US012453557B2

(12) United States Patent
Baxter, III et al.

(10) Patent No.: US 12,453,557 B2
(45) Date of Patent: Oct. 28, 2025

(54) LAYER OF MATERIAL FOR A SURGICAL END EFFECTOR

(71) Applicant: Cilag GmbH International, Zug (CH)

(72) Inventors: Chester O. Baxter, III, Loveland, OH (US); Frederick E. Shelton, IV, Hillsboro, OH (US); Charles J. Scheib, Loveland, OH (US); Christopher W. Widenhouse, Clarksville, OH (US); William B. Weisenburgh, II, Maineville, OH (US); John L. Stammen, Cincinnati, OH (US); Mark H. Ransick, West Chester, OH (US); Stephanie A. Mutchler, Loveland, OH (US); Gary W. Knight, Lebanon, OH (US); Michael S. Cropper, Edgewood, KY (US); Sean P. Conlon, Loveland, OH (US); Jeffrey S. Swayze, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/376,228

(22) Filed: Oct. 3, 2023

(65) Prior Publication Data

US 2024/0032922 A1 Feb. 1, 2024

Related U.S. Application Data

(63) Continuation of application No. 16/434,317, filed on Jun. 7, 2019, now Pat. No. 11,812,965, which is a (Continued)

(51) Int. Cl.
*A61B 17/072* (2006.01)
*A61B 17/00* (2006.01)
(Continued)

(52) U.S. Cl.
CPC .. *A61B 17/07292* (2013.01); *A61B 17/00491* (2013.01); *A61B 17/068* (2013.01); (Continued)

(58) Field of Classification Search
CPC ........ A61B 17/07292; A61B 17/00491; A61B 17/0068; A61B 17/0072; A61B 17/02707; A61B 17/1155; A61L 17/005
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2012203035 A1 6/2012
(Continued)

OTHER PUBLICATIONS

ASTM procedure D2240-00, "Standard Test Method for Rubber Property-Durometer Hardness," (Published Aug. 2000).
(Continued)

*Primary Examiner* — James D Sells

(57) ABSTRACT

A method of creating a tissue thickness compensator is disclosed. The method comprises dispensing oxidized regenerated cellulose onto a cover sheet, folding the cover sheet to at least partially capture the oxidized regenerated cellulose therein, and creating the tissue thickness compensator by applying a seal to the folded cover sheet.

13 Claims, 153 Drawing Sheets

Related U.S. Application Data continuation-in-part of application No. 15/800,713, filed on Nov. 1, 2017, now Pat. No. 11,504,116, which is a continuation of application No. 13/766,325, filed on Feb. 13, 2013, now abandoned, which is a continuation of application No. 13/433,129, filed on Mar. 28, 2012, now Pat. No. 9,211,120, said application No. 16/434,317 is a continuation-in-part of application No. 16/188,107, filed on Nov. 12, 2018, now Pat. No. 10,945,731, which is a continuation of application No. 13/433,141, filed on Mar. 28, 2012, now Pat. No. 10,123,798, which is a continuation-in-part of application No. 13/097,891, filed on Apr. 29, 2011, now Pat. No. 8,864,009, which is a continuation-in-part of application No. 12/894,377, filed on Sep. 30, 2010, now Pat. No. 8,393,514.

(51) Int. Cl.

| | |
|---|---|
| ***A61B 17/068*** | (2006.01) |
| ***A61B 17/115*** | (2006.01) |
| ***A61L 17/00*** | (2006.01) |
| *A61B 17/064* | (2006.01) |
| *A61B 17/29* | (2006.01) |
| *A61B 17/32* | (2006.01) |
| *A61B 90/00* | (2016.01) |

(52) U.S. Cl.

CPC ...... *A61B 17/072* (2013.01); *A61B 17/07207* (2013.01); *A61B 17/1155* (2013.01); *A61L 17/005* (2013.01); *A61B 2017/00004* (2013.01); *A61B 2017/00477* (2013.01); *A61B 2017/00526* (2013.01); *A61B 2017/0053* (2013.01); *A61B 2017/00561* (2013.01); *A61B 2017/00818* (2013.01); *A61B 2017/00862* (2013.01); *A61B 2017/00884* (2013.01); *A61B 2017/00889* (2013.01); *A61B 2017/00893* (2013.01); *A61B 2017/00898* (2013.01); *A61B 2017/00942* (2013.01); *A61B 2017/00951* (2013.01); *A61B 17/0644* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/07285* (2013.01); *A61B 2017/2908* (2013.01); *A61B 17/2909* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/2946* (2013.01); *A61B 2017/320052* (2013.01); *A61B 2090/0811* (2016.02); *A61B 2090/3966* (2016.02); *A61L 2300/102* (2013.01); *A61L 2300/232* (2013.01); *A61L 2300/45* (2013.01); *F04C 2270/0421* (2013.01); *Y10T 29/49826* (2015.01)

(58) Field of Classification Search

USPC .......................................................... 156/196

See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |

(56) References Cited

U.S. PATENT DOCUMENTS

| | | | |
|---|---|---|---|
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,616,278 | A | 10/1971 | Jansen |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,797,494 | A | 3/1974 | Zaffaroni |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,825,007 | A | 7/1974 | Rand |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,993,072 | A | 11/1976 | Zaffaroni |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,160,857 | A | 7/1979 | Nardella et al. |
| 4,169,476 | A | 10/1979 | Hiltebrandt |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,191,377 | A | 3/1980 | Burnside |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |

(56) References Cited

U.S. PATENT DOCUMENTS 4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.

(56) References Cited

U.S. PATENT DOCUMENTS 4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,868,958 A 9/1989 Suzuki et al.
4,869,414 A 9/1989 Green et al.
4,869,415 A 9/1989 Fox
4,870,966 A 10/1989 Dellon et al.
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,039 A 4/1990 Nutter
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
D316,875 S 5/1991 Momot et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,019,077 A 5/1991 De Bastiani et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.

(56) References Cited

U.S. PATENT DOCUMENTS 5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,100,422 A 3/1992 Berguer et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,134,229 A * 7/1992 Saferstein .............. C08B 15/02
424/443
5,135,483 A 8/1992 Wagner et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,151 A 10/1992 Imran
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,163,842 A 11/1992 Nonomura
5,164,652 A 11/1992 Johnson et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,180,375 A 1/1993 Feibus
5,181,514 A 1/1993 Solomon et al.
5,187,422 A 2/1993 Izenbaard et al.
5,188,102 A 2/1993 Idemoto et al.
5,188,111 A 2/1993 Yates et al.
5,188,126 A 2/1993 Fabian et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D337,962 S 8/1993 Avitan
D338,729 S 8/1993 Sprecklemeier et al.
5,234,447 A 8/1993 Kaster et al.
5,236,269 A 8/1993 Handy
5,236,424 A 8/1993 Imran
5,236,440 A 8/1993 Hlavacek
5,236,629 A 8/1993 Mahabadi et al.
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,251,801 A 10/1993 Ruckdeschel et al.
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,269,794 A 12/1993 Rexroth
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,714 A 3/1994 Kramer
5,300,087 A 4/1994 Knoepfler
5,302,148 A 4/1994 Heinz
5,303,606 A 4/1994 Kokinda
5,304,204 A 4/1994 Bregen

(56) References Cited

U.S. PATENT DOCUMENTS

D347,474 S 5/1994 Olson
5,307,976 A 5/1994 Olson et al.
5,308,353 A 5/1994 Beurrier
5,308,358 A 5/1994 Bond et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller nee Degwitz et al.
5,314,466 A 5/1994 Stern et al.
5,318,221 A 6/1994 Green et al.
5,318,589 A 6/1994 Lichtman
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Lacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,215 A 10/1994 Viracola
5,354,250 A 10/1994 Christensen
5,354,303 A 10/1994 Spaeth et al.
5,355,897 A 10/1994 Pietrafitta et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,368,599 A 11/1994 Hirsch et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,738 A 1/1995 Herbermann
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,388,748 A 2/1995 Davignon et al.
5,389,072 A 2/1995 Imran
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.

(56) References Cited

U.S. PATENT DOCUMENTS

| | | | |
|---|---|---|---|
| 5,431,323 | A | 7/1995 | Smith et al. |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,644 | A | 8/1995 | Pietrafitta et al. |
| 5,446,646 | A | 8/1995 | Miyazaki |
| 5,447,265 | A | 9/1995 | Vidal et al. |
| 5,447,417 | A | 9/1995 | Kuhl et al. |
| 5,447,513 | A | 9/1995 | Davison et al. |
| 5,449,355 | A | 9/1995 | Rhum et al. |
| 5,449,365 | A | 9/1995 | Green et al. |
| 5,449,370 | A | 9/1995 | Vaitekunas |
| 5,452,836 | A | 9/1995 | Huitema et al. |
| 5,452,837 | A | 9/1995 | Williamson, IV et al. |
| 5,454,378 | A | 10/1995 | Palmer et al. |
| 5,454,822 | A | 10/1995 | Schob et al. |
| 5,454,824 | A | 10/1995 | Fontayne et al. |
| 5,454,827 | A | 10/1995 | Aust et al. |
| 5,456,401 | A | 10/1995 | Green et al. |
| 5,456,917 | A | 10/1995 | Wise et al. |
| 5,458,279 | A | 10/1995 | Plyley |
| 5,458,579 | A | 10/1995 | Chodorow et al. |
| 5,462,215 | A | 10/1995 | Viola et al. |
| 5,464,013 | A | 11/1995 | Lemelson |
| 5,464,144 | A | 11/1995 | Guy et al. |
| 5,464,300 | A | 11/1995 | Crainich |
| 5,465,819 | A | 11/1995 | Weilant et al. |
| 5,465,894 | A | 11/1995 | Clark et al. |
| 5,465,895 | A | 11/1995 | Knodel et al. |
| 5,465,896 | A | 11/1995 | Allen et al. |
| 5,466,020 | A | 11/1995 | Page et al. |
| 5,467,911 | A | 11/1995 | Tsuruta et al. |
| 5,468,253 | A | 11/1995 | Bezwada et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,470,010 | A | 11/1995 | Rothfuss et al. |
| 5,471,129 | A | 11/1995 | Mann |
| 5,472,132 | A | 12/1995 | Savage et al. |
| 5,472,442 | A | 12/1995 | Klicek |
| 5,473,204 | A | 12/1995 | Temple |
| 5,474,057 | A | 12/1995 | Makower et al. |
| 5,474,223 | A | 12/1995 | Viola et al. |
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,630 | A | 1/1996 | Unuma et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,508,080 | A | 4/1996 | Sorimachi et al. |
| 5,509,596 | A | 4/1996 | Green et al. |
| 5,509,916 | A | 4/1996 | Taylor |
| 5,509,918 | A | 4/1996 | Romano |
| 5,510,138 | A | 4/1996 | Sanftleben et al. |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |

(56) References Cited

U.S. PATENT DOCUMENTS 5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,694 A 10/1996 Sauer et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
D378,500 S 3/1997 Nakai et al.
5,607,094 A 3/1997 Clark et al.
5,607,095 A 3/1997 Smith et al.
5,607,303 A 3/1997 Nakamura
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,415 A 4/1997 Lucey et al.
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.

(56) References Cited

U.S. PATENT DOCUMENTS 5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,683,432 A 11/1997 Goedeke et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,265 A 12/1997 Romano
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,746,770 A 5/1998 Zeitels et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
D395,645 S 6/1998 Cappa et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,186 A 6/1998 Faraz et al.
5,766,188 A 6/1998 Gaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,798,752 A 8/1998 Buxton et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger

(56) References Cited

U.S. PATENT DOCUMENTS

| | | | |
|---|---|---|---|
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,240 | A | 9/1998 | Robertson |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,855 | A | 4/1999 | Jacobs |
| 5,893,863 | A | 4/1999 | Yoon |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,907,664 | A | 5/1999 | Wang et al. |
| 5,908,149 | A | 6/1999 | Welch et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,922,001 | A | 7/1999 | Yoon |
| 5,922,003 | A | 7/1999 | Anctil et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,980,569 | A | 11/1999 | Scirica |
| 5,984,949 | A | 11/1999 | Levin |
| 5,988,479 | A | 11/1999 | Palmer |
| 5,990,379 | A | 11/1999 | Gregory |
| 5,993,464 | A | 11/1999 | Knodel |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |

(56) References Cited

U.S. PATENT DOCUMENTS 6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,275 A 2/2000 Horvitz et al.
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,031,148 A 2/2000 Hayes et al.
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
D422,545 S 4/2000 Palalau et al.
6,045,560 A 4/2000 Mckean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,144 A 5/2000 Wolf et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
6,094,021 A 7/2000 Noro et al.
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
RE36,923 E 10/2000 Hiroi et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,148,979 A 11/2000 Roach et al.
6,149,660 A 11/2000 Laufer et al.
6,151,323 A 11/2000 O'Connell et al.
6,152,935 A 11/2000 Kammerer et al.
6,155,083 A 12/2000 Goeser et al.
6,155,473 A 12/2000 Tompkins et al.
6,156,056 A 12/2000 Kearns et al.
6,157,169 A 12/2000 Lee
6,157,303 A 12/2000 Bodie et al.
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam

(56) References Cited

U.S. PATENT DOCUMENTS 6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,235,036 B1 5/2001 Gardner et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,607 B1 10/2001 Milbocker
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,338,738 B1 1/2002 Bellotti et al.
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.

(56) References Cited

U.S. PATENT DOCUMENTS 6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,463,824 B1 10/2002 Prell et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,844 B2 4/2003 Lee et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,569,173 B1 5/2003 Blatter et al.
6,572,629 B2 6/2003 Kalloo et al.
6,575,969 B1 6/2003 Rittman, III et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,623,482 B2 9/2003 Pendekanti et al.
6,625,517 B1 9/2003 Bogdanov et al.
6,626,834 B2 9/2003 Dunne et al.
6,626,901 B1 9/2003 Treat et al.
6,626,938 B1 9/2003 Butaric et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi

(56) References Cited

U.S. PATENT DOCUMENTS 6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,750,622 B2 6/2004 Simizu et al.
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,819,269 B2 11/2004 Flick
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble

(56) References Cited

U.S. PATENT DOCUMENTS 6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
6,958,070 B2 10/2005 Witt et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,960,894 B2 11/2005 Carusillo et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.

(56) References Cited

U.S. PATENT DOCUMENTS 7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,412 B1 7/2006 Reynolds et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,201 B2 9/2006 Truckai et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,846 B2 1/2007 Dycus et al.
7,156,863 B2 1/2007 Sonnenschein et al.
7,159,750 B2 1/2007 Racenet et al.
7,160,296 B2 1/2007 Pearson et al.

(56) References Cited

U.S. PATENT DOCUMENTS 7,160,299 B2 1/2007 Baily
7,160,311 B2 1/2007 Blatter et al.
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,169,146 B2 1/2007 Truckai et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,197,965 B1 4/2007 Anderson
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,205,959 B2 4/2007 Henriksson
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,311,709 B2 12/2007 Truckai et al.
7,313,430 B2 12/2007 Urquhart et al.
7,314,473 B2 1/2008 Jinno et al.
7,317,955 B2 1/2008 McGreevy
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.

(56) References Cited

U.S. PATENT DOCUMENTS

| | | | |
|---|---|---|---|
| 7,344,532 | B2 | 3/2008 | Goble et al. |
| 7,344,533 | B2 | 3/2008 | Pearson et al. |
| 7,346,344 | B2 | 3/2008 | Fontaine |
| 7,346,406 | B2 | 3/2008 | Brotto et al. |
| 7,348,763 | B1 | 3/2008 | Reinhart et al. |
| 7,348,875 | B2 | 3/2008 | Hughes et al. |
| RE40,237 | E | 4/2008 | Bilotti et al. |
| 7,351,258 | B2 | 4/2008 | Ricotta et al. |
| 7,354,398 | B2 | 4/2008 | Kanazawa |
| 7,354,440 | B2 | 4/2008 | Truckal et al. |
| 7,354,447 | B2 | 4/2008 | Shelton, IV et al. |
| 7,354,502 | B2 | 4/2008 | Polat et al. |
| 7,357,287 | B2 | 4/2008 | Shelton, IV et al. |
| 7,357,806 | B2 | 4/2008 | Rivera et al. |
| 7,361,168 | B2 | 4/2008 | Makower et al. |
| 7,361,195 | B2 | 4/2008 | Schwartz et al. |
| 7,362,062 | B2 | 4/2008 | Schneider et al. |
| 7,364,060 | B2 | 4/2008 | Milliman |
| 7,364,061 | B2 | 4/2008 | Swayze et al. |
| 7,367,485 | B2 | 5/2008 | Shelton, IV et al. |
| 7,367,973 | B2 | 5/2008 | Manzo et al. |
| 7,368,124 | B2 | 5/2008 | Chun et al. |
| 7,371,210 | B2 | 5/2008 | Brock et al. |
| 7,371,403 | B2 | 5/2008 | McCarthy et al. |
| 7,375,493 | B2 | 5/2008 | Calhoon et al. |
| 7,377,918 | B2 | 5/2008 | Amoah |
| 7,377,928 | B2 | 5/2008 | Zubik et al. |
| 7,378,817 | B2 | 5/2008 | Calhoon et al. |
| RE40,388 | E | 6/2008 | Gines |
| D570,868 | S | 6/2008 | Hosokawa et al. |
| 7,380,695 | B2 | 6/2008 | Doll et al. |
| 7,380,696 | B2 | 6/2008 | Shelton, IV et al. |
| 7,384,403 | B2 | 6/2008 | Sherman |
| 7,384,417 | B2 | 6/2008 | Cucin |
| 7,386,365 | B2 | 6/2008 | Nixon |
| 7,386,730 | B2 | 6/2008 | Uchikubo |
| 7,388,217 | B2 | 6/2008 | Buschbeck et al. |
| 7,388,484 | B2 | 6/2008 | Hsu |
| 7,391,173 | B2 | 6/2008 | Schena |
| 7,394,190 | B2 | 7/2008 | Huang |
| 7,396,356 | B2 | 7/2008 | Mollenauer |
| 7,397,364 | B2 | 7/2008 | Govari |
| 7,398,707 | B2 | 7/2008 | Morley et al. |
| 7,398,907 | B2 | 7/2008 | Racenet et al. |
| 7,398,908 | B2 | 7/2008 | Holsten et al. |
| 7,400,107 | B2 | 7/2008 | Schneider et al. |
| 7,400,752 | B2 | 7/2008 | Zacharias |
| 7,401,000 | B2 | 7/2008 | Nakamura |
| 7,401,721 | B2 | 7/2008 | Holsten et al. |
| 7,404,449 | B2 | 7/2008 | Bermingham et al. |
| 7,404,508 | B2 | 7/2008 | Smith et al. |
| 7,404,509 | B2 | 7/2008 | Ortiz et al. |
| 7,404,822 | B2 | 7/2008 | Viart et al. |
| D575,793 | S | 8/2008 | Ording |
| 7,407,074 | B2 | 8/2008 | Ortiz et al. |
| 7,407,075 | B2 | 8/2008 | Holsten et al. |
| 7,407,076 | B2 | 8/2008 | Racenet et al. |
| 7,407,077 | B2 | 8/2008 | Ortiz et al. |
| 7,407,078 | B2 | 8/2008 | Shelton, IV et al. |
| 7,408,310 | B2 | 8/2008 | Hong et al. |
| 7,410,085 | B2 | 8/2008 | Wolf et al. |
| 7,410,086 | B2 | 8/2008 | Ortiz et al. |
| 7,410,483 | B2 | 8/2008 | Danitz et al. |
| 7,413,563 | B2 | 8/2008 | Corcoran et al. |
| 7,416,101 | B2 | 8/2008 | Shelton, IV et al. |
| 7,418,078 | B2 | 8/2008 | Blanz et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,419,321 | B2 | 9/2008 | Tereschouk |
| 7,419,495 | B2 | 9/2008 | Menn et al. |
| 7,422,136 | B1 | 9/2008 | Marczyk |
| 7,422,138 | B2 | 9/2008 | Bilotti et al. |
| 7,422,139 | B2 | 9/2008 | Shelton, IV et al. |
| 7,422,582 | B2 | 9/2008 | Malackowski et al. |
| 7,424,965 | B2 | 9/2008 | Racenet et al. |
| 7,427,607 | B2 | 9/2008 | Suzuki |
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,443,547 | B2 | 10/2008 | Moreno et al. |
| D580,942 | S | 11/2008 | Oshiro et al. |
| 7,446,131 | B1 | 11/2008 | Liu et al. |
| 7,448,525 | B2 | 11/2008 | Shelton, IV et al. |
| 7,450,010 | B1 | 11/2008 | Gravelle et al. |
| 7,450,991 | B2 | 11/2008 | Smith et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,455,687 | B2 | 11/2008 | Saunders et al. |
| D582,934 | S | 12/2008 | Byeon |
| 7,461,767 | B2 | 12/2008 | Viola et al. |
| 7,462,187 | B2 | 12/2008 | Johnston et al. |
| 7,464,845 | B2 | 12/2008 | Chou |
| 7,464,846 | B2 | 12/2008 | Shelton, IV et al. |
| 7,464,847 | B2 | 12/2008 | Viola et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,489,055 | B2 | 2/2009 | Jeong et al. |
| 7,490,749 | B2 | 2/2009 | Schall et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,566 | B2 | 3/2009 | Jacobs et al. |
| 7,513,407 | B1 | 4/2009 | Chang |
| 7,513,408 | B2 | 4/2009 | Shelton, IV et al. |
| 7,517,356 | B2 | 4/2009 | Heinrich |
| 7,524,320 | B2 | 4/2009 | Tierney et al. |

(56) References Cited

U.S. PATENT DOCUMENTS 7,527,632 B2 5/2009 Houghton et al.
7,530,984 B2 5/2009 Sonnenschein et al.
7,530,985 B2 5/2009 Takemoto et al.
7,533,790 B1 5/2009 Knodel et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,572,298 B2 8/2009 Roller et al.
7,575,144 B2 8/2009 Ortiz et al.
7,578,825 B2 8/2009 Huebner
D600,703 S 9/2009 LaManna et al.
D600,712 S 9/2009 LaManna et al.
7,582,086 B2 9/2009 Privitera et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
D601,578 S 10/2009 Poulet et al.
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,605,826 B2 10/2009 Sauer
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
7,618,427 B2 11/2009 Ortiz et al.
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,625,662 B2 12/2009 Vaisnys et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,639,598 B2 12/2009 Sovenyi
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,016 B2 1/2010 Nycz et al.
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.

(56) References Cited

U.S. PATENT DOCUMENTS

| | | | |
|---|---|---|---|
| 7,695,493 | B2 | 4/2010 | Saadat et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,717,873 | B2 | 5/2010 | Swick |
| 7,717,915 | B2 | 5/2010 | Miyazawa |
| 7,717,926 | B2 | 5/2010 | Whitfield et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,932 | B2 | 5/2010 | Cole et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shalton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |
| 7,725,214 | B2 | 5/2010 | Diolaiti |
| 7,726,171 | B2 | 6/2010 | Langlotz et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,727,954 | B2 | 6/2010 | McKay |
| 7,728,553 | B2 | 6/2010 | Carrier et al. |
| 7,729,742 | B2 | 6/2010 | Govari |
| 7,731,072 | B2 | 6/2010 | Timm et al. |
| 7,731,073 | B2 | 6/2010 | Wixey et al. |
| 7,731,724 | B2 | 6/2010 | Huitema et al. |
| 7,735,703 | B2 | 6/2010 | Morgan et al. |
| 7,735,704 | B2 | 6/2010 | Bilotti |
| 7,736,254 | B2 | 6/2010 | Schena |
| 7,736,306 | B2 | 6/2010 | Brustad et al. |
| 7,736,356 | B2 | 6/2010 | Cooper et al. |
| 7,736,374 | B2 | 6/2010 | Vaughan et al. |
| 7,738,971 | B2 | 6/2010 | Swayze et al. |
| 7,740,159 | B2 | 6/2010 | Shelton, IV et al. |
| 7,742,036 | B2 | 6/2010 | Grant et al. |
| 7,743,960 | B2 | 6/2010 | Whitman et al. |
| 7,744,624 | B2 | 6/2010 | Bettuchi |
| 7,744,627 | B2 | 6/2010 | Orban, III et al. |
| 7,744,628 | B2 | 6/2010 | Viola |
| 7,747,146 | B2 | 6/2010 | Milano et al. |
| 7,748,587 | B2 | 7/2010 | Haramiishi et al. |
| 7,748,632 | B2 | 7/2010 | Coleman et al. |
| 7,749,204 | B2 | 7/2010 | Dhanaraj et al. |
| 7,749,240 | B2 | 7/2010 | Takahashi et al. |
| 7,751,870 | B2 | 7/2010 | Whitman |
| 7,753,245 | B2 | 7/2010 | Boudreaux et al. |
| 7,753,246 | B2 | 7/2010 | Scirica |
| 7,753,904 | B2 | 7/2010 | Shelton, IV et al. |
| 7,757,924 | B2 | 7/2010 | Gerbi et al. |
| 7,758,594 | B2 | 7/2010 | Lamson et al. |
| 7,758,612 | B2 | 7/2010 | Shipp |
| 7,758,613 | B2 | 7/2010 | Whitman |
| 7,762,462 | B2 | 7/2010 | Gelbman |
| 7,762,998 | B2 | 7/2010 | Birk et al. |
| D622,286 | S | 8/2010 | Umezawa |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,770,658 | B2 | 8/2010 | Ito et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,772,725 | B2 | 8/2010 | Siman-Tov |
| 7,775,972 | B2 | 8/2010 | Brock et al. |
| 7,776,037 | B2 | 8/2010 | Odom |
| 7,776,060 | B2 | 8/2010 | Mooradian et al. |
| 7,776,065 | B2 | 8/2010 | Griffiths et al. |
| 7,778,004 | B2 | 8/2010 | Nerheim et al. |
| 7,779,614 | B1 | 8/2010 | McGonagle et al. |
| 7,779,737 | B2 | 8/2010 | Newman, Jr. et al. |
| 7,780,054 | B2 | 8/2010 | Wales |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,283 | B2 | 9/2010 | Shah |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |

(56) References Cited

U.S. PATENT DOCUMENTS

| | | | |
|---|---|---|---|
| 7,832,612 | B2 | 11/2010 | Baxter, III et al. |
| 7,833,234 | B2 | 11/2010 | Bailly et al. |
| 7,835,823 | B2 | 11/2010 | Sillman et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,425 | B2 | 11/2010 | Saeki et al. |
| 7,837,685 | B2 | 11/2010 | Weinberg et al. |
| 7,837,687 | B2 | 11/2010 | Harp |
| 7,837,694 | B2 | 11/2010 | Tethrake et al. |
| 7,838,789 | B2 | 11/2010 | Stoffers et al. |
| 7,839,109 | B2 | 11/2010 | Carmen, Jr. et al. |
| 7,840,253 | B2 | 11/2010 | Tremblay et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,843,158 | B2 | 11/2010 | Prisco |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,845,538 | B2 | 12/2010 | Whitman |
| 7,845,912 | B2 | 12/2010 | Sung et al. |
| 7,846,085 | B2 | 12/2010 | Silverman et al. |
| 7,846,149 | B2 | 12/2010 | Jankowski |
| 7,846,161 | B2 | 12/2010 | Dumbauld et al. |
| 7,848,066 | B2 | 12/2010 | Yanagishima |
| 7,850,623 | B2 | 12/2010 | Griffin et al. |
| 7,850,642 | B2 | 12/2010 | Moll et al. |
| 7,850,982 | B2 | 12/2010 | Stopek et al. |
| 7,853,813 | B2 | 12/2010 | Lee |
| 7,854,735 | B2 | 12/2010 | Houser et al. |
| 7,854,736 | B2 | 12/2010 | Ryan |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,502 | B2 | 1/2011 | Pool et al. |
| 7,862,546 | B2 | 1/2011 | Conlon et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,871,440 | B2 | 1/2011 | Schwartz et al. |
| 7,875,055 | B2 | 1/2011 | Cichocki, Jr. |
| 7,877,869 | B2 | 2/2011 | Mehdizadeh et al. |
| 7,879,063 | B2 | 2/2011 | Khosravi |
| 7,879,070 | B2 | 2/2011 | Ortiz et al. |
| 7,879,367 | B2 | 2/2011 | Heublein et al. |
| 7,883,461 | B2 | 2/2011 | Albrecht et al. |
| 7,883,465 | B2 | 2/2011 | Donofrio et al. |
| 7,883,540 | B2 | 2/2011 | Niwa et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,887,536 | B2 | 2/2011 | Johnson et al. |
| 7,887,563 | B2 | 2/2011 | Cummins |
| 7,887,755 | B2 | 2/2011 | Mingerink et al. |
| 7,891,531 | B1 | 2/2011 | Ward |
| 7,891,532 | B2 | 2/2011 | Mastri et al. |
| 7,892,200 | B2 | 2/2011 | Birk et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,671 | B2 | 3/2011 | Kim et al. |
| 7,896,869 | B2 | 3/2011 | DiSilvestro et al. |
| 7,896,877 | B2 | 3/2011 | Hall et al. |
| 7,896,895 | B2 | 3/2011 | Boudreaux et al. |
| 7,896,897 | B2 | 3/2011 | Gresham et al. |
| 7,896,900 | B2 | 3/2011 | Frank et al. |
| 7,898,198 | B2 | 3/2011 | Murphree |
| 7,900,805 | B2 | 3/2011 | Shelton, IV et al. |
| 7,900,806 | B2 | 3/2011 | Chen et al. |
| 7,901,381 | B2 | 3/2011 | Birk et al. |
| 7,905,380 | B2 | 3/2011 | Shelton, IV et al. |
| 7,905,381 | B2 | 3/2011 | Baxter, III et al. |
| 7,905,881 | B2 | 3/2011 | Masuda et al. |
| 7,905,889 | B2 | 3/2011 | Catanese, III et al. |
| 7,905,890 | B2 | 3/2011 | Whitfield et al. |
| 7,905,902 | B2 | 3/2011 | Huitema et al. |
| 7,909,039 | B2 | 3/2011 | Hur |
| 7,909,191 | B2 | 3/2011 | Baker et al. |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,521 | B2 | 3/2011 | Wang et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,845 | B2 | 4/2011 | Saadat et al. |
| 7,918,848 | B2 | 4/2011 | Lau et al. |
| 7,918,861 | B2 | 4/2011 | Brock et al. |
| 7,918,867 | B2 | 4/2011 | Dana et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,926,692 | B2 | 4/2011 | Racenet et al. |
| 7,927,328 | B2 | 4/2011 | Orszulak et al. |
| 7,928,281 | B2 | 4/2011 | Augustine |
| 7,930,040 | B1 | 4/2011 | Kelsch et al. |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,931,877 | B2 | 4/2011 | Steffens et al. |
| D638,028 | S | 5/2011 | Cook et al. |
| 7,934,630 | B2 | 5/2011 | Shelton, IV et al. |
| 7,934,631 | B2 | 5/2011 | Balbierz et al. |
| 7,934,896 | B2 | 5/2011 | Schnier |
| 7,935,130 | B2 | 5/2011 | Williams |
| 7,935,773 | B2 | 5/2011 | Hadba et al. |
| 7,936,142 | B2 | 5/2011 | Otsuka et al. |
| 7,938,307 | B2 | 5/2011 | Bettuchi |
| 7,939,152 | B2 | 5/2011 | Haskin et al. |
| 7,941,865 | B2 | 5/2011 | Seman, Jr. et al. |
| 7,942,300 | B2 | 5/2011 | Rethy et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,945,798 | B2 | 5/2011 | Carlson et al. |
| 7,946,453 | B2 | 5/2011 | Voegele et al. |
| 7,947,011 | B2 | 5/2011 | Birk et al. |
| 7,948,381 | B2 | 5/2011 | Lindsay et al. |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,951,071 | B2 | 5/2011 | Whitman et al. |
| 7,951,166 | B2 | 5/2011 | Orban, III et al. |
| 7,952,464 | B2 | 5/2011 | Nikitin et al. |
| 7,954,682 | B2 | 6/2011 | Giordano et al. |
| 7,954,684 | B2 | 6/2011 | Boudreaux |
| 7,954,685 | B2 | 6/2011 | Viola |
| 7,954,686 | B2 | 6/2011 | Baxter et al. |
| 7,954,687 | B2 | 6/2011 | Zemlok et al. |
| 7,954,688 | B2 | 6/2011 | Argentine et al. |
| 7,955,253 | B2 | 6/2011 | Ewers et al. |
| 7,955,257 | B2 | 6/2011 | Frasier et al. |
| 7,955,322 | B2 | 6/2011 | Devengenzo et al. |
| 7,955,327 | B2 | 6/2011 | Sartor et al. |
| 7,955,380 | B2 | 6/2011 | Chu et al. |

(56) References Cited

U.S. PATENT DOCUMENTS

| | | | |
|---|---|---|---|
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,996,064 | B2 | 8/2011 | Simon et al. |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,741 | B2 | 9/2011 | Cole et al. |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,024 | B2 | 11/2011 | Viola et al. |
| 8,052,636 | B2 | 11/2011 | Moll et al. |
| 8,052,697 | B2 | 11/2011 | Phillips |
| 8,056,787 | B2 | 11/2011 | Boudreaux et al. |
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| D652,048 | S | 1/2012 | Joseph |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |

(56) References Cited

U.S. PATENT DOCUMENTS 8,102,138 B2 1/2012 Sekine et al.
8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,114,345 B2 2/2012 Dlugos, Jr. et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,150 B2 4/2012 Viola et al.
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
D661,314 S 6/2012 Marchetti
D661,315 S 6/2012 Marchetti et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,413 B2 7/2012 Whitman et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,230,235 B2 7/2012 Goodman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,536 B2 8/2012 Marczyk
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.

(56) References Cited

U.S. PATENT DOCUMENTS

| | | | |
|---|---|---|---|
| 8,245,594 | B2 | 8/2012 | Rogers et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,245,901 | B2 | 8/2012 | Stopek |
| 8,246,608 | B2 | 8/2012 | Omori et al. |
| 8,246,637 | B2 | 8/2012 | Viola et al. |
| 8,251,921 | B2 | 8/2012 | Briggs et al. |
| 8,252,009 | B2 | 8/2012 | Weller et al. |
| D667,450 | S | 9/2012 | Eby et al. |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,257,251 | B2 | 9/2012 | Shelton, IV et al. |
| 8,257,356 | B2 | 9/2012 | Bleich et al. |
| 8,257,386 | B2 | 9/2012 | Lee et al. |
| 8,257,391 | B2 | 9/2012 | Orban, III et al. |
| 8,257,634 | B2 | 9/2012 | Scirica |
| 8,258,745 | B2 | 9/2012 | Smith et al. |
| 8,261,958 | B1 | 9/2012 | Knodel |
| 8,262,560 | B2 | 9/2012 | Whitman |
| 8,262,655 | B2 | 9/2012 | Ghabrial et al. |
| 8,266,232 | B2 | 9/2012 | Piper et al. |
| 8,267,300 | B2 | 9/2012 | Boudreaux |
| 8,267,849 | B2 | 9/2012 | Wazer et al. |
| 8,267,924 | B2 | 9/2012 | Zemlok et al. |
| 8,267,946 | B2 | 9/2012 | Whitfield et al. |
| 8,267,951 | B2 | 9/2012 | Whayne et al. |
| 8,268,344 | B2 | 9/2012 | Ma et al. |
| 8,269,121 | B2 | 9/2012 | Smith |
| 8,272,553 | B2 | 9/2012 | Mastri et al. |
| 8,272,554 | B2 | 9/2012 | Whitman et al. |
| 8,272,918 | B2 | 9/2012 | Lam |
| 8,273,404 | B2 | 9/2012 | Dave et al. |
| 8,276,594 | B2 | 10/2012 | Shah |
| 8,276,801 | B2 | 10/2012 | Zemlok et al. |
| 8,276,802 | B2 | 10/2012 | Kostrzewski |
| 8,277,473 | B2 | 10/2012 | Sunaoshi et al. |
| 8,281,446 | B2 | 10/2012 | Moskovich |
| 8,281,973 | B2 | 10/2012 | Wenchell et al. |
| 8,281,974 | B2 | 10/2012 | Hessler et al. |
| 8,282,654 | B2 | 10/2012 | Ferrari et al. |
| 8,285,367 | B2 | 10/2012 | Hyde et al. |
| 8,286,723 | B2 | 10/2012 | Puzio et al. |
| 8,286,845 | B2 | 10/2012 | Perry et al. |
| 8,286,846 | B2 | 10/2012 | Smith et al. |
| 8,286,847 | B2 | 10/2012 | Taylor |
| 8,287,487 | B2 | 10/2012 | Estes |
| 8,287,522 | B2 | 10/2012 | Moses et al. |
| 8,287,561 | B2 | 10/2012 | Nunez et al. |
| 8,288,984 | B2 | 10/2012 | Yang |
| 8,289,403 | B2 | 10/2012 | Dobashi et al. |
| 8,290,883 | B2 | 10/2012 | Takeuchi et al. |
| 8,292,147 | B2 | 10/2012 | Viola |
| 8,292,148 | B2 | 10/2012 | Viola |
| 8,292,150 | B2 | 10/2012 | Bryant |
| 8,292,151 | B2 | 10/2012 | Viola |
| 8,292,152 | B2 | 10/2012 | Milliman et al. |
| 8,292,155 | B2 | 10/2012 | Shelton, IV et al. |
| 8,292,157 | B2 | 10/2012 | Smith et al. |
| 8,292,158 | B2 | 10/2012 | Sapienza |
| 8,292,801 | B2 | 10/2012 | Dejima et al. |
| 8,292,888 | B2 | 10/2012 | Whitman |
| 8,292,906 | B2 | 10/2012 | Taylor et al. |
| 8,294,399 | B2 | 10/2012 | Suzuki et al. |
| 8,298,161 | B2 | 10/2012 | Vargas |
| 8,298,189 | B2 | 10/2012 | Fisher et al. |
| 8,298,233 | B2 | 10/2012 | Mueller |
| 8,298,677 | B2 | 10/2012 | Wiesner et al. |
| 8,302,323 | B2 | 11/2012 | Fortier et al. |
| 8,303,621 | B2 | 11/2012 | Miyamoto et al. |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,046 | B2 | 11/2012 | Prommersberger |
| 8,308,659 | B2 | 11/2012 | Scheibe et al. |
| 8,308,725 | B2 | 11/2012 | Bell et al. |
| 8,310,188 | B2 | 11/2012 | Nakai |
| 8,313,444 | B2 | 11/2012 | Thompson et al. |
| 8,313,496 | B2 | 11/2012 | Sauer et al. |
| 8,313,499 | B2 | 11/2012 | Magnusson et al. |
| 8,313,509 | B2 | 11/2012 | Kostrzewski |
| 8,317,070 | B2 | 11/2012 | Hueil et al. |
| 8,317,071 | B1 | 11/2012 | Knodel |
| 8,317,074 | B2 | 11/2012 | Ortiz et al. |
| 8,317,437 | B2 | 11/2012 | Merkley et al. |
| 8,317,744 | B2 | 11/2012 | Kirschenman |
| 8,317,790 | B2 | 11/2012 | Bell et al. |
| 8,319,002 | B2 | 11/2012 | Daniels et al. |
| D672,784 | S | 12/2012 | Clanton et al. |
| 8,322,455 | B2 | 12/2012 | Shelton, IV et al. |
| 8,322,589 | B2 | 12/2012 | Boudreaux |
| 8,322,590 | B2 | 12/2012 | Patel et al. |
| 8,322,901 | B2 | 12/2012 | Michelotti |
| 8,323,271 | B2 | 12/2012 | Humayun et al. |
| 8,323,789 | B2 | 12/2012 | Rozhin et al. |
| 8,324,585 | B2 | 12/2012 | McBroom et al. |
| 8,327,514 | B2 | 12/2012 | Kim |
| 8,328,061 | B2 | 12/2012 | Kasvikis |
| 8,328,062 | B2 | 12/2012 | Viola |
| 8,328,063 | B2 | 12/2012 | Milliman et al. |
| 8,328,064 | B2 | 12/2012 | Racenet et al. |
| 8,328,065 | B2 | 12/2012 | Shah |
| 8,328,802 | B2 | 12/2012 | Deville et al. |
| 8,328,823 | B2 | 12/2012 | Aranyi et al. |
| 8,333,313 | B2 | 12/2012 | Boudreaux et al. |
| 8,333,691 | B2 | 12/2012 | Schaaf |
| 8,333,764 | B2 | 12/2012 | Francischelli et al. |
| 8,333,779 | B2 | 12/2012 | Smith et al. |
| 8,334,468 | B2 | 12/2012 | Palmer et al. |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,343,150 | B2 | 1/2013 | Artale |
| 8,347,978 | B2 | 1/2013 | Forster et al. |
| 8,348,118 | B2 | 1/2013 | Segura |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,348,837 | B2 | 1/2013 | Wenchell |
| 8,348,948 | B2 | 1/2013 | Bahney |
| 8,348,959 | B2 | 1/2013 | Wolford et al. |
| 8,348,972 | B2 | 1/2013 | Soltz et al. |
| 8,349,987 | B2 | 1/2013 | Kapiamba et al. |
| 8,352,004 | B2 | 1/2013 | Mannheimer et al. |
| 8,353,437 | B2 | 1/2013 | Boudreaux |
| 8,353,438 | B2 | 1/2013 | Baxter, III et al. |
| 8,353,439 | B2 | 1/2013 | Baxter, III et al. |
| 8,356,740 | B1 | 1/2013 | Knodel |
| 8,357,144 | B2 | 1/2013 | Whitman et al. |
| 8,357,158 | B2 | 1/2013 | McKenna et al. |
| 8,357,161 | B2 | 1/2013 | Mueller |
| 8,359,174 | B2 | 1/2013 | Nakashima et al. |
| 8,360,296 | B2 | 1/2013 | Zingman |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,361,501 | B2 | 1/2013 | DiTizio et al. |
| D676,866 | S | 2/2013 | Chaudhri |
| 8,365,972 | B2 | 2/2013 | Aranyi et al. |
| 8,365,973 | B1 | 2/2013 | White et al. |
| 8,365,975 | B1 | 2/2013 | Manoux et al. |
| 8,365,976 | B2 | 2/2013 | Hess et al. |
| 8,366,559 | B2 | 2/2013 | Papenfuss et al. |
| 8,366,719 | B2 | 2/2013 | Markey et al. |

(56) References Cited

U.S. PATENT DOCUMENTS 8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,381,834 B2 2/2013 Barhitte et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,395,342 B2 3/2013 Prisco
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D679,726 S 4/2013 Kobayashi
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,409,234 B2 4/2013 Stahler et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,424,742 B2 4/2013 Bettuchi
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
D681,674 S 5/2013 Koehn et al.
8,435,257 B2 5/2013 Smith et al.
8,439,246 B1 5/2013 Knodel
8,439,830 B2 5/2013 McKinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,460,207 B2 6/2013 Burdorff et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,491,624 B2 7/2013 Kerr et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno

(56) References Cited

U.S. PATENT DOCUMENTS 8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,505,802 B2 8/2013 Viola et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
D690,614 S 10/2013 Mascadri et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
D695,310 S 12/2013 Jang et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf

(56) References Cited

U.S. PATENT DOCUMENTS

| | | | |
|---|---|---|---|
| 8,668,129 | B2 | 3/2014 | Olson |
| 8,668,130 | B2 | 3/2014 | Hess et al. |
| 8,672,206 | B2 | 3/2014 | Aranyi et al. |
| 8,672,207 | B2 | 3/2014 | Shelton, IV et al. |
| 8,672,208 | B2 | 3/2014 | Hess et al. |
| 8,672,209 | B2 | 3/2014 | Crainich |
| 8,672,922 | B2 | 3/2014 | Loh et al. |
| 8,672,935 | B2 | 3/2014 | Okada et al. |
| 8,672,951 | B2 | 3/2014 | Smith et al. |
| 8,673,210 | B2 | 3/2014 | Deshays |
| 8,675,820 | B2 | 3/2014 | Baic et al. |
| 8,678,263 | B2 | 3/2014 | Viola |
| 8,678,994 | B2 | 3/2014 | Sonnenschein et al. |
| 8,679,093 | B2 | 3/2014 | Farra |
| 8,679,098 | B2 | 3/2014 | Hart |
| 8,679,114 | B2 | 3/2014 | Chapman et al. |
| 8,679,137 | B2 | 3/2014 | Bauman et al. |
| 8,679,154 | B2 | 3/2014 | Smith et al. |
| 8,679,156 | B2 | 3/2014 | Smith et al. |
| 8,679,454 | B2 | 3/2014 | Guire et al. |
| 8,684,248 | B2 | 4/2014 | Milliman |
| 8,684,249 | B2 | 4/2014 | Racenet et al. |
| 8,684,250 | B2 | 4/2014 | Bettuchi et al. |
| 8,684,253 | B2 | 4/2014 | Giordano et al. |
| 8,684,962 | B2 | 4/2014 | Kirschenman et al. |
| 8,685,004 | B2 | 4/2014 | Zemlock et al. |
| 8,685,020 | B2 | 4/2014 | Weizman et al. |
| 8,690,893 | B2 | 4/2014 | Deitch et al. |
| 8,695,866 | B2 | 4/2014 | Leimbach et al. |
| 8,696,665 | B2 | 4/2014 | Hunt et al. |
| 8,701,958 | B2 | 4/2014 | Shelton, IV et al. |
| 8,701,959 | B2 | 4/2014 | Shah |
| 8,706,316 | B1 | 4/2014 | Hoevenaar |
| 8,708,210 | B2 | 4/2014 | Zemlok et al. |
| 8,708,211 | B2 | 4/2014 | Zemlok et al. |
| 8,708,212 | B2 | 4/2014 | Williams |
| 8,708,213 | B2 | 4/2014 | Shelton, IV et al. |
| 8,709,012 | B2 | 4/2014 | Muller |
| 8,712,549 | B2 | 4/2014 | Zdeblick et al. |
| 8,714,352 | B2 | 5/2014 | Farascioni et al. |
| 8,714,429 | B2 | 5/2014 | Demmy |
| 8,714,430 | B2 | 5/2014 | Natarajan et al. |
| 8,715,256 | B2 | 5/2014 | Greener |
| 8,715,302 | B2 | 5/2014 | Ibrahim et al. |
| 8,720,766 | B2 | 5/2014 | Hess et al. |
| 8,721,630 | B2 | 5/2014 | Ortiz et al. |
| 8,721,666 | B2 | 5/2014 | Schroeder et al. |
| 8,727,197 | B2 | 5/2014 | Hess et al. |
| 8,727,199 | B2 | 5/2014 | Wenchell |
| 8,727,200 | B2 | 5/2014 | Roy |
| 8,727,961 | B2 | 5/2014 | Ziv |
| 8,728,099 | B2 | 5/2014 | Cohn et al. |
| 8,728,119 | B2 | 5/2014 | Cummins |
| 8,733,470 | B2 | 5/2014 | Matthias et al. |
| 8,733,611 | B2 | 5/2014 | Milliman |
| 8,733,612 | B2 | 5/2014 | Ma |
| 8,733,613 | B2 | 5/2014 | Huitema et al. |
| 8,733,614 | B2 | 5/2014 | Ross et al. |
| 8,734,336 | B2 | 5/2014 | Bonadio et al. |
| 8,734,359 | B2 | 5/2014 | Ibanez et al. |
| 8,734,431 | B2 | 5/2014 | Shimada et al. |
| 8,734,478 | B2 | 5/2014 | Widenhouse et al. |
| 8,734,831 | B2 | 5/2014 | Kim et al. |
| 8,739,033 | B2 | 5/2014 | Rosenberg |
| 8,739,417 | B2 | 6/2014 | Tokunaga et al. |
| 8,740,034 | B2 | 6/2014 | Morgan et al. |
| 8,740,037 | B2 | 6/2014 | Shelton, IV et al. |
| 8,740,038 | B2 | 6/2014 | Shelton, IV et al. |
| 8,740,987 | B2 | 6/2014 | Geremakis et al. |
| 8,746,529 | B2 | 6/2014 | Shelton, IV et al. |
| 8,746,530 | B2 | 6/2014 | Giordano et al. |
| 8,746,533 | B2 | 6/2014 | Whitman et al. |
| 8,746,535 | B2 | 6/2014 | Shelton, IV et al. |
| 8,747,238 | B2 | 6/2014 | Shelton, IV et al. |
| 8,747,441 | B2 | 6/2014 | Konieczynski et al. |
| 8,752,264 | B2 | 6/2014 | Ackley et al. |
| 8,752,699 | B2 | 6/2014 | Morgan et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,753,664 | B2 | 6/2014 | Dao et al. |
| 8,757,287 | B2 | 6/2014 | Mak et al. |
| 8,757,465 | B2 | 6/2014 | Woodard, Jr. et al. |
| 8,758,235 | B2 | 6/2014 | Jaworek |
| 8,758,366 | B2 | 6/2014 | McLean et al. |
| 8,758,391 | B2 | 6/2014 | Swayze et al. |
| 8,758,438 | B2 | 6/2014 | Boyce et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,764,732 | B2 | 7/2014 | Hartwell |
| 8,765,942 | B2 | 7/2014 | Feraud et al. |
| 8,770,458 | B2 | 7/2014 | Scirica |
| 8,770,459 | B2 | 7/2014 | Racenet et al. |
| 8,770,460 | B2 | 7/2014 | Belzer |
| 8,771,169 | B2 | 7/2014 | Whitman et al. |
| 8,771,260 | B2 | 7/2014 | Conlon et al. |
| 8,777,004 | B2 | 7/2014 | Shelton, IV et al. |
| 8,777,082 | B2 | 7/2014 | Scirica |
| 8,777,083 | B2 | 7/2014 | Racenet et al. |
| 8,777,898 | B2 | 7/2014 | Suon et al. |
| 8,783,541 | B2 | 7/2014 | Shelton, IV et al. |
| 8,783,542 | B2 | 7/2014 | Riestenberg et al. |
| 8,783,543 | B2 | 7/2014 | Shelton, IV et al. |
| 8,784,304 | B2 | 7/2014 | Mikkaichi et al. |
| 8,784,404 | B2 | 7/2014 | Doyle et al. |
| 8,784,415 | B2 | 7/2014 | Malackowski et al. |
| 8,789,737 | B2 | 7/2014 | Hodgkinson et al. |
| 8,789,739 | B2 | 7/2014 | Swensgard |
| 8,789,740 | B2 | 7/2014 | Baxter et al. |
| 8,789,741 | B2 | 7/2014 | Baxter et al. |
| 8,790,658 | B2 | 7/2014 | Cigarini et al. |
| 8,790,684 | B2 | 7/2014 | Dave et al. |
| D711,905 | S | 8/2014 | Morrison et al. |
| 8,794,098 | B2 | 8/2014 | Long |
| 8,794,496 | B2 | 8/2014 | Scirica |
| 8,794,497 | B2 | 8/2014 | Zingman |
| 8,795,159 | B2 | 8/2014 | Moriyama |
| 8,795,276 | B2 | 8/2014 | Dietz et al. |
| 8,795,308 | B2 | 8/2014 | Valin |
| 8,795,324 | B2 | 8/2014 | Kawai et al. |
| 8,796,995 | B2 | 8/2014 | Cunanan et al. |
| 8,800,681 | B2 | 8/2014 | Rousson et al. |
| 8,800,837 | B2 | 8/2014 | Zemlok |
| 8,800,838 | B2 | 8/2014 | Shelton, IV |
| 8,800,839 | B2 | 8/2014 | Beetel |
| 8,800,840 | B2 | 8/2014 | Jankowski |
| 8,800,841 | B2 | 8/2014 | Ellerhorst et al. |
| 8,801,710 | B2 | 8/2014 | Ullrich et al. |
| 8,801,734 | B2 | 8/2014 | Shelton, IV et al. |
| 8,801,735 | B2 | 8/2014 | Shelton, IV et al. |
| 8,801,752 | B2 | 8/2014 | Fortier et al. |
| 8,801,801 | B2 | 8/2014 | Datta et al. |
| 8,806,973 | B2 | 8/2014 | Ross et al. |
| 8,807,414 | B2 | 8/2014 | Ross et al. |
| 8,808,161 | B2 | 8/2014 | Gregg et al. |
| 8,808,164 | B2 | 8/2014 | Hoffman et al. |
| 8,808,274 | B2 | 8/2014 | Hartwell |
| 8,808,294 | B2 | 8/2014 | Fox et al. |
| 8,808,308 | B2 | 8/2014 | Boukhny et al. |
| 8,808,311 | B2 | 8/2014 | Heinrich et al. |
| 8,808,325 | B2 | 8/2014 | Hess et al. |
| 8,810,197 | B2 | 8/2014 | Juergens |
| 8,811,017 | B2 | 8/2014 | Fujii et al. |
| 8,813,866 | B2 | 8/2014 | Suzuki |
| 8,814,024 | B2 | 8/2014 | Woodard, Jr. et al. |
| 8,814,025 | B2 | 8/2014 | Miller et al. |
| 8,814,836 | B2 | 8/2014 | Ignon et al. |
| 8,815,594 | B2 | 8/2014 | Harris et al. |
| 8,818,523 | B2 | 8/2014 | Olson et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |

(56) References Cited

U.S. PATENT DOCUMENTS 8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,852,473 B1 10/2014 Tan
8,855,822 B2 10/2014 Bartol et al.
8,857,692 B2 10/2014 Shima et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roßkamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
D716,820 S 11/2014 Wood
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,634 B2 11/2014 Devengenzo et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,915,842 B2 12/2014 Weisenburgh, II et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,931,692 B2 1/2015 Sancak
8,936,614 B2 1/2015 Allen, IV
8,937,408 B2 1/2015 Ganem et al.
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.
8,945,098 B2 2/2015 Seibold et al.
8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,961,542 B2 2/2015 Whitfield et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.
8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux
8,982,195 B2 3/2015 Claus et al.
8,984,711 B2 3/2015 Ota et al.
8,985,240 B2 3/2015 Winnard
8,985,429 B2 3/2015 Balek et al.

(56) References Cited

U.S. PATENT DOCUMENTS 8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,004,799 B1 4/2015 Tibbits
9,005,230 B2 4/2015 Yates et al.
9,005,238 B2 4/2015 DeSantis et al.
9,005,243 B2 4/2015 Stopek et al.
9,010,606 B2 4/2015 Aranyi et al.
9,010,608 B2 4/2015 Casasanta, Jr. et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
D730,393 S 5/2015 Bray et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,468 B2 5/2015 Scarfogliero et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,028,529 B2 5/2015 Fox et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,039,736 B2 5/2015 Scirica et al.
9,040,062 B2 5/2015 Maeda et al.
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
D733,727 S 7/2015 Cojuangco et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,317 B2 7/2015 Burdorff et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,877 B1 8/2015 Whitman et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.

(56) References Cited

U.S. PATENT DOCUMENTS

| | | | |
|---|---|---|---|
| 9,125,654 | B2 | 9/2015 | Aronhalt et al. |
| 9,125,662 | B2 | 9/2015 | Shelton, IV |
| 9,126,317 | B2 | 9/2015 | Lawton et al. |
| 9,131,835 | B2 | 9/2015 | Widenhouse et al. |
| 9,131,940 | B2 | 9/2015 | Huitema et al. |
| 9,131,950 | B2 | 9/2015 | Matthew |
| 9,131,957 | B2 | 9/2015 | Skarbnik et al. |
| 9,138,225 | B2 | 9/2015 | Huang et al. |
| 9,138,226 | B2 | 9/2015 | Racenet et al. |
| 9,144,455 | B2 | 9/2015 | Kennedy et al. |
| D740,414 | S | 10/2015 | Katsura |
| D741,882 | S | 10/2015 | Shmilov et al. |
| 9,149,274 | B2 | 10/2015 | Spivey et al. |
| 9,149,324 | B2 | 10/2015 | Huang et al. |
| 9,149,325 | B2 | 10/2015 | Worrell et al. |
| 9,153,994 | B2 | 10/2015 | Wood et al. |
| 9,154,189 | B2 | 10/2015 | Von Novak et al. |
| 9,161,753 | B2 | 10/2015 | Prior |
| 9,161,769 | B2 | 10/2015 | Stoddard et al. |
| 9,161,803 | B2 | 10/2015 | Yates et al. |
| 9,161,807 | B2 | 10/2015 | Garrison |
| 9,161,855 | B2 | 10/2015 | Rousseau et al. |
| 9,164,271 | B2 | 10/2015 | Ebata et al. |
| 9,167,960 | B2 | 10/2015 | Yamaguchi et al. |
| 9,168,038 | B2 | 10/2015 | Shelton, IV et al. |
| 9,168,039 | B1 | 10/2015 | Knodel |
| 9,168,042 | B2 | 10/2015 | Milliman |
| 9,168,054 | B2 | 10/2015 | Turner et al. |
| 9,168,144 | B2 | 10/2015 | Rivin et al. |
| 9,171,244 | B2 | 10/2015 | Endou et al. |
| 9,179,832 | B2 | 11/2015 | Diolaiti |
| 9,179,911 | B2 | 11/2015 | Morgan et al. |
| 9,179,912 | B2 | 11/2015 | Yates et al. |
| 9,180,223 | B2 | 11/2015 | Yu et al. |
| 9,182,244 | B2 | 11/2015 | Luke et al. |
| 9,186,046 | B2 | 11/2015 | Ramamurthy et al. |
| 9,186,137 | B2 | 11/2015 | Farascioni et al. |
| 9,186,140 | B2 | 11/2015 | Hiles et al. |
| 9,186,142 | B2 | 11/2015 | Fanelli et al. |
| 9,186,143 | B2 | 11/2015 | Timm et al. |
| 9,186,148 | B2 | 11/2015 | Felder et al. |
| 9,186,221 | B2 | 11/2015 | Burbank |
| 9,192,376 | B2 | 11/2015 | Almodovar |
| 9,192,380 | B2 | 11/2015 | Racenet et al. |
| 9,192,384 | B2 | 11/2015 | Bettuchi |
| 9,192,430 | B2 | 11/2015 | Rachlin et al. |
| 9,192,434 | B2 | 11/2015 | Twomey et al. |
| 9,193,045 | B2 | 11/2015 | Saur et al. |
| 9,197,079 | B2 | 11/2015 | Yip et al. |
| D744,528 | S | 12/2015 | Agrawal |
| D746,459 | S | 12/2015 | Kaercher et al. |
| 9,198,642 | B2 | 12/2015 | Storz |
| 9,198,644 | B2 | 12/2015 | Balek et al. |
| 9,198,661 | B2 | 12/2015 | Swensgard |
| 9,198,662 | B2 | 12/2015 | Barton et al. |
| 9,198,683 | B2 | 12/2015 | Friedman et al. |
| 9,204,830 | B2 | 12/2015 | Zand et al. |
| 9,204,877 | B2 | 12/2015 | Whitman et al. |
| 9,204,878 | B2 | 12/2015 | Hall et al. |
| 9,204,879 | B2 | 12/2015 | Shelton, IV |
| 9,204,880 | B2 | 12/2015 | Baxter, III et al. |
| 9,204,881 | B2 | 12/2015 | Penna |
| 9,204,923 | B2 | 12/2015 | Manzo et al. |
| 9,204,924 | B2 | 12/2015 | Marczyk et al. |
| 9,211,120 | B2 | 12/2015 | Scheib et al. |
| 9,211,121 | B2 | 12/2015 | Hall et al. |
| 9,211,122 | B2 | 12/2015 | Hagerty et al. |
| 9,216,013 | B2 | 12/2015 | Scirica et al. |
| 9,216,019 | B2 | 12/2015 | Schmid et al. |
| 9,216,020 | B2 | 12/2015 | Zhang et al. |
| 9,216,030 | B2 | 12/2015 | Fan et al. |
| 9,216,062 | B2 | 12/2015 | Duque et al. |
| 9,220,500 | B2 | 12/2015 | Swayze et al. |
| 9,220,501 | B2 | 12/2015 | Baxter, III et al. |
| 9,220,502 | B2 | 12/2015 | Zemlok et al. |
| 9,220,504 | B2 | 12/2015 | Viola et al. |
| 9,220,508 | B2 | 12/2015 | Dannaher |
| 9,220,559 | B2 | 12/2015 | Worrell et al. |
| 9,220,570 | B2 | 12/2015 | Kim et al. |
| D746,854 | S | 1/2016 | Shardlow et al. |
| 9,226,686 | B2 | 1/2016 | Blair |
| 9,226,750 | B2 | 1/2016 | Weir et al. |
| 9,226,751 | B2 | 1/2016 | Shelton, IV et al. |
| 9,226,754 | B2 | 1/2016 | D'Agostino et al. |
| 9,226,760 | B2 | 1/2016 | Shelton, IV |
| 9,226,761 | B2 | 1/2016 | Burbank |
| 9,226,767 | B2 | 1/2016 | Stulen et al. |
| 9,226,799 | B2 | 1/2016 | Lightcap et al. |
| 9,232,941 | B2 | 1/2016 | Mandakolathur Vasudevan et al. |
| 9,232,945 | B2 | 1/2016 | Zingman |
| 9,232,979 | B2 | 1/2016 | Parihar et al. |
| 9,233,610 | B2 | 1/2016 | Kim et al. |
| 9,237,891 | B2 | 1/2016 | Shelton, IV |
| 9,237,892 | B2 | 1/2016 | Hodgkinson |
| 9,237,895 | B2 | 1/2016 | McCarthy et al. |
| 9,237,900 | B2 | 1/2016 | Boudreaux et al. |
| 9,237,921 | B2 | 1/2016 | Messerly et al. |
| 9,239,064 | B2 | 1/2016 | Helbig et al. |
| 9,240,740 | B2 | 1/2016 | Zeng et al. |
| 9,241,711 | B2 | 1/2016 | Ivanko |
| 9,241,712 | B2 | 1/2016 | Zemlok et al. |
| 9,241,714 | B2 | 1/2016 | Timm et al. |
| 9,241,716 | B2 | 1/2016 | Whitman |
| 9,241,731 | B2 | 1/2016 | Boudreaux et al. |
| 9,241,758 | B2 | 1/2016 | Franer et al. |
| 9,244,524 | B2 | 1/2016 | Inoue et al. |
| D748,668 | S | 2/2016 | Kim et al. |
| D749,128 | S | 2/2016 | Perez et al. |
| D749,623 | S | 2/2016 | Gray et al. |
| D750,122 | S | 2/2016 | Shardlow et al. |
| D750,129 | S | 2/2016 | Kwon |
| 9,254,131 | B2 | 2/2016 | Soltz et al. |
| 9,254,170 | B2 | 2/2016 | Parihar et al. |
| 9,259,265 | B2 | 2/2016 | Harris et al. |
| 9,259,268 | B2 | 2/2016 | Behnke, II et al. |
| 9,259,274 | B2 | 2/2016 | Prisco |
| 9,259,275 | B2 | 2/2016 | Burbank |
| 9,261,172 | B2 | 2/2016 | Solomon et al. |
| 9,265,500 | B2 | 2/2016 | Sorrentino et al. |
| 9,265,510 | B2 | 2/2016 | Dietzel et al. |
| 9,265,516 | B2 | 2/2016 | Casey et al. |
| 9,265,585 | B2 | 2/2016 | Wingardner et al. |
| 9,271,718 | B2 | 3/2016 | Milad et al. |
| 9,271,727 | B2 | 3/2016 | McGuckin, Jr. et al. |
| 9,271,753 | B2 | 3/2016 | Butler et al. |
| 9,271,799 | B2 | 3/2016 | Shelton, IV et al. |
| 9,272,406 | B2 | 3/2016 | Aronhalt et al. |
| 9,274,095 | B2 | 3/2016 | Humayun et al. |
| 9,277,919 | B2 | 3/2016 | Timmer et al. |
| 9,277,922 | B2 | 3/2016 | Carter et al. |
| 9,277,969 | B2 | 3/2016 | Brannan et al. |
| 9,282,962 | B2 | 3/2016 | Schmid et al. |
| 9,282,963 | B2 | 3/2016 | Bryant |
| 9,282,966 | B2 | 3/2016 | Shelton, IV et al. |
| 9,282,974 | B2 | 3/2016 | Shelton, IV |
| 9,283,028 | B2 | 3/2016 | Johnson |
| 9,283,045 | B2 | 3/2016 | Rhee et al. |
| 9,283,054 | B2 | 3/2016 | Morgan et al. |
| 9,283,334 | B2 | 3/2016 | Mantell et al. |
| 9,289,206 | B2 | 3/2016 | Hess et al. |
| 9,289,207 | B2 | 3/2016 | Shelton, IV |
| 9,289,210 | B2 | 3/2016 | Baxter, III et al. |
| 9,289,211 | B2 | 3/2016 | Williams et al. |
| 9,289,212 | B2 | 3/2016 | Shelton, IV et al. |
| 9,289,225 | B2 | 3/2016 | Shelton, IV et al. |
| 9,289,256 | B2 | 3/2016 | Shelton, IV et al. |
| 9,293,757 | B2 | 3/2016 | Toussaint et al. |
| 9,295,464 | B2 | 3/2016 | Shelton, IV et al. |
| 9,295,465 | B2 | 3/2016 | Farascioni |
| 9,295,466 | B2 | 3/2016 | Hodgkinson et al. |
| 9,295,467 | B2 | 3/2016 | Scirica |
| 9,295,468 | B2 | 3/2016 | Heinrich et al. |
| 9,295,514 | B2 | 3/2016 | Shelton, IV et al. |
| 9,295,522 | B2 | 3/2016 | Kostrzewski |

(56) References Cited

U.S. PATENT DOCUMENTS 9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 Van Der Walt et al.
9,339,342 B2 5/2016 Prisco et al.
9,345,477 B2 5/2016 Anim et al.
9,345,479 B2 5/2016 Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,408,668 B2 8/2016 Durant et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,418 B2 9/2016 Whitman et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.

(56) References Cited

U.S. PATENT DOCUMENTS 9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,528 B2 10/2016 Marczyk
9,474,540 B2 10/2016 Stokes et al.
9,474,581 B2 10/2016 Niemeyer
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,519,341 B2 12/2016 Hasegawa et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,554,854 B2 1/2017 Yates et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,561,072 B2 2/2017 Ko
9,561,082 B2 2/2017 Yen et al.
9,566,061 B2 2/2017 Aronhalt et al.
9,566,062 B2 2/2017 Boudreaux
9,566,064 B2 2/2017 Williams et al.
9,566,065 B2 2/2017 Knodel
9,566,067 B2 2/2017 Milliman et al.
9,566,124 B2 2/2017 Prisco et al.
9,572,552 B1 2/2017 Bodor et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,039 B2 2/2017 Jansen et al.
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.

(56) References Cited

U.S. PATENT DOCUMENTS 9,610,412 B2 4/2017 Zemlok et al.
9,614,258 B2 4/2017 Takahashi et al.
9,615,826 B2 4/2017 Shelton, IV et al.
9,622,745 B2 4/2017 Ingmanson et al.
9,622,746 B2 4/2017 Simms et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,651,032 B2 5/2017 Weaver et al.
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,111 B2 5/2017 Holsten et al.
9,662,116 B2 5/2017 Smith et al.
9,662,130 B2 5/2017 Bartels et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,700,381 B2 7/2017 Amat Girbau
9,702,823 B2 7/2017 Maher et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.

(56) References Cited

U.S. PATENT DOCUMENTS 9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Take
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh et al.
9,839,480 B2 12/2017 Pribanic et al.
9,839,481 B2 12/2017 Blumenkranz et al.
9,844,313 B2 12/2017 DiCarlo et al.
9,844,368 B2 12/2017 Boudreaux et al.
9,844,369 B2 12/2017 Huitema et al.
9,844,371 B2 12/2017 Scirica et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,499 B2 12/2017 Baylink et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,718 B2 1/2018 Weir et al.
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,552 B2 3/2018 Measamer et al.
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.

(56) References Cited

U.S. PATENT DOCUMENTS 9,913,642 B2 3/2018 Leimbach et al.
9,913,644 B2 3/2018 McCuen
9,913,646 B2 3/2018 Shelton, IV
9,913,647 B2 3/2018 Weisenburgh et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,005 B2 6/2018 Viola et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
D823,858 S 7/2018 Li et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.
10,022,125 B2 7/2018 Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.

(56) References Cited

U.S. PATENT DOCUMENTS 10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.
10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
10,136,949 B2 11/2018 Felder et al.
D835,659 S 12/2018 Anzures et al.
D836,124 S 12/2018 Fan
10,143,474 B2 12/2018 Bucciaglia et al.
10,146,423 B1 12/2018 Reed et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.
10,188,389 B2 1/2019 Vendely et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,911 B2 2/2019 Miller et al.
10,194,912 B2 2/2019 Scheib et al.
10,194,913 B2 2/2019 Nalagatla et al.
10,194,976 B2 2/2019 Boudreaux
10,194,981 B2 2/2019 Margallo Balbas et al.
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.

(56) References Cited

U.S. PATENT DOCUMENTS

| | | | |
|---|---|---|---|
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,038 | B2 | 4/2019 | Hopkins et al. |
| 10,245,058 | B2 | 4/2019 | Omori et al. |
| 10,251,645 | B2 | 4/2019 | Kostrzewski |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,363 | B2 | 4/2019 | Worrell et al. |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,271,840 | B2 | 4/2019 | Sapre |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,847 | B2 | 4/2019 | Racenet et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,696 | B2 | 5/2019 | Marczyk |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |

(56) References Cited

U.S. PATENT DOCUMENTS 10,383,634 B2 8/2019 Shelton, IV et al.
10,390,823 B2 8/2019 Shelton, IV et al.
10,390,825 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D859,466 S 9/2019 Okada et al.
D860,219 S 9/2019 Rasmussen et al.
D861,035 S 9/2019 Park et al.
10,398,433 B2 9/2019 Boudreaux et al.
10,398,434 B2 9/2019 Shelton, IV et al.
10,398,436 B2 9/2019 Shelton, IV et al.
10,398,460 B2 9/2019 Overmyer
10,404,136 B2 9/2019 Oktavec et al.
10,405,854 B2 9/2019 Schmid et al.
10,405,857 B2 9/2019 Shelton, IV et al.
10,405,859 B2 9/2019 Harris et al.
10,405,863 B2 9/2019 Wise et al.
10,405,914 B2 9/2019 Manwaring et al.
10,405,932 B2 9/2019 Overmyer
10,405,937 B2 9/2019 Black et al.
10,413,155 B2 9/2019 Inoue
10,413,291 B2 9/2019 Worthington et al.
10,413,293 B2 9/2019 Shelton, IV et al.
10,413,294 B2 9/2019 Shelton, IV et al.
10,413,297 B2 9/2019 Harris et al.
10,413,370 B2 9/2019 Yates et al.
10,413,373 B2 9/2019 Yates et al.
10,420,548 B2 9/2019 Whitman et al.
10,420,549 B2 9/2019 Yates et al.
10,420,550 B2 9/2019 Shelton, IV
10,420,551 B2 9/2019 Calderoni
10,420,552 B2 9/2019 Shelton, IV et al.
10,420,553 B2 9/2019 Shelton, IV et al.
10,420,554 B2 9/2019 Collings et al.
10,420,555 B2 9/2019 Shelton, IV et al.
10,420,558 B2 9/2019 Nalagatla et al.
10,420,559 B2 9/2019 Marczyk et al.
10,420,560 B2 9/2019 Shelton, IV et al.
10,420,561 B2 9/2019 Shelton, IV et al.
10,420,577 B2 9/2019 Chowaniec et al.
D861,707 S 10/2019 Yang
D862,518 S 10/2019 Niven et al.
D863,343 S 10/2019 Mazlish et al.
D864,388 S 10/2019 Barber
D865,174 S 10/2019 Auld et al.
D865,175 S 10/2019 Widenhouse et al.
10,426,463 B2 10/2019 Shelton, IV et al.
10,426,466 B2 10/2019 Contini et al.
10,426,467 B2 10/2019 Miller et al.
10,426,468 B2 10/2019 Contini et al.
10,426,469 B2 10/2019 Shelton, IV et al.
10,426,471 B2 10/2019 Shelton, IV et al.
10,426,476 B2 10/2019 Harris et al.
10,426,477 B2 10/2019 Harris et al.
10,426,478 B2 10/2019 Shelton, IV et al.
10,426,481 B2 10/2019 Aronhalt et al.
10,426,555 B2 10/2019 Crowley et al.
10,433,837 B2 10/2019 Worthington et al.
10,433,839 B2 10/2019 Scheib et al.
10,433,840 B2 10/2019 Shelton, IV et al.
10,433,842 B2 10/2019 Amariglio et al.
10,433,844 B2 10/2019 Shelton, IV et al.
10,433,845 B2 10/2019 Baxter, III et al.
10,433,846 B2 10/2019 Vendely et al.
10,433,849 B2 10/2019 Shelton, IV et al.
10,433,918 B2 10/2019 Shelton, IV et al.
10,441,279 B2 10/2019 Shelton, IV et al.
10,441,280 B2 10/2019 Timm et al.
10,441,281 B2 10/2019 Shelton, IV et al.
10,441,285 B2 10/2019 Shelton, IV et al.
10,441,286 B2 10/2019 Shelton, IV et al.
10,441,345 B2 10/2019 Aldridge et al.
10,441,369 B2 10/2019 Shelton, IV et al.
10,448,948 B2 10/2019 Shelton, IV et al.
10,448,950 B2 10/2019 Shelton, IV et al.
10,448,952 B2 10/2019 Shelton, IV et al.
10,456,122 B2 10/2019 Koltz et al.
10,456,132 B2 10/2019 Gettinger et al.
10,456,133 B2 10/2019 Yates et al.
10,456,137 B2 10/2019 Vendely et al.
10,456,140 B2 10/2019 Shelton, IV et al.
D865,796 S 11/2019 Xu et al.
10,463,367 B2 11/2019 Kostrzewski et al.
10,463,369 B2 11/2019 Shelton, IV et al.
10,463,370 B2 11/2019 Yates et al.
10,463,371 B2 11/2019 Kostrzewski
10,463,372 B2 11/2019 Shelton, IV et al.
10,463,373 B2 11/2019 Mozdzierz et al.
10,463,382 B2 11/2019 Ingmanson et al.
10,463,383 B2 11/2019 Shelton, IV et al.
10,463,384 B2 11/2019 Shelton, IV et al.
10,470,762 B2 11/2019 Leimbach et al.
10,470,763 B2 11/2019 Yates et al.
10,470,764 B2 11/2019 Baxter, III et al.
10,470,767 B2 11/2019 Gleiman et al.
10,470,768 B2 11/2019 Harris et al.
10,470,769 B2 11/2019 Shelton, IV et al.
10,471,282 B2 11/2019 Kirk et al.
10,471,576 B2 11/2019 Totsu
10,471,607 B2 11/2019 Butt et al.
10,478,181 B2 11/2019 Shelton, IV et al.
10,478,182 B2 11/2019 Taylor
10,478,185 B2 11/2019 Nicholas
10,478,187 B2 11/2019 Shelton, IV et al.
10,478,188 B2 11/2019 Harris et al.
10,478,189 B2 11/2019 Bear et al.
10,478,190 B2 11/2019 Miller et al.
10,478,207 B2 11/2019 Lathrop
10,482,292 B2 11/2019 Clouser et al.
10,485,536 B2 11/2019 Ming et al.
10,485,537 B2 11/2019 Yates et al.
10,485,539 B2 11/2019 Shelton, IV et al.
10,485,541 B2 11/2019 Shelton, IV et al.
10,485,542 B2 11/2019 Shelton, IV et al.
10,485,543 B2 11/2019 Shelton, IV et al.
10,485,546 B2 11/2019 Shelton, IV et al.
10,485,547 B2 11/2019 Shelton, IV et al.
D869,655 S 12/2019 Shelton, IV et al.
D870,742 S 12/2019 Cornell
10,492,783 B2 12/2019 Shelton, IV et al.
10,492,785 B2 12/2019 Overmyer et al.
10,492,787 B2 12/2019 Smith et al.
10,492,814 B2 12/2019 Snow et al.
10,492,847 B2 12/2019 Godara et al.
10,492,851 B2 12/2019 Hughett, Sr. et al.
10,498,269 B2 12/2019 Zemlok et al.
10,499,890 B2 12/2019 Shelton, IV et al.
10,499,914 B2 12/2019 Huang et al.
10,499,917 B2 12/2019 Scheib et al.
10,499,918 B2 12/2019 Schellin et al.
10,500,000 B2 12/2019 Swayze et al.
10,500,004 B2 12/2019 Hanuschik et al.
10,500,309 B2 12/2019 Shah et al.
10,507,034 B2 12/2019 Timm
10,508,720 B2 12/2019 Nicholas
10,512,461 B2 12/2019 Gupta et al.
10,512,462 B2 12/2019 Felder et al.
10,512,464 B2 12/2019 Park et al.
10,517,590 B2 12/2019 Giordano et al.
10,517,592 B2 12/2019 Shelton, IV et al.
10,517,594 B2 12/2019 Shelton, IV et al.
10,517,595 B2 12/2019 Hunter et al.
10,517,596 B2 12/2019 Hunter et al.
10,517,599 B2 12/2019 Baxter, III et al.
10,517,682 B2 12/2019 Giordano et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.

(56) References Cited

U.S. PATENT DOCUMENTS 10,524,870 B2 1/2020 Saraliev et al.
10,531,874 B2 1/2020 Morgan et al.
10,531,887 B2 1/2020 Shelton, IV et al.
10,537,323 B2 1/2020 Racenet et al.
10,537,324 B2 1/2020 Shelton, IV et al.
10,537,325 B2 1/2020 Bakos et al.
10,537,351 B2 1/2020 Shelton, IV et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,988 B2 1/2020 Schellin et al.
10,542,991 B2 1/2020 Shelton, IV et al.
D876,478 S 2/2020 Sakata et al.
10,548,504 B2 2/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,412 B2 2/2020 Bookbinder et al.
10,561,418 B2 2/2020 Richard et al.
10,561,419 B2 2/2020 Beardsley
10,561,420 B2 2/2020 Harris et al.
10,561,422 B2 2/2020 Schellin et al.
10,561,432 B2 2/2020 Estrella et al.
10,561,474 B2 2/2020 Adams et al.
10,562,160 B2 2/2020 Iwata et al.
10,568,493 B2 2/2020 Blase et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,568,652 B2 2/2020 Hess et al.
10,569,071 B2 2/2020 Harris et al.
D879,808 S 3/2020 Harris et al.
D879,809 S 3/2020 Harris et al.
10,575,868 B2 3/2020 Hall et al.
10,580,320 B2 3/2020 Kamiguchi et al.
10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,614,184 B2 4/2020 Solki
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,038 B2 5/2020 Scott et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.
10,653,417 B2 5/2020 Shelton, IV et al.
10,653,435 B2 5/2020 Shelton, IV et al.
10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
D890,805 S 7/2020 Echeverri et al.
10,702,266 B2 7/2020 Parihar et al.
10,702,267 B2 7/2020 Hess et al.

(56) References Cited

U.S. PATENT DOCUMENTS

| | | | |
|---|---|---|---|
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,495 | B2 | 7/2020 | Broderick et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| D893,717 | S | 8/2020 | Messerly et al. |
| 10,729,432 | B2 | 8/2020 | Shelton, IV et al. |
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,736,702 | B2 | 8/2020 | Harris et al. |
| 10,737,398 | B2 | 8/2020 | Remirez et al. |
| 10,743,849 | B2 | 8/2020 | Shelton, IV et al. |
| 10,743,850 | B2 | 8/2020 | Hibner et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,051 | B2 | 8/2020 | Weir et al. |
| 10,751,053 | B2 | 8/2020 | Harris et al. |
| 10,751,076 | B2 | 8/2020 | Laurent et al. |
| 10,751,104 | B2 | 8/2020 | Mistry et al. |
| 10,751,138 | B2 | 8/2020 | Giordano et al. |
| 10,758,226 | B2 | 9/2020 | Weir et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| D898,767 | S | 10/2020 | Shah et al. |
| D899,455 | S | 10/2020 | Rondoni et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,874,474 | B2 | 12/2020 | Wu et al. |
| 10,879,275 | B2 | 12/2020 | Li et al. |
| D907,647 | S | 1/2021 | Siebel et al. |
| D907,648 | S | 1/2021 | Siebel et al. |

(56) References Cited

U.S. PATENT DOCUMENTS

D908,216 S 1/2021 Messerly et al.
10,881,339 B2 1/2021 Peyser et al.
10,881,395 B2 1/2021 Merchant et al.
10,881,396 B2 1/2021 Shelton, IV et al.
10,881,398 B2 1/2021 Whitman et al.
10,881,399 B2 1/2021 Shelton, IV et al.
10,881,401 B2 1/2021 Baber et al.
10,881,446 B2 1/2021 Strobl
10,888,318 B2 1/2021 Parihar et al.
10,888,321 B2 1/2021 Shelton, IV et al.
10,888,322 B2 1/2021 Morgan et al.
10,888,323 B2 1/2021 Chen et al.
10,888,325 B2 1/2021 Harris et al.
10,888,328 B2 1/2021 Shelton, IV et al.
10,888,329 B2 1/2021 Moore et al.
10,888,330 B2 1/2021 Moore et al.
10,888,369 B2 1/2021 Messerly et al.
10,892,899 B2 1/2021 Shelton, IV et al.
10,893,853 B2 1/2021 Shelton, IV et al.
10,893,863 B2 1/2021 Shelton, IV et al.
10,893,864 B2 1/2021 Harris et al.
10,893,867 B2 1/2021 Leimbach et al.
10,898,183 B2 1/2021 Shelton, IV et al.
10,898,184 B2 1/2021 Yates et al.
10,898,185 B2 1/2021 Overmyer et al.
10,898,186 B2 1/2021 Bakos et al.
10,898,190 B2 1/2021 Yates et al.
10,898,193 B2 1/2021 Shelton, IV et al.
10,898,194 B2 1/2021 Moore et al.
10,898,195 B2 1/2021 Moore et al.
10,903,685 B2 1/2021 Yates et al.
D910,847 S 2/2021 Shelton, IV et al.
10,905,415 B2 2/2021 DiNardo et al.
10,905,418 B2 2/2021 Shelton, IV et al.
10,905,420 B2 2/2021 Jasemian et al.
10,905,422 B2 2/2021 Bakos et al.
10,905,423 B2 2/2021 Baber et al.
10,905,426 B2 2/2021 Moore et al.
10,905,427 B2 2/2021 Moore et al.
10,911,515 B2 2/2021 Biasi et al.
10,912,559 B2 2/2021 Harris et al.
10,912,562 B2 2/2021 Dunki-Jacobs et al.
10,912,575 B2 2/2021 Shelton, IV et al.
10,918,364 B2 2/2021 Applegate et al.
10,918,380 B2 2/2021 Morgan et al.
10,918,385 B2 2/2021 Overmyer et al.
10,918,386 B2 2/2021 Shelton, IV et al.
10,919,156 B2 2/2021 Roberts et al.
10,925,600 B2 2/2021 McCuen
10,925,605 B2 2/2021 Moore et al.
D914,878 S 3/2021 Shelton, IV et al.
10,932,772 B2 3/2021 Shelton, IV et al.
10,932,774 B2 3/2021 Shelton, IV
10,932,775 B2 3/2021 Shelton, IV et al.
10,932,778 B2 3/2021 Smith et al.
10,932,779 B2 3/2021 Vendely et al.
10,932,784 B2 3/2021 Mozdzierz et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,945,727 B2 3/2021 Shelton, IV et al.
10,945,728 B2 3/2021 Morgan et al.
10,945,729 B2 3/2021 Shelton, IV et al.
10,945,731 B2 3/2021 Baxter, III et al.
10,952,708 B2 3/2021 Scheib et al.
10,952,726 B2 3/2021 Chowaniec
10,952,727 B2 3/2021 Giordano et al.
10,952,728 B2 3/2021 Shelton, IV et al.
10,952,759 B2 3/2021 Messerly et al.
10,952,767 B2 3/2021 Kostrzewski et al.
10,959,722 B2 3/2021 Morgan et al.
10,959,725 B2 3/2021 Kerr et al.
10,959,726 B2 3/2021 Williams et al.
10,959,727 B2 3/2021 Hunter et al.
10,959,731 B2 3/2021 Casasanta, Jr. et al.
10,959,744 B2 3/2021 Shelton, IV et al.
10,959,797 B2 3/2021 Licht et al.
D917,500 S 4/2021 Siebel et al.
10,966,627 B2 4/2021 Shelton, IV et al.
10,966,717 B2 4/2021 Shah et al.
10,966,718 B2 4/2021 Shelton, IV et al.
10,966,791 B2 4/2021 Harris et al.
10,973,515 B2 4/2021 Harris et al.
10,973,516 B2 4/2021 Shelton, IV et al.
10,973,517 B2 4/2021 Wixey
10,973,519 B2 4/2021 Weir et al.
10,973,520 B2 4/2021 Shelton, IV et al.
10,980,534 B2 4/2021 Yates et al.
10,980,535 B2 4/2021 Yates et al.
10,980,536 B2 4/2021 Weaner et al.
10,980,537 B2 4/2021 Shelton, IV et al.
10,980,538 B2 4/2021 Nalagatla et al.
10,980,539 B2 4/2021 Harris et al.
10,980,560 B2 4/2021 Shelton, IV et al.
10,983,646 B2 4/2021 Yoon et al.
10,987,102 B2 4/2021 Gonzalez et al.
10,987,178 B2 4/2021 Shelton, IV et al.
10,993,713 B2 5/2021 Shelton, IV et al.
10,993,715 B2 5/2021 Shelton, IV et al.
10,993,716 B2 5/2021 Shelton, IV et al.
10,993,717 B2 5/2021 Shelton, IV et al.
11,000,274 B2 5/2021 Shelton, IV et al.
11,000,275 B2 5/2021 Shelton, IV et al.
11,000,277 B2 5/2021 Giordano et al.
11,000,278 B2 5/2021 Shelton, IV et al.
11,000,279 B2 5/2021 Shelton, IV et al.
11,005,291 B2 5/2021 Calderoni
11,006,951 B2 5/2021 Giordano et al.
11,006,955 B2 5/2021 Shelton, IV et al.
11,007,004 B2 5/2021 Shelton, IV et al.
11,007,022 B2 5/2021 Shelton, IV et al.
11,013,511 B2 5/2021 Huang et al.
11,013,552 B2 5/2021 Widenhouse et al.
11,013,563 B2 5/2021 Shelton, IV et al.
11,020,016 B2 6/2021 Wallace et al.
11,020,112 B2 6/2021 Shelton, IV et al.
11,020,113 B2 6/2021 Shelton, IV et al.
11,020,114 B2 6/2021 Shelton, IV et al.
11,020,115 B2 6/2021 Scheib et al.
11,020,172 B2 6/2021 Garrison
11,026,678 B2 6/2021 Overmyer et al.
11,026,680 B2 6/2021 Shelton, IV et al.
11,026,684 B2 6/2021 Shelton, IV et al.
11,026,687 B2 6/2021 Shelton, IV et al.
11,026,712 B2 6/2021 Shelton, IV et al.
11,026,713 B2 6/2021 Stokes et al.
11,026,751 B2 6/2021 Shelton, IV et al.
11,033,267 B2 6/2021 Shelton, IV et al.
11,039,834 B2 6/2021 Harris et al.
11,039,836 B2 6/2021 Shelton, IV et al.
11,039,837 B2 6/2021 Shelton, IV et al.
11,039,849 B2 6/2021 Bucciaglia et al.
11,045,189 B2 6/2021 Yates et al.
11,045,191 B2 6/2021 Shelton, IV et al.
11,045,192 B2 6/2021 Harris et al.
11,045,196 B2 6/2021 Olson et al.
11,045,197 B2 6/2021 Shelton, IV et al.
11,045,199 B2 6/2021 Mozdzierz et al.
11,045,270 B2 6/2021 Shelton, IV et al.
D925,563 S 7/2021 Melvin et al.
11,051,807 B2 7/2021 Shelton, IV et al.
11,051,810 B2 7/2021 Harris et al.
11,051,811 B2 7/2021 Shelton, IV et al.
11,051,813 B2 7/2021 Shelton, IV et al.
11,051,836 B2 7/2021 Shelton, IV et al.
11,051,840 B2 7/2021 Shelton, IV et al.
11,051,873 B2 7/2021 Wiener et al.
11,058,418 B2 7/2021 Shelton, IV et al.
11,058,420 B2 7/2021 Shelton, IV et al.
11,058,422 B2 7/2021 Harris et al.
11,058,423 B2 7/2021 Shelton, IV et al.
11,058,424 B2 7/2021 Shelton, IV et al.
11,058,425 B2 7/2021 Widenhouse et al.

(56) References Cited

U.S. PATENT DOCUMENTS

| | | | |
|---|---|---|---|
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,000 | B2 | 7/2021 | Shankarsetty et al. |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,687 | B2 | 8/2021 | Flanagan et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,103,301 | B2 | 8/2021 | Messerly et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 | 9/2021 | Beardsley |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,152 | B2 | 10/2021 | Ingmanson et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| D936,684 | S | 11/2021 | Luo et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner, II |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,089 | B2 | 12/2021 | Kostrzewski et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| D946,025 | S | 3/2022 | Vogler-Ivashchanka et al. |
| D946,617 | S | 3/2022 | Ahmed |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |

(56) References Cited

U.S. PATENT DOCUMENTS 11,266,405 B2 3/2022 Shelton, IV et al.
11,266,406 B2 3/2022 Leimbach et al.
11,266,409 B2 3/2022 Huitema et al.
11,266,410 B2 3/2022 Shelton, IV et al.
11,266,468 B2 3/2022 Shelton, IV et al.
11,272,927 B2 3/2022 Swayze et al.
11,272,928 B2 3/2022 Shelton, IV
11,272,931 B2 3/2022 Boudreaux et al.
11,272,938 B2 3/2022 Shelton, IV et al.
11,278,279 B2 3/2022 Morgan et al.
11,278,280 B2 3/2022 Shelton, IV et al.
11,278,284 B2 3/2022 Shelton, IV et al.
11,278,288 B2 3/2022 Rector et al.
11,284,890 B2 3/2022 Nalagatla et al.
11,284,891 B2 3/2022 Shelton, IV et al.
11,284,898 B2 3/2022 Baxter, III et al.
11,284,953 B2 3/2022 Shelton, IV et al.
11,291,440 B2 4/2022 Harris et al.
11,291,441 B2 4/2022 Giordano et al.
11,291,442 B2 4/2022 Wixey et al.
11,291,443 B2 4/2022 Viola et al.
11,291,444 B2 4/2022 Boudreaux et al.
11,291,445 B2 4/2022 Shelton, IV et al.
11,291,447 B2 4/2022 Shelton, IV et al.
11,291,449 B2 4/2022 Swensgard et al.
11,291,451 B2 4/2022 Shelton, IV
11,291,465 B2 4/2022 Parihar et al.
11,291,510 B2 4/2022 Shelton, IV et al.
11,298,125 B2 4/2022 Ming et al.
11,298,127 B2 4/2022 Shelton, IV
11,298,128 B2 4/2022 Messerly et al.
11,298,129 B2 4/2022 Bakos et al.
11,298,130 B2 4/2022 Bakos et al.
11,298,132 B2 4/2022 Shelton, IV et al.
11,298,134 B2 4/2022 Huitema et al.
11,304,695 B2 4/2022 Shelton, IV et al.
11,304,696 B2 4/2022 Shelton, IV et al.
11,304,697 B2 4/2022 Fanelli et al.
11,304,699 B2 4/2022 Shelton, IV et al.
11,304,704 B2 4/2022 Thomas et al.
11,311,290 B2 4/2022 Shelton, IV et al.
11,311,292 B2 4/2022 Shelton, IV et al.
11,311,294 B2 4/2022 Swayze et al.
11,311,295 B2 4/2022 Wingardner et al.
11,311,342 B2 4/2022 Parihar et al.
D950,728 S 5/2022 Bakos et al.
D952,144 S 5/2022 Boudreaux
11,317,910 B2 5/2022 Miller et al.
11,317,912 B2 5/2022 Jenkins et al.
11,317,913 B2 5/2022 Shelton, IV et al.
11,317,915 B2 5/2022 Boudreaux et al.
11,317,917 B2 5/2022 Shelton, IV et al.
11,317,919 B2 5/2022 Shelton, IV et al.
11,317,978 B2 5/2022 Cameron et al.
11,324,501 B2 5/2022 Shelton, IV et al.
11,324,503 B2 5/2022 Shelton, IV et al.
11,324,506 B2 5/2022 Beckman et al.
11,324,557 B2 5/2022 Shelton, IV et al.
11,331,100 B2 5/2022 Boudreaux et al.
11,331,101 B2 5/2022 Harris et al.
11,337,691 B2 5/2022 Widenhouse et al.
11,337,693 B2 5/2022 Hess et al.
11,337,698 B2 5/2022 Baxter, III et al.
11,344,299 B2 5/2022 Yates et al.
11,344,303 B2 5/2022 Shelton, IV et al.
D954,736 S 6/2022 Teague et al.
11,350,843 B2 6/2022 Shelton, IV et al.
11,350,916 B2 6/2022 Shelton, IV et al.
11,350,928 B2 6/2022 Shelton, IV et al.
11,350,929 B2 6/2022 Giordano et al.
11,350,932 B2 6/2022 Shelton, IV et al.
11,350,934 B2 6/2022 Bakos et al.
11,350,935 B2 6/2022 Shelton, IV et al.
11,350,938 B2 6/2022 Shelton, IV et al.
11,357,503 B2 6/2022 Bakos et al.
11,361,176 B2 6/2022 Shelton, IV et al.
11,364,027 B2 6/2022 Harris et al.
11,364,046 B2 6/2022 Shelton, IV et al.
11,369,366 B2 6/2022 Scheib et al.
11,369,368 B2 6/2022 Shelton, IV et al.
11,369,376 B2 6/2022 Simms et al.
11,369,377 B2 6/2022 Boudreaux et al.
11,373,755 B2 6/2022 Shelton, IV et al.
11,376,001 B2 7/2022 Shelton, IV et al.
11,376,002 B2 7/2022 Shelton, IV et al.
11,376,082 B2 7/2022 Shelton, IV et al.
11,376,098 B2 7/2022 Shelton, IV et al.
11,382,625 B2 7/2022 Huitema et al.
11,382,626 B2 7/2022 Shelton, IV et al.
11,382,627 B2 7/2022 Huitema et al.
11,382,628 B2 7/2022 Baxter, III et al.
11,382,638 B2 7/2022 Harris et al.
11,382,697 B2 7/2022 Shelton, IV et al.
11,382,704 B2 7/2022 Overmyer et al.
11,389,160 B2 7/2022 Shelton, IV et al.
11,389,161 B2 7/2022 Shelton, IV et al.
11,389,162 B2 7/2022 Baber et al.
11,389,164 B2 7/2022 Yates et al.
11,395,651 B2 7/2022 Shelton, IV et al.
11,395,652 B2 7/2022 Parihar et al.
11,399,828 B2 8/2022 Swayze et al.
11,399,829 B2 8/2022 Leimbach et al.
11,399,831 B2 8/2022 Overmyer et al.
11,399,837 B2 8/2022 Shelton, IV et al.
11,406,377 B2 8/2022 Schmid et al.
11,406,378 B2 8/2022 Baxter, III et al.
11,406,380 B2 8/2022 Yates et al.
11,406,381 B2 8/2022 Parihar et al.
11,406,382 B2 8/2022 Shelton, IV et al.
11,406,386 B2 8/2022 Baber et al.
11,406,390 B2 8/2022 Shelton, IV et al.
11,406,442 B2 8/2022 Davison et al.
11,410,259 B2 8/2022 Harris et al.
11,413,041 B2 8/2022 Viola et al.
11,413,042 B2 8/2022 Shelton, IV et al.
11,413,102 B2 8/2022 Shelton, IV et al.
11,419,606 B2 8/2022 Overmyer et al.
11,419,630 B2 8/2022 Yates et al.
11,424,027 B2 8/2022 Shelton, IV
11,426,160 B2 8/2022 Shelton, IV et al.
11,426,167 B2 8/2022 Shelton, IV et al.
11,426,251 B2 8/2022 Kimball et al.
D962,980 S 9/2022 Frenkler et al.
D964,564 S 9/2022 Boudreaux
11,432,816 B2 9/2022 Leimbach et al.
11,432,819 B2 9/2022 Rector et al.
11,432,885 B2 9/2022 Shelton, IV et al.
11,439,391 B2 9/2022 Bruns et al.
11,439,470 B2 9/2022 Spivey et al.
11,446,029 B2 9/2022 Shelton, IV et al.
11,446,034 B2 9/2022 Shelton, IV et al.
11,452,526 B2 9/2022 Ross et al.
11,452,528 B2 9/2022 Leimbach et al.
D966,512 S 10/2022 Shelton, IV et al.
D967,421 S 10/2022 Shelton, IV et al.
11,457,918 B2 10/2022 Shelton, IV et al.
11,464,511 B2 10/2022 Timm et al.
11,464,512 B2 10/2022 Shelton, IV et al.
11,464,513 B2 10/2022 Shelton, IV et al.
11,464,514 B2 10/2022 Yates et al.
11,464,601 B2 10/2022 Shelton, IV et al.
11,471,155 B2 10/2022 Shelton, IV et al.
11,471,156 B2 10/2022 Shelton, IV et al.
11,471,157 B2 10/2022 Baxter, III et al.
11,478,241 B2 10/2022 Shelton, IV et al.
11,478,242 B2 10/2022 Shelton, IV et al.
11,478,244 B2 10/2022 DiNardo et al.
D969,849 S 11/2022 Stipech et al.
D971,232 S 11/2022 Siebel et al.
11,484,307 B2 11/2022 Hall et al.
11,484,309 B2 11/2022 Harris et al.
11,484,310 B2 11/2022 Shelton, IV et al.
11,484,311 B2 11/2022 Shelton, IV et al.
11,484,312 B2 11/2022 Shelton, IV et al.

(56) References Cited

U.S. PATENT DOCUMENTS 11,490,889 B2 11/2022 Overmyer et al.
11,497,488 B2 11/2022 Leimbach et al.
11,497,489 B2 11/2022 Baxter, III et al.
11,497,492 B2 11/2022 Shelton, IV
11,497,499 B2 11/2022 Shelton, IV et al.
11,504,116 B2 11/2022 Schmid et al.
11,504,119 B2 11/2022 Shelton, IV et al.
11,504,122 B2 11/2022 Shelton, IV et al.
11,504,192 B2 11/2022 Shelton, IV et al.
11,510,671 B2 11/2022 Shelton, IV et al.
11,510,673 B1 11/2022 Chen et al.
11,510,741 B2 11/2022 Shelton, IV et al.
11,517,304 B2 12/2022 Yates et al.
11,517,306 B2 12/2022 Miller et al.
11,517,309 B2 12/2022 Bakos et al.
11,517,311 B2 12/2022 Lytle, IV et al.
11,517,315 B2 12/2022 Huitema et al.
11,517,325 B2 12/2022 Shelton, IV et al.
11,517,390 B2 12/2022 Baxter, III
11,523,821 B2 12/2022 Harris et al.
11,523,822 B2 12/2022 Shelton, IV et al.
11,523,823 B2 12/2022 Hunter et al.
11,523,824 B2 12/2022 Williams
11,523,859 B2 12/2022 Shelton, IV et al.
11,529,137 B2 12/2022 Shelton, IV et al.
11,529,138 B2 12/2022 Jaworek et al.
11,529,139 B2 12/2022 Shelton, IV et al.
11,529,140 B2 12/2022 Shelton, IV et al.
11,529,142 B2 12/2022 Leimbach et al.
11,534,162 B2 12/2022 Shelton, IV
11,534,259 B2 12/2022 Leimbach et al.
D974,560 S 1/2023 Shelton, IV et al.
D975,278 S 1/2023 Shelton, IV et al.
D975,850 S 1/2023 Shelton, IV et al.
D975,851 S 1/2023 Shelton, IV et al.
D976,401 S 1/2023 Shelton, IV et al.
11,540,824 B2 1/2023 Shelton, IV et al.
11,540,829 B2 1/2023 Shelton, IV et al.
11,547,403 B2 1/2023 Shelton, IV et al.
11,547,404 B2 1/2023 Shelton, IV et al.
11,553,911 B2 1/2023 Shelton, IV et al.
11,553,916 B2 1/2023 Vendely et al.
11,553,919 B2 1/2023 Shelton, IV et al.
11,553,971 B2 1/2023 Shelton, IV et al.
11,559,302 B2 1/2023 Timm et al.
11,559,303 B2 1/2023 Shelton, IV et al.
11,559,304 B2 1/2023 Boudreaux et al.
11,559,307 B2 1/2023 Shelton, IV et al.
11,559,308 B2 1/2023 Yates et al.
11,559,496 B2 1/2023 Widenhouse et al.
11,564,679 B2 1/2023 Parihar et al.
11,564,682 B2 1/2023 Timm et al.
11,564,686 B2 1/2023 Yates et al.
11,564,688 B2 1/2023 Swayze et al.
11,564,703 B2 1/2023 Shelton, IV et al.
11,564,756 B2 1/2023 Shelton, IV et al.
11,571,207 B2 2/2023 Shelton, IV et al.
11,571,210 B2 2/2023 Shelton, IV et al.
11,571,212 B2 2/2023 Yates et al.
11,571,215 B2 2/2023 Shelton, IV et al.
11,571,231 B2 2/2023 Hess et al.
11,576,668 B2 2/2023 Shelton, IV et al.
11,576,672 B2 2/2023 Shelton, IV et al.
11,576,673 B2 2/2023 Shelton, IV
11,576,677 B2 2/2023 Shelton, IV et al.
11,583,274 B2 2/2023 Widenhouse et al.
11,583,277 B2 2/2023 Shelton, IV et al.
11,583,278 B2 2/2023 Shelton, IV et al.
11,583,279 B2 2/2023 Smith et al.
11,589,863 B2 2/2023 Weir et al.
11,589,865 B2 2/2023 Shelton, IV et al.
11,589,888 B2 2/2023 Shelton, IV et al.
D980,425 S 3/2023 Baxter, III
11,596,406 B2 3/2023 Huitema et al.
11,602,340 B2 3/2023 Schmid et al.
11,602,346 B2 3/2023 Shelton, IV
11,602,366 B2 3/2023 Shelton, IV et al.
11,607,219 B2 3/2023 Shelton, IV et al.
11,607,239 B2 3/2023 Swensgard et al.
11,607,278 B2 3/2023 Shelton, IV et al.
11,612,393 B2 3/2023 Morgan et al.
11,612,394 B2 3/2023 Morgan et al.
11,612,395 B2 3/2023 Yates et al.
11,617,575 B2 4/2023 Yates et al.
11,617,576 B2 4/2023 Yates et al.
11,617,577 B2 4/2023 Huang
11,622,763 B2 4/2023 Parihar et al.
11,622,766 B2 4/2023 Shelton, IV
11,622,785 B2 4/2023 Hess et al.
11,627,959 B2 4/2023 Shelton, IV et al.
11,627,960 B2 4/2023 Shelton, IV et al.
11,628,006 B2 4/2023 Henderson et al.
11,633,183 B2 4/2023 Parihar et al.
11,633,185 B2 4/2023 Wilson et al.
D985,009 S 5/2023 Barrett et al.
D985,617 S 5/2023 Bahatyrevich et al.
11,638,581 B2 5/2023 Parihar et al.
11,638,582 B2 5/2023 Bakos et al.
11,638,583 B2 5/2023 Yates et al.
11,638,587 B2 5/2023 Shelton, IV et al.
11,642,125 B2 5/2023 Harris et al.
11,642,128 B2 5/2023 Shelton, IV et al.
11,648,005 B2 5/2023 Yates et al.
11,648,006 B2 5/2023 Timm et al.
11,648,008 B2 5/2023 Shelton, IV et al.
11,648,009 B2 5/2023 Jenkins
11,648,022 B2 5/2023 Shelton, IV
11,648,024 B2 5/2023 Shelton, IV et al.
11,653,914 B2 5/2023 Shelton, IV et al.
11,653,915 B2 5/2023 Shelton, IV et al.
11,653,917 B2 5/2023 Scott et al.
11,653,918 B2 5/2023 Swayze et al.
11,653,920 B2 5/2023 Shelton, IV et al.
11,659,023 B2 5/2023 Shelton, IV et al.
11,660,090 B2 5/2023 Bakos et al.
11,660,110 B2 5/2023 Shelton, IV et al.
11,660,163 B2 5/2023 Shelton, IV et al.
11,666,327 B2 6/2023 Whitman et al.
11,666,332 B2 6/2023 Giordano et al.
11,672,531 B2 6/2023 Timm et al.
11,672,532 B2 6/2023 Shelton, IV et al.
11,672,536 B2 6/2023 Shelton, IV et al.
11,672,605 B2 6/2023 Messerly et al.
11,678,877 B2 6/2023 Shelton, IV et al.
11,678,880 B2 6/2023 Shelton, IV et al.
11,678,881 B2 6/2023 Yates et al.
11,678,882 B2 6/2023 Shelton, IV et al.
11,684,360 B2 6/2023 Shelton, IV et al.
11,684,361 B2 6/2023 Yates et al.
11,684,365 B2 6/2023 Shelton, IV et al.
11,684,369 B2 6/2023 Shelton, IV et al.
11,684,434 B2 6/2023 Shelton, IV
11,690,615 B2 7/2023 Parihar et al.
11,690,623 B2 7/2023 Shelton, IV et al.
11,696,757 B2 7/2023 Shelton, IV et al.
11,696,759 B2 7/2023 Shelton, IV et al.
11,696,761 B2 7/2023 Shelton, IV
11,696,778 B2 7/2023 Shelton, IV et al.
11,701,110 B2 7/2023 Yates et al.
11,701,111 B2 7/2023 Shelton, IV et al.
11,701,113 B2 7/2023 Shelton, IV et al.
11,701,114 B2 7/2023 Shelton, IV et al.
11,701,115 B2 7/2023 Harris et al.
11,701,118 B2 7/2023 Viola et al.
11,707,273 B2 7/2023 Kerr et al.
11,712,244 B2 8/2023 Vendely et al.
11,712,303 B2 8/2023 Shelton, IV et al.
11,717,285 B2 8/2023 Yates et al.
11,717,289 B2 8/2023 Leimbach
11,717,291 B2 8/2023 Morgan et al.
11,717,294 B2 8/2023 Huitema et al.
11,717,297 B2 8/2023 Baber et al.
11,723,657 B2 8/2023 Shelton, IV et al.
11,723,658 B2 8/2023 Bakos et al.

(56) References Cited

U.S. PATENT DOCUMENTS 11,723,662 B2 8/2023 Leimbach et al.
11,730,471 B2 8/2023 Worthington et al.
11,730,473 B2 8/2023 Creamer et al.
11,730,474 B2 8/2023 Shelton, IV
11,730,477 B2 8/2023 Smith et al.
11,737,749 B2 8/2023 Shelton, IV et al.
11,737,751 B2 8/2023 Shelton, IV et al.
11,737,754 B2 8/2023 Shelton, IV et al.
11,744,581 B2 9/2023 Shelton, IV et al.
11,744,583 B2 9/2023 Shelton, IV et al.
11,744,588 B2 9/2023 Beckman et al.
11,744,593 B2 9/2023 Shelton, IV et al.
11,744,603 B2 9/2023 Shelton, IV et al.
11,744,604 B2 9/2023 Shelton, IV et al.
11,749,877 B2 9/2023 Shelton, IV et al.
11,751,867 B2 9/2023 Shelton, IV et al.
11,751,869 B2 9/2023 Shelton, IV et al.
11,751,872 B2 9/2023 Zeiner et al.
11,751,937 B2 9/2023 Harlev et al.
11,759,202 B2 9/2023 Morgan et al.
11,759,208 B2 9/2023 Harris et al.
11,759,224 B2 9/2023 Shelton, IV et al.
11,766,257 B2 9/2023 Shelton, IV et al.
11,766,258 B2 9/2023 Shelton, IV et al.
11,766,259 B2 9/2023 Shelton, IV et al.
11,766,260 B2 9/2023 Harris et al.
11,771,419 B2 10/2023 Shelton, IV et al.
11,771,425 B2 10/2023 Swayze et al.
11,771,426 B2 10/2023 Giordano et al.
11,771,454 B2 10/2023 Swensgard et al.
2001/0000531 A1 4/2001 Casscells et al.
2001/0025183 A1 9/2001 Shahidi
2001/0025184 A1 9/2001 Messerly
2001/0030219 A1 10/2001 Green et al.
2001/0034530 A1 10/2001 Malackowski et al.
2001/0045442 A1 11/2001 Whitman
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0045905 A1 4/2002 Gerbi et al.
2002/0054158 A1 5/2002 Asami
2002/0065535 A1 5/2002 Kneifel et al.
2002/0066764 A1 6/2002 Perry et al.
2002/0077660 A1 6/2002 Kayan et al.
2002/0082612 A1 6/2002 Moll et al.
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0099374 A1 7/2002 Pendekanti et al.
2002/0103494 A1 8/2002 Pacey
2002/0111621 A1 8/2002 Wallace et al.
2002/0111624 A1 8/2002 Witt et al.
2002/0116063 A1 8/2002 Giannetti et al.
2002/0117533 A1 8/2002 Milliman et al.
2002/0117534 A1 8/2002 Green et al.
2002/0127265 A1 9/2002 Bowman et al.
2002/0128633 A1 9/2002 Brock et al.
2002/0133236 A1 9/2002 Rousseau
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0156497 A1 10/2002 Nagase et al.
2002/0158593 A1 10/2002 Henderson et al.
2002/0161277 A1 10/2002 Boone et al.
2002/0165559 A1 11/2002 Grant et al.
2002/0165562 A1 11/2002 Grant et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0004610 A1 1/2003 Niemeyer et al.
2003/0009193 A1 1/2003 Corsaro
2003/0011245 A1 1/2003 Fiebig
2003/0012805 A1 1/2003 Chen et al.
2003/0018323 A1 1/2003 Wallace et al.
2003/0028236 A1 2/2003 Gillick et al.
2003/0040670 A1 2/2003 Govari
2003/0045835 A1 3/2003 Anderson et al.
2003/0045900 A1 3/2003 Hahnen et al.
2003/0047230 A1 3/2003 Kim
2003/0047582 A1 3/2003 Sonnenschein et al.
2003/0050628 A1 3/2003 Whitman et al.
2003/0050654 A1 3/2003 Whitman et al.
2003/0066858 A1 4/2003 Holgersson
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0093160 A1 5/2003 Maksimovic et al.
2003/0094356 A1 5/2003 Waldron
2003/0096158 A1 5/2003 Takano et al.
2003/0105475 A1 6/2003 Sancoff et al.
2003/0114851 A1 6/2003 Truckai et al.
2003/0121586 A1 7/2003 Mitra et al.
2003/0129382 A1 7/2003 Treat
2003/0135204 A1 7/2003 Lee et al.
2003/0135388 A1 7/2003 Martucci et al.
2003/0139741 A1 7/2003 Goble et al.
2003/0144660 A1 7/2003 Mollenauer
2003/0149406 A1 8/2003 Martineau et al.
2003/0153908 A1 8/2003 Goble et al.
2003/0153968 A1 8/2003 Geis et al.
2003/0158463 A1 8/2003 Julian et al.
2003/0163029 A1 8/2003 Sonnenschein et al.
2003/0163085 A1 8/2003 Tanner et al.
2003/0164172 A1 9/2003 Chumas et al.
2003/0181800 A1 9/2003 Bonutti
2003/0181900 A1 9/2003 Long
2003/0190584 A1 10/2003 Heasley
2003/0195387 A1 10/2003 Kortenbach et al.
2003/0205029 A1 11/2003 Chapolini et al.
2003/0212005 A1 11/2003 Petito et al.
2003/0216619 A1 11/2003 Scirica et al.
2003/0216732 A1 11/2003 Truckai et al.
2003/0220541 A1 11/2003 Salisbury et al.
2003/0236505 A1 12/2003 Bonadio et al.
2004/0006335 A1 1/2004 Garrison
2004/0006340 A1 1/2004 Latterell et al.
2004/0007608 A1 1/2004 Ehrenfels et al.
2004/0024457 A1 2/2004 Boyce et al.
2004/0028502 A1 2/2004 Cummins
2004/0030333 A1 2/2004 Goble
2004/0034287 A1 2/2004 Hickle
2004/0034357 A1 2/2004 Beane et al.
2004/0044295 A1 3/2004 Reinert et al.
2004/0044364 A1 3/2004 DeVries et al.
2004/0049121 A1 3/2004 Yaron
2004/0049172 A1 3/2004 Root et al.
2004/0059362 A1 3/2004 Knodel et al.
2004/0068161 A1 4/2004 Couvillon
2004/0068224 A1 4/2004 Couvillon et al.
2004/0068307 A1 4/2004 Goble
2004/0070369 A1 4/2004 Sakakibara
2004/0073222 A1 4/2004 Koseki
2004/0078037 A1 4/2004 Batchelor et al.
2004/0082952 A1 4/2004 Dycus et al.
2004/0085180 A1 5/2004 Juang
2004/0092967 A1 5/2004 Sancoff et al.
2004/0092992 A1 5/2004 Adams et al.
2004/0093020 A1 5/2004 Sinton
2004/0093024 A1 5/2004 Lousararian et al.
2004/0098040 A1 5/2004 Taniguchi et al.
2004/0101822 A1 5/2004 Wiesner et al.
2004/0102783 A1 5/2004 Sutterlin et al.
2004/0108357 A1 6/2004 Milliman et al.
2004/0110439 A1 6/2004 Chaikof et al.

(56) References Cited

U.S. PATENT DOCUMENTS

| | | | |
|---|---|---|---|
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0230230 | A1 | 11/2004 | Lindstrom et al. |
| 2004/0231870 | A1 | 11/2004 | McCormick et al. |
| 2004/0232194 | A1 | 11/2004 | Pedicini et al. |
| 2004/0232197 | A1 | 11/2004 | Shelton, IV et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0254680 | A1 | 12/2004 | Sunaoshi |
| 2004/0260315 | A1 | 12/2004 | Dell et al. |
| 2004/0267310 | A1 | 12/2004 | Racenet et al. |
| 2004/0267362 | A1 | 12/2004 | Hwang et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0023325 | A1 | 2/2005 | Gresham et al. |
| 2005/0032511 | A1 | 2/2005 | Malone et al. |
| 2005/0033136 | A1 | 2/2005 | Govari et al. |
| 2005/0033352 | A1 | 2/2005 | Zepf et al. |
| 2005/0044489 | A1 | 2/2005 | Yamagami et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0067548 | A1 | 3/2005 | Inoue |
| 2005/0070925 | A1 | 3/2005 | Shelton et al. |
| 2005/0070929 | A1 | 3/2005 | Dalessandro et al. |
| 2005/0074593 | A1 | 4/2005 | Day et al. |
| 2005/0075561 | A1 | 4/2005 | Golden |
| 2005/0079088 | A1 | 4/2005 | Wirth et al. |
| 2005/0080342 | A1 | 4/2005 | Gilreath et al. |
| 2005/0085693 | A1 | 4/2005 | Belson et al. |
| 2005/0085838 | A1 | 4/2005 | Thompson et al. |
| 2005/0090709 | A1 | 4/2005 | Okada et al. |
| 2005/0090817 | A1 | 4/2005 | Phan |
| 2005/0096683 | A1 | 5/2005 | Ellins et al. |
| 2005/0108643 | A1 | 5/2005 | Schybergson et al. |
| 2005/0116673 | A1 | 6/2005 | Carl et al. |
| 2005/0119524 | A1 | 6/2005 | Sekine et al. |
| 2005/0120836 | A1 | 6/2005 | Anderson |
| 2005/0121390 | A1 | 6/2005 | Wallace et al. |
| 2005/0124855 | A1 | 6/2005 | Jaffe et al. |
| 2005/0125028 | A1 | 6/2005 | Looper et al. |
| 2005/0125897 | A1 | 6/2005 | Wyslucha et al. |
| 2005/0129730 | A1 | 6/2005 | Pang et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139635 | A1 | 6/2005 | Wukusick et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0145672 | A1 | 7/2005 | Schwemberger et al. |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0178813 | A1 | 8/2005 | Swayze et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0191936 | A1 | 9/2005 | Marine et al. |
| 2005/0197859 | A1 | 9/2005 | Wilson et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |
| 2005/0240178 | A1 | 10/2005 | Morley et al. |
| 2005/0242950 | A1 | 11/2005 | Lindsay et al. |
| 2005/0245965 | A1 | 11/2005 | Orban Iii et al. |
| 2005/0246881 | A1 | 11/2005 | Kelly et al. |
| 2005/0251063 | A1 | 11/2005 | Basude |
| 2005/0251110 | A1 | 11/2005 | Nixon |
| 2005/0256452 | A1 | 11/2005 | DeMarchi et al. |
| 2005/0256546 | A1 | 11/2005 | Vaisnys et al. |
| 2005/0258963 | A1 | 11/2005 | Rodriguez et al. |
| 2005/0261676 | A1 | 11/2005 | Hall et al. |
| 2005/0263563 | A1 | 12/2005 | Racenet et al. |
| 2005/0267455 | A1 | 12/2005 | Eggers et al. |
| 2005/0267464 | A1 | 12/2005 | Truckai et al. |
| 2005/0267529 | A1 | 12/2005 | Crockett et al. |
| 2005/0274034 | A1 | 12/2005 | Hayashida et al. |
| 2005/0283188 | A1 | 12/2005 | Loshakove et al. |
| 2005/0283226 | A1 | 12/2005 | Haverkost |
| 2006/0000867 | A1 | 1/2006 | Shelton et al. |
| 2006/0008504 | A1 | 1/2006 | Kerr et al. |
| 2006/0008787 | A1 | 1/2006 | Hayman et al. |
| 2006/0011698 | A1 | 1/2006 | Okada et al. |
| 2006/0015009 | A1 | 1/2006 | Jaffe et al. |
| 2006/0019056 | A1 | 1/2006 | Turner et al. |
| 2006/0020167 | A1 | 1/2006 | Sitzmann |
| 2006/0020258 | A1 | 1/2006 | Strauss et al. |
| 2006/0020272 | A1 | 1/2006 | Gildenberg |
| 2006/0020336 | A1 | 1/2006 | Liddicoat |
| 2006/0025812 | A1 | 2/2006 | Shelton |
| 2006/0041188 | A1 | 2/2006 | Dirusso et al. |
| 2006/0047275 | A1 | 3/2006 | Goble |
| 2006/0049229 | A1 | 3/2006 | Milliman et al. |
| 2006/0052824 | A1 | 3/2006 | Ransick et al. |
| 2006/0052825 | A1 | 3/2006 | Ransick et al. |
| 2006/0053951 | A1 | 3/2006 | Revelis et al. |
| 2006/0064086 | A1 | 3/2006 | Odom |
| 2006/0079735 | A1 | 4/2006 | Martone et al. |

(56) References Cited

U.S. PATENT DOCUMENTS

2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0089628 A1 4/2006 Whitman
2006/0097026 A1 5/2006 Shelton
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0111738 A1 5/2006 Wenchell
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0189440 A1 8/2006 Gravagne
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0235368 A1 10/2006 Oz
2006/0241666 A1 10/2006 Briggs et al.
2006/0241691 A1 10/2006 Wilk
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0016272 A1 1/2007 Thompson et al.
2007/0018958 A1 1/2007 Tavakoli et al.
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0034668 A1 2/2007 Holsten et al.
2007/0034669 A1 2/2007 de la Torre et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0102476 A1 5/2007 Shelton et al.
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0207186 A1 9/2007 Scanlon et al.
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0250093 A1 10/2007 Makower et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0270790 A1 11/2007 Smith et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.

(56) References Cited

U.S. PATENT DOCUMENTS

| | | | |
|---|---|---|---|
| 2008/0029574 | A1 | 2/2008 | Shelton et al. |
| 2008/0029575 | A1 | 2/2008 | Shelton et al. |
| 2008/0029576 | A1 | 2/2008 | Shelton et al. |
| 2008/0030170 | A1 | 2/2008 | Dacquay et al. |
| 2008/0039746 | A1 | 2/2008 | Hissong et al. |
| 2008/0042861 | A1 | 2/2008 | Dacquay et al. |
| 2008/0046000 | A1 | 2/2008 | Lee et al. |
| 2008/0051833 | A1 | 2/2008 | Gramuglia et al. |
| 2008/0064920 | A1 | 3/2008 | Bakos et al. |
| 2008/0064921 | A1 | 3/2008 | Larkin et al. |
| 2008/0065153 | A1 | 3/2008 | Allard et al. |
| 2008/0069736 | A1 | 3/2008 | Mingerink et al. |
| 2008/0071328 | A1 | 3/2008 | Haubrich et al. |
| 2008/0077158 | A1 | 3/2008 | Haider et al. |
| 2008/0078802 | A1 | 4/2008 | Hess et al. |
| 2008/0081948 | A1 | 4/2008 | Weisenburgh et al. |
| 2008/0082114 | A1 | 4/2008 | Mckenna et al. |
| 2008/0082125 | A1 | 4/2008 | Murray et al. |
| 2008/0082126 | A1 | 4/2008 | Murray et al. |
| 2008/0083807 | A1 | 4/2008 | Beardsley et al. |
| 2008/0083811 | A1 | 4/2008 | Marczyk |
| 2008/0085296 | A1 | 4/2008 | Powell et al. |
| 2008/0086078 | A1 | 4/2008 | Powell et al. |
| 2008/0091072 | A1 | 4/2008 | Omori et al. |
| 2008/0094228 | A1 | 4/2008 | Welch et al. |
| 2008/0108443 | A1 | 5/2008 | Jinno et al. |
| 2008/0114250 | A1 | 5/2008 | Urbano et al. |
| 2008/0125634 | A1 | 5/2008 | Ryan et al. |
| 2008/0125749 | A1 | 5/2008 | Olson |
| 2008/0126984 | A1 | 5/2008 | Fleishman et al. |
| 2008/0128469 | A1 | 6/2008 | Dalessandro et al. |
| 2008/0129253 | A1 | 6/2008 | Shiue et al. |
| 2008/0135600 | A1 | 6/2008 | Hiranuma et al. |
| 2008/0140088 | A1 | 6/2008 | Orban, III |
| 2008/0140115 | A1 | 6/2008 | Stopek |
| 2008/0140159 | A1 | 6/2008 | Bornhoft et al. |
| 2008/0149682 | A1 | 6/2008 | Uhm |
| 2008/0154299 | A1 | 6/2008 | Livneh |
| 2008/0154335 | A1 | 6/2008 | Thrope et al. |
| 2008/0169328 | A1 | 7/2008 | Shelton |
| 2008/0169330 | A1 | 7/2008 | Shelton et al. |
| 2008/0169332 | A1 | 7/2008 | Shelton et al. |
| 2008/0169333 | A1 | 7/2008 | Shelton et al. |
| 2008/0172087 | A1 | 7/2008 | Fuchs et al. |
| 2008/0177392 | A1 | 7/2008 | Williams et al. |
| 2008/0190989 | A1 | 8/2008 | Crews et al. |
| 2008/0196253 | A1 | 8/2008 | Ezra et al. |
| 2008/0196419 | A1 | 8/2008 | Dube |
| 2008/0197167 | A1 | 8/2008 | Viola et al. |
| 2008/0200755 | A1 | 8/2008 | Bakos |
| 2008/0200762 | A1 | 8/2008 | Stokes et al. |
| 2008/0200835 | A1 | 8/2008 | Monson et al. |
| 2008/0200911 | A1 | 8/2008 | Long |
| 2008/0200933 | A1 | 8/2008 | Bakos et al. |
| 2008/0200934 | A1 | 8/2008 | Fox |
| 2008/0206186 | A1 | 8/2008 | Butler et al. |
| 2008/0208058 | A1 | 8/2008 | Sabata et al. |
| 2008/0214967 | A1 | 9/2008 | Aranyi et al. |
| 2008/0216704 | A1 | 9/2008 | Eisenbeis et al. |
| 2008/0217376 | A1 | 9/2008 | Clauson et al. |
| 2008/0234709 | A1 | 9/2008 | Houser |
| 2008/0234866 | A1 | 9/2008 | Kishi et al. |
| 2008/0237296 | A1 | 10/2008 | Boudreaux et al. |
| 2008/0242939 | A1 | 10/2008 | Johnston |
| 2008/0243088 | A1 | 10/2008 | Evans |
| 2008/0243143 | A1 | 10/2008 | Kuhns et al. |
| 2008/0249536 | A1 | 10/2008 | Stahler et al. |
| 2008/0249608 | A1 | 10/2008 | Dave |
| 2008/0255413 | A1 | 10/2008 | Zemlok et al. |
| 2008/0255420 | A1 | 10/2008 | Lee et al. |
| 2008/0255421 | A1 | 10/2008 | Hegeman et al. |
| 2008/0255663 | A1 | 10/2008 | Akpek et al. |
| 2008/0262654 | A1 | 10/2008 | Omori et al. |
| 2008/0269596 | A1 | 10/2008 | Revie et al. |
| 2008/0281171 | A1 | 11/2008 | Fennell et al. |
| 2008/0281332 | A1 | 11/2008 | Taylor |
| 2008/0287944 | A1 | 11/2008 | Pearson et al. |
| 2008/0293910 | A1 | 11/2008 | Kapiamba et al. |
| 2008/0294179 | A1 | 11/2008 | Balbierz et al. |
| 2008/0296343 | A1 | 12/2008 | Schall et al. |
| 2008/0296346 | A1 | 12/2008 | Shelton, IV et al. |
| 2008/0296347 | A1 | 12/2008 | Shelton, IV et al. |
| 2008/0297287 | A1 | 12/2008 | Shachar et al. |
| 2008/0298784 | A1 | 12/2008 | Kastner |
| 2008/0300579 | A1 | 12/2008 | Broehl et al. |
| 2008/0308504 | A1 | 12/2008 | Hallan et al. |
| 2008/0308602 | A1 | 12/2008 | Timm et al. |
| 2008/0308603 | A1 | 12/2008 | Shelton et al. |
| 2008/0308607 | A1 | 12/2008 | Timm et al. |
| 2008/0308608 | A1 | 12/2008 | Prommersberger |
| 2008/0308807 | A1 | 12/2008 | Yamazaki et al. |
| 2008/0312686 | A1 | 12/2008 | Ellingwood |
| 2008/0312687 | A1 | 12/2008 | Blier |
| 2008/0315829 | A1 | 12/2008 | Jones et al. |
| 2009/0001121 | A1 | 1/2009 | Hess et al. |
| 2009/0001130 | A1 | 1/2009 | Hess et al. |
| 2009/0004455 | A1 | 1/2009 | Gravagna et al. |
| 2009/0005809 | A1 | 1/2009 | Hess et al. |
| 2009/0007014 | A1 | 1/2009 | Coomer et al. |
| 2009/0012534 | A1 | 1/2009 | Madhani et al. |
| 2009/0015195 | A1 | 1/2009 | Loth-Krausser |
| 2009/0020958 | A1 | 1/2009 | Soul |
| 2009/0030437 | A1 | 1/2009 | Houser et al. |
| 2009/0043253 | A1 | 2/2009 | Podaima |
| 2009/0048583 | A1 | 2/2009 | Williams et al. |
| 2009/0048589 | A1 | 2/2009 | Takashino et al. |
| 2009/0053288 | A1 | 2/2009 | Eskridge, Jr. et al. |
| 2009/0057369 | A1 | 3/2009 | Smith et al. |
| 2009/0069806 | A1 | 3/2009 | De La Mora Levy et al. |
| 2009/0076506 | A1 | 3/2009 | Baker |
| 2009/0076510 | A1 | 3/2009 | Bell et al. |
| 2009/0078736 | A1 | 3/2009 | Van Lue |
| 2009/0078739 | A1 | 3/2009 | Viola |
| 2009/0081313 | A1 | 3/2009 | Aghion et al. |
| 2009/0088659 | A1 | 4/2009 | Graham et al. |
| 2009/0090763 | A1 | 4/2009 | Zemlok et al. |
| 2009/0099579 | A1 | 4/2009 | Nentwick et al. |
| 2009/0099876 | A1 | 4/2009 | Whitman |
| 2009/0110533 | A1 | 4/2009 | Jinno |
| 2009/0112234 | A1 | 4/2009 | Crainich et al. |
| 2009/0114701 | A1 | 5/2009 | Zemlok et al. |
| 2009/0118762 | A1 | 5/2009 | Crainch et al. |
| 2009/0119011 | A1 | 5/2009 | Kondo et al. |
| 2009/0120994 | A1 | 5/2009 | Murray et al. |
| 2009/0131819 | A1 | 5/2009 | Ritchie et al. |
| 2009/0132400 | A1 | 5/2009 | Conway |
| 2009/0135280 | A1 | 5/2009 | Johnston et al. |
| 2009/0138003 | A1 | 5/2009 | Deville et al. |
| 2009/0143797 | A1 | 6/2009 | Smith et al. |
| 2009/0143855 | A1 | 6/2009 | Weber et al. |
| 2009/0149871 | A9 | 6/2009 | Kagan et al. |
| 2009/0167548 | A1 | 7/2009 | Sugahara |
| 2009/0171147 | A1 | 7/2009 | Lee et al. |
| 2009/0177218 | A1 | 7/2009 | Young et al. |
| 2009/0177226 | A1 | 7/2009 | Reinprecht et al. |
| 2009/0181290 | A1 | 7/2009 | Baldwin et al. |
| 2009/0188964 | A1 | 7/2009 | Orlov |
| 2009/0192534 | A1 | 7/2009 | Ortiz et al. |
| 2009/0196903 | A1 | 8/2009 | Kliman |
| 2009/0198272 | A1 | 8/2009 | Kerver et al. |
| 2009/0204108 | A1 | 8/2009 | Steffen |
| 2009/0204109 | A1 | 8/2009 | Grove et al. |
| 2009/0204126 | A1 | 8/2009 | Le |
| 2009/0204925 | A1 | 8/2009 | Bhat et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh et al. |
| 2009/0206133 | A1 | 8/2009 | Morgan et al. |
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0218384 | A1 | 9/2009 | Aranyi |

(56) References Cited

U.S. PATENT DOCUMENTS

| | | | |
|---|---|---|---|
| 2009/0221993 | A1 | 9/2009 | Sohi et al. |
| 2009/0227834 | A1 | 9/2009 | Nakamoto et al. |
| 2009/0234273 | A1 | 9/2009 | Intoccia et al. |
| 2009/0236401 | A1 | 9/2009 | Cole et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248100 | A1 | 10/2009 | Vaisnys et al. |
| 2009/0253959 | A1 | 10/2009 | Yoshie et al. |
| 2009/0255974 | A1 | 10/2009 | Viola |
| 2009/0255977 | A1 | 10/2009 | Zemlok |
| 2009/0261141 | A1 | 10/2009 | Stratton et al. |
| 2009/0262078 | A1 | 10/2009 | Pizzi |
| 2009/0264940 | A1 | 10/2009 | Beale et al. |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0287300 | A1 | 11/2009 | Dave et al. |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0318936 | A1 | 12/2009 | Harris et al. |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0032470 | A1 | 2/2010 | Hess et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076433 | A1 | 3/2010 | Taylor et al. |
| 2010/0076483 | A1 | 3/2010 | Imuta |
| 2010/0076489 | A1 | 3/2010 | Stopek et al. |
| 2010/0081883 | A1 | 4/2010 | Murray et al. |
| 2010/0094312 | A1 | 4/2010 | Ruiz Morales et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0106167 | A1 | 4/2010 | Boulnois et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0181364 | A1 | 7/2010 | Shelton, IV et al. |
| 2010/0187285 | A1 | 7/2010 | Harris et al. |
| 2010/0191255 | A1 | 7/2010 | Crainich et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0218019 | A1 | 8/2010 | Eckhard |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241115 | A1 | 9/2010 | Benamou et al. |
| 2010/0241137 | A1 | 9/2010 | Doyle et al. |
| 2010/0243707 | A1 | 9/2010 | Olson et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |
| 2010/0298636 | A1 | 11/2010 | Castro et al. |
| 2010/0298642 | A1 | 11/2010 | Trusty et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0009863 | A1 | 1/2011 | Marczyk et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029003 | A1 | 2/2011 | Lavigne et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0066243 | A1 | 3/2011 | Rivin et al. |
| 2011/0071473 | A1 | 3/2011 | Rogers et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112513 | A1 | 5/2011 | Hester et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | El-Galley et al. |
| 2011/0125176 | A1 | 5/2011 | Yates et al. |
| 2011/0127945 | A1 | 6/2011 | Yoneda |
| 2011/0129706 | A1 | 6/2011 | Takahashi et al. |
| 2011/0144764 | A1 | 6/2011 | Bagga et al. |
| 2011/0147433 | A1 | 6/2011 | Shelton, IV et al. |
| 2011/0160725 | A1 | 6/2011 | Kabaya et al. |
| 2011/0163146 | A1 | 7/2011 | Ortiz et al. |
| 2011/0172495 | A1 | 7/2011 | Armstrong |
| 2011/0174861 | A1 | 7/2011 | Shelton, IV et al. |
| 2011/0189957 | A1 | 8/2011 | Hocke |
| 2011/0192882 | A1 | 8/2011 | Hess et al. |
| 2011/0198381 | A1 | 8/2011 | McCardle et al. |

(56) References Cited

U.S. PATENT DOCUMENTS

| | | | |
|---|---|---|---|
| 2011/0199225 | A1 | 8/2011 | Touchberry et al. |
| 2011/0218400 | A1 | 9/2011 | Ma et al. |
| 2011/0218550 | A1 | 9/2011 | Ma |
| 2011/0220381 | A1 | 9/2011 | Friese et al. |
| 2011/0224543 | A1 | 9/2011 | Johnson et al. |
| 2011/0225105 | A1 | 9/2011 | Scholer et al. |
| 2011/0230713 | A1 | 9/2011 | Kleemann et al. |
| 2011/0235168 | A1 | 9/2011 | Sander |
| 2011/0238044 | A1 | 9/2011 | Main et al. |
| 2011/0241597 | A1 | 10/2011 | Zhu et al. |
| 2011/0251606 | A1 | 10/2011 | Kerr |
| 2011/0256266 | A1 | 10/2011 | Orme et al. |
| 2011/0271186 | A1 | 11/2011 | Owens |
| 2011/0275901 | A1 | 11/2011 | Shelton, IV |
| 2011/0276083 | A1 | 11/2011 | Shelton, IV et al. |
| 2011/0278035 | A1 | 11/2011 | Chen |
| 2011/0278343 | A1 | 11/2011 | Knodel et al. |
| 2011/0279268 | A1 | 11/2011 | Konishi et al. |
| 2011/0285507 | A1 | 11/2011 | Nelson |
| 2011/0290856 | A1 | 12/2011 | Shelton, IV et al. |
| 2011/0290858 | A1 | 12/2011 | Whitman et al. |
| 2011/0292258 | A1 | 12/2011 | Adler et al. |
| 2011/0293690 | A1 | 12/2011 | Griffin et al. |
| 2011/0295295 | A1 | 12/2011 | Shelton, IV et al. |
| 2011/0295299 | A1 | 12/2011 | Braithwaite et al. |
| 2011/0313894 | A1 | 12/2011 | Dye et al. |
| 2011/0315413 | A1 | 12/2011 | Fisher et al. |
| 2012/0004636 | A1 | 1/2012 | Lo |
| 2012/0007442 | A1 | 1/2012 | Rhodes et al. |
| 2012/0008880 | A1 | 1/2012 | Toth |
| 2012/0010615 | A1 | 1/2012 | Cummings et al. |
| 2012/0016239 | A1 | 1/2012 | Barthe et al. |
| 2012/0016413 | A1 | 1/2012 | Timm et al. |
| 2012/0016467 | A1 | 1/2012 | Chen et al. |
| 2012/0018487 | A1 | 1/2012 | Bettuchi et al. |
| 2012/0029272 | A1 | 2/2012 | Shelton, IV et al. |
| 2012/0029550 | A1 | 2/2012 | Forsell |
| 2012/0033360 | A1 | 2/2012 | Hsu |
| 2012/0043100 | A1 | 2/2012 | Isobe et al. |
| 2012/0059286 | A1 | 3/2012 | Hastings et al. |
| 2012/0064483 | A1 | 3/2012 | Lint et al. |
| 2012/0074200 | A1 | 3/2012 | Schmid et al. |
| 2012/0078243 | A1 | 3/2012 | Worrell et al. |
| 2012/0078244 | A1 | 3/2012 | Worrell et al. |
| 2012/0080336 | A1 | 4/2012 | Shelton, IV et al. |
| 2012/0080344 | A1 | 4/2012 | Shelton, IV |
| 2012/0080478 | A1 | 4/2012 | Morgan et al. |
| 2012/0080491 | A1 | 4/2012 | Shelton, IV et al. |
| 2012/0080498 | A1 | 4/2012 | Shelton, IV et al. |
| 2012/0083836 | A1 | 4/2012 | Shelton, IV et al. |
| 2012/0086276 | A1 | 4/2012 | Sawyers |
| 2012/0095458 | A1 | 4/2012 | Cybulski et al. |
| 2012/0101488 | A1 | 4/2012 | Aldridge et al. |
| 2012/0109186 | A1 | 5/2012 | Parrott et al. |
| 2012/0116261 | A1 | 5/2012 | Mumaw et al. |
| 2012/0116262 | A1 | 5/2012 | Houser et al. |
| 2012/0116263 | A1 | 5/2012 | Houser et al. |
| 2012/0116265 | A1 | 5/2012 | Houser et al. |
| 2012/0116266 | A1 | 5/2012 | Houser et al. |
| 2012/0116381 | A1 | 5/2012 | Houser et al. |
| 2012/0118595 | A1 | 5/2012 | Pellenc |
| 2012/0123463 | A1 | 5/2012 | Jacobs |
| 2012/0125792 | A1 | 5/2012 | Cassivi |
| 2012/0130217 | A1 | 5/2012 | Kauphusman et al. |
| 2012/0132286 | A1 | 5/2012 | Lim et al. |
| 2012/0132663 | A1 | 5/2012 | Kasvikis et al. |
| 2012/0143173 | A1 | 6/2012 | Steege et al. |
| 2012/0143175 | A1 | 6/2012 | Hermann et al. |
| 2012/0171539 | A1 | 7/2012 | Rejman et al. |
| 2012/0175398 | A1 | 7/2012 | Sandborn et al. |
| 2012/0190964 | A1 | 7/2012 | Hyde et al. |
| 2012/0197239 | A1 | 8/2012 | Smith et al. |
| 2012/0197272 | A1 | 8/2012 | Oray et al. |
| 2012/0203213 | A1 | 8/2012 | Kimball et al. |
| 2012/0211542 | A1 | 8/2012 | Racenet |
| 2012/0220990 | A1 | 8/2012 | Mckenzie et al. |
| 2012/0233298 | A1 | 9/2012 | Verbandt et al. |
| 2012/0234895 | A1 | 9/2012 | O'Connor et al. |
| 2012/0234897 | A1 | 9/2012 | Shelton, IV et al. |
| 2012/0239068 | A1 | 9/2012 | Morris et al. |
| 2012/0241494 | A1 | 9/2012 | Marczyk |
| 2012/0241503 | A1 | 9/2012 | Baxter, III et al. |
| 2012/0248169 | A1 | 10/2012 | Widenhouse et al. |
| 2012/0251861 | A1 | 10/2012 | Liang et al. |
| 2012/0253328 | A1 | 10/2012 | Cunningham et al. |
| 2012/0256494 | A1 | 10/2012 | Kesler et al. |
| 2012/0271327 | A1 | 10/2012 | West et al. |
| 2012/0283707 | A1 | 11/2012 | Giordano et al. |
| 2012/0286019 | A1 | 11/2012 | Hueil et al. |
| 2012/0289811 | A1 | 11/2012 | Viola et al. |
| 2012/0289979 | A1 | 11/2012 | Eskaros et al. |
| 2012/0292367 | A1 | 11/2012 | Morgan et al. |
| 2012/0296316 | A1 | 11/2012 | Imuta |
| 2012/0296342 | A1 | 11/2012 | Haglund Wendelschafer |
| 2012/0298722 | A1 | 11/2012 | Hess et al. |
| 2012/0301498 | A1 | 11/2012 | Altreuter et al. |
| 2012/0310254 | A1 | 12/2012 | Manzo et al. |
| 2012/0312861 | A1 | 12/2012 | Gurumurthy et al. |
| 2012/0316424 | A1 | 12/2012 | Stopek |
| 2012/0330285 | A1 | 12/2012 | Hartoumbekis et al. |
| 2012/0330329 | A1 | 12/2012 | Harris et al. |
| 2013/0006227 | A1 | 1/2013 | Takashino |
| 2013/0008937 | A1 | 1/2013 | Viola |
| 2013/0012983 | A1 | 1/2013 | Kleyman |
| 2013/0018400 | A1 | 1/2013 | Milton et al. |
| 2013/0020375 | A1 | 1/2013 | Shelton, IV et al. |
| 2013/0020376 | A1 | 1/2013 | Shelton, IV et al. |
| 2013/0023861 | A1 | 1/2013 | Shelton, IV et al. |
| 2013/0023910 | A1 | 1/2013 | Solomon et al. |
| 2013/0023915 | A1 | 1/2013 | Mueller |
| 2013/0026208 | A1 | 1/2013 | Shelton, IV et al. |
| 2013/0026210 | A1 | 1/2013 | Shelton, IV et al. |
| 2013/0030462 | A1 | 1/2013 | Keating et al. |
| 2013/0041292 | A1 | 2/2013 | Cunningham |
| 2013/0056522 | A1 | 3/2013 | Swensgard |
| 2013/0057162 | A1 | 3/2013 | Pollischansky |
| 2013/0068816 | A1 | 3/2013 | Mandakolathur Vasudevan et al. |
| 2013/0069088 | A1 | 3/2013 | Speck et al. |
| 2013/0075447 | A1 | 3/2013 | Weisenburgh, II et al. |
| 2013/0087597 | A1 | 4/2013 | Shelton, IV et al. |
| 2013/0090534 | A1 | 4/2013 | Burns et al. |
| 2013/0096568 | A1 | 4/2013 | Justis |
| 2013/0098968 | A1 | 4/2013 | Aranyi et al. |
| 2013/0098970 | A1 | 4/2013 | Racenet et al. |
| 2013/0106352 | A1 | 5/2013 | Nagamine |
| 2013/0112729 | A1 | 5/2013 | Beardsley et al. |
| 2013/0116669 | A1 | 5/2013 | Shelton, IV et al. |
| 2013/0123816 | A1 | 5/2013 | Hodgkinson et al. |
| 2013/0126202 | A1 | 5/2013 | Oomori et al. |
| 2013/0131476 | A1 | 5/2013 | Siu et al. |
| 2013/0131651 | A1 | 5/2013 | Strobl et al. |
| 2013/0136969 | A1 | 5/2013 | Yasui et al. |
| 2013/0153639 | A1 | 6/2013 | Hodgkinson et al. |
| 2013/0153641 | A1 | 6/2013 | Shelton, IV et al. |
| 2013/0158390 | A1 | 6/2013 | Tan et al. |
| 2013/0162198 | A1 | 6/2013 | Yokota et al. |
| 2013/0165908 | A1 | 6/2013 | Purdy et al. |
| 2013/0169217 | A1 | 7/2013 | Watanabe et al. |
| 2013/0172713 | A1 | 7/2013 | Kirschenman |
| 2013/0172878 | A1 | 7/2013 | Smith |
| 2013/0175315 | A1 | 7/2013 | Milliman |
| 2013/0175317 | A1 | 7/2013 | Yates et al. |
| 2013/0183769 | A1 | 7/2013 | Tajima |
| 2013/0186936 | A1 | 7/2013 | Shelton, IV |
| 2013/0211244 | A1 | 8/2013 | Nathaniel |
| 2013/0214025 | A1 | 8/2013 | Zemlok et al. |
| 2013/0215449 | A1 | 8/2013 | Yamasaki |
| 2013/0231681 | A1 | 9/2013 | Robinson et al. |
| 2013/0233906 | A1 | 9/2013 | Hess et al. |
| 2013/0238021 | A1 | 9/2013 | Gross et al. |
| 2013/0248578 | A1 | 9/2013 | Arteaga Gonzalez |
| 2013/0253480 | A1 | 9/2013 | Kimball et al. |
| 2013/0253499 | A1 | 9/2013 | Kimball et al. |
| 2013/0256373 | A1 | 10/2013 | Schmid et al. |

(56) References Cited

U.S. PATENT DOCUMENTS

2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0310849 A1 11/2013 Malkowski
2013/0327552 A1 12/2013 Lovelass et al.
2013/0331826 A1 12/2013 Steege
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100554 A1 4/2014 Williams
2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166718 A1 6/2014 Swayze et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0194874 A1 7/2014 Dietz et al.
2014/0207124 A1 7/2014 Aldridge et al.
2014/0209658 A1 7/2014 Skalla et al.
2014/0215242 A1 7/2014 Jung
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0262408 A1 9/2014 Woodard
2014/0263535 A1 9/2014 Rajani et al.
2014/0263541 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2014/0379000 A1 12/2014 Romo et al.
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0133957 A1 5/2015 Kostrzewski
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0202013 A1 7/2015 Teichtmann et al.
2015/0209045 A1 7/2015 Hodgkinson et al.

(56) References Cited

U.S. PATENT DOCUMENTS

| | | | |
|---|---|---|---|
| 2015/0216605 | A1 | 8/2015 | Baldwin |
| 2015/0222212 | A1 | 8/2015 | Iwata |
| 2015/0223868 | A1 | 8/2015 | Brandt et al. |
| 2015/0230697 | A1 | 8/2015 | Phee et al. |
| 2015/0230794 | A1 | 8/2015 | Wellman et al. |
| 2015/0230861 | A1 | 8/2015 | Woloszko et al. |
| 2015/0231409 | A1 | 8/2015 | Racenet et al. |
| 2015/0238118 | A1 | 8/2015 | Legassey et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272606 | A1 | 10/2015 | Nobis |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297824 | A1 | 10/2015 | Cabiri et al. |
| 2015/0303417 | A1 | 10/2015 | Koeder et al. |
| 2015/0305743 | A1 | 10/2015 | Casasanta et al. |
| 2015/0313594 | A1 | 11/2015 | Shelton, IV et al. |
| 2015/0324317 | A1 | 11/2015 | Collins et al. |
| 2015/0352699 | A1 | 12/2015 | Sakai et al. |
| 2015/0366585 | A1 | 12/2015 | Lemay et al. |
| 2015/0367497 | A1 | 12/2015 | Ito et al. |
| 2015/0372265 | A1 | 12/2015 | Morisaku et al. |
| 2015/0374372 | A1 | 12/2015 | Zergiebel et al. |
| 2015/0374378 | A1 | 12/2015 | Giordano et al. |
| 2016/0000437 | A1 | 1/2016 | Giordano et al. |
| 2016/0000452 | A1 | 1/2016 | Yates et al. |
| 2016/0029998 | A1 | 2/2016 | Brister et al. |
| 2016/0030042 | A1 | 2/2016 | Heinrich et al. |
| 2016/0030043 | A1 | 2/2016 | Fanelli et al. |
| 2016/0030076 | A1 | 2/2016 | Faller et al. |
| 2016/0034167 | A1 | 2/2016 | Wilson et al. |
| 2016/0047423 | A1 | 2/2016 | Bodtker |
| 2016/0051316 | A1 | 2/2016 | Boudreaux |
| 2016/0066913 | A1 | 3/2016 | Swayze et al. |
| 2016/0069449 | A1 | 3/2016 | Kanai et al. |
| 2016/0074035 | A1 | 3/2016 | Whitman et al. |
| 2016/0074040 | A1 | 3/2016 | Widenhouse et al. |
| 2016/0081678 | A1 | 3/2016 | Kappel et al. |
| 2016/0082161 | A1 | 3/2016 | Zilberman et al. |
| 2016/0089175 | A1 | 3/2016 | Hibner et al. |
| 2016/0099601 | A1 | 4/2016 | Leabman et al. |
| 2016/0100838 | A1 | 4/2016 | Beaupréet al. |
| 2016/0118201 | A1 | 4/2016 | Nicholas et al. |
| 2016/0132026 | A1 | 5/2016 | Wingardner et al. |
| 2016/0135835 | A1 | 5/2016 | Onuma |
| 2016/0135895 | A1 | 5/2016 | Faasse et al. |
| 2016/0139666 | A1 | 5/2016 | Rubin et al. |
| 2016/0174969 | A1 | 6/2016 | Kerr et al. |
| 2016/0174983 | A1 | 6/2016 | Shelton, IV et al. |
| 2016/0175021 | A1 | 6/2016 | Hassler, Jr. |
| 2016/0183939 | A1 | 6/2016 | Shelton, IV et al. |
| 2016/0183944 | A1 | 6/2016 | Swensgard et al. |
| 2016/0192927 | A1 | 7/2016 | Kostrzewski |
| 2016/0192960 | A1 | 7/2016 | Bueno et al. |
| 2016/0199063 | A1 | 7/2016 | Mandakolathur Vasudevan et al. |
| 2016/0199956 | A1 | 7/2016 | Shelton, IV et al. |
| 2016/0220150 | A1 | 8/2016 | Sharonov |
| 2016/0235494 | A1 | 8/2016 | Shelton, IV et al. |
| 2016/0242783 | A1 | 8/2016 | Shelton, IV et al. |
| 2016/0242855 | A1 | 8/2016 | Fichtinger et al. |
| 2016/0249910 | A1 | 9/2016 | Shelton, IV et al. |
| 2016/0249922 | A1 | 9/2016 | Morgan et al. |
| 2016/0249929 | A1 | 9/2016 | Cappola et al. |
| 2016/0256159 | A1 | 9/2016 | Pinjala et al. |
| 2016/0256184 | A1 | 9/2016 | Shelton, IV et al. |
| 2016/0256221 | A1 | 9/2016 | Smith |
| 2016/0256229 | A1 | 9/2016 | Morgan et al. |
| 2016/0262745 | A1 | 9/2016 | Morgan et al. |
| 2016/0262921 | A1 | 9/2016 | Balbierz et al. |
| 2016/0270781 | A1 | 9/2016 | Scirica |
| 2016/0287265 | A1 | 10/2016 | Macdonald et al. |
| 2016/0287279 | A1 | 10/2016 | Bovay et al. |
| 2016/0302820 | A1 | 10/2016 | Hibner et al. |
| 2016/0310143 | A1 | 10/2016 | Bettuchi |
| 2016/0314716 | A1 | 10/2016 | Grubbs |
| 2016/0314717 | A1 | 10/2016 | Grubbs |
| 2016/0345972 | A1 | 12/2016 | Beardsley et al. |
| 2016/0367122 | A1 | 12/2016 | Ichimura et al. |
| 2016/0374669 | A1 | 12/2016 | Overmyer et al. |
| 2016/0374716 | A1 | 12/2016 | Kessler |
| 2017/0000549 | A1 | 1/2017 | Gilbert et al. |
| 2017/0007234 | A1 | 1/2017 | Chin et al. |
| 2017/0007244 | A1 | 1/2017 | Shelton, IV et al. |
| 2017/0007245 | A1 | 1/2017 | Shelton, IV et al. |
| 2017/0007347 | A1 | 1/2017 | Jaworek et al. |
| 2017/0020616 | A1 | 1/2017 | Vale et al. |
| 2017/0035419 | A1 | 2/2017 | Decker et al. |
| 2017/0055819 | A1 | 3/2017 | Hansen et al. |
| 2017/0055980 | A1 | 3/2017 | Vendely et al. |
| 2017/0056008 | A1 | 3/2017 | Shelton, IV et al. |
| 2017/0056016 | A1 | 3/2017 | Barton et al. |
| 2017/0056018 | A1 | 3/2017 | Zeiner et al. |
| 2017/0066054 | A1 | 3/2017 | Birky |
| 2017/0079642 | A1 | 3/2017 | Overmyer et al. |
| 2017/0086829 | A1 | 3/2017 | Vendely et al. |
| 2017/0086830 | A1 | 3/2017 | Yates et al. |
| 2017/0086930 | A1 | 3/2017 | Thompson et al. |
| 2017/0086932 | A1 | 3/2017 | Auld et al. |
| 2017/0095252 | A1 | 4/2017 | Smith et al. |
| 2017/0095922 | A1 | 4/2017 | Licht et al. |
| 2017/0105727 | A1 | 4/2017 | Scheib et al. |
| 2017/0105733 | A1 | 4/2017 | Scheib et al. |
| 2017/0105786 | A1 | 4/2017 | Scheib et al. |
| 2017/0106302 | A1 | 4/2017 | Cummings et al. |
| 2017/0135711 | A1 | 5/2017 | Overmyer et al. |
| 2017/0135717 | A1 | 5/2017 | Boudreaux et al. |
| 2017/0135747 | A1 | 5/2017 | Broderick et al. |
| 2017/0143336 | A1 | 5/2017 | Shah et al. |
| 2017/0168187 | A1 | 6/2017 | Calderoni et al. |
| 2017/0172382 | A1 | 6/2017 | Nir et al. |
| 2017/0172549 | A1 | 6/2017 | Smaby et al. |
| 2017/0172662 | A1 | 6/2017 | Panescu et al. |
| 2017/0181803 | A1 | 6/2017 | Mayer-Ullmann et al. |
| 2017/0182195 | A1 | 6/2017 | Wagner |
| 2017/0182211 | A1 | 6/2017 | Raxworthy et al. |
| 2017/0196558 | A1 | 7/2017 | Morgan et al. |
| 2017/0196649 | A1 | 7/2017 | Yates et al. |
| 2017/0202605 | A1 | 7/2017 | Shelton, IV et al. |
| 2017/0202607 | A1 | 7/2017 | Shelton, IV et al. |
| 2017/0202770 | A1 | 7/2017 | Friedrich et al. |
| 2017/0224332 | A1 | 8/2017 | Hunter et al. |
| 2017/0224428 | A1 | 8/2017 | Kopp |
| 2017/0231628 | A1 | 8/2017 | Shelton, IV et al. |
| 2017/0231629 | A1 | 8/2017 | Stopek et al. |
| 2017/0238962 | A1 | 8/2017 | Hansen et al. |
| 2017/0238991 | A1 | 8/2017 | Worrell et al. |
| 2017/0242455 | A1 | 8/2017 | Dickens |
| 2017/0245880 | A1 | 8/2017 | Honda et al. |
| 2017/0245949 | A1 | 8/2017 | Randle |
| 2017/0249431 | A1 | 8/2017 | Shelton, IV et al. |
| 2017/0252060 | A1 | 9/2017 | Ellingson et al. |
| 2017/0255799 | A1 | 9/2017 | Zhao et al. |
| 2017/0258471 | A1 | 9/2017 | DiNardo et al. |
| 2017/0262110 | A1 | 9/2017 | Polishchuk et al. |
| 2017/0265774 | A1 | 9/2017 | Johnson et al. |
| 2017/0281186 | A1 | 10/2017 | Shelton, IV et al. |
| 2017/0296173 | A1 | 10/2017 | Shelton, IV et al. |
| 2017/0303984 | A1 | 10/2017 | Malackowski |
| 2017/0308665 | A1 | 10/2017 | Heck et al. |
| 2017/0312042 | A1 | 11/2017 | Giordano et al. |
| 2017/0319047 | A1 | 11/2017 | Poulsen et al. |
| 2017/0319201 | A1 | 11/2017 | Morgan et al. |
| 2017/0333034 | A1 | 11/2017 | Morgan et al. |
| 2017/0333035 | A1 | 11/2017 | Morgan et al. |
| 2017/0348010 | A1 | 12/2017 | Chiang |
| 2017/0348042 | A1 | 12/2017 | Drochner et al. |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |

(56) References Cited

U.S. PATENT DOCUMENTS

2018/0008265 A1 1/2018 Hatanaka et al.
2018/0036024 A1 2/2018 Allen, IV
2018/0036025 A1 2/2018 Drochner et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.
2018/0067004 A1 3/2018 Sgroi, Jr.
2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271526 A1 9/2018 Zammataro
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280026 A1 10/2018 Zhang et al.
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0310995 A1 11/2018 Gliner et al.
2018/0317905 A1 11/2018 Olson et al.
2018/0317915 A1 11/2018 Mcdonald, II
2018/0325514 A1 11/2018 Harris et al.
2018/0333169 A1 11/2018 Leimbach et al.
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000481 A1 1/2019 Harris et al.
2019/0000533 A1 1/2019 Messerly et al.
2019/0000535 A1 1/2019 Messerly et al.
2019/0000536 A1 1/2019 Yates et al.
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0038281 A1 2/2019 Shelton, IV et al.
2019/0038283 A1 2/2019 Shelton, IV et al.
2019/0038285 A1 2/2019 Mozdzierz
2019/0059890 A1 2/2019 Shelton, IV et al.
2019/0059891 A1 2/2019 Shelton, IV et al.
2019/0059984 A1 2/2019 Otrembiak et al.
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117220 A1 4/2019 Nativ et al.
2019/0117224 A1 4/2019 Setser et al.
2019/0117287 A1 4/2019 Nativ et al.
2019/0122840 A1 4/2019 Zergiebel et al.
2019/0125320 A1 5/2019 Shelton, IV et al.
2019/0125336 A1 5/2019 Deck et al.
2019/0125338 A1 5/2019 Shelton, IV et al.
2019/0125342 A1 5/2019 Beardsley et al.
2019/0125344 A1 5/2019 DiNardo et al.
2019/0125361 A1 5/2019 Shelton, IV et al.
2019/0125378 A1 5/2019 Shelton, IV et al.
2019/0125432 A1 5/2019 Shelton, IV et al.
2019/0125454 A1 5/2019 Stokes et al.
2019/0125476 A1 5/2019 Shelton, IV et al.
2019/0133422 A1 5/2019 Nakamura
2019/0133577 A1 5/2019 Weadock et al.
2019/0138770 A1 5/2019 Compaijen et al.
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183502 A1 6/2019 Shelton, IV et al.
2019/0192147 A1 6/2019 Shelton, IV et al.
2019/0192148 A1 6/2019 Shelton, IV et al.
2019/0192151 A1 6/2019 Shelton, IV et al.
2019/0192155 A1 6/2019 Shelton, IV et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.

(56) References Cited

U.S. PATENT DOCUMENTS

| | | | |
|---|---|---|---|
| 2019/0201034 | A1 | 7/2019 | Shelton, IV et al. |
| 2019/0201045 | A1 | 7/2019 | Yates et al. |
| 2019/0201079 | A1 | 7/2019 | Shelton, IV et al. |
| 2019/0201104 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201146 | A1 | 7/2019 | Shelton, IV et al. |
| 2019/0201158 | A1 | 7/2019 | Shelton, IV et al. |
| 2019/0201594 | A1 | 7/2019 | Shelton, IV et al. |
| 2019/0205567 | A1 | 7/2019 | Shelton, IV et al. |
| 2019/0206555 | A1 | 7/2019 | Morgan et al. |
| 2019/0206561 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0239873 | A1 | 8/2019 | Laurent et al. |
| 2019/0247048 | A1 | 8/2019 | Gasparovich et al. |
| 2019/0261982 | A1 | 8/2019 | Holsten |
| 2019/0261983 | A1 | 8/2019 | Granger et al. |
| 2019/0261984 | A1 | 8/2019 | Nelson et al. |
| 2019/0261987 | A1 | 8/2019 | Viola et al. |
| 2019/0262153 | A1 | 8/2019 | Tassoni et al. |
| 2019/0269400 | A1 | 9/2019 | Mandakolathur Vasudevan et al. |
| 2019/0269402 | A1 | 9/2019 | Murray et al. |
| 2019/0269428 | A1 | 9/2019 | Allen et al. |
| 2019/0274685 | A1 | 9/2019 | Olson et al. |
| 2019/0274716 | A1 | 9/2019 | Nott et al. |
| 2019/0282233 | A1 | 9/2019 | Burbank et al. |
| 2019/0290264 | A1 | 9/2019 | Morgan et al. |
| 2019/0290266 | A1 | 9/2019 | Scheib et al. |
| 2019/0290267 | A1 | 9/2019 | Baxter, III et al. |
| 2019/0290297 | A1 | 9/2019 | Haider et al. |
| 2019/0298353 | A1 | 10/2019 | Shelton, IV et al. |
| 2019/0298360 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0298381 | A1 | 10/2019 | Kreidler et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |
| 2019/0307456 | A1 | 10/2019 | Shelton, IV et al. |
| 2019/0314015 | A1 | 10/2019 | Shelton, IV et al. |
| 2019/0321062 | A1 | 10/2019 | Williams |
| 2019/0328387 | A1 | 10/2019 | Overmyer et al. |
| 2019/0388091 | A1 | 12/2019 | Eschbach et al. |
| 2020/0008802 | A1 | 1/2020 | Aronhalt et al. |
| 2020/0008809 | A1 | 1/2020 | Shelton, IV et al. |
| 2020/0008827 | A1 | 1/2020 | Dearden et al. |
| 2020/0015817 | A1 | 1/2020 | Harris et al. |
| 2020/0015836 | A1 | 1/2020 | Nicholas et al. |
| 2020/0015915 | A1 | 1/2020 | Swayze et al. |
| 2020/0030020 | A1 | 1/2020 | Wang et al. |
| 2020/0037939 | A1 | 2/2020 | Castagna et al. |
| 2020/0038016 | A1 | 2/2020 | Shelton, IV et al. |
| 2020/0038018 | A1 | 2/2020 | Shelton, IV et al. |
| 2020/0038021 | A1 | 2/2020 | Contini et al. |
| 2020/0046355 | A1 | 2/2020 | Harris et al. |
| 2020/0046356 | A1 | 2/2020 | Baxter et al. |
| 2020/0054320 | A1 | 2/2020 | Harris et al. |
| 2020/0054321 | A1 | 2/2020 | Harris et al. |
| 2020/0054329 | A1 | 2/2020 | Shelton, IV et al. |
| 2020/0054332 | A1 | 2/2020 | Shelton, IV et al. |
| 2020/0054333 | A1 | 2/2020 | Shelton, IV et al. |
| 2020/0054334 | A1 | 2/2020 | Shelton, IV et al. |
| 2020/0054355 | A1 | 2/2020 | Laurent et al. |
| 2020/0060523 | A1 | 2/2020 | Matsuda et al. |
| 2020/0060713 | A1 | 2/2020 | Leimbach et al. |
| 2020/0061385 | A1 | 2/2020 | Schwarz et al. |
| 2020/0085435 | A1 | 3/2020 | Shelton, IV et al. |
| 2020/0085518 | A1 | 3/2020 | Giordano et al. |
| 2020/0093484 | A1 | 3/2020 | Shelton, IV et al. |
| 2020/0093506 | A1 | 3/2020 | Leimbach et al. |
| 2020/0093550 | A1 | 3/2020 | Spivey et al. |
| 2020/0107829 | A1 | 4/2020 | Shelton, IV et al. |
| 2020/0113563 | A1 | 4/2020 | Gupta et al. |
| 2020/0114505 | A1 | 4/2020 | Kikuchi |
| 2020/0138507 | A1 | 5/2020 | Davison et al. |
| 2020/0138534 | A1 | 5/2020 | Garcia Kilroy et al. |
| 2020/0146166 | A1 | 5/2020 | Sgroi, Jr. |
| 2020/0146741 | A1 | 5/2020 | Long et al. |
| 2020/0187943 | A1 | 6/2020 | Shelton, IV et al. |
| 2020/0197027 | A1 | 6/2020 | Hershberger et al. |
| 2020/0205810 | A1 | 7/2020 | Posey et al. |
| 2020/0205811 | A1 | 7/2020 | Posey et al. |
| 2020/0205823 | A1 | 7/2020 | Vendely et al. |
| 2020/0214706 | A1 | 7/2020 | Vendely et al. |
| 2020/0214731 | A1 | 7/2020 | Shelton, IV et al. |
| 2020/0229814 | A1 | 7/2020 | Amariglio et al. |
| 2020/0237371 | A1 | 7/2020 | Huitema et al. |
| 2020/0268377 | A1 | 8/2020 | Schmid et al. |
| 2020/0268381 | A1 | 8/2020 | Roberts et al. |
| 2020/0275927 | A1 | 9/2020 | Shelton, IV et al. |
| 2020/0280219 | A1 | 9/2020 | Laughery et al. |
| 2020/0289112 | A1 | 9/2020 | Whitfield et al. |
| 2020/0289119 | A1 | 9/2020 | Viola et al. |
| 2020/0305863 | A1 | 10/2020 | Yates et al. |
| 2020/0305864 | A1 | 10/2020 | Yates et al. |
| 2020/0305872 | A1 | 10/2020 | Weidner et al. |
| 2020/0315623 | A1 | 10/2020 | Eisinger et al. |
| 2020/0323526 | A1 | 10/2020 | Huang et al. |
| 2020/0330181 | A1 | 10/2020 | Junger et al. |
| 2020/0337706 | A1 | 10/2020 | Truckai et al. |
| 2020/0337791 | A1 | 10/2020 | Shelton, IV et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345356 | A1 | 11/2020 | Leimbach et al. |
| 2020/0345357 | A1 | 11/2020 | Leimbach et al. |
| 2020/0345359 | A1 | 11/2020 | Baxter, III et al. |
| 2020/0345363 | A1 | 11/2020 | Shelton, IV et al. |
| 2020/0345435 | A1 | 11/2020 | Traina |
| 2020/0352562 | A1 | 11/2020 | Timm et al. |
| 2020/0352569 | A1 | 11/2020 | Viola et al. |
| 2020/0367886 | A1 | 11/2020 | Shelton, IV et al. |
| 2020/0375585 | A1 | 12/2020 | Swayze et al. |
| 2020/0375597 | A1 | 12/2020 | Shelton, IV et al. |
| 2020/0390444 | A1 | 12/2020 | Harris et al. |
| 2020/0397430 | A1 | 12/2020 | Patel et al. |
| 2020/0397439 | A1 | 12/2020 | Eisinger |
| 2020/0405292 | A1 | 12/2020 | Shelton, IV et al. |
| 2020/0405302 | A1 | 12/2020 | Shelton, IV et al. |
| 2020/0405304 | A1 | 12/2020 | Mozdzierz et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405375 | A1 | 12/2020 | Shelton, IV et al. |
| 2020/0405403 | A1 | 12/2020 | Shelton, IV et al. |
| 2020/0410177 | A1 | 12/2020 | Shelton, IV |
| 2021/0000466 | A1 | 1/2021 | Leimbach et al. |
| 2021/0000467 | A1 | 1/2021 | Shelton, IV et al. |
| 2021/0007742 | A1 | 1/2021 | Rector et al. |
| 2021/0007826 | A1 | 1/2021 | Shafer et al. |
| 2021/0015480 | A1 | 1/2021 | Shelton, IV et al. |
| 2021/0045742 | A1 | 2/2021 | Shelton, IV et al. |
| 2021/0052271 | A1 | 2/2021 | Harris et al. |
| 2021/0059661 | A1 | 3/2021 | Schmid et al. |
| 2021/0059662 | A1 | 3/2021 | Shelton, IV |
| 2021/0059664 | A1 | 3/2021 | Hensel et al. |
| 2021/0059670 | A1 | 3/2021 | Overmyer et al. |
| 2021/0059672 | A1 | 3/2021 | Giordano et al. |
| 2021/0059673 | A1 | 3/2021 | Shelton, IV et al. |
| 2021/0068829 | A1 | 3/2021 | Miller et al. |
| 2021/0068835 | A1 | 3/2021 | Shelton, IV et al. |
| 2021/0077099 | A1 | 3/2021 | Shelton, IV et al. |

(56) References Cited

U.S. PATENT DOCUMENTS

2021/0077109 A1 3/2021 Harris et al.
2021/0084700 A1 3/2021 Daniels
2021/0085313 A1 3/2021 Morgan et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.
2021/0093321 A1 4/2021 Auld et al.
2021/0093323 A1 4/2021 Scirica et al.
2021/0100541 A1 4/2021 Shelton, IV et al.
2021/0100982 A1 4/2021 Laby et al.
2021/0107031 A1 4/2021 Bales, Jr. et al.
2021/0121175 A1 4/2021 Yates et al.
2021/0128153 A1 5/2021 Sgroi
2021/0137522 A1 5/2021 Shelton, IV et al.
2021/0145441 A1 5/2021 Weir et al.
2021/0153866 A1 5/2021 Knapp et al.
2021/0177401 A1 6/2021 Abramek et al.
2021/0177411 A1 6/2021 Williams
2021/0177528 A1 6/2021 Cappelleri et al.
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0196265 A1 7/2021 Shelton, IV et al.
2021/0196269 A1 7/2021 Shelton, IV et al.
2021/0196270 A1 7/2021 Shelton, IV et al.
2021/0196425 A1 7/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212776 A1 7/2021 Schmitt et al.
2021/0225140 A1 7/2021 Adachi et al.
2021/0228209 A1 7/2021 Shelton, IV et al.
2021/0244407 A1 8/2021 Shelton, IV et al.
2021/0244411 A1 8/2021 Smith et al.
2021/0251720 A1 8/2021 Jhaveri et al.
2021/0259681 A1 8/2021 Shelton, IV et al.
2021/0259687 A1 8/2021 Gonzalez et al.
2021/0259790 A1 8/2021 Kaiser
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0282767 A1 9/2021 Shelton, IV et al.
2021/0282769 A1 9/2021 Baxter, III et al.
2021/0282776 A1 9/2021 Overmyer et al.
2021/0290226 A1 9/2021 Mandakolathur Vasudevan et al.
2021/0290231 A1 9/2021 Baxter et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0313975 A1 10/2021 Shan et al.
2021/0315566 A1 10/2021 Yates et al.
2021/0315570 A1 10/2021 Shelton, IV
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0346082 A1 11/2021 Adams et al.
2021/0353284 A1 11/2021 Yang et al.
2021/0369271 A1 12/2021 Schings et al.
2021/0378669 A1 12/2021 Shelton, IV et al.
2021/0393366 A1 12/2021 Shelton, IV et al.
2021/0401487 A1 12/2021 Apostolopoulos et al.
2021/0401513 A1 12/2021 Apostolopoulos et al.
2022/0000478 A1 1/2022 Shelton, IV et al.
2022/0000479 A1 1/2022 Shelton, IV et al.
2022/0015760 A1 1/2022 Beardsley et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061642 A1 3/2022 Park et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079595 A1 3/2022 Huitema et al.
2022/0079596 A1 3/2022 Huitema et al.
2022/0104695 A1 4/2022 Russell
2022/0104814 A1 4/2022 Shelton, IV et al.
2022/0104816 A1 4/2022 Fernandes et al.
2022/0104820 A1 4/2022 Shelton, IV et al.
2022/0110673 A1 4/2022 Boronyak et al.
2022/0117602 A1 4/2022 Wise et al.
2022/0125472 A1 4/2022 Beckman et al.
2022/0133299 A1 5/2022 Baxter, III
2022/0133300 A1 5/2022 Leimbach et al.
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133312 A1 5/2022 Huang
2022/0133318 A1 5/2022 Hudson et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160355 A1 5/2022 Harris et al.
2022/0160358 A1 5/2022 Wixey
2022/0167970 A1 6/2022 Aronhalt et al.
2022/0167972 A1 6/2022 Shelton, IV et al.
2022/0167973 A1 6/2022 Shelton, IV et al.
2022/0167977 A1 6/2022 Shelton, IV et al.
2022/0167979 A1 6/2022 Yates et al.
2022/0167981 A1 6/2022 Shelton, IV et al.
2022/0167982 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0183687 A1 6/2022 Wixey et al.

(56) References Cited

U.S. PATENT DOCUMENTS

| | | | |
|---|---|---|---|
| 2022/0202487 | A1 | 6/2022 | Shelton, IV et al. |
| 2022/0211367 | A1 | 7/2022 | Schmid et al. |
| 2022/0218332 | A1 | 7/2022 | Shelton, IV et al. |
| 2022/0218336 | A1 | 7/2022 | Timm et al. |
| 2022/0218338 | A1 | 7/2022 | Shelton, IV et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218347 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225986 | A1 | 7/2022 | Shelton, IV et al. |
| 2022/0225993 | A1 | 7/2022 | Huitema et al. |
| 2022/0225994 | A1 | 7/2022 | Setser et al. |
| 2022/0226013 | A1 | 7/2022 | Hall et al. |
| 2022/0233186 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0265272 | A1 | 8/2022 | Li et al. |
| 2022/0273293 | A1 | 9/2022 | Shelton, IV et al. |
| 2022/0273294 | A1 | 9/2022 | Creamer et al. |
| 2022/0273300 | A1 | 9/2022 | Shelton, IV et al. |
| 2022/0273303 | A1 | 9/2022 | Creamer et al. |
| 2022/0273304 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0346776 | A1 | 11/2022 | Aronhalt et al. |
| 2022/0346781 | A1 | 11/2022 | Shelton, IV et al. |
| 2022/0346783 | A1 | 11/2022 | Shelton, IV et al. |
| 2022/0346785 | A1 | 11/2022 | Aronhalt et al. |
| 2022/0354492 | A1 | 11/2022 | Baril |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |
| 2023/0016171 | A1 | 1/2023 | Yates et al. |
| 2023/0018950 | A1 | 1/2023 | Shelton, IV et al. |
| 2023/0055711 | A1 | 2/2023 | Chen et al. |
| 2023/0088531 | A1 | 3/2023 | Hall et al. |
| 2023/0094712 | A1 | 3/2023 | Shelton, IV et al. |
| 2023/0120983 | A1 | 4/2023 | Stokes et al. |
| 2023/0121131 | A1 | 4/2023 | Swayze et al. |
| 2023/0121658 | A1 | 4/2023 | Stokes et al. |
| 2023/0133811 | A1 | 5/2023 | Huang |
| 2023/0134883 | A1 | 5/2023 | Leimbach |
| 2023/0135070 | A1 | 5/2023 | Shelton, IV et al. |
| 2023/0135282 | A1 | 5/2023 | Schings et al. |
| 2023/0135811 | A1 | 5/2023 | Guest |
| 2023/0138314 | A1 | 5/2023 | Jenkins |
| 2023/0138743 | A1 | 5/2023 | Ross et al. |
| 2023/0165582 | A1 | 6/2023 | Harris et al. |
| 2023/0165584 | A1 | 6/2023 | Leimbach et al. |
| 2023/0172607 | A1 | 6/2023 | DiNardo et al. |
| 2023/0200831 | A1 | 6/2023 | Swensgard et al. |
| 2023/0210525 | A1 | 7/2023 | Shelton, IV et al. |
| 2023/0218296 | A1 | 7/2023 | Yates et al. |
| 2023/0240677 | A1 | 8/2023 | Ming et al. |
| 2023/0240678 | A1 | 8/2023 | Overmyer et al. |
| 2023/0255631 | A1 | 8/2023 | Vendely et al. |
| 2023/0270438 | A1 | 8/2023 | Jaworek et al. |
| 2023/0277175 | A1 | 9/2023 | Shelton, IV et al. |
| 2023/0285021 | A1 | 9/2023 | Shelton, IV |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2550059 | C | 8/2008 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |

(56) References Cited

FOREIGN PATENT DOCUMENTS

| | | | |
|---|---|---|---|
| CN | 101273908 | A | 10/2008 |
| CN | 101378791 | A | 3/2009 |
| CN | 101401736 | A | 4/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | L | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 104321021 | A | 1/2015 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |

(56) References Cited

FOREIGN PATENT DOCUMENTS

| | | | |
|---|---|---|---|
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |

(56) References Cited

FOREIGN PATENT DOCUMENTS

| | | | |
|---|---|---|---|
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |

(56) References Cited

FOREIGN PATENT DOCUMENTS

| | | | |
|---|---|---|---|
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |
| WO | WO-2022249091 | A1 | 12/2022 |
| WO | WO-2022249094 | A1 | 12/2022 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell- synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A

(56) References Cited

OTHER PUBLICATIONS

Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d9395 03e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications," Research Article*, Nov. 14, 2011, pp. 1-12, vol. 2012, Article ID 879294, Hindawi Publishing Corporation Pushing Pixels (GIF), published on dribble.com, 2013.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.

(56) References Cited

OTHER PUBLICATIONS

IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, November/Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

* cited by examiner

JAW OPEN

JAW CLOSED

STAPLES FORMING

COMPLETELY FORMED

LAYER OF MATERIAL FOR A SURGICAL END EFFECTOR

CROSS-REFERENCE TO RELATED APPLICATIONS

This application is a continuation application claiming priority under 35 U.S.C. § 120 to U.S. patent application Ser. No. 16/434,317, entitled LAYER OF MATERIAL FOR A SURGICAL END EFFECTOR, filed Jun. 7, 2019, which issued on Nov. 14, 2023 as U.S. Pat. No. 11,812,965, which is a continuation-in-part application claiming priority under U.S.C. § 120 to U.S. patent application Ser. No. 15/800,713, entitled LAYER OF MATERIAL FOR A SURGICAL END EFFECTOR, filed Nov. 1, 2017, which issued on Nov. 22, 2022 as U.S. Pat. No. 11,504,116, which is a continuation application claiming priority under U.S.C. § 120 to U.S. patent application Ser. No. 13/766,325, entitled LAYER OF MATERIAL FOR A SURGICAL END EFFECTOR, filed Feb. 13, 2013, now U.S. Patent Application Publication No. 2013/0256380, which is a continuation application claiming priority under 35 U.S.C. § 120 to U.S. patent application Ser. No. 13/433,129, entitled TISSUE THICKNESS COMPENSATOR COMPRISING A PLURALITY OF MEDICAMENTS, filed on Mar. 28, 2012, which issued on Dec. 15, 2015 as U.S. Pat. No. 9,211,120, the entire disclosures of which are hereby incorporated by reference herein.

This application is a continuation application claiming priority under 35 U.S.C. § 120 to U.S. patent application Ser. No. 16/434,317, entitled LAYER OF MATERIAL FOR A SURGICAL END EFFECTOR, filed Jun. 7, 2019, which issued on Nov. 14, 2023 as U.S. Pat. No. 11,812,965, which is a continuation-in-part application claiming priority under U.S.C. § 120 to U.S. patent application Ser. No. 16/188,107, entitled TISSUE THICKNESS COMPENSATOR COMPRISING CONTROLLED RELEASE AND EXPANSION, filed Nov. 12, 2018, which issued on Mar. 16, 2021 as U.S. Pat. No. 10,945,731, which is a continuation application claiming priority under 35 U.S.C. § 120 to U.S. patent application Ser. No. 13/433,141, entitled TISSUE THICKNESS COMPENSATOR COMPRISING CONTROLLED RELEASE AND EXPANSION, filed Mar. 28, 2012, which issued on Nov. 13, 2018 as U.S. Pat. No. 10,123,798, which is a continuation-in-part application claiming priority under 35 U.S.C. § 120 to U.S. patent application Ser. No. 13/097,891, entitled TISSUE THICKNESS COMPENSATOR FOR A SURGICAL STAPLER COMPRISING AN ADJUSTABLE ANVIL, filed Apr. 29, 2011, which issued on Oct. 21, 2014 as U.S. Pat. No. 8,864,009, which is a continuation-in-part application claiming priority under 35 U.S.C. § 120 to U.S. patent application Ser. No. 12/894,377, entitled SELECTIVELY ORIENTABLE IMPLANTABLE FASTENER CARTRIDGE, filed Sep. 30, 2010, which issued on Mar. 12, 2013 as U.S. Pat. No. 8,393,514, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 113 illustrates the retainer assembly of FIG. 110 being inserted into a surgical instrument comprising an anvil and a staple cartridge channel, wherein a portion of the insertion tool is removed for the purposes of illustration;

FIG. 114 illustrates the insertion tool of FIG. 105 being moved relative to the retainer to engage the staple cartridge in the staple cartridge channel and to engage the tissue thickness compensator with the anvil, wherein a portion of the insertion tool is removed for the purposes of illustration;

FIG. 115 illustrates the insertion tool of FIG. 105 being moved relative to the retainer to disengage the retainer from the tissue thickness compensator and from the staple cartridge, wherein a portion of the insertion tool is removed for the purposes of illustration;

FIG. 116 is a cross-sectional view of a tissue thickness compensator attached to an anvil of a surgical stapling instrument in accordance with at least one embodiment;

FIG. 117 is a diagram illustrating deformed staples at least partially capturing the tissue thickness compensator of FIG. 116 therein;

FIG. 118 is a cross-sectional view of an end effector of a surgical stapling instrument including a staple cartridge comprising a first tissue thickness compensator and an anvil comprising a second tissue thickness compensator in accordance with at least one embodiment;

FIG. 119 is a cross-sectional view of the end effector of FIG. 118 illustrating staples from the staple cartridge moved from an unfired position to a fired position;

FIG. 120 is a perspective view of a tissue thickness compensator attached to an anvil of an end effector wherein the tissue thickness compensator comprises a plurality of capsules in accordance with at least one embodiment;

FIG. 120A is a partial perspective view of the tissue thickness compensator of FIG. 120;

FIG. 121 is a cross-sectional view of staples being moved from an unfired position to a fired position to puncture the capsules of the tissue thickness compensator of FIG. 120;

FIG. 122 is an exploded view of an anvil and a tissue thickness compensator in accordance with at least one embodiment;

FIG. 123 is a cross-sectional view of an anvil comprising a plurality of staple forming pockets and a tissue thickness compensator comprising a plurality of capsules aligned with the forming pockets in accordance with at least one embodiment;

Figure 123:
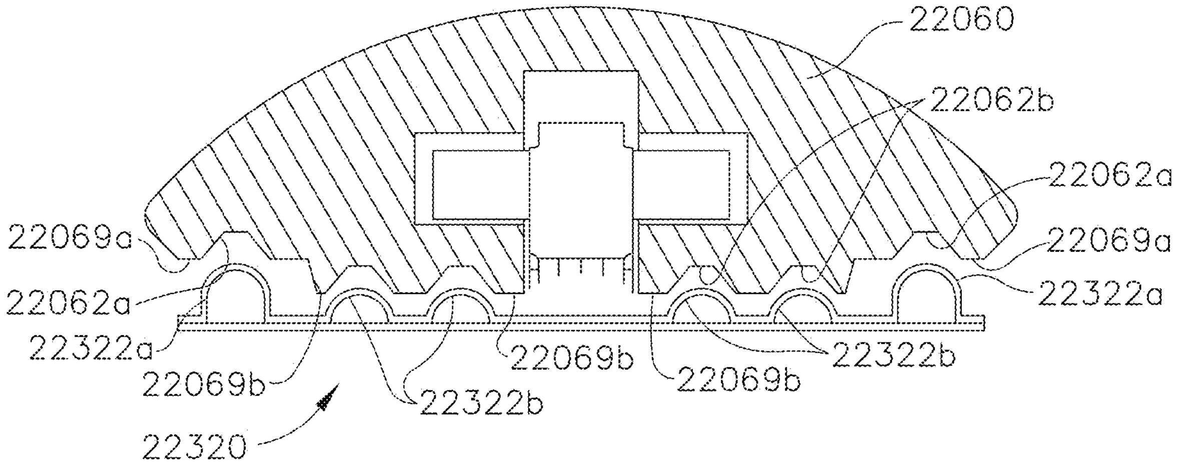
Figure 124:
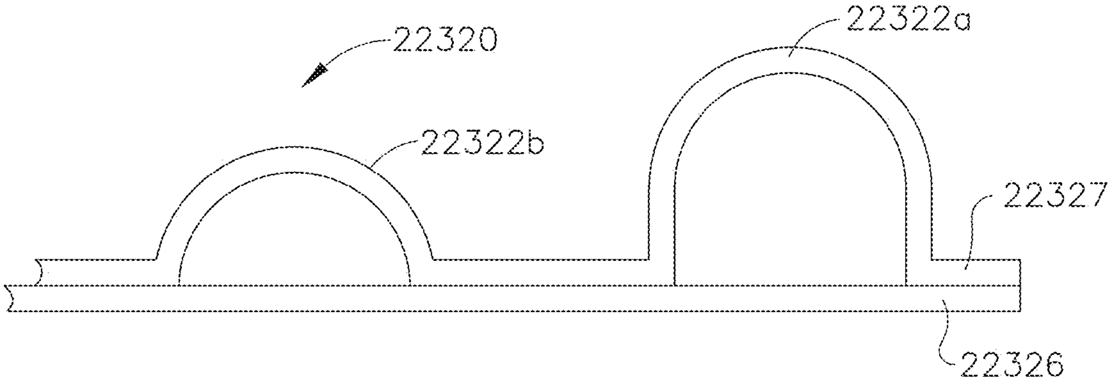
Figure 125:
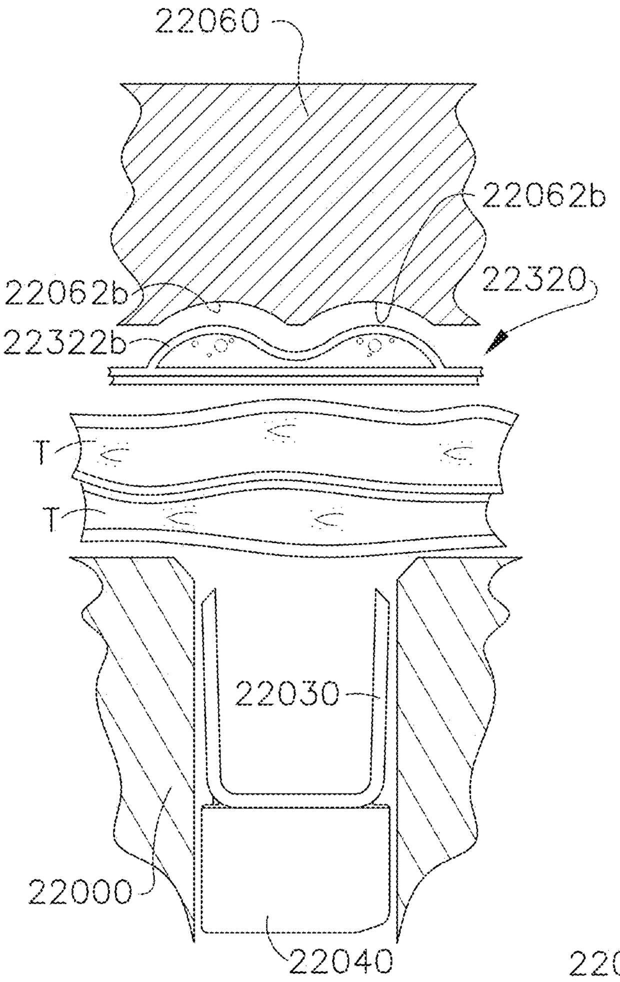
Figure 126:
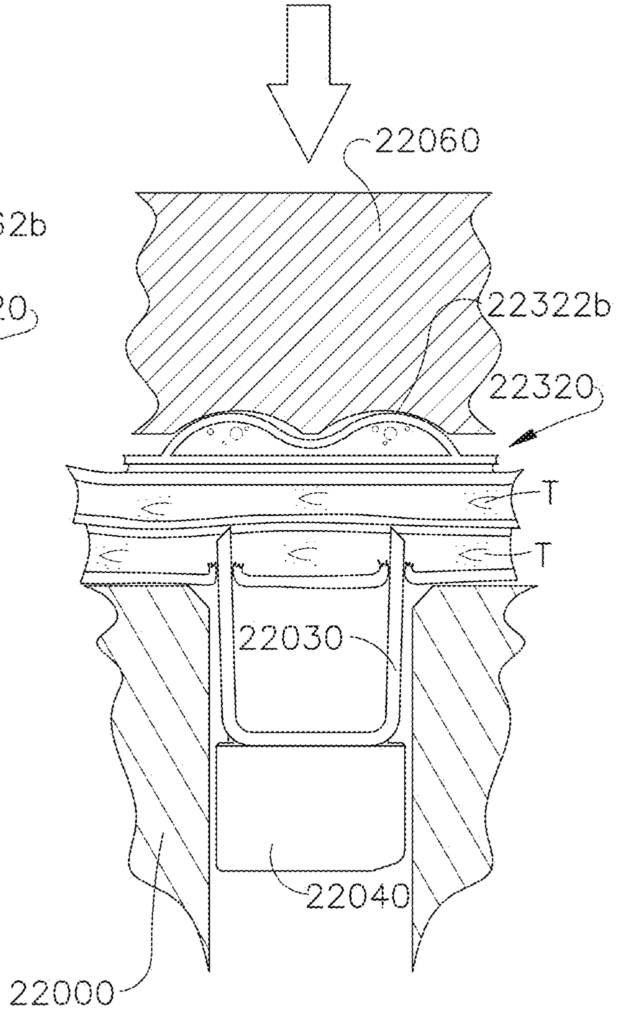
Figure 127:
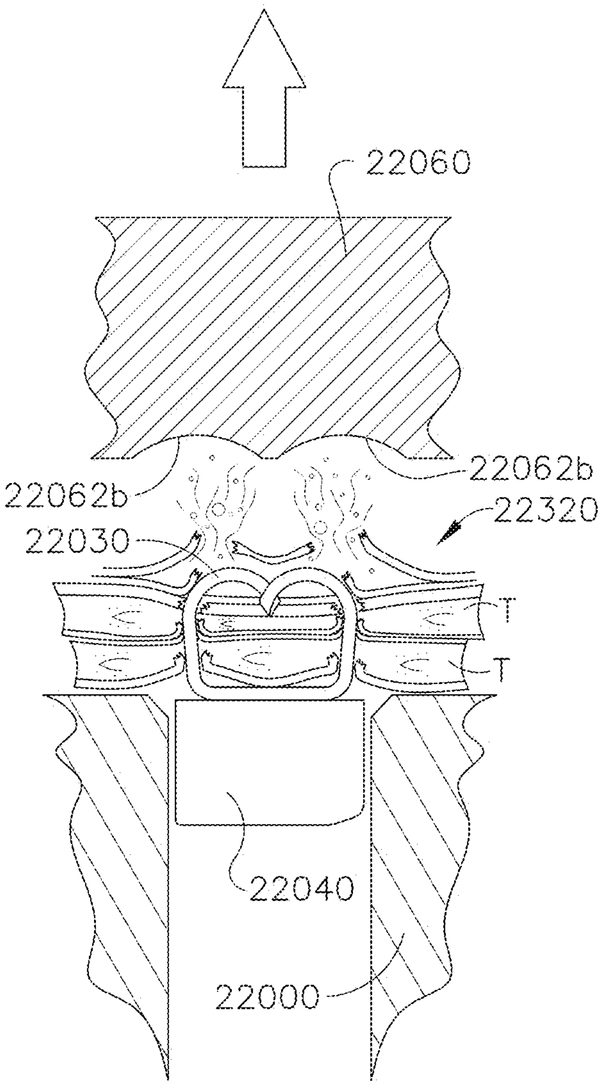
Figure 128:
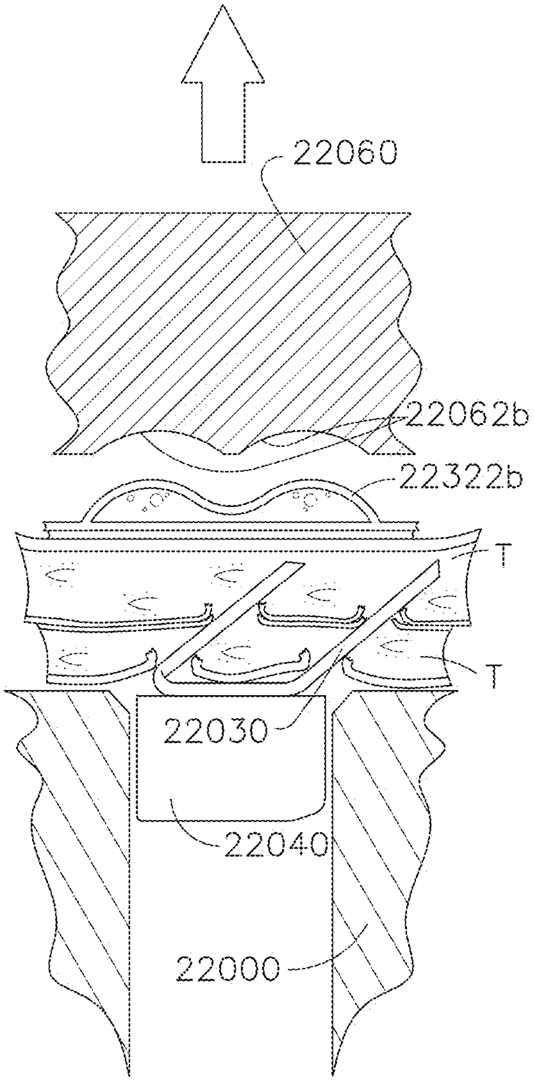
Figure 129:
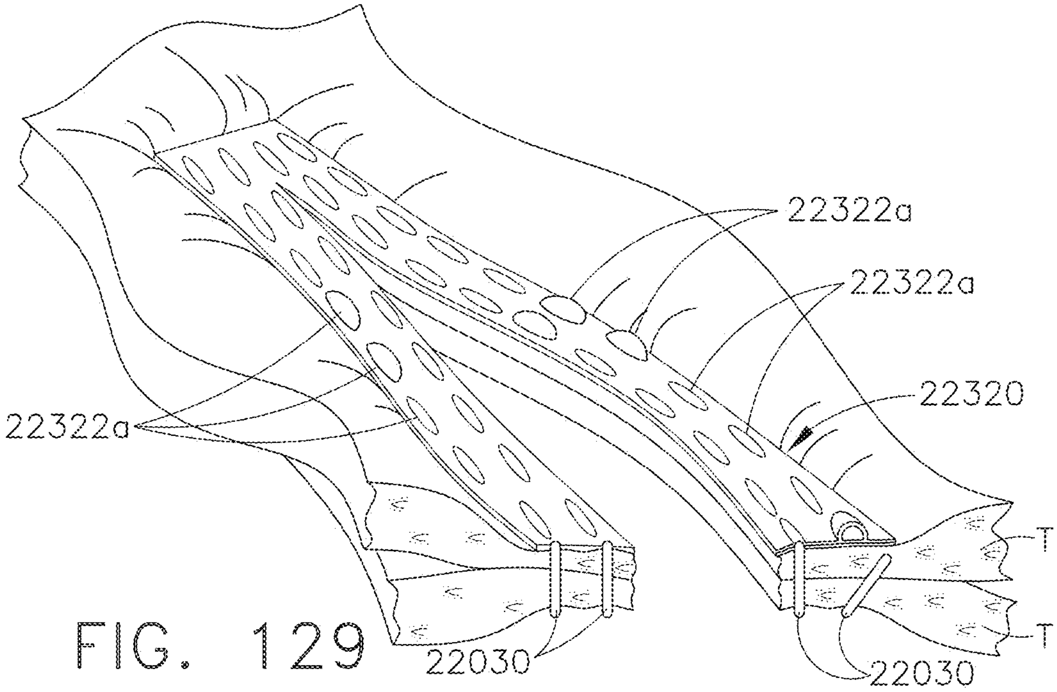
Figure 130:
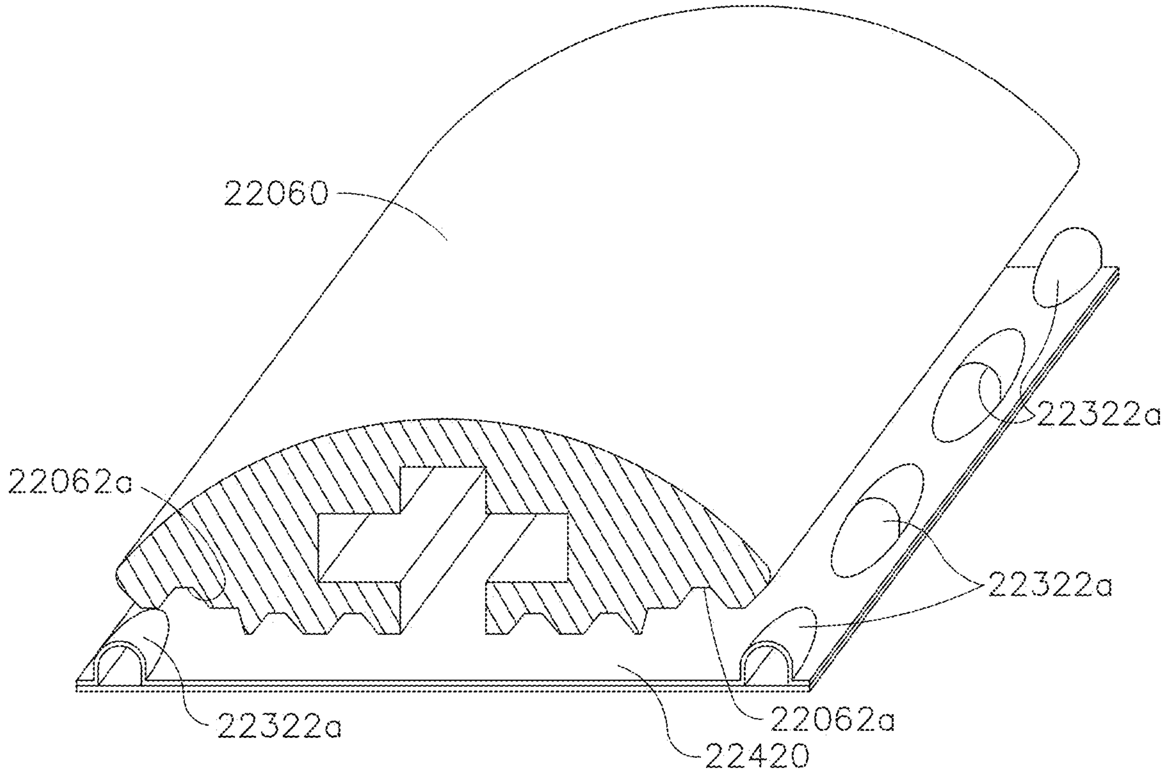
Figure 131:
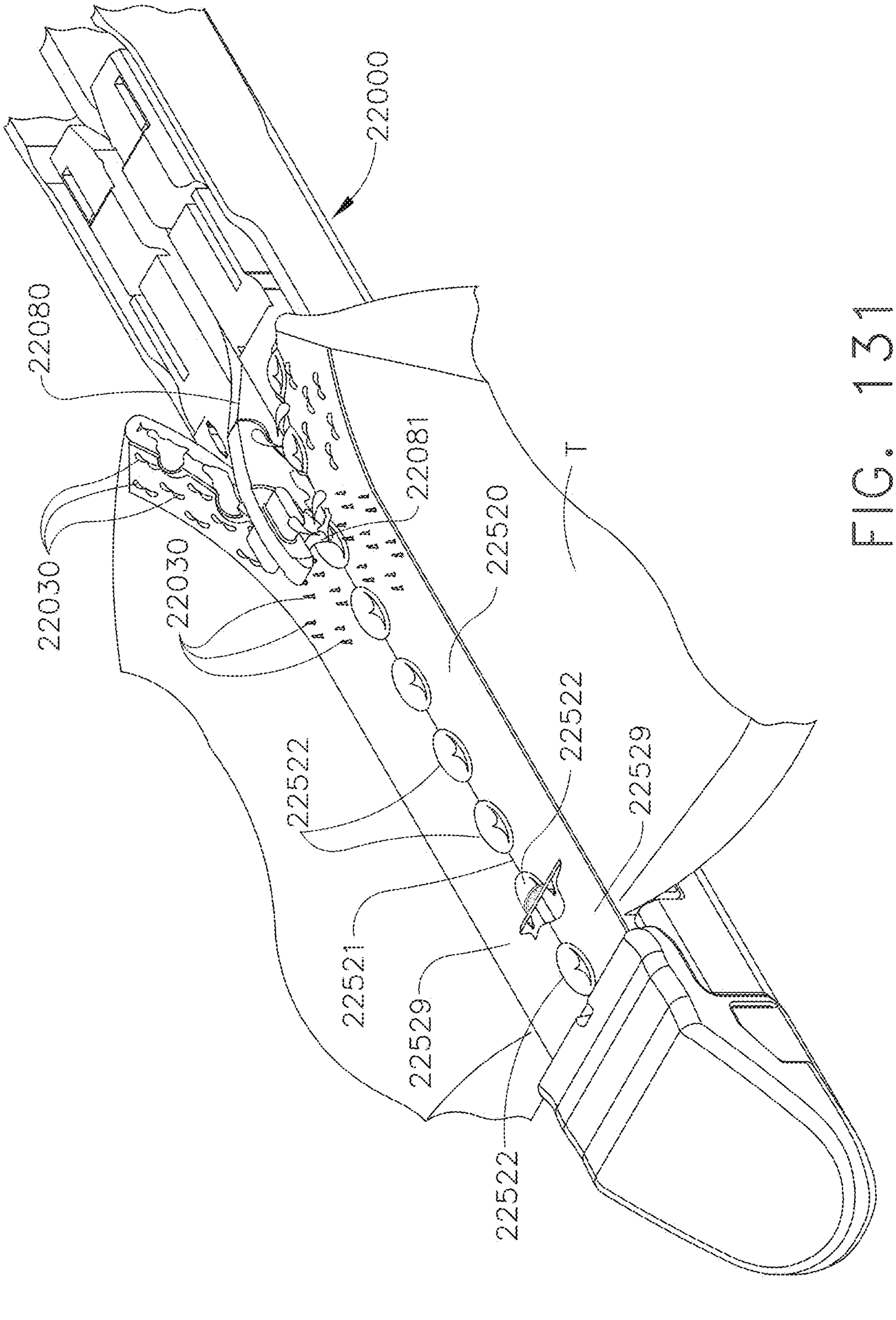
Figure 132:
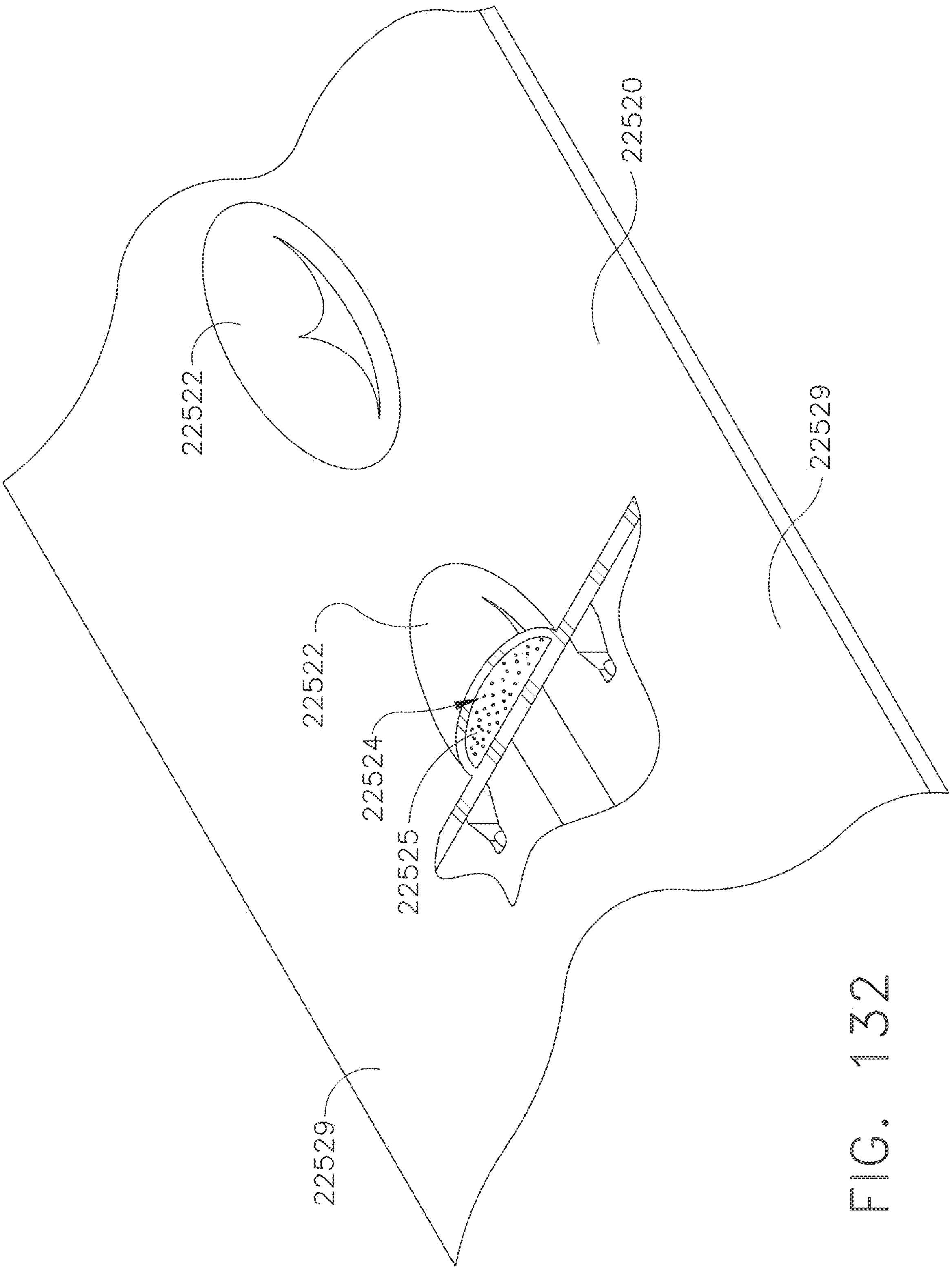
Figure 133:
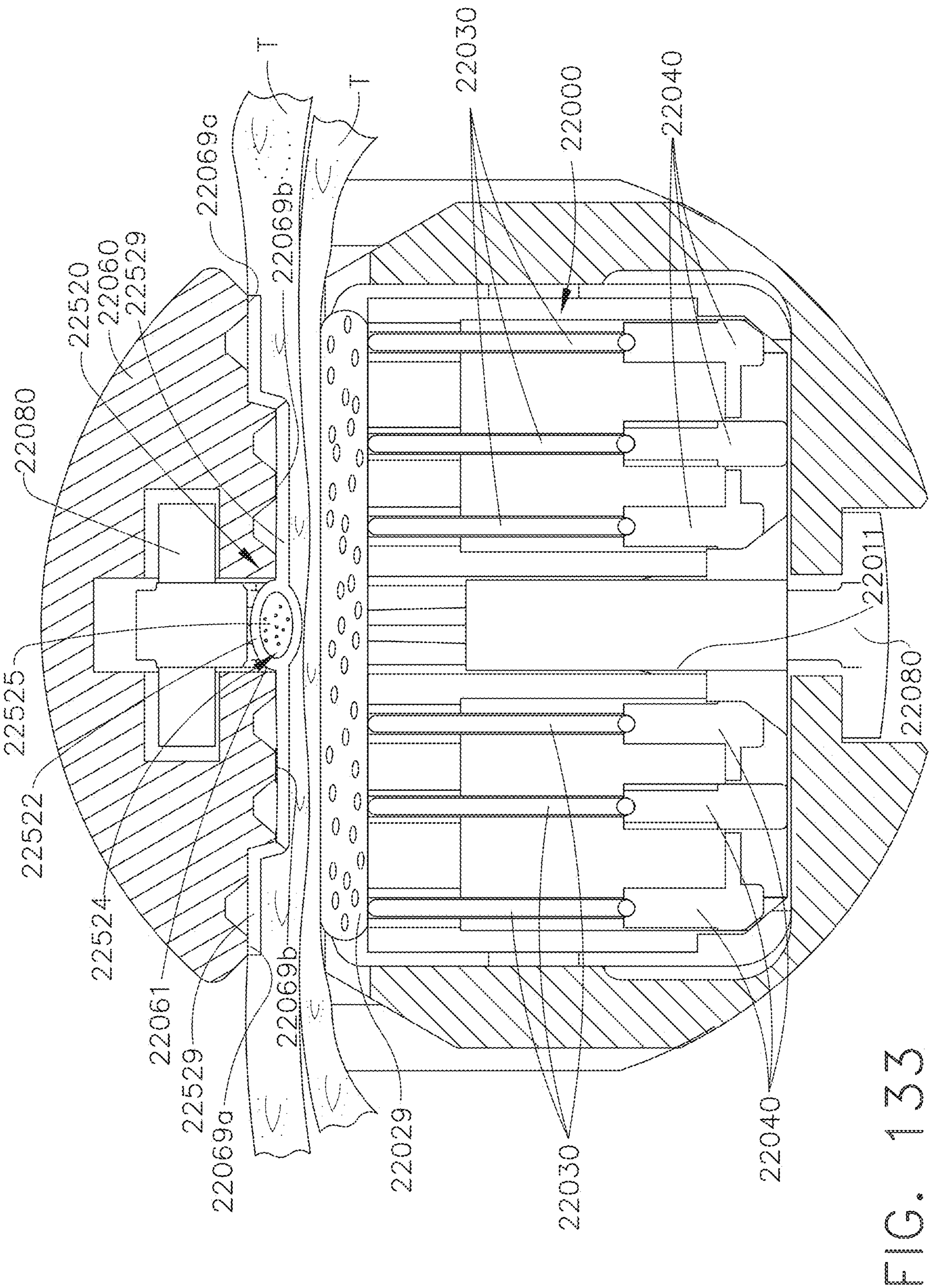
Figure 134:
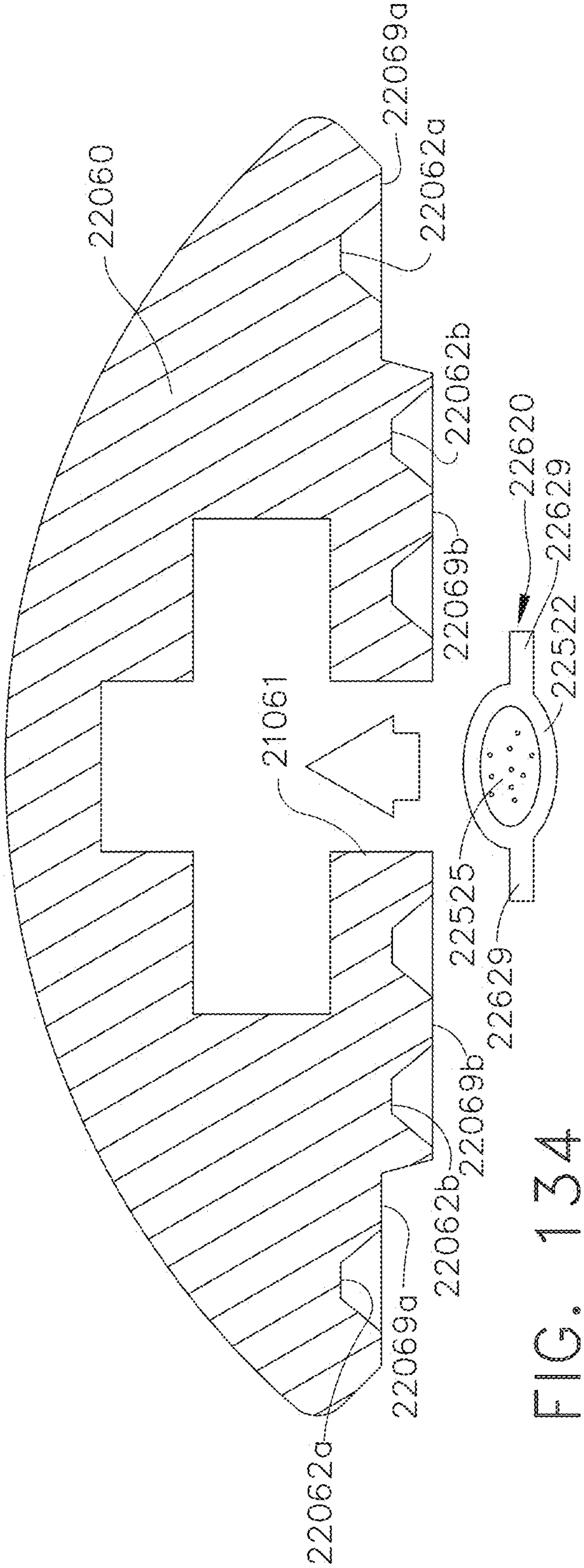
Figure 135:
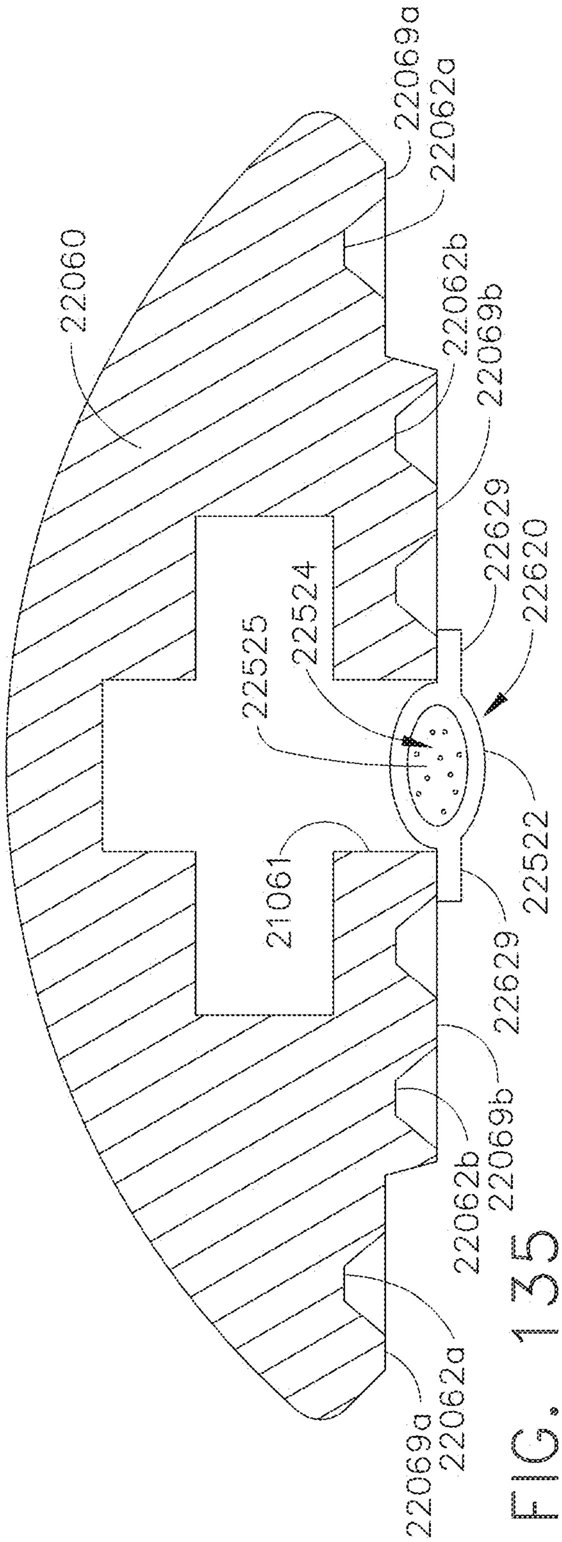
Figure 136:
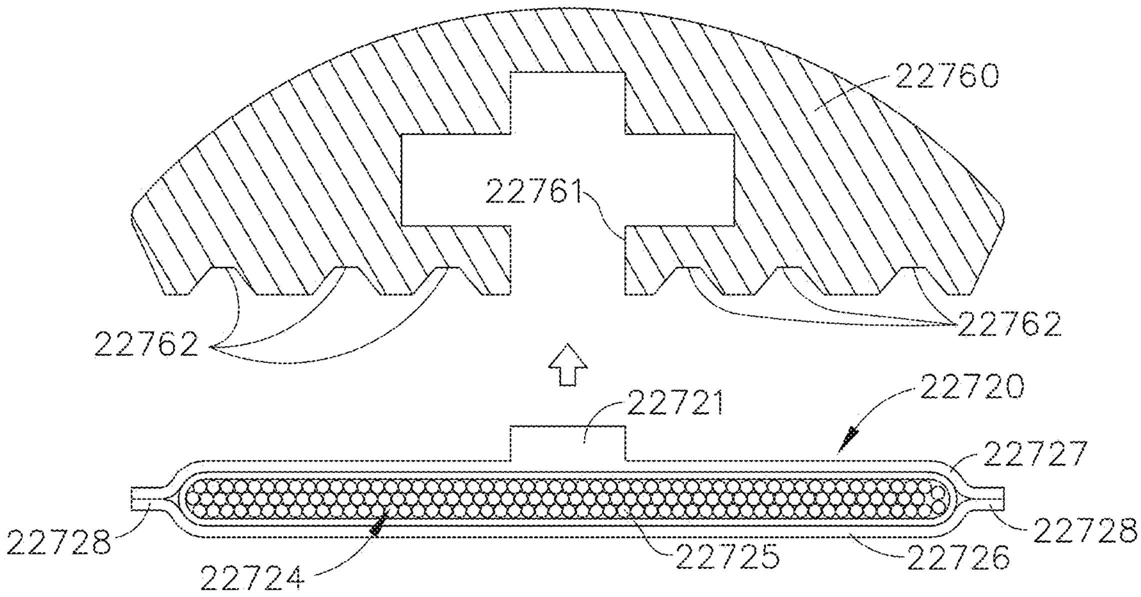
Figure 137:
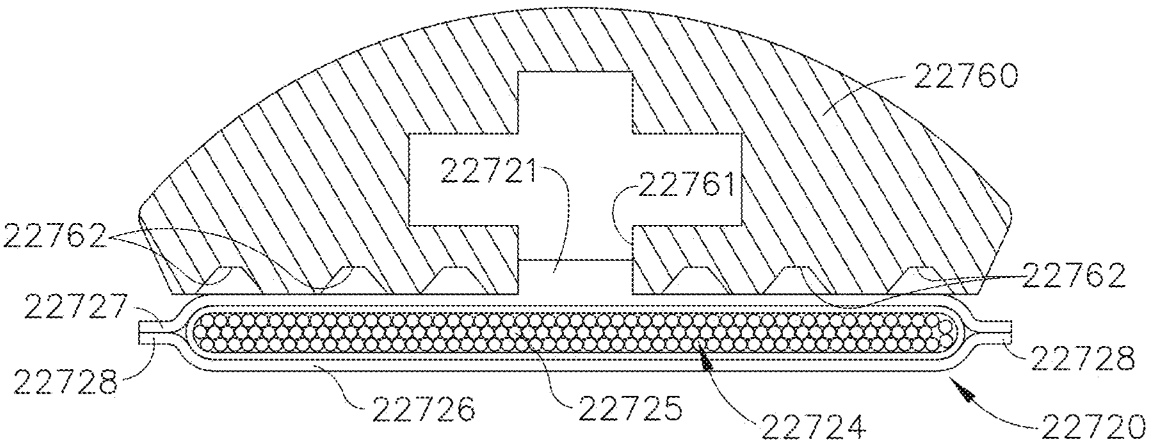
Figure 138:
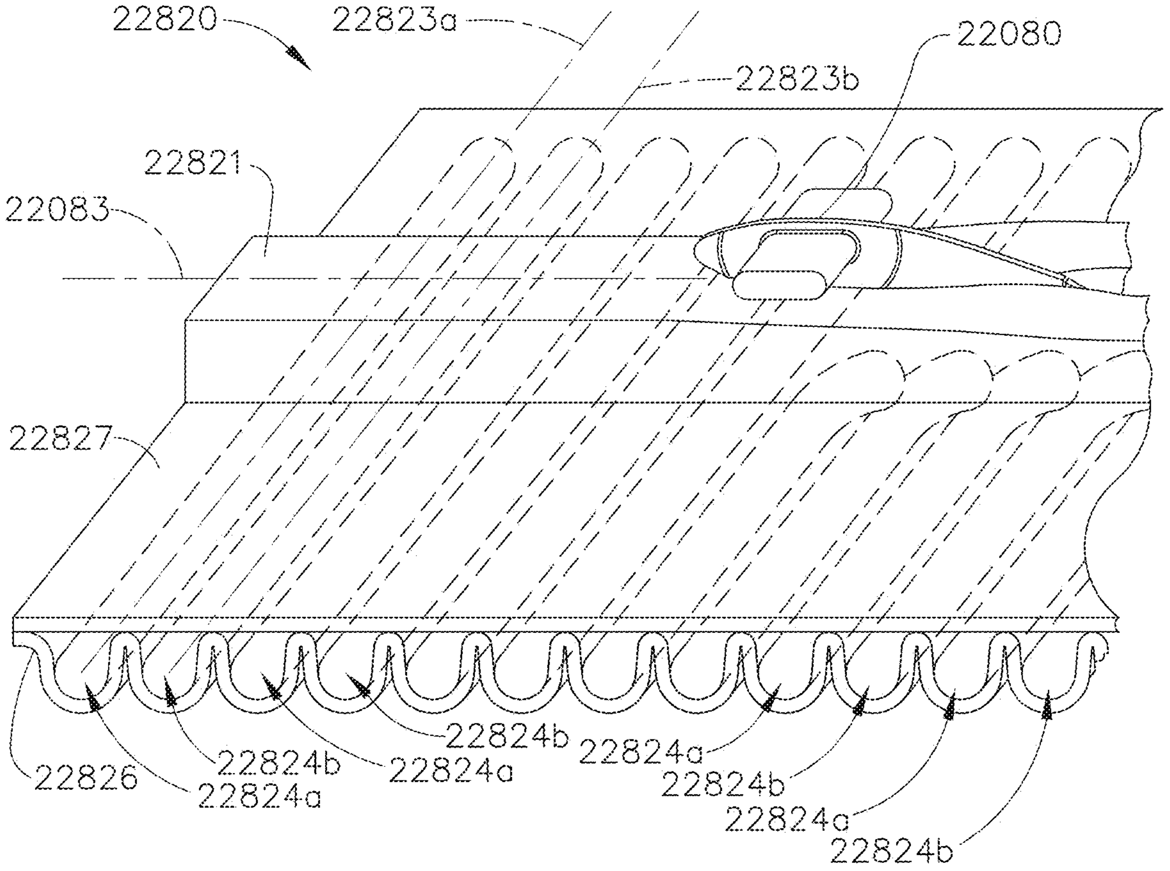
Figure 139:
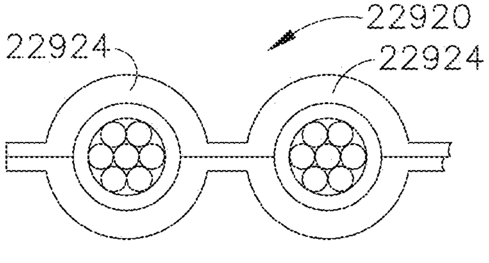
Figure 140:
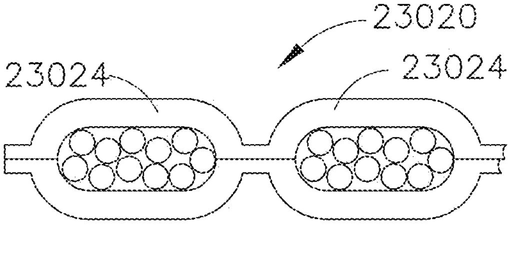
Figure 141:
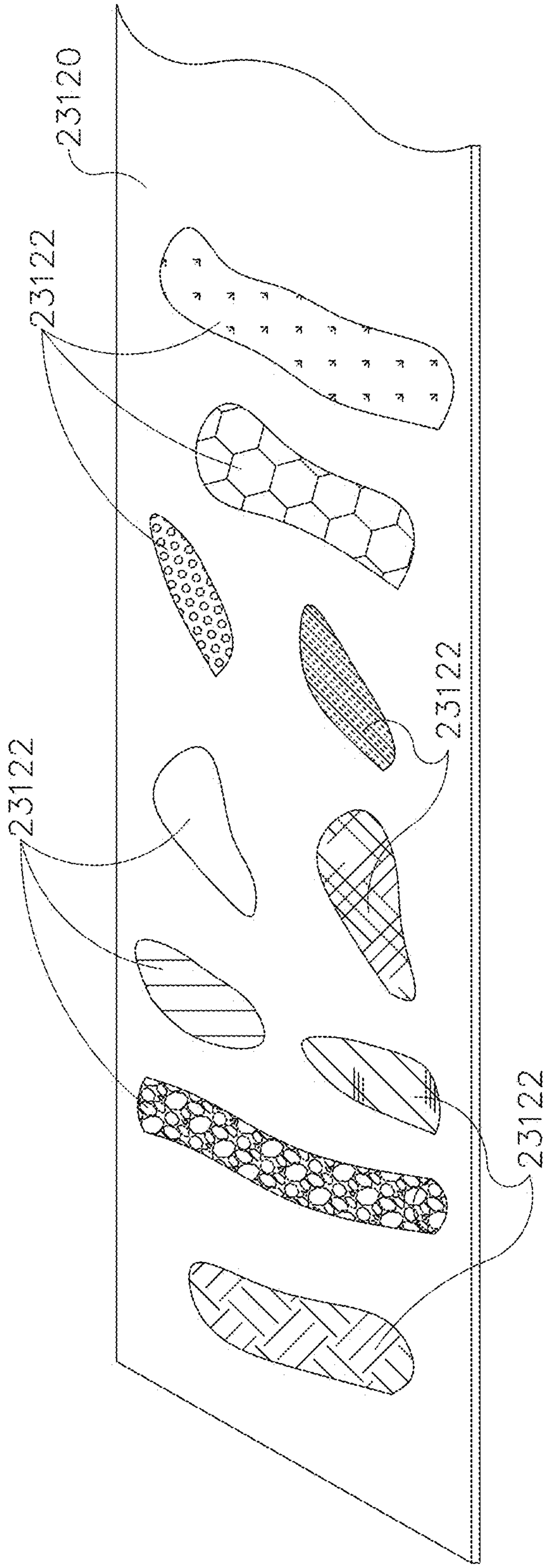
Figure 142:
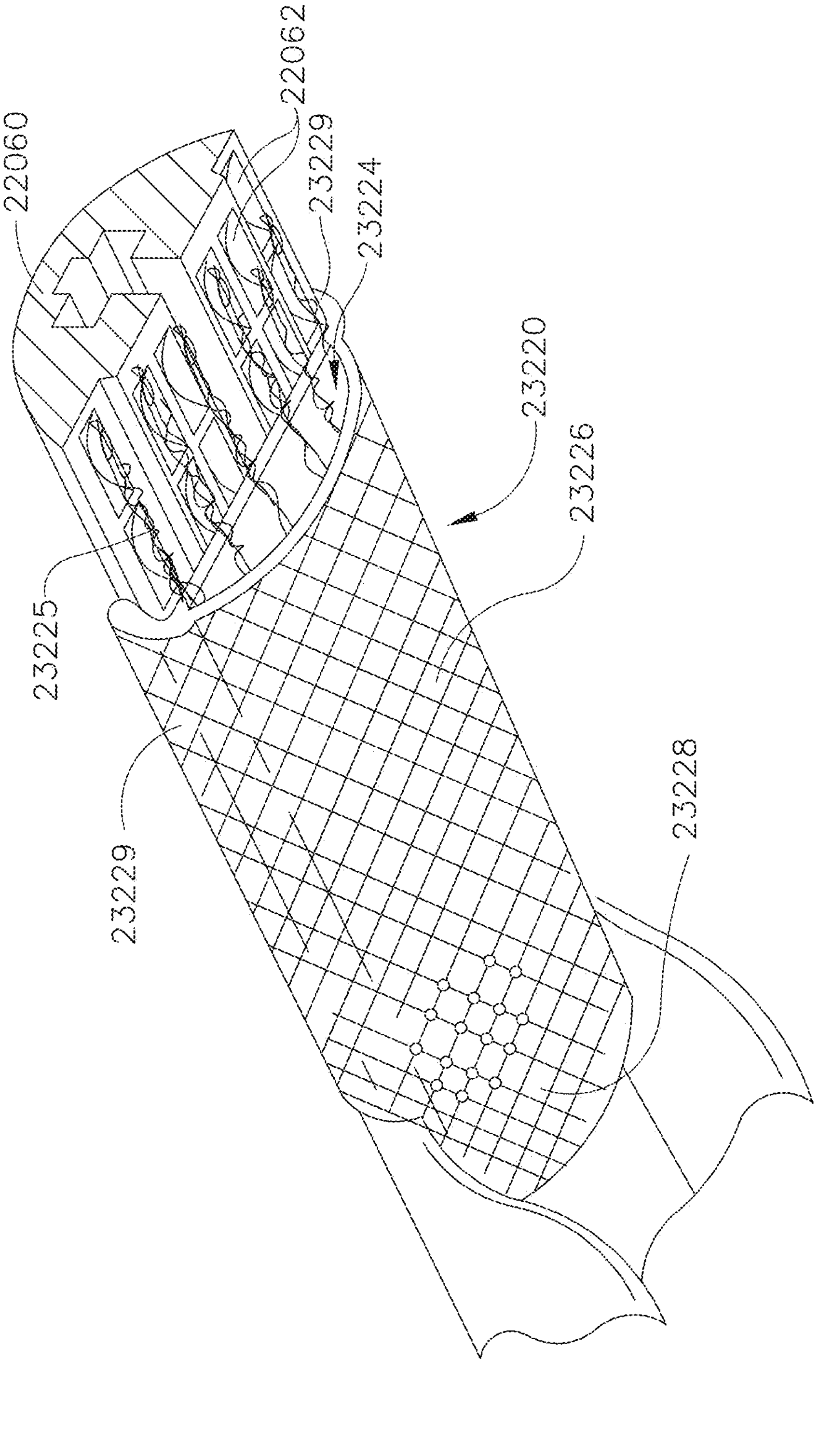
Figure 143:
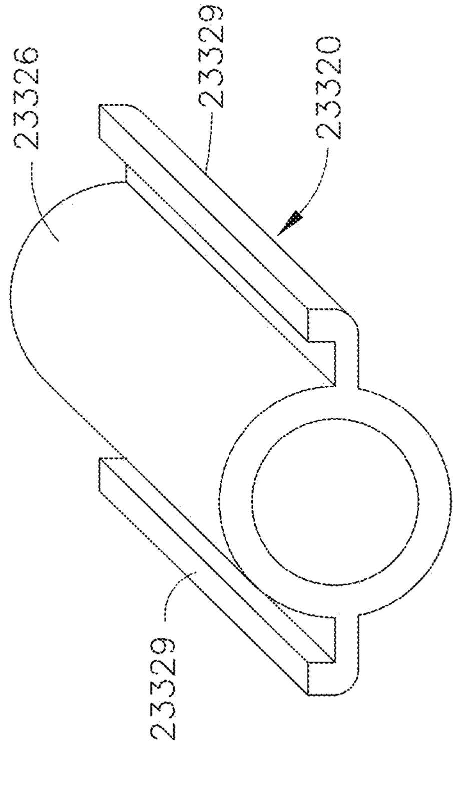
Figure 144:
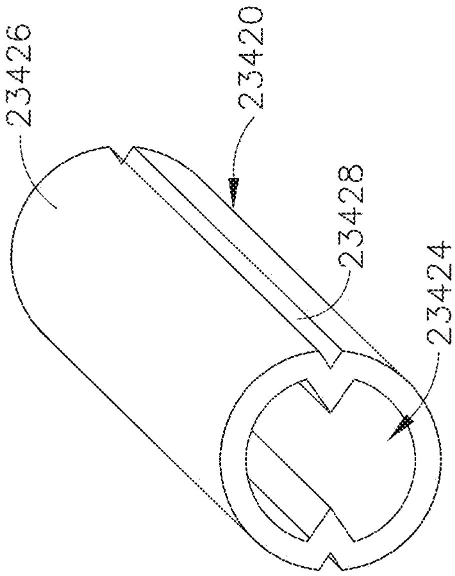
Figure 145:
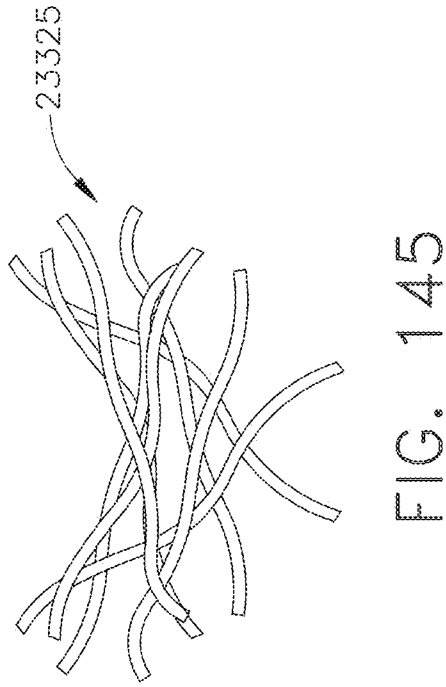
Figure 146:
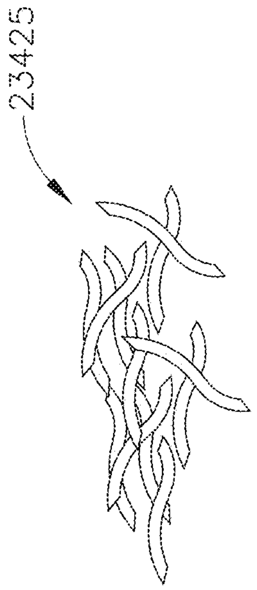
Figure 147:
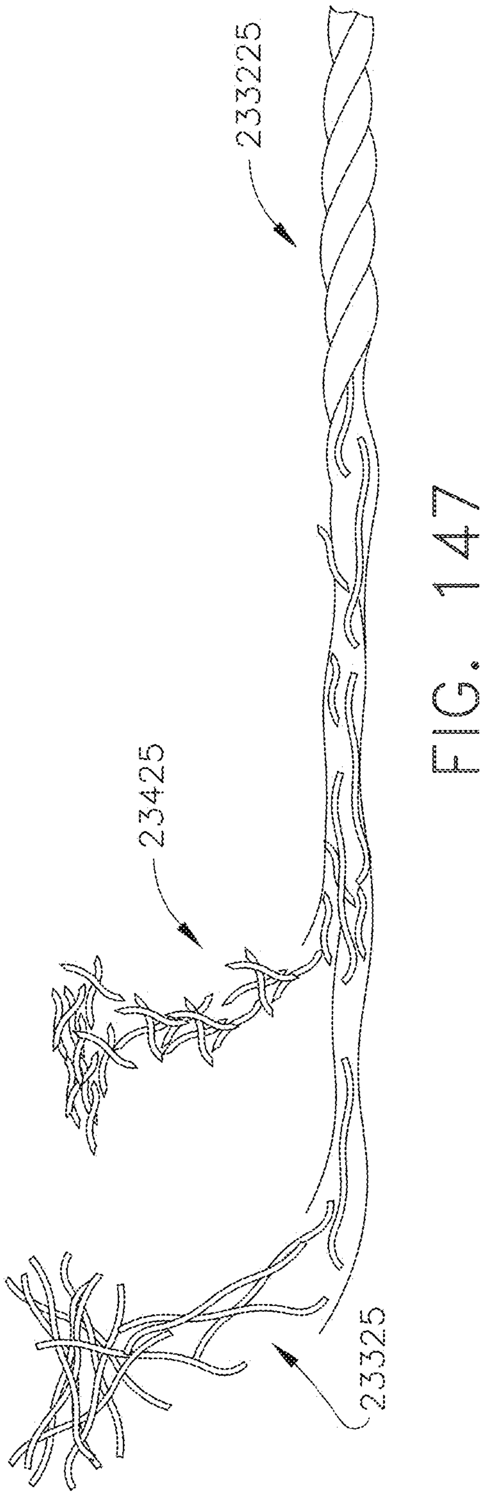
Figure 148:
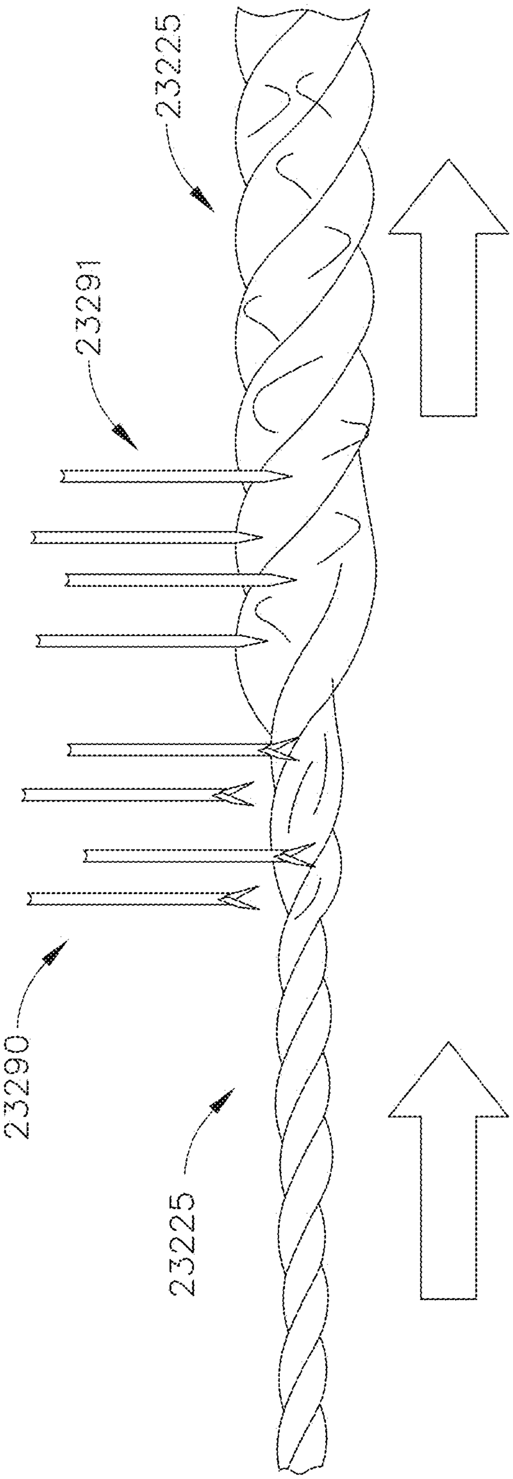
Figures 149, 150, 151:
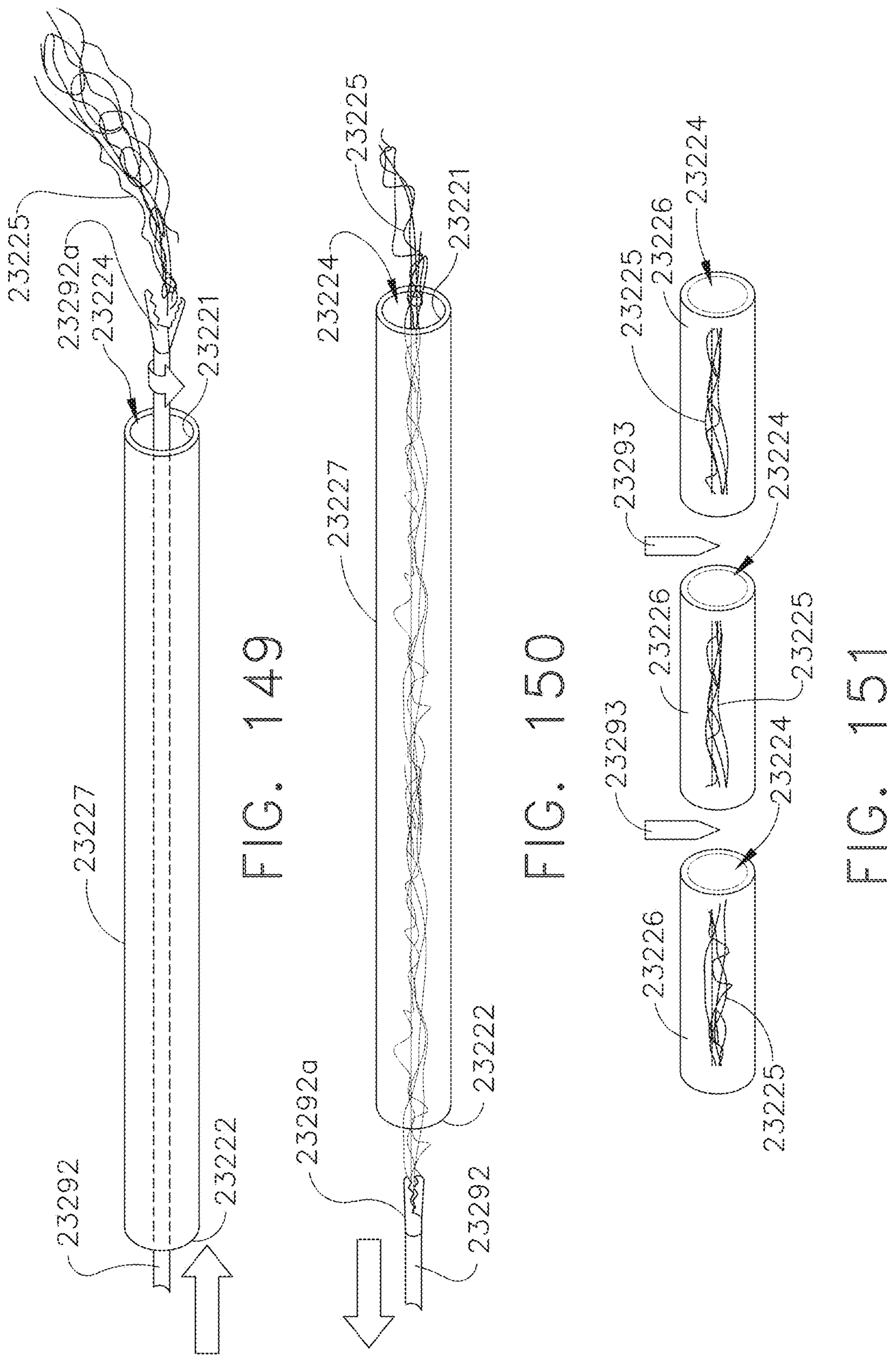
Figure 152:
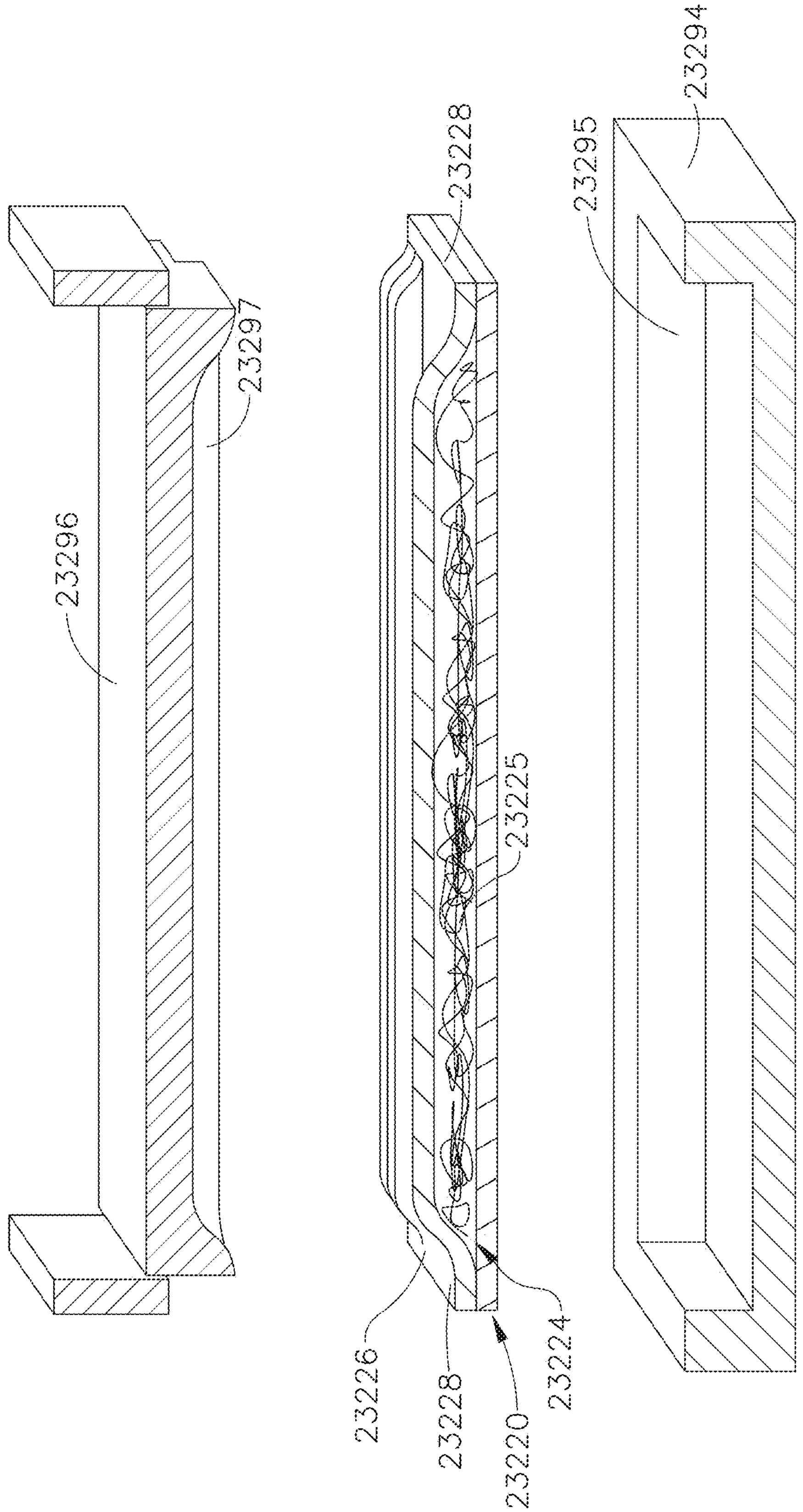
Figure 153:
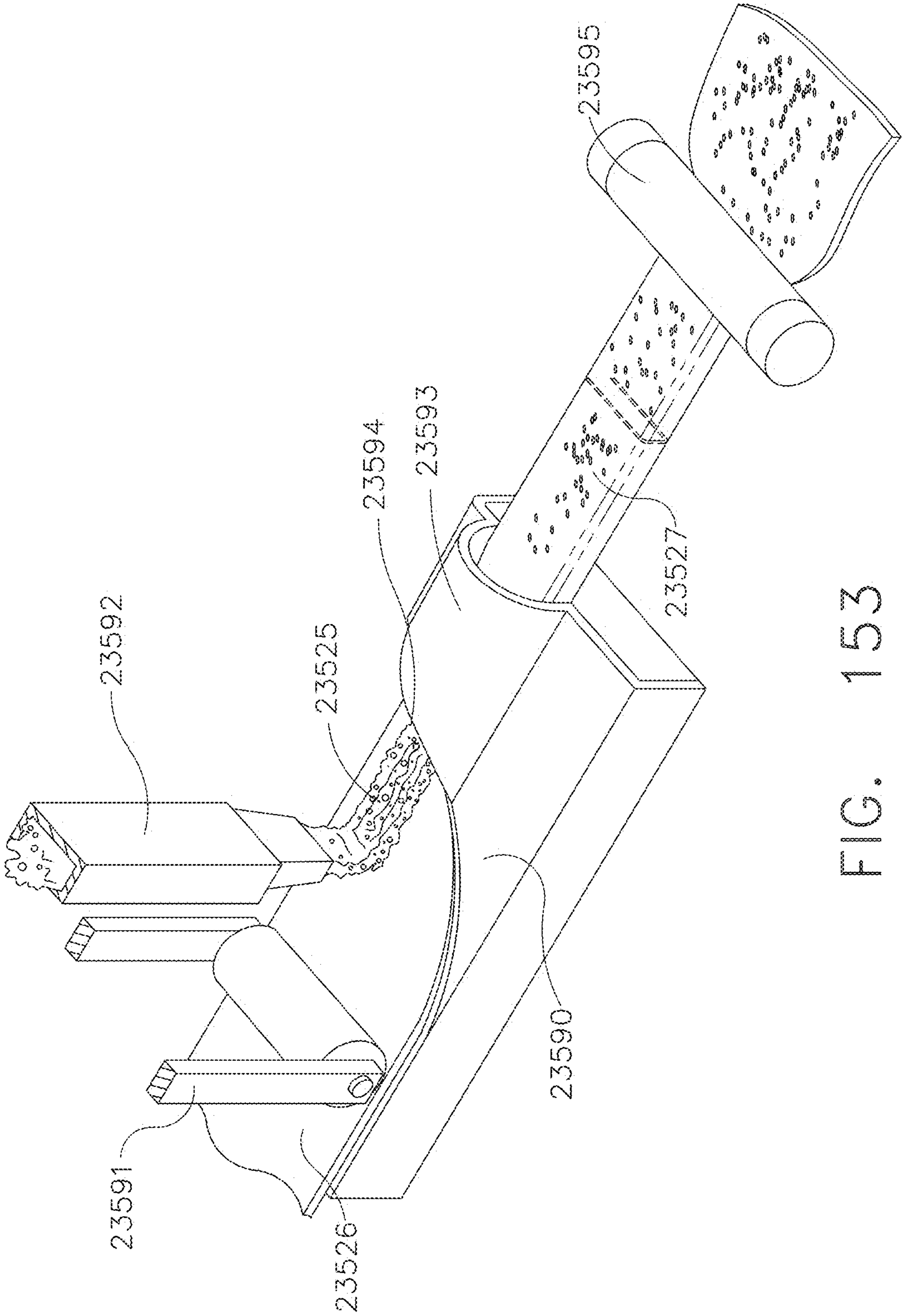
Figure 154:
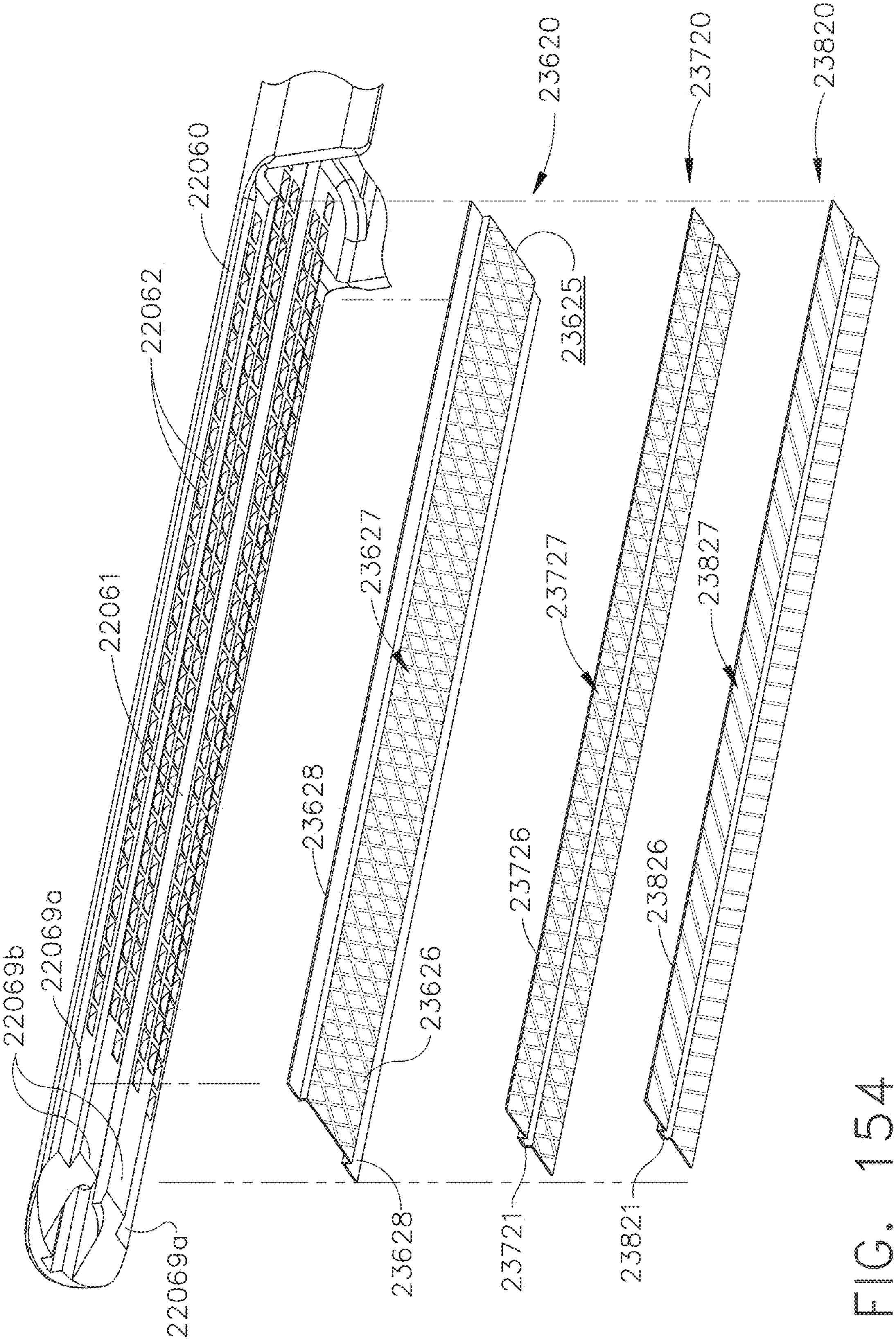
Figure 155:
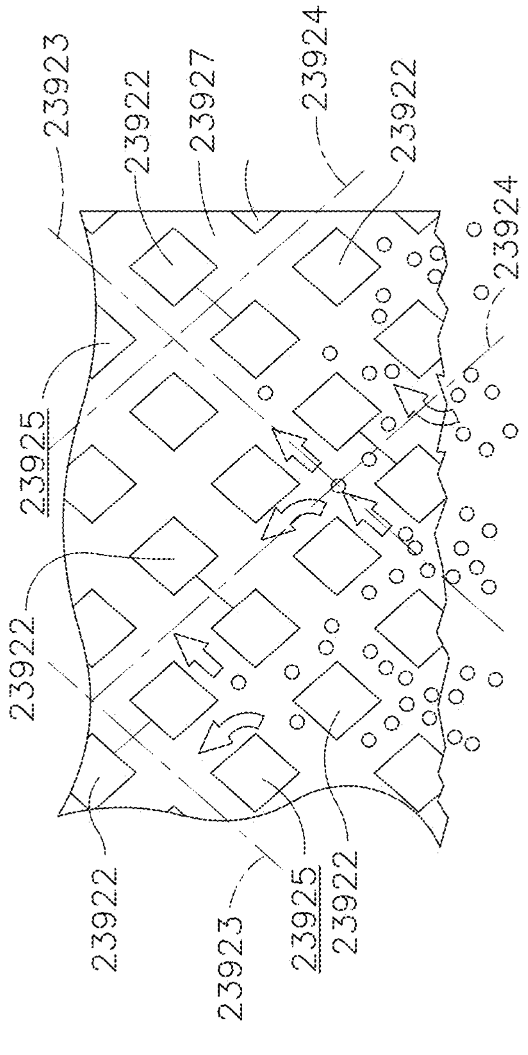
Figure 156:
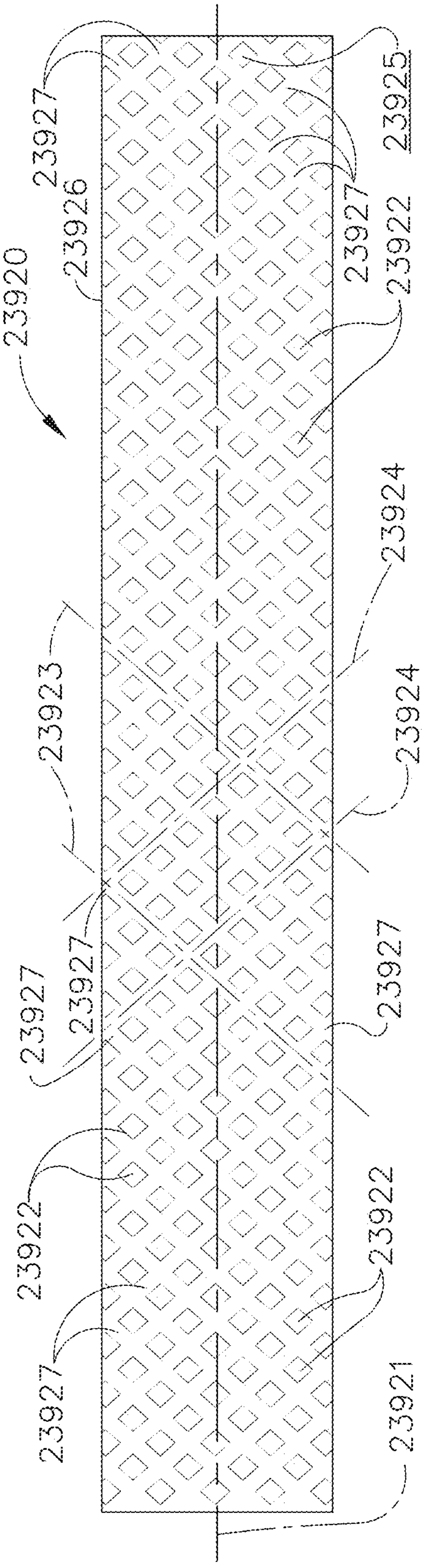
Figure 157:
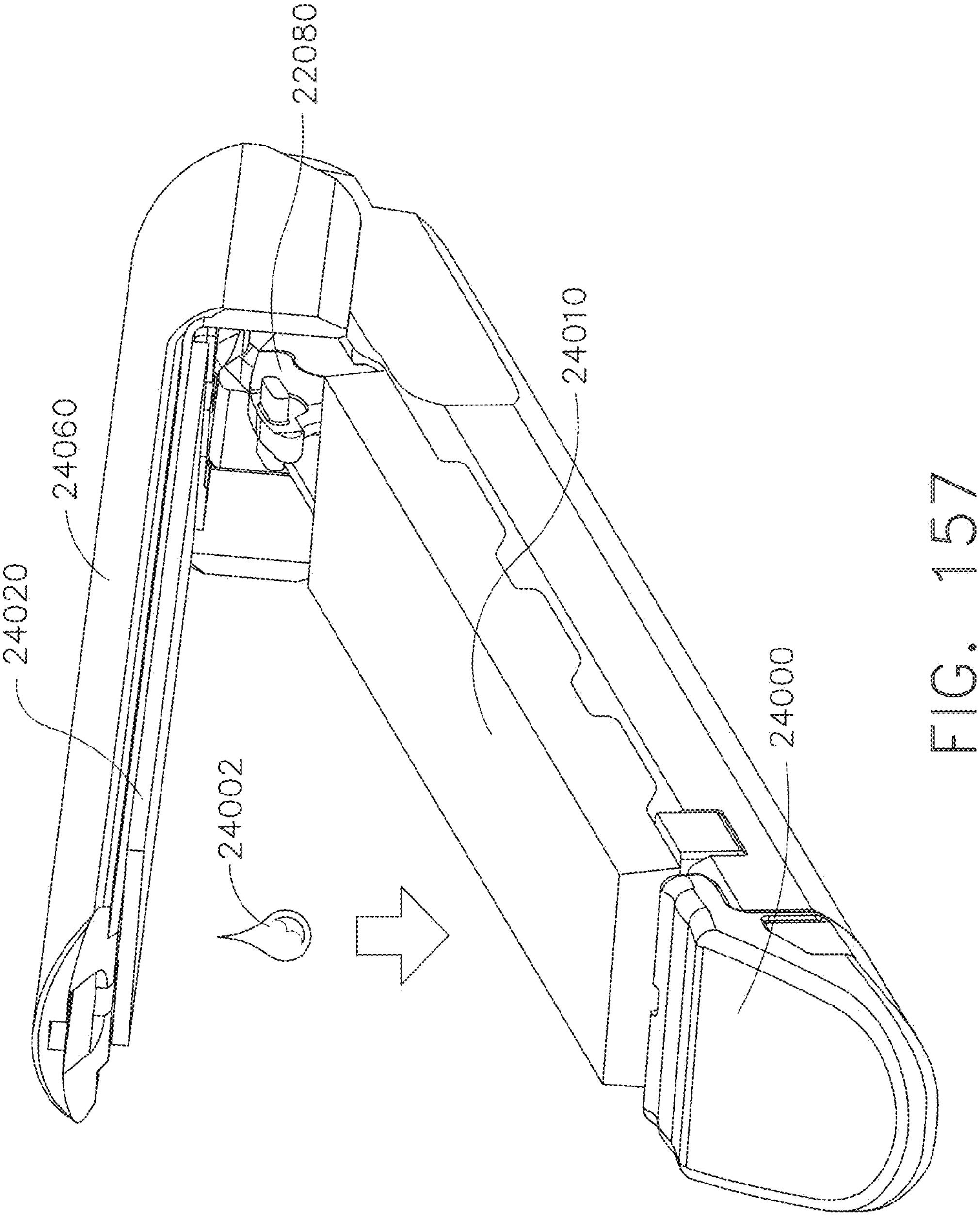
Figure 158:
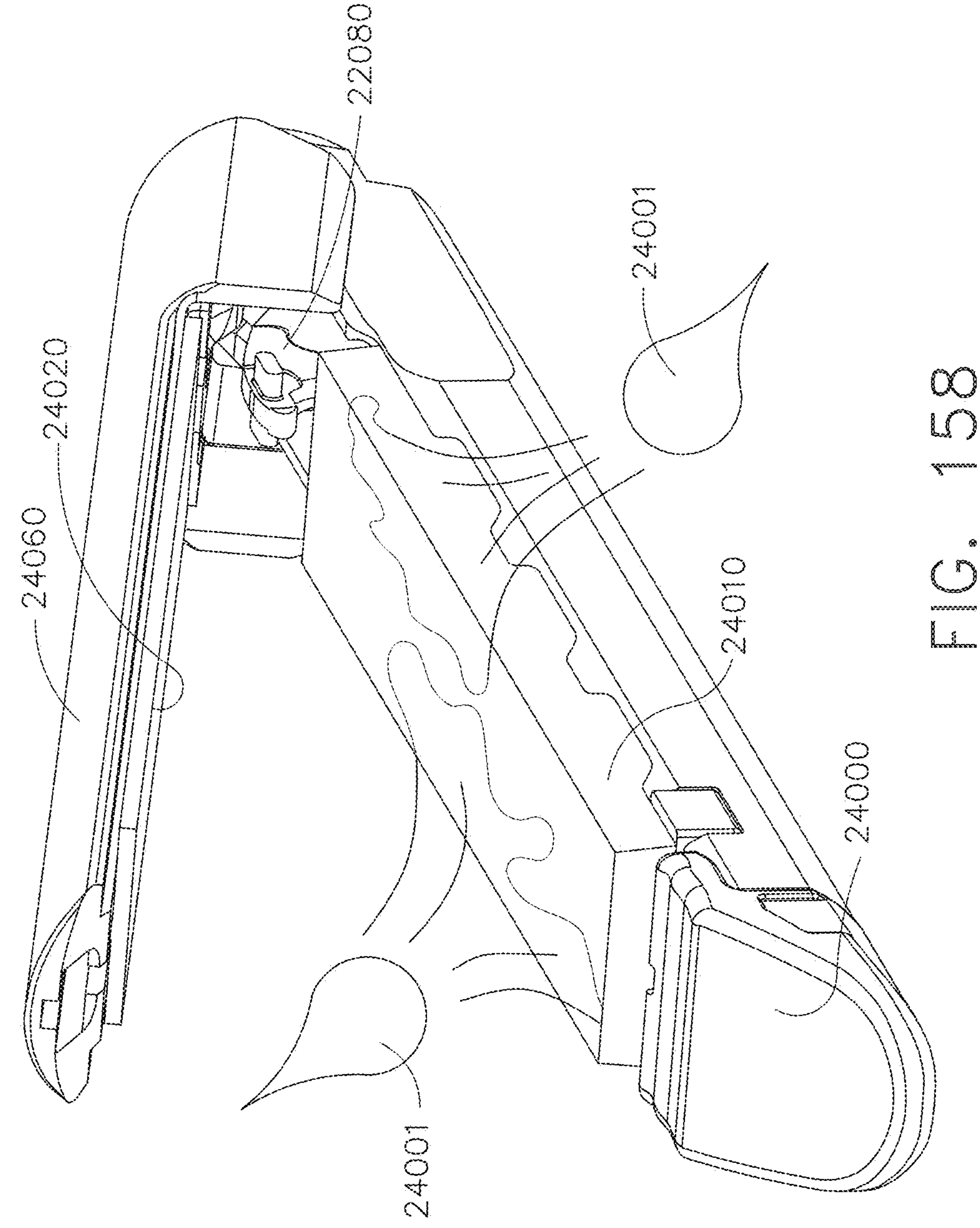
Figure 159:
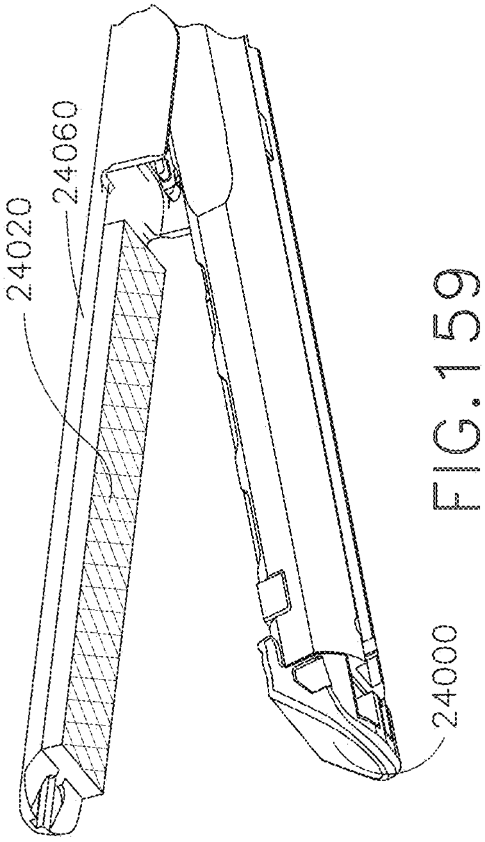
Figure 160:
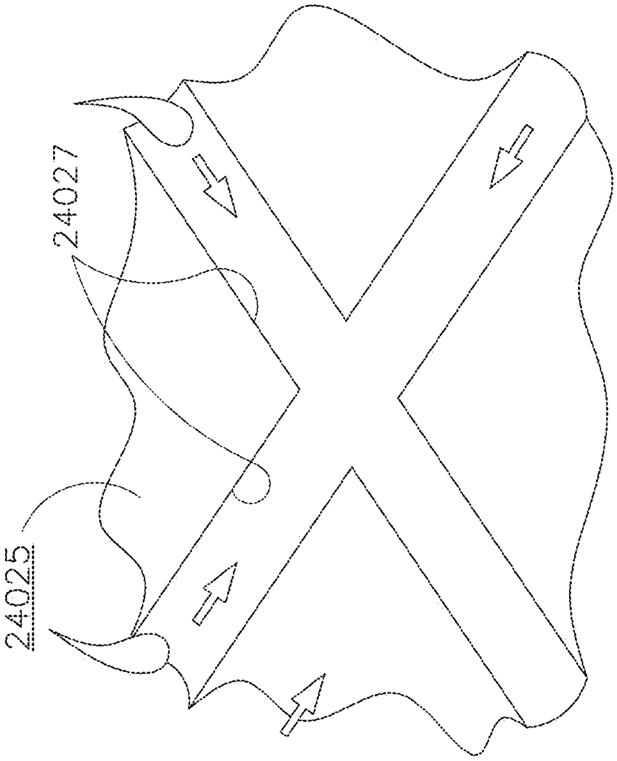
Figure 161:
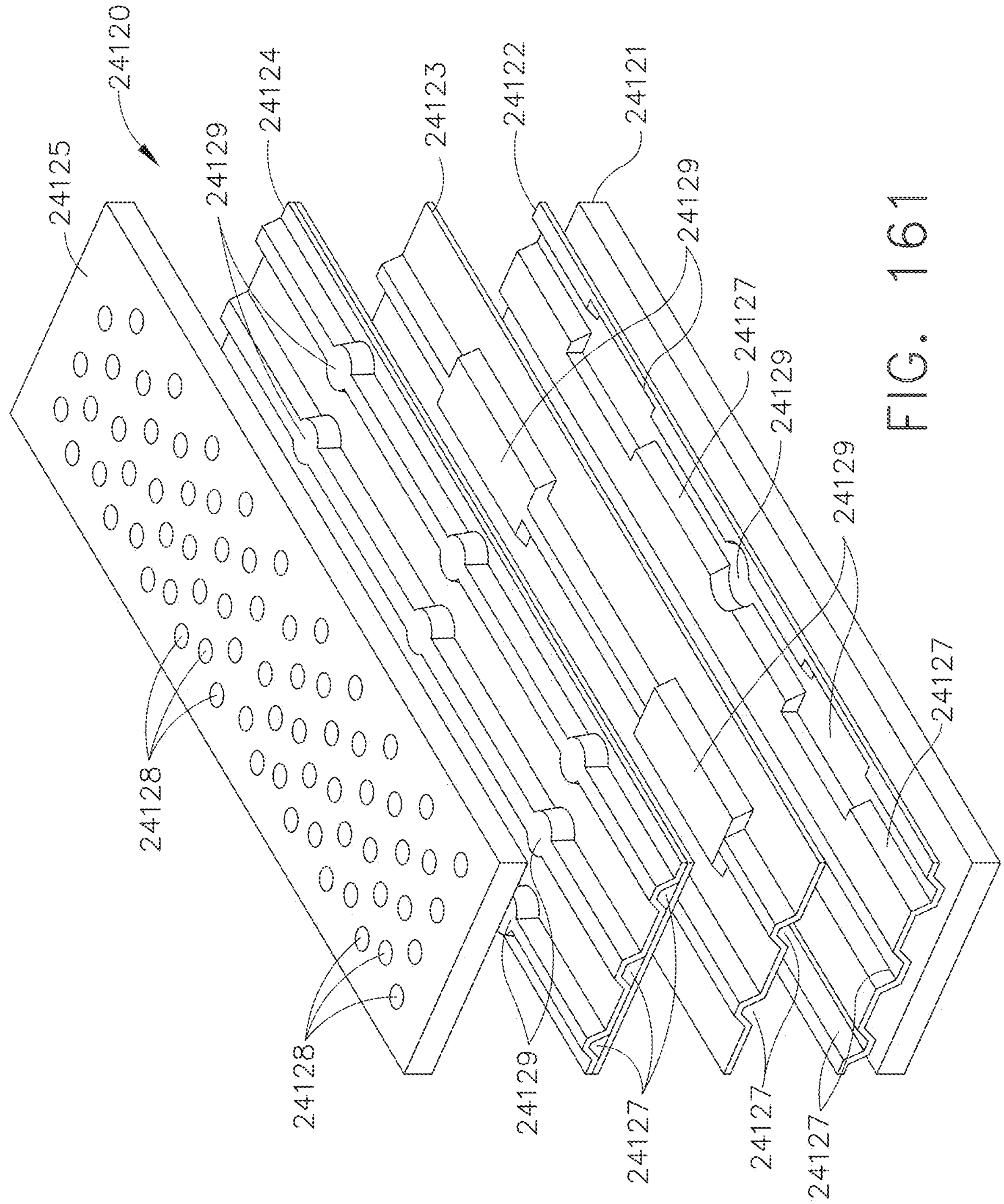
Figure 162:
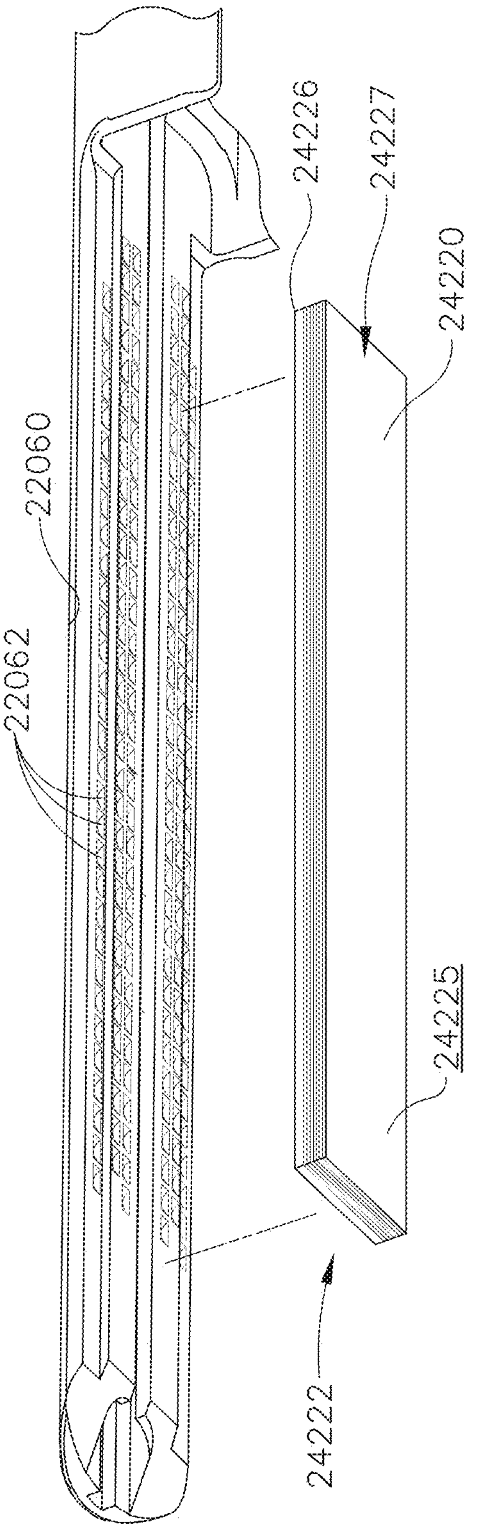
Figure 163:
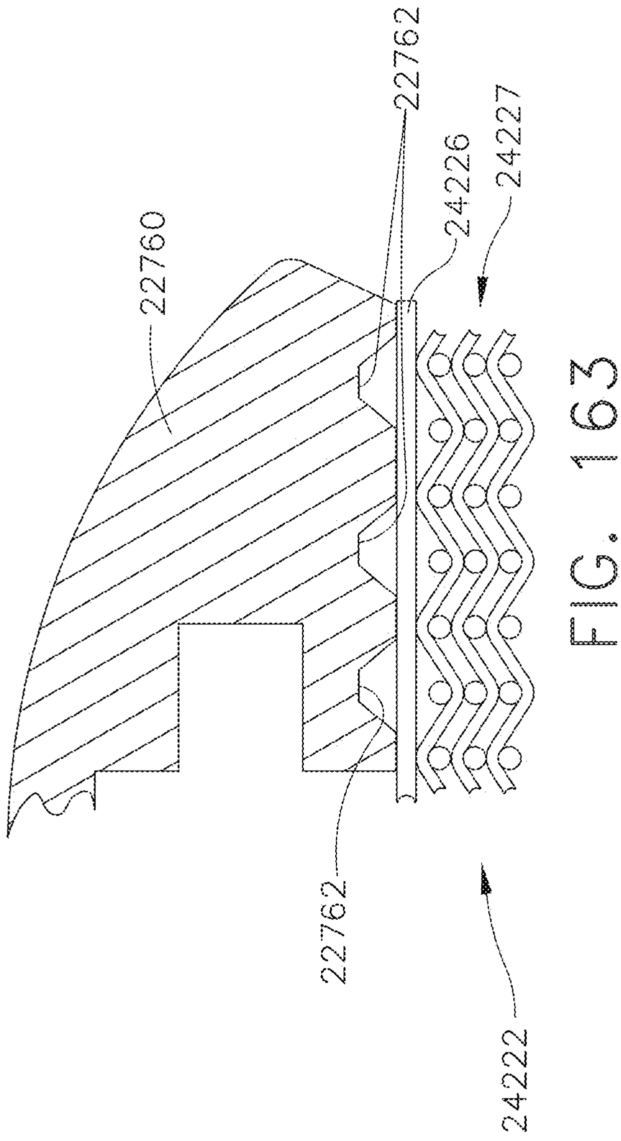
Figure 164:
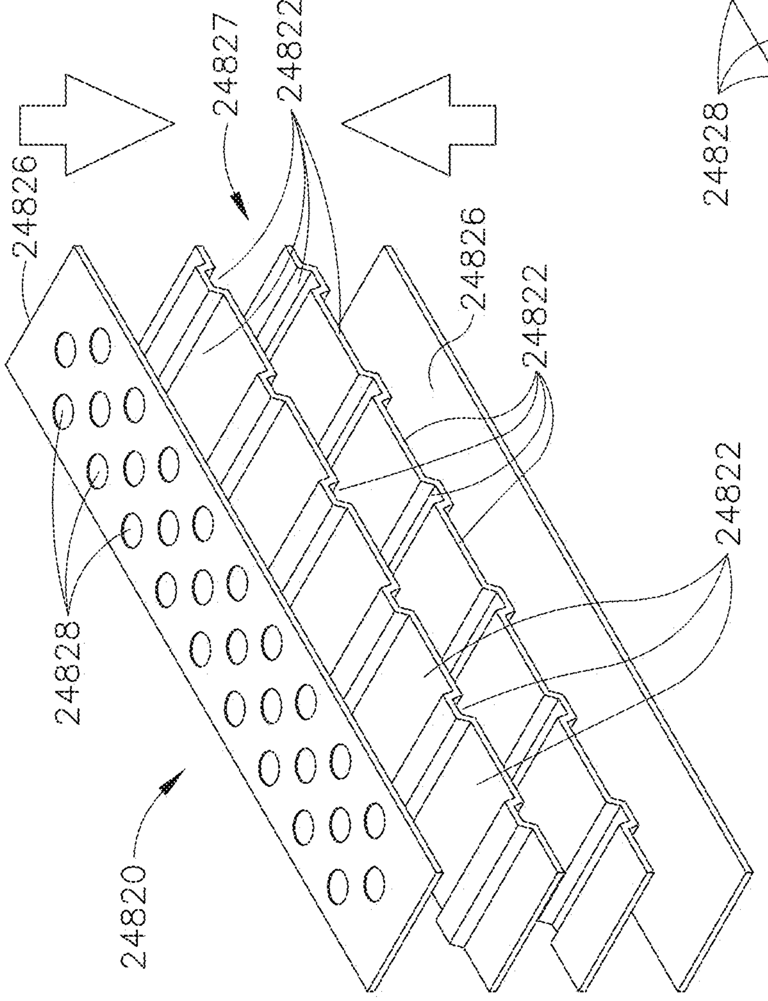
Figure 165:
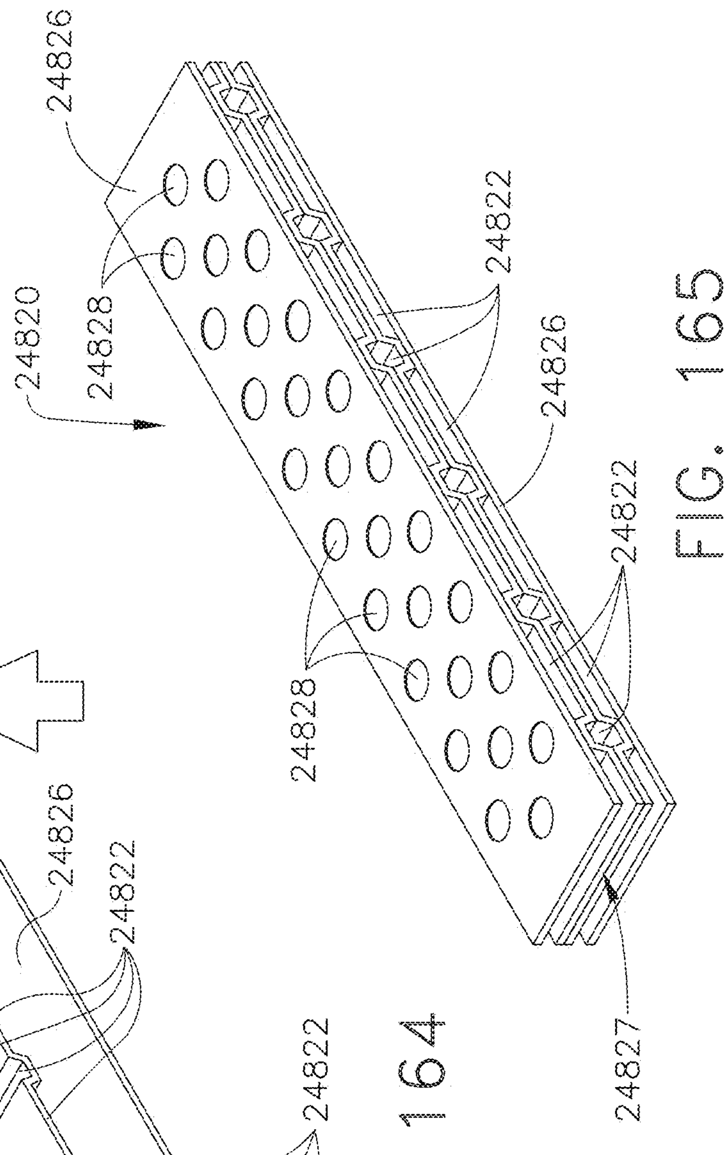
Figure 166:
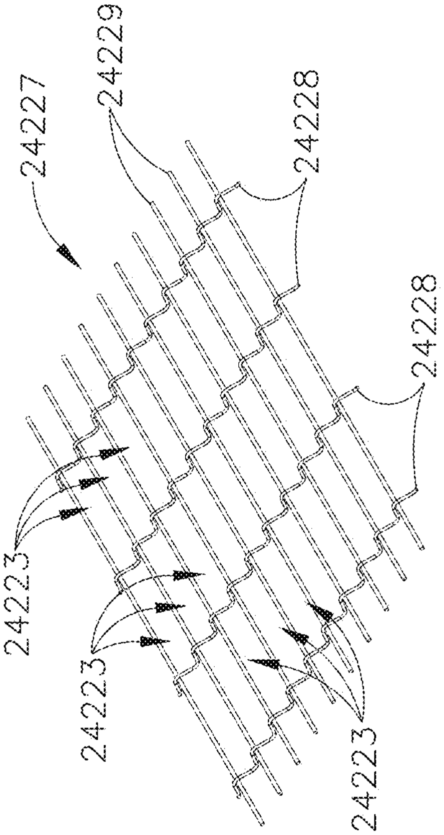
Figure 167:
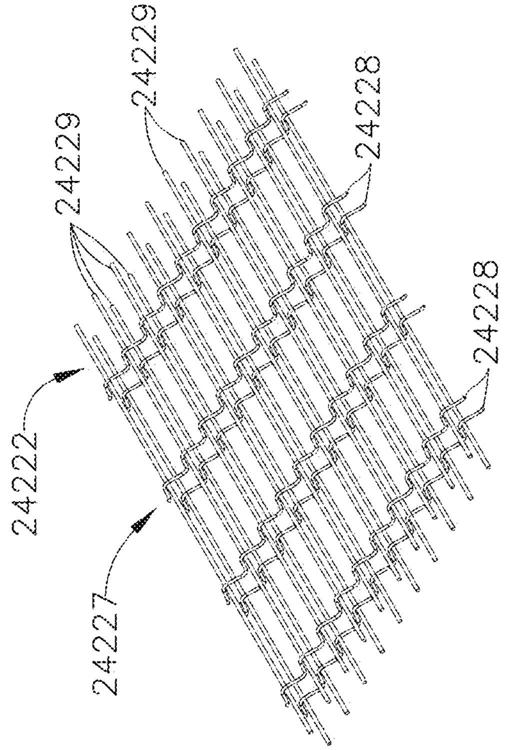
Figure 168:
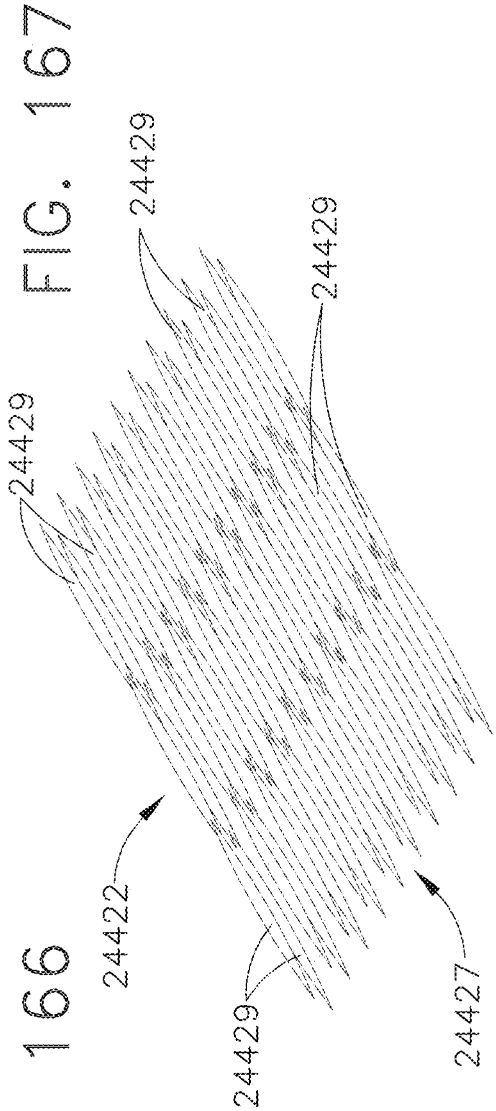
Figure 170:
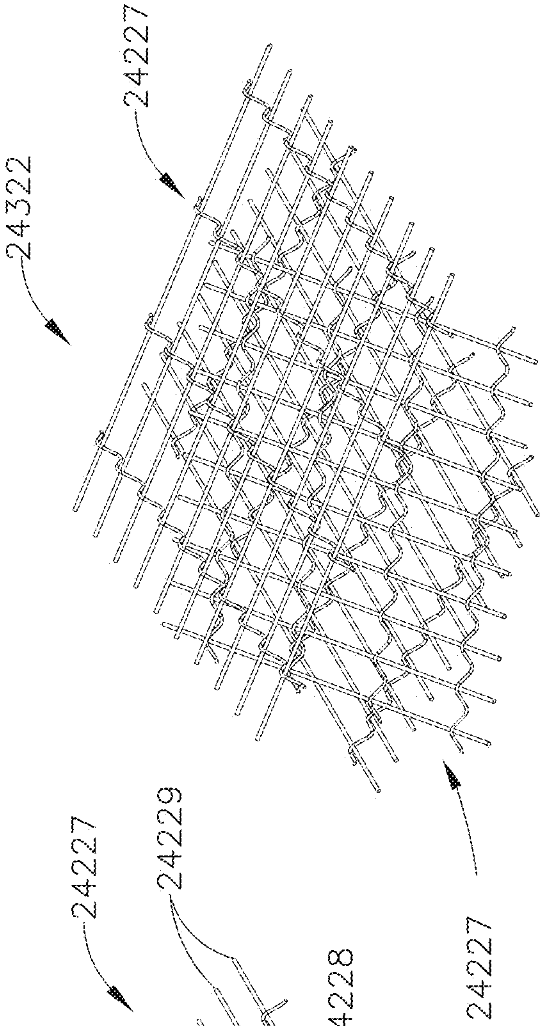
Figure 169:
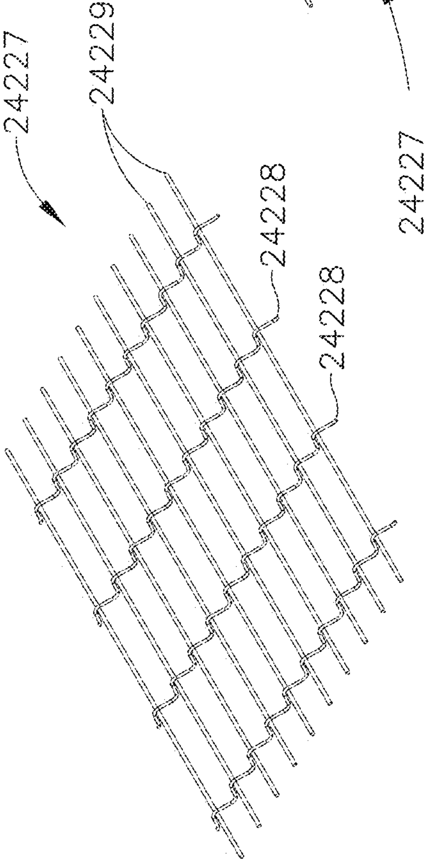
Figure 171:
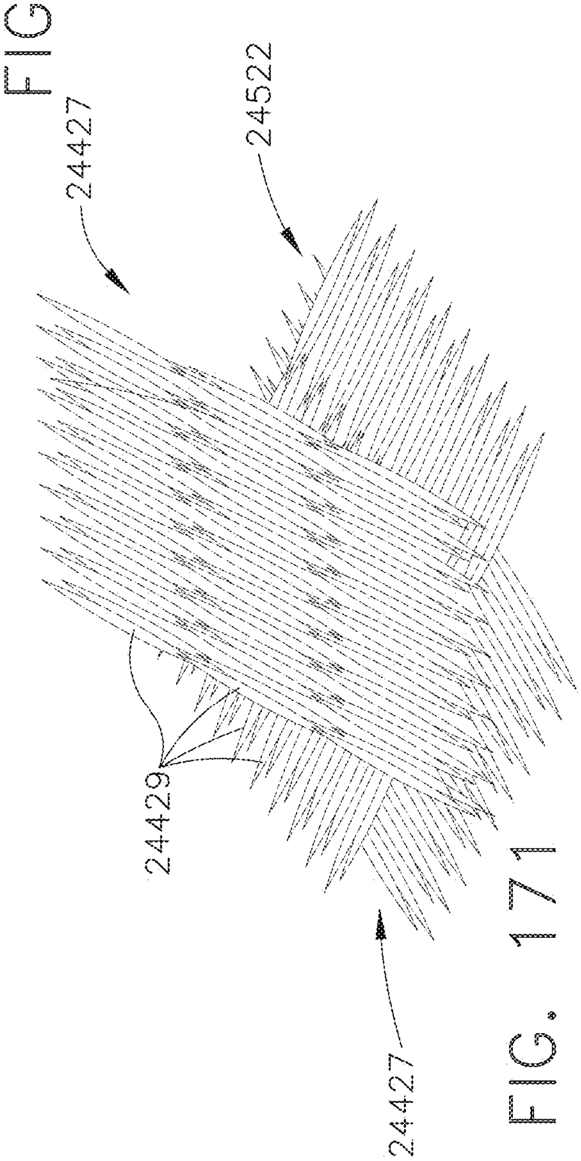
Figure 172:
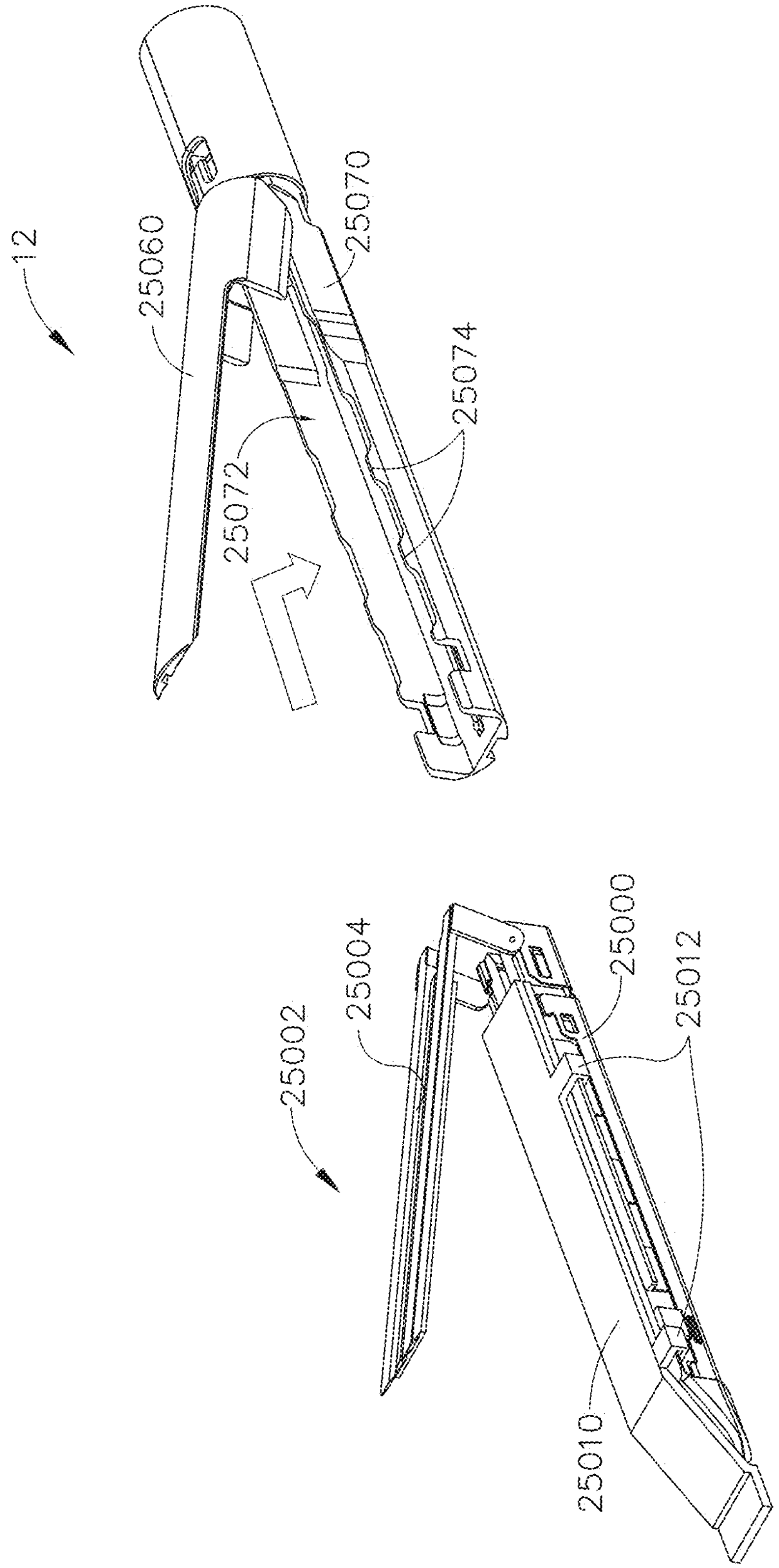
Figure 173:
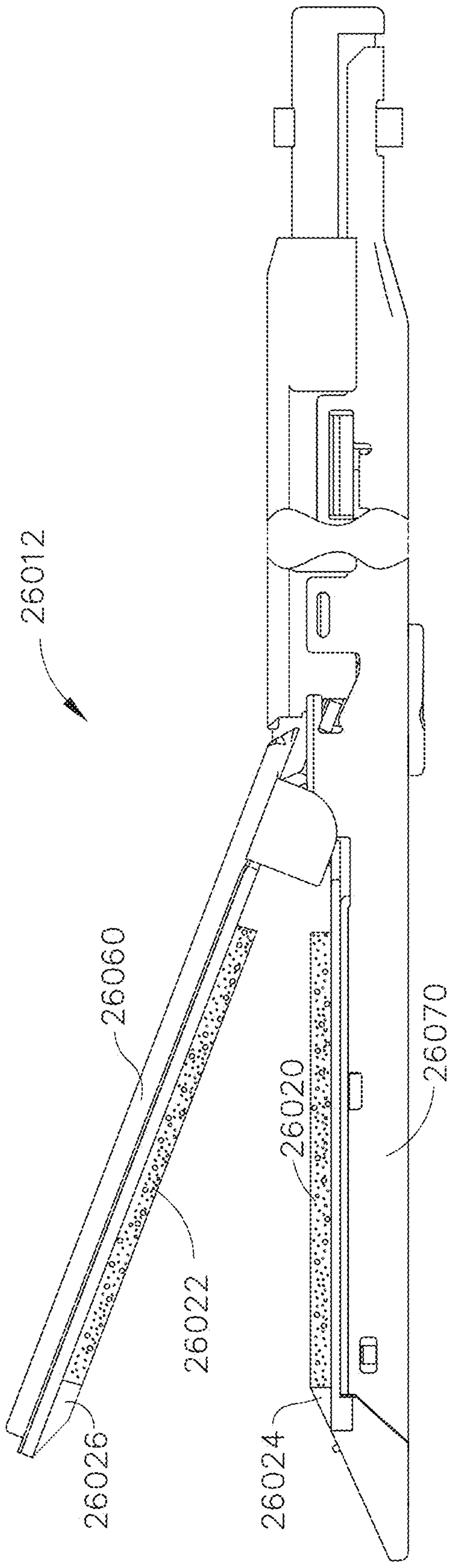
Figure 174:
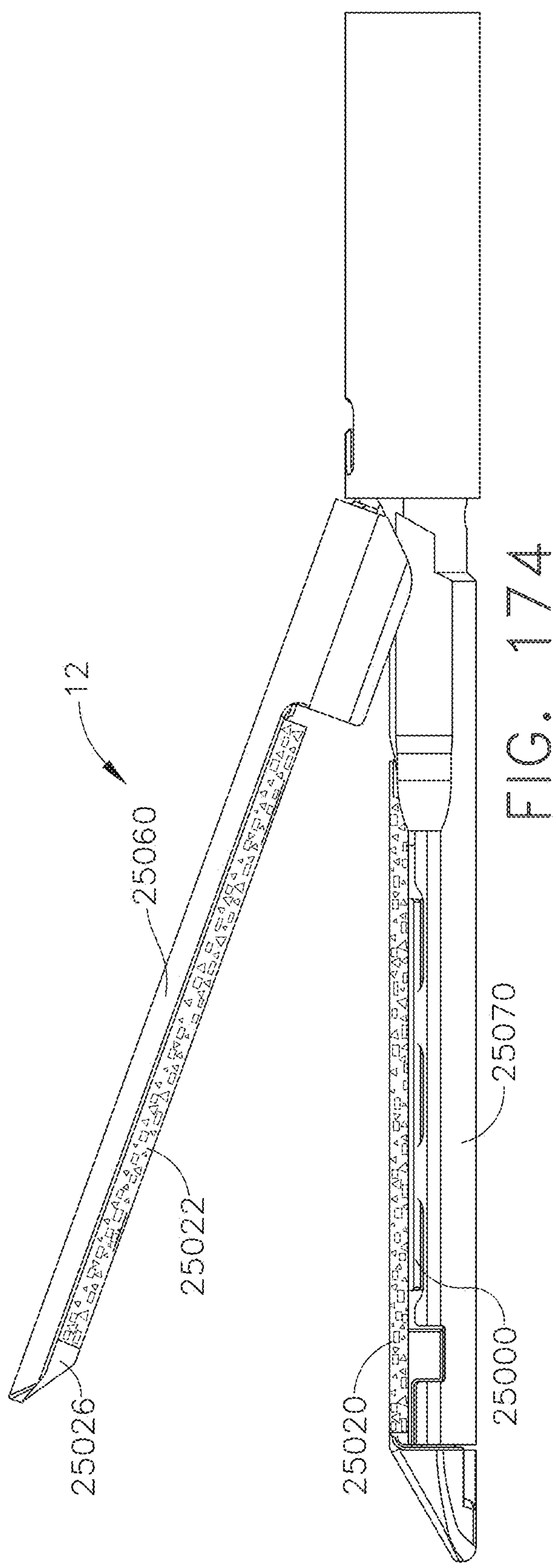
Figure 175:
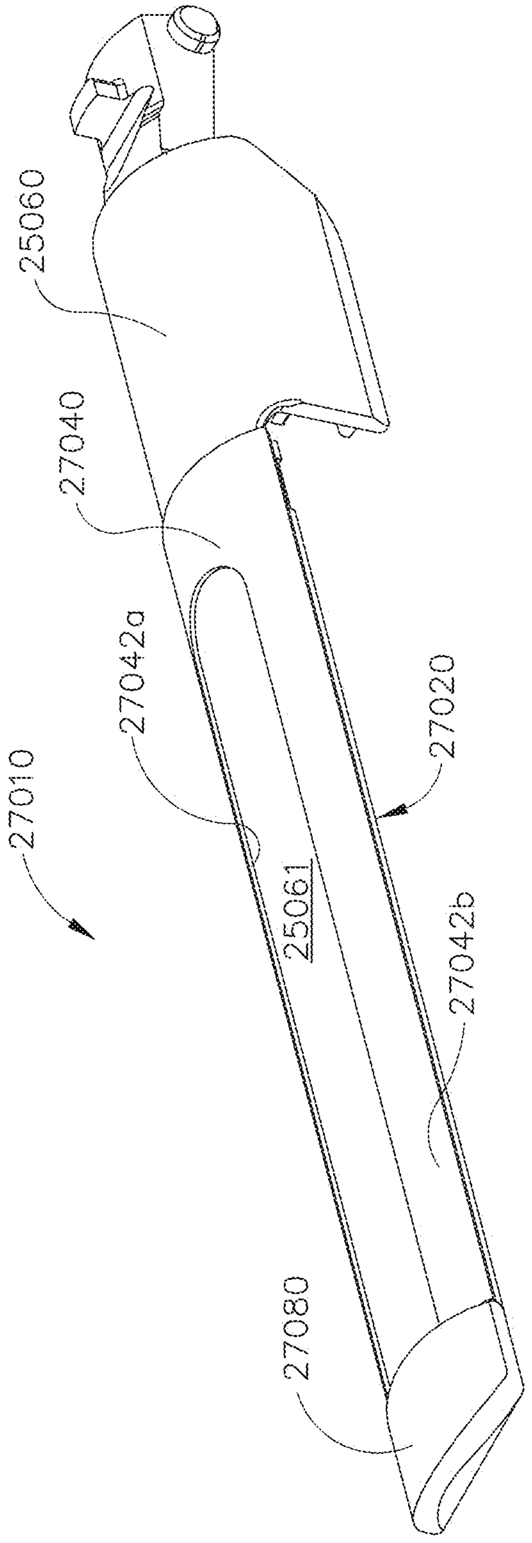
Figure 176:
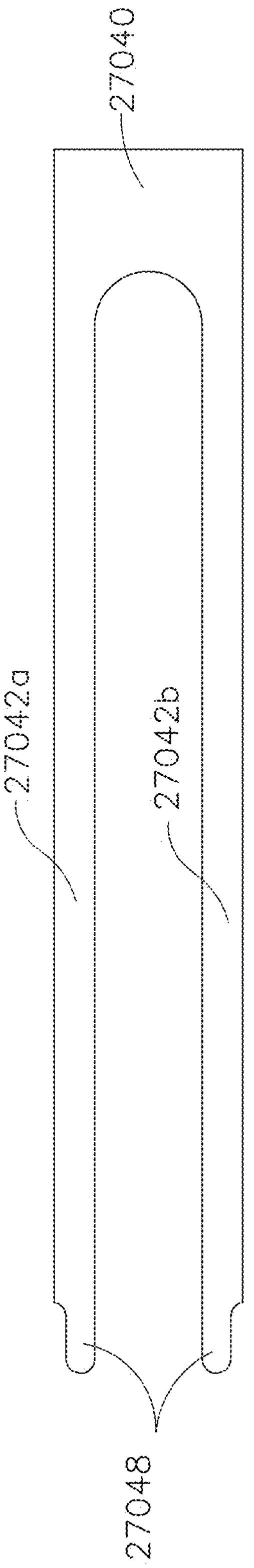
Figure 177:
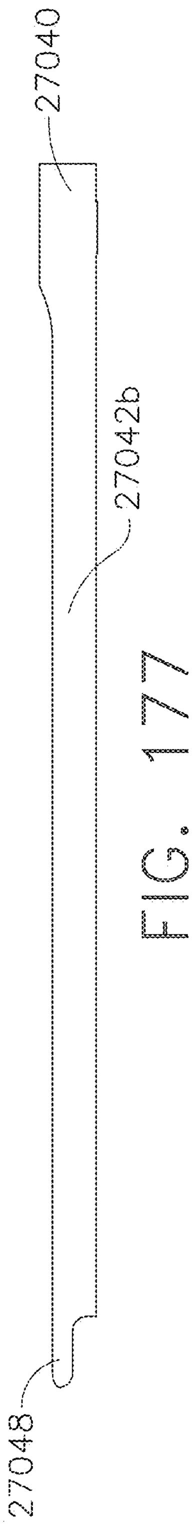
Figure 179:
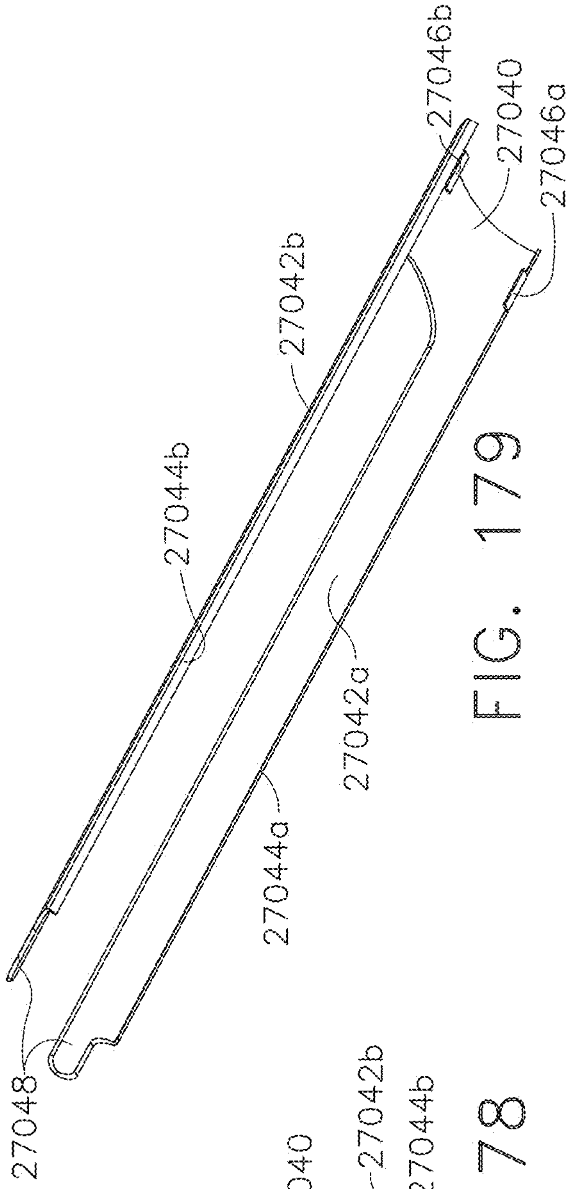
Figure 178:
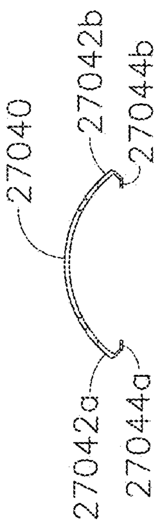
Figure 181:
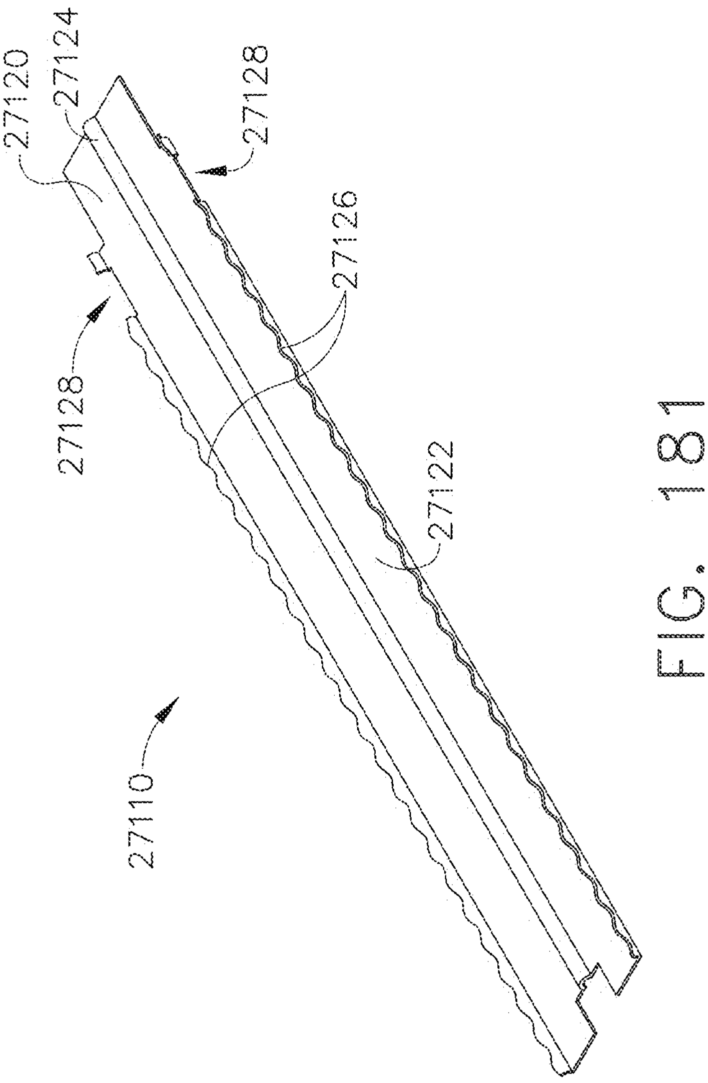
Figure 182:
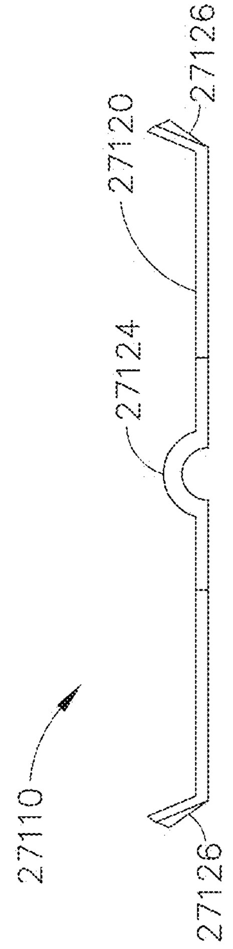
Figure 180:
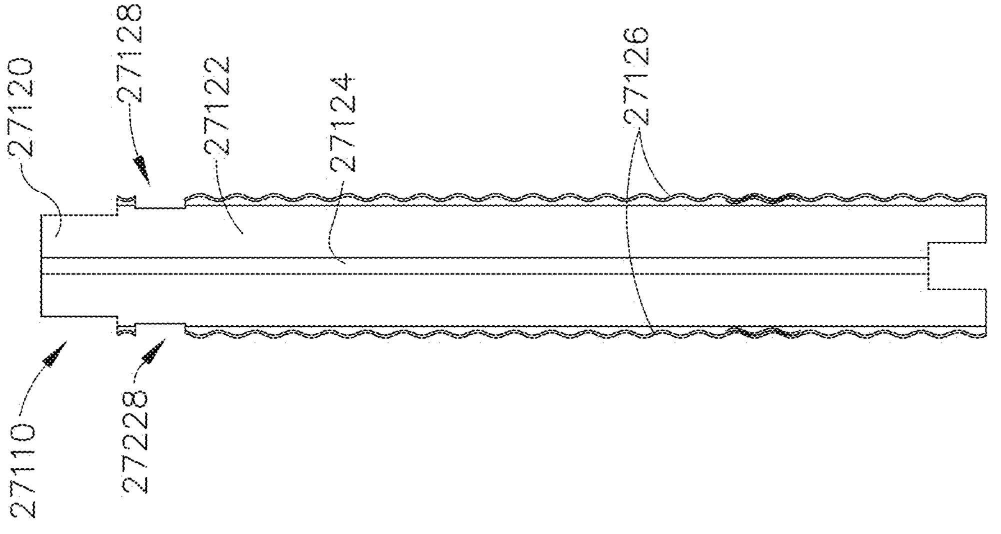
Figure 184:
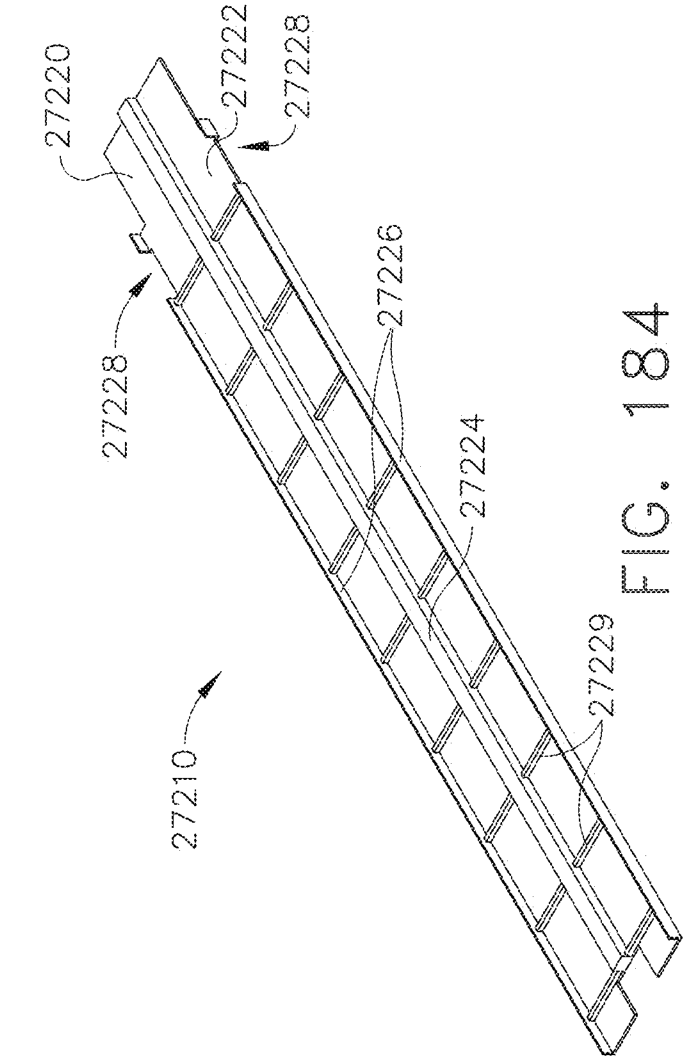
Figure 185:
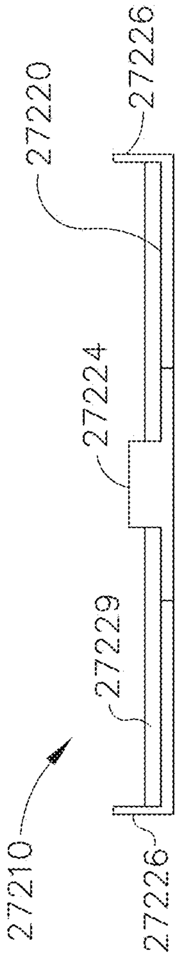
Figure 183:
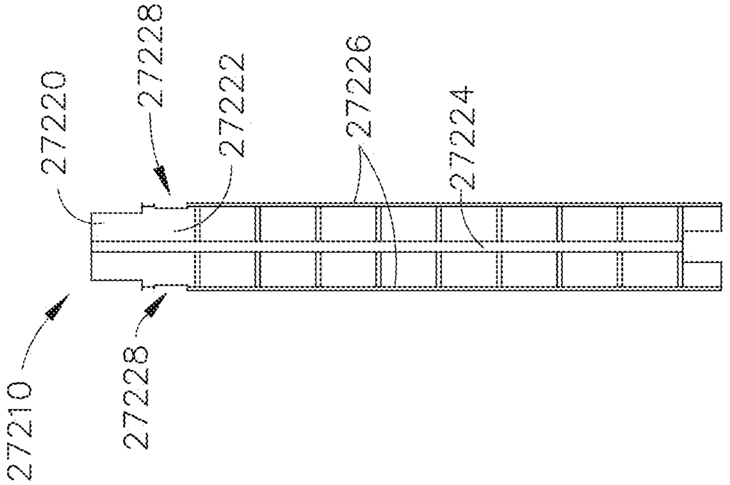
Figure 188:
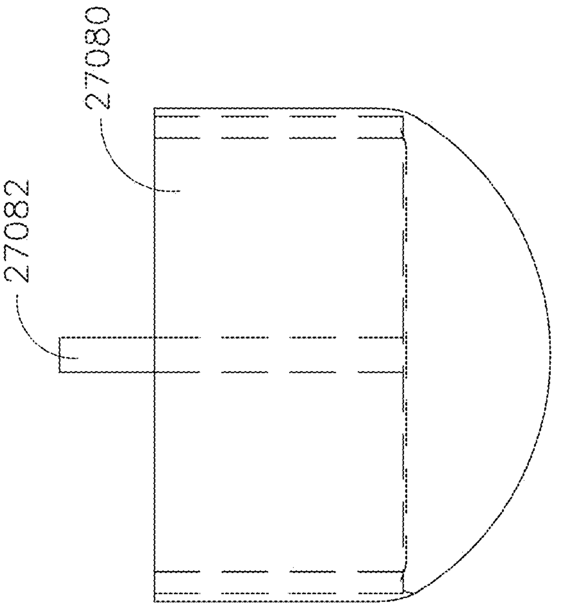
Figure 189:
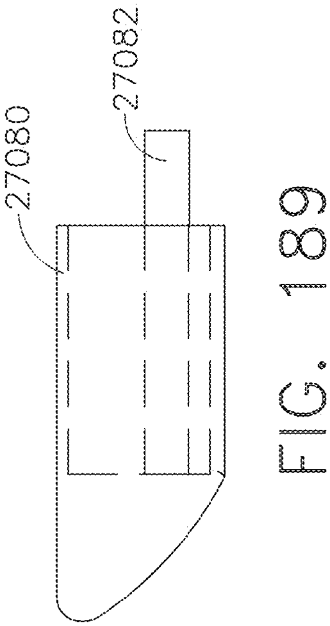
Figure 186:
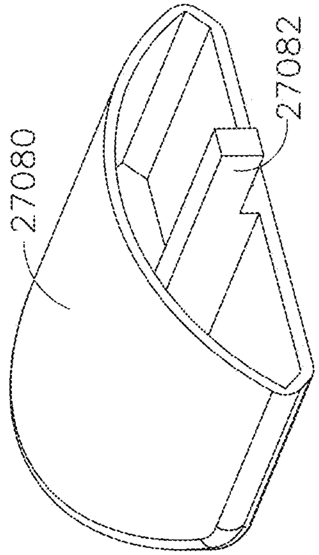
Figure 187:
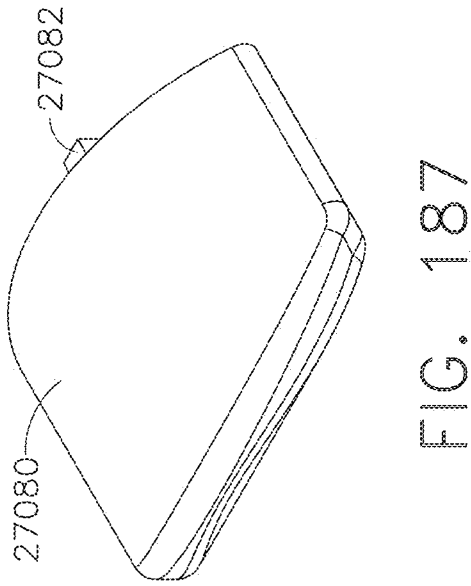
Figure 190:
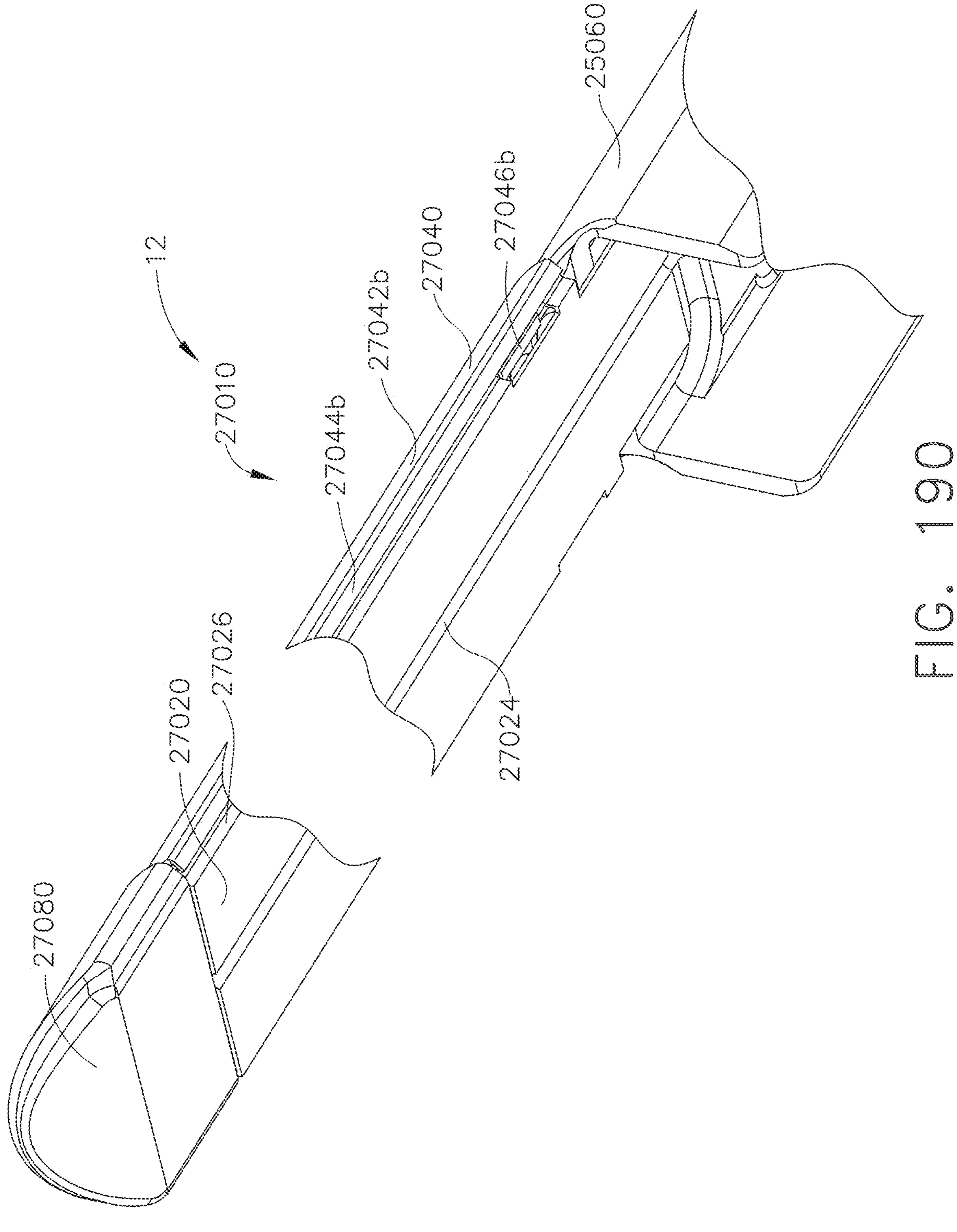
Figure 191:
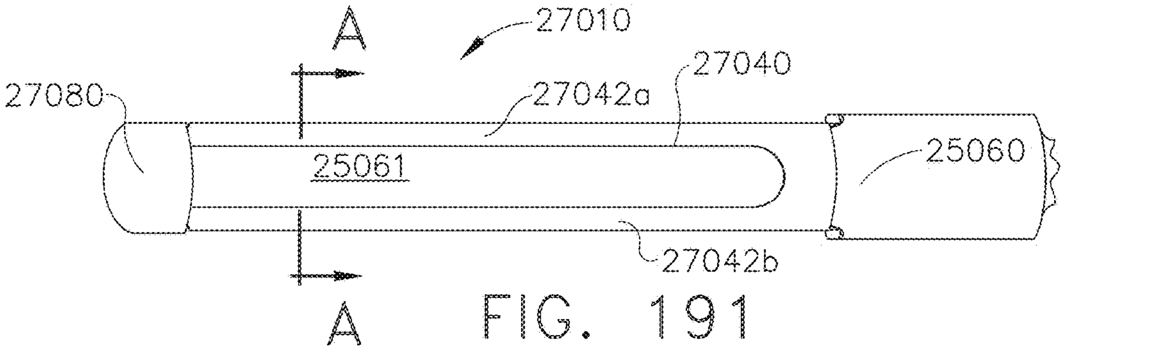
Figure 192:
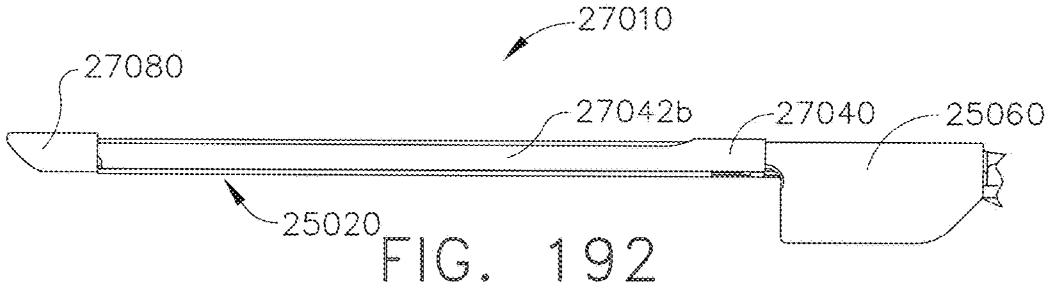
Figure 193:
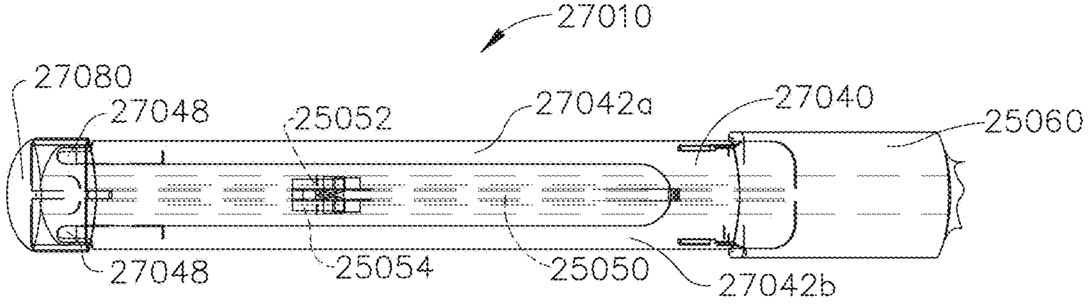
Figure 194:
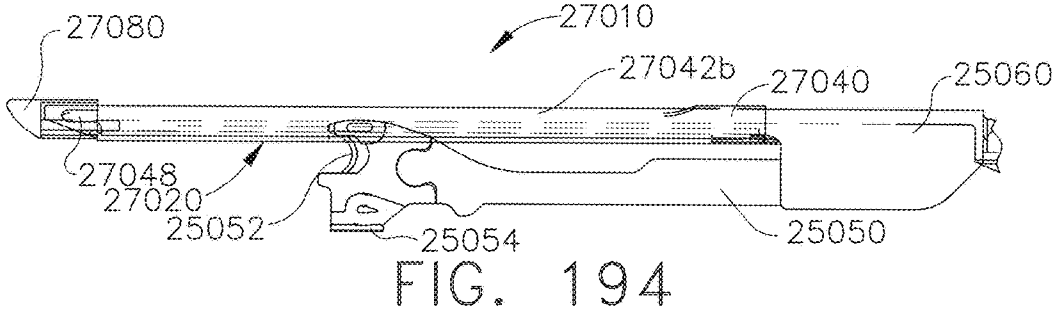
Figure 195:
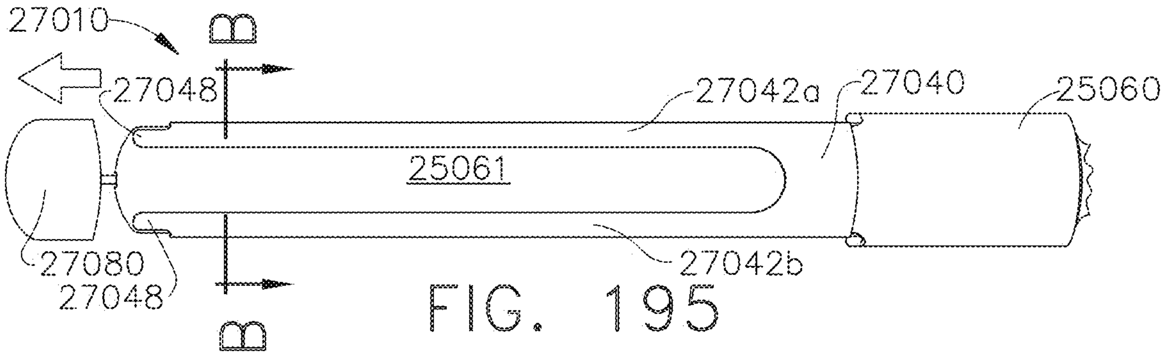
Figure 196:
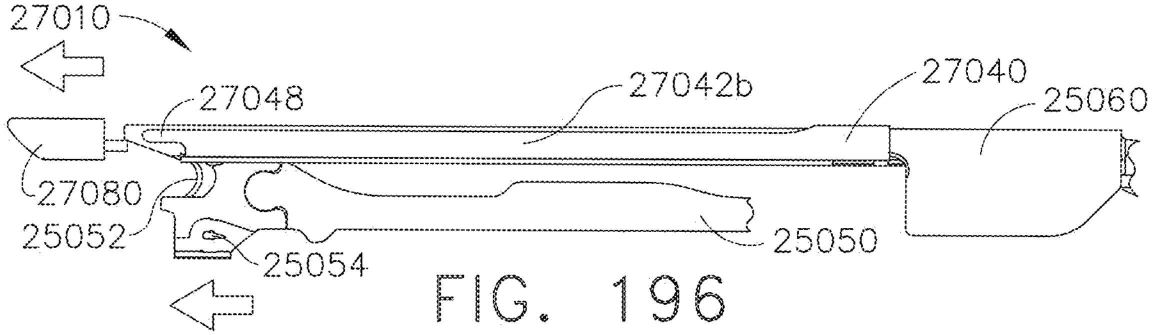
Figure 197:
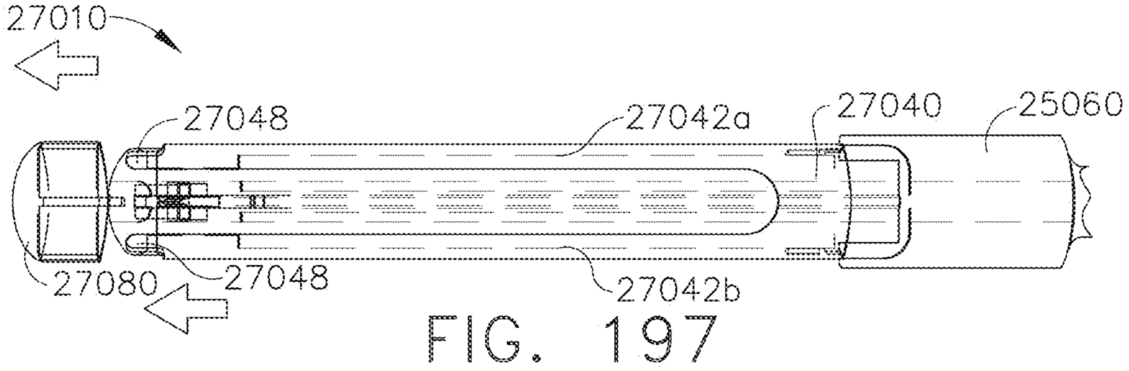
Figure 198:
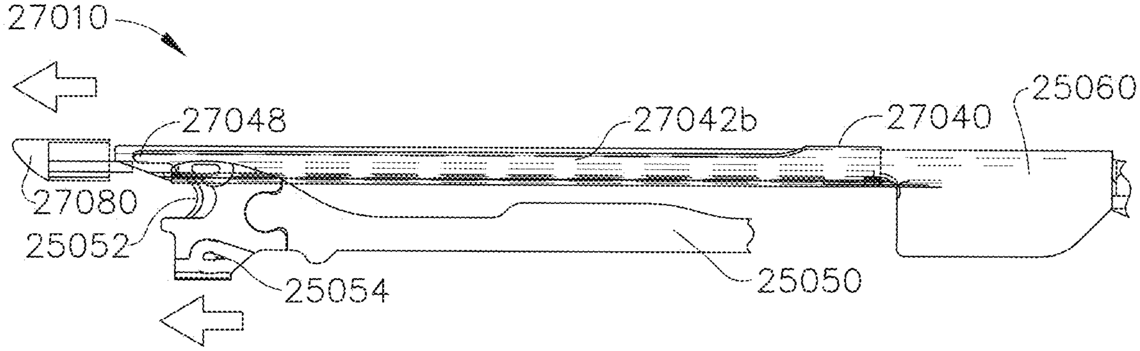
Figure 199:
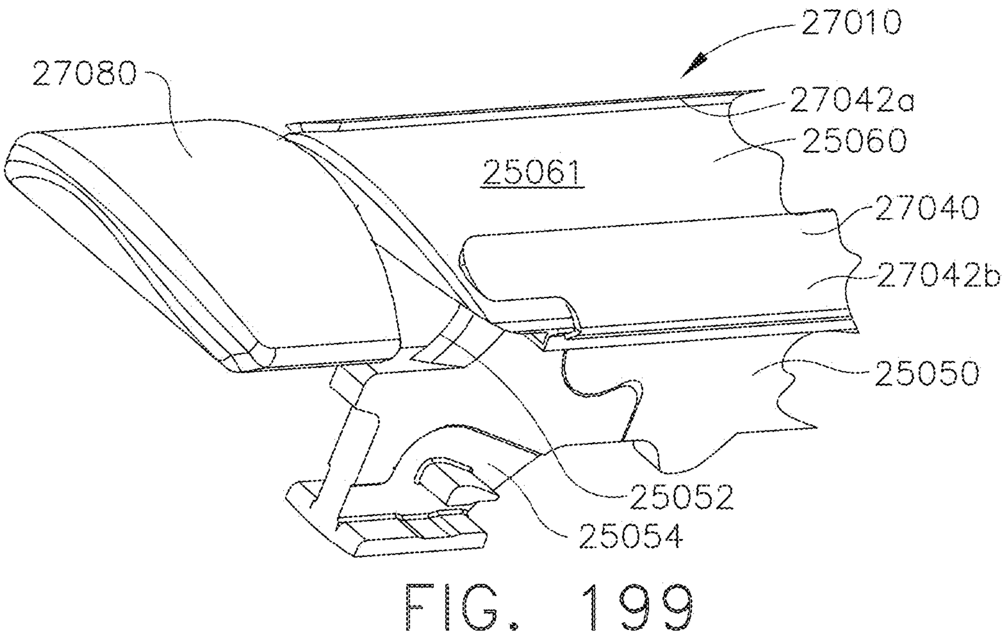
Figure 200:
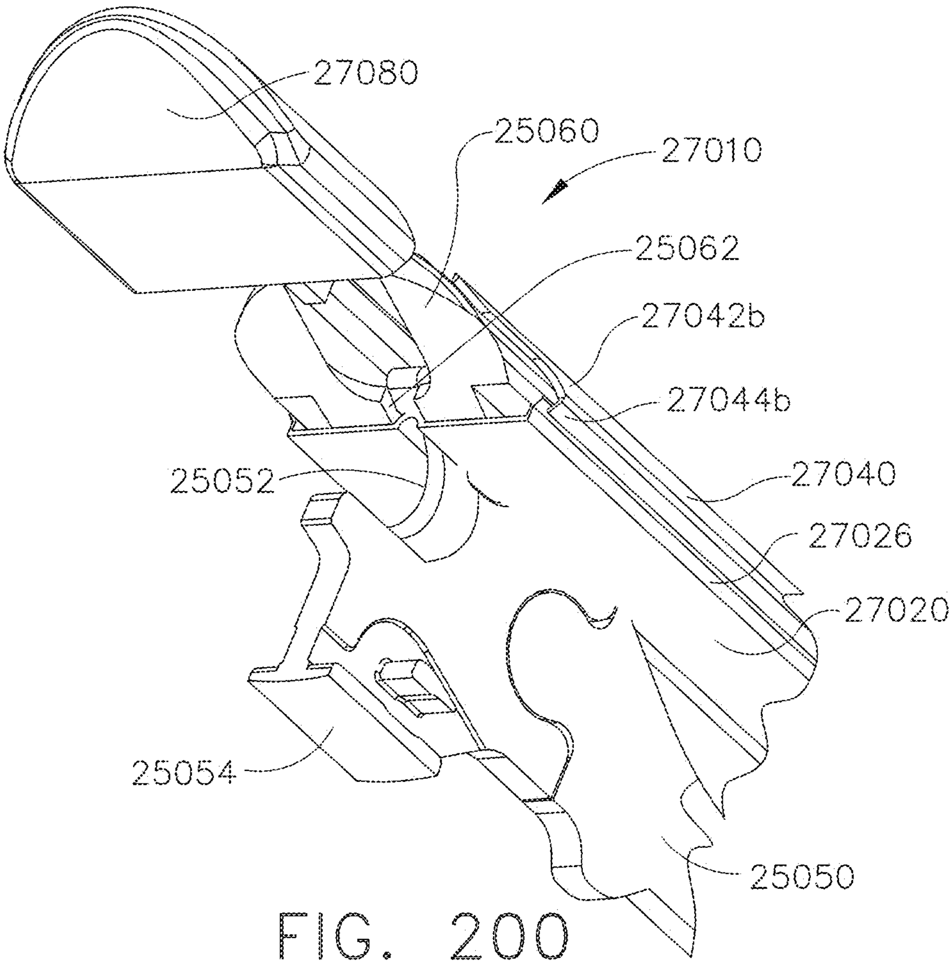
Figure 201:
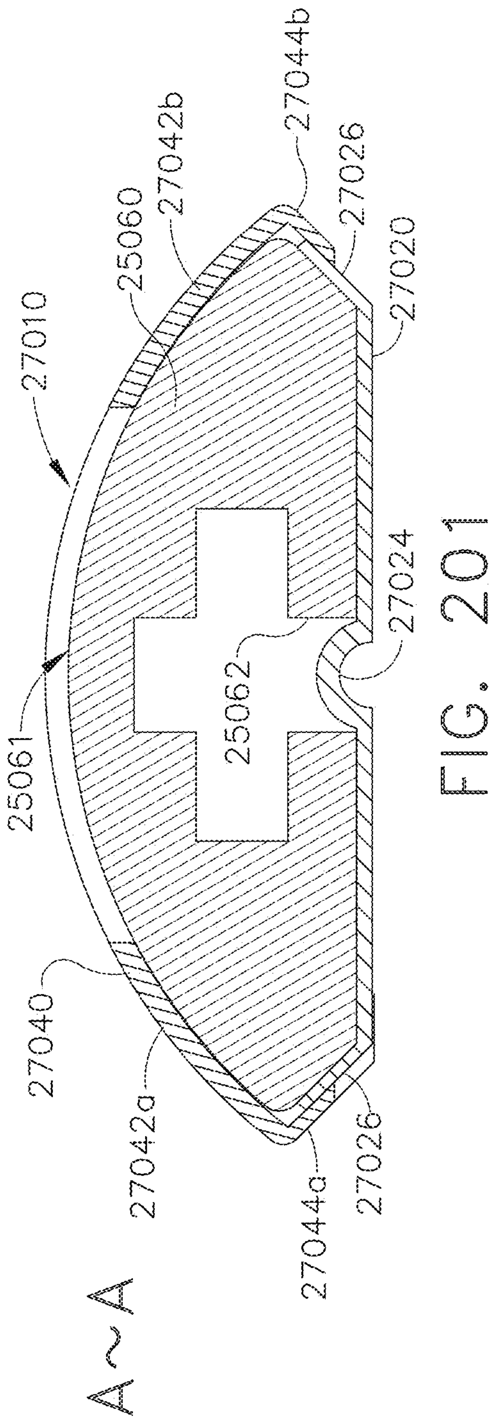
Figure 202:
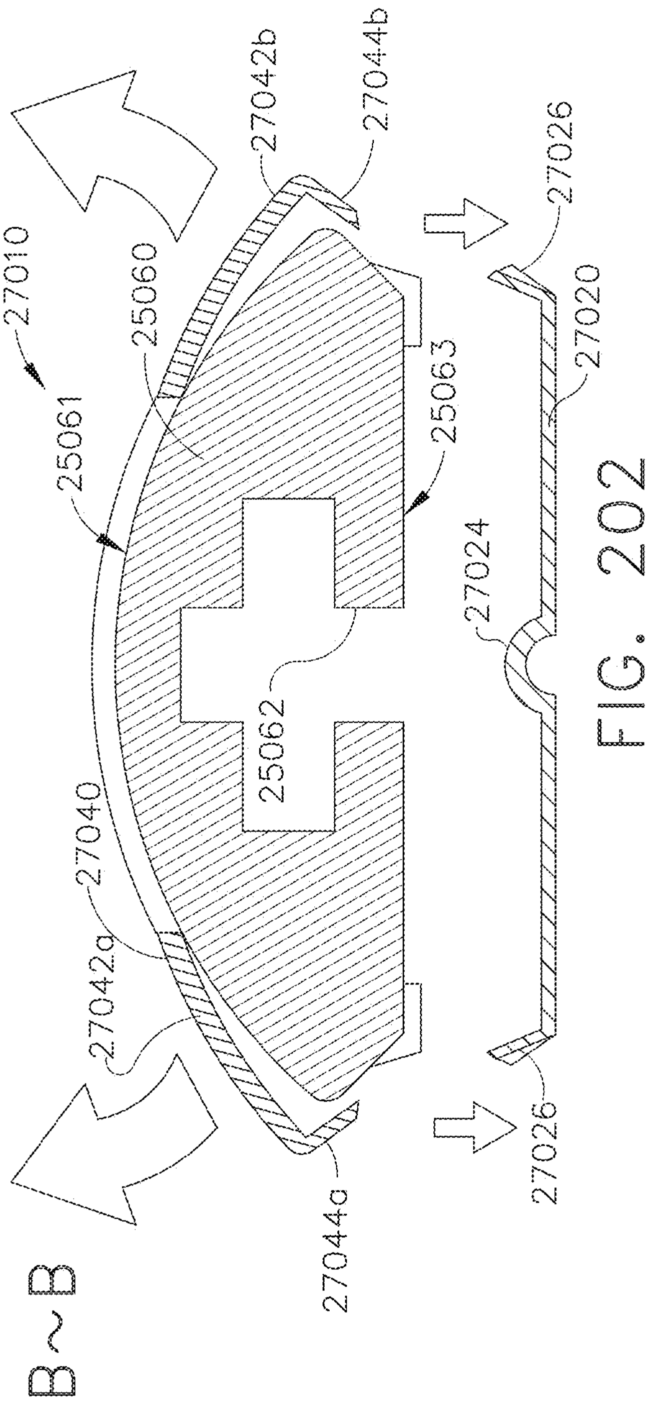
Figure 203:
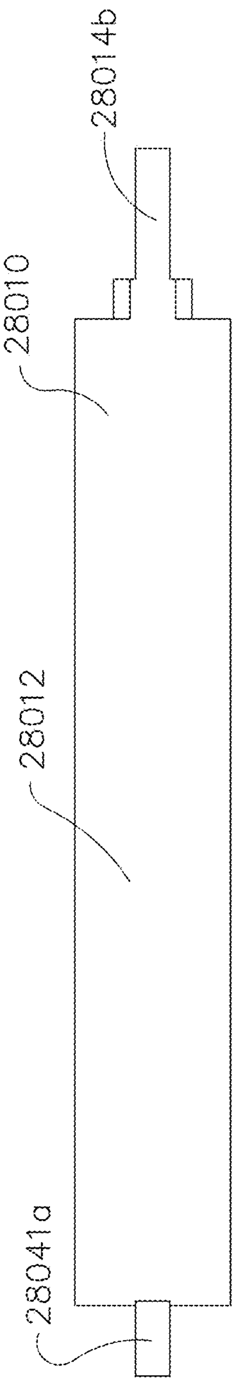
Figure 204:
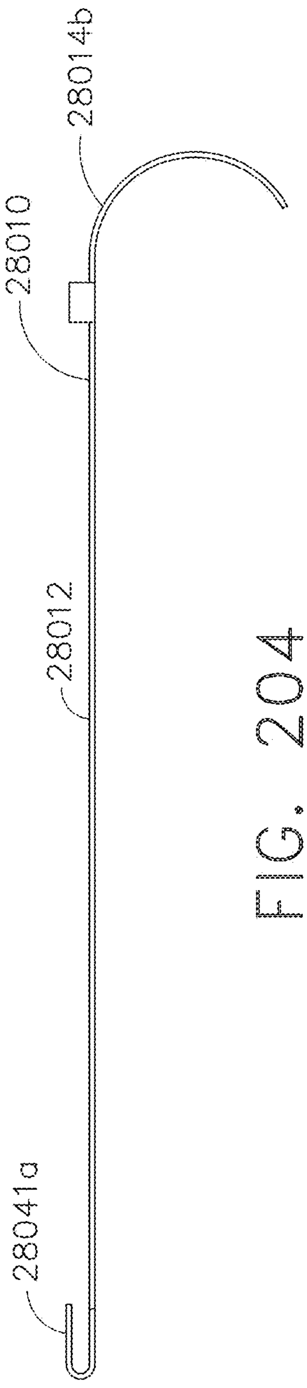
Figure 205:
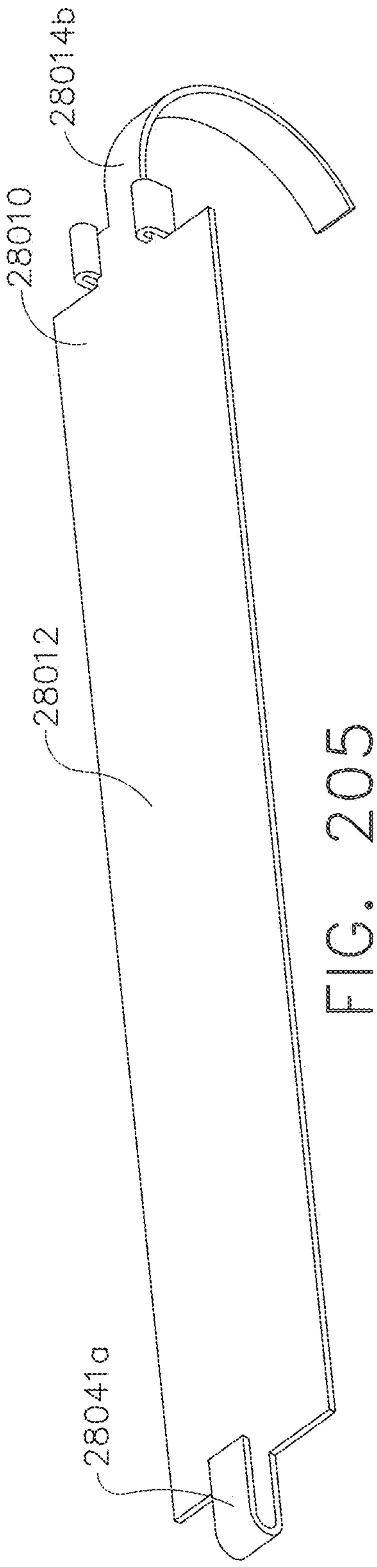
Figure 206:
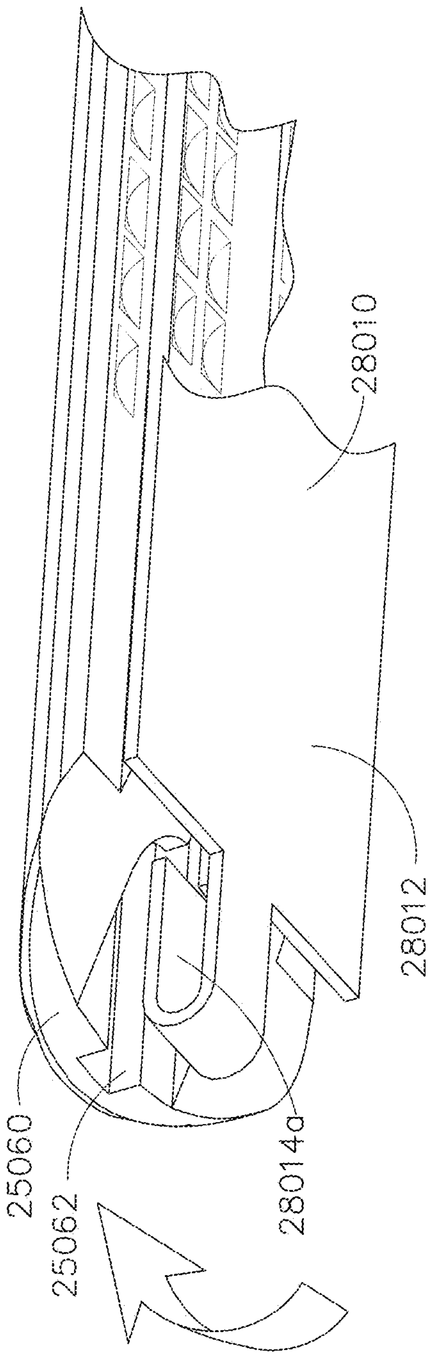
Figure 207:
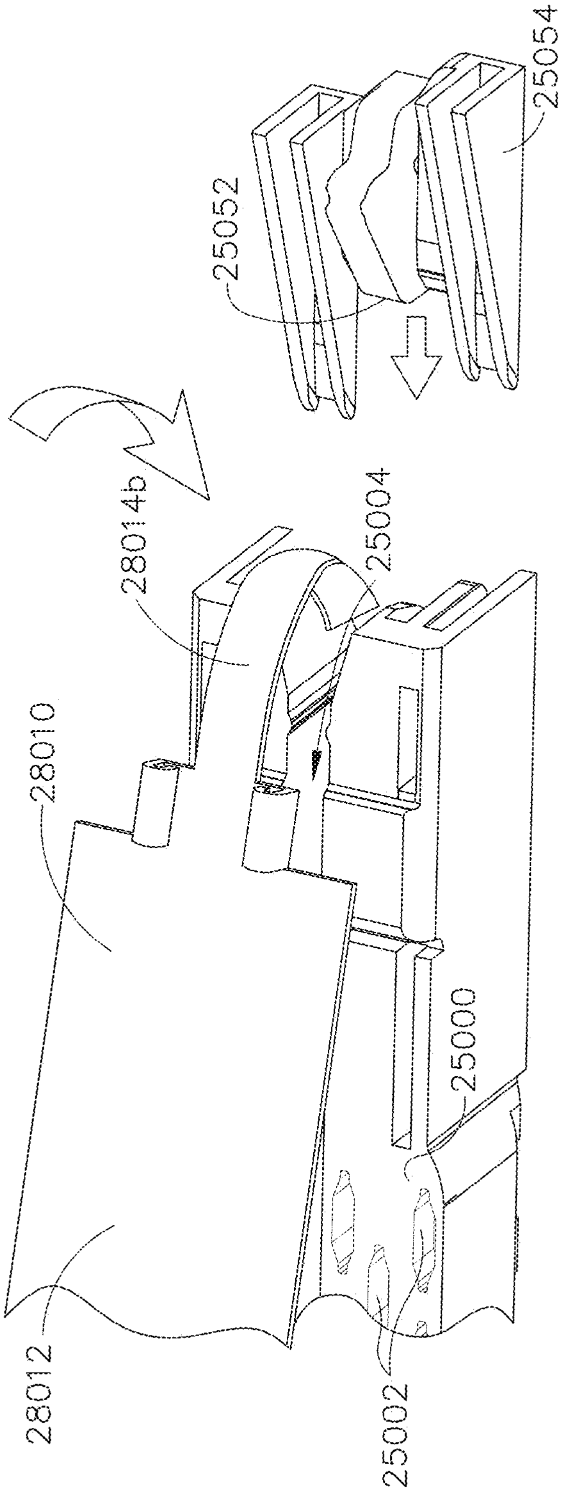
Figure 208:
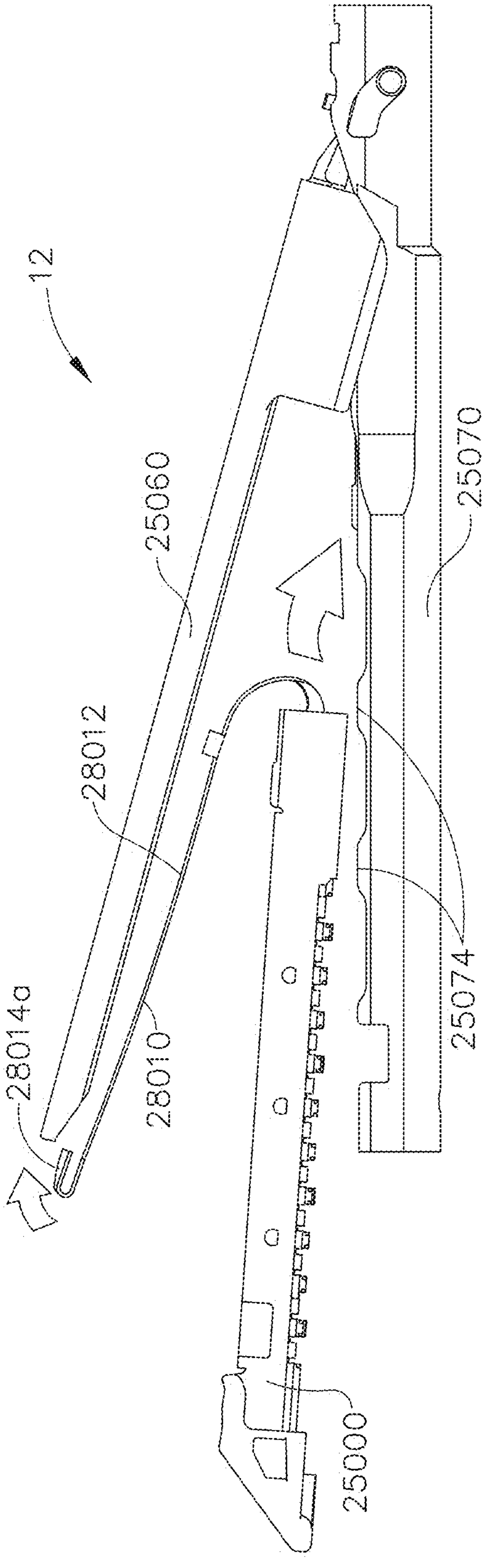
Figure 209:
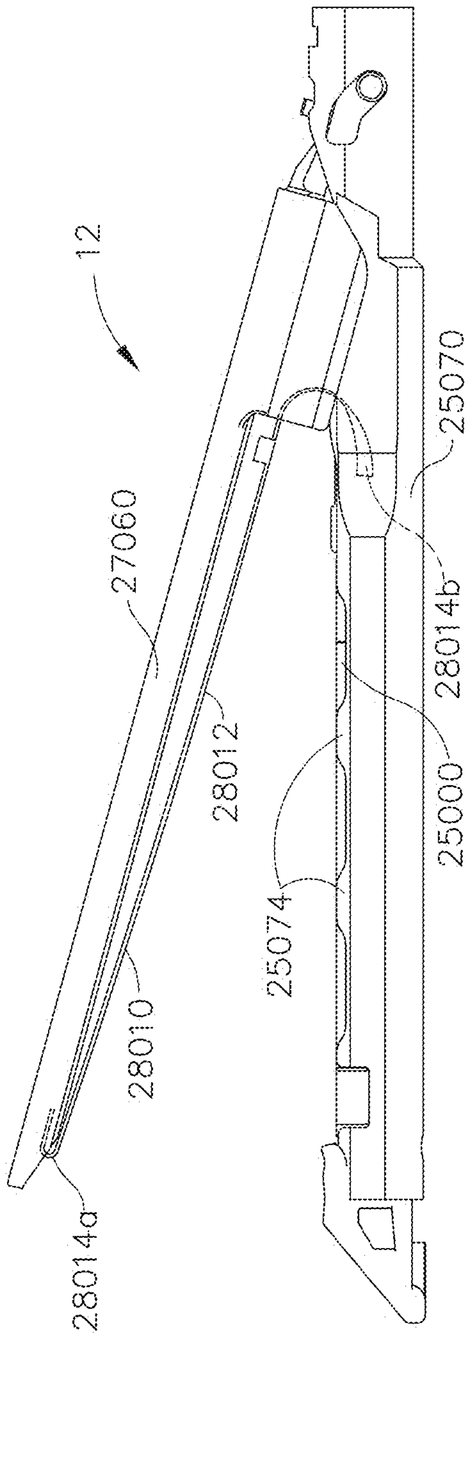
Figure 210:
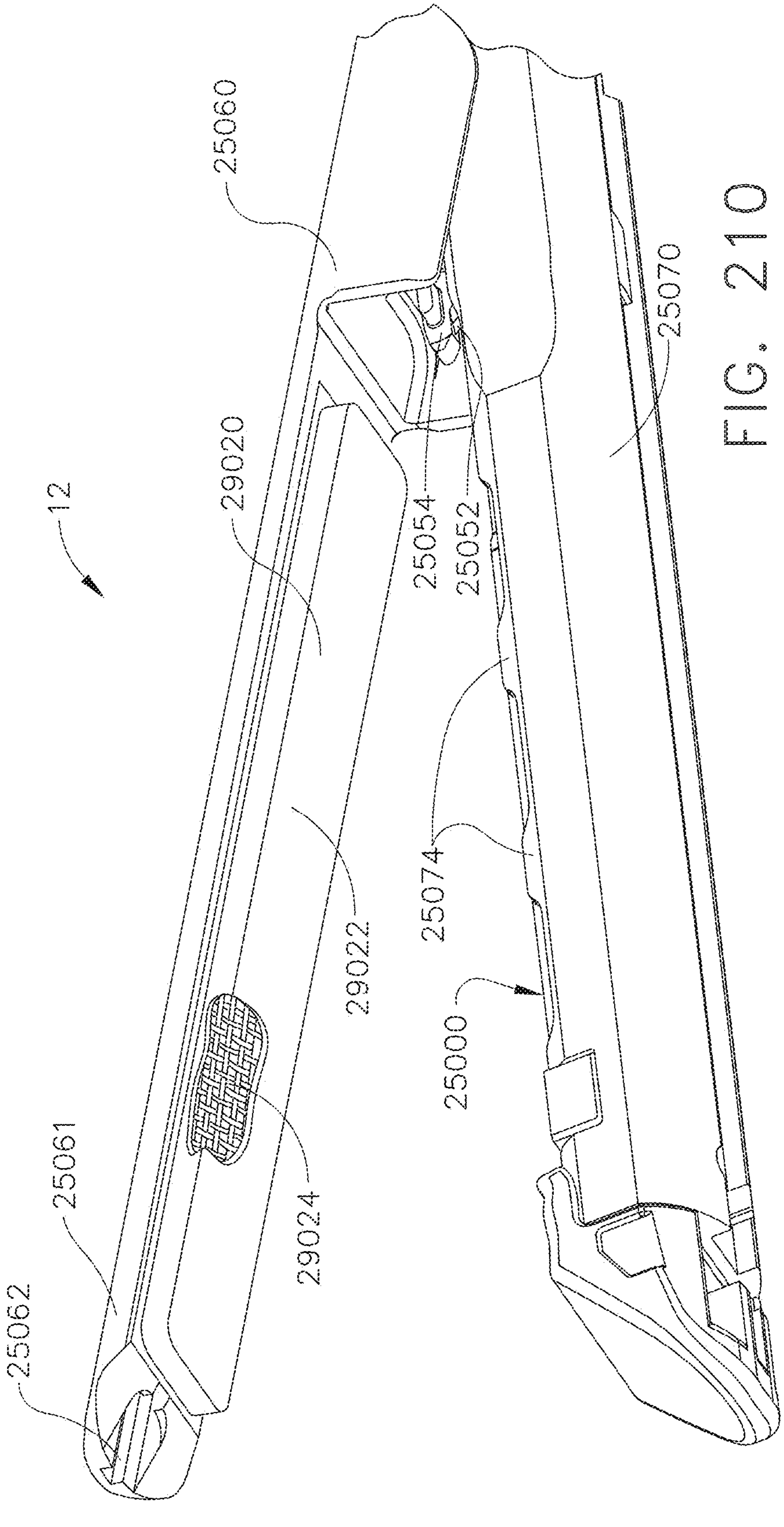
Figure 211:
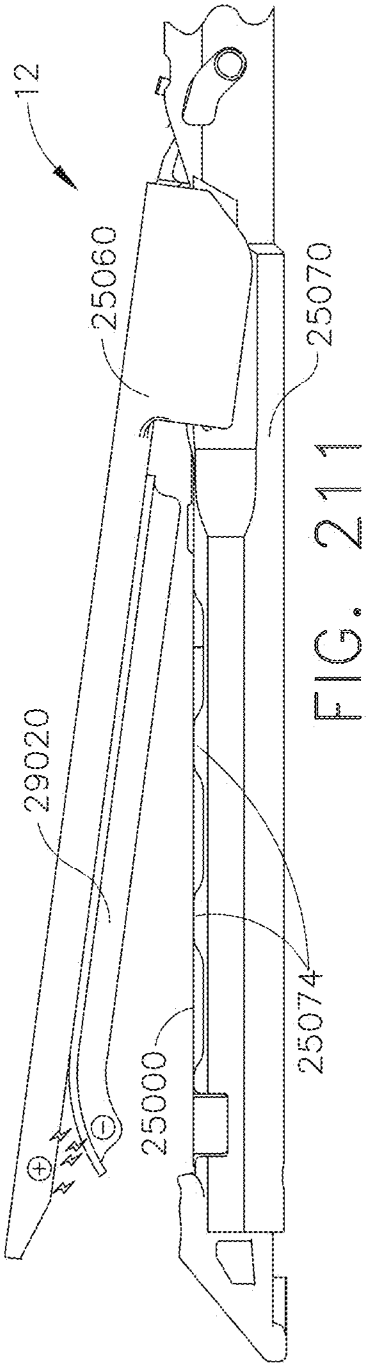
Figure 212:
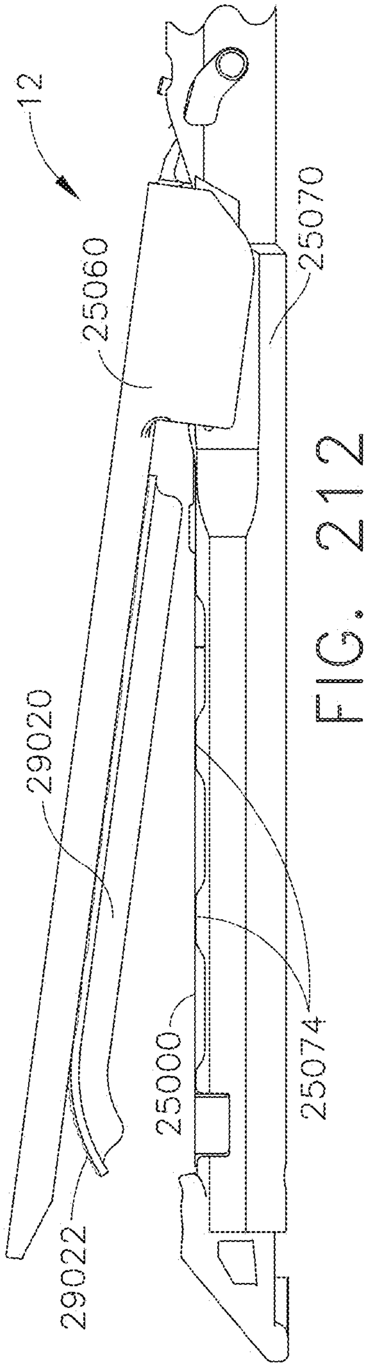
Figure 213:
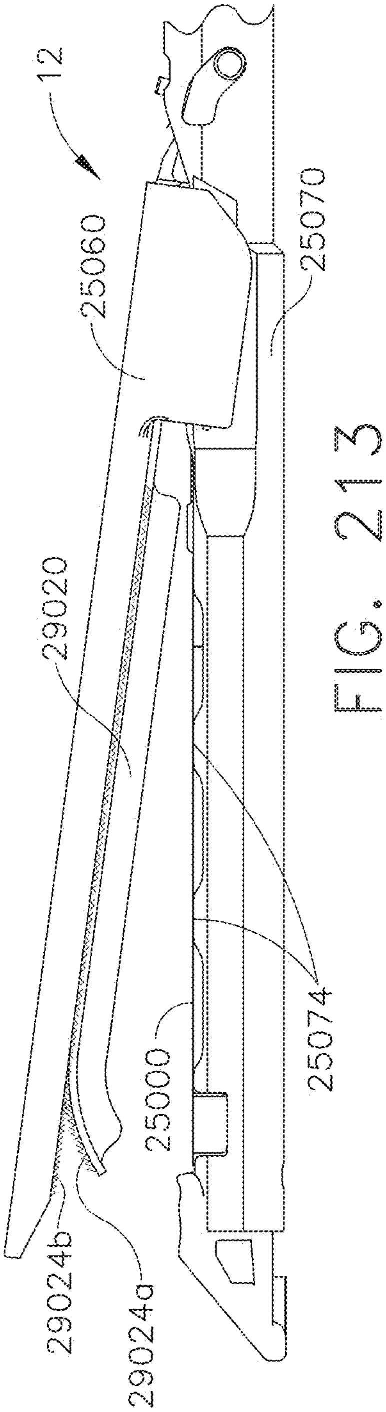
Figure 214:
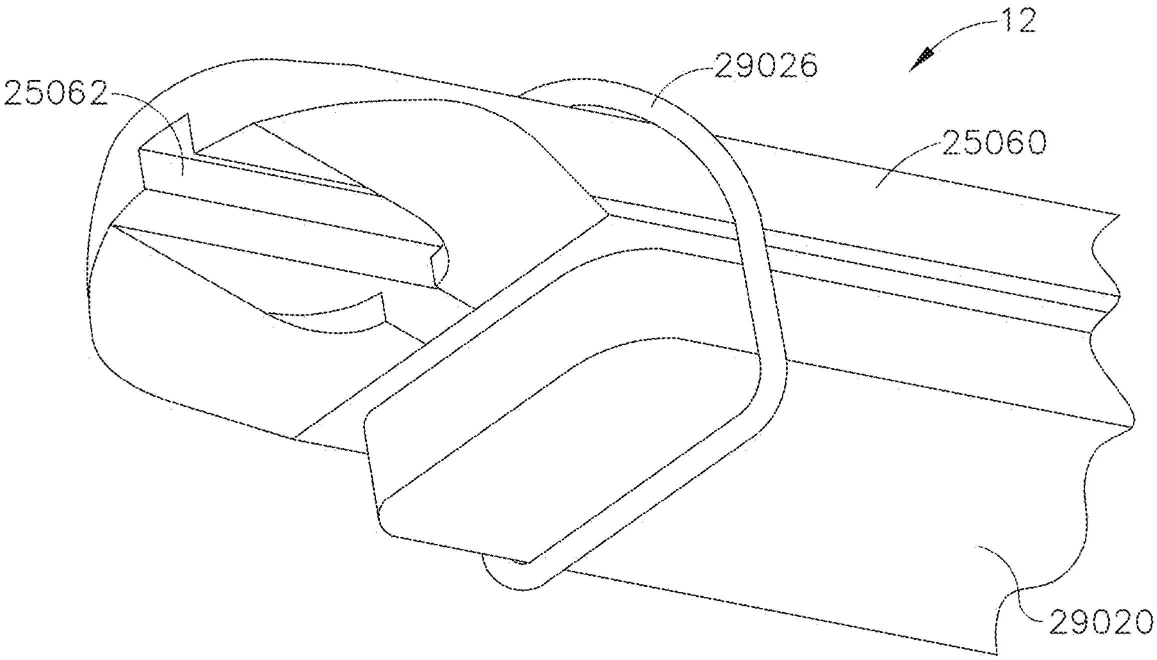
Figure 215:
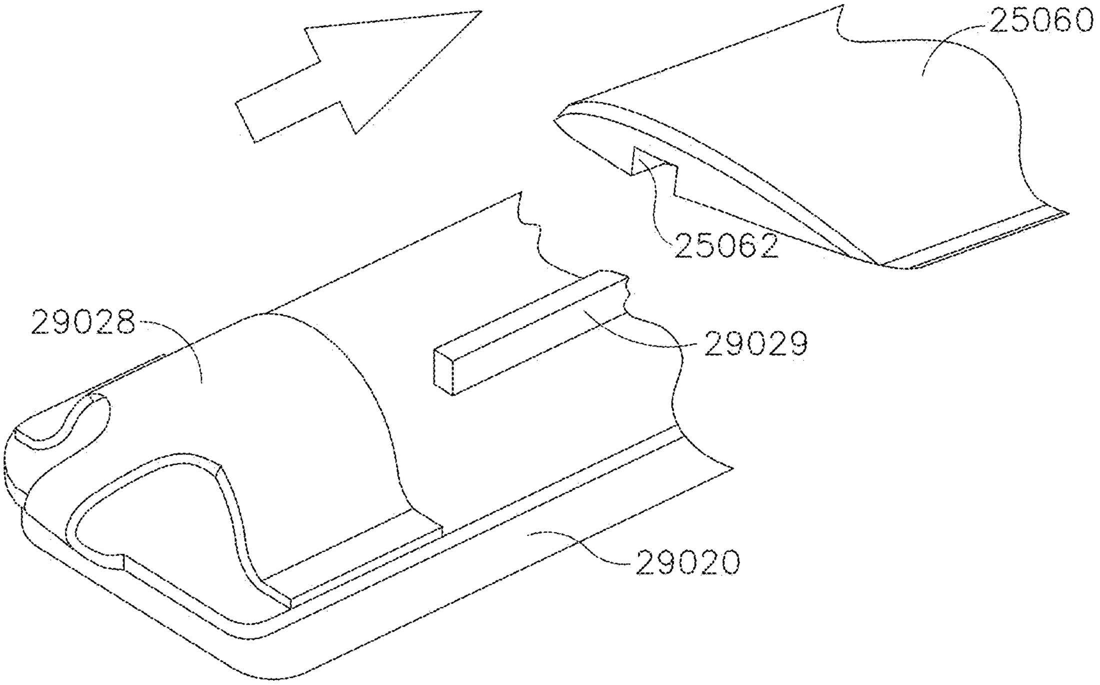
Figure 216:
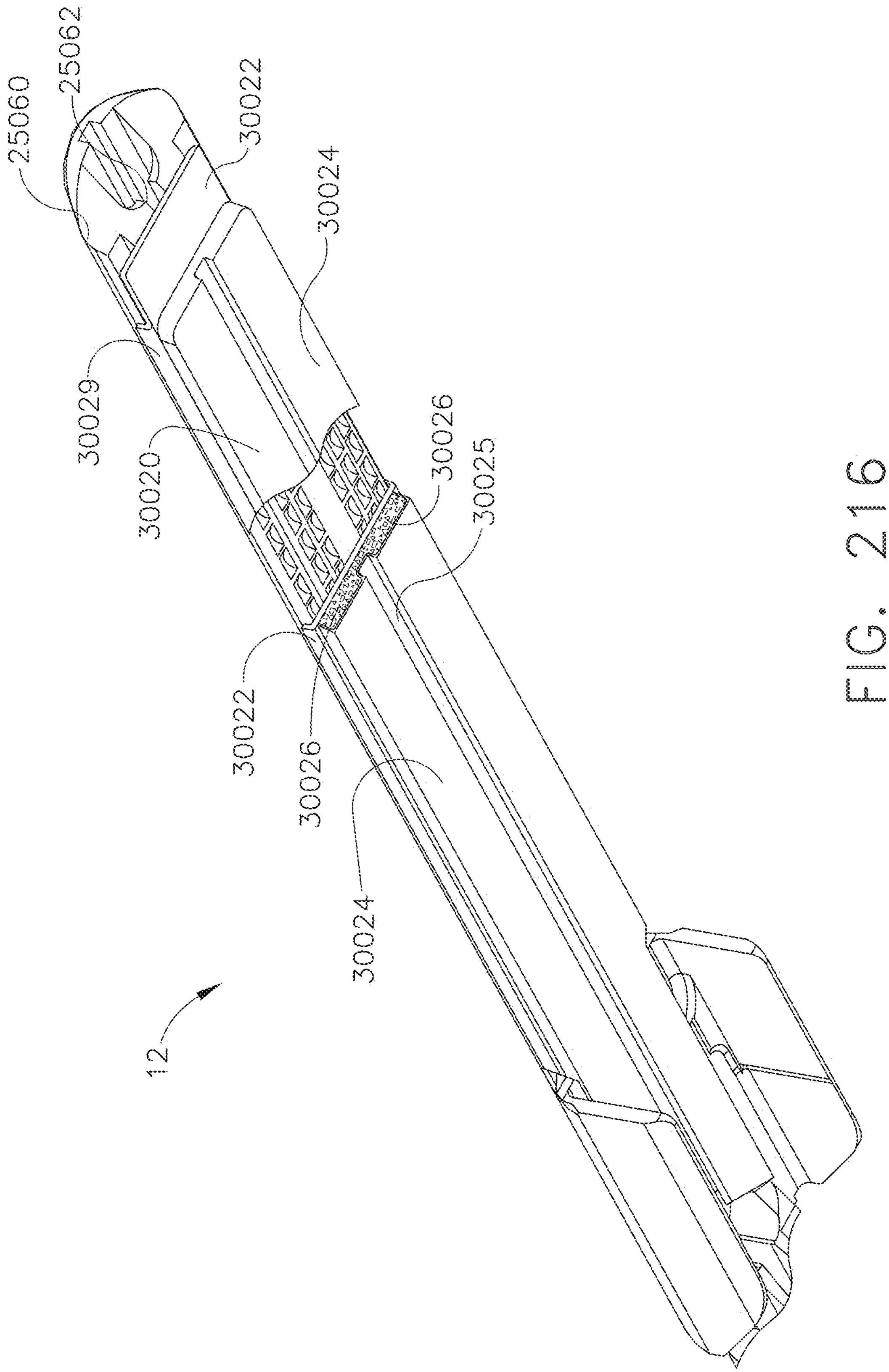
Figure 217:
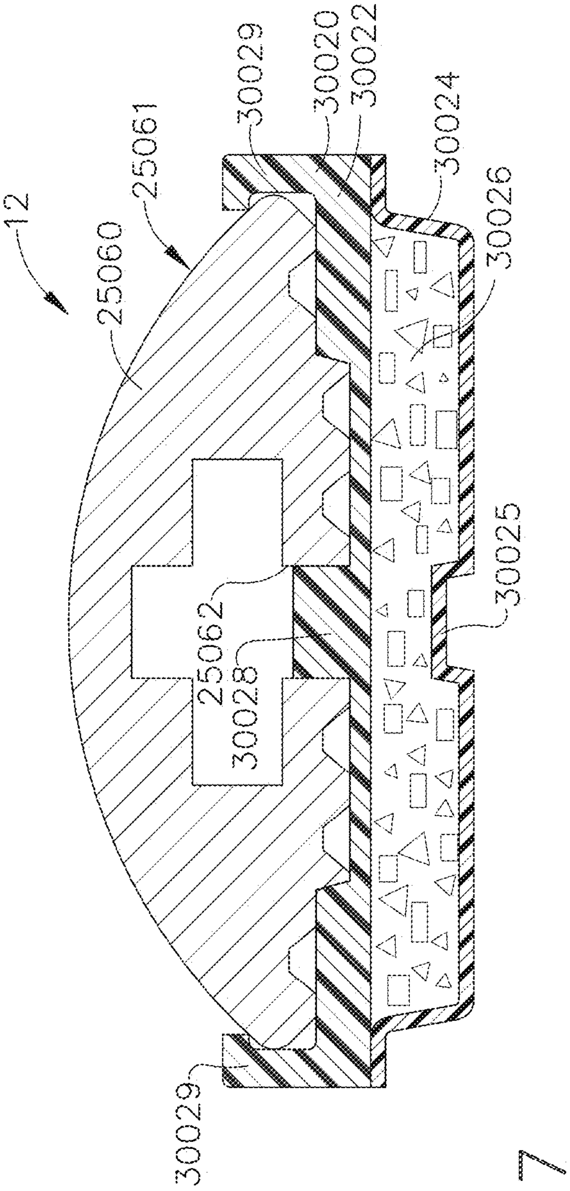
Figure 218:
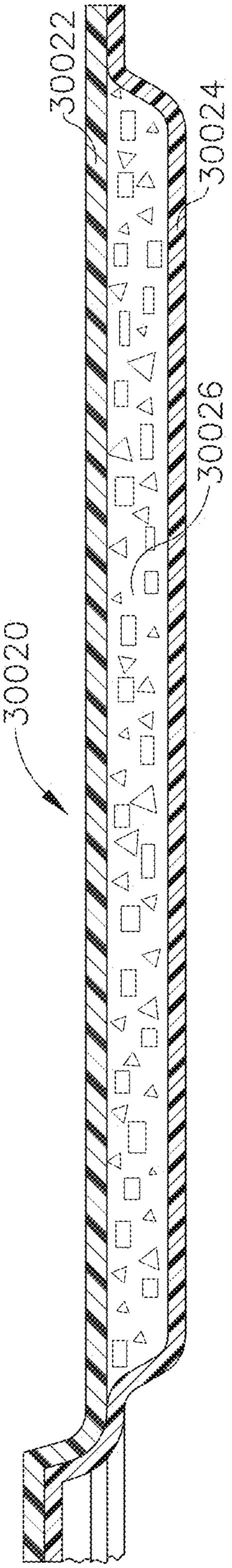
Figure 219:
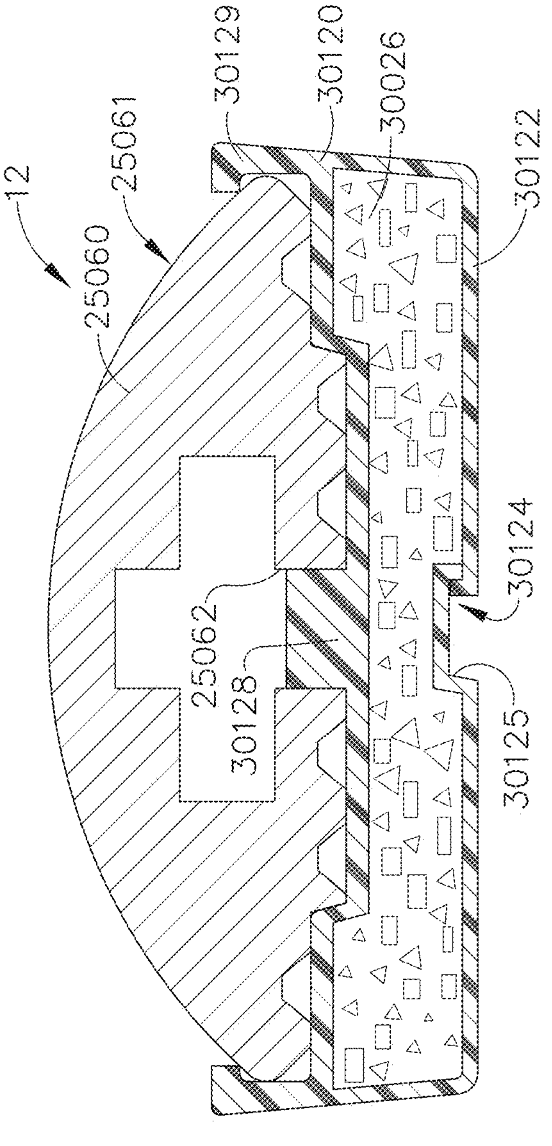
Figure 220:
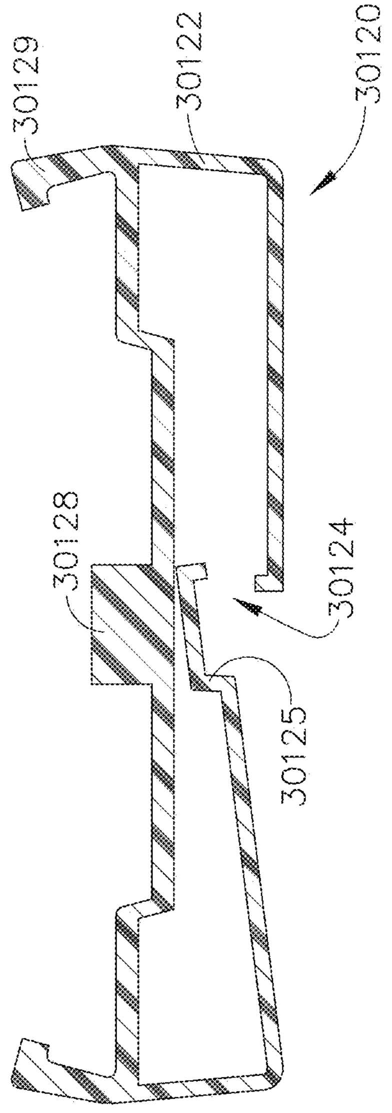
Figure 221:
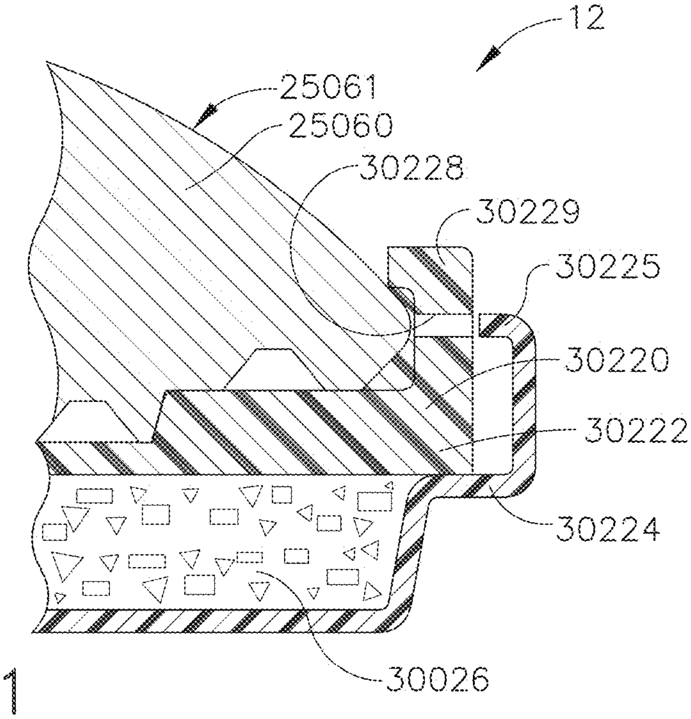
Figure 222:
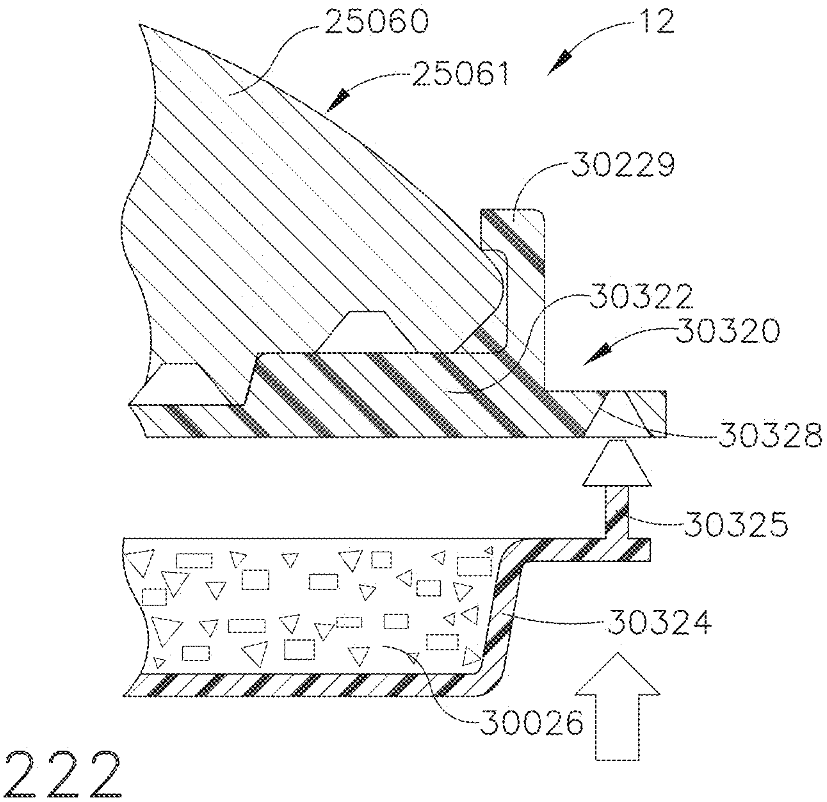
Figure 223:
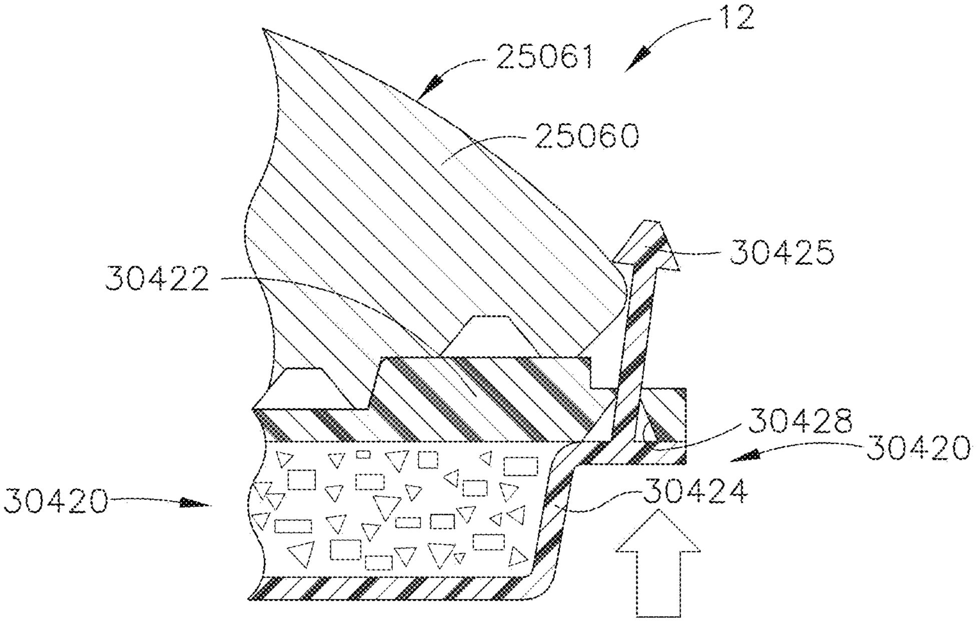
Figure 224:
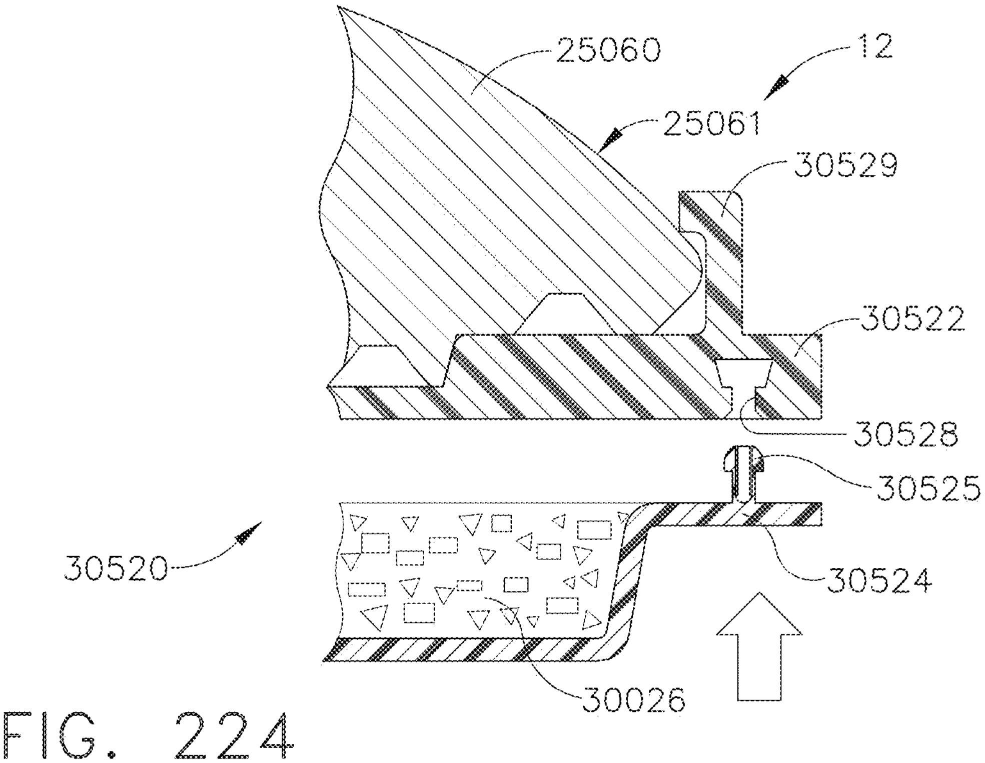
Figure 225:
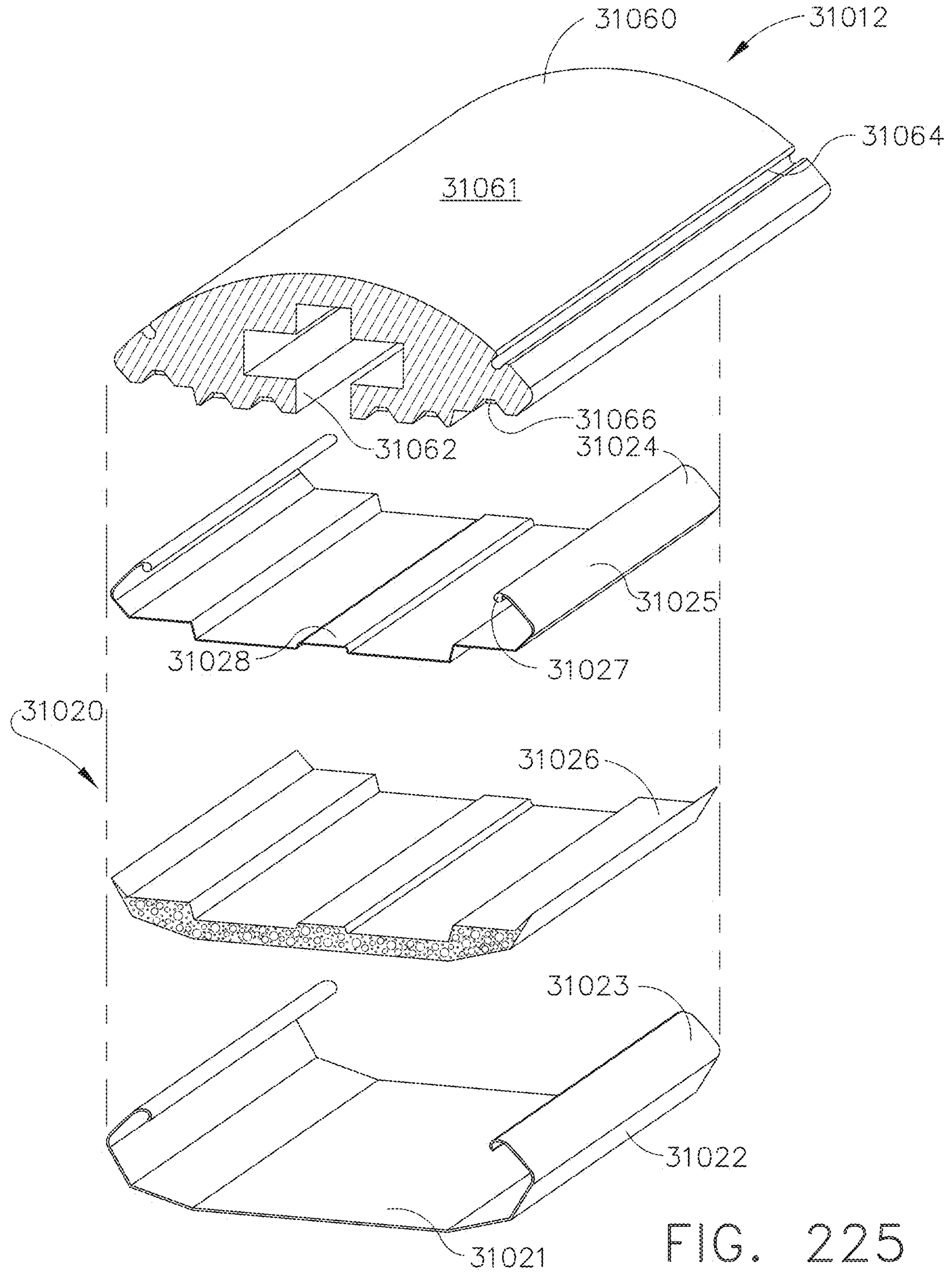
Figure 226:
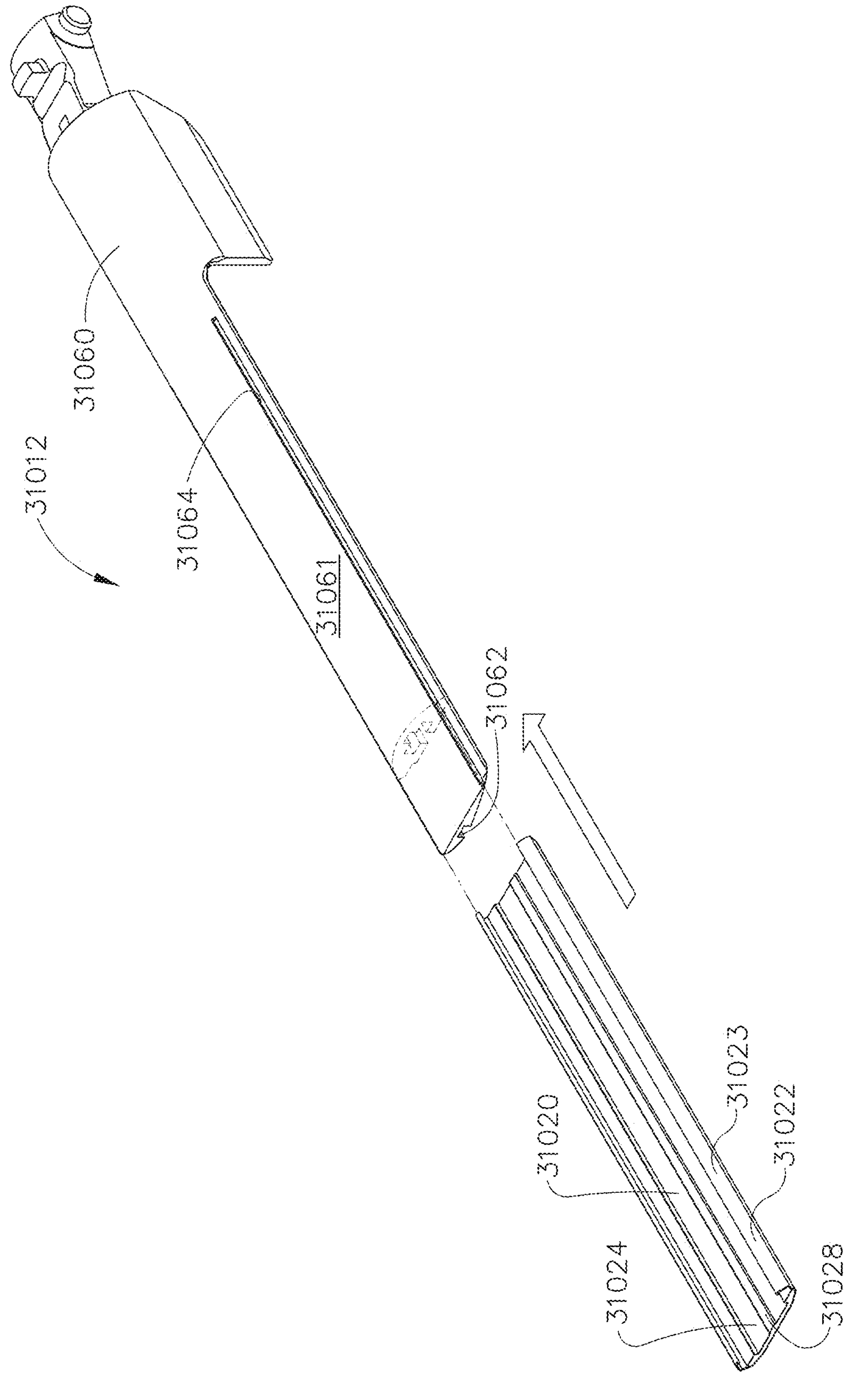
Figure 227:
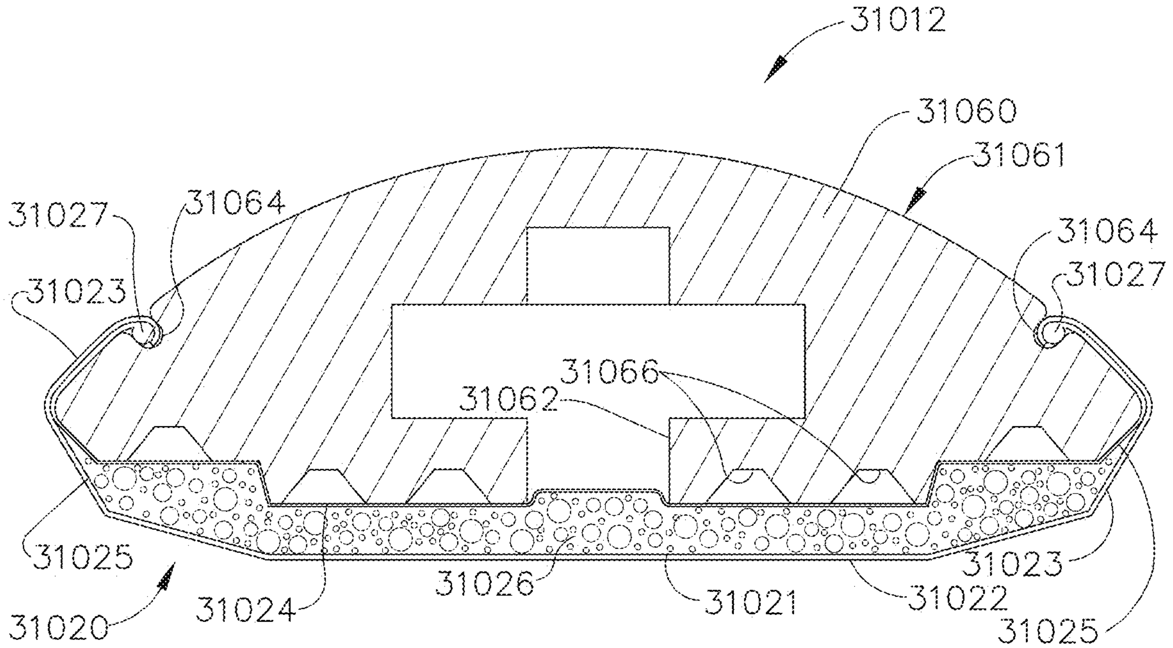
Figure 228:
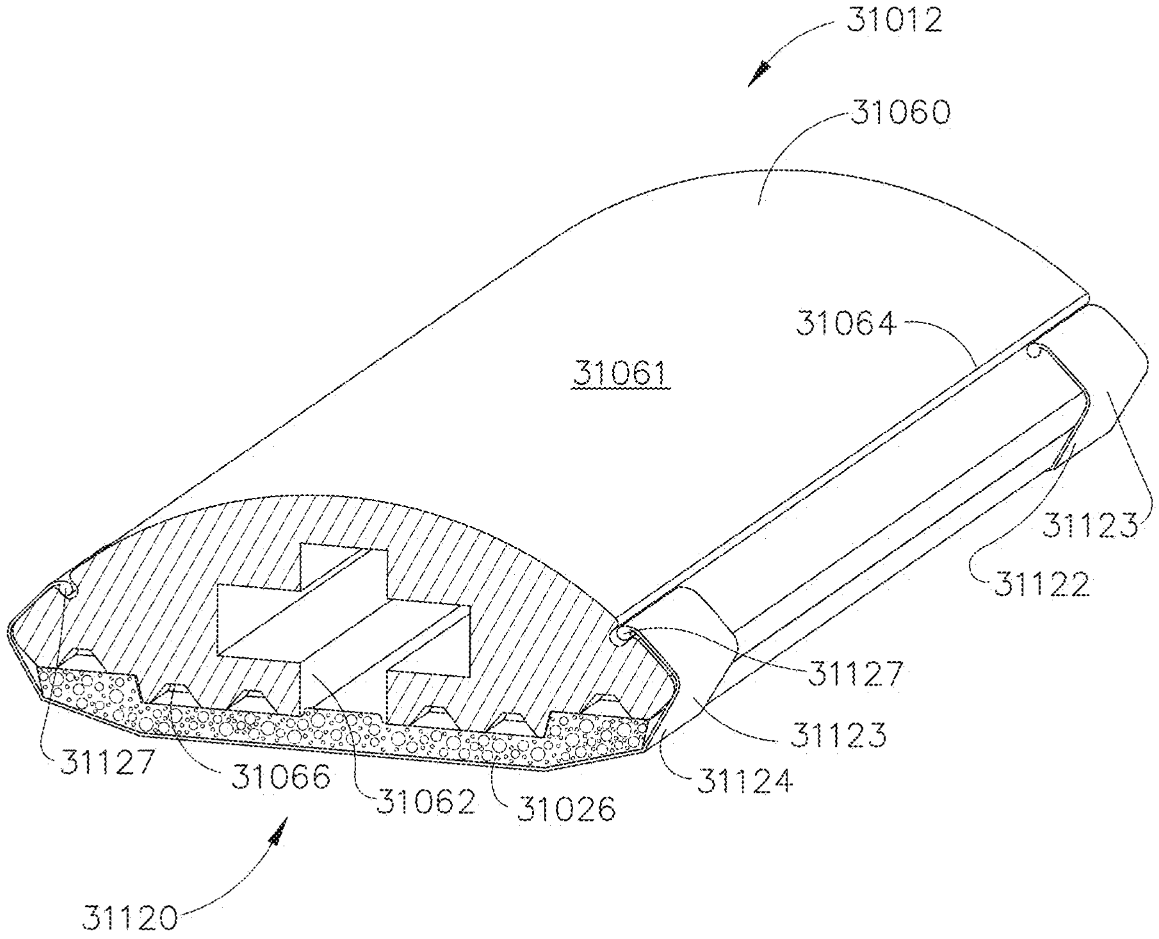
Figure 229:
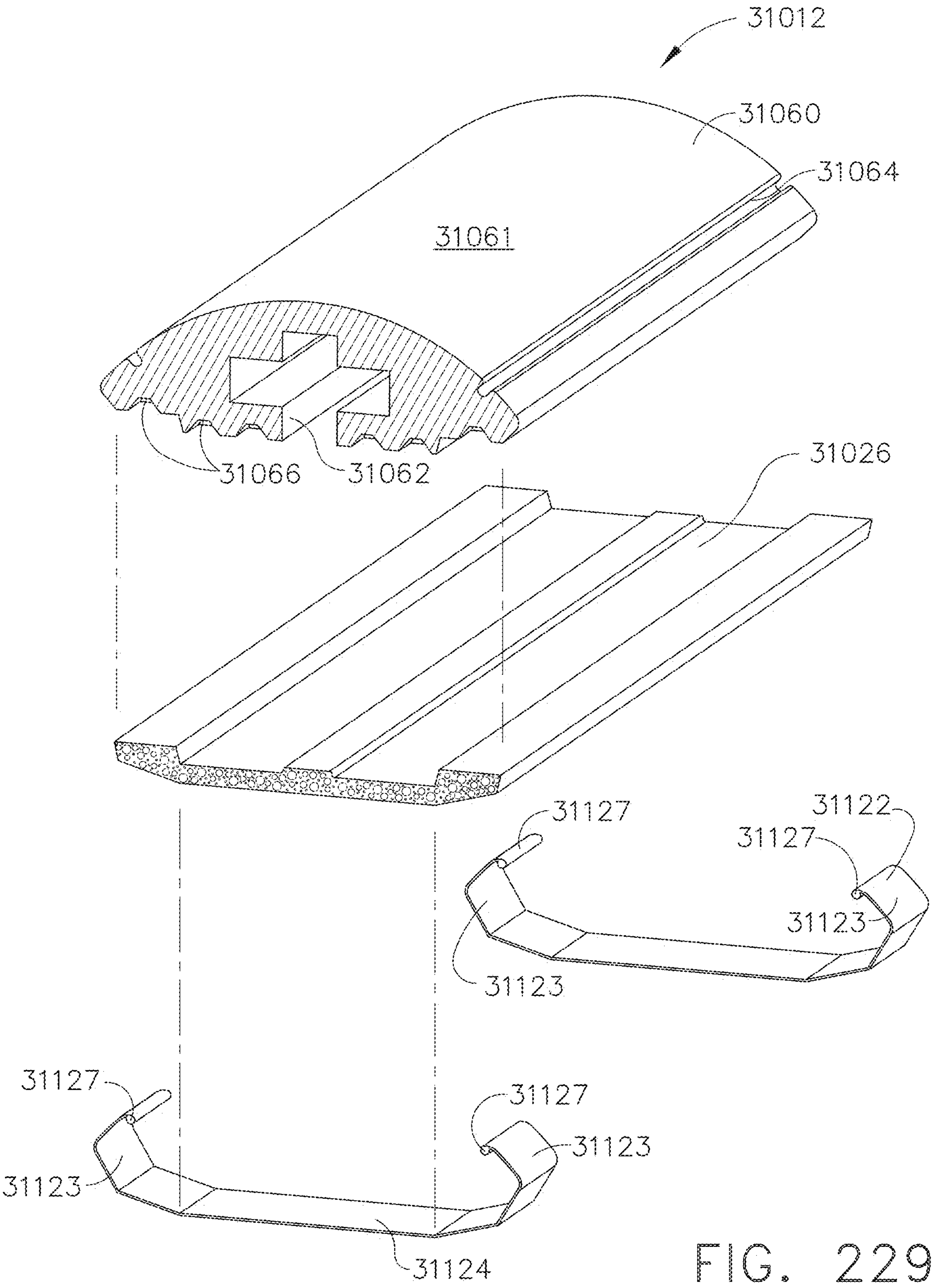
Figure 230:
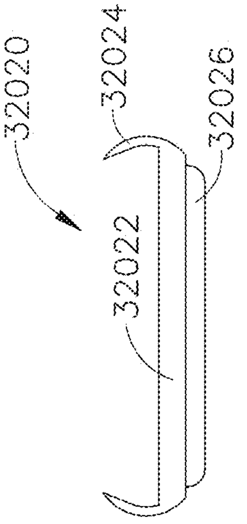
Figure 231:
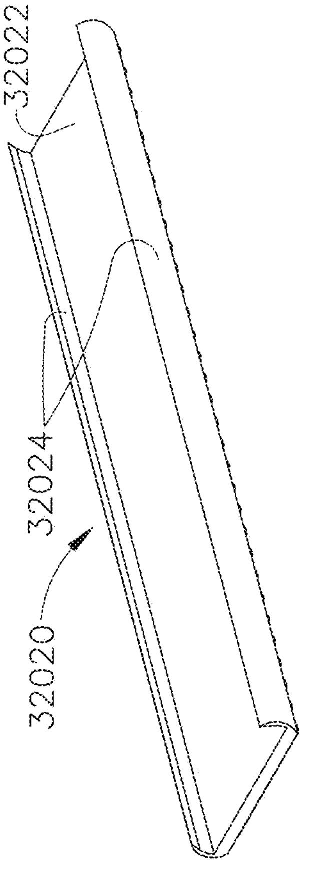
Figure 232:
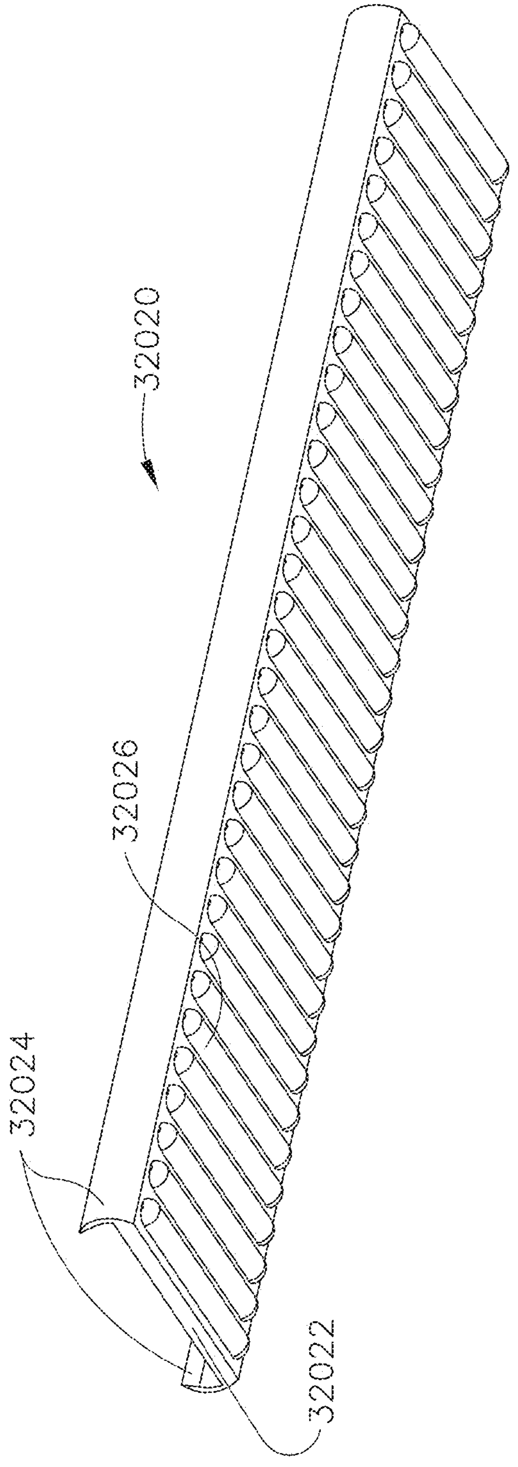
Figure 233:
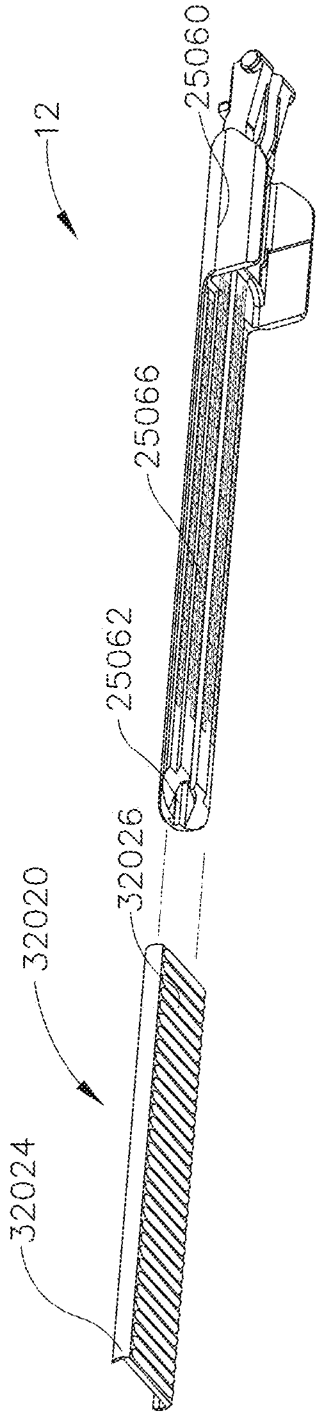
Figure 234:
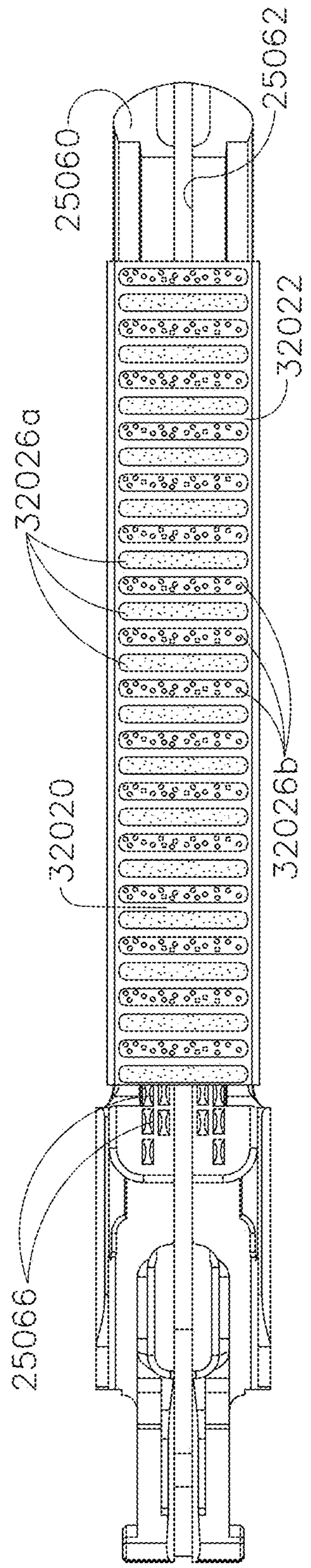
Figure 235:
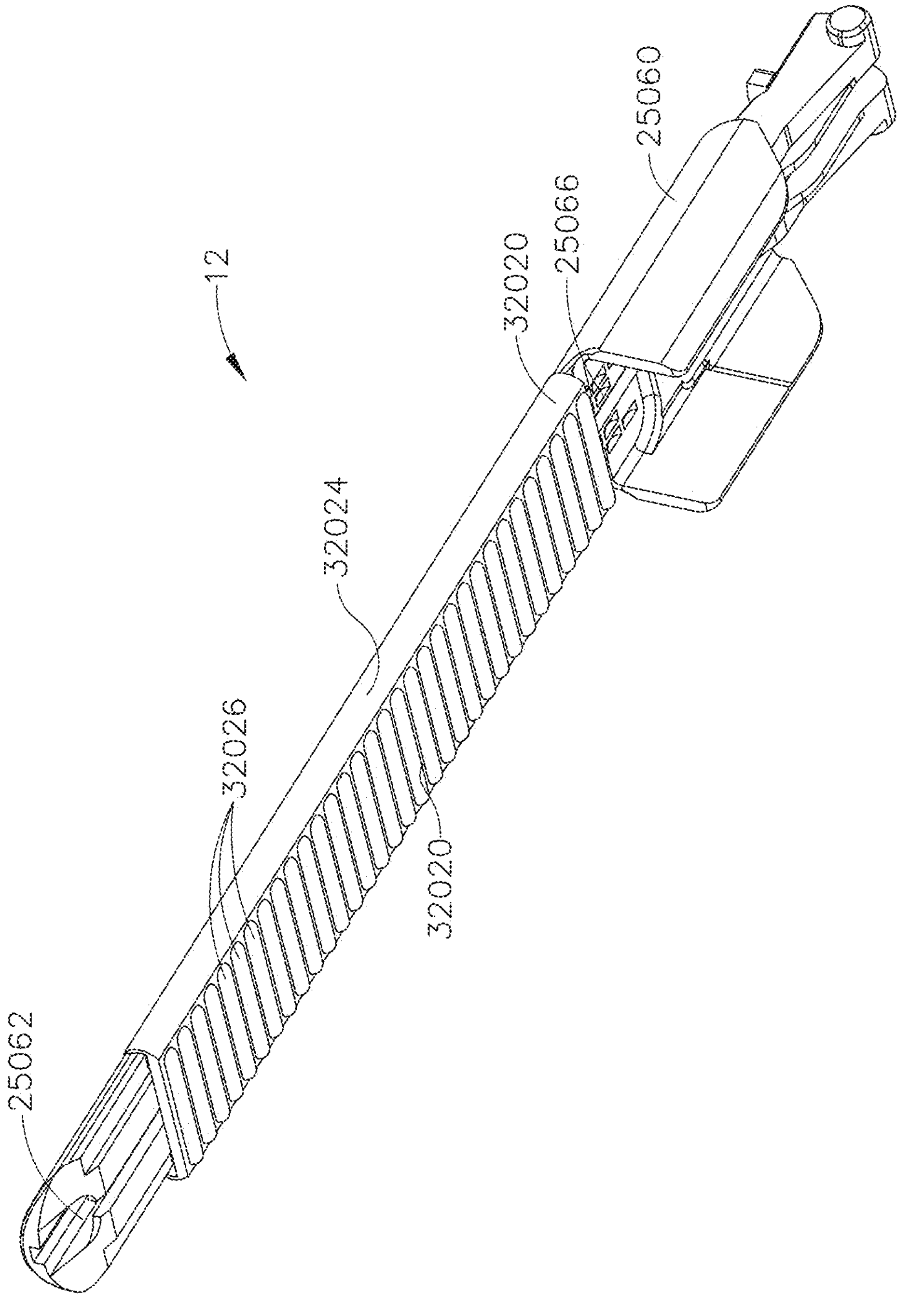
Figure 236:
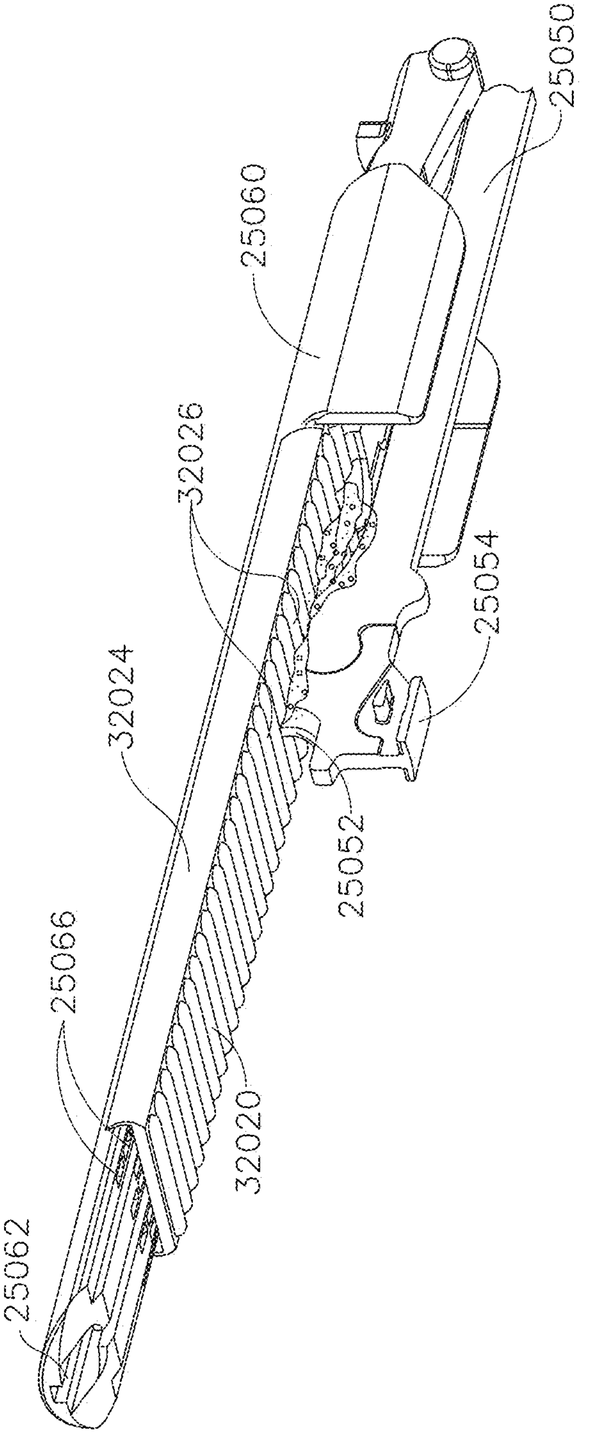
Figure 237:
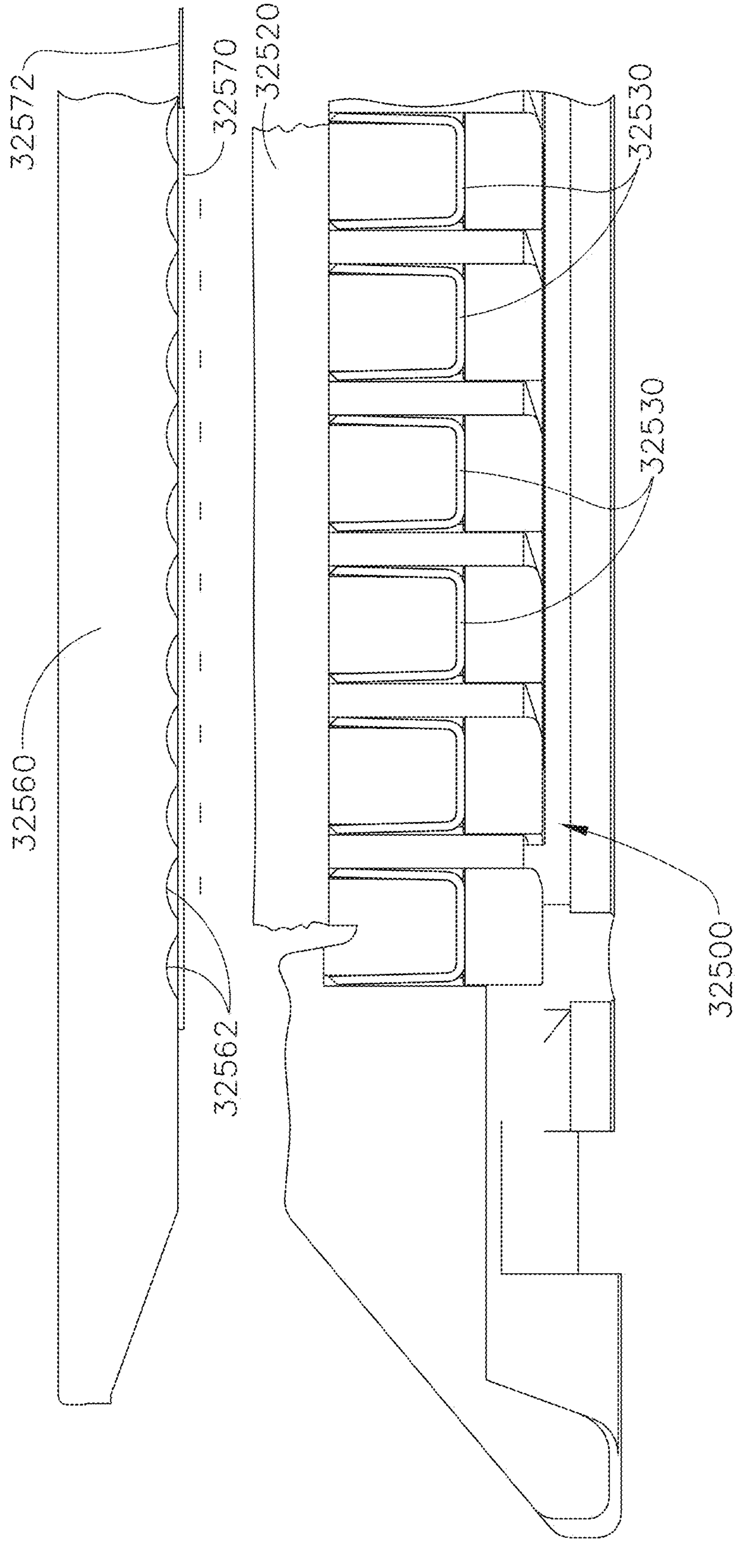
Figure 238:
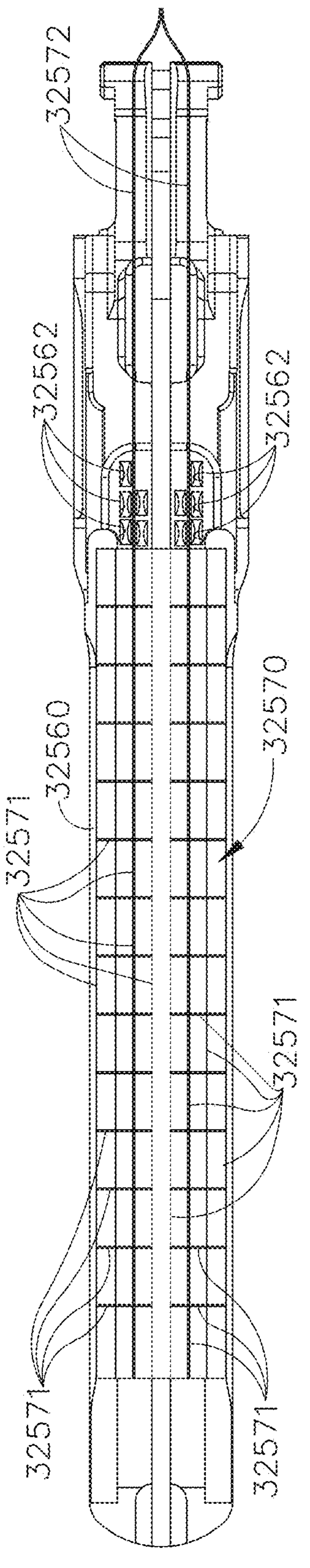
Figure 239:
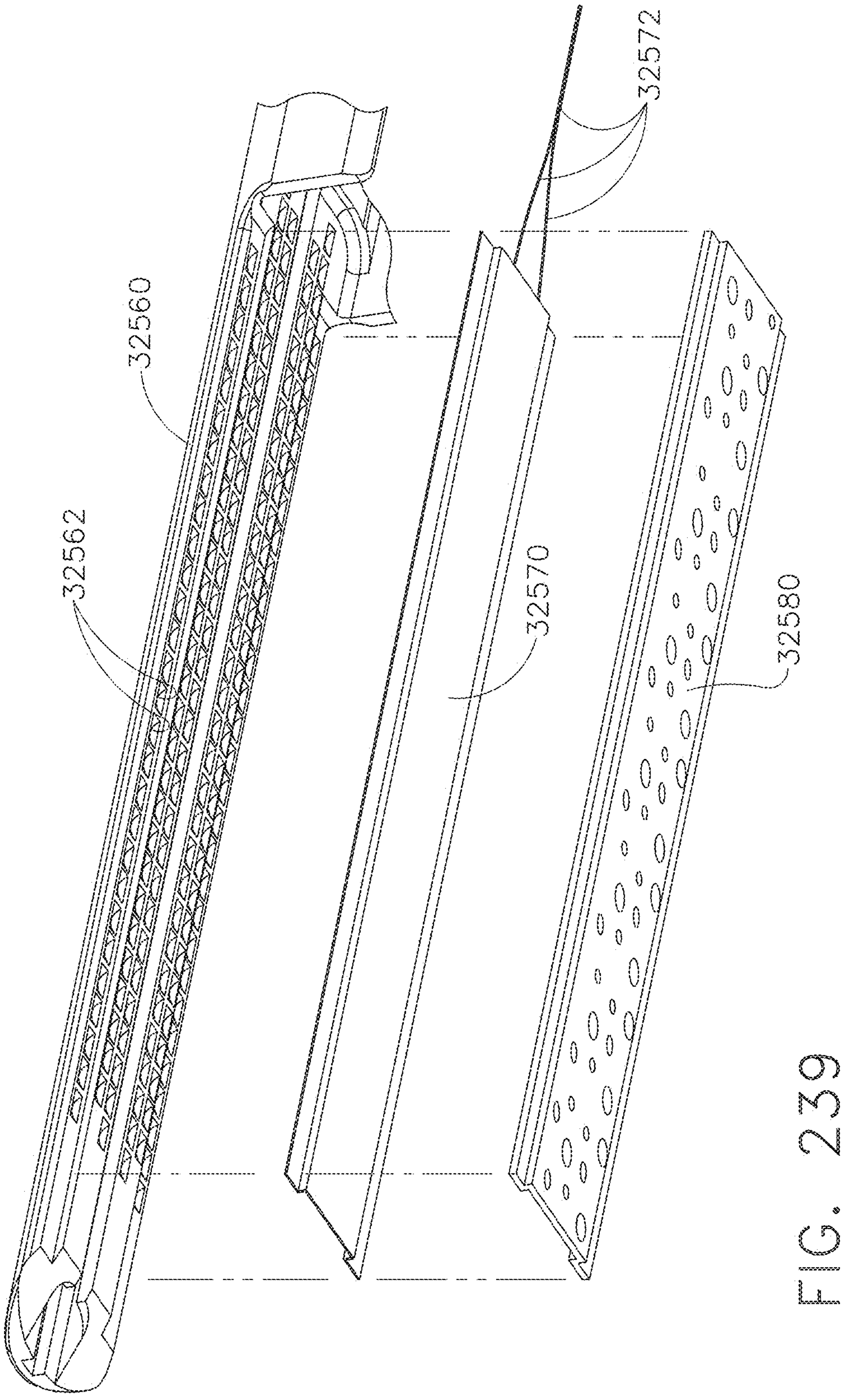
Figure 240:
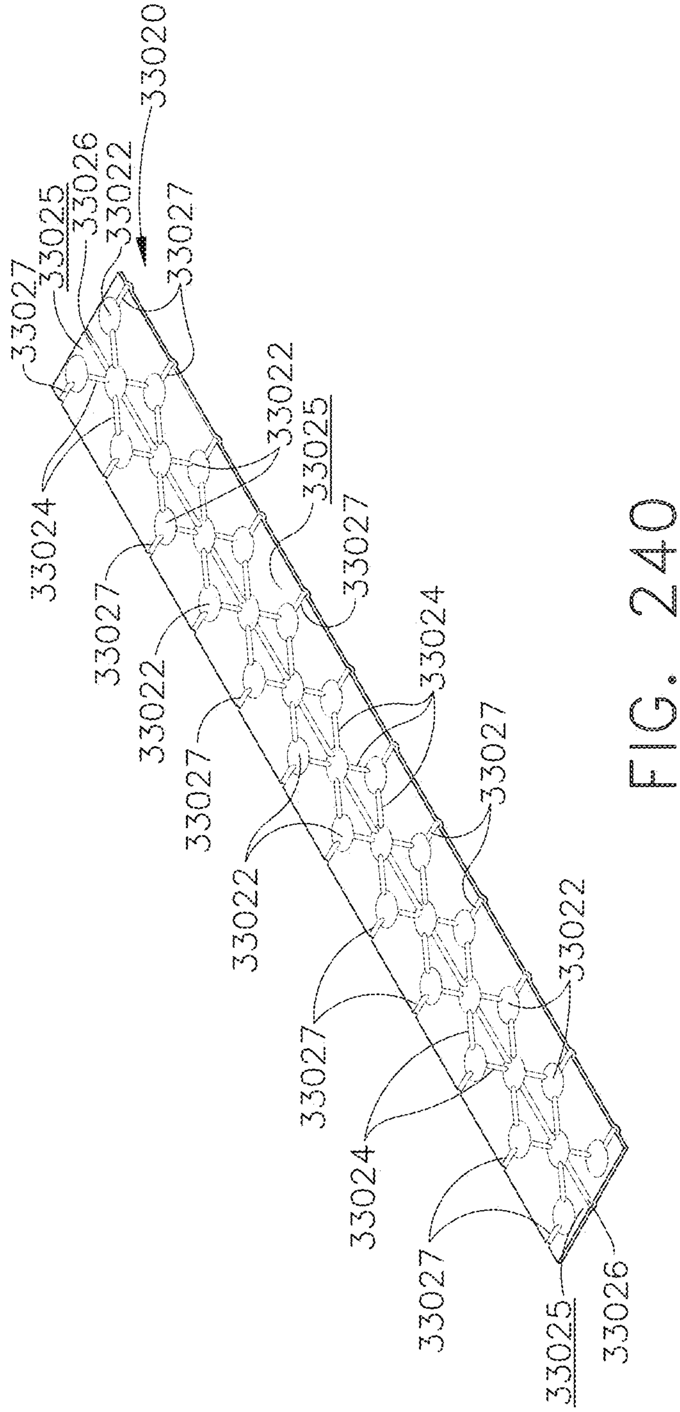
Figure 241:
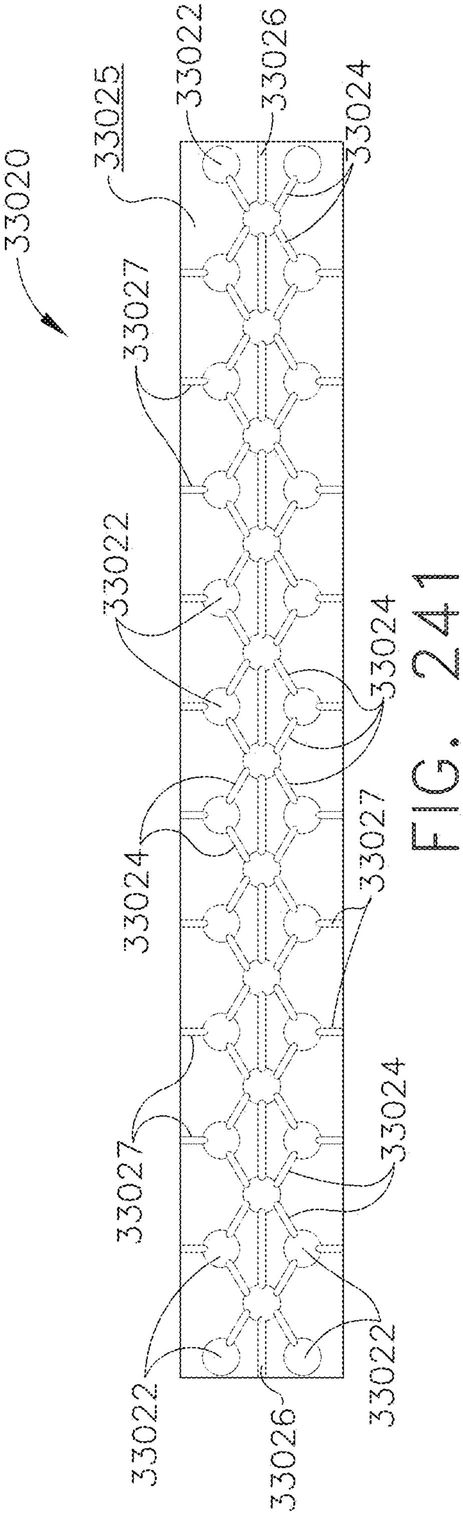
Figure 240A:
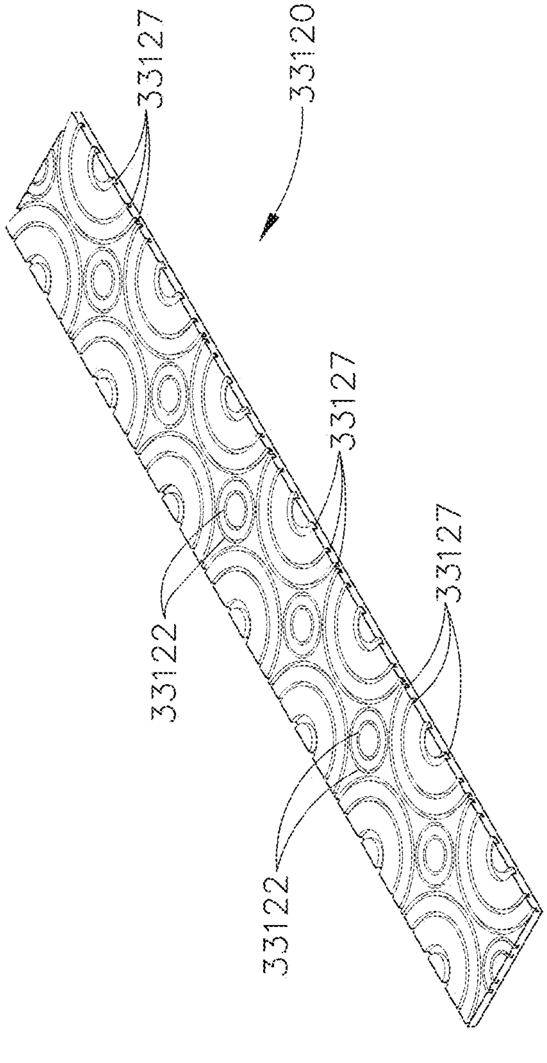
Figure 241A:
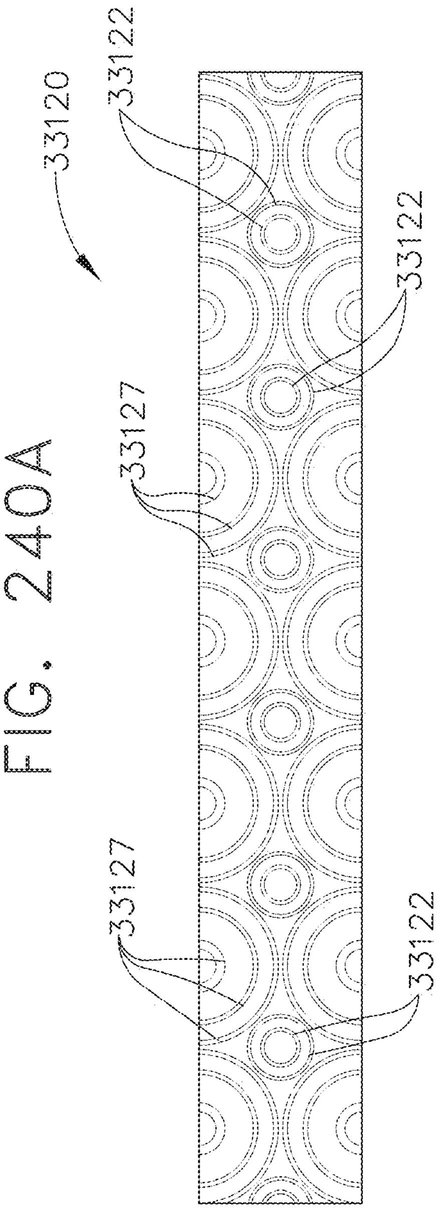
Figure 242:
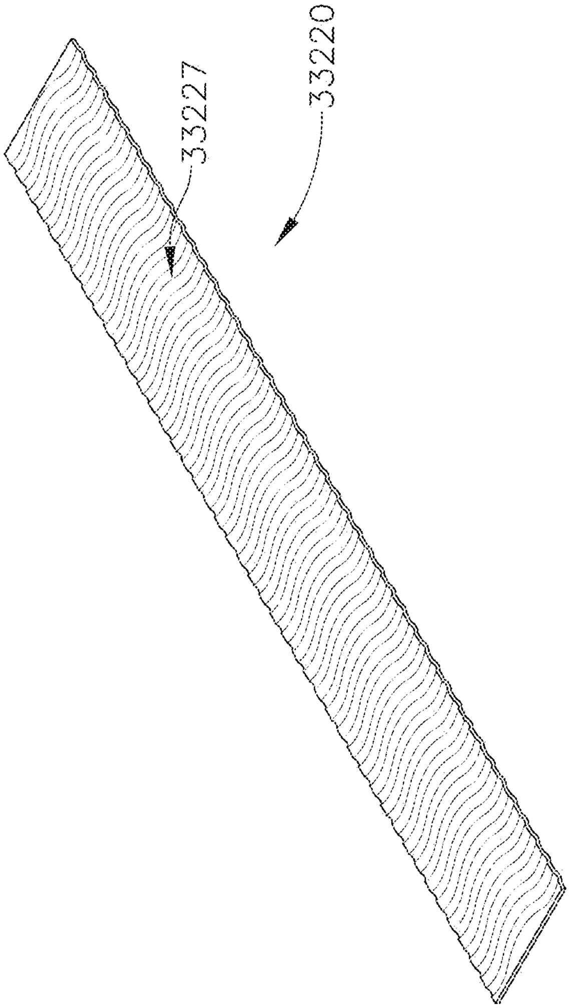
Figure 243:
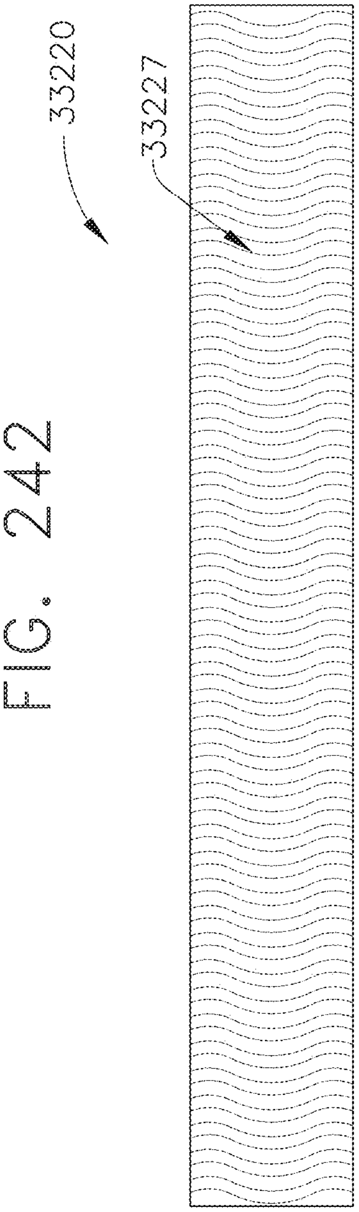
Figure 244:
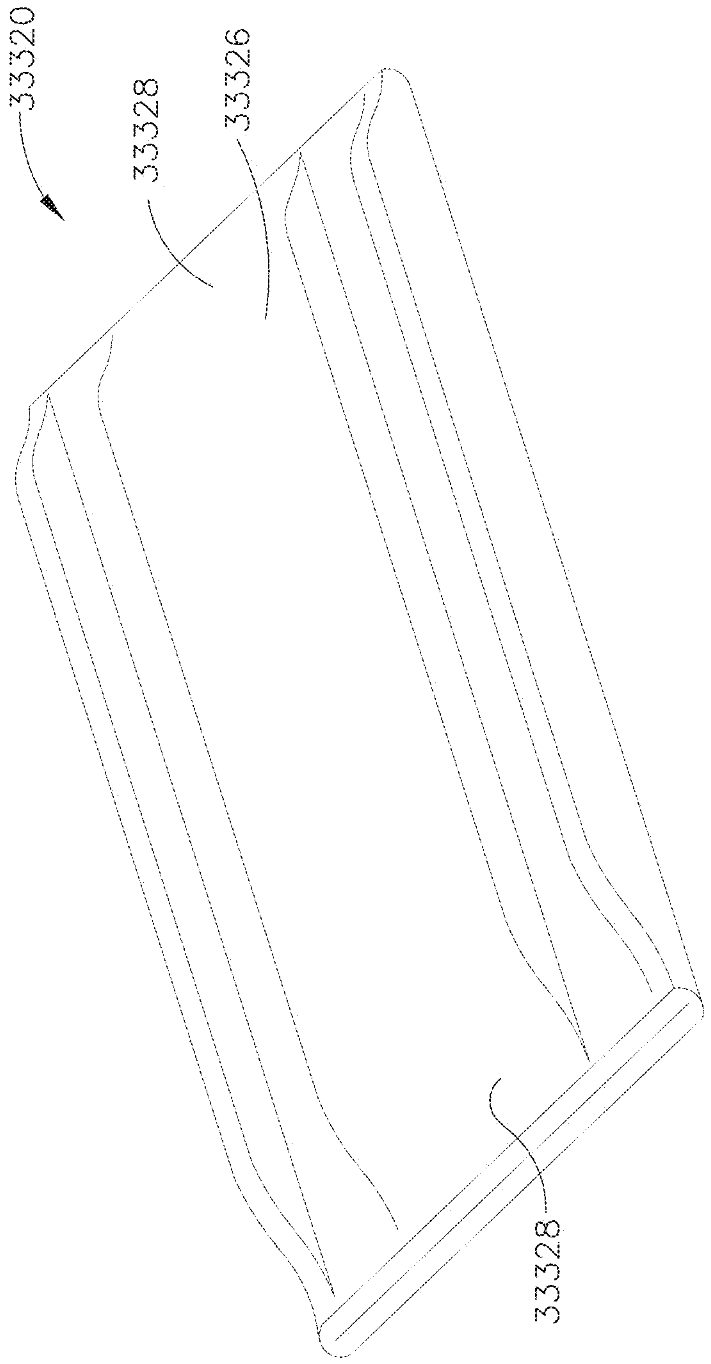
Figure 245:
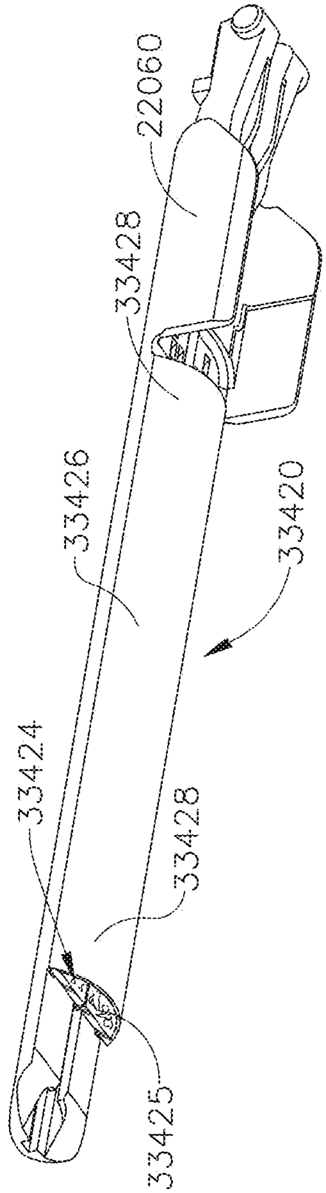
Figure 247:
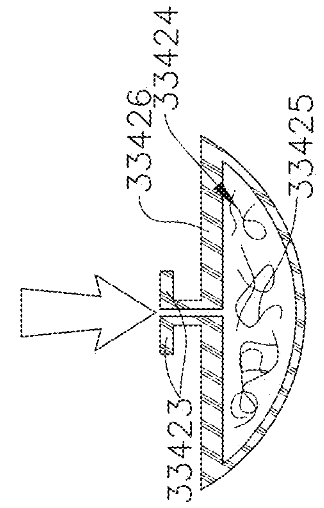
Figure 246:
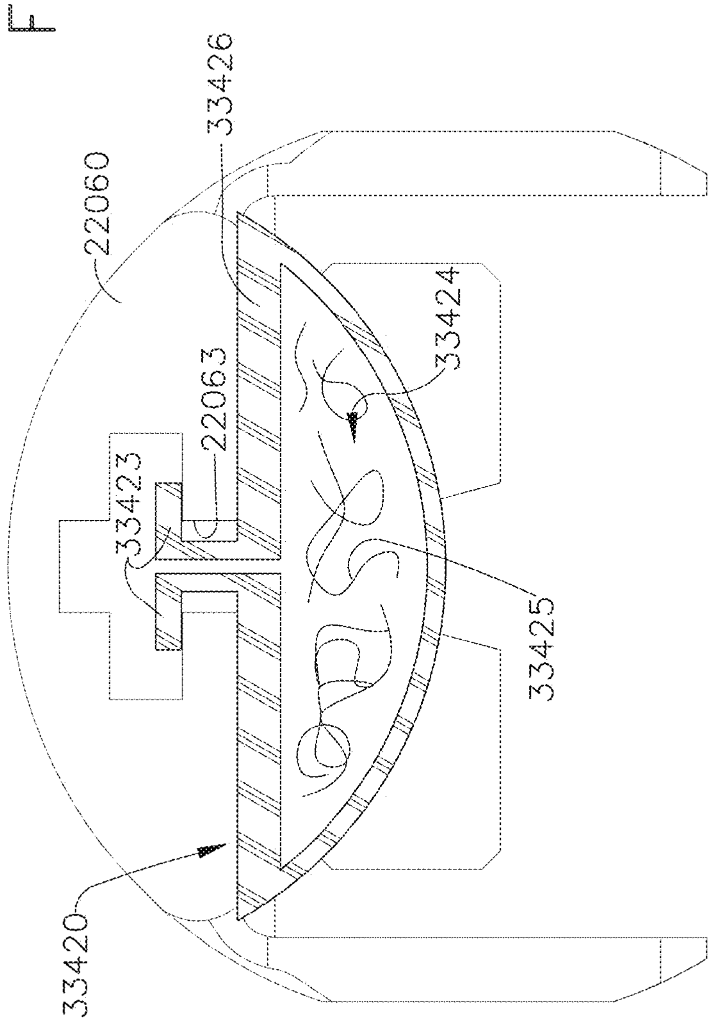
Figure 248:
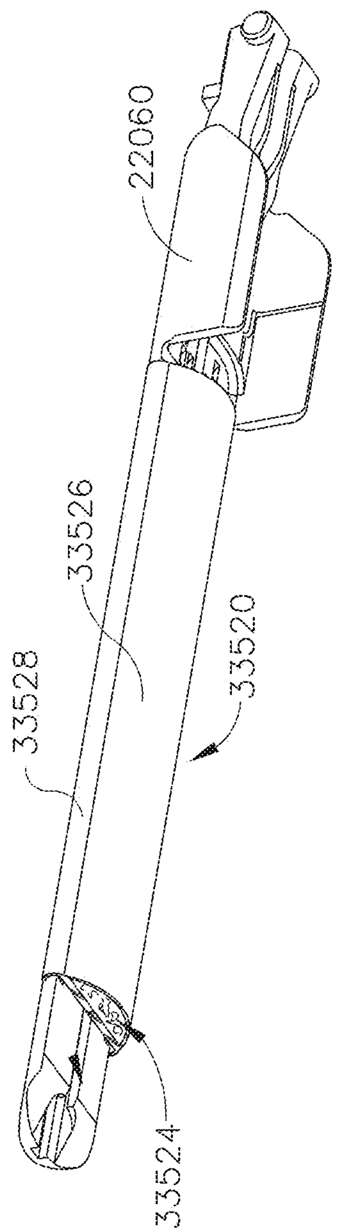
Figure 250:
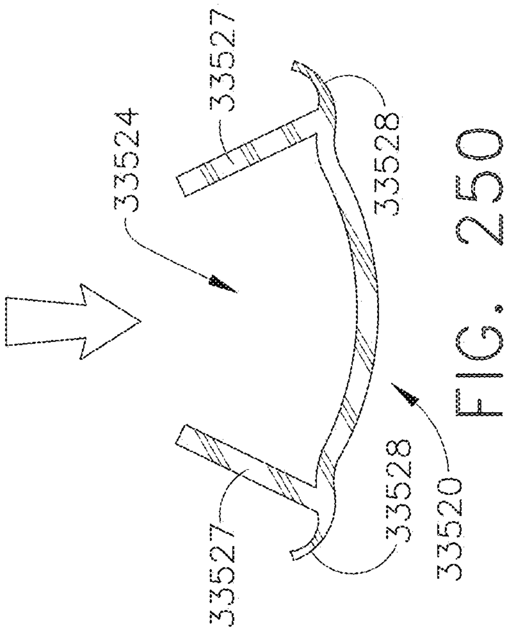
Figure 249:
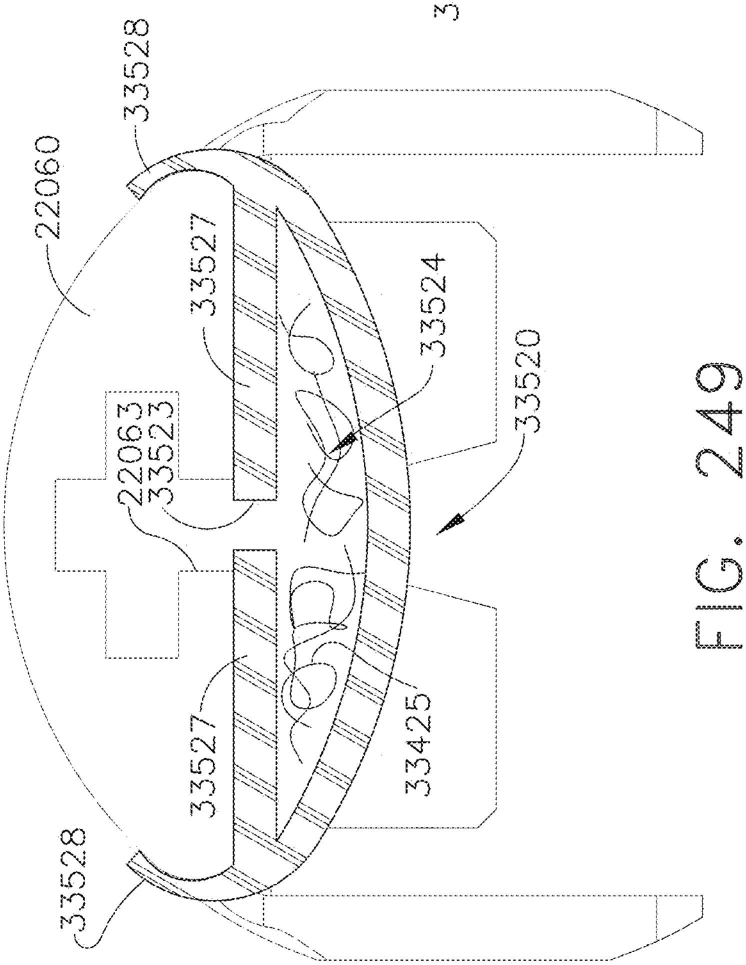
Figure 251:
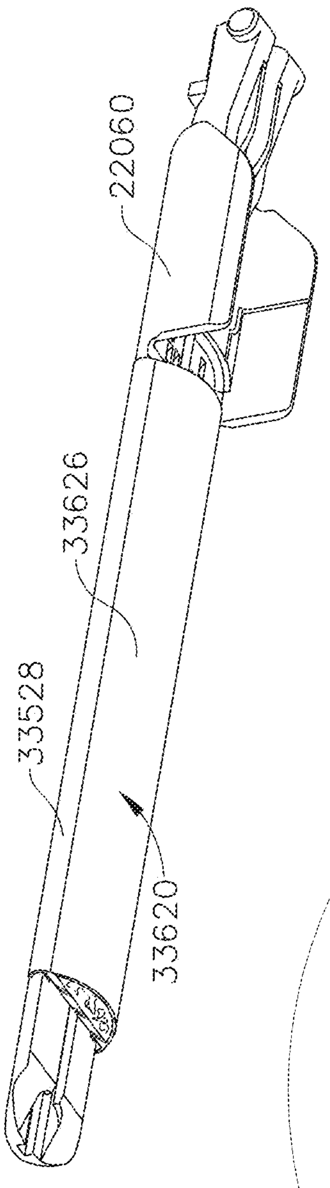
Figure 252:
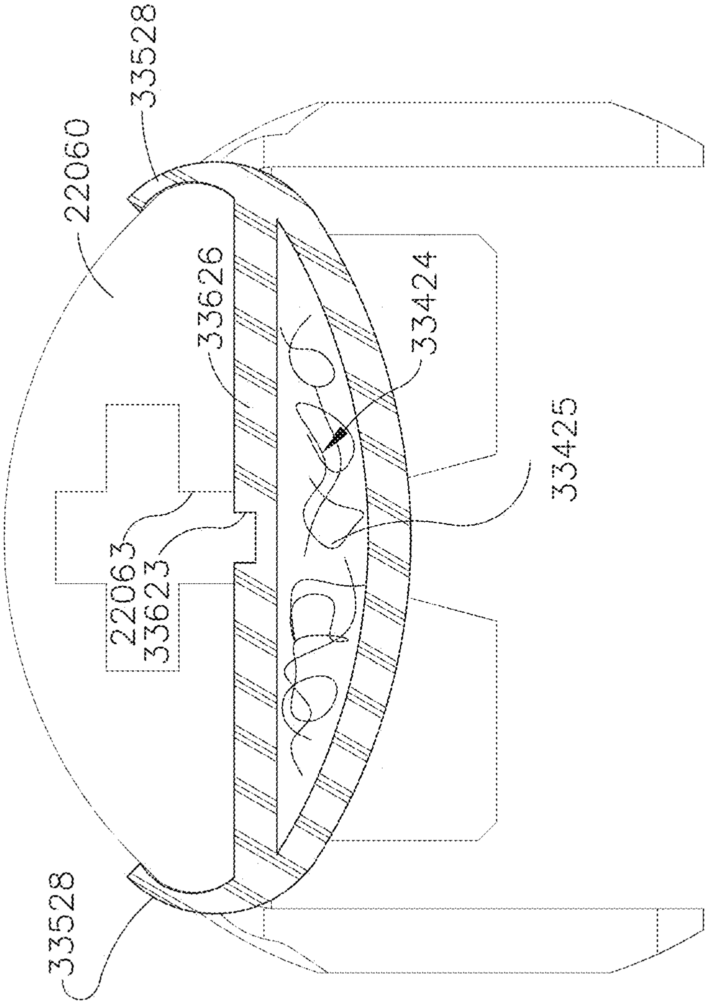
Figure 253:
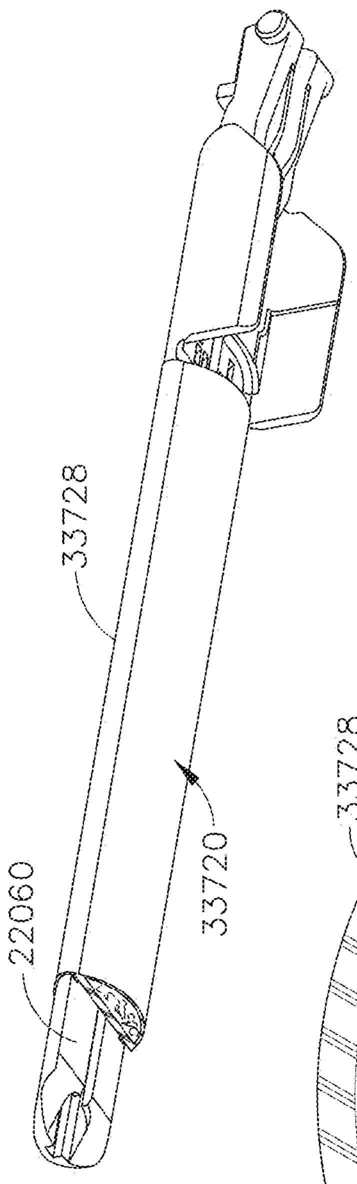
Figure 254:
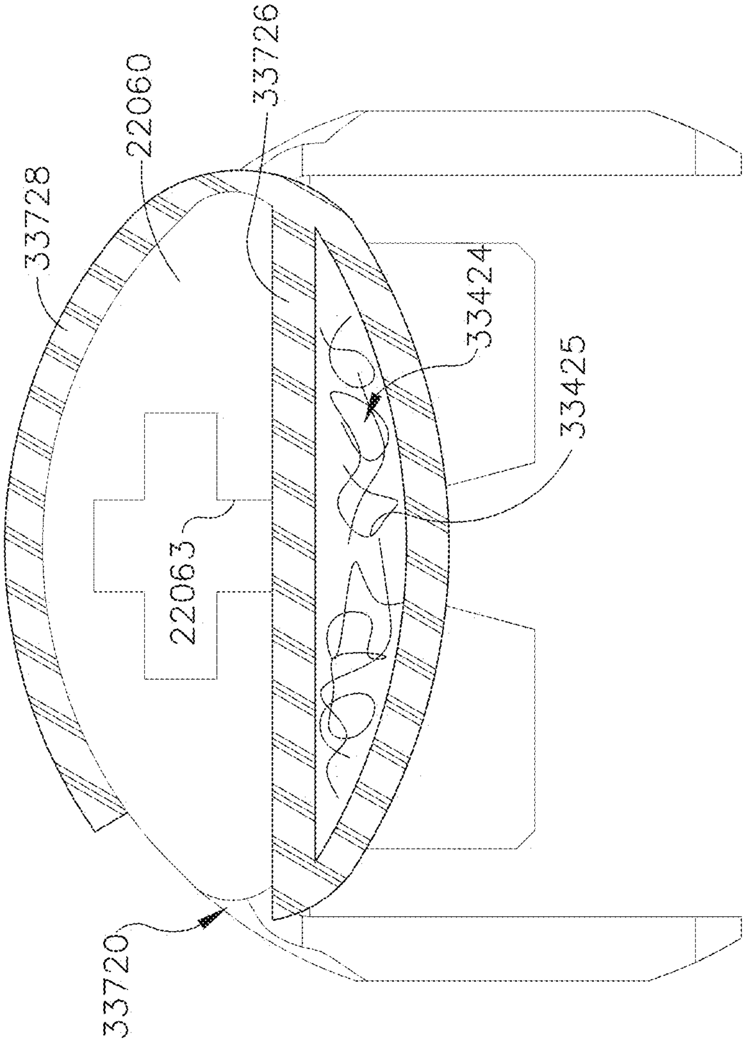
Figure 255:
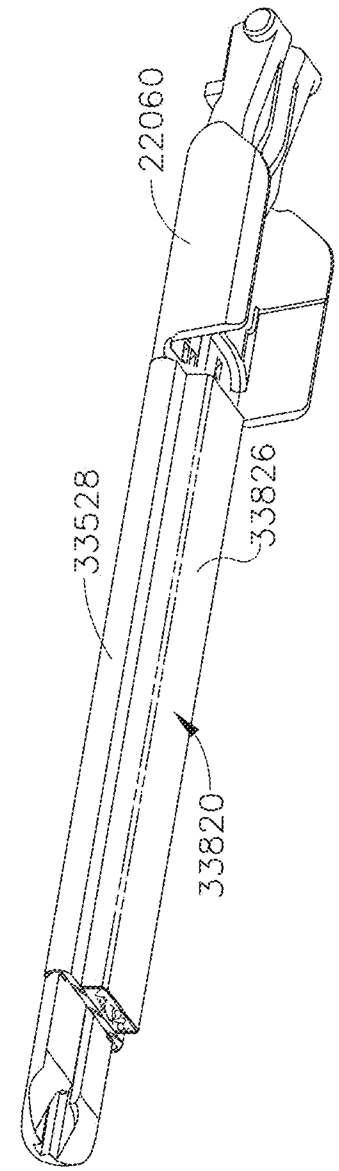
Figure 256:
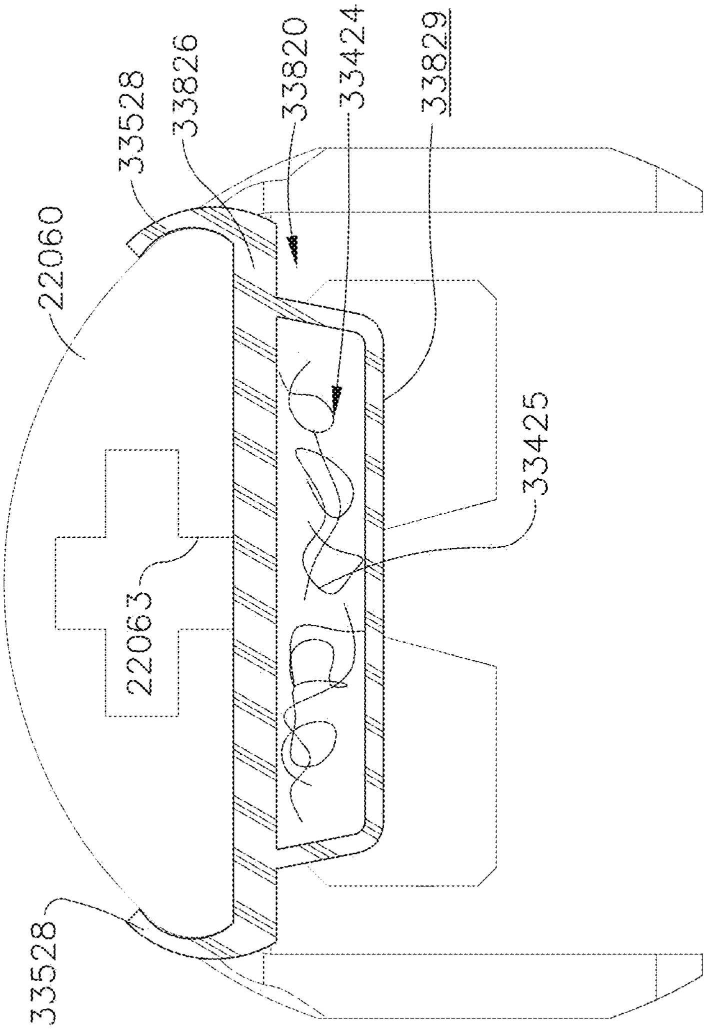
Figure 257:
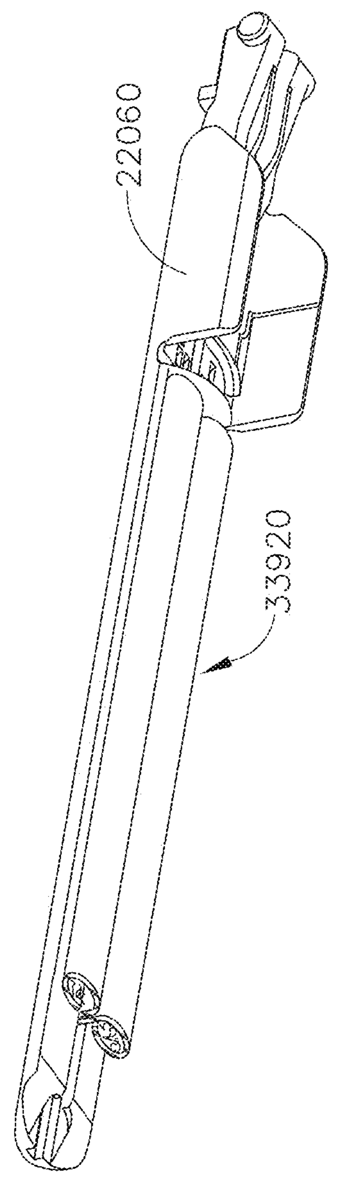
Figure 258:
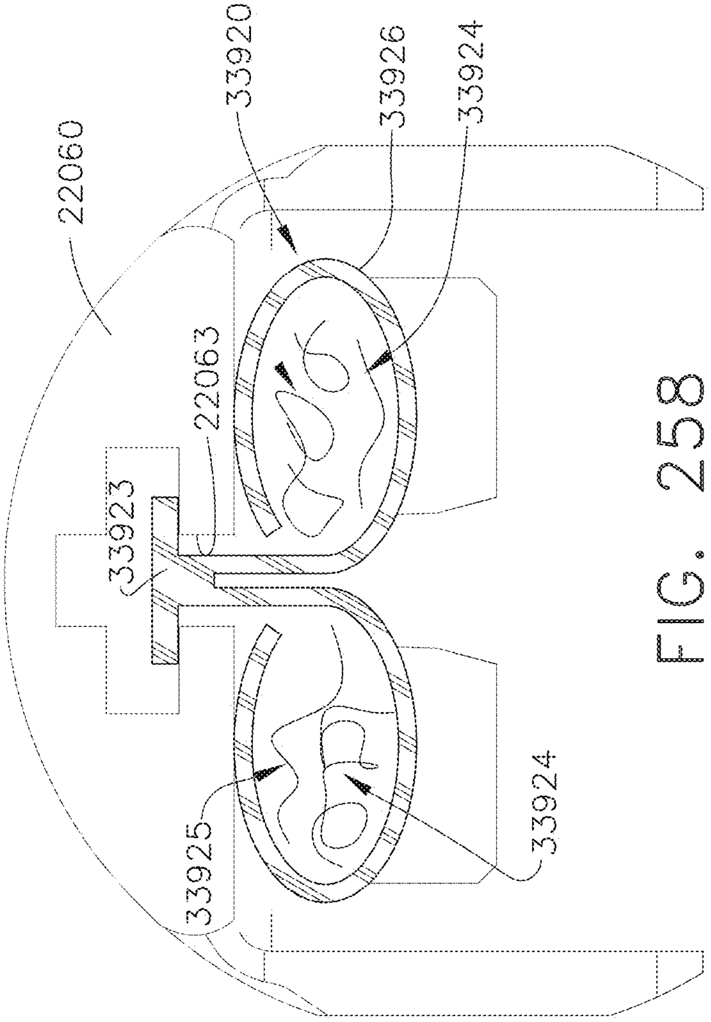

FIG. 124 is a detail view of the capsules of the tissue thickness compensator of FIG. 123;

FIG. 125 is a diagram illustrating the anvil and the tissue thickness compensator of FIG. 123 positioned relative to tissue which is to be stapled by staples from a staple cartridge positioned on the opposite side of the tissue;

FIG. 126 is a diagram illustrating the anvil of FIG. 123 moved toward the staple cartridge of FIG. 125 and staples partially fired from the staple cartridge;

FIG. 127 is a diagram illustrating the staples of FIG. 126 in a fully-fired configuration and the capsules of the tissue thickness compensator of FIG. 123 in a ruptured state;

FIG. 128 is a diagram illustrating a staple of FIG. 126 in a misfired condition;

FIG. 129 is a diagram illustrating the staples of FIG. 126 in a fully-fired configuration and the tissue thickness compensator of FIG. 123 in at least partially transected condition;

FIG. 130 is a cross-sectional perspective view of an alternative embodiment of a tissue thickness compensator in accordance with at least one embodiment;

FIG. 131 is a perspective view of an alternative embodiment of a tissue thickness compensator comprising a plurality of capsules aligned with a cutting member of a surgical stapling instrument;

FIG. 132 is a detail view of the capsules of FIG. 131;

FIG. 133 is a cross-sectional view of the tissue thickness compensator of FIG. 131 comprising a plurality of capsules aligned with a knife slot of an anvil of a surgical stapling instrument;

FIGS. 134 and 135 illustrate an alternative embodiment of a tissue thickness compensator being attached to an anvil;

FIG. 136 is a cross-sectional exploded view of an anvil and a compensator in accordance with at least one embodiment;

FIG. 137 illustrates the compensator of FIG. 136 attached to the anvil;

FIG. 138 is a partial perspective view of a tissue thickness compensator and a cutting member incising the tissue thickness compensator in accordance with at least one embodiment;

FIG. 139 is a partial cross-sectional view of an alternative embodiment of a tissue thickness compensator in accordance with at least one embodiment;

FIG. 140 is a partial cross-sectional view of another alternative embodiment of a tissue thickness compensator in accordance with at least one embodiment;

FIG. 141 is an illustration depicting a tissue thickness compensator comprising a plurality of irregular and/or asymmetrical cavities in accordance with various embodiments;

FIG. 142 is a partial cut-away view of a tissue thickness compensator attached to an anvil of a surgical stapling instrument in accordance with at least one embodiment;

FIG. 143 is a perspective view of a seamless extruded casing, or outer tube, of a tissue thickness compensator in accordance with at least one embodiment;

FIG. 144 is a perspective view of another seamless extruded casing, or outer tube, of a tissue thickness compensator in accordance with at least one embodiment;

FIG. 145 is a perspective view of oxidized regenerated cellulose fibers;

FIG. 146 is a perspective view of oxidized regenerated cellulose fibers which are shorter than the fibers of FIG. 145;

FIG. 147 is a diagram illustrating the fibers of FIG. 145 being woven into a strand utilizing the fibers of FIG. 146;

FIG. 148 depicts the strand of FIG. 147 being fluffed and at least partially cut;

FIG. 149 depicts a grasper inserted through a casing, or outer tube, of a tissue thickness compensator and positioned to grasp the strand of FIG. 147;

FIG. 150 illustrates the grasper of FIG. 149 being withdrawn from the casing and the strand of FIG. 147 being pulled through the casing;

FIG. 151 illustrates the casing and the strand of FIG. 150 being segmented;

FIG. 152 illustrates the ends of the casing being heat-welded and/or sealed;

FIG. 153 illustrates a process for creating a tissue thickness compensator without lateral seams;

FIG. 154 illustrates an anvil of a surgical stapling instrument and a plurality of compensators which can be selectively attached to the anvil, wherein each of the compensators comprises an array of capillary channels;

FIG. 155 is a plan view of a compensator configured to be attached to an anvil;

FIG. 156 is a detail view of a portion of the compensator of FIG. 155;

FIG. 157 is a perspective view of an end effector of a surgical stapling instrument;

FIG. 158 is another perspective view of the end effector of FIG. 157 illustrating a fluid being placed on a tissue thickness compensator of the end effector;

FIG. 159 is another perspective view of the end effector of FIG. 159 illustrating a compensator attached to an anvil of the end effector;

FIG. 160 is a detail view of an array of capillary channels on the compensator of FIG. 159;

FIG. 161 is an exploded view of a compensator comprising a plurality of layers in accordance with at least one embodiment;

FIG. 162 is an exploded view of a compensator and an anvil of a surgical stapling instrument in accordance with at least one embodiment;

FIG. 163 is a partial cross-sectional view of the compensator and the anvil of FIG. 162;

FIG. 164 is an exploded view of a compensator comprising a cellular ingrowth matrix in accordance with at least one embodiment;

FIG. 165 is a perspective view of the compensator of FIG. 164;

FIG. 166 is a perspective view of a fibrous layer of material for a compensator;

FIG. 167 is a perspective view of a plurality of fibrous layers stacked on one another in accordance with at least one embodiment;

FIG. 168 is a perspective view of another plurality of fibrous layers stacked on one another in accordance with at least one embodiment;

FIG. 169 is a perspective view of a fibrous layer of material for a compensator;

FIG. 170 is a perspective view of a plurality of fibrous layers stacked on one another wherein the fibers are arranged in different directions in accordance with at least one embodiment;

FIG. 171 is a perspective view of another plurality of fibrous layers stacked on one another in accordance with at least one embodiment;

FIG. 172 is a perspective view of an end effector insert and an end effector of a surgical instrument in accordance with at least one embodiment;

FIG. 173 is an elevational view of a tissue thickness compensator positioned in an end effector of a surgical instrument in accordance with at least one embodiment;

FIG. 174 is an elevational view of a tissue thickness compensator positioned in the end effector of the surgical instrument in accordance with at least one embodiment;

FIG. 175 is a perspective view of a sleeve positioned on an anvil for the end effector of the surgical instrument in accordance with at least one embodiment;

FIG. 176 is a plan view of a pronged portion of the sleeve of FIG. 175;

FIG. 177 is an elevational view of the pronged portion of the sleeve of FIG. 175;

FIG. 178 is an end view of the pronged portion of the sleeve of FIG. 175;

FIG. 179 is a perspective view of the pronged portion of the sleeve of FIG. 175;

FIG. 180 is a plan view of a tissue compensator of a sleeve in accordance with at least one embodiment;

FIG. 181 is a perspective view of the tissue compensator of FIG. 180;

FIG. 182 is an elevational view of the tissue compensator of FIG. 180;

FIG. 183 is a plan view of a tissue compensator of a sleeve in accordance with at least one embodiment;

FIG. 184 is a perspective view of the tissue compensator of FIG. 183;

FIG. 185 is an elevational view of the tissue compensator of FIG. 183;

FIG. 186 is a perspective view of a nose of the sleeve of FIG. 175;

FIG. 187 is another perspective view of the nose of FIG. 186;

FIG. 188 is a plan view of the nose of FIG. 186 depicting the inner geometry in phantom lines;

FIG. 189 is an elevational view of the nose of FIG. 186 depicting the inner geometry in phantom lines;

FIG. 190 is another perspective view of the sleeve of FIG. 175 positioned on the anvil;

FIG. 191 is a plan view of the sleeve of FIG. 175 positioned on the anvil;

FIG. 192 is an elevational view of the sleeve of FIG. 175 positioned on the anvil;

FIG. 193 is a plan view of the sleeve of FIG. 175 positioned on the anvil depicting a translating firing bar shown in phantom lines;

FIG. 194 is an elevational view of the sleeve of FIG. 175 positioned on the anvil depicting a translating firing bar shown in phantom lines;

FIG. 195 is a plan view of the sleeve of FIG. 175 positioned on the anvil depicting the release of the nose from the sleeve;

FIG. 196 is an elevational view of the sleeve of FIG. 175 positioned on the anvil depicting the release of the nose from the sleeve;

FIG. 197 is a plan view of the sleeve of FIG. 175 positioned on the anvil depicting the firing bar in phantom lines and the release of the nose from the sleeve;

FIG. 198 is an elevational view of the sleeve of FIG. 175 positioned on the anvil depicting the firing bar in phantom lines and the release of the nose from the sleeve;

FIG. 199 is a partial perspective view of the sleeve, the anvil, and the firing bar of FIG. 197;

FIG. 200 is another partial perspective view of the sleeve, the anvil, and the firing bar of FIG. 197;

FIG. 201 is an elevational cross-sectional view of the sleeve and the anvil of FIG. 175;

FIG. 202 is an elevational cross-sectional view of the anvil of FIG. 175 depicting the release of the tissue compensator from the sleeve;

FIG. 203 is a plan view of an end effector insert in accordance with at least one embodiment;

FIG. 204 is an elevational view of the end effector insert of FIG. 203;

FIG. 205 is a perspective view of the end effector insert of FIG. 205;

FIG. 206 is a partial perspective view of the end effector insert of FIG. 203 depicting the end effector insert engaging the anvil of the end effector of a surgical instrument;

FIG. 207 is a partial perspective view of the end effector insert of FIG. 203 depicting the end effector insert engaging the staple cartridge of the end effector of a surgical instrument;

FIG. 208 is an elevational view of the end effector insert of FIG. 203 depicting the end effector insert engaging the end effector of a surgical instrument;

FIG. 209 is an elevational view of the end effector insert of FIG. 203 positioned in the end effector of a surgical instrument;

FIG. 210 is a perspective view of a tissue thickness compensator positioned in the end effector of a surgical instrument in accordance with at least one embodiment illustrated with a portion of the tissue thickness compensator cut away;

FIG. 211 is a perspective view of the tissue thickness compensator of FIG. 210 secured to the anvil of the end effector by a static charge;

FIG. 212 is a perspective view of the tissue thickness compensator of FIG. 210 secured to the anvil of the end effector by suction elements;

FIG. 213 is a perspective view of the tissue thickness compensator of FIG. 210 secured to the anvil of the end effector by hook and loop fasteners;

FIG. 214 is a partial perspective view of the tissue thickness compensator of FIG. 210 secured to the anvil of the end effector by a band;

FIG. 215 is a partial perspective view of the tissue thickness compensator of FIG. 210 secured to the anvil of the end effector by a sock at the distal end of the tissue thickness compensator;

FIG. 216 is a perspective partial cross-sectional view of a tissue thickness compensator secured to the anvil of the end effector of a surgical instrument in accordance with at least one embodiment;

FIG. 217 is an elevational cross-sectional view of the tissue thickness compensator of FIG. 216;

FIG. 218 is another elevational cross-sectional view of the tissue thickness compensator of FIG. 216;

FIG. 219 is an elevational cross-sectional view of a tissue thickness compensator secured to the anvil of the end effector of a surgical instrument depicting a latch in a closed position in accordance with at least one embodiment;

FIG. 220 is an elevational cross-sectional view the tissue thickness compensator of FIG. 219 depicting the latch in the open position;

FIG. 221 is an elevational cross-sectional view of a tissue thickness compensator secured to the anvil of the end effector of a surgical instrument in accordance with at least one embodiment;

FIG. 222 is an elevational cross-sectional view of a tissue thickness compensator secured to the anvil of the end effector of a surgical instrument in accordance with at least one embodiment;

FIG. 223 is an elevational cross-sectional view of a tissue thickness compensator secured to the anvil of the end effector of a surgical instrument in accordance with at least one embodiment;

FIG. 224 is an elevational cross-sectional view of a tissue thickness compensator secured to the anvil of the end effector of the surgical instrument in accordance with at least one embodiment;

FIG. 225 is a perspective cross-sectional exploded view of a tissue thickness compensator secured to an anvil of an end effector of the surgical instrument in accordance with at least one embodiment;

FIG. 226 is a perspective view of the tissue thickness compensator of FIG. 225 depicting movement of the tissue thickness compensator towards the anvil;

FIG. 227 is an elevational cross-sectional view of the tissue thickness compensator of FIG. 225 engaged with the anvil;

FIG. 228 is a perspective cross-sectional view of a tissue thickness compensator secured to the anvil of the end effector of a surgical instrument in accordance with at least one embodiment;

FIG. 229 is a perspective cross-sectional exploded view of the tissue thickness compensator and the anvil of FIG. 228;

FIG. 230 is an elevational view of a tissue thickness compensator in accordance with at least one embodiment;

FIG. 231 is a perspective view of the tissue thickness compensator of FIG. 230;

FIG. 232 is another perspective of the tissue thickness compensator of FIG. 230;

FIG. 233 is a perspective view of the tissue thickness compensator of FIG. 230 depicting movement of the tissue thickness compensator towards the anvil of the end effector of a surgical instrument;

FIG. 234 is a plan cross-sectional view of the tissue thickness compensator of FIG. 230 positioned on the anvil;

FIG. 235 is a perspective view of the tissue thickness compensator of FIG. 230 positioned on the anvil;

FIG. 236 is a perspective view of the tissue thickness compensator of FIG. 230 positioned on the anvil illustrating a cutting element severing the tissue thickness compensator;

FIG. 237 is a cross-sectional elevational view of an end effector of a surgical stapling instrument comprising an anvil and a chargeable layer in accordance with at least one embodiment;

FIG. 238 is a bottom view of the anvil and the chargeable layer of FIG. 237;

FIG. 239 is an exploded view of the anvil and the chargeable layer of FIG. 237 and a tissue thickness compensator releasably attachable to the chargeable layer;

FIG. 240 is a perspective view of a tissue thickness compensator in accordance with at least one embodiment;

FIG. 241 is a plan view of the tissue thickness compensator of FIG. 240;

FIG. 240A is a perspective view of a tissue thickness compensator in accordance with at least one alternative embodiment;

FIG. 241A is a plan view of the tissue thickness compensator of FIG. 240A;

FIG. 242 is a perspective view of a tissue thickness compensator in accordance with at least one alternative embodiment;

FIG. 243 is a plan view of the tissue thickness compensator of FIG. 242;

FIG. 244 is a perspective view of a tissue thickness compensator in accordance with at least one embodiment;

FIG. 245 is a perspective view of a tissue thickness compensator attached to an anvil in accordance with at least one embodiment;

FIG. 246 is a cross-sectional view of the anvil and the tissue thickness compensator of FIG. 245;

FIG. 247 is a cross-sectional view of the tissue thickness compensator of FIG. 245;

FIG. 248 is a perspective view of a tissue thickness compensator attached to an anvil in accordance with at least one alternative embodiment;

FIG. 249 is a cross-sectional view of the anvil and the tissue thickness compensator of FIG. 248;

FIG. 250 is a cross-sectional view of the tissue thickness compensator of FIG. 248 in an open configuration;

FIG. 251 is a perspective view of a tissue thickness compensator attached to an anvil in accordance with at least one alternative embodiment;

FIG. 252 is a cross-sectional view of the anvil and the tissue thickness compensator of FIG. 251;

FIG. 253 is a perspective view of a tissue thickness compensator attached to an anvil in accordance with at least one alternative embodiment;

FIG. 254 is a cross-sectional view of the anvil and the tissue thickness compensator of FIG. 253;

FIG. 255 is a perspective view of a tissue thickness compensator attached to an anvil in accordance with at least one alternative embodiment;

FIG. 256 is a cross-sectional view of the anvil and the tissue thickness compensator of FIG. 255;

FIG. 257 is a perspective view of a tissue thickness compensator attached to an anvil in accordance with at least one alternative embodiment; and FIG. 258 is a cross-sectional view of the anvil and the tissue thickness compensator of FIG. 257.

Figure 259:
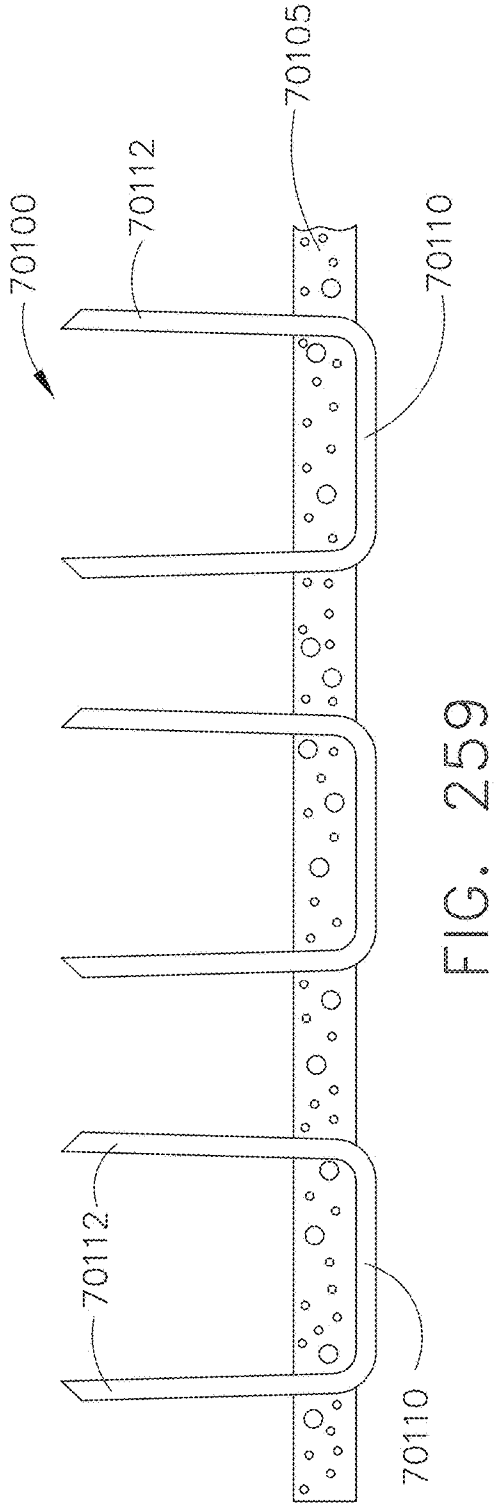
Figure 260:
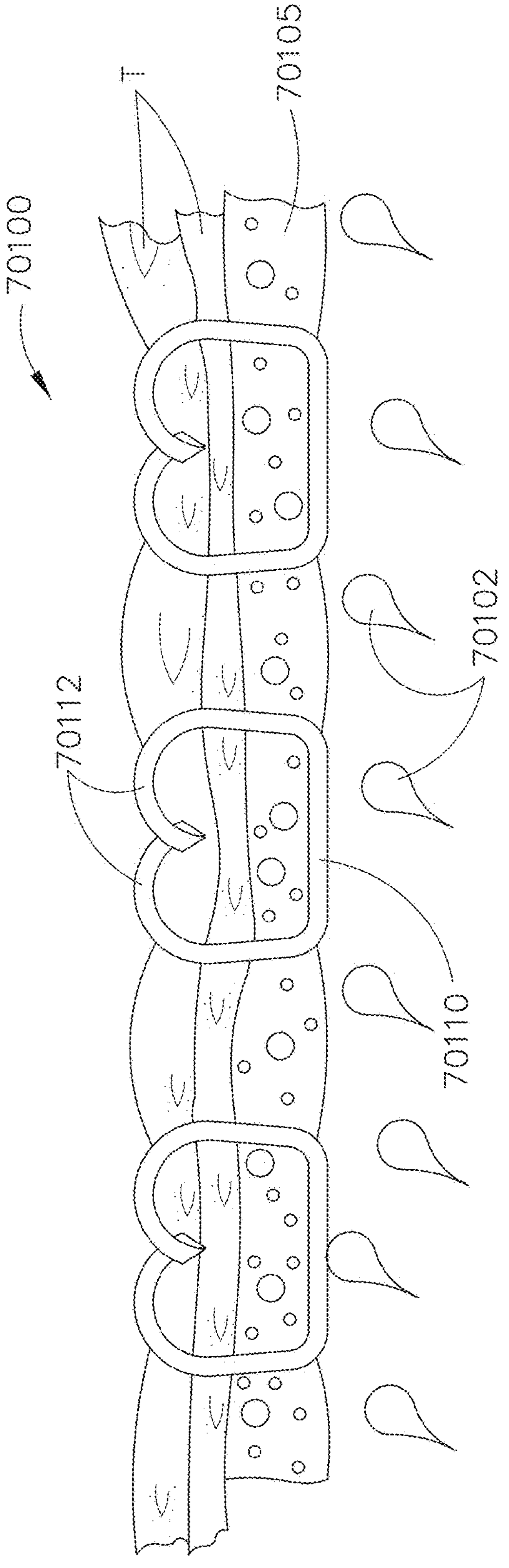
Figure 261:
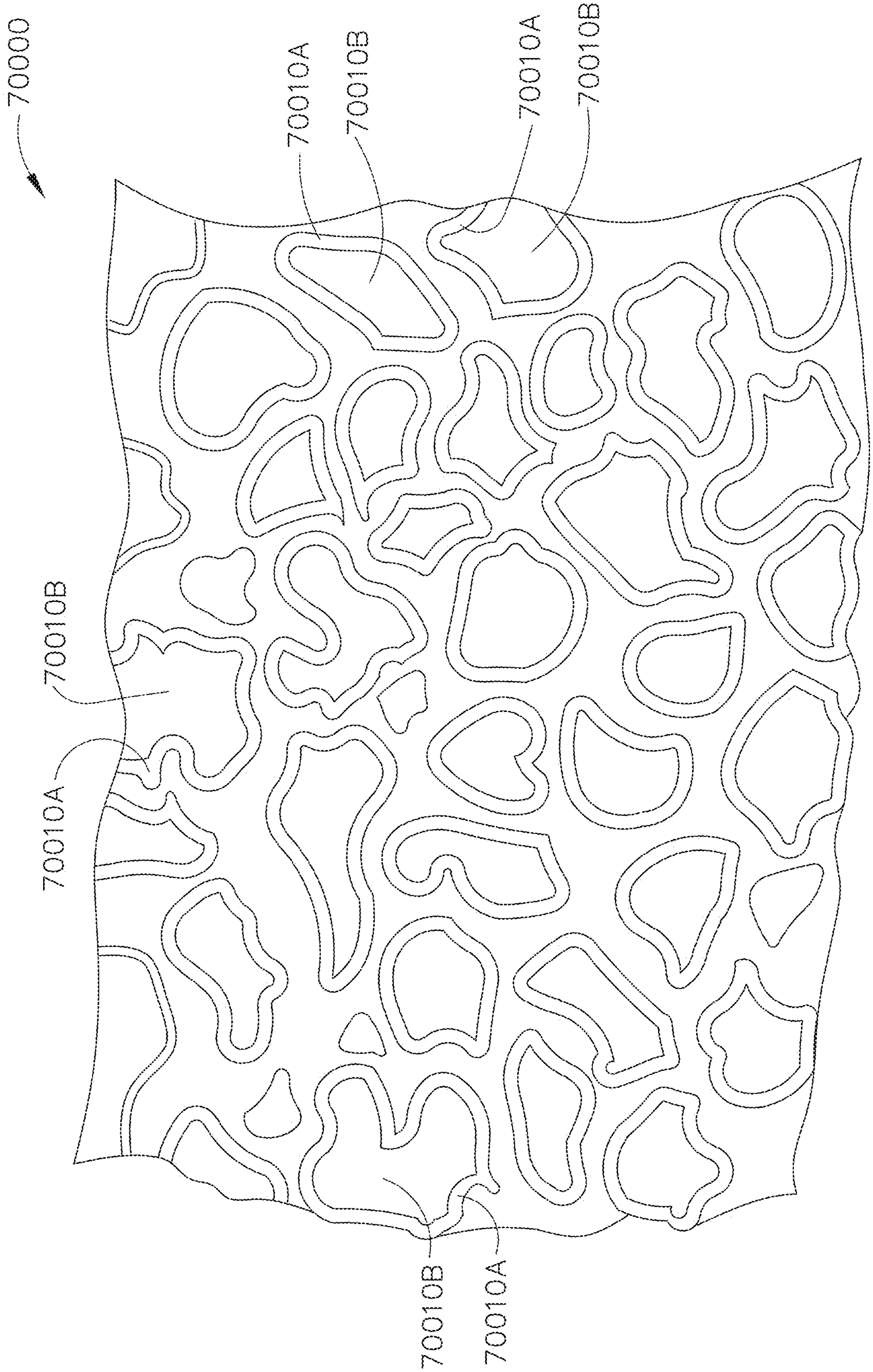
Figure 262:
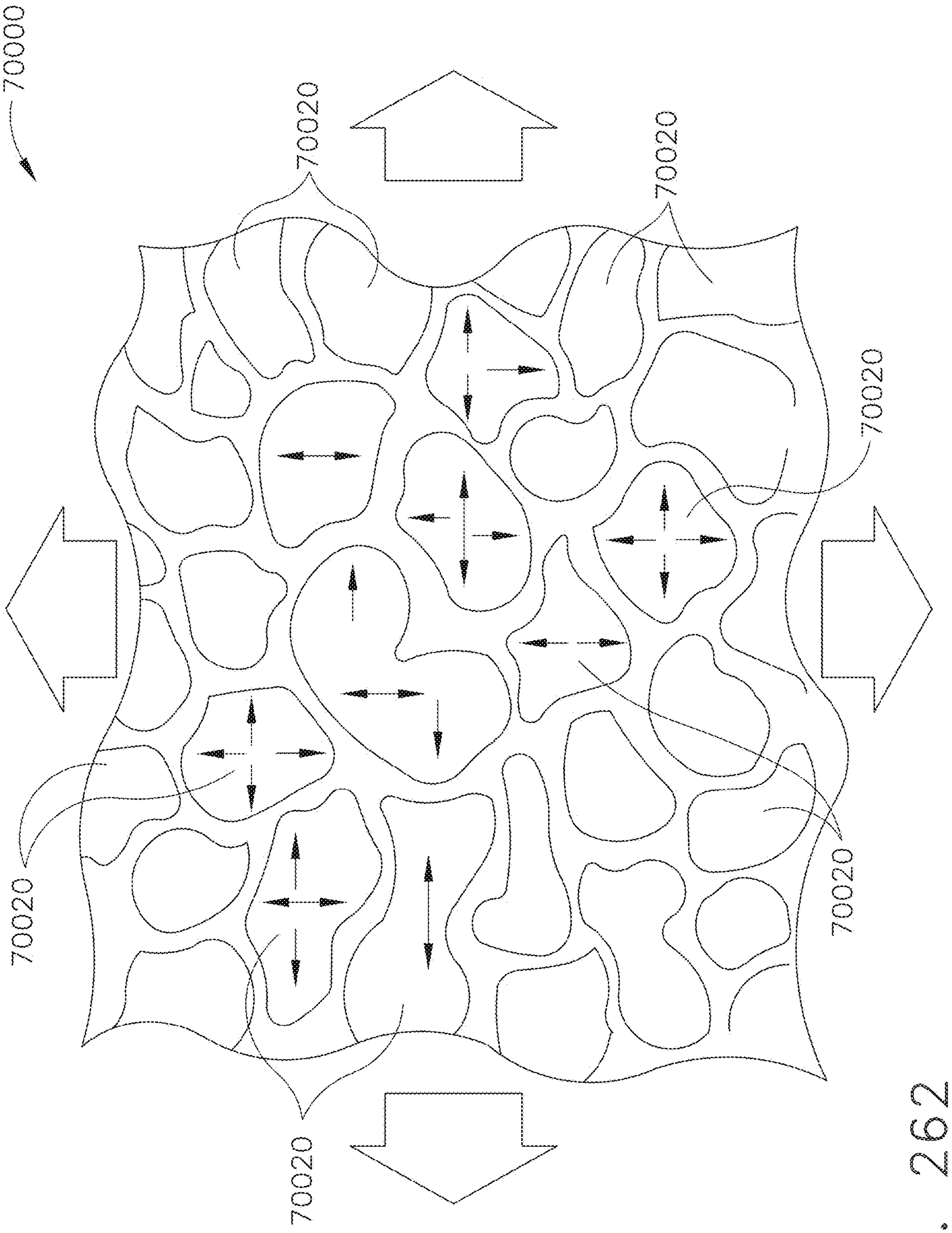
Figure 263:
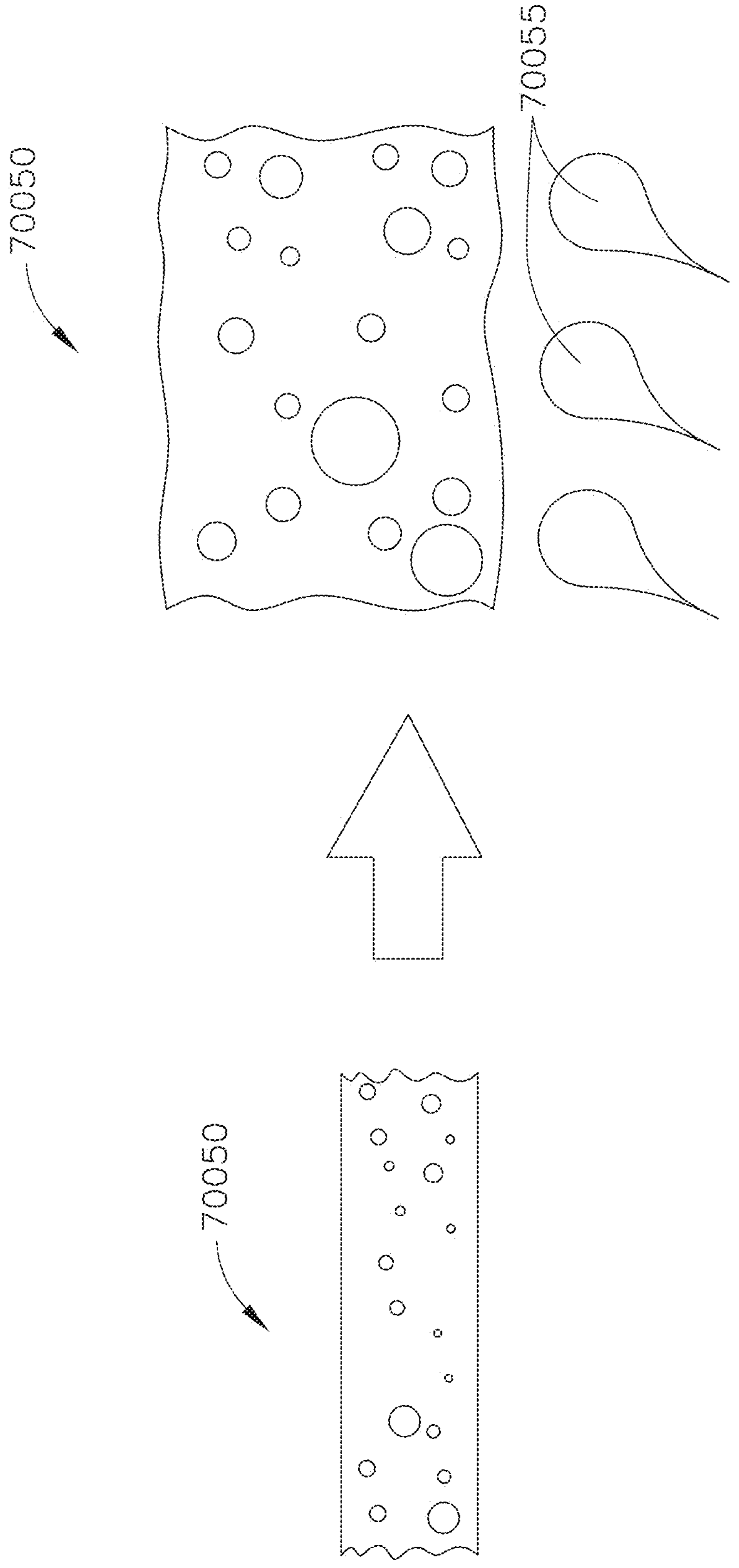
Figure 264:
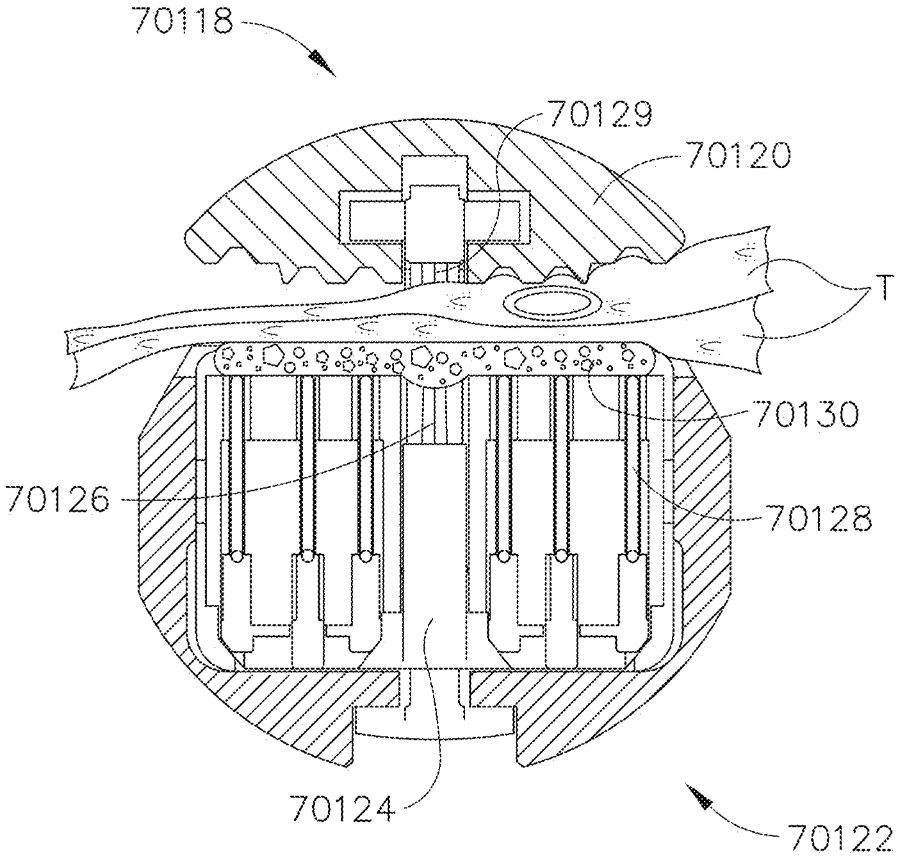
Figure 265:
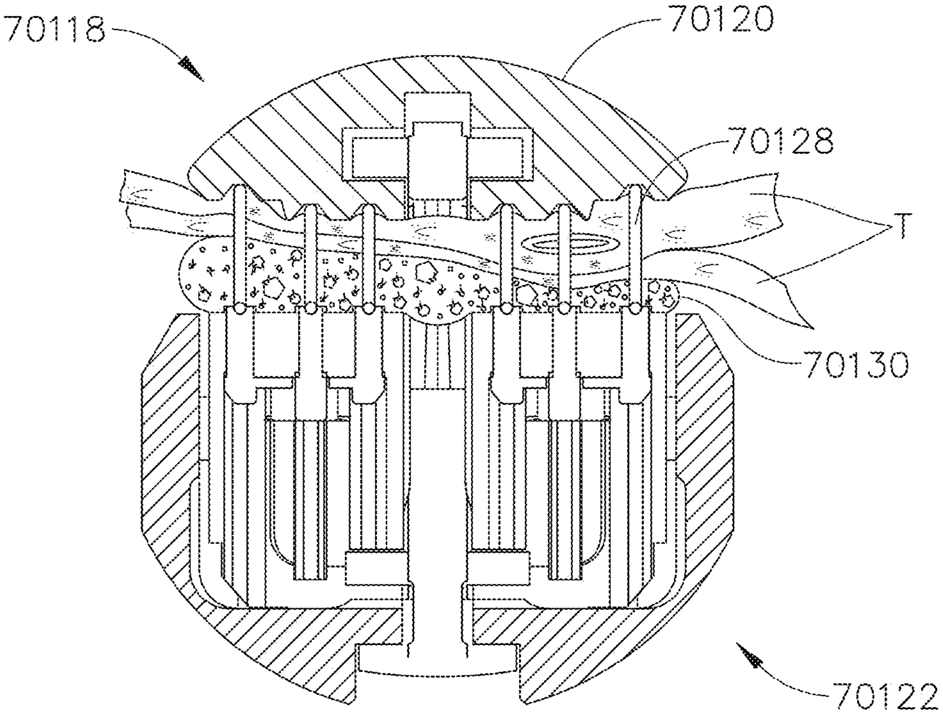
Figure 266:
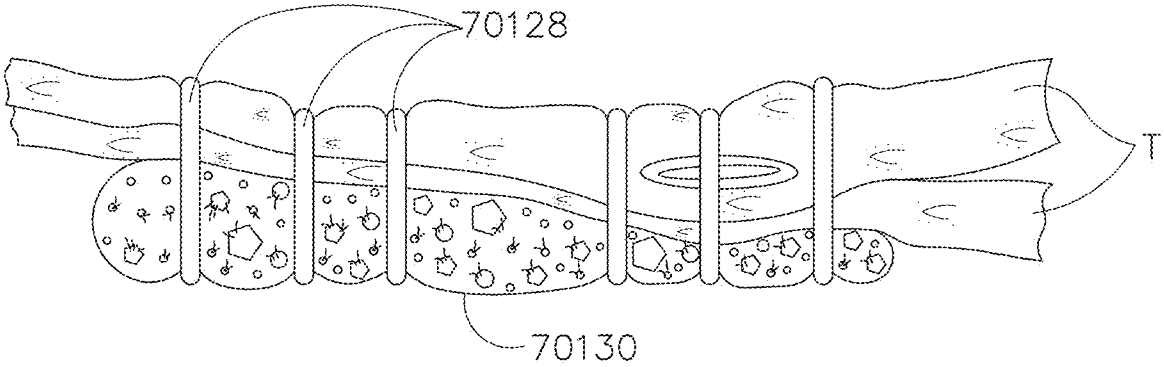

FIG. 259 is a cross-sectional view of a staple cartridge in accordance with various embodiments;

FIG. 260 is a partial cross-section view of FIG. 259 in an implanted condition;

FIG. 261 is a partial perspective view of a tissue thickness compensator prior to expansion;

FIG. 262 is a partial perspective view of a tissue thickness compensator of FIG. 261 during expansion;

FIG. 263 is a partial perspective view of a tissue thickness compensator comprising a fluid swellable composition according to various embodiments;

FIG. 264 is a cross-sectional view of tissue positioned adjacent a tissue thickness compensator according to various embodiments;

FIG. 265 is a partial cross-sectional view of FIG. 264 after the staple cartridge has been fired; and FIG. 266 is a diagram illustrating the tissue thickness compensator of FIG. 264 implanted adjacent the tissue.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. patent applications identified below which are each herein incorporated by reference in their respective entirety:

- U.S. patent application Ser. No. 12/894,311, entitled SURGICAL INSTRUMENTS WITH RECONFIGURABLE SHAFT SEGMENTS, now U.S. Pat. No. 8,763,877;
- U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;
- U.S. patent application Ser. No. 12/894,327, entitled JAW CLOSURE ARRANGEMENTS FOR SURGICAL INSTRUMENTS, now U.S. Pat. No. 8,978,956;
- U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;
- U.S. patent application Ser. No. 12/894,338, entitled IMPLANTABLE FASTENER CARTRIDGE HAVING A NON-UNIFORM ARRANGEMENT, now U.S. Pat. No. 8,864,007;
- U.S. patent application Ser. No. 12/894,369, entitled IMPLANTABLE FASTENER CARTRIDGE COMPRISING A SUPPORT RETAINER, now U.S. Patent Application Publication No. 2012/0080344;
- U.S. patent application Ser. No. 12/894,312, entitled IMPLANTABLE FASTENER CARTRIDGE COMPRISING MULTIPLE LAYERS, now U.S. Pat. No. 8,925,782;
- U.S. patent application Ser. No. 12/894,377, entitled SELECTIVELY ORIENTABLE IMPLANTABLE FASTENER CARTRIDGE, now U.S. Pat. No. 8,393,514;
- U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;
- U.S. patent application Ser. No. 12/894,360, entitled SURGICAL STAPLING INSTRUMENT WITH A VARIABLE STAPLE FORMING SYSTEM, now U.S. Pat. No. 9,113,862;
- U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;
- U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application Publication No. 2012/0080478;
- U.S. patent application Ser. No. 12/894,383, entitled IMPLANTABLE FASTENER CARTRIDGE COMPRISING BIOABSORBABLE LAYERS, now U.S. Pat. No. 8,752,699;
- U.S. patent application Ser. No. 12/894,389, entitled COMPRESSIBLE FASTENER CARTRIDGE, now U.S. Pat. No. 8,740,037;
- U.S. patent application Ser. No. 12/894,345, entitled FASTENERS SUPPORTED BY A FASTENER CARTRIDGE SUPPORT, now U.S. Pat. No. 8,783,542;
- U.S. patent application Ser. No. 12/894,306, entitled COLLAPSIBLE FASTENER CARTRIDGE, now U.S. Pat. No. 9,044,227;
- U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;
- U.S. patent application Ser. No. 12/894,330, entitled FASTENER SYSTEM COMPRISING A RETENTION MATRIX AND AN ALIGNMENT MATRIX, now U.S. Pat. No. 8,757,465;
- U.S. patent application Ser. No. 12/894,361, entitled FASTENER SYSTEM COMPRISING A RETENTION MATRIX, now U.S. Pat. No. 8,529,600;
- U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;
U.S. patent application Ser. No. 12/894,376, entitled FASTENER SYSTEM COMPRISING A PLURALITY OF FASTENER CARTRIDGES, now U.S. Pat. No. 9,044,228;
U.S. patent application Ser. No. 13/097,865, entitled SURGICAL STAPLER ANVIL COMPRISING A PLURALITY OF FORMING POCKETS, now U.S. Pat. No. 9,295,464;
U.S. patent application Ser. No. 13/097,936, entitled TISSUE THICKNESS COMPENSATOR FOR A SURGICAL STAPLER, now U.S. Pat. No. 8,657,176;
U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;
U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;
U.S. patent application Ser. No. 13/097,928, entitled TISSUE THICKNESS COMPENSATOR COMPRISING DETACHABLE PORTIONS, now U.S. Pat. No. 8,746,535;
U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;
U.S. patent application Ser. No. 13/097,948, entitled STAPLE CARTRIDGE COMPRISING AN ADJUSTABLE DISTAL PORTION, now U.S. Pat. No. 8,978,954;
U.S. patent application Ser. No. 13/097,907, entitled COMPRESSIBLE STAPLE CARTRIDGE ASSEMBLY, now U.S. Pat. No. 9,301,755;
U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;
U.S. patent application Ser. No. 13/097,869, entitled STAPLE CARTRIDGE LOADING ASSEMBLY, now U.S. Pat. No. 8,857,694;
U.S. patent application Ser. No. 13/097,917, entitled COMPRESSIBLE STAPLE CARTRIDGE COMPRISING ALIGNMENT MEMBERS, now U.S. Pat. No. 8,777,004;
U.S. patent application Ser. No. 13/097,873, entitled STAPLE CARTRIDGE COMPRISING A RELEASABLE PORTION, now U.S. Pat. No. 8,740,038;
U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;
U.S. patent application Ser. No. 13/097,924, entitled STAPLE CARTRIDGE COMPRISING A TISSUE THICKNESS COMPENSATOR, now U.S. Pat. No. 9,168,038;
U.S. patent application Ser. No. 13/242,029, entitled SURGICAL STAPLER WITH FLOATING ANVIL, now U.S. Pat. No. 8,893,949;
U.S. patent application Ser. No. 13/242,066, entitled CURVED END EFFECTOR FOR A STAPLING INSTRUMENT, now U.S. Patent Application Publication No. 2012/0080498;
U.S. patent application Ser. No. 13/242,086, entitled STAPLE CARTRIDGE INCLUDING COLLAPSIBLE DECK, now U.S. Pat. No. 9,055,941;
U.S. patent application Ser. No. 13/241,912, entitled STAPLE CARTRIDGE INCLUDING COLLAPSIBLE DECK ARRANGEMENT, now U.S. Pat. No. 9,050,084;
U.S. patent application Ser. No. 13/241,922, entitled SURGICAL STAPLER WITH STATIONARY STAPLE DRIVERS, now U.S. Pat. No. 9,216,019;
U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741; and
U.S. patent application Ser. No. 13/241,629, entitled SURGICAL INSTRUMENT WITH SELECTIVELY ARTICULATABLE END EFFECTOR, now U.S. Patent Application Publication No. 2012/0074200.

The Applicant of the present application also owns the U.S. patent applications identified below which were filed on Mar. 28, 2012 and which are each herein incorporated by reference in their respective entirety:
U.S. patent application Ser. No. 13/433,096, entitled TISSUE THICKNESS COMPENSATOR COMPRISING A PLURALITY OF CAPSULES, now U.S. Pat. No. 9,301,752;
U.S. patent application Ser. No. 13/433,103, entitled TISSUE THICKNESS COMPENSATOR COMPRISING A PLURALITY OF LAYERS, now U.S. Pat. No. 9,433,419;
U.S. patent application Ser. No. 13/433,098 entitled EXPANDABLE TISSUE THICKNESS COMPENSATOR, now U.S. Pat. No. 9,301,753;
U.S. patent application Ser. No. 13/433,102, entitled TISSUE THICKNESS COMPENSATOR COMPRISING A RESERVOIR, now U.S. Pat. No. 9,232,941;
U.S. patent application Ser. No. 13/433,114, entitled RETAINER ASSEMBLY INCLUDING A TISSUE THICKNESS COMPENSATOR, now U.S. Pat. No. 9,386,988;
U.S. patent application Ser. No. 13/433,136, entitled TISSUE THICKNESS COMPENSATOR COMPRISING AT LEAST ONE MEDICAMENT, now U.S. Patent Application Publication No. 2012/0241492;
U.S. patent application Ser. No. 13/433,141, entitled TISSUE THICKNESS COMPENSATOR COMPRISING CONTROLLED RELEASE AND EXPANSION, now U.S. Patent Application Publication No. 2012/0241493;
U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;
U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;
U.S. patent application Ser. No. 13/433,155, entitled TISSUE THICKNESS COMPENSATOR COMPRISING RESILIENT MEMBERS, now U.S. Pat. No. 9,480,476;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. patent application Ser. No. 13/433,118, entitled TISSUE THICKNESS COMPENSATOR COMPRISED OF A PLURALITY OF MATERIALS, now U.S. Pat. No. 9,414,838;

U.S. patent application Ser. No. 13/433,135, entitled MOVABLE MEMBER FOR USE WITH A TISSUE THICKNESS COMPENSATOR, now U.S. Pat. No. 9,517,063;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/433,126, entitled TISSUE THICKNESS COMPENSATOR COMPRISING TISSUE INGROWTH FEATURES, now U.S. Pat. No. 9,320,523; and U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
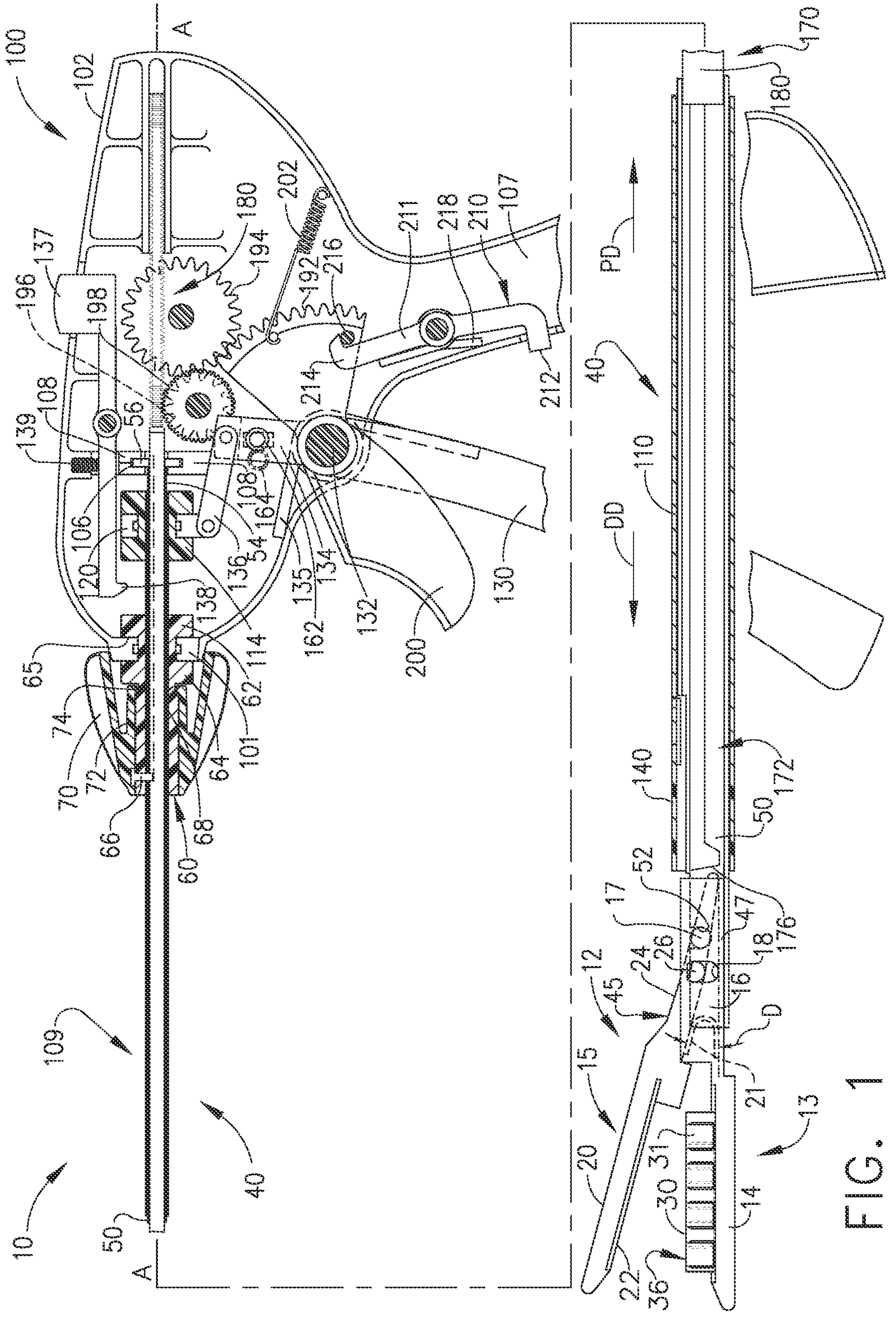
FIG. 1 is a cross-sectional view of a surgical instrument embodiment.

Turning to the Drawings wherein like numerals denote like components throughout the several views, FIG. 1 depicts a surgical instrument 10 that is capable of practicing several unique benefits. The surgical stapling instrument 10 is designed to manipulate and/or actuate various forms and sizes of end effectors 12 that are operably attached thereto. In the embodiment depicted in FIGS. 1-1E, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Figure 1A:
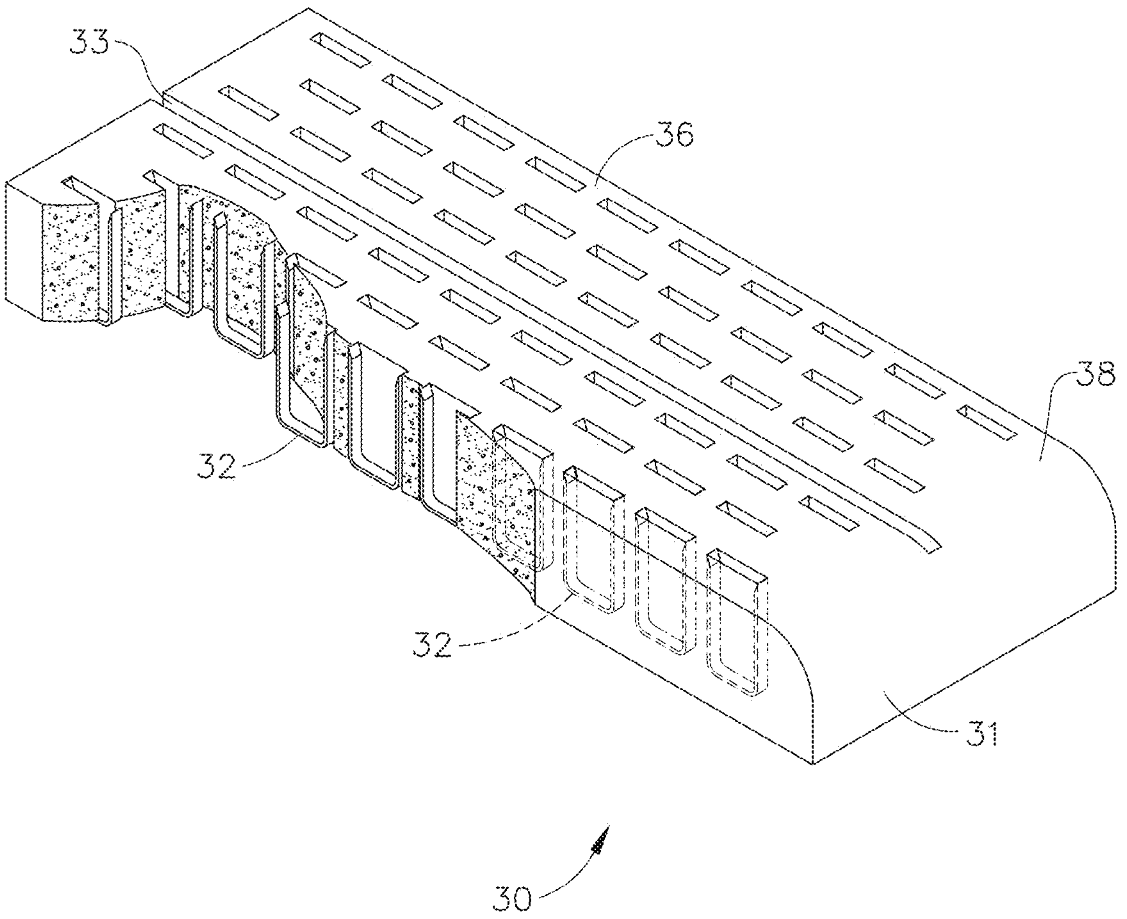
FIG. 1A is a perspective view of one embodiment of an implantable staple cartridge.

Various forms of implantable staple cartridges may be employed with the various embodiments of the surgical instruments disclosed herein. Specific staple cartridge configurations and constructions will be discussed in further detail below. However, in the embodiment depicted in FIG. 1A, an implantable staple cartridge 30 is shown. In at least one embodiment, the staple cartridge 30 has a body portion 31 that consists of a compressible hemostat material such as, for example, oxidized regenerated cellulose ("ORC") or a bioabsorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FF".

Figures 1B, 1C, 1D, 1E:
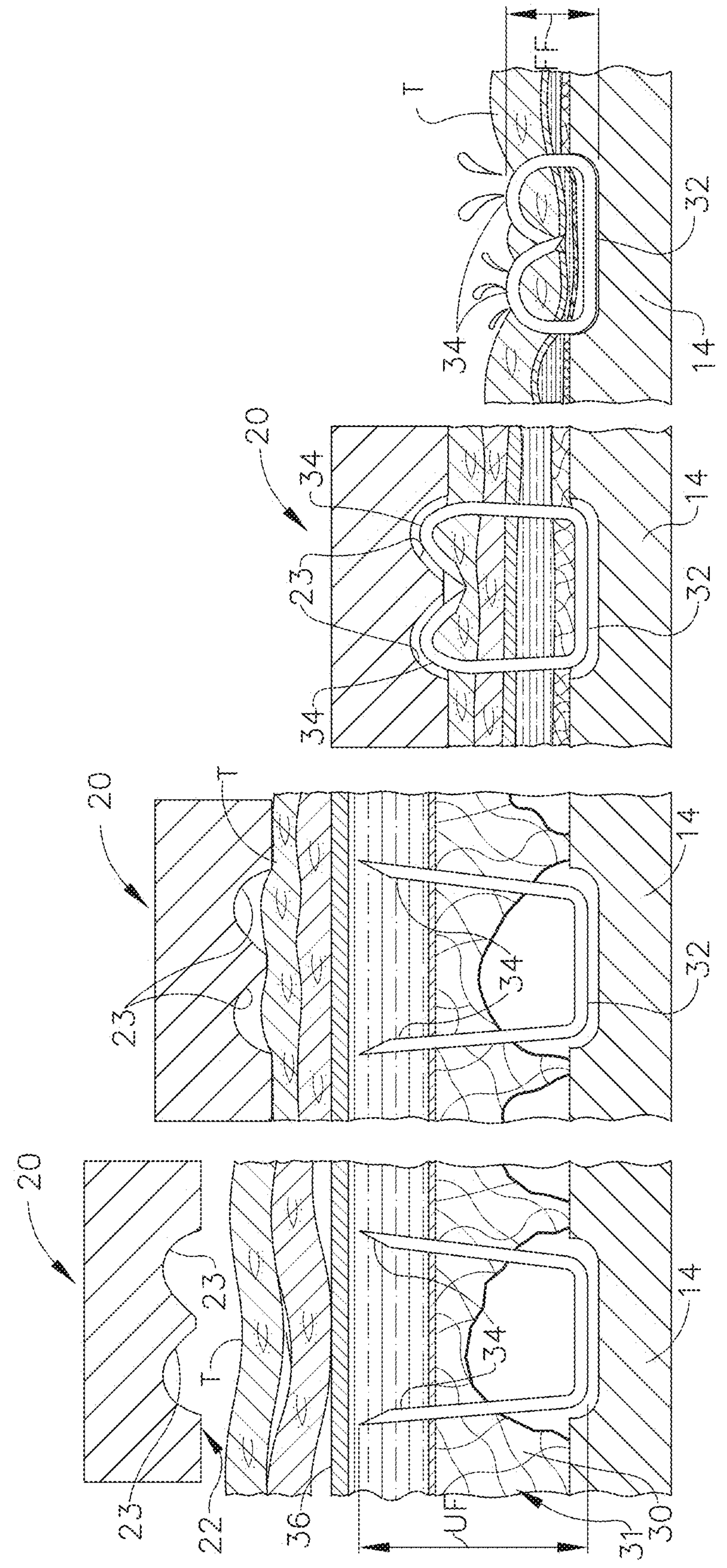
FIGS. 1B-1E illustrate portions of an end effector clamping and stapling tissue with an implantable staple cartridge.

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes. Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and may eventually be absorbed by the patient's body. Such implantable staple cartridges are distinguishable from prior cartridge arrangements that remain positioned within the end effector in their entirety after they have been fired.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunnions 17 protruding therefrom that are sized to be received within corresponding trunnion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member (not illustrated) that are molded or otherwise fabricated from a polymer or plastic material and are designed to mate together. Such case members may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

As can be further seen in FIG. 1, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 and/or another biasing arrangement. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end that is attached to a firing yoke 114 of the firing system 109. In various embodiments for example, the firing yoke 114 may be over-molded to the proximal end of the firing tube 110. However, other fastener arrangements may be employed.

As can be seen in FIG. 1, the firing yoke 114 may be rotatably supported within a support collar 120 that is configured to move axially within the handle assembly 100. In various embodiments, the support collar 120 has a pair of laterally extending fins that are sized to be slidably received within fin slots formed in the right and left hand case members. Thus, the support collar 120 may slide axially within the handle housing 100 while enabling the firing yoke 114 and firing tube 110 to rotate relative thereto about the longitudinal axis A-A. In various embodiments, a longitudinal slot is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIG. 1, the firing trigger 130 has an upper portion 134 that is movably attached to (pinned) firing links 136 that are movably attached to (pinned) the support collar 120. Thus, movement of the firing trigger 130 from the starting position (FIG. 1) toward an ending position adjacent the pistol grip portion 107 of the handle assembly 100 will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter. In still other embodiments, the elongated shaft assembly 40 may configured to be attached to only one form or size of end effector.

One method of removably coupling the end effector 12 to the spine member 50 will now be explained. The coupling process is commenced by inserting the retention trunnions 17 on the elongated channel 14 into the trunnion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunnions 17 in their respective cradles 52. Such position of the first firing adapter 140 over the trunnions 17 is referred to herein as the "coupled position". Various embodiments of the present invention may also have an end effector locking assembly for locking the firing trigger 130 in position after an end effector 12 has been attached to the spine member 50.

More specifically, one embodiment of the end effector locking assembly 160 includes a retention pin 162 that is movably supported in the upper portion 134 of the firing trigger 130. As discussed above, the firing tube 110 must initially be advanced distally to the coupled position wherein the first firing adapter 140 retains the retention trunnions 17 of the end effector 12 in the trunnion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 is moved distally until the firing tube 110 has advanced the first firing adapter 140 to the coupled position at which point the retention pin 162 is biased into a locking cavity 164 formed in the case member. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

Various embodiments of the present invention may further include a firing system lock button 137 that is pivotally attached to the handle assembly 100. In one form, the firing system lock button 137 has a latch 138 formed on a distal end thereof that is oriented to engage the firing yoke 114 when the firing release button is in a first latching position. As can be seen in FIG. 1, a latch spring 139 serves to bias the firing system lock button 137 to the first latching position. In various circumstances, the latch 138 serves to engage the firing yoke 114 at a point where the position of the firing yoke 114 on the spine member 50 corresponds to a point wherein the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. After depressing the firing system lock button 137, the surgeon continues to actuate the firing trigger 130 towards the pistol grip 107 thereby driving the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 to an actuated position by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot in the anvil 20 and a centrally disposed slot 33 in the staple cartridge 30 to cut through tissue that is clamped in the end effector 12. In various embodiments, the knife rod 180 extends through the spine member 50 and has a proximal end portion which drivingly interfaces with a knife transmission that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position.

Various embodiments of the knife transmission also include a second knife gear 194 that is rotatably supported on a second gear spindle and in meshing engagement with the first knife gear 192. The second knife gear 194 is in meshing engagement with a third knife gear 196 that is supported on a third gear spindle. Also supported on the third gear spindle 195 is a fourth knife gear 198. The fourth knife gear 198 is adapted to drivingly engage a series of annular gear teeth or rings on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 172 unless the firing trigger 130 has been pulled to the fully fired position. Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 172 through the target tissue to the end of the end effector. Thereafter, the surgeon may release the knife advancement trigger 200 to enable the firing return spring 202 to cause the firing transmission to return the knife bar 172 to the starting (un-actuated) position. Once the knife bar 172 has been returned to the starting position, the surgeon may open the end effector jaws 13, 15 to release the implantable cartridge 30 within the patient and then withdraw the end effector 12 from the patient. Thus, such surgical instruments facilitate the use of small implantable staple cartridges that may be inserted through relatively smaller working channels and passages, while providing the surgeon with the option to fire the staples without cutting tissue or if desired to also cut tissue after the staples have been fired.

Various unique and novel embodiments of the present invention employ a compressible staple cartridge that supports staples in a substantially stationary position for forming contact by the anvil. In various embodiments, the anvil is driven into the unformed staples wherein, in at least one such embodiment, the degree of staple formation attained is dependent upon how far the anvil is driven into the staples. Such an arrangement provides the surgeon with the ability to adjust the amount of forming or firing pressure applied to the staples and thereby alter the final formed height of the staples. In other various embodiments of the present invention, surgical stapling arrangements can employ staple driving elements which can lift the staples toward the anvil. Such embodiments are described in greater detail further below.

In various embodiments, with regard to the embodiments described in detail above, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

Figures 2, 3, 4:
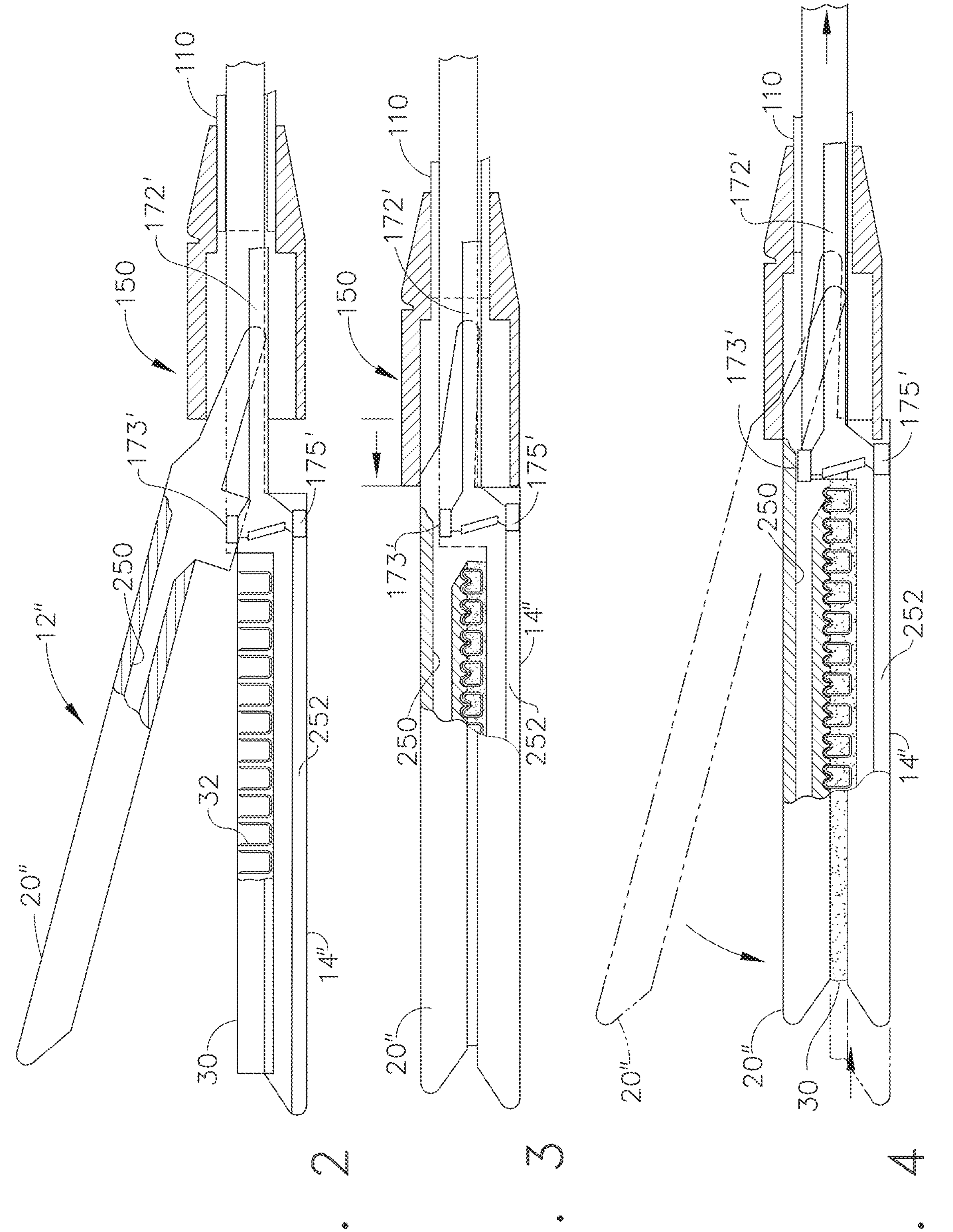
FIG. 2 is a partial cross-sectional side view of another end effector coupled to a portion of a surgical instrument with the end effector supporting a surgical staple cartridge and with the anvil thereof in an open position.
FIG. 3 is another partial cross-sectional side view of the end effector of FIG. 2 in a closed position.
FIG. 4 is another partial cross-sectional side view of the end effector of FIGS. 2 and 3 as the knife bar is starting to advance through the end effector.

FIGS. 2 and 3 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provided in the anvil 20" such that when the knife bar 172' has been driven to an ending position within end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

Figure 5:
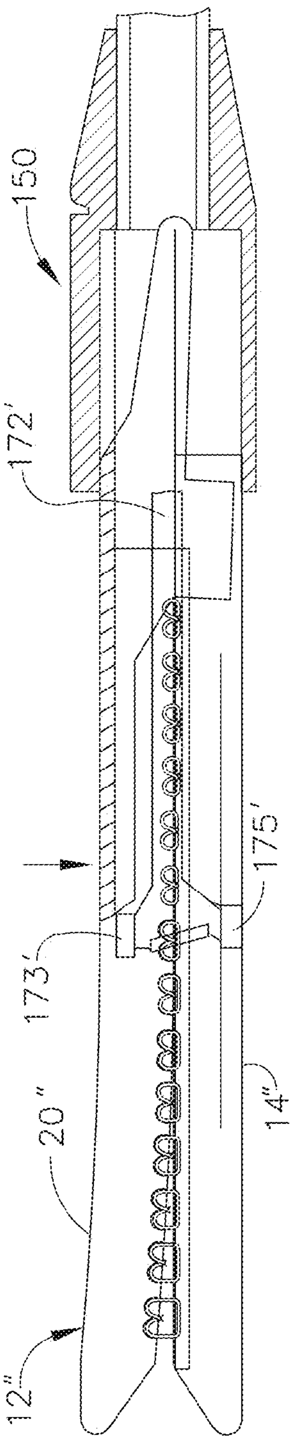
FIG. 5 is another partial cross-sectional side view of the end effector of FIGS. 2-4 with the knife bar partially advanced therethrough.

In these embodiments, the anvil 20" is biased to a fully open position (FIG. 2) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 3), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 4 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 5. Thus, in this embodiment, staple formation occurs simultaneously with tissue cutting, but the staples themselves may be sequentially formed as the knife bar 172" is driven distally.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, the lines of staples on each side of the elongated slot may have a zigzag appearance.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Figures 6A, 6B, 6C, 6D:
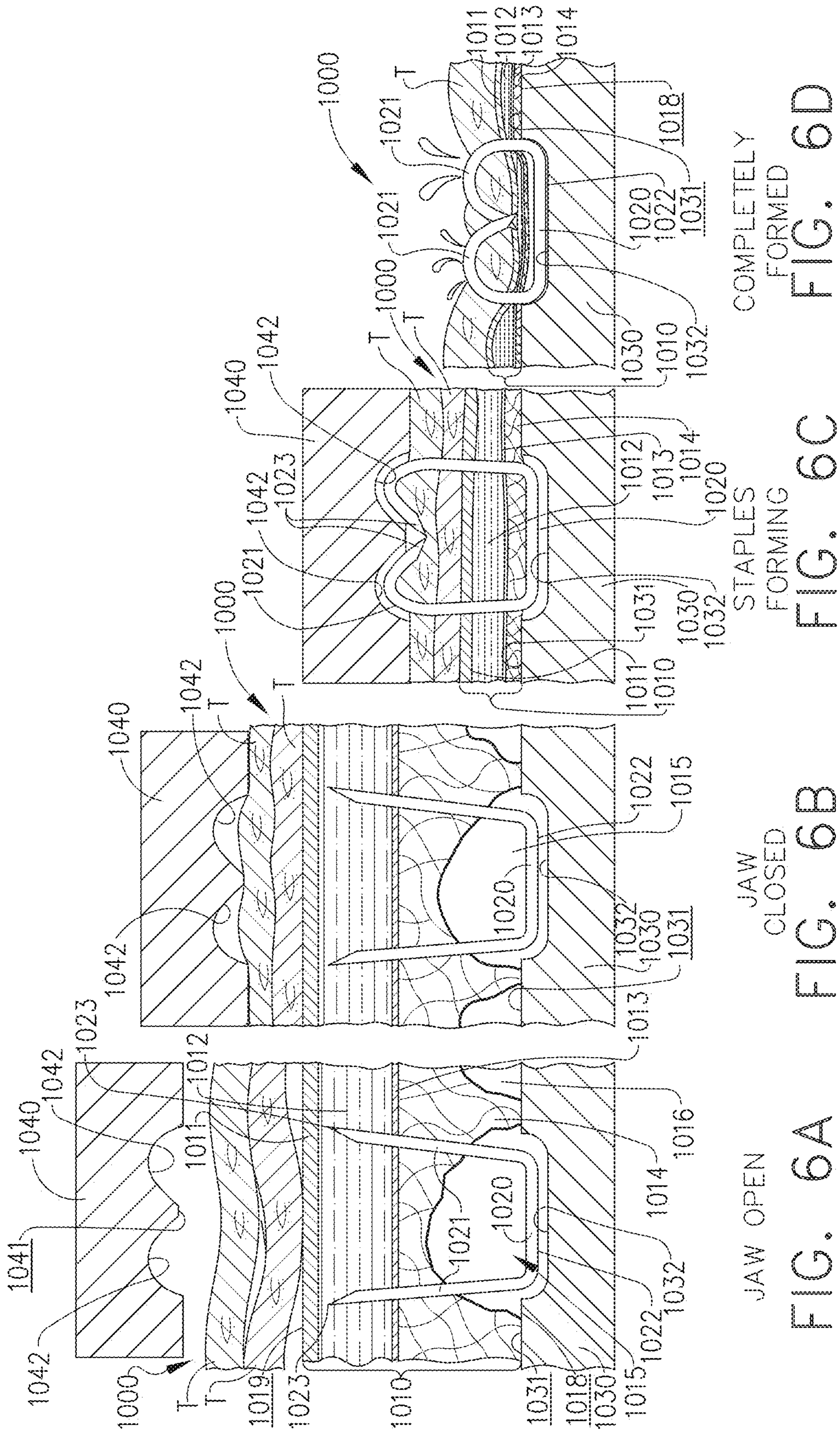
FIGS. 6A-6D diagram the deformation of a surgical staple positioned within a collapsible staple cartridge body in accordance with at least one embodiment.

Referring now to FIGS. 6A-6D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 6A-6D. FIG. 6A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 6B and position the tissue T against the cartridge body 1010. Even though the anvil 1040 can position the tissue T against a tissue-contacting surface 1019 of staple cartridge body 1010, referring again to FIG. 6B, the staple cartridge body 1010 may be subjected to little, if any, compressive force or pressure at such point and the staples 1020 may remain in an unformed, or unfired, condition. As illustrated in FIGS. 6A and 6B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible haemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one haemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 6C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 6C. As the staple legs 1021 are being deformed, as also illustrated in FIG. 6C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 6C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 6B and FIG. 6C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 6D. Referring to FIG. 6D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 6C and 6D, it is further evident that the second layer 1012 and the fourth layer 1014 have been further substantially compressed by the compressive pressure applied by the anvil 1040. It may also be noted upon comparing FIGS. 6C and 6D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 6D, and as a result of the above, the cartridge body 1010 can be implanted with the staples 1020. In various circumstances, the implanted cartridge body 1010 can support the tissue along the staple line. In some circumstances, a haemostatic agent, and/or any other suitable therapeutic medicament, contained within the implanted cartridge body 1010 can treat the tissue over time. A haemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulose), extracellular proteins such as collagen, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or anti-microbial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 7A:
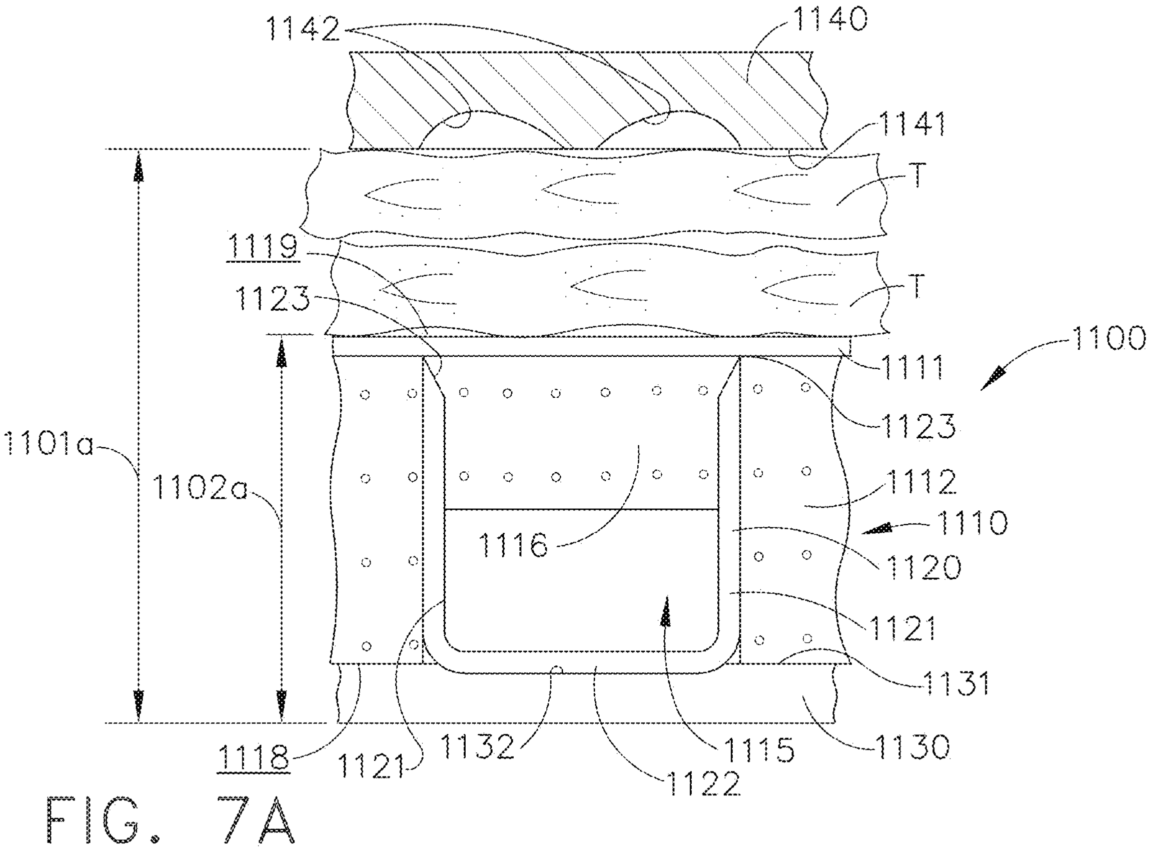
FIG. 7A is a diagram illustrating a staple positioned in a crushable staple cartridge body.
Figure 7B:
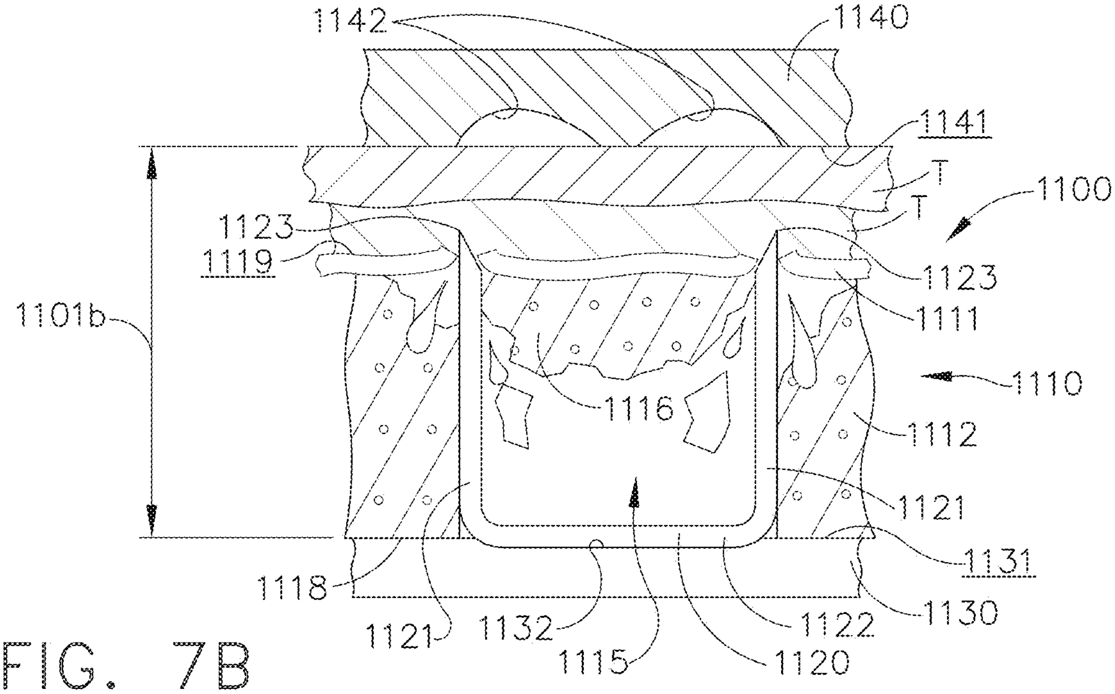
FIG. 7B is a diagram illustrating the crushable staple cartridge body of FIG. 7A being crushed by an anvil.
Figure 7C:
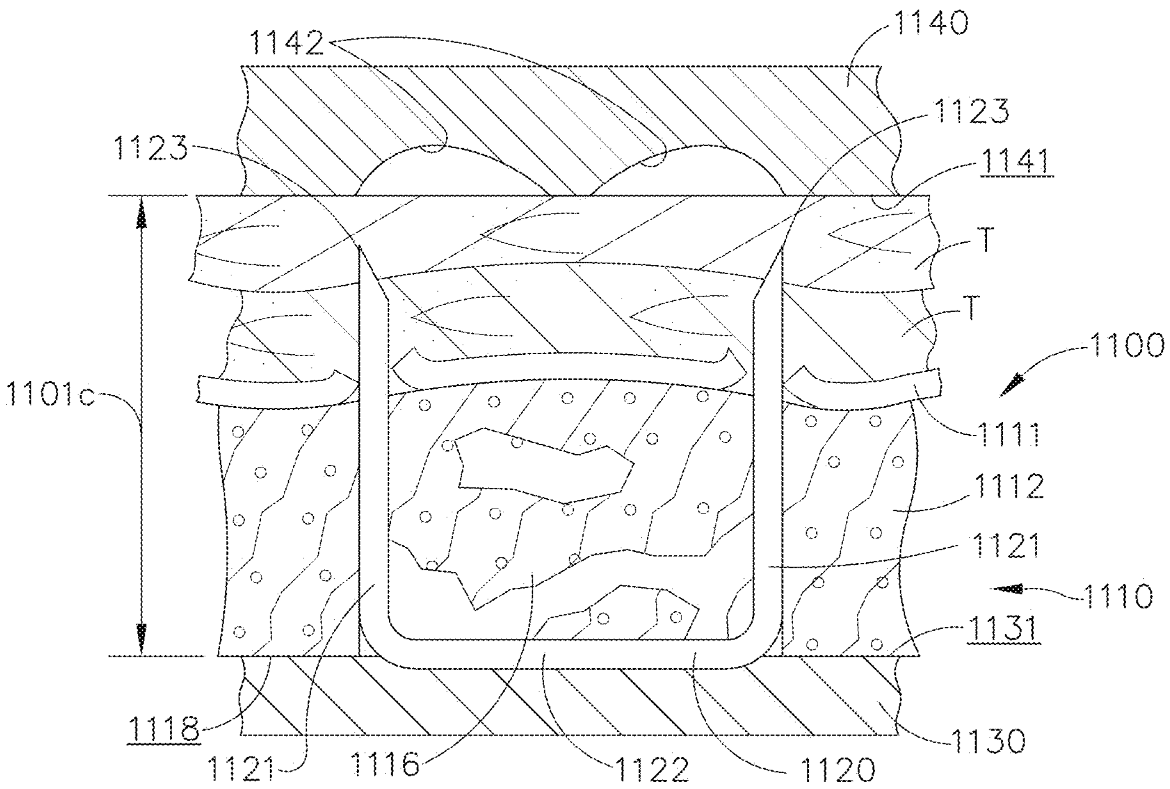
FIG. 7C is a diagram illustrating the crushable staple cartridge body of FIG. 7A being further crushed by the anvil.

In various embodiments, referring now to FIGS. 7A-7D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 7A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101*a* away from the staple cartridge support surface 1131 and the tissue-contacting surface 1119 can be positioned a distance 1102*a* away from the staple cartridge support surface 1131. Thereafter, as the anvil 1140 is moved toward the staple cartridge support 1130, referring now to FIG. 7B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 7B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 7B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 7D:
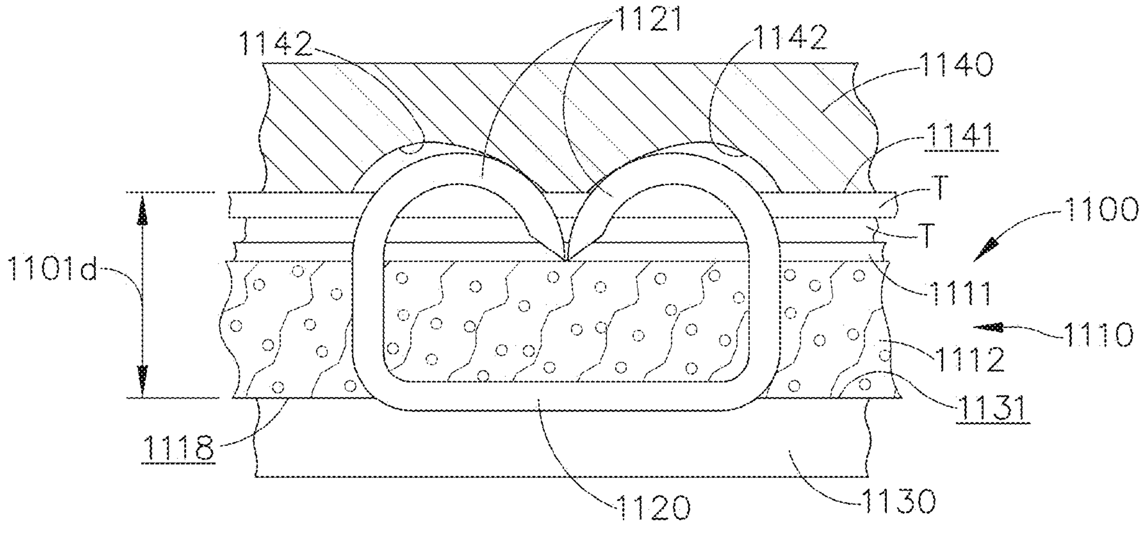
FIG. 7D is a diagram illustrating the staple of FIG. 7A in a fully formed configuration and the crushable staple cartridge of FIG. 7A in a fully crushed condition.

When the anvil 1140 is in a partially closed, unfired position, referring again to FIG. 7A, the anvil 1140 can be positioned a distance 1101*a* away from the cartridge support surface 1131 such that a gap is defined therebetween. This gap can be filled by the staple cartridge 1100, having a staple cartridge height 1102*a*, and the tissue T. As the anvil 1140 is moved downwardly to compress the staple cartridge 1100, referring again to FIG. 7B, the distance between the tissue contacting surface 1141 and the cartridge support surface 1131 can be defined by a distance 1101*b* which is shorter than the distance 1101*a*. In various circumstances, the gap between the tissue-contacting surface 1141 of anvil 1140 and the cartridge support surface 1131, defined by distance 1101*b*, may be larger than the original, undeformed staple cartridge height 1102*a*. As the anvil 1140 is moved closer to the cartridge support surface 1131, referring now to FIG. 7C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101*c* which, in various embodiments, may be greater than, equal to, or less than the original, undeformed cartridge height 1102*a*. Referring now to FIG. 7D, the anvil 1140 can be moved into a final, fired position in which the staples 1120 have been fully formed, or at least formed to a desired height. In such a position, the tissue-contacting surface 1141 of anvil 1140 can be a distance 1101*d* away from the cartridge support surface 1131, wherein the distance 1101*d* can be shorter than the original, undeformed cartridge height 1102*a*. As also illustrated in FIG. 7D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 7A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 7A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 7A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

Figure 8:
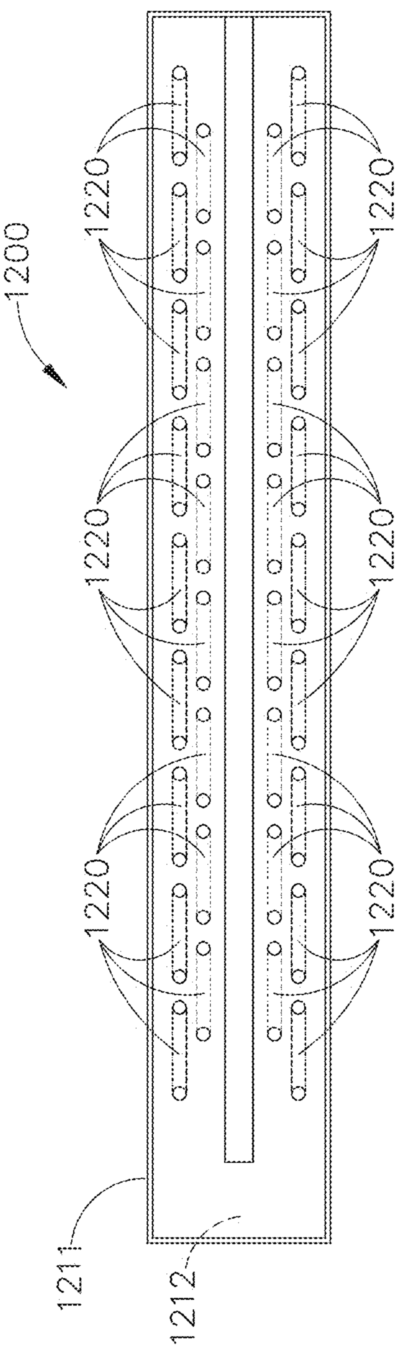
FIG. 8 is a top view of a staple cartridge in accordance with at least one embodiment comprising staples embedded in a collapsible staple cartridge body.
Figure 9:
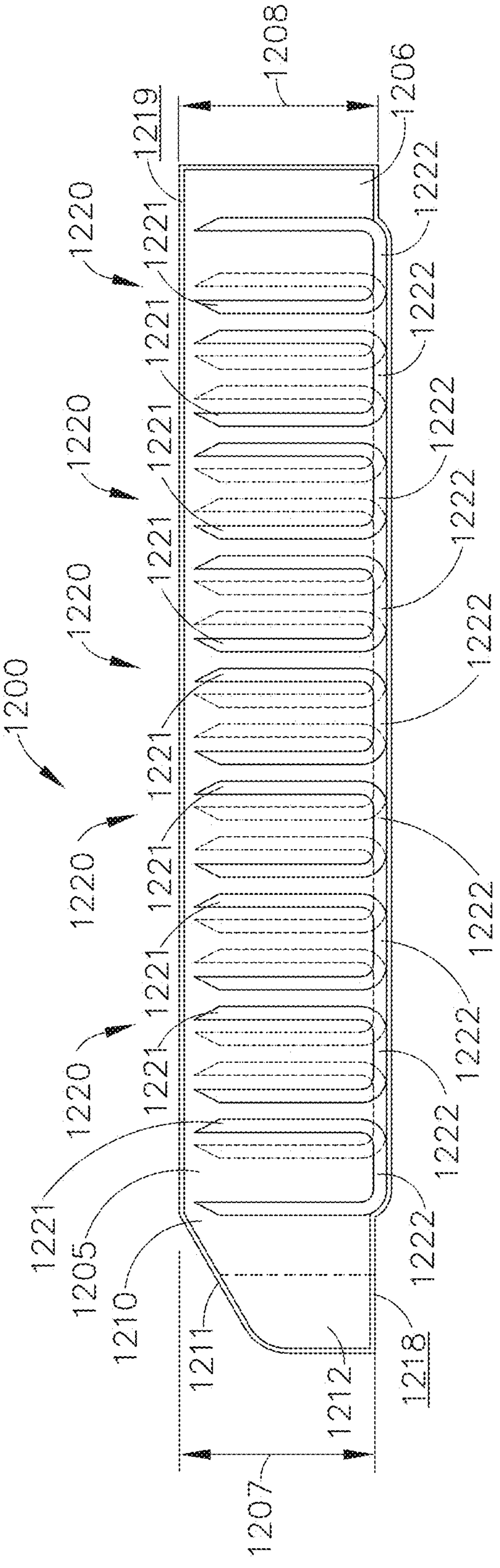
FIG. 9 is an elevational view of the staple cartridge of FIG. 8.

In various embodiments, referring now to FIGS. 8 and 9, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 8 and 9, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgicel and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 8 and 9, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 10:
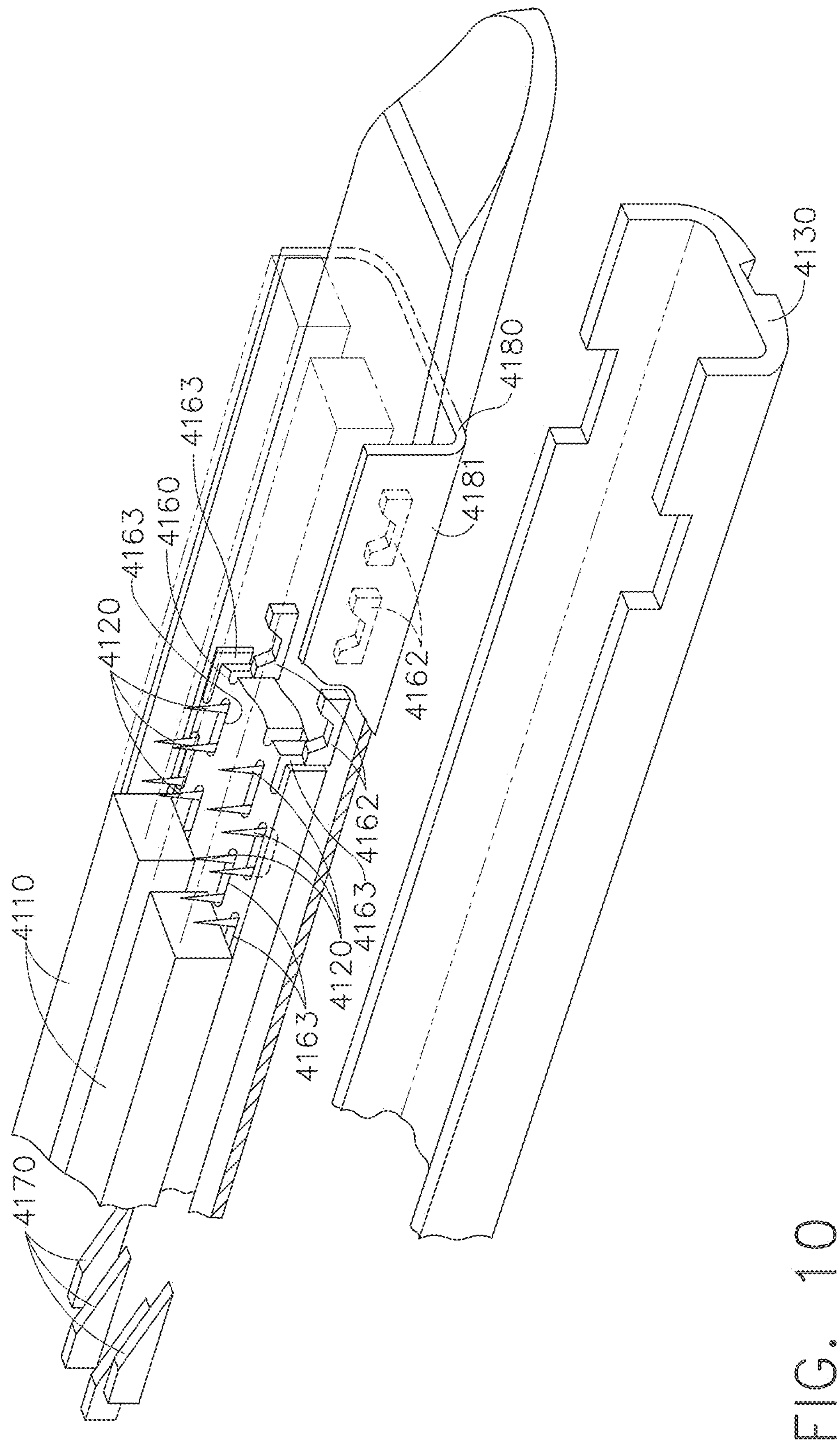
FIG. 10 is an exploded perspective view of an alternative embodiment of a compressible staple cartridge comprising staples therein and a system for driving the staples against an anvil.
Figure 10A:
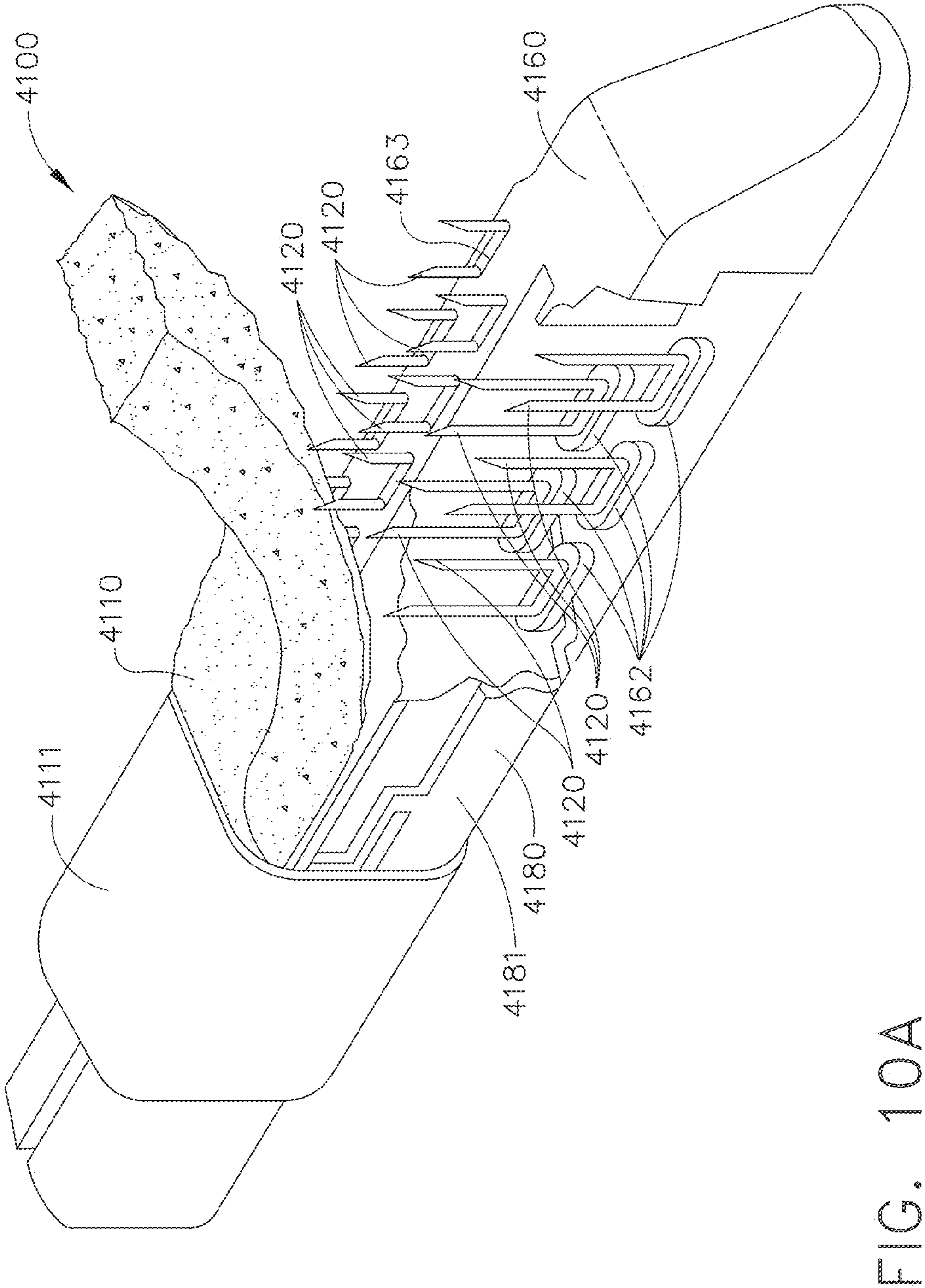
FIG. 10A is a partial cut-away view of an alternative embodiment of the staple cartridge of FIG. 10.
Figure 11:
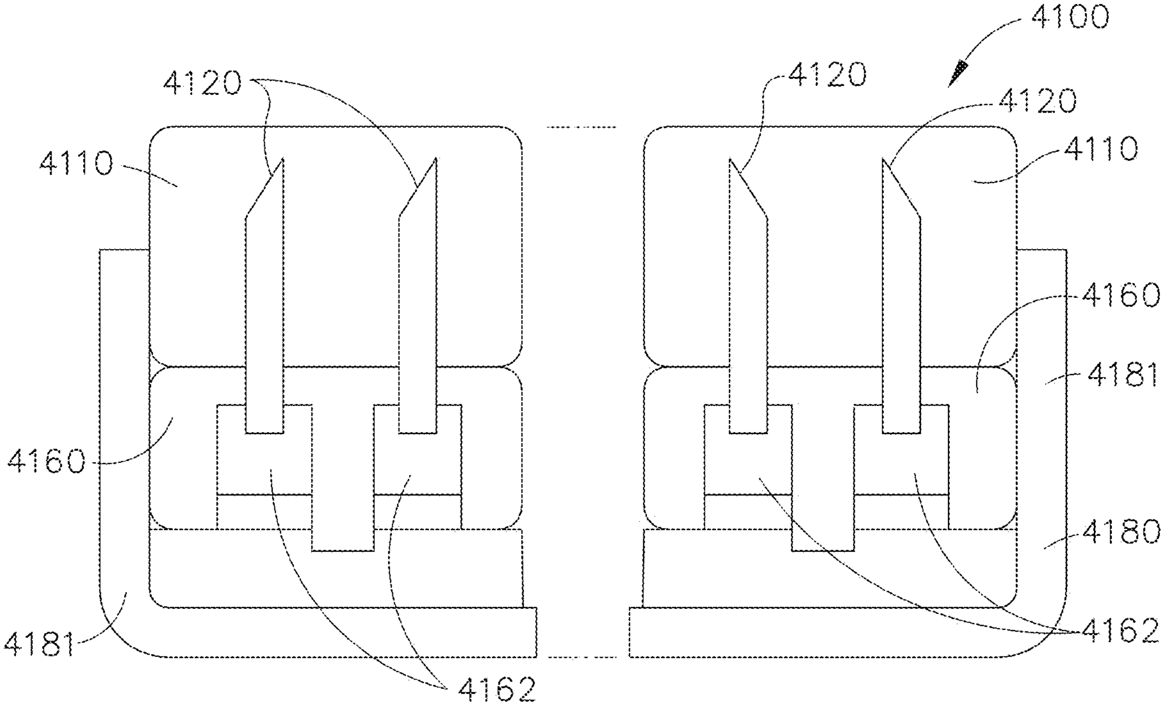
FIG. 11 is a cross-sectional view of the staple cartridge of FIG. 10.
Figure 12:
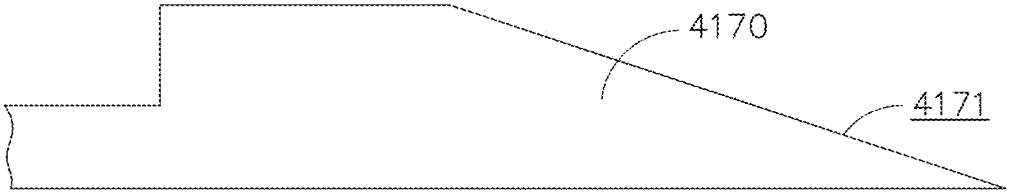
FIG. 12 is an elevational view of a sled configured to traverse the staple cartridge of FIG. 10 and move the staples to toward the anvil.

In various embodiments described herein, the staples of a staple cartridge can be fully formed by an anvil when the anvil is moved into a closed position. In various other embodiments, referring now to FIGS. 10-13, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 11, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 10A, the staple cartridge 4100 can further comprise a water impermeable wrap or membrane 4111 surrounding the cartridge body 4110 and the driver holder 4160, for example.

Figure 13:
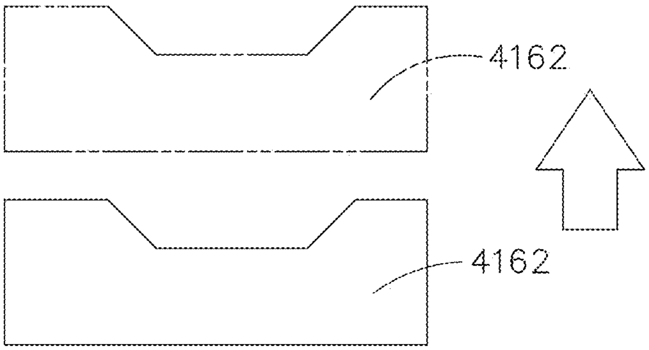
FIG. 13 is a diagram of a staple driver which can be lifted toward the anvil by the sled of FIG. 12.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 12, the sleds 4170 can each comprise at least one angled or inclined surface 4711 which can be configured to slide underneath the staple drivers 4162 and lift the staple drivers 4162 as illustrated in FIG. 13.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 10, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist. Surgical stapling instruments are disclosed in U.S. Pat. No. 7,380,696, which issued on Jun. 3, 2008, the entire disclosure of which is incorporated by reference herein. An illustrative multi-stroke handle for the surgical stapling and severing instrument is described in greater detail in the commonly-owned U.S. patent application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in commonly owned U.S. patent application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

In various embodiments described herein, a staple cartridge can comprise means for compensating for the thickness of the tissue captured within the staples deployed from the staple cartridge. In various embodiments, referring to FIG. 14, a staple cartridge, such as staple cartridge 10000, for example, can include a rigid first portion, such as support portion 10010, for example, and a compressible second portion, such as tissue thickness compensator 10020, for example. In at least one embodiment, referring primarily to FIG. 16, the support portion 10010 can comprise a cartridge body, a top deck surface 10011, and a plurality of staple cavities 10012 wherein, similar to the above, each staple cavity 10012 can define an opening in the deck surface 10011. A staple 10030, for example, can be removably positioned in each staple cavity 10012. In at least one such embodiment, each staple 10030 can comprise a base 10031 and one or more legs 10032 extending from the base 10031. Prior to the staples 10030 being deployed, as also described in greater detail below, the bases 10031 of the staples 10030 can be supported by staple drivers positioned within the support portion 10010 and, concurrently, the legs 10032 of the staples 10030 can be at least partially contained within the staple cavities 10012. In various embodiments, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area 10039 in which the tissue T and the tissue thickness compensator 10020 can be captured. In various circumstances, the staple entrapment area 10039 can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

Figure 49:
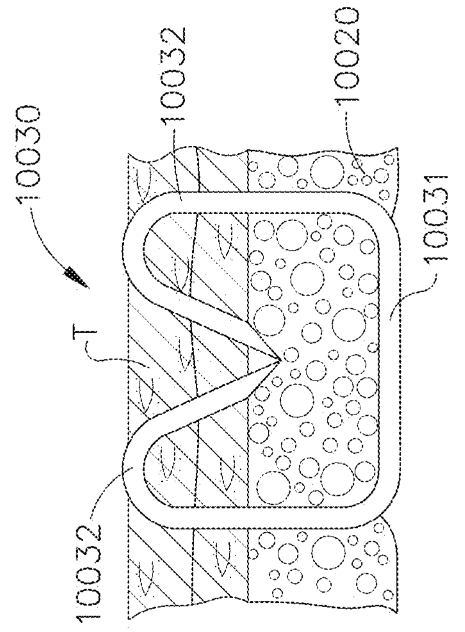
FIG. 49 is a diagram illustrating tissue and a tissue thickness compensator captured within a staple.
Figure 48:
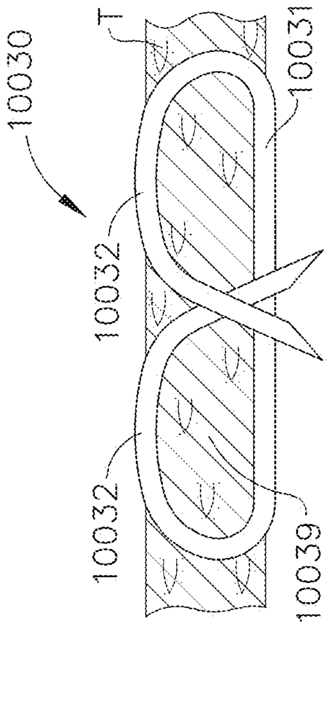
FIG. 48 is a diagram illustrating tissue captured within a staple.
Figure 51:
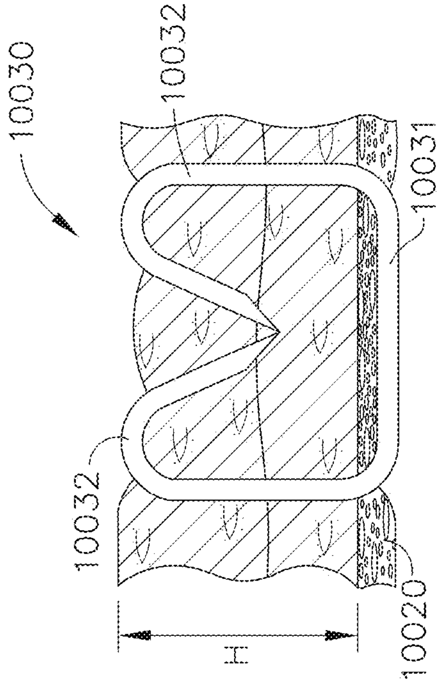
FIG. 51 is a diagram illustrating thick tissue and a tissue thickness compensator captured within a staple.

In previous embodiments, a surgeon was often required to select the appropriate staples having the appropriate staple height for the tissue being stapled. For example, a surgeon could select tall staples for use with thick tissue and short staples for use with thin tissue. In some circumstances, however, the tissue being stapled did not have a consistent thickness and, thus, some staples were unable to achieve the desired fired configuration. For example, FIG. 48 illustrates a tall staple used in thin tissue. Referring now to FIG. 49, when a tissue thickness compensator, such as tissue thickness compensator 10020, for example, is used with thin tissue, for example, the larger staple may be formed to a desired fired configuration.

Figure 43:
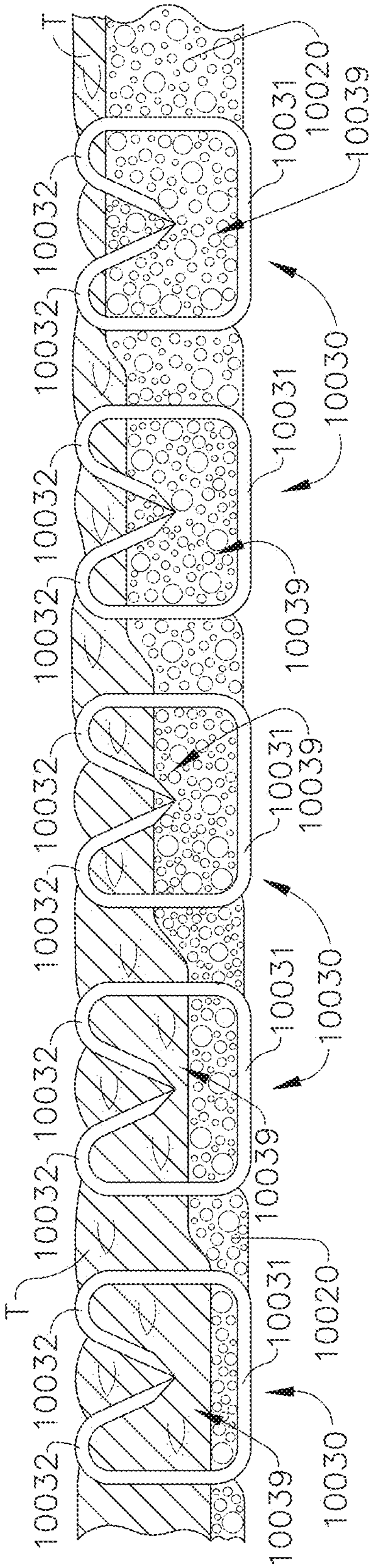
FIG. 43 is a diagram illustrating a tissue thickness compensator which is compensating for different tissue thickness captured within different staples.
Figure 44:
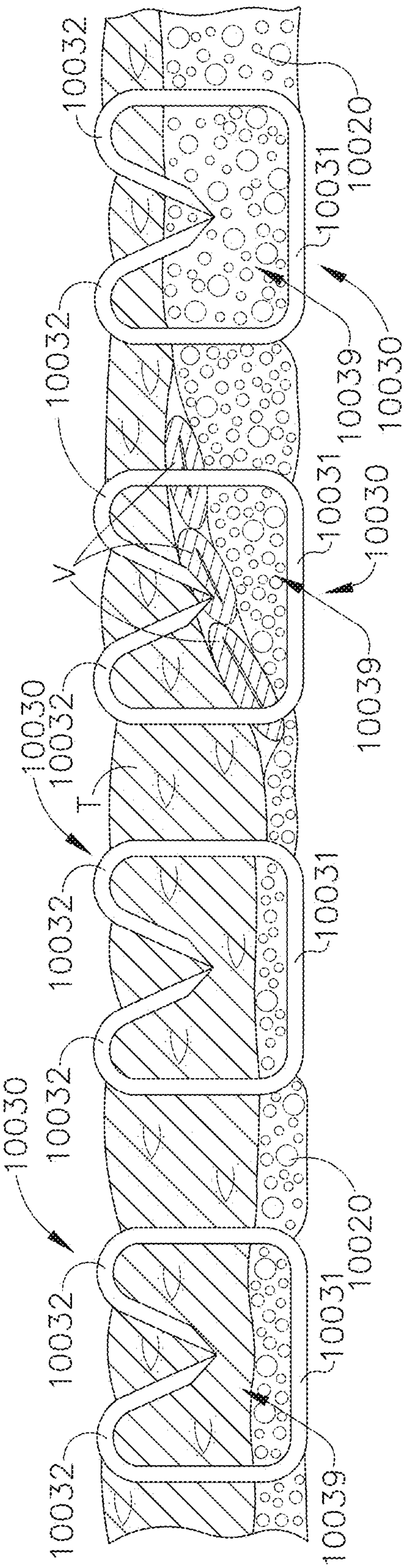
FIG. 44 is a diagram illustrating a tissue thickness compensator applying a compressive pressure to one or more vessels that have been transected by a staple line.
Figure 45:
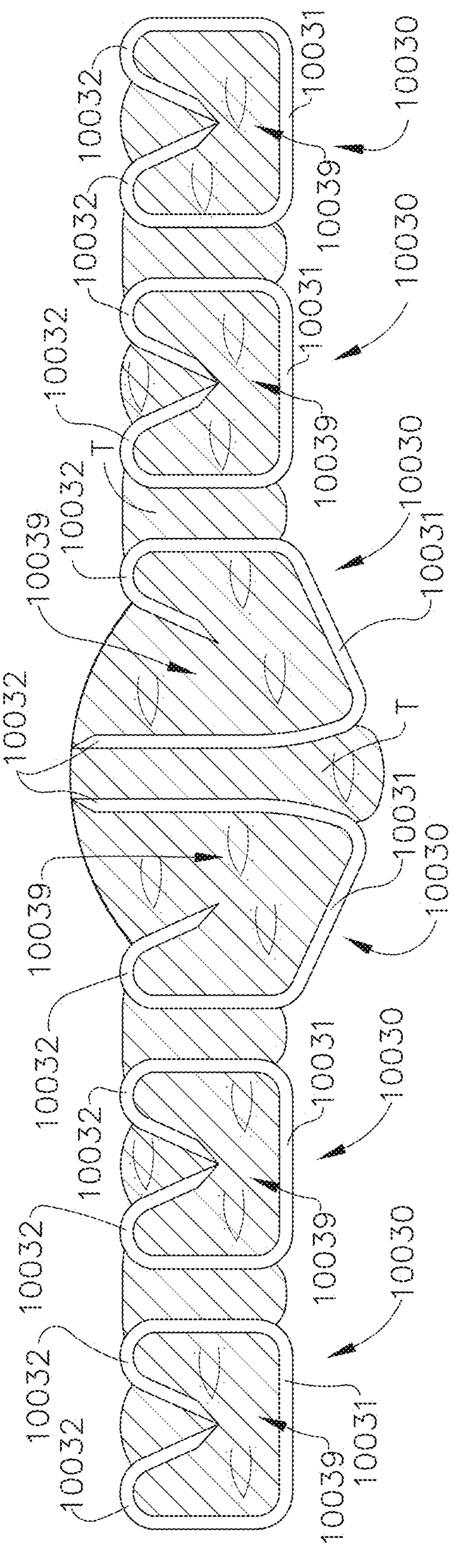
FIG. 45 is a diagram illustrating a circumstance wherein one or more staples have been improperly formed.
Figure 46:
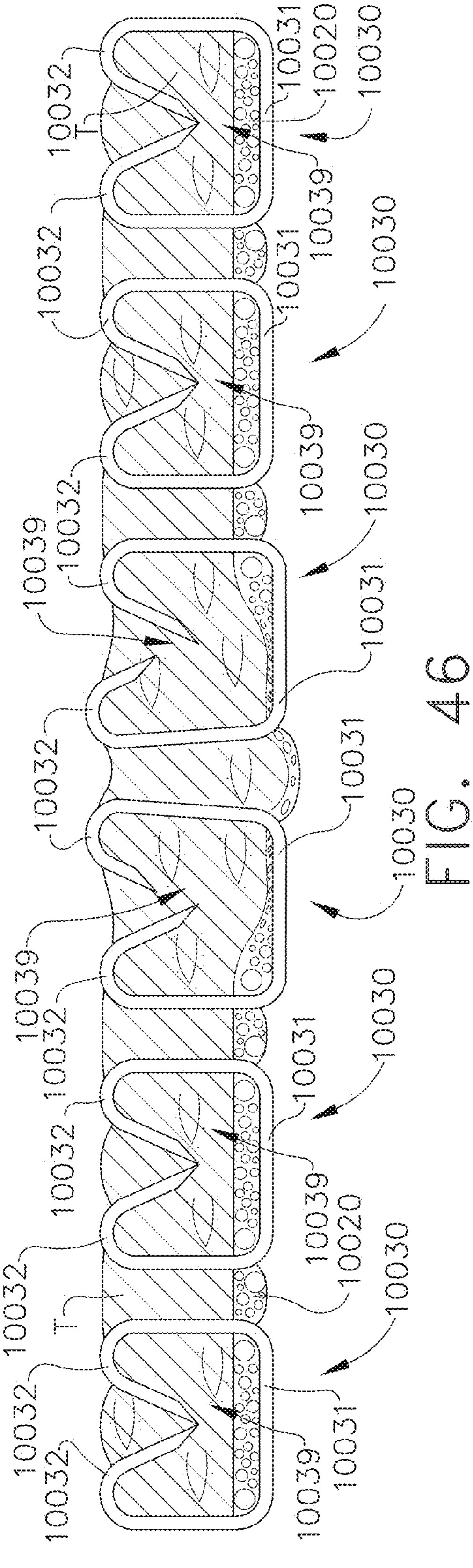
FIG. 46 is a diagram illustrating a tissue thickness compensator which could compensate for improperly formed staples.
Figure 47:
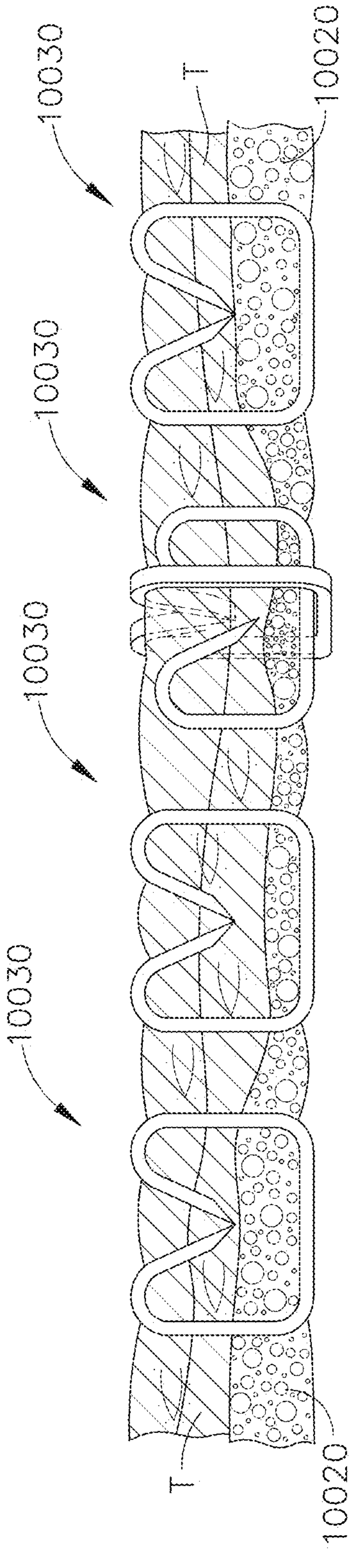
FIG. 47 is a diagram illustrating a tissue thickness compensator positioned in a region of tissue in which multiple staples lines have intersected.

Owing to the compressibility of the tissue thickness compensator, the tissue thickness compensator can compensate for the thickness of the tissue captured within each staple. More particularly, referring now to FIGS. 43 and 44, a tissue thickness compensator, such as tissue thickness compensator 10020, for example, can consume larger and/or smaller portions of the staple entrapment area 10039 of each staple 10030 depending on the thickness and/or type of tissue contained within the staple entrapment area 10039. For example, if thinner tissue T is captured within a staple 10030, the tissue thickness compensator 10020 can consume a larger portion of the staple entrapment area 10039 as compared to circumstances where thicker tissue T is captured within the staple 10030. Correspondingly, if thicker tissue T is captured within a staple 10030, the tissue thickness compensator 10020 can consume a smaller portion of the staple entrapment area 10039 as compared to the circumstances where thinner tissue T is captured within the staple 10030. In this way, the tissue thickness compensator can compensate for thinner tissue and/or thicker tissue and assure that a compressive pressure is applied to the tissue irrespective, or at least substantially irrespective, of the tissue thickness captured within the staples. In addition to the above, the tissue thickness compensator 10020 can compensate for different types, or compressibilities, of tissues captured within different staples 10030. Referring now to FIG. 44, the tissue thickness compensator 10020 can apply a compressive force to vascular tissue T which can include vessels V and, as a result, restrict the flow of blood through the less compressible vessels V while still applying a desired compressive pressure to the surrounding tissue T. In various circumstances, further to the above, the tissue thickness compensator 10020 can also compensate for malformed staples. Referring to FIG. 45, the malformation of various staples 10030 can result in larger staple entrapment areas 10039 being defined within such staples. Owing to the resiliency of the tissue thickness compensator 10020, referring now to FIG. 46, the tissue thickness compensator 10020 positioned within malformed staples 10030 may still apply a sufficient compressive pressure to the tissue T even though the staple entrapment areas 10039 defined within such malformed staples 10030 may be enlarged. In various circumstances, the tissue thickness compensator 10020 located intermediate adjacent staples 10030 can be biased against the tissue T by properly-formed staples 10030 surrounding a malformed staple 10030 and, as a result, apply a compressive pressure to the tissue surrounding and/or captured within the malformed staple 10030, for example. In various circumstances, a tissue thickness compensator can compensate for different tissue densities which can arise due to calcifications, fibrous areas, and/or tissue that has been previously stapled or treated, for example.

Figure 53:
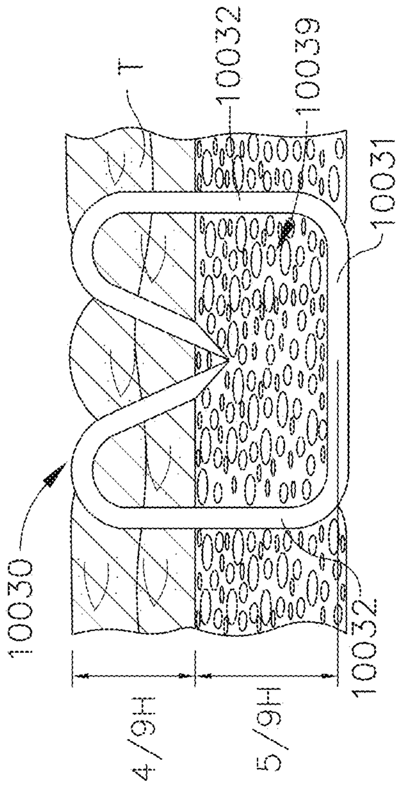
FIG. 53 is a diagram illustrating tissue having an intermediate thickness and a tissue thickness compensator captured within a staple.
Figure 50:
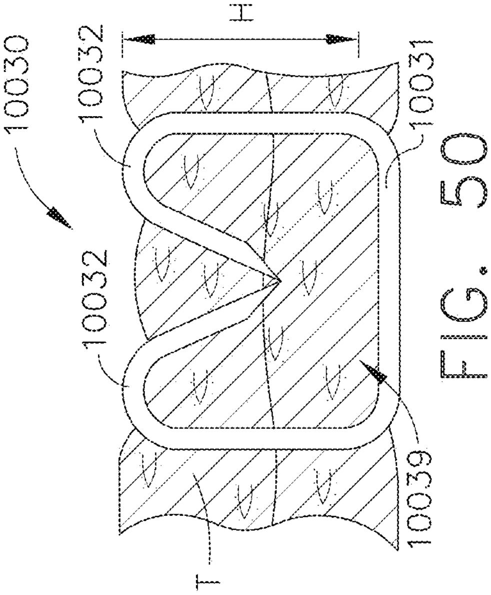
FIG. 50 is a diagram illustrating tissue captured within a staple.
Figure 52:
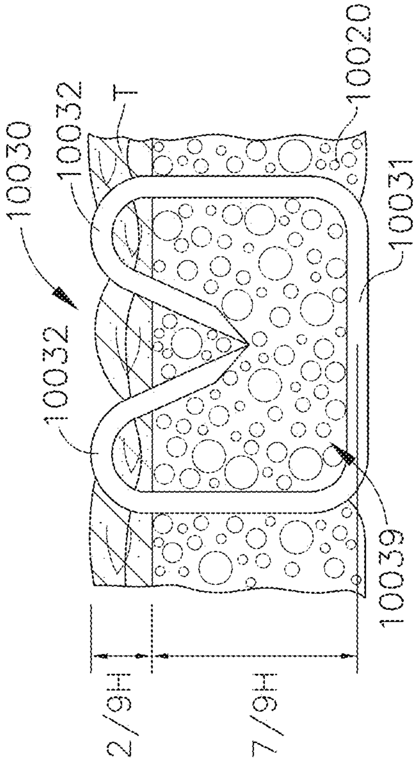
FIG. 52 is a diagram illustrating thin tissue and a tissue thickness compensator captured within a staple.
Figure 55:
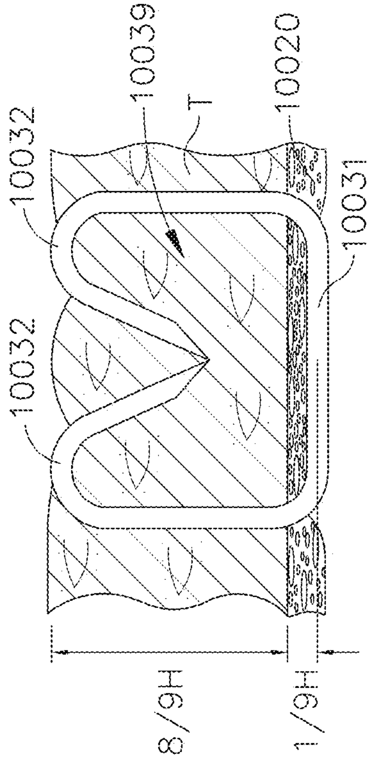
FIG. 55 is a diagram illustrating thick tissue and a tissue thickness compensator captured within a staple.
Figure 54:
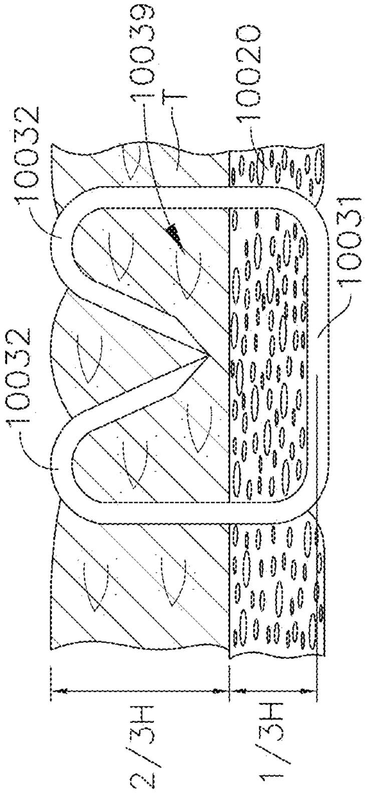
FIG. 54 is a diagram illustrating tissue having another intermediate thickness and a tissue thickness compensator captured within a staple.
Figure 57:
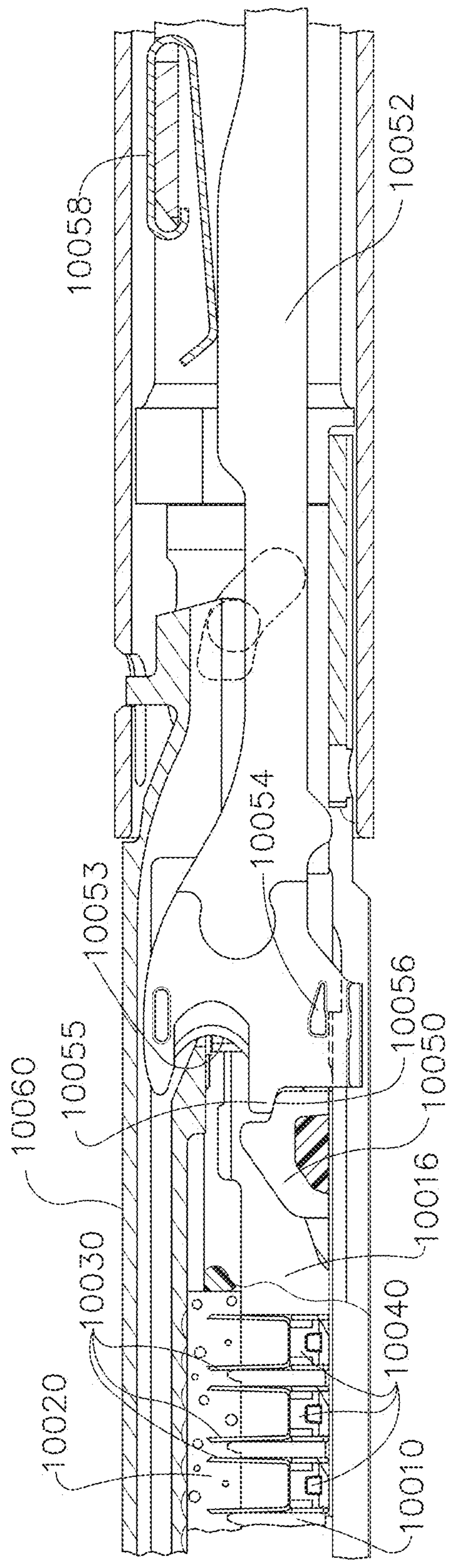
FIG. 57 is another partial cross-sectional view of the end effector of FIG. 56 illustrating the firing bar and the staple-firing sled in a partially advanced position.

In various embodiments, a fixed, or unchangeable, tissue gap can be defined between the support portion and the anvil and, as a result, the staples may be deformed to a predetermined height regardless of the thickness of the tissue captured within the staples. When a tissue thickness compensator is used with these embodiments, the tissue thickness compensator can adapt to the tissue captured between the anvil and the support portion staple cartridge and, owing to the resiliency of the tissue thickness compensator, the tissue thickness compensator can apply an additional compressive pressure to the tissue. Referring now to FIGS. 50-55, a staple 10030 has been formed to a predefined height H. With regard to FIG. 50, a tissue thickness compensator has not been utilized and the tissue T consumes the entirety of the staple entrapment area 10039. With regard to FIG. 57, a portion of a tissue thickness compensator 10020 has been captured within the staple 10030, compressed the tissue T, and consumed at least a portion of the staple entrapment area 10039. Referring now to FIG. 52, thin tissue T has been captured within the staple 10030. In this embodiment, the compressed tissue T has a height of approximately $\frac{2}{9}$H and the compressed tissue thickness compensator 10020 has a height of approximately $\frac{7}{9}$H, for example. Referring now to FIG. 53, tissue T having an intermediate thickness has been captured within the staple 10030. In this embodiment, the compressed tissue T has a height of approximately $\frac{4}{9}$H and the compressed tissue thickness compensator 10020 has a height of approximately $\frac{5}{9}$H, for example. Referring now to FIG. 54, tissue T having an intermediate thickness has been captured within the staple 10030. In this embodiment, the compressed tissue T has a height of approximately $\frac{2}{3}$H and the compressed tissue thickness compensator 10020 has a height of approximately $\frac{1}{3}$H, for example. Referring now to FIG. 53, thick tissue T has been captured within the staple 10030. In this embodiment, the compressed tissue T has a height of approximately $\frac{8}{9}$H and the compressed tissue thickness compensator 10020 has a height of approximately $\frac{1}{9}$H, for example. In various circumstances, the tissue thickness compensator can comprise a compressed height which comprises approximately 10% of the staple entrapment height, approximately 20% of the staple entrapment height, approximately 30% of the staple entrapment height, approximately 40% of the staple entrapment height, approximately 50% of the staple entrapment height, approximately 60% of the staple entrapment height, approximately 70% of the staple entrapment height, approximately 80% of the staple entrapment height, and/or approximately 90% of the staple entrapment height, for example.

In various embodiments, the staples 10030 can comprise any suitable unformed height. In certain embodiments, the staples 10030 can comprise an unformed height between approximately 2 mm and approximately 4.8 mm, for example. The staples 10030 can comprise an unformed height of approximately 2.0 mm, approximately 2.5 mm, approximately 3.0 mm, approximately 3.4 mm, approximately 3.5 mm, approximately 3.8 mm, approximately 4.0 mm, approximately 4.1 mm, and/or approximately 4.8 mm, for example. In various embodiments, the height H to which the staples can be deformed can be dictated by the distance between the deck surface 10011 of the support portion 10010 and the opposing anvil. In at least one embodiment, the distance between the deck surface 10011 and the tissue-contacting surface of the anvil can be approximately 0.097", for example. The height H can also be dictated by the depth of the forming pockets defined within the anvil. In at least one embodiment, the forming pockets can have a depth measured from the tissue-contacting surface, for example. In various embodiments, as described in greater detail below, the staple cartridge 10000 can further comprise staple drivers which can lift the staples 10030 toward the anvil and, in at least one embodiment, lift, or "overdrive", the staples above the deck surface 10011. In such embodiments, the height H to which the staples 10030 are formed can also be dictated by the distance in which the staples 10030 are overdriven. In at least one such embodiment, the staples 10030 can be overdriven by approximately 0.028", for example, and can result in the staples 10030 being formed to a height of approximately 0.189", for example. In various embodiments, the staples 10030 can be formed to a height of approximately 0.8 mm, approximately 1.0 mm, approximately 1.5 mm, approximately 1.8 mm, approximately 2.0 mm, and/or approximately 2.25 mm, for example. In certain embodiments, the staples can be formed to a height between approximately 2.25 mm and approximately 3.0 mm, for example. Further to the above, the height of the staple entrapment area of a staple can be determined by the formed height of the staple and the width, or diameter, of the wire comprising the staple. In various embodiments, the height of the staple entrapment area 10039 of a staple 10030 can comprise the formed height H of the staple less two diameter widths of the wire. In certain embodiments, the staple wire can comprise a diameter of approximately 0.0089", for example. In various embodiments, the staple wire can comprise a diameter between approximately 0.0069" and approximately 0.0119", for example. In at least one exemplary embodiment, the formed height H of a staple 10030 can be approximately 0.189" and the staple wire diameter can be approximately 0.0089" resulting in a staple entrapment height of approximately 0.171", for example.

In various embodiments, further to the above, the tissue thickness compensator can comprise an uncompressed, or pre-deployed, height and can be configured to deform to one of a plurality of compressed heights. In certain embodiments, the tissue thickness compensator can comprise an uncompressed height of approximately 0.125", for example. In various embodiments, the tissue thickness compensator can comprise an uncompressed height of greater than or equal to approximately 0.080", for example. In at least one embodiment, the tissue thickness compensator can comprise an uncompressed, or pre-deployed, height which is greater than the unfired height of the staples. In at least one embodiment, the uncompressed, or pre-deployed, height of the tissue thickness compensator can be approximately 10% taller, approximately 20% taller, approximately 30% taller, approximately 40% taller, approximately 50% taller, approximately 60% taller, approximately 70% taller, approximately 80% taller, approximately 90% taller, and/or approximately 100% taller than the unfired height of the staples, for example. In at least one embodiment, the uncompressed, or pre-deployed, height of the tissue thickness compensator can be up to approximately 100% taller than the unfired height of the staples, for example. In certain embodiments, the uncompressed, or pre-deployed, height of the tissue thickness compensator can be over 100% taller than the unfired height of the staples, for example. In at least one embodiment, the tissue thickness compensator can comprise an uncompressed height which is equal to the unfired height of the staples. In at least one embodiment, the tissue thickness compensator can comprise an uncompressed height which is less than the unfired height of the staples. In at least one embodiment, the uncompressed, or pre-deployed, height of the thickness compensator can be approximately 10% shorter, approximately 20% shorter, approximately 30% shorter, approximately 40% shorter, approximately 50% shorter, approximately 60% shorter, approximately 70% shorter, approximately 80% shorter, and/or approximately 90% shorter than the unfired height of the staples, for example. In various embodiments, the compressible second portion can comprise an uncompressed height which is taller than an uncompressed height of the tissue T being stapled. In certain embodiments, the tissue thickness compensator can comprise an uncompressed height which is equal to an uncompressed height of the tissue T being stapled. In various embodiments, the tissue thickness compensator can comprise an uncompressed height which is shorter than an uncompressed height of the tissue T being stapled.

As described above, a tissue thickness compensator can be compressed within a plurality of formed staples regardless of whether thick tissue or thin tissue is captured within the staples. In at least one exemplary embodiment, the staples within a staple line, or row, can be deformed such that the staple entrapment area of each staple comprises a height of approximately 2.0 mm, for example, wherein the tissue T and the tissue thickness compensator can be compressed within this height. In certain circumstances, the tissue T can comprise a compressed height of approximately 1.75 mm within the staple entrapment area while the tissue thickness compensator can comprise a compressed height of approximately 0.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 1.25 mm within the staple entrapment area while the tissue thickness compensator can comprise a compressed height of approximately 0.75 mm within the staple entrapment area, thereby totaling the approximately 2.0 mm staple entrapment area height, for example. In certain circumstances, the tissue T can comprise a compressed height of approximately 1.0 mm within the staple entrapment area while the tissue thickness compensator can comprise a compressed height of approximately 1.0 mm within the staple entrapment area, thereby totaling the approximately 2.0 mm staple entrapment area height, for example. In certain circumstances, the tissue T can comprise a compressed height of approximately 0.75 mm within the staple entrapment area while the tissue thickness compensator can comprise a compressed height of approximately 1.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 0.25 mm within the staple entrapment area while the tissue thickness compensator can comprise a compressed height of approximately 1.75 mm within the staple entrapment area, thereby totaling the approximately 2.0 mm staple entrapment area height, for example.

In various embodiments, further to the above, the tissue thickness compensator can comprise an uncompressed height which is less than the fired height of the staples. In certain embodiments, the tissue thickness compensator can comprise an uncompressed height which is equal to the fired height of the staples. In certain other embodiments, the tissue thickness compensator can comprise an uncompressed height which is taller than the fired height of the staples. In at least one such embodiment, the uncompressed height of a tissue thickness compensator can comprise a thickness which is approximately 110% of the formed staple height, approximately 120% of the formed staple height, approximately 130% of the formed staple height, approximately 140% of the formed staple height, approximately 150% of the formed staple height, approximately 160% of the formed staple height, approximately 170% of the formed staple height, approximately 180% of the formed staple height, approximately 190% of the formed staple height, and/or approximately 200% of the formed staple height, for example. In certain embodiments, the tissue thickness compensator can comprise an uncompressed height which is more than twice the fired height of the staples. In various embodiments, the tissue thickness compensator can comprise a compressed height which is from approximately 85% to approximately 150% of the formed staple height, for example. In various embodiments, as described above, the tissue thickness compensator can be compressed between an uncompressed thickness and a compressed thickness. In certain embodiments, the compressed thickness of a tissue thickness compensator can be approximately 10% of its uncompressed thickness, approximately 20% of its uncompressed thickness, approximately 30% of its uncompressed thickness, approximately 40% of its uncompressed thickness, approximately 50% of its uncompressed thickness, approximately 60% of its uncompressed thickness, approximately 70% of its uncompressed thickness, approximately 80% of its uncompressed thickness, and/or approximately 90% of its uncompressed thickness, for example. In various embodiments, the uncompressed thickness of the tissue thickness compensator can be approximately two times, approximately ten times, approximately fifty times, and/or approximately one hundred times thicker than its compressed thickness, for example. In at least one embodiment, the compressed thickness of the tissue thickness compensator can be between approximately 60% and approximately 99% of its uncompressed thickness. In at least one embodiment, the uncompressed thickness of the tissue thickness compensator can be at least 50% thicker than its compressed thickness. In at least one embodiment, the uncompressed thickness of the tissue thickness compensator can be up to one hundred times thicker than its compressed thickness. In various embodiments, the compressible second portion can be elastic, or at least partially elastic, and can bias the tissue T against the deformed legs of the staples. In at least one such embodiment, the compressible second portion can resiliently expand between the tissue T and the base of the staple in order to push the tissue T against the legs of the staple. In certain embodiments, discussed in further detail below, the tissue thickness compensator can be positioned intermediate the tissue T and the deformed staple legs. In various circumstances, as a result of the above, the tissue thickness compensator can be configured to consume any gaps within the staple entrapment area.

In various embodiments, the tissue thickness compensator may comprise materials characterized by one or more of the following properties: biocompatible, bioabsorbable, bioresorbable, biodurable, biodegradable, compressible, fluid absorbable, swellable, self-expandable, bioactive, medicament, pharmaceutically active, anti-adhesion, haemostatic, antibiotic, anti-microbial, anti-viral, nutritional, adhesive, permeable, hydrophilic and/or hydrophobic, for example. In various embodiments, a surgical instrument comprising an anvil and a staple cartridge may comprise a tissue thickness compensator associated with the anvil and/or staple cartridge comprising at least one of a haemostatic agent, such as fibrin and thrombin, an antibiotic, such as doxycpl, and medicament, such as matrix metalloproteinases (MMPs).

In various embodiments, the tissue thickness compensator may comprise synthetic and/or non-synthetic materials. The tissue thickness compensator may comprise a polymeric composition comprising one or more synthetic polymers and/or one or more non-synthetic polymers. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam may have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In various embodiments, the tissue thickness compensator may comprise a microgel or a nanogel. The hydrogel may comprise carbohydrate-derived microgels and/or nanogels. In certain embodiments, a tissue thickness compensator may be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or haemostatic behavior. Further, the gradient could be also compositional with a varying bioabsorption profile. A short term absorption profile may be preferred to address hemostasis while a long term absorption profile may address better tissue healing without leakages.

Examples of non-synthetic materials include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof.

Examples of synthetic absorbable materials include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and F-caprolactone (PGCL), a copolymer of glycolide and -trimethylene carbonate, poly(glycerol sebacate) (PGS), poly(dioxanone) (PDS), polyesters, poly (orthoesters), polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly(E-caprolactone), polyethyleneglycol (PEG), poly[bis (carboxylatophenoxy) phosphazene] poly(amino acids), pseudo-poly(amino acids), absorbable polyurethanes, poly (phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. In various embodiments, the polyester is may be selected from the group consisting of polylactides, polyglycolides, trimethylene carbonates, polydioxanones, polycaprolactones, polybutesters, and combinations thereof.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-ε-caprolactone-poliglecaprolactone 25) copolymer, commercially available from Ethicon under the trade designation MONOCRYL, for example.

Examples of synthetic non-absorbable materials include, but are not limited to, polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, silicons, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of ε-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and ε-caprolactone. In another embodiment, the elastomeric copolymer is a copolymer of lactide and ε-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the tissue thickness compensator may comprise an emulsifier. Examples of emulsifiers may include, but are not limited to, water-soluble polymers, such as, polyvinyl alcohol (PVA), polyvinyl pyrrolidone (PVP), polyethylene glycol (PEG), polypropylene glycol (PPG), PLURONICS, TWEENS, polysaccharides and combinations thereof.

In various embodiments, the tissue thickness compensator may comprise a surfactant. Examples of surfactants may include, but are not limited to, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers.

In various embodiments, the polymeric composition may comprise a pharmaceutically active agent. The polymeric composition may release a therapeutically effective amount of the pharmaceutically active agent. In various embodiments, the pharmaceutically active agent may be released as the polymeric composition is desorbed/absorbed. In various embodiments, the pharmaceutically active agent may be released into fluid, such as, for example, blood, passing over or through the polymeric composition. Examples of pharmaceutically active agents may include, but are not limited to, haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

In various embodiments, the polymeric composition may comprise a haemostatic material. The tissue thickness compensator may comprise haemostatic materials comprising poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, ε-amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof. The tissue thickness compensator may be characterized by haemostatic properties.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example.

According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, the tissue thickness compensator may comprise a material that expands. As discussed above, the tissue thickness compensator may comprise a compressed material that expands when uncompressed or deployed, for example. In various embodiments, the tissue thickness compensator may comprise a self-expanding material formed in situ. In various embodiments, the tissue thickness compensator may comprise at least one precursor selected to spontaneously crosslink when contacted with at least one of other precursor(s), water, and/or bodily fluids. In various embodiments, a first precursor may contact one or more other precursors to form an expandable and/or swellable tissue thickness compensator. In various embodiments, the tissue thickness compensator may comprise a fluid-swellable composition, such as a water-swellable composition, for example. In various embodiments, the tissue thickness compensator may comprise a gel comprising water.

In various embodiments, the tissue thickness compensator may comprise a biodegradable foam having an encapsulation comprising dry hydrogel particles or granules embedded therein. Without wishing to be bound to any particular theory, the encapsulations in the foam may be formed by contacting an aqueous solution of a hydrogel precursor and an organic solution of biocompatible materials to form the foam. In various embodiments, the aqueous solution and organic solution may form micelles. The aqueous solution and organic solution may be dried to encapsulate dry hydrogel particles or granules within the foam. For example, a hydrogel precursor, such as a hydrophilic polymer, may be dissolved in water to form a dispersion of micelles. The aqueous solution may contact an organic solution of dioxane comprising poly(glycolic acid) and polycaprolactone. The aqueous and organic solutions may be lyophilized to form a biodegradable foam having dry hydrogel particles or granules dispersed therein. Without wishing to be bound to any particular theory, it is believed that the micelles form the encapsulation having the dry hydrogel particles or granules dispersed within the foam structure. In certain embodiments, the encapsulation may be ruptured, and the dry hydrogel particles or granules may contact a fluid, such as a bodily fluid, and expand.

In various embodiments, as described above, the tissue thickness compensator may comprise an initial thickness and an expanded thickness. In certain embodiments, the initial thickness of a tissue thickness compensator can be approximately 0.001% of its expanded thickness, approximately 0.01% of its expanded thickness, approximately 0.1% of its expanded thickness, approximately 1% of its expanded thickness, approximately 10% of its expanded thickness, approximately 20% of its expanded thickness, approximately 30% of its expanded thickness, approximately 40% of its expanded thickness, approximately 50% of its expanded thickness, approximately 60% of its expanded thickness, approximately 70% of its expanded thickness, approximately 80% of its expanded thickness, and/or approximately 90% of its expanded thickness, for example. In various embodiments, the expanded thickness of the tissue thickness compensator can be approximately two times, approximately five times, approximately ten times, approximately fifty times, approximately one hundred times, approximately two hundred times, approximately three hundred times, approximately four hundred times, approximately five hundred times, approximately six hundred times, approximately seven hundred times, approximately eight hundred times, approximately nine hundred times, and/or approximately one thousand times thicker than its initial thickness, for example. In various embodiments, the initial thickness of the tissue thickness compensator can be up to 1% its expanded thickness, up to 5% its expanded thickness, up to 10% its expanded thickness, and up to 50% its expanded thickness. In various embodiments, the expanded thickness of the tissue thickness compensator can be at least 50% thicker than its initial thickness, at least 100% thicker than its initial thickness, at least 300% thicker than its initial thickness, and at least 500% thicker than its initial thickness. As described above, in various circumstances, as a result of the above, the tissue thickness compensator can be configured to consume any gaps within the staple entrapment area.

As discussed above, in various embodiments, the tissue thickness compensator may comprise a hydrogel. In various embodiments, the hydrogel may comprise homopolymer hydrogels, copolymer hydrogels, multipolymer hydrogels, interpenetrating polymer hydrogels, and combinations thereof. In various embodiments, the hydrogel may comprise microgels, nanogels, and combinations thereof. The hydrogel may generally comprise a hydrophilic polymer network capable of absorbing and/or retaining fluids. In various embodiments, the hydrogel may comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking. The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In certain embodiments, the precursor may crosslink with endogenous materials and/or tissues.

In various embodiments, the hydrogel may comprise an environmentally sensitive hydrogel (ESH). The ESH may comprise materials having fluid-swelling properties that relate to environmental conditions. The environmental conditions may include, but are not limited to, the physical conditions, biological conditions, and/or chemical conditions at the surgical site. In various embodiments, the hydrogel may swell or shrink in response to temperature, pH, electric fields, ionic strength, enzymatic and/or chemical reactions, electrical and/or magnetic stimuli, and other physiological and environmental variables, for example. In various embodiments, the ESH may comprise multifunctional acrylates, hydroxyethylmethacrylate (HEMA), elastomeric acrylates, and related monomers.

In various embodiments, the tissue thickness compensator comprising a hydrogel may comprise at least one of the non-synthetic materials and synthetic materials described above. The hydrogel may comprise a synthetic hydrogel and/or a non-synthetic hydrogel. In various embodiments, the tissue thickness compensator may comprise a plurality of layers. The plurality of the layers may comprise porous layers and/or non-porous layers. For example, the tissue thickness compensator may comprise a non-porous layer and a porous layer. In another example, the tissue thickness compensator may comprise a porous layer intermediate a first non-porous layer and a second non-porous layer. In another example, the tissue thickness compensator may comprise a non-porous layer intermediate a first porous layer and a second porous layer. The non-porous layers and porous layers may be positioned in any order relative to the surfaces of the staple cartridge and/or anvil.

Examples of the non-synthetic material may include, but are not limited to, albumin, alginate, carbohydrate, casein, cellulose, chitin, chitosan, collagen, blood, dextran, elastin, fibrin, fibrinogen, gelatin, heparin, hyaluronic acid, keratin, protein, serum, and starch. The cellulose may comprise hydroxyethyl cellulose, oxidized cellulose, oxidized regenerated cellulose (ORC), hydroxypropyl cellulose, carboxyethyl cellulose, carboxymethylcellulose, and combinations thereof. The collagen may comprise bovine pericardium. The carbohydrate may comprise a polysaccharide, such as lyophilized polysaccharide. The protein may comprise glycoprotein, proteoglycan, and combinations thereof.

Examples of the synthetic material may include, but are not limited to, poly(lactic acid), poly(glycolic acid), poly (hydroxybutyrate), poly(phosphazine), polyesters, polyethylene glycols, polyethylene oxide, polyethylene oxide-co-polypropylene oxide, co-polyethylene oxide, polyalkyleneoxides, polyacrylamides, polyhydroxyethylmethylacrylate, poly(vinylpyrrolidone), polyvinyl alcohols, poly(caprolactone), poly(dioxanone), polyacrylic acid, polyacetate, polypropylene, aliphatic polyesters, glycerols, poly (amino acids), copoly(ether-esters), polyalkylene oxalates, polyamides, poly(iminocarbonates), polyoxaesters, polyorthoesters, polyphosphazenes and combinations thereof. In certain embodiments, the above non-synthetic materials may be synthetically prepared, e.g., synthetic hyaluronic acid, utilizing conventional methods.

In various embodiments, the hydrogel may be made from one or more hydrogel precursors. The precursor may comprise a monomer and/or a macromer. The hydrogel precursor may comprise an electrophile functional group and/or a nucleophile electrophile functional group. In general, electrophiles may react with nucleophiles to form a bond. The term "functional group" as used herein refers to electrophilic or nucleophilic groups capable of reacting with each other to form a bond. Examples of electrophilic functional groups may include, but are not limited to, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In at least one embodiment, the electrophilic functional group may comprise a succinimidyl ester. Examples of nucleophile functional groups may include, but are not limited to, $—NH_2$, —SH, —OH, $—PH_2$, and $—CO—NH—NH_2$.

In various embodiments, the hydrogel may be formed from a single precursor or multiple precursors. In certain embodiments, the hydrogel may be formed from a first precursor and a second precursor. The first hydrogel precursor and second hydrogel precursor may form a hydrogel in situ and/or in vivo upon contact. The hydrogel precursor may generally refer to a polymer, functional group, macromolecule, small molecule, and/or crosslinker that can take part in a reaction to form a hydrogel. The precursor may comprise a homogeneous solution, heterogeneous, or phase separated solution in a suitable solvent, such as water or a buffer, for example. The buffer may have a pH from about 8 to about 12, such as, about 8.2 to about 9, for example. Examples of buffers may include, but are not limited to borate buffers. In certain embodiments, the precursor(s) may be in an emulsion. In various embodiments, a first precursor may react with a second precursor to form a hydrogel. In various embodiments, the first precursor may spontaneously crosslink when contacted with the second precursor. In various embodiments, a first set of electrophilic functional groups on a first precursor may react with a second set of nucleophilic functional groups on a second precursor. When the precursors are mixed in an environment that permits reaction (e.g., as relating to pH, temperature, and/or solvent), the functional groups may react with each other to form covalent bonds. The precursors may become cross-linked when at least some of the precursors react with more than one other precursor.

In various embodiments, the tissue thickness compensator may comprise at least one monomer selected from the group consisting of 3-sulfopropyl acrylate potassium salt ("KSPA"), sodium acrylate ("NaA"), N-(tris(hydroxylmethyl)methyl)acrylamide ("tris acryl"), and 2-acrylamido-2-methyl-1-propane sulfonic acid (AMPS). The tissue thickness compensator may comprise a copolymer comprising two or more monomers selected from the group consisting of KSPA, NaA, tris acryl, AMPS. The tissue thickness compensator may comprise homopolymers derived from KSPA, NaA, trisacryl and AMPS. The tissue thickness compensator may comprise hydrophilicity modifying monomers copolymerizable therewith. The hydrophilicity modifying monomers may comprise methylmethacrylate, butylacrylate, cyclohexylacrylate, styrene, styrene sulphonic acid.

In various embodiments, the tissue thickness compensator may comprise a crosslinker. The crosslinker may comprise a low molecular weight di- or polyvinylic crosslinking agent, such as ethylenglycol diacrylate or dimethacrylate, di-, tri- or tetraethylen-glycol diacrylate or dimethacrylate, allyl (meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or bismethacrylamide, ethylene bisacrylamide or ethylene bismethacrylamide, triallyl phthalate or diallyl phthalate. In at least one embodiment, the crosslinker may comprise N,N'-methylenebisacrylamide ("MBAA").

In various embodiments, the tissue thickness compensator may comprise at least one of acrylate and/or methacrylate functional hydrogels, biocompatible photoinitiator, alkyl-cyanoacrylates, isocyanate functional macromers, optionally comprising amine functional macromers, succinimidyl ester functional macromers, optionally comprising amine and/or sulfhydryl functional macromers, epoxy functional macromers, optionally comprising amine functional macromers, mixtures of proteins and/or polypeptides and aldehyde crosslinkers, Genipin, and water-soluble carbodiimides, anionic polysaccharides and polyvalent cations.

In various embodiments, the tissue thickness compensator may comprise unsaturated organic acid monomers, acrylic substituted alcohols, and/or acrylamides. In various embodiments, the tissue thickness compensator may comprise methacrylic acids, acrylic acids, glycerolacrylate, glycerolmethacryulate, 2-hydroxyethylmethacrylate, 2-hydroxyethylacrylate, 2-(dimethylaminoethyl) methacrylate, N-vinyl pyrrolidone, methacrylamide, and/or N, N-dimethylacrylamide poly(methacrylic acid).

In various embodiments, the tissue thickness compensator may comprise a reinforcement material. In various embodiments, the reinforcement material may comprise at least one of the non-synthetic materials and synthetic materials described above. In various embodiments, the reinforcement material may comprise collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethylcellulose, chitan, chitosan, alginate, poly(lactic acid), poly(glycolic acid), poly(hydroxybutyrate), poly(phosphazine), polyesters, polyethylene glycols, polyalkyleneoxides, polyacrylamides, polyhydroxyethylmethylacrylate, polyvinylpyrrolidone, polyvinyl alcohols, poly(caprolactone), poly(dioxanone), polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and combinations thereof.

In various embodiments, the tissue thickness compensator may comprise a layer comprising the reinforcement material. In certain embodiments, a porous layer and/or a non-porous layer of a tissue thickness compensator may comprise the reinforcement material. For example, the porous layer may comprise the reinforcement material and the non-porous layer may not comprise the reinforcement material. In various embodiments, the reinforcement layer may comprise an inner layer intermediate a first non-porous layer and a second non-porous layer. In certain embodiments, the reinforcement layer may comprise an outer layer of the tissue thickness compensator. In certain embodiments, the reinforcement layer may comprise an exterior surface of the tissue thickness compensator.

In various embodiments, the reinforcement material may comprise meshes, monofilaments, multifilament braids, fibers, mats, felts, particles, and/or powders. In certain embodiments, the reinforcement material may be incorporated into a layer of the tissue thickness compensator. The reinforcement material may be incorporated into at least one of a non-porous layer and a porous layer. A mesh comprising the reinforcement material may be formed using conventional techniques, such as, for example, knitting, weaving, tatting, and/or knipling. In various embodiments, a plurality of reinforcement materials may be oriented in a random direction and/or a common direction. In certain embodiments, the common direction may be one of parallel to the staple line and perpendicular to the staple line, for example. For example, the monofilaments and/or multifilament braids may be oriented in a random direction and/or a common direction. The monofilaments and multifilament braids may be associated with the non-porous layer and/or the porous layer. In various embodiments, the tissue thickness compensator may comprise a plurality of reinforcement fibers oriented in a random direction within a non-porous layer. In various embodiments, the tissue thickness compensator may comprise a plurality of reinforcement fibers oriented in a common direction within a non-porous layer.

The fibers may form a non-woven material, such as, for example, a mat and a felt. The fibers may have any suitable length, such as, for example from 0.1 mm to 100 mm and 0.4 mm to 50 mm. The reinforcement material may be ground to a powder. The powder may have a particle size from 10 micrometers to 1 cm, for example. The powder may be incorporated into the tissue thickness compensator.

In various embodiments, the tissue thickness compensator may be formed in situ. In various embodiments, the hydrogel may be formed in situ. The tissue thickness compensator may be formed in situ by covalent, ionic, and/or hydrophobic bonds. Physical (non-covalent) crosslinks may result from complexation, hydrogen bonding, desolvation, Van der Waals interactions, ionic bonding, and combinations thereof. Chemical (covalent) crosslinking may be accomplished by any of a number of mechanisms, including: free radical polymerization, condensation polymerization, anionic or cationic polymerization, step growth polymerization, electrophile-nucleophile reactions, and combinations thereof.

In various embodiments, in situ formation of the tissue thickness compensator may comprise reacting two or more precursors that are physically separated until contacted in situ and/or react to an environmental condition to react with each other to form the hydrogel. In situ polymerizable polymers may be prepared from precursor(s) that can be reacted to form a polymer at the surgical site. The tissue thickness compensator may be formed by crosslinking reactions of the precursor(s) in situ. In certain embodiments, the precursor may comprise an initiator capable of initiating a polymerization reaction for the formation of the in situ tissue thickness compensator. The tissue thickness compensator may comprise a precursor that can be activated at the time of application to create, in various embodiments, a cross-linked hydrogel. In situ formation of the tissue thickness compensator may comprise activating at least one precursor to form bonds to form the tissue thickness compensator. In various embodiments, activation may be achieved by changes in the physical conditions, biological conditions, and/or chemical conditions at the surgical site, including, but not limited to temperature, pH, electric fields, ionic strength, enzymatic and/or chemical reactions, electrical and/or magnetic stimuli, and other physiological and environmental variables. In various embodiments, the precursors may be contacted outside the body and introduced to the surgical site.

In various embodiments, the tissue thickness compensator may comprise one or more encapsulations, or cells, which can be configured to store at least one component therein. In certain embodiments, the encapsulation may be configured to store a hydrogel precursor therein. In certain embodiments, the encapsulation may be configured to store two components therein, for example. In certain embodiments, the encapsulation may be configured to store a first hydrogel precursor and a second hydrogel precursor therein. In certain embodiments, a first encapsulation may be configured to store a first hydrogel precursor therein and a second encapsulation may be configured to store a second hydrogel precursor therein. As described above, the encapsulations can be aligned, or at least substantially aligned, with the staple legs to puncture and/or otherwise rupture the encapsulations when the staple legs contact the encapsulation. In certain embodiments, the encapsulations may be compressed, crushed, collapsed, and/or otherwise ruptured when the staples are deployed. After the encapsulations have been ruptured, the component(s) stored therein can flow out of the encapsulation. The component stored therein may contact other components, layers of the tissue thickness compensator, and/or the tissue. In various embodiments, the other components may be flowing from the same or different encapsulations, provided in the layers of the tissue thickness compensator, and/or provided to the surgical site by the clinician. As a result of the above, the component(s) stored within the encapsulations can provide expansion and/or swelling of the tissue thickness compensator.

In various embodiments, the tissue thickness compensator may comprise a layer comprising the encapsulations. In various embodiments, the encapsulation may comprise a void, a pocket, a dome, a tube, and combinations thereof associated with the layer. In certain embodiments, the encapsulations may comprise voids in the layer. In at least one embodiment, the layer can comprise two layers that can be attached to one another wherein the encapsulations can be defined between the two layers. In certain embodiments, the encapsulations may comprise domes on the surface of the layer. For example, at least a portion of the encapsulations can be positioned within domes extending upwardly from the layer. In certain embodiments, the encapsulations may comprise pockets formed within the layer. In certain embodiments, a first portion of the encapsulations may comprise a dome and a second portion of the encapsulations may comprise a pocket. In certain embodiments, the encapsulations may comprise a tube embedded within the layer. In certain embodiments, the tube may comprise the non-synthetic materials and/or synthetic materials described herein, such as PLA. In at least one embodiment, the tissue thickness compensator may comprise a bioabsorbable foam, such as ORC, comprising PLA tubes embedded therein, and the tube may encapsulate a hydrogel, for example. In certain embodiments, the encapsulations may comprise discrete cells that are unconnected to each other. In certain embodiments, one or more of the encapsulations can be in fluid communication with each other via one or more passageways, conduits, and/or channels, for example, extending through the layer.

The rate of release of a component from the encapsulation may be controlled by the thickness of the tissue thickness compensator, the composition of tissue thickness compensator, the size of the component, the hydrophilicity of the component, and/or the physical and/or chemical interactions among the component, the composition of the tissue thickness compensator, and/or the surgical instrument, for example. In various embodiments, the layer can comprise one or more thin sections or weakened portions, such as partial perforations, for example, which can facilitate the incision of the layer and the rupture of the encapsulations. In various embodiments, the partial perforations may not completely extend through a layer while, in certain embodiments, perforations may completely extend through the layer.

In various embodiments, an anvil may comprise a tissue thickness compensator comprising an encapsulated component comprising at least one microsphere particle. In certain embodiments, the tissue thickness compensator may comprise an encapsulation comprising a first encapsulated component and a second encapsulated component. In certain embodiments, the tissue thickness compensator may comprise an encapsulation comprising a first microsphere particle and a second microsphere particle.

In various embodiments, the tissue thickness compensator may be suitable for use with a surgical instrument. As described above the tissue thickness compensator may be associated with the staple cartridge and/or the anvil. The tissue thickness compensator may be configured into any shape, size and/or dimension suitable to fit the staple cartridge and/or anvil. As described herein, the tissue thickness compensator may be releasably attached to the staple cartridge and/or anvil. The tissue thickness compensator may be attached to the staple cartridge and/or anvil in any mechanical and/or chemical manner capable of retaining the tissue thickness compensator in contact with the staple cartridge and/or anvil prior to and during the stapling process. The tissue thickness compensator may be removed or released from the staple cartridge and/or anvil after the staple penetrates the tissue thickness compensator. The tissue thickness compensator may be removed or released from the staple cartridge and/or anvil as the staple cartridge and/or anvil is moved away from the tissue thickness compensator.

Figure 14:
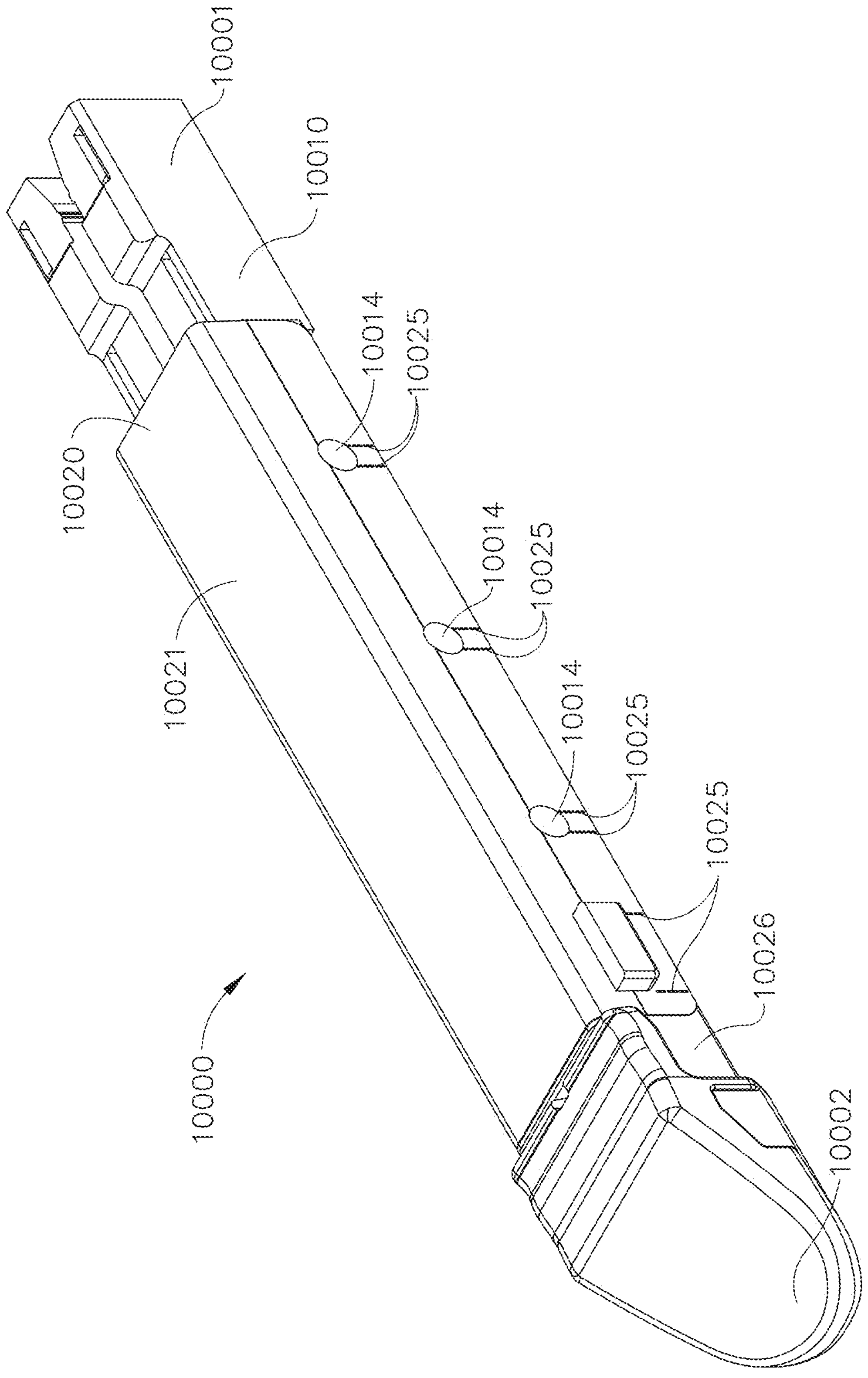
FIG. 14 is a perspective view of a staple cartridge comprising a rigid support portion and a compressible tissue thickness compensator for use with a surgical stapling instrument in accordance with at least one embodiment of the invention.
Figure 16:
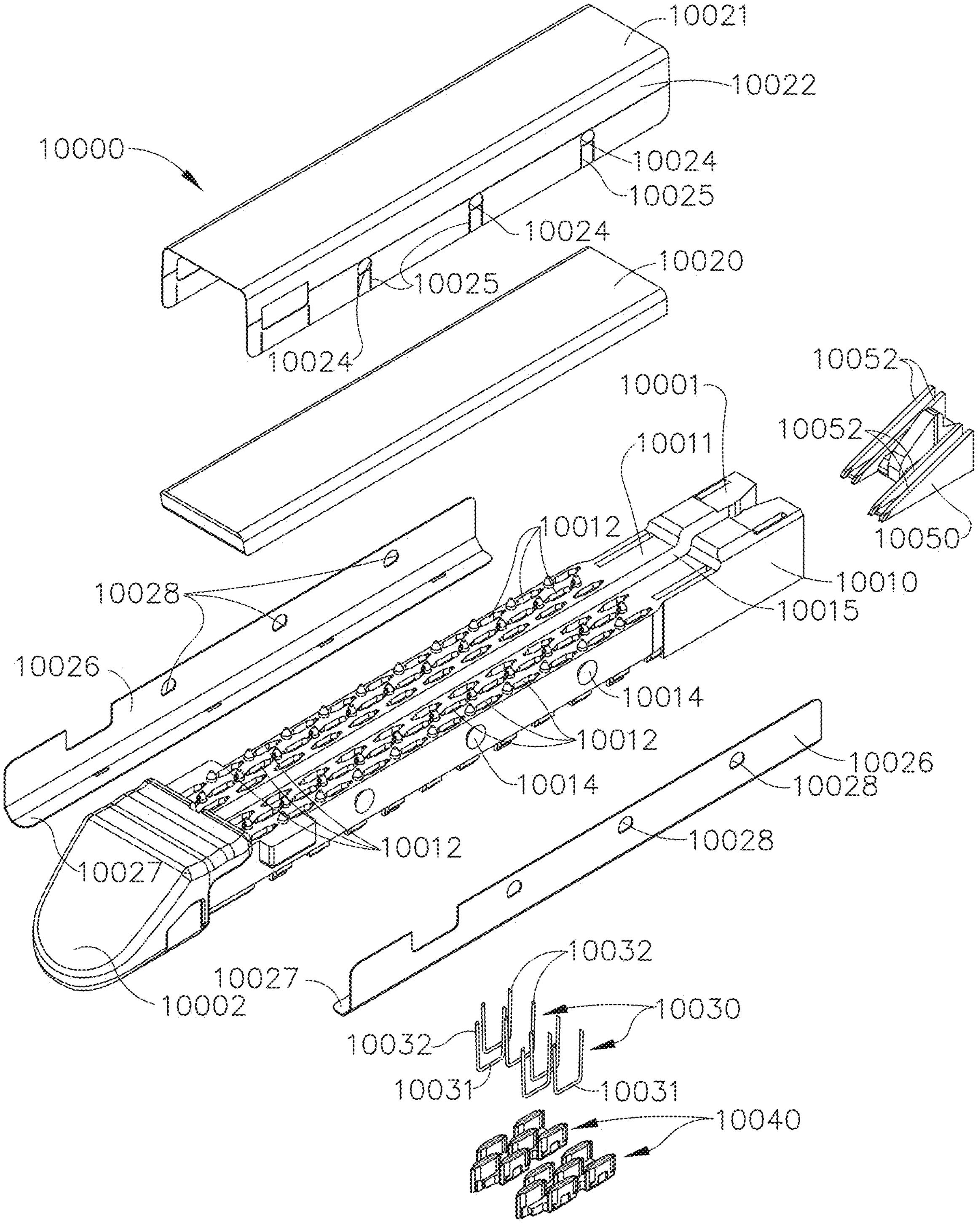
FIG. 16 is a fully exploded view of the staple cartridge of FIG. 14.
Figure 17:
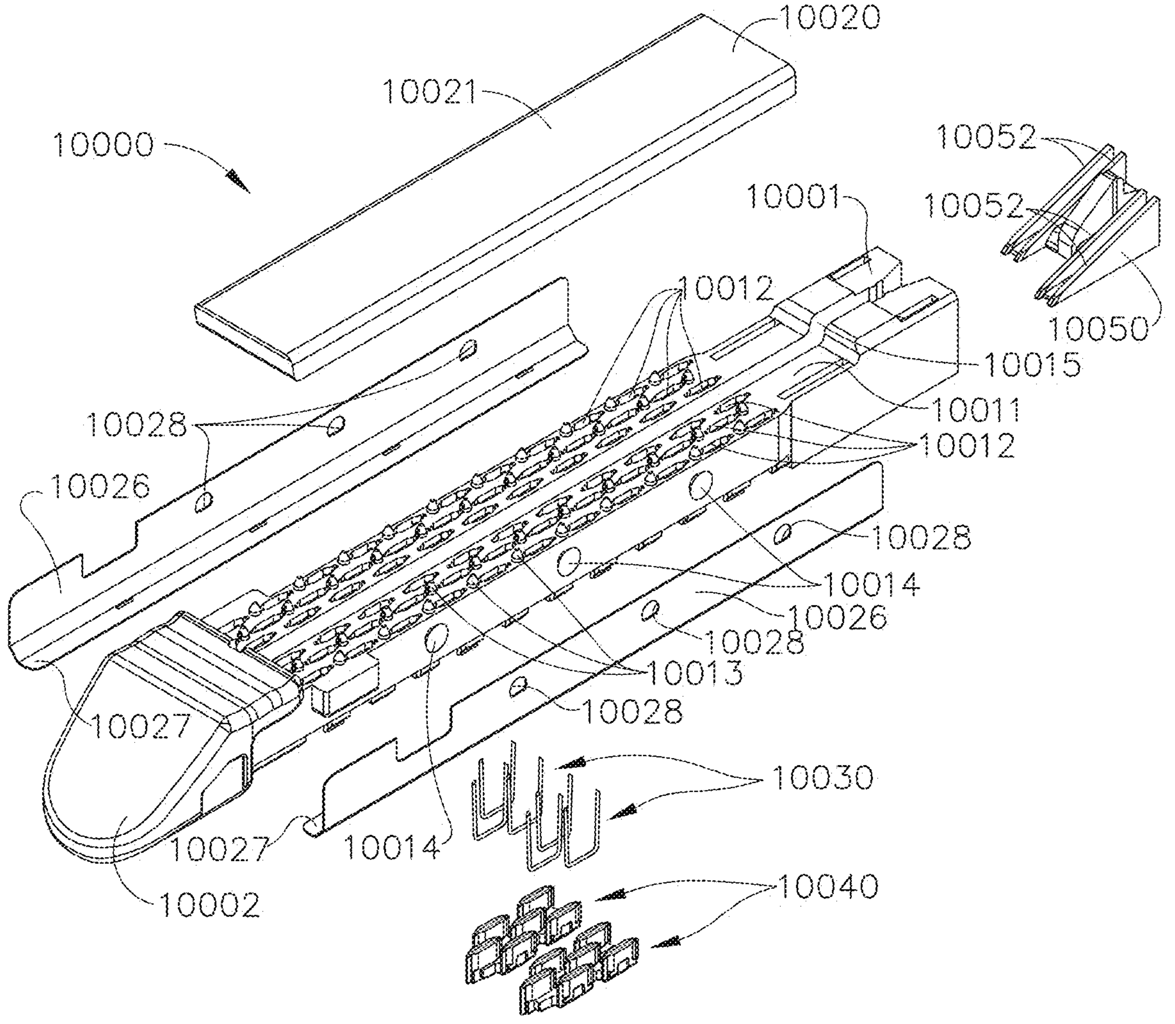
FIG. 17 is another exploded view of the staple cartridge of FIG. 14 without a warp covering the tissue thickness compensator.
Figure 18:
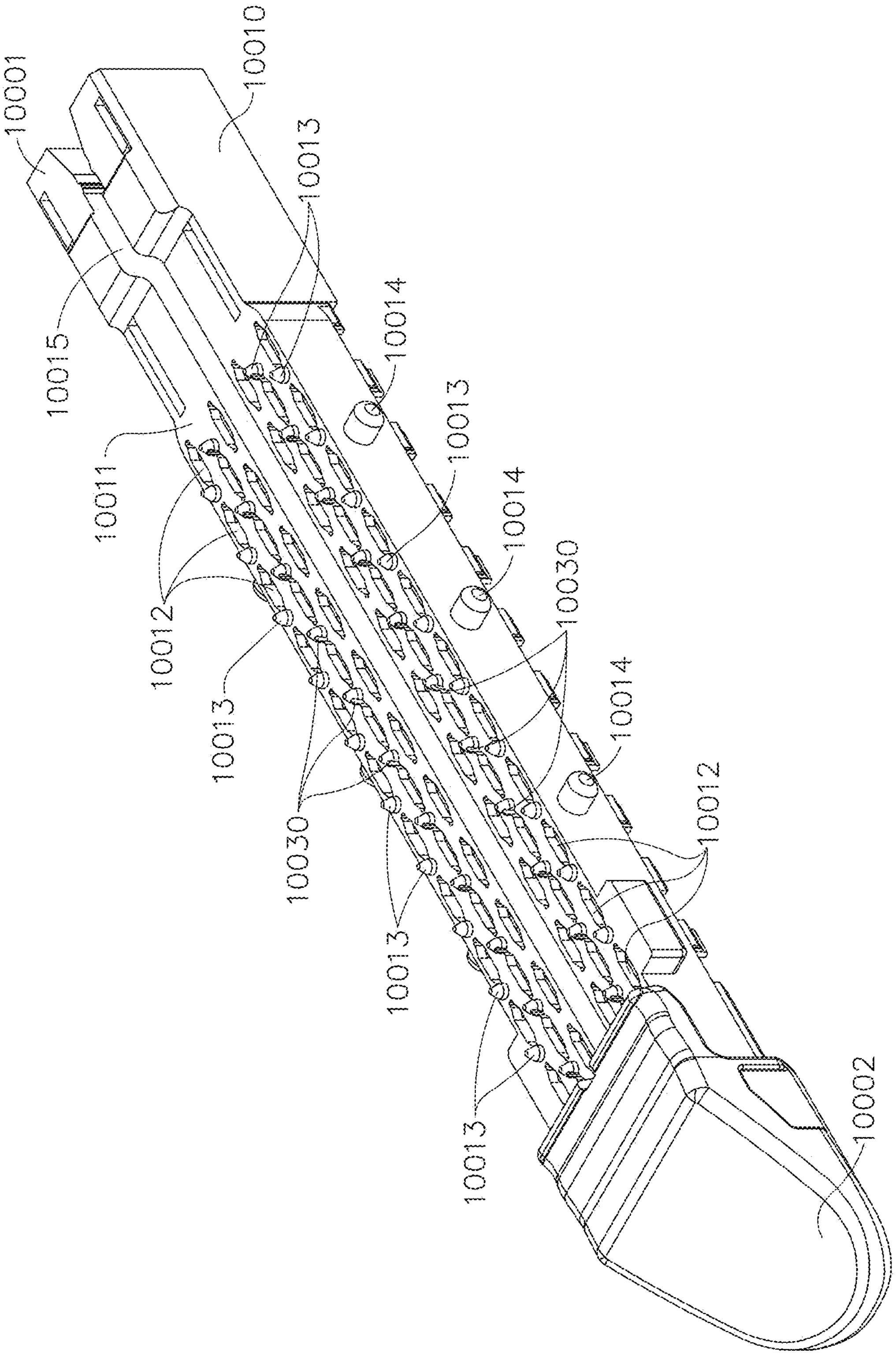
FIG. 18 is a perspective view of a cartridge body, or support portion, of the staple cartridge of FIG. 14.
Figure 19:
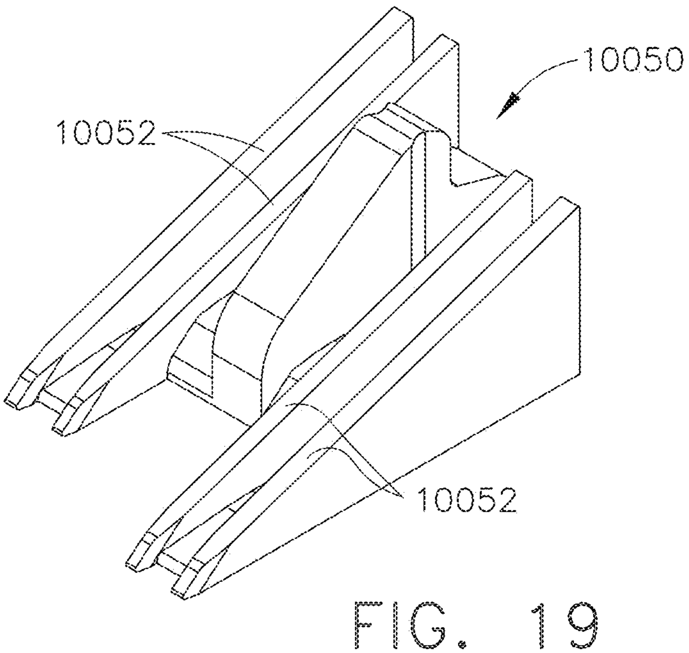
FIG. 19 is a top perspective view of a sled movable within the staple cartridge of FIG. 14 to deploy staples from the staple cartridge.
Figure 20:
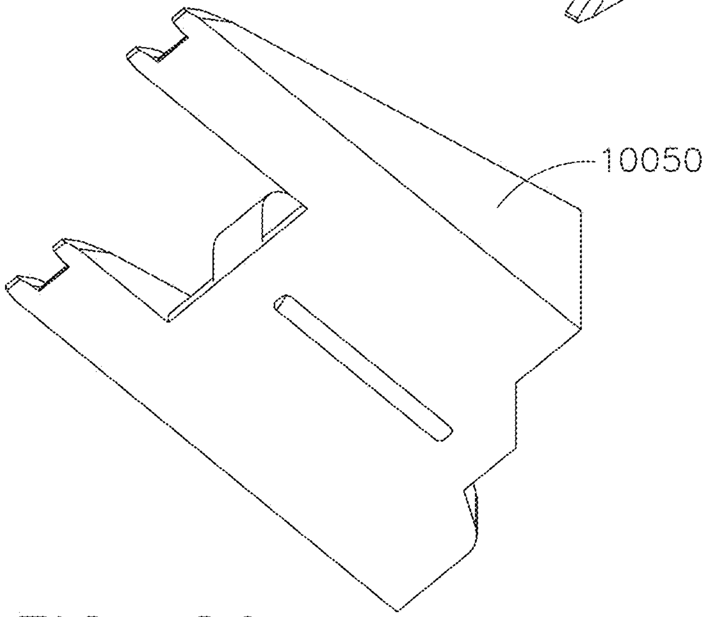
FIG. 20 is a bottom perspective view of the sled of FIG. 19.
Figure 21:
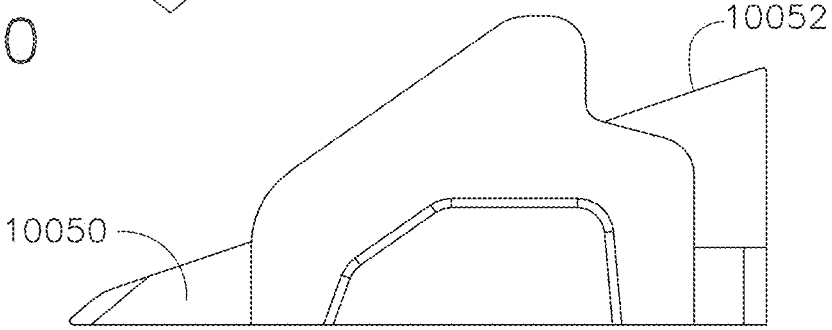
FIG. 21 is an elevational view of the sled of FIG. 19.
Figure 22:
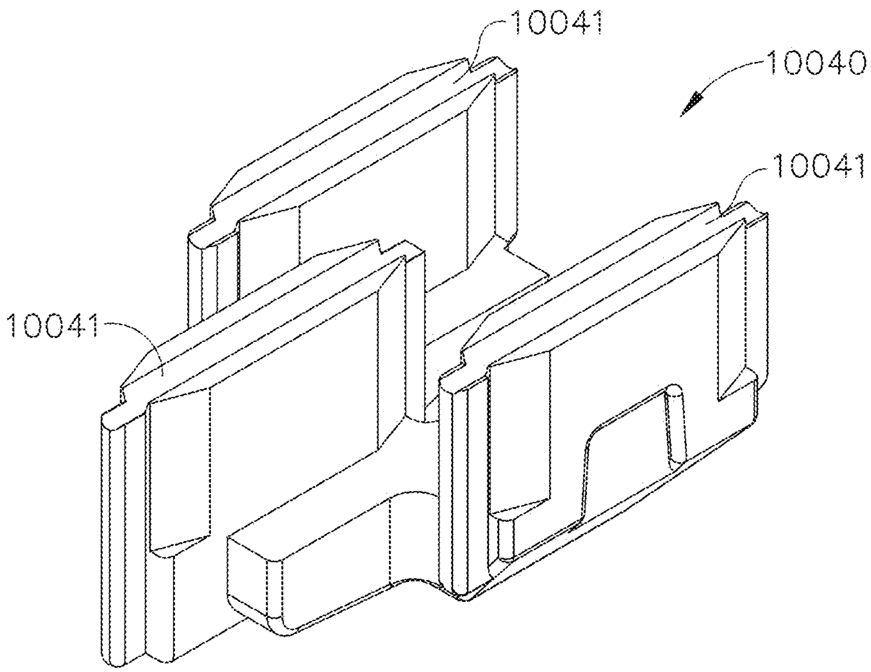
FIG. 22 is a top perspective view of a driver configured to support one or more staples and to be lifted upwardly by the sled of FIG. 19 to eject the staples from the staple cartridge.
Figure 23:
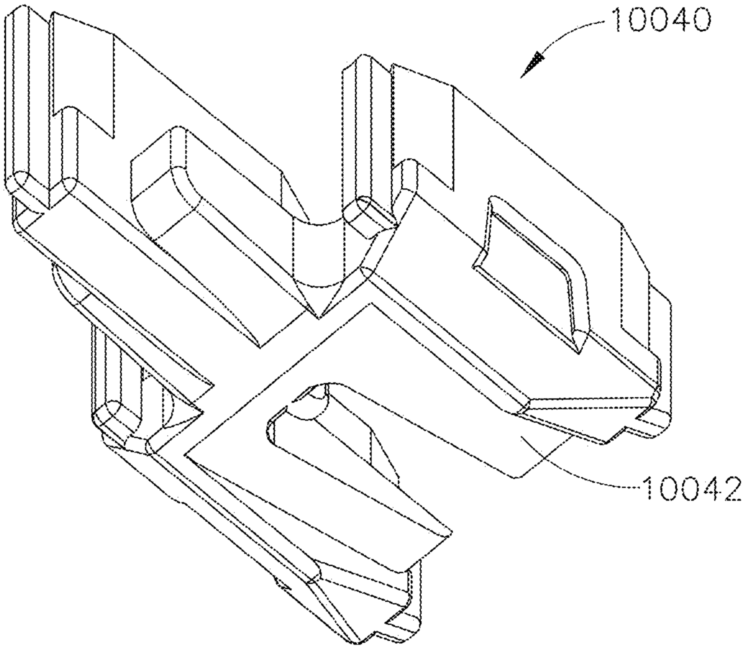
FIG. 23 is a bottom perspective view of the driver of FIG. 22.

In various embodiments, referring now to FIG. 14, a staple cartridge, such as staple cartridge 10000, for example, can comprise a support portion 10010 and a compressible tissue thickness compensator 10020. Referring now to FIGS. 16-18, the support portion 10010 can comprise a deck surface 10011 and a plurality of staple cavities 10012 defined within the support portion 10010. Each staple cavity 10012 can be sized and configured to removably store a staple, such as a staple 10030, for example, therein. The staple cartridge 10000 can further comprise a plurality of staple drivers 10040 which can each be configured to support one or more staples 10030 within the staple cavities 10012 when the staples 10030 and the staple drivers 10040 are in their unfired positions. In at least one such embodiment, referring primarily to FIGS. 22 and 23, each staple driver 10040 can comprise one or more cradles, or troughs, 10041, for example, which can be configured to support the staples and limit relative movement between the staples 10030 and the staple drivers 10040. In various embodiments, referring again to FIG. 16, the staple cartridge 10000 can further comprise a staple-firing sled 10050 which can be moved from a proximal end 10001 to a distal end 10002 of the staple cartridge in order to sequentially lift the staple drivers 10040 and the staples 10030 from their unfired positions toward an anvil positioned opposite the staple cartridge 10000. In certain embodiments, referring primarily to FIGS. 16 and 18, each staple 10030 can comprise a base 10031 and one or more legs 10032 extending from the base 10031 wherein each staple can be at least one of substantially U-shaped and substantially V-shaped, for example. In at least one embodiment, the staples 10030 can be configured such that the tips of the staple legs 10032 are recessed with respect to the deck surface 10011 of the support portion 10010 when the staples 10030 are in their unfired positions. In at least one embodiment, the staples 10030 can be configured such that the tips of the staple legs 10032 are flush with respect to the deck surface 10011 of the support portion 10010 when the staples 10030 are in their unfired positions. In at least one embodiment, the staples 10030 can be configured such that the tips of the staple legs 10032, or at least some portion of the staple legs 10032, extend above the deck surface 10011 of the support portion 10010 when the staples 10030 are in their unfired positions. In such embodiments, the staple legs 10032 can extend into and can be embedded within the tissue thickness compensator 10020 when the staples 10030 are in their unfired positions. In at least one such embodiment, the staple legs 10032 can extend above the deck surface 10011 by approximately 0.075", for example. In various embodiments, the staple legs 10032 can extend above the deck surface 10011 by a distance between approximately 0.025" and approximately 0.125", for example. In certain embodiments, further to the above, the tissue thickness compensator 10020 can comprise an uncompressed thickness between approximately 0.08" and approximately 0.125", for example.

Figure 25:
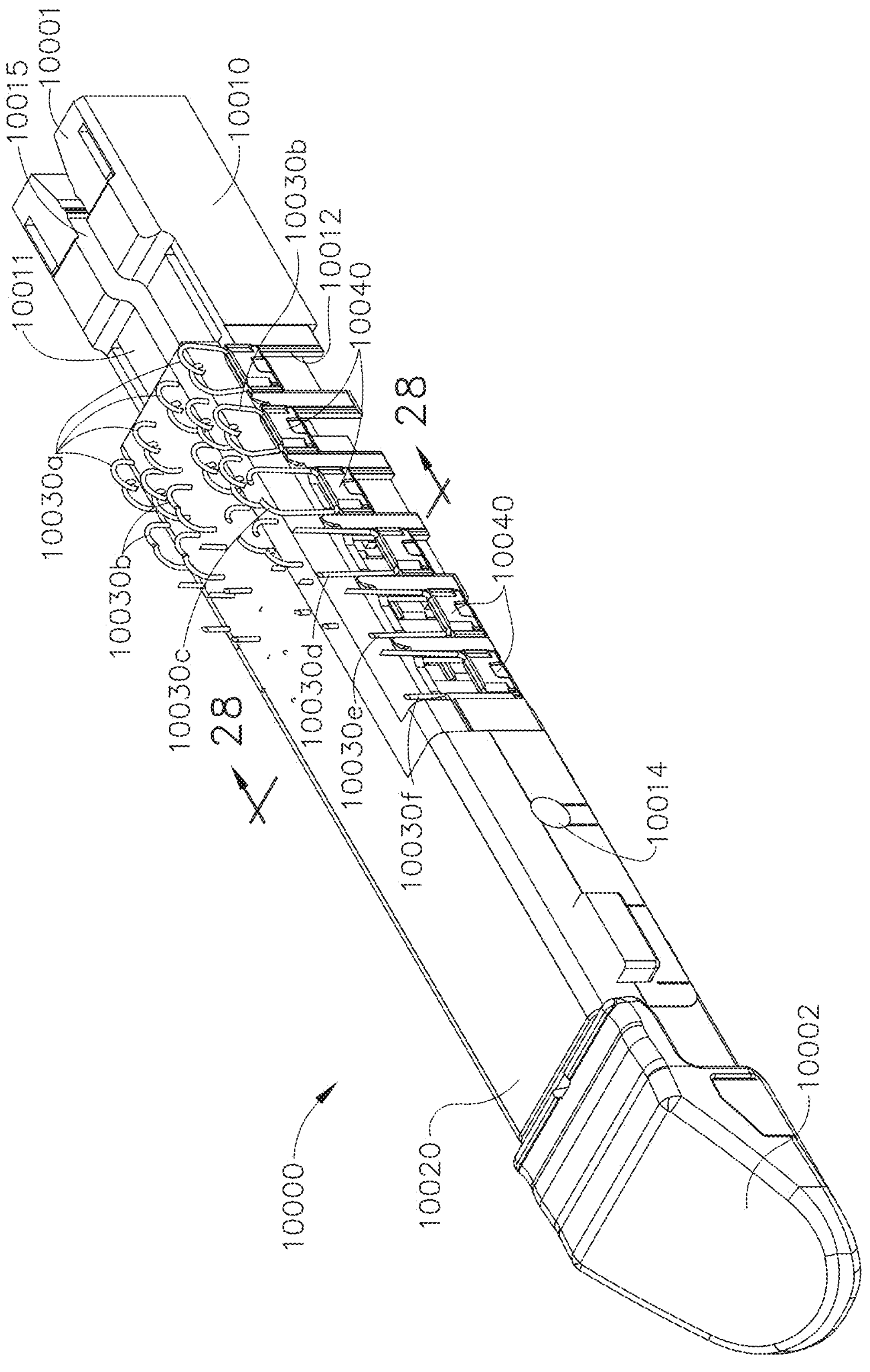
FIG. 25 is a partial cut away view of a staple cartridge comprising a rigid support portion and a compressible tissue thickness compensator illustrated with staples being moved from an unfired position to a fired position during a first sequence.
Figure 26:
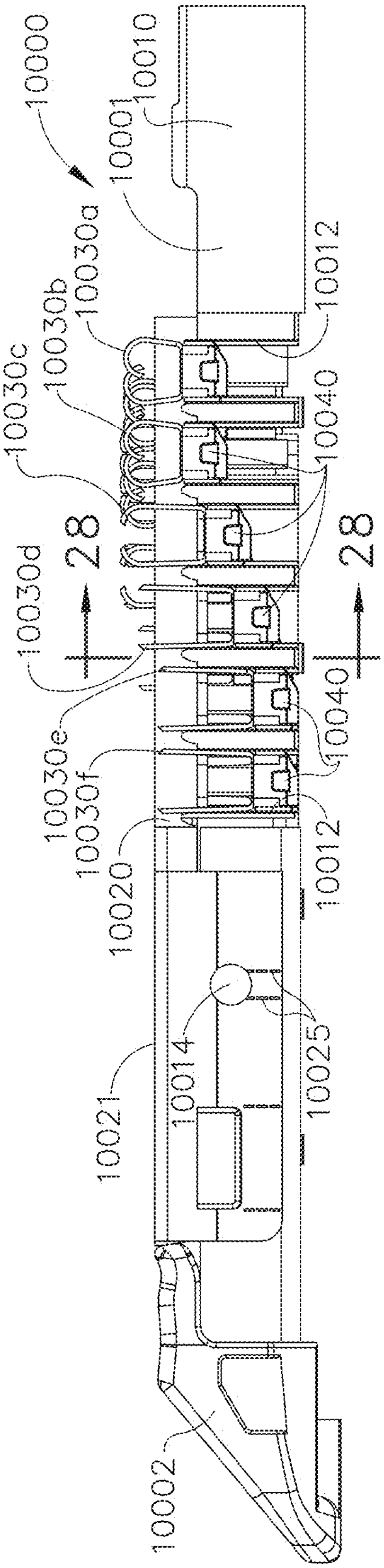
FIG. 26 is an elevational view of the staple cartridge of FIG. 25.
Figure 27:
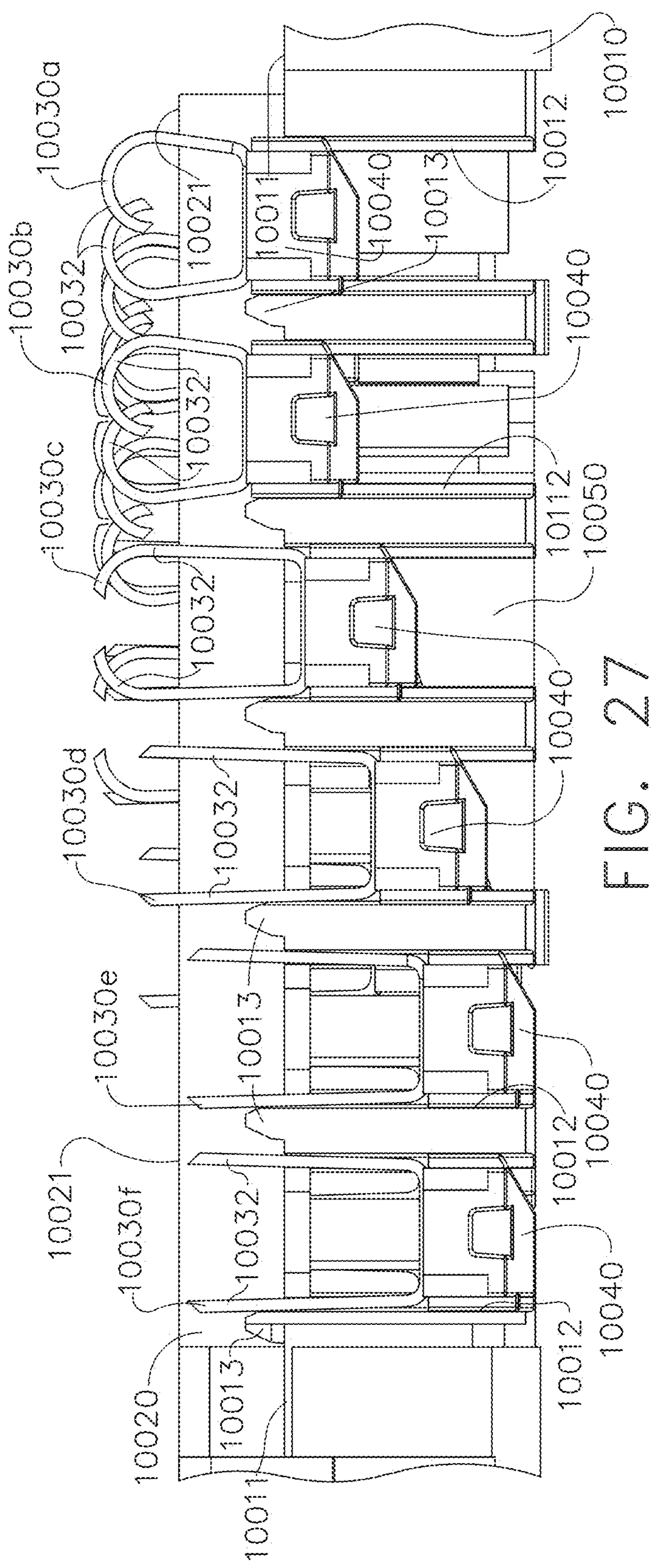
FIG. 27 is a detail elevational view of the staple cartridge of FIG. 25.
Figure 28:
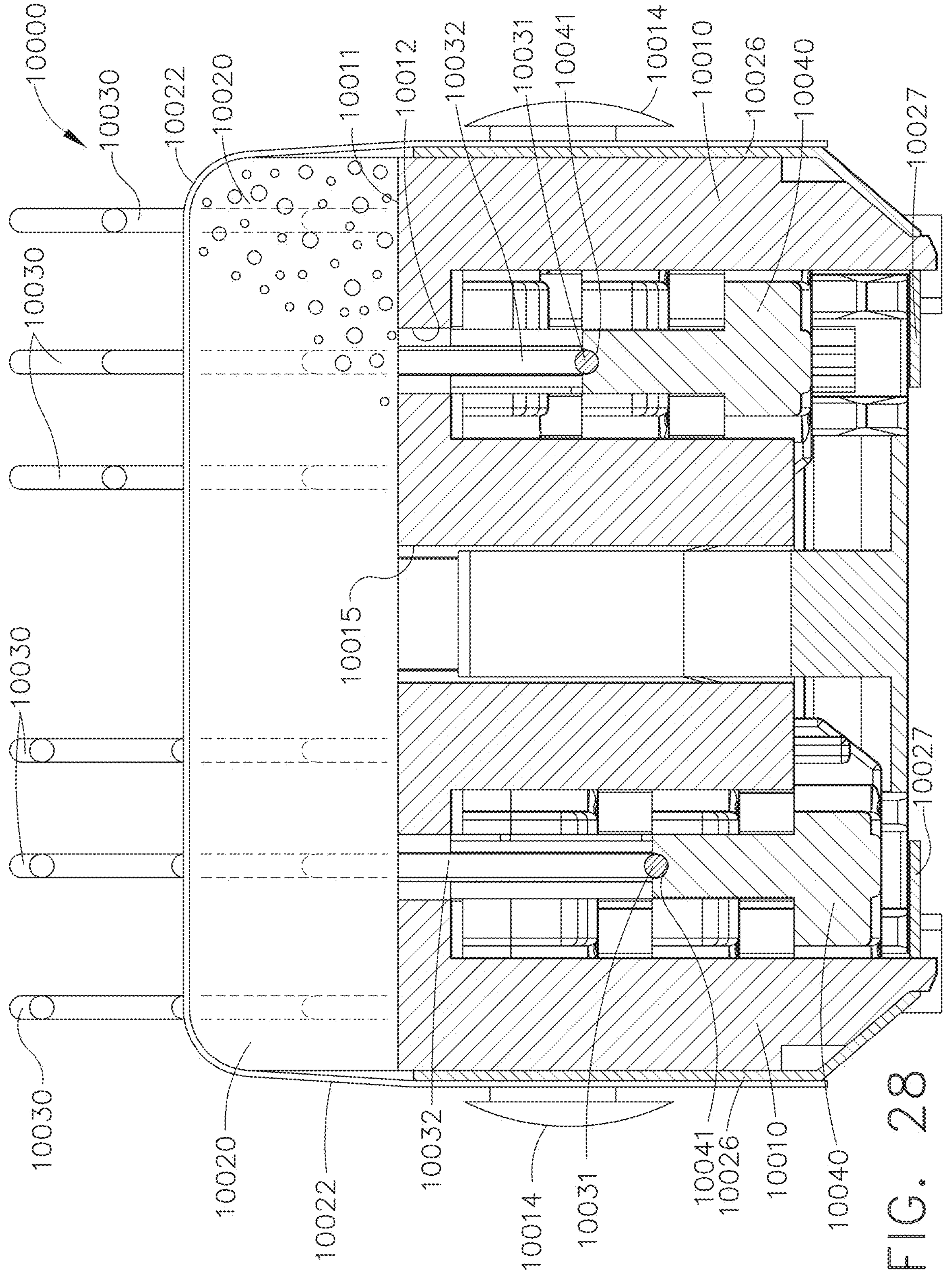
FIG. 28 is a cross-sectional end view of the staple cartridge of FIG. 25.
Figure 29:
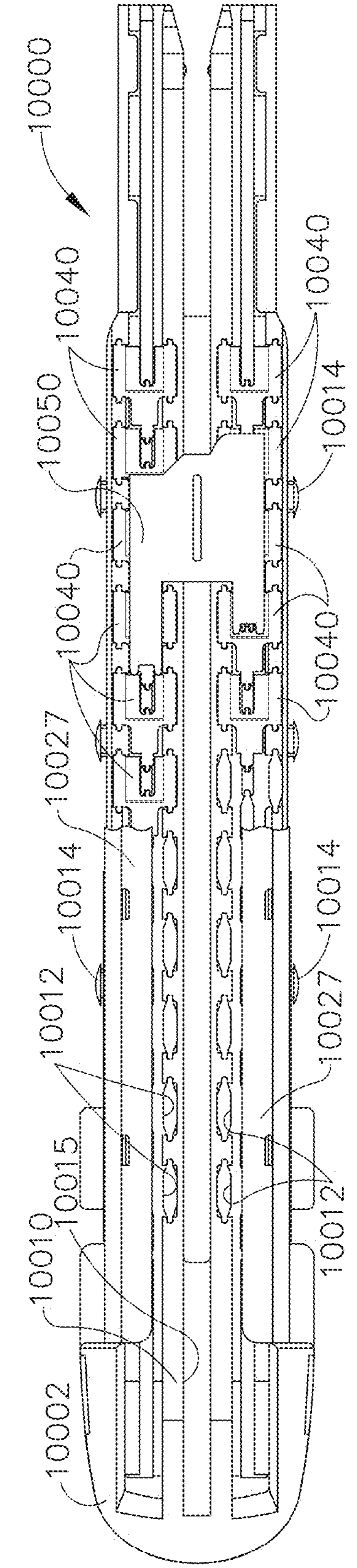
FIG. 29 is a bottom view of the staple cartridge of FIG. 25.
Figure 30:
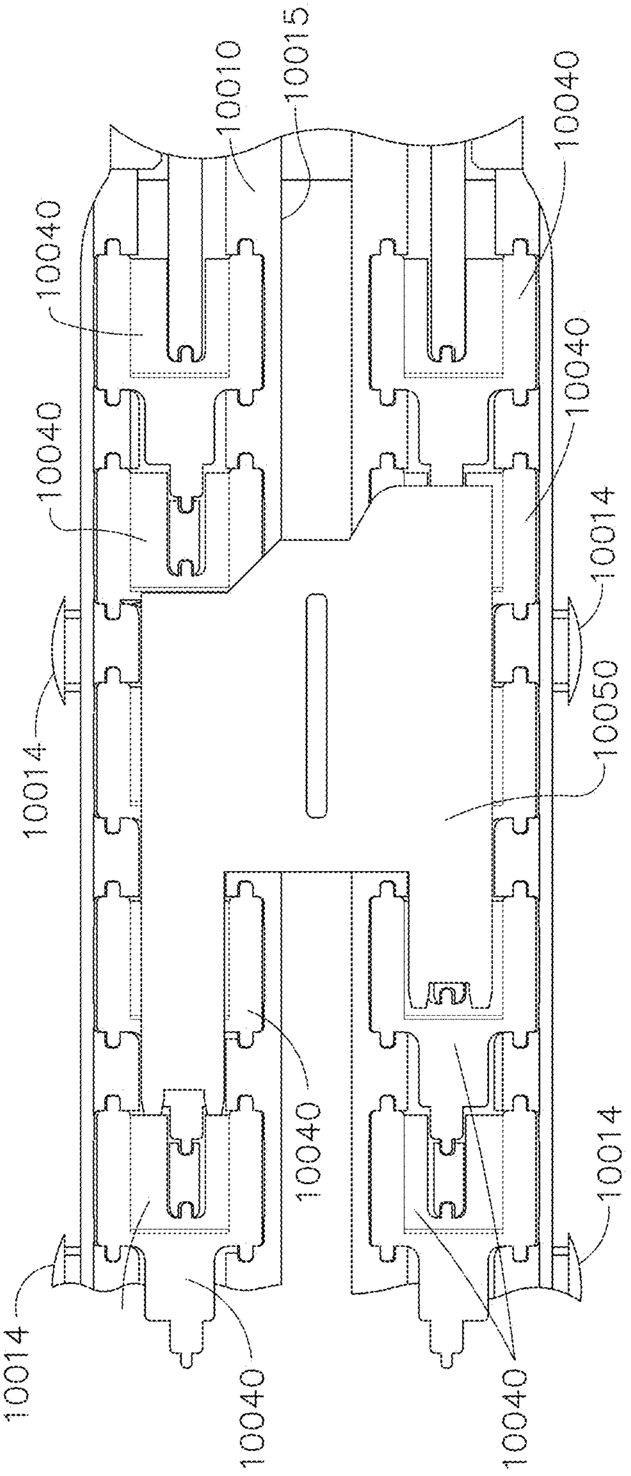
FIG. 30 is a detail bottom view of the staple cartridge of FIG. 25.
Figure 31:
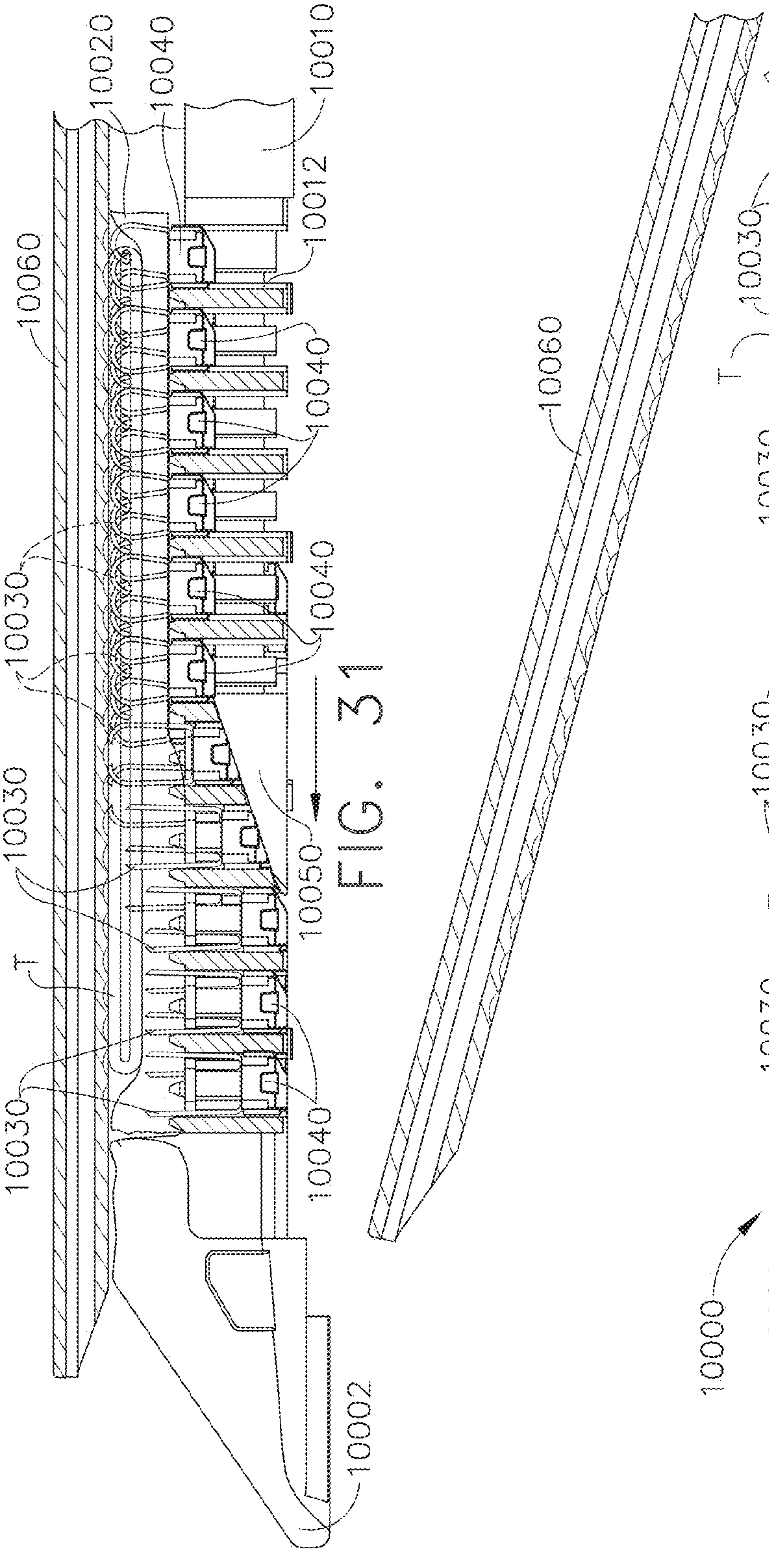
FIG. 31 is a longitudinal cross-sectional view of an anvil in a closed position and a staple cartridge comprising a rigid support portion and a compressible tissue thickness compensator illustrated with staples being moved from an unfired position to a fired position during a first sequence.
Figure 32:
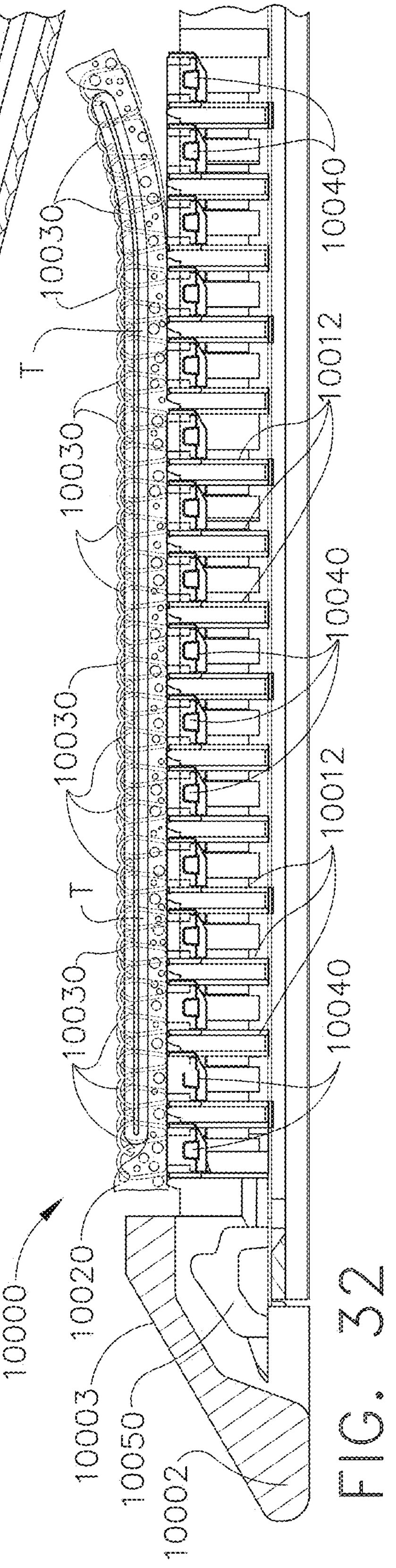
FIG. 32 is another cross-sectional view of the anvil and the staple cartridge of FIG. 31 illustrating the anvil in an open position after the firing sequence has been completed.

In use, further to the above and referring primarily to FIG. 31, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 31. In various embodiments, as mentioned above, the staple-firing sled 10050 can be moved from the proximal end 10001 of the staple cartridge 10000 toward the distal end 10002, as illustrated in FIG. 32. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, referring to FIGS. 19-23, each staple driver 10040 can comprise at least one inclined surface 10042 and the sled 10050 can comprise one or more inclined surfaces 10052 which can be configured such that the inclined surfaces 10052 can slide under the inclined surface 10042 as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011. During an exemplary firing sequence, referring primarily to FIGS. 25-27, the sled 10050 can first contact staple **10030*a* and begin to lift the staple 10030*a* upwardly. As the sled 10050 is advanced further distally, the sled 10050 can begin to lift staples 10030*b*, 10030*c*, 10030*d*, 10030*e*, and 10030*f*, and any other subsequent staples, in a sequential order. As illustrated in FIG. 27, the sled 10050 can drive the staples 10030 upwardly such that the legs 10032 of the staples contact the opposing anvil, are deformed to a desired shape, and ejected therefrom the support portion 10010. In various circumstances, the sled 10030 can move several staples upwardly at the same time as part of a firing sequence. With regard to the firing sequence illustrated in FIG. 27, the staples 10030*a* and 10030*b* have been moved into their fully fired positions and ejected from the support portion 10010, the staples 10030*c* and 10030*d* are in the process of being fired and are at least partially contained within the support portion 10010, and the staples 10030*e* and 10030*f*** are still in their unfired positions.

Figure 33:
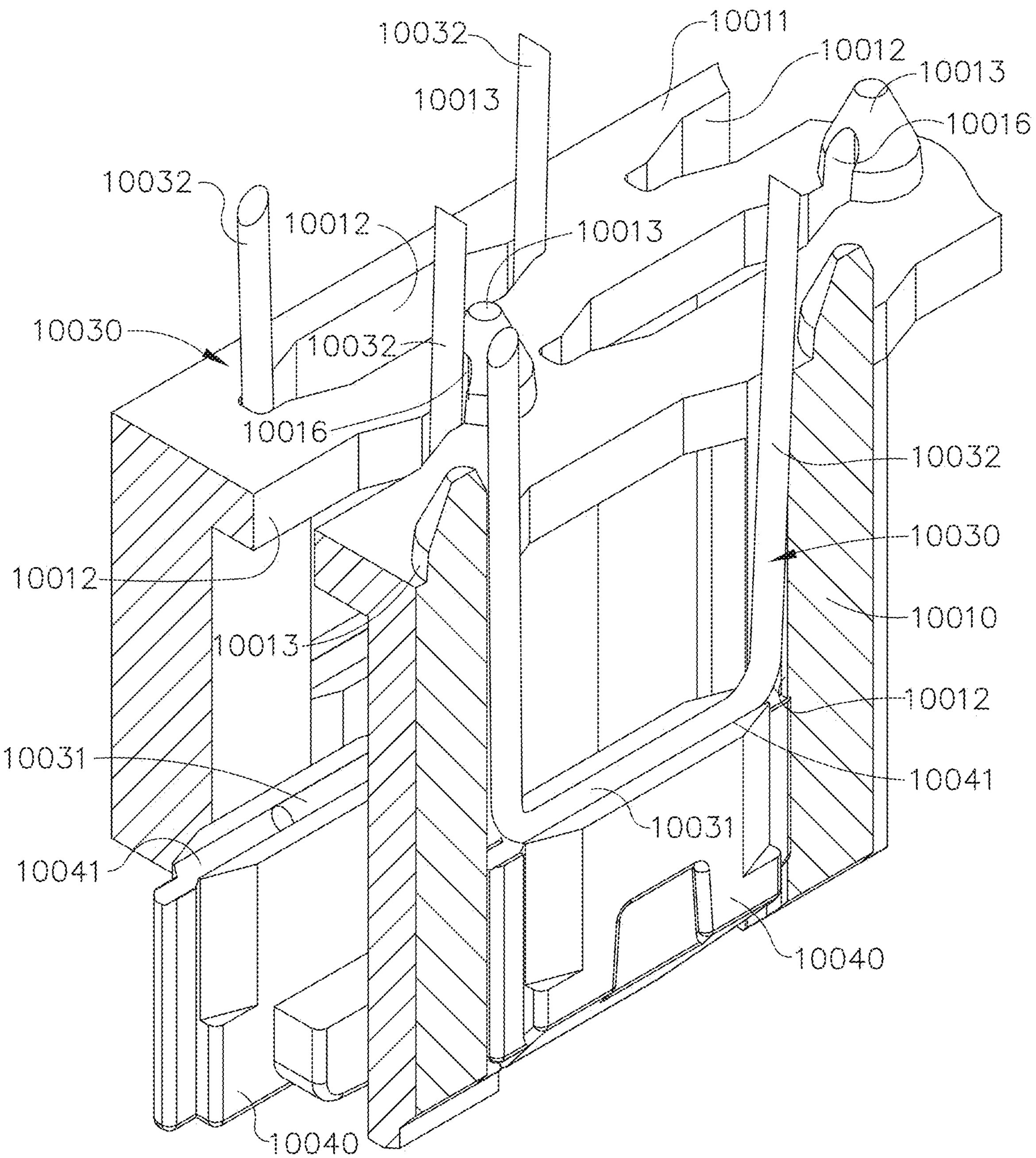
FIG. 33 is a partial detail view of the staple cartridge of FIG. 31 illustrating the staples in an unfired position.
Figure 34:
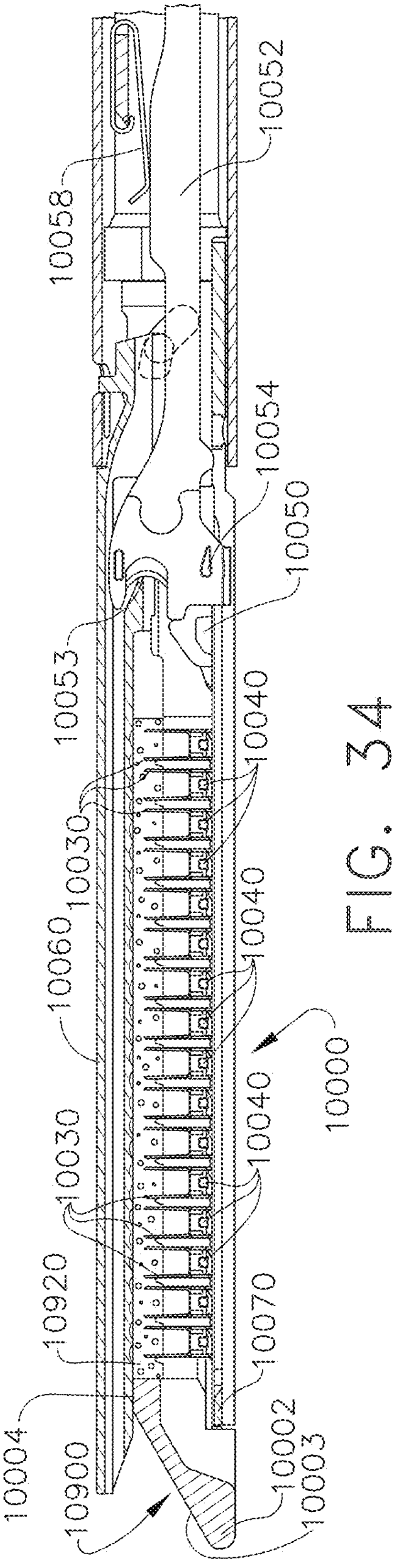
FIG. 34 is a cross-sectional elevational view of a staple cartridge comprising a rigid support portion and a compressible tissue thickness compensator illustrating the staples in an unfired position.
Figure 35:
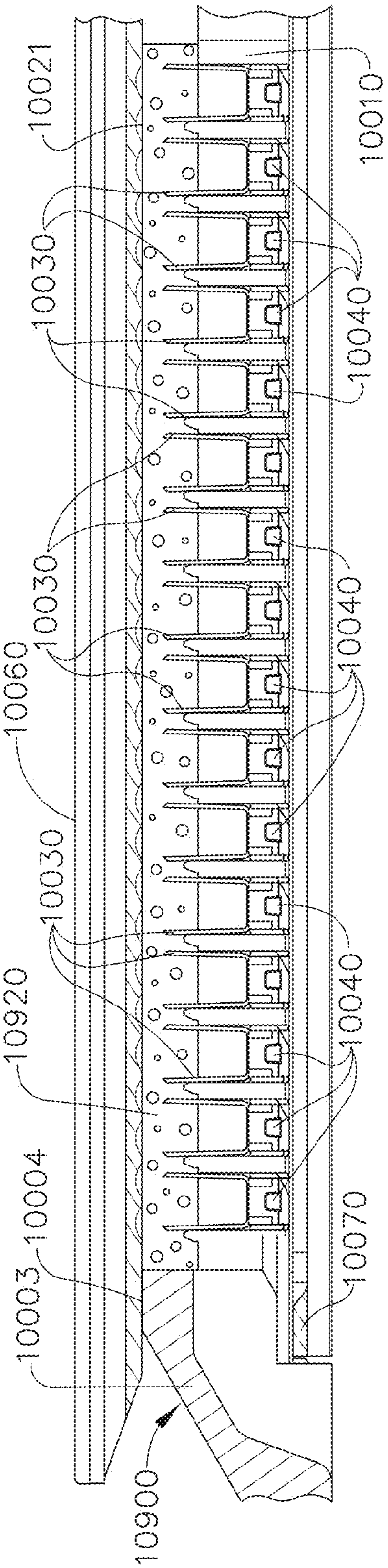
FIG. 35 is a detail view of the staple cartridge of FIG. 34.
Figure 36:
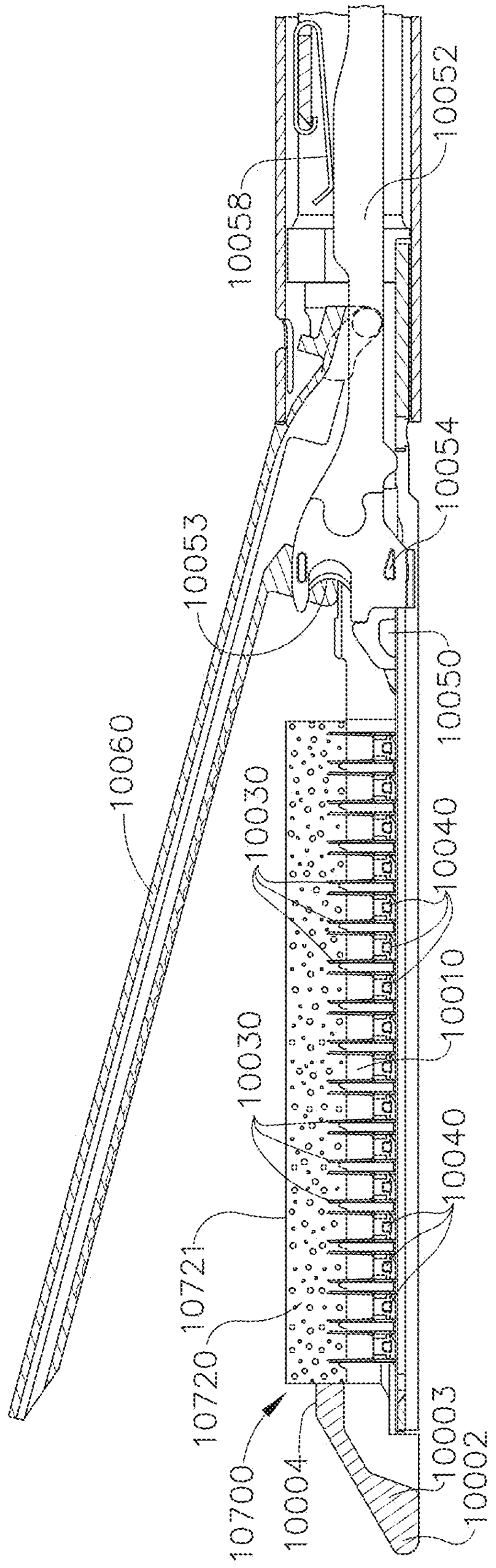
FIG. 36 is an elevational view of an anvil in an open position and a staple cartridge comprising a rigid support portion and a compressible tissue thickness compensator illustrating the staples in an unfired position.
Figure 37:
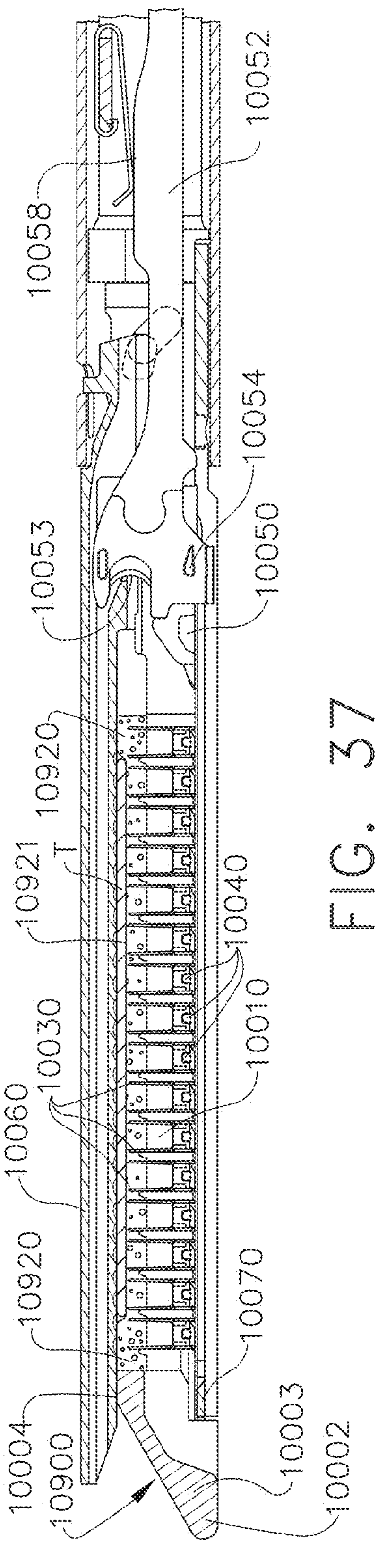
FIG. 37 is an elevational view of an anvil in a closed position and a staple cartridge comprising a rigid support portion and a compressible tissue thickness compensator illustrating the staples in an unfired position and tissue captured between the anvil and the tissue thickness compensator.
Figure 38:
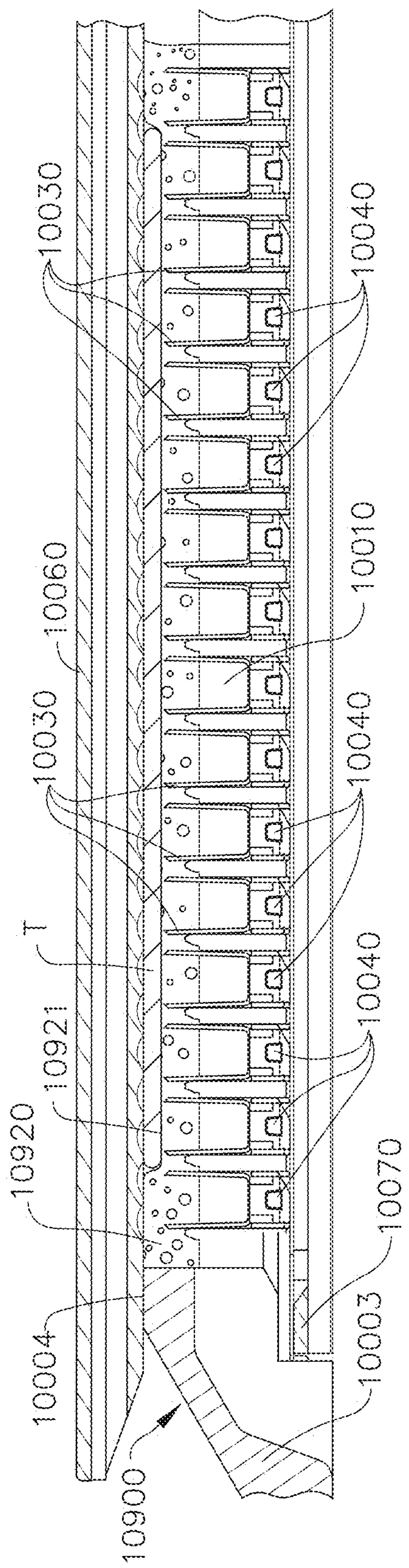
FIG. 38 is a detail view of the anvil and staple cartridge of FIG. 37.
Figure 39:
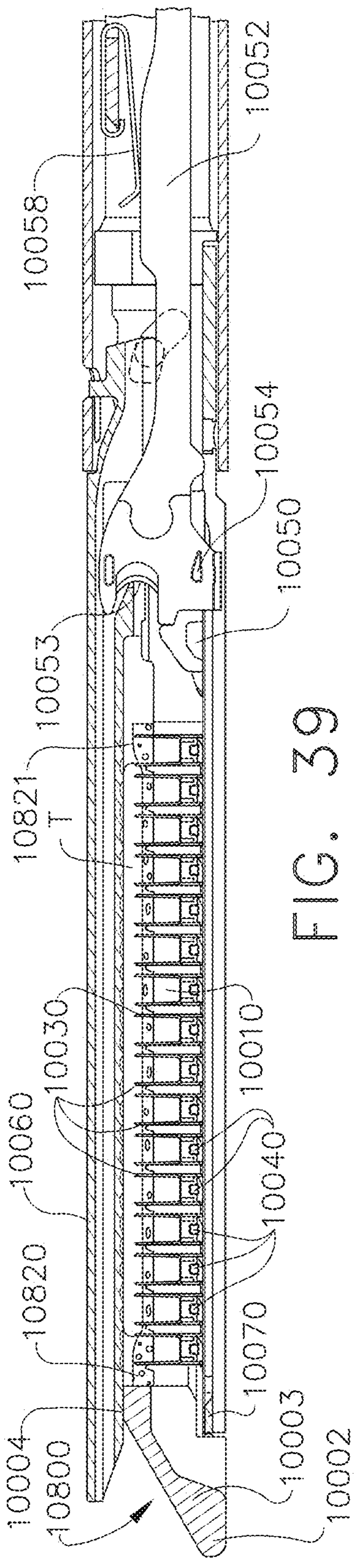
FIG. 39 is an elevational view of an anvil in a closed position and a staple cartridge comprising a rigid support portion and a compressible tissue thickness compensator illustrating the staples in an unfired position illustrating thicker tissue positioned between the anvil and the staple cartridge.
Figure 40:
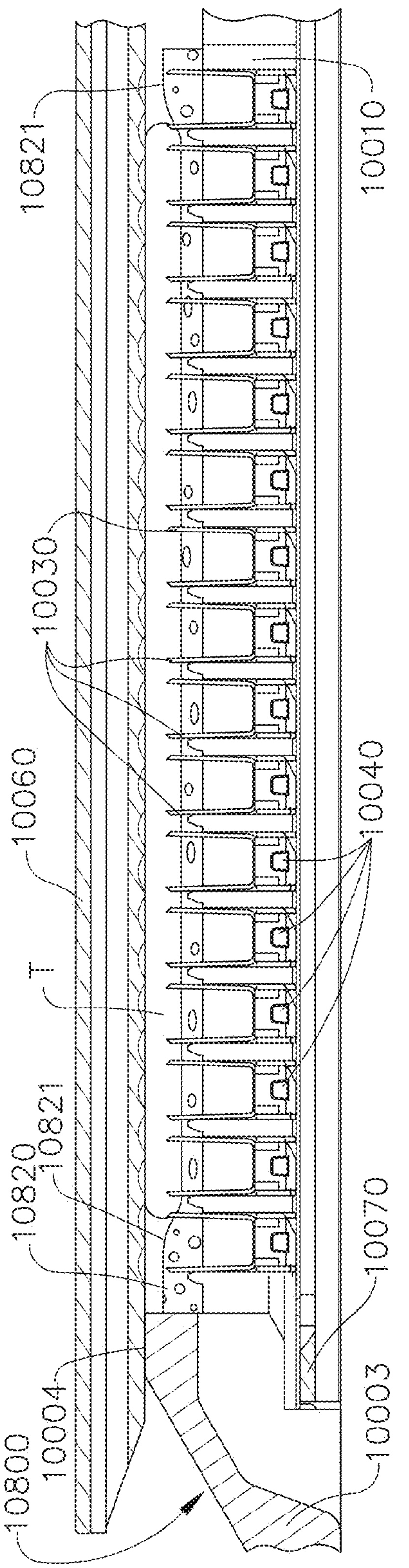
FIG. 40 is a detail view of the anvil and staple cartridge of FIG. 39.
Figure 41:
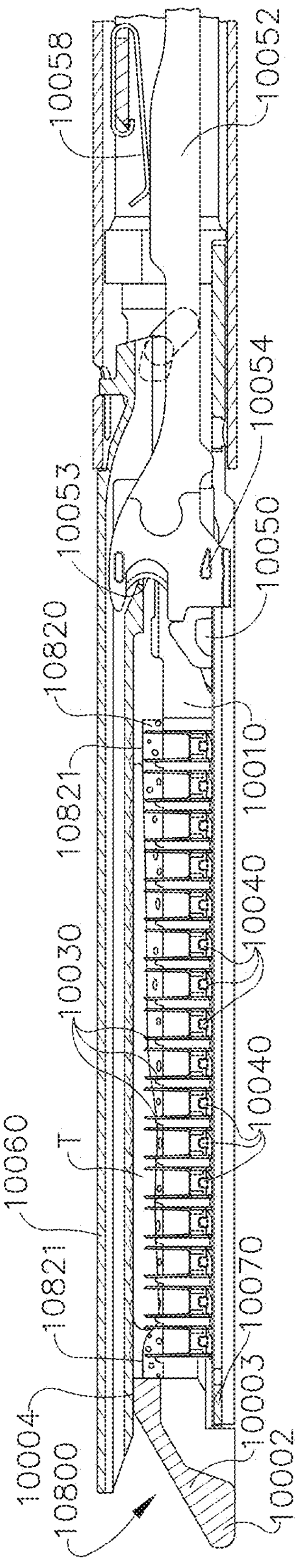
FIG. 41 is an elevational view of the anvil and staple cartridge of FIG. 39 illustrating tissue having different thicknesses positioned between the anvil and the staple cartridge.
Figure 42:
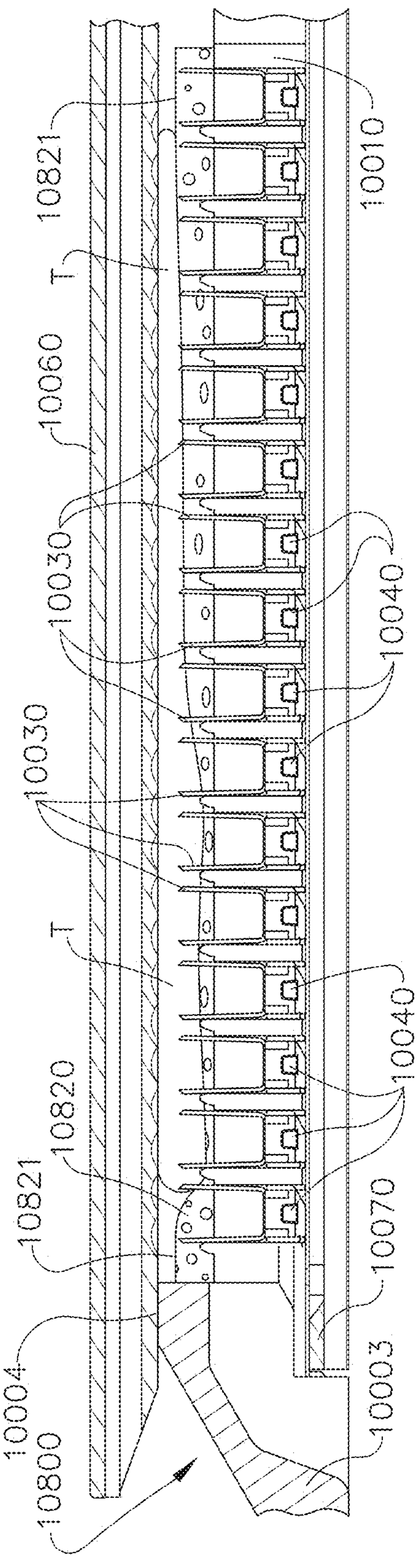
FIG. 42 is a detail view of the anvil and staple cartridge of FIG. 39 as illustrated in FIG. 41.

As discussed above, and referring to FIG. 33, the staple legs 10032 of the staples 10030 can extend above the deck surface 10011 of the support portion 10010 when the staples 10030 are in their unfired positions. With further regard to this firing sequence illustrated in FIG. 27, the staples **10030*e* and 10030*f* are illustrated in their unfired position and their staple legs 10032 extend above the deck surface 10011 and into the tissue thickness compensator 10020. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, as illustrated in FIG. 27, the tips of the staple legs can protrude through the tissue-contacting surface 10032. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013** can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 33, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

Figure 15:
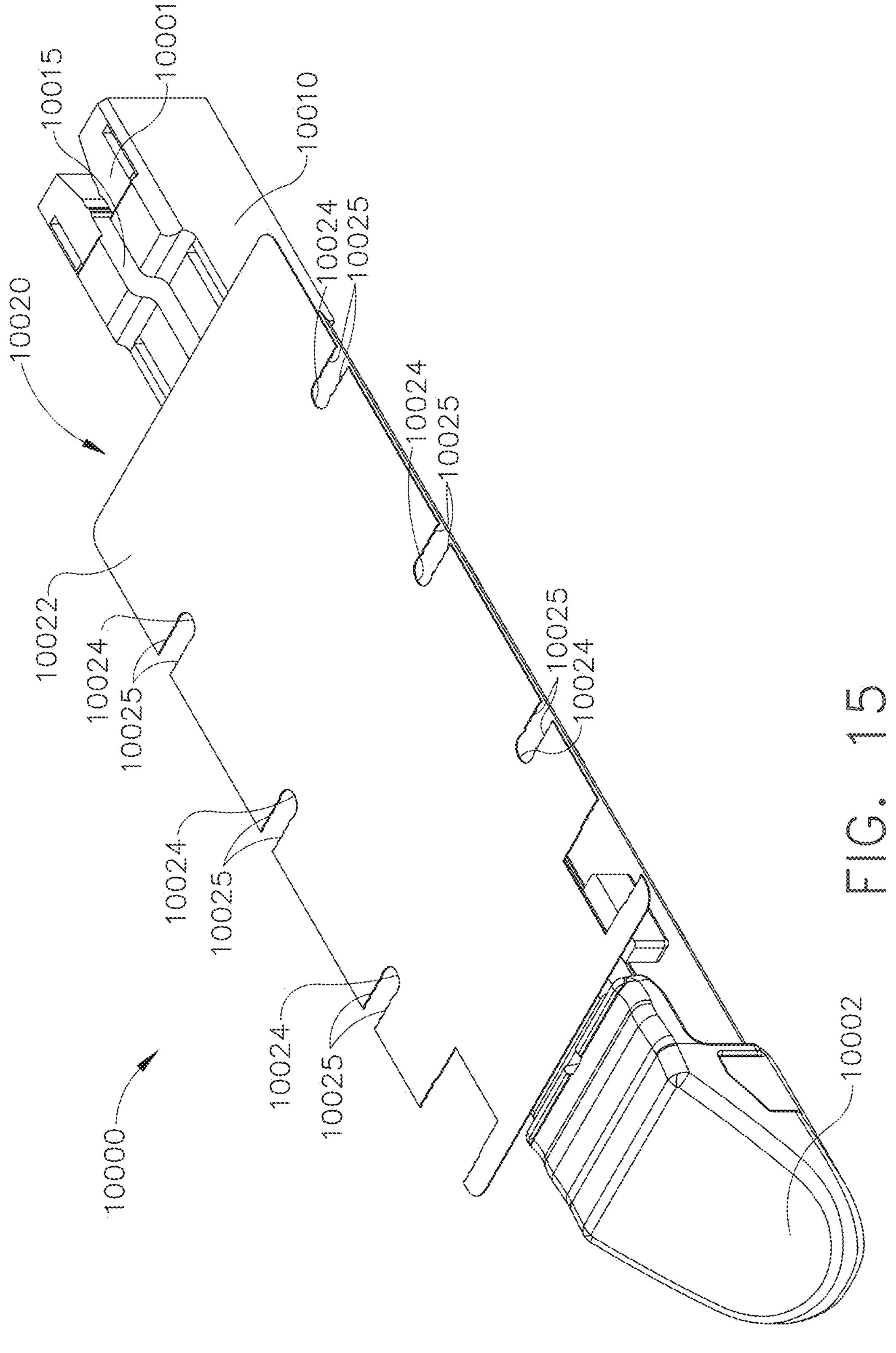
FIG. 15 is a partially exploded view of the staple cartridge of FIG. 14.
Figure 24:
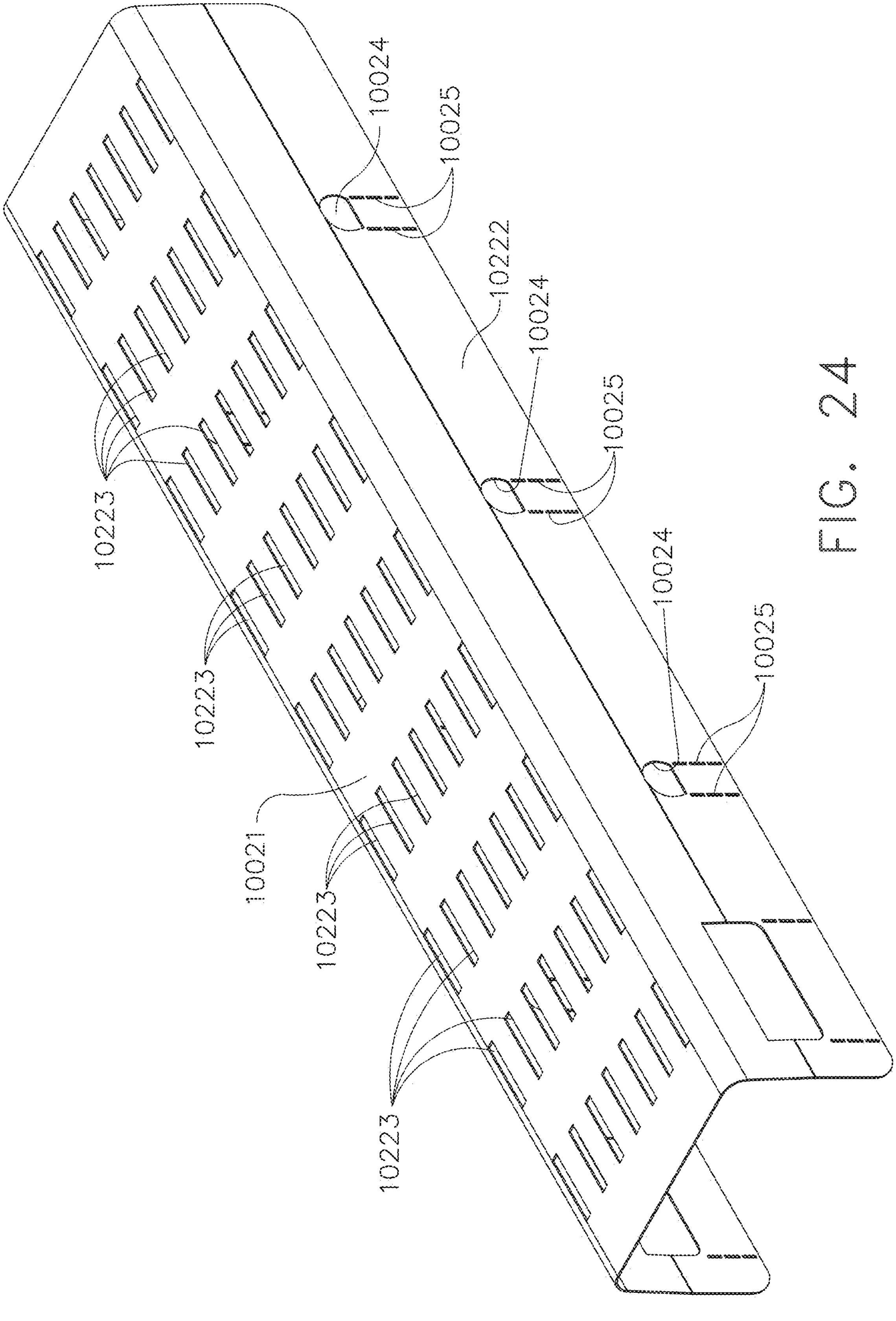
FIG. 24 is a wrap configured to at least partially surround a compressible tissue thickness compensator of a staple cartridge.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, referring now to FIG. 15, a tissue thickness compensator can comprise a compressible core and a wrap surrounding the compressible core. In certain embodiments, a wrap 10022 can be configured to releasably hold the compressible core to the support portion 10010. In at least one such embodiment, the support portion 10010 can comprise one or more projections, such as projections 10014 (FIG. 18), for example, extending therefrom which can be received within one or more apertures and/or slots, such as apertures 10024, for example, defined in the wrap 10022. The projections 10014 and the apertures 10024 can be configured such that the projections 10014 can retain the wrap 10022 to the support portion 10010. In at least one embodiment, the ends of the projections 10014 can be deformed, such as by a heat-stake process, for example, in order to enlarge the ends of the projections 10014 and, as a result, limit the relative movement between the wrap 10022 and the support portion 10010. In at least one embodiment, the wrap 10022 can comprise one or more perforations 10025 which can facilitate the release of the wrap 10022 from the support portion 10010, as illustrated in FIG. 15. Referring now to FIG. 24, a tissue thickness compensator can comprise a wrap 10222 including a plurality of apertures 10223, wherein the apertures 10223 can be aligned, or at least partially aligned, with the staple cavity openings in the support portion 10010. In certain embodiments, the core of the tissue thickness compensator can also comprise apertures which are aligned, or at least partially aligned, with the apertures 10223 in the wrap 10222. In other embodiments, the core of the tissue thickness compensator can comprise a continuous body and can extend underneath the apertures 10223 such that the continuous body covers the staple cavity openings in the deck surface 10011.

In various embodiments, as described above, a tissue thickness compensator can comprise a wrap for releasably holding a compressible core to the support portion 10010. In at least one such embodiment, referring to FIG. 16, a staple cartridge can further comprise retainer clips 10026 which can be configured to inhibit the wrap, and the compressible core, from prematurely detaching from the support portion 10010. In various embodiments, each retainer clip 10026 can comprise apertures 10028 which can be configured to receive the projections 10014 extending from the support portion 10010 such that the retainer clips 10026 can be retained to the support portion 10010. In certain embodiments, the retainer clips 10026 can each comprise at least one pan portion 10027 which can extend underneath the support portion 10010 and can support and retain the staple drivers 10040 within the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

Figure 56:
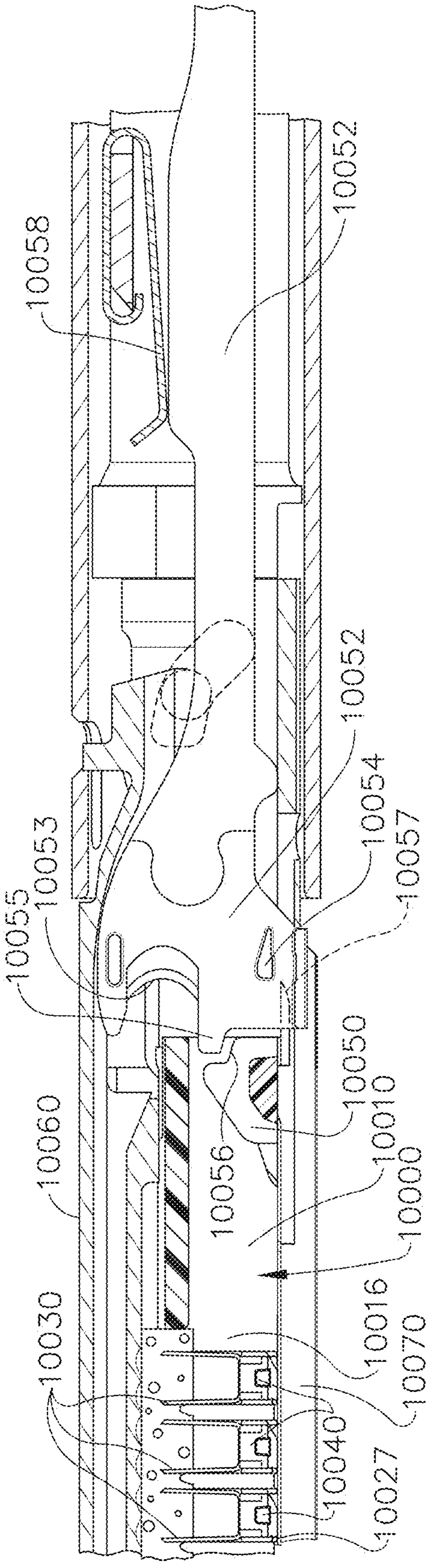
FIG. 56 is a partial cross-sectional view of an end effector of a surgical stapling instrument illustrating a firing bar and staple-firing sled in a retracted, unfired position.
Figure 58:
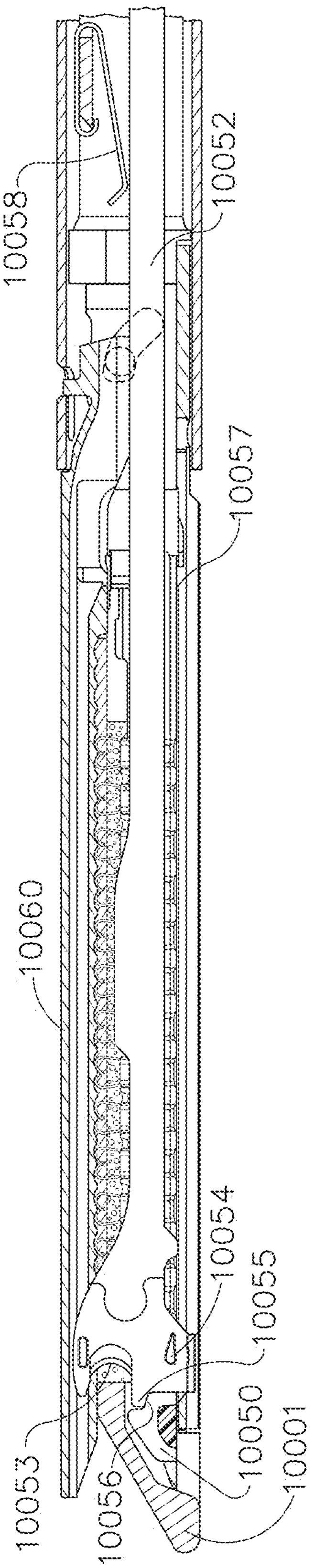
FIG. 58 is a cross-sectional view of the end effector of FIG. 56 illustrating the firing bar in a fully advanced, or fired, position.
Figure 59:
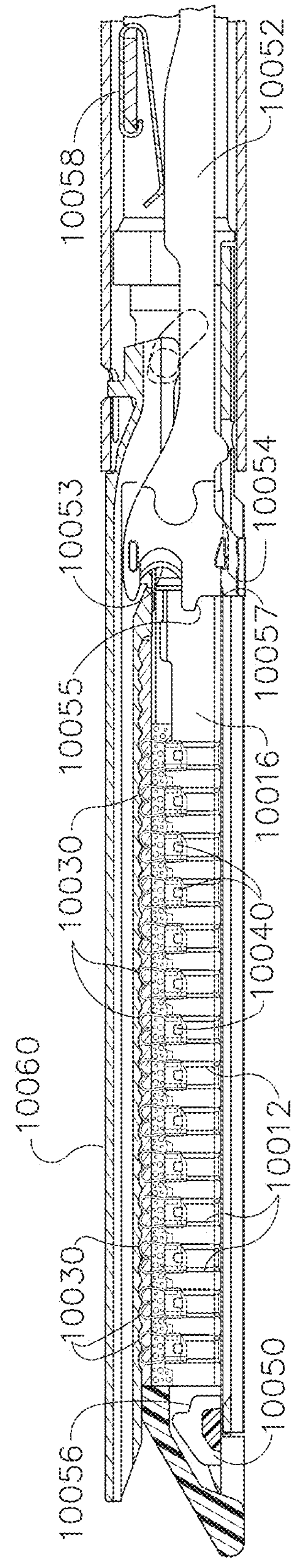
FIG. 59 is a cross-sectional view of the end effector of FIG. 56 illustrating the firing bar in a retracted position after being fired and the staple-firing sled left in its fully fired position.

In various embodiments, further to the above, the sled 10050 can be advanced from the proximal end 10001 to the distal end 10002 to fully deploy all of the staples 10030 contained within the staple cartridge 10000. In at least one embodiment, referring now to FIGS. 56-60, the sled 10050 can be advanced distally within a longitudinal cavity 10016 within the support portion 10010 by a firing member, or knife bar, 10052 of a surgical stapler. In use, the staple cartridge 10000 can be inserted into a staple cartridge channel in a jaw of the surgical stapler, such as staple cartridge channel 10070, for example, and the firing member 10052 can be advanced into contact with the sled 10050, as illustrated in FIG. 56. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 56, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end 10002 of the staple cartridge 10000, as illustrated in FIG. 58. At such point, the firing member 10052 can be retracted proximally. In some embodiments, the sled 10050 can be retracted proximally with the firing member 10052 but, in various embodiments, referring now to FIG. 59, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel 10070.

Figure 60:
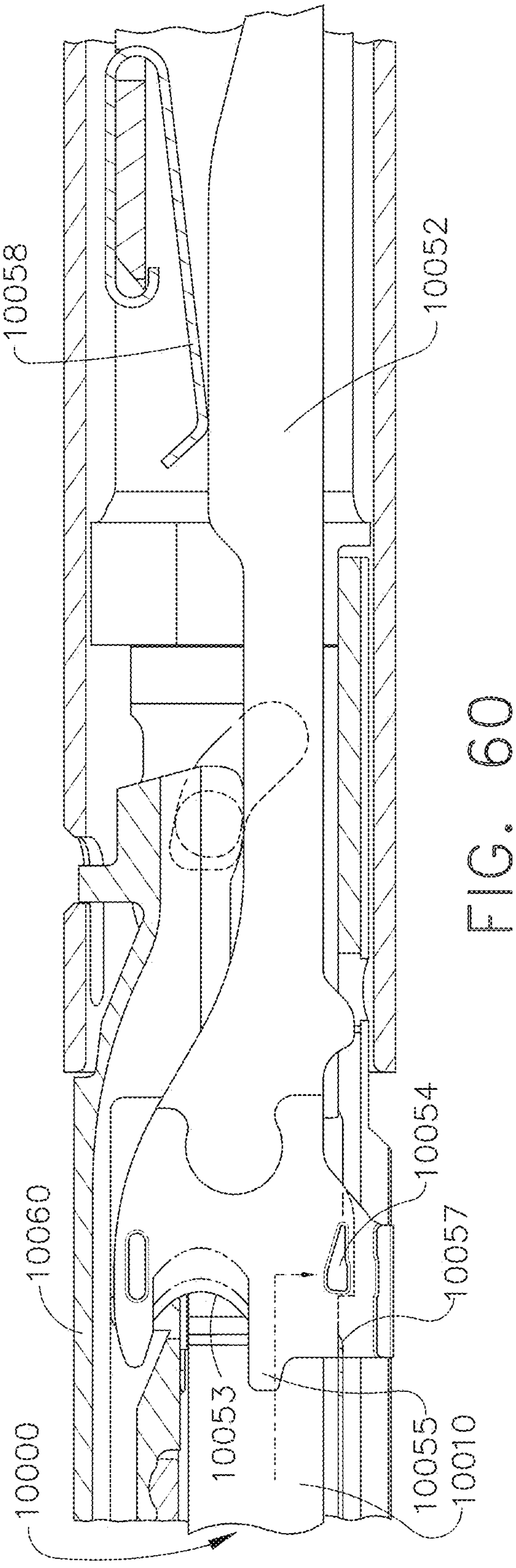
FIG. 60 is a detail view of the firing bar in the retracted position of FIG. 59.

After the expended staple cartridge 10000 has been removed from the staple cartridge channel, further to the above, a new staple cartridge 10000, or any other suitable staple cartridge, can be inserted into the staple cartridge channel 10070. In various embodiments, further to the above, the staple cartridge channel 10070, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, referring again to FIG. 56, as the firing member 10052 is advanced into contact with the sled 10050 and, when the sled 10050 is in its proximal unfired position, a support nose 10055 of the firing member 10052 can be positioned on and/or over a support ledge 10056 on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall 10057 of the lock recess as the firing member 10052 is advanced. As the firing member 10052 pushes the sled 10050 distally, the firing member 10052 can be supported in its upward firing position owing to the support nose 10055 resting on the support ledge 10056. When the firing member 10052 is retracted relative to the sled 10050, as discussed above and illustrated in FIG. 59, the firing member 10052 can drop downwardly from its upward position as the support nose 10055 is no longer resting on the support ledge 10056 of the sled 10050. In at least one such embodiment, the surgical staple can comprise a spring 10058, and/or any other suitable biasing element, which can be configured to bias the firing member 10052 into its downward position. Once the firing member 10052 has been completely retracted, as illustrated in FIG. 60, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end 10002 of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, now U.S. Pat. No. 7,794,475, is hereby incorporated by reference in its entirety.

As described above, a surgical stapling instrument can comprise a staple cartridge channel configured to receive a staple cartridge, an anvil rotatably coupled to the staple cartridge channel, and a firing member comprising a knife edge which is movable relative to the anvil and the staple cartridge channel. In use, a staple cartridge can be positioned within the staple cartridge channel and, after the staple cartridge has been at least partially expended, the staple cartridge can be removed from the staple cartridge channel and replaced with a new staple cartridge. In some such embodiments, the staple cartridge channel, the anvil, and/or the firing member of the surgical stapling instrument may be re-used with the replacement staple cartridge. In certain other embodiments, a staple cartridge may comprise a part of a disposable loading unit assembly which can include a staple cartridge channel, an anvil, and/or a firing member, for example, which can be replaced along with the staple cartridge as part of replacing the disposable loading unit assembly. Certain disposable loading unit assemblies are disclosed in U.S. patent application Ser. No. 12/031,817, entitled END EFFECTOR COUPLING ARRANGEMENTS FOR A SURGICAL CUTTING AND STAPLING INSTRUMENT, which was filed on Feb. 15, 2008, now U.S. Patent Application Publication No. 2009/0206131, the entire disclosure of which is incorporated by reference herein.

In various embodiments, the tissue thickness compensator may comprise an extrudable, a castable, and/or moldable composition comprising at least one of the synthetic and/or non-synthetic materials described herein. In various embodiments, the tissue thickness compensator may comprise a film or sheet comprising two or more layers. The tissue thickness compensator may be obtained using conventional methods, such as, for example, mixing, blending, compounding, spraying, wicking, solvent evaporating, dipping, brushing, vapor deposition, extruding, calendaring, casting, molding and the like. In extrusion, an opening may be in the form of a die comprising at least one opening to impart a shape to the emerging extrudate. In calendering, an opening may comprise a nip between two rolls. Conventional molding methods may include, but are not limited to, blow molding, injection molding, foam injection, compression molding, thermoforming, extrusion, foam extrusion, film blowing, calendaring, spinning, solvent welding, coating methods, such as dip coating and spin coating, solution casting and film casting, plastisol processing (including knife coating, roller coating and casting), and combinations thereof. In injection molding, an opening may comprise a nozzle and/or channels/runners and/or mold cavities and features. In compression molding, the composition may be positioned in a mold cavity, heated to a suitable temperature, and shaped by exposure to compression under relatively high pressure. In casting, the composition may comprise a liquid or slurry that may be poured or otherwise provided into, onto and/or around a mold or object to replicate features of the mold or object. After casting, the composition may be dried, cooled, and/or cured to form a solid.

In various embodiments, a method of manufacturing a tissue thickness compensator comprising at least one medicament stored and/or absorbed therein may generally comprise providing a tissue thickness compensator and contacting the tissue thickness compensator and the medicament to retain the medicament in the tissue thickness compensator. In at least one embodiment, a method of manufacturing a tissue thickness compensator comprising an antibacterial material may comprise providing a hydrogel, drying the hydrogel, swelling the hydrogel in an aqueous solution of silver nitrate, contacting the hydrogel and a solution of sodium chloride to form the tissue thickness compensator having antibacterial properties. The tissue thickness compensator may comprise silver dispersed therein.

Figure 116:
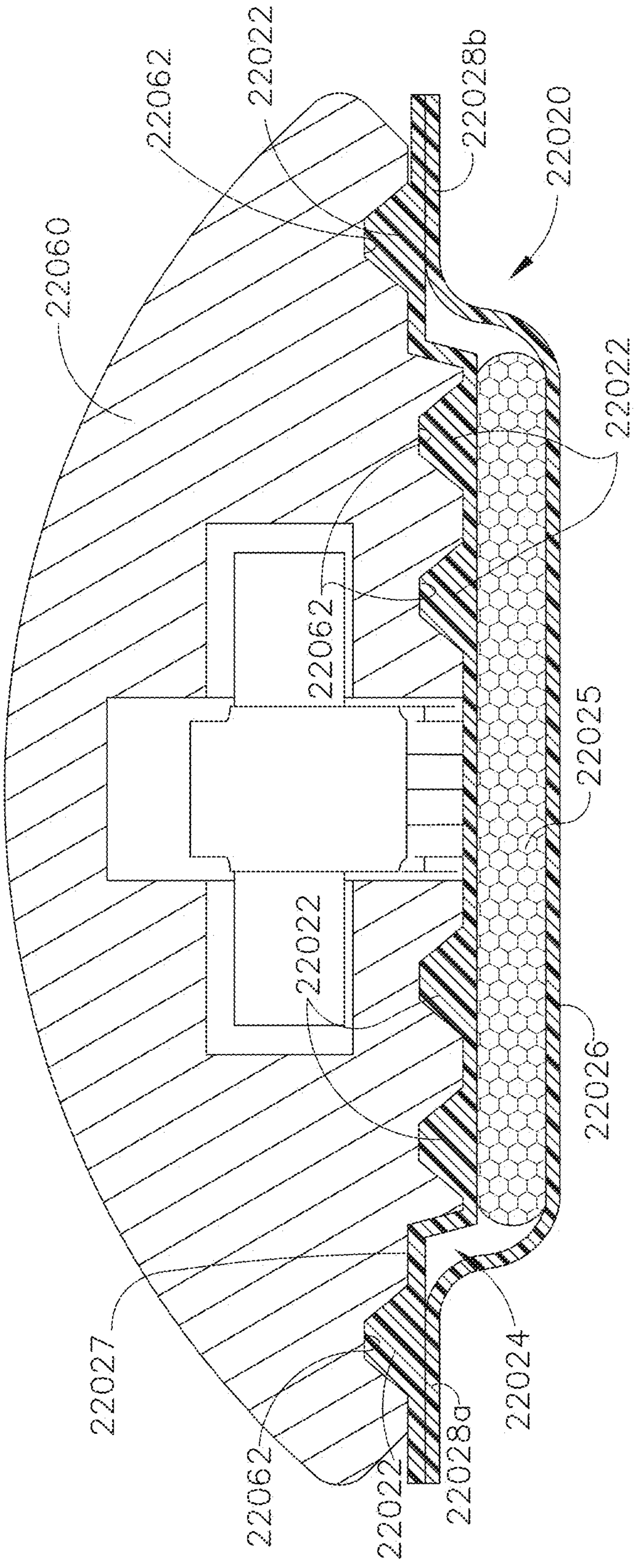

In various embodiments, referring now to FIG. 116, a tissue thickness compensator, such as tissue thickness compensator 22020, for example, can be attached to an anvil of a surgical stapling instrument, such as anvil 22060, for example. The tissue thickness compensator 22020 can include, in at least one embodiment, a cavity 22024 defined between a first film 22026 and a second film 22027, wherein at least portions of the first film 22026 are attached to the second film 22027. In at least one such embodiment, the first film 22026 can be attached to the second film 22027 along lateral seams 22028*a* and 22028*b*, for example. In various embodiments, the first film 22026 can be attached to the second film 22027 along a sealed perimeter in order to sealingly enclose the cavity 22024. In certain embodiments, the first film 22026 and the second film 22027 can be thermally welded along the lateral seams 22028*a*, 22028*b* and/or any other seams connecting the films 22026 and 22027, for example. Referring again to FIG. 116, the anvil 22060 can comprise a plurality of staple forming pockets 22062 which can each be configured to receive and deform the leg of staple wherein, in at least one embodiment, the second film 22027 can comprise projections 22022 which can extend into the forming pockets 22062. In certain embodiments, the projections 22022 can be sized and configured such that they fit snugly within the forming pockets 22062 and can retain the tissue thickness compensator 22020 to the anvil 22060. In the illustrated embodiment, the anvil 22060 can comprise six rows of forming pockets 22062 wherein the tissue thickness compensator 22020 can similarly comprise six rows of projections 22022 which are aligned with the forming pockets 22062, for example. Other embodiments comprising more than or less than six rows of forming pockets 22062 and/or projections 22022 could be utilized. In certain embodiments, one or more adhesives could be utilized to retain the tissue thickness compensator 22020 to the anvil 20060.

Figure 117:
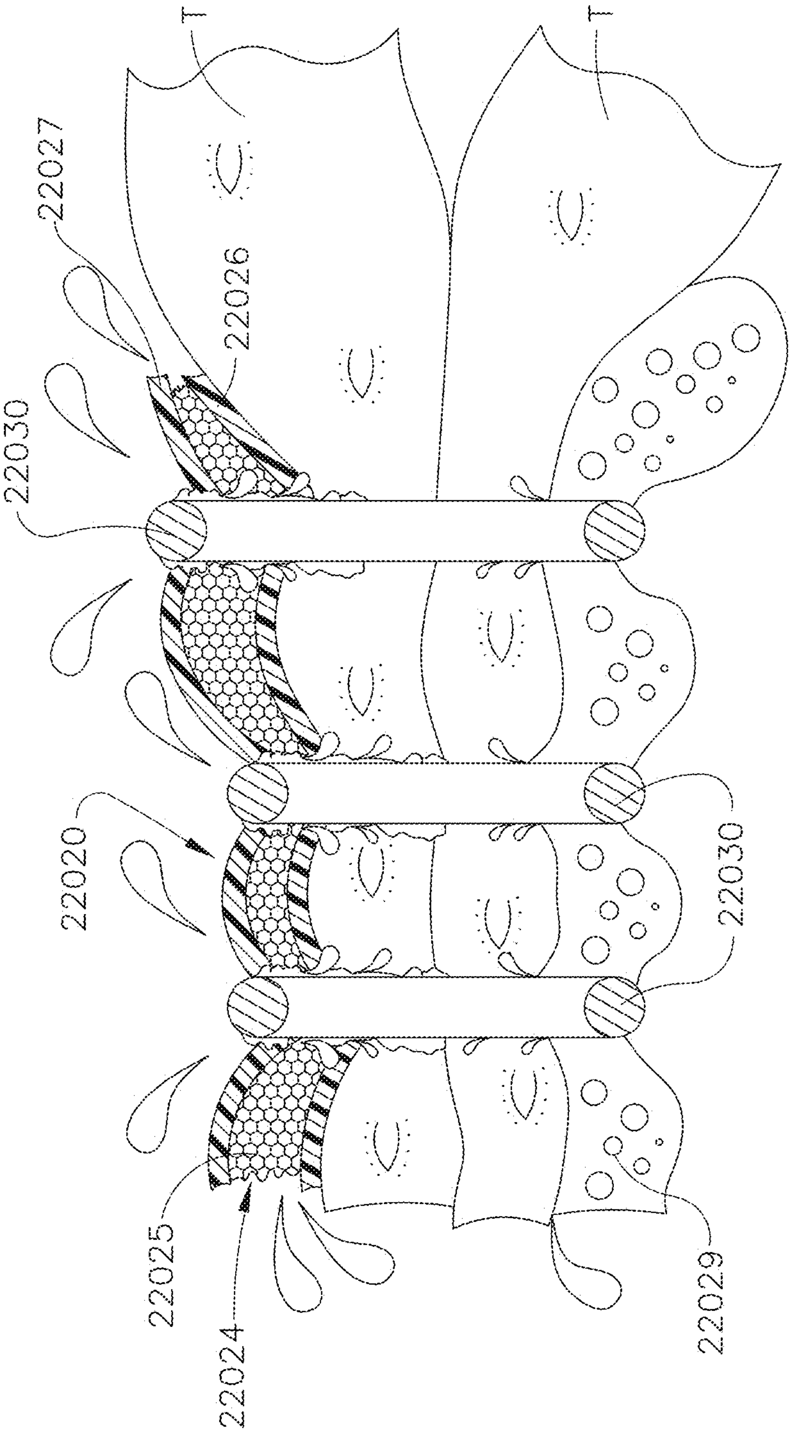

As discussed above, the tissue thickness compensator 22020 can comprise a cavity 22024 defined therein. In various embodiments, the cavity 22024 can extend longitudinally along the anvil 22060. Referring again to FIG. 116, the tissue thickness compensator 22020 can comprise a compressible material positioned within the cavity 22024. In at least one embodiment, referring now to FIG. 117, staples, such as staples 22030, for example, can be ejected from a staple cartridge such that the staples 22030 penetrate the tissue T and then penetrate the tissue thickness compensator 22020 before contacting the anvil 22060. As the legs of the staples 22030 are deformed by the anvil 22060, in various embodiments, the legs can be turned downwardly to repenetrate the tissue thickness compensator 22020 once again. In any event, once the staples 22030 have penetrated the tissue thickness compensator 22020, one or more fluids contained in the cavity 22024, for example, can flow or weep out of the tissue thickness compensator 22020 and onto the tissue T. In certain embodiments, the cavity 22024 can comprise one or more powders contained therein which can escape the cavity 22024 once the tissue thickness compensator 22020 has been at least partially ruptured by the staples 22030, for example. In various embodiments, a material 22025 positioned within the cavity 22024 can be compressed or squeezed within the staples 22030 when the staples 22030 are deformed into their fired configurations such that, in at least one embodiment, a fluid stored within the material 22025 can be expressed from the material 22025, for example. In various embodiments, referring again to FIG. 117, the staples 22030 can also be configured to capture a tissue thickness compensator, such as compensator 22029, for example, removably attached to the staple cartridge against the other side of the tissue T.

In various embodiments, further to the above, the material 22025 can comprise freeze-dried thrombin, freeze-dried fibrin, and/or small fiber non-woven oxidized regenerated cellulose, for example. In certain embodiments, the material 22025 can comprise a compressed powder wafer. In at least one embodiment, the sealed cavity 22024 can comprise an internal atmosphere having a pressure below that of the atmosphere surrounding the tissue thickness compensator 22020. In such an embodiment, the pressure difference between the atmosphere in the internal cavity 22024 and the atmosphere can cause the films 22027 and 22028 to be drawn inwardly. When the internal cavity 22024 is ruptured by the staples 22030, as described above, the vacuum within the internal cavity 22024 can equalize with the surrounding atmosphere and the material 22025 can escape the internal cavity 22024, as also described above. In such circumstances, the tissue thickness compensator 22020 can expand and apply a compressive force to the tissue T captured within the staples 20030. In embodiments in which the material 22025 is vacuum-packed within the tissue thickness compensator 22020, the material 22025 can expand after the internal cavity 22024 has been punctured. In certain embodiments, the films 22026, 22027 can be comprised of a bioabsorbable material and can be configured to dissolve once placed in the patient. In at least one such embodiment, each film 22026, 22027 can be comprised of a layer, or laminate, which is between approximately 0.25 mils and approximately 0.50 mils thick, for example. In any event, further to the above, the tissue thickness compensator 22020, including the material 22025, can be transected by a cutting element as the staples 22030 are fired from their staple cartridge.

Figure 118:
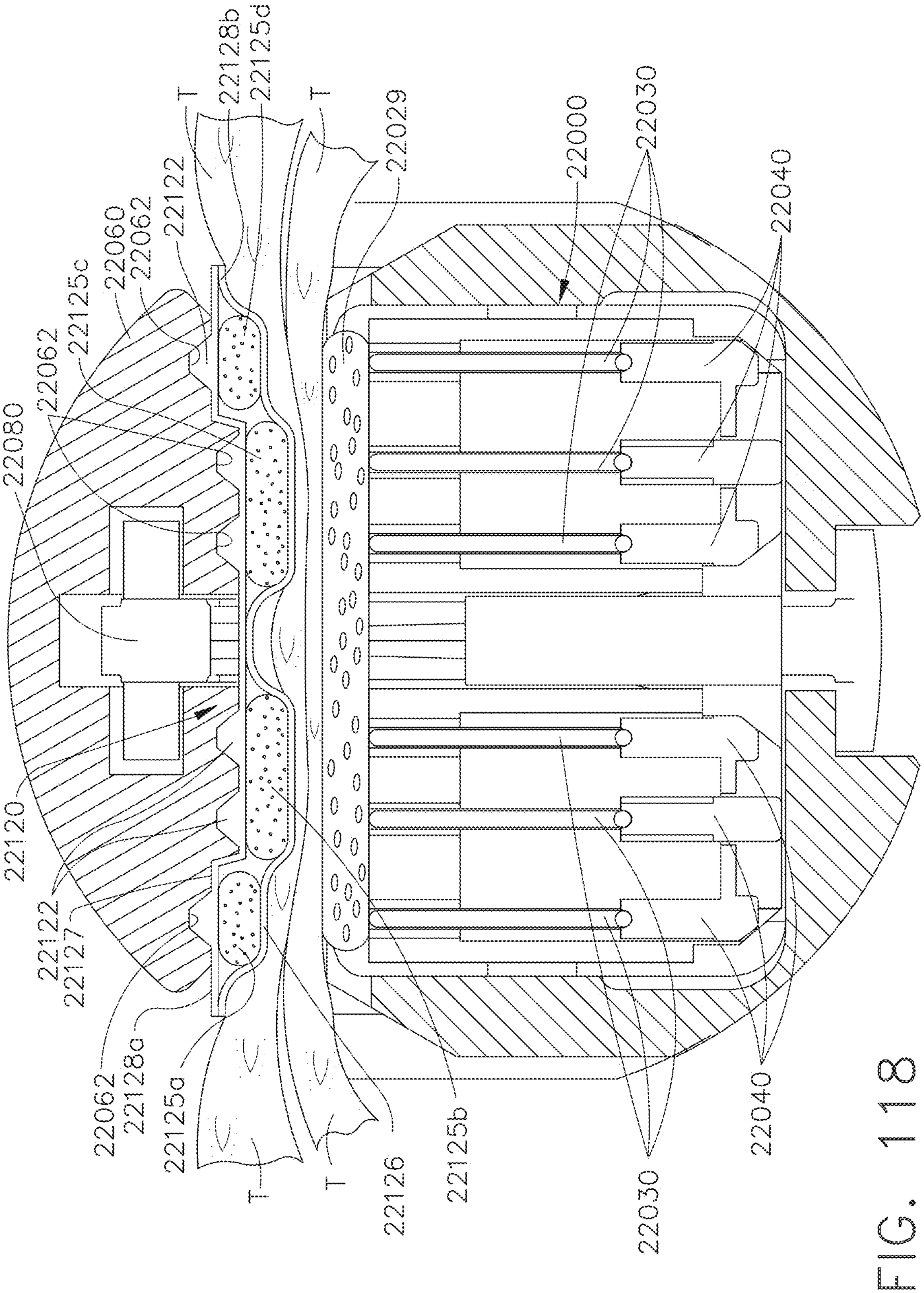
Figure 119:
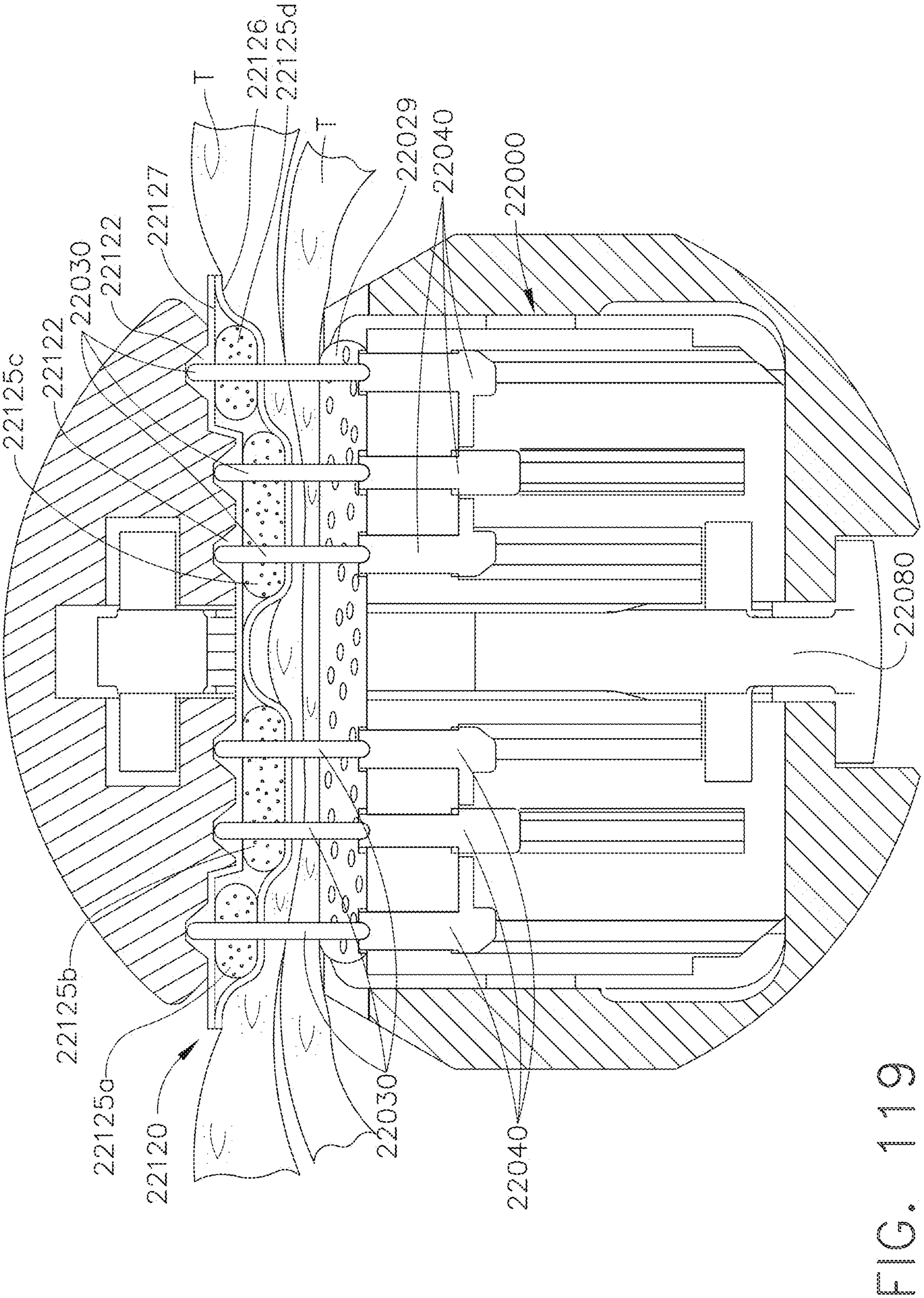

In certain embodiments, referring again to FIG. 116, the cavity 22024 and the material 22025 of the tissue thickness compensator 22020 can be positioned underneath the inner four rows of staple forming pockets 22062 while the seams 22028*a*, 22028*b* can be positioned underneath the outer rows of forming pockets 22062. In such embodiments, the staples in the outer rows of staples may not engage the material 22025 and, thus, they may not capture the material 22025 therein. Rather, such staples may only capture the films 22026 and 22027 along seams 22028*a*, 22028*b*. In various alternative embodiments, referring now to FIGS. 118 and 119, a tissue thickness compensator 22120 can comprise, similar to the above, a first film 22126, a second film 22127, and a plurality of materials 22125*a-d* captured between the first film 22126 and the second film 22127. In at least one such embodiment, referring primarily to FIG. 118, the first material 22125*a* can be aligned with an outer row of staples 22030 in staple cartridge 22000 and an outer row of staple cavities 22062 in anvil 22060, the second material 22125*b* and the third material 22125*c* can each be aligned with two inner rows of staples 22030 and staple cavities 22062, and the fourth material 22126*d* can be aligned with another outer row of staples 22030 and staple cavities 22062. In such an embodiment, referring now to FIG. 119, all of the staples 22030 can be arranged such that they can capture at least one of the materials 22125*a*-22125*d* therein. As illustrated in FIGS. 118 and 119, further to the above, the staples 22030 can be lifted upwardly between an unfired position and a fired position by staple drivers 22040 positioned within the staple cartridge 22000.

In various embodiments, referring again to FIGS. 118 and 119, the layers 22126 and 22127 can define one or more sealed cavities in which the materials 22125*a-d* can be positioned. In at least one embodiment, the layers 22126 and 22127 can be sealed together along a perimeter which can include lateral seams 22128*a* and 22128*b*, for example, utilizing any suitable process, such as thermal and/or laser welding, for example. In certain embodiments, each of the materials 22125*a*-22125*d* can be sealed within separate cavities while, in other embodiments, two or more of the materials 22125*a*-22125*d* can be sealed within the same cavity. In various embodiments, the materials 22125*a*-22125*d* can be comprised of the same material or materials while, in other embodiments, one or more of the materials 22125*a*-22125*d* can be comprised of different materials. In at least one embodiment, one or more of the materials 22125*a*-22125*d* can be comprised of sodium sterate and/or LAE, for example. In certain embodiments, the materials 22125*a*-22125*d* can comprise a lubricant. In such embodiments, the legs of the staples 22030 can be exposed to the lubricant when the staple legs penetrate the materials 22125*a*-22125*d* of the tissue thickness compensator 22120. After the legs pass through the tissue thickness compensator 22120, the legs can contact the anvil 22060 wherein the lubricant can reduce the coefficient of friction, and the friction forces, between the staple legs and the anvil 22060. In such circumstances, the force needed to fire the staples 22030 can be reduced. Owing to the position of the tissue thickness compensator 22120 against the anvil 22060, in at least one embodiment, the staple legs of the staples 22030 can contact the anvil 22060 directly after exiting the tissue thickness compensator 22120 thereby reducing the possibility that the lubricant may be wiped off the staple legs before they contact the anvil 22060. Similarly, the staple legs of the staples 22030 can contact the anvil 22060 directly after being exposed to one or medicaments in the tissue thickness compensator 22120 thereby reducing the possibility that medicaments may be wiped off the staple legs before they re-enter the tissue T. In some circumstances, the staple legs can re-enter the tissue thickness compensator 22120 as the staple legs are being deformed downwardly such that the staple legs can be re-exposed to the medicaments before re-entering the tissue T, for example. In various embodiments, similar to the above, the second film 22127 can comprise a plurality of projections 22122, for example, which can be snugly received within the staple cavities 22062 in order to retain the tissue thickness compensator 22120 to the anvil 22060, for example.

Figure 120A:
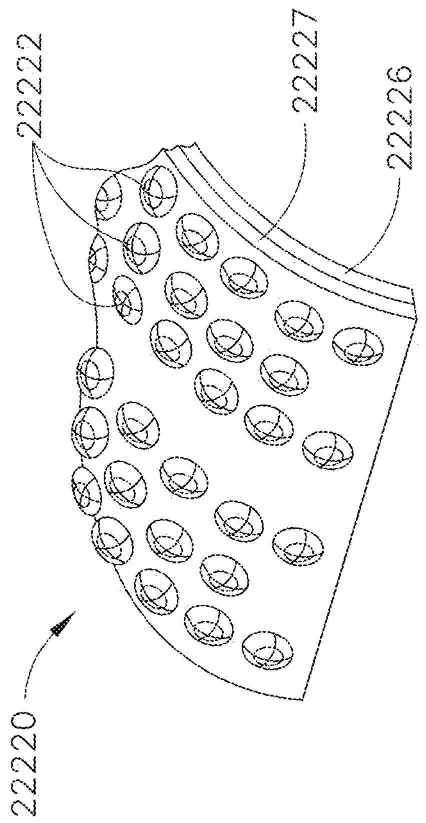
Figure 120:
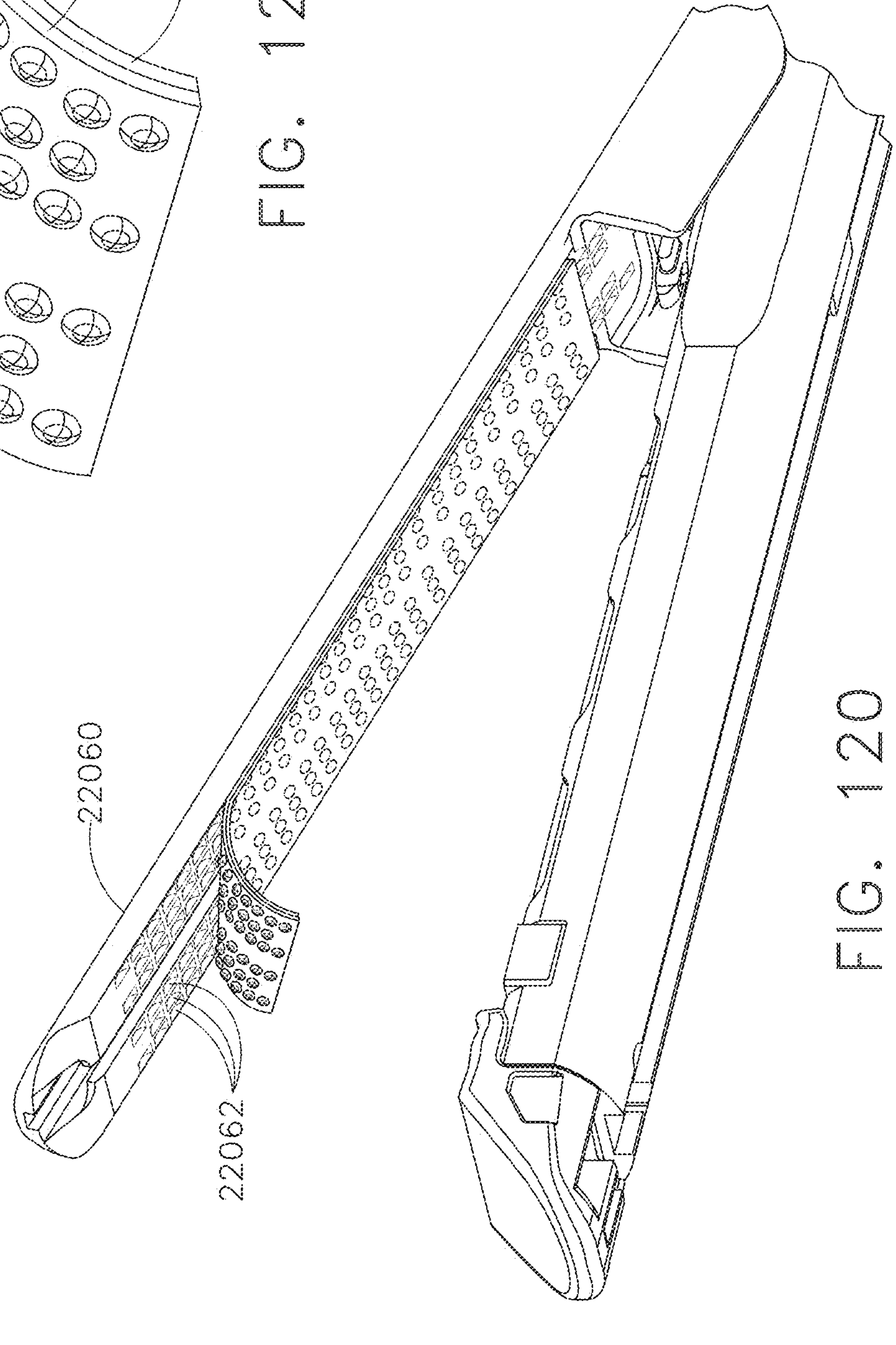
Figure 121:
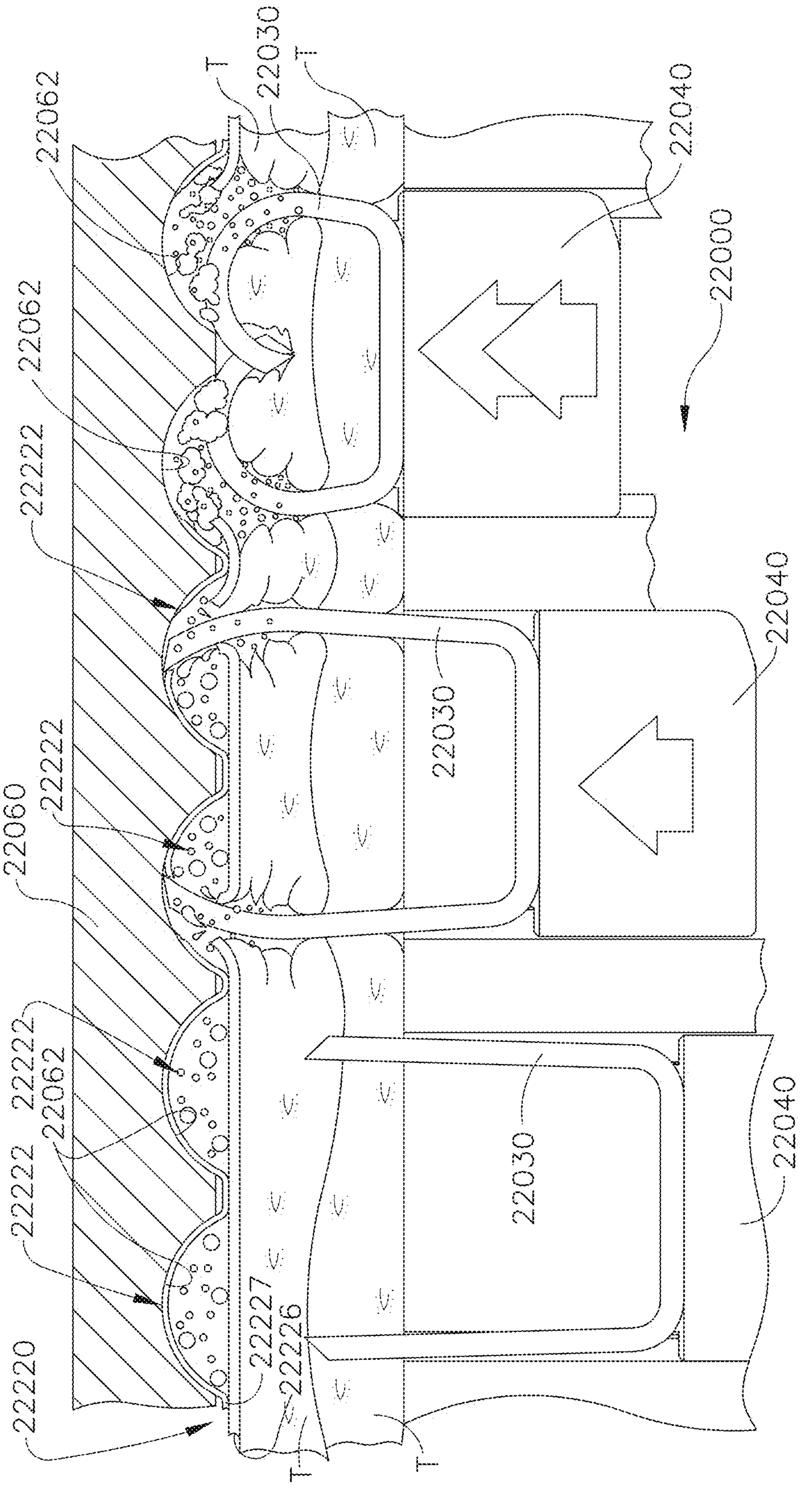

In various embodiments, referring now to FIGS. 120 and 121, an end effector of a surgical stapling instrument can comprise a tissue thickness compensator, such as compensator 22220, for example, which can comprise a plurality of cavities 22222 aligned with the staple forming pockets 22062 of the anvil 22060. In at least one embodiment, the compensator 22220 can be comprised of a first, or bottom, layer 22226 and a second, or top, layer 22227 wherein the first layer 22226 and/or the second layer 22227 can comprise a plurality of raised portions or partial bubbles which can define the cavities 22222. As illustrated in FIG. 120, the compensator 22220 can be attached to the anvil 22060 such that the cavities 22222 are aligned, or at least substantially aligned, with the staple forming pockets 22062 of the anvil 22060. In various embodiments, each cavity 22222 can include one or more medicaments contained therein, such as, for example, oxidized regenerated cellulose, calcium, and/or alginate. In use, in certain embodiments, each cavity 22222 can be in a sealed, unpunctured state prior to being punctured by the staples 22030 ejected from the staple cartridge 22000, for example. After the legs of the staples 22030 have passed through the tissue T, referring now to FIG. 121, each staple leg can pierce and penetrate the first layer 22226 and enter into a cavity 22222 where the staple leg can then pass through one or more medicaments contained therein before piercing and penetrating the second layer 22227. Similar to the above, the legs of the staples 22030 can then contact the anvil 22060.

In various embodiments, the cavities 22222 can maintain the one or more medicaments stored therein in a dry or an at least substantially dry state before being ruptured. After a cavity 22222 has been ruptured, a fluid, such as blood, for example, can enter into the cavity 22222 and mix with the one or more medicaments. In at least one embodiment, the mixture of the fluid with a medicament can cause the medicament to expand within the cavity 22222 wherein, in at least one such embodiment, the medicament can comprise at least one hydrogel, for example. In certain embodiments, the medicament can comprise at least one haemostatic material, for example. In various embodiments, the first layer 22226 and/or the second layer 22227 can be comprised of a flexible material which can stretch to accommodate the expansion of the medicament. In at least one embodiment, the layers 22226, 22227 can be comprised of a CAP/GLY material, for example. In any event, the expansion of the medicament can apply a compressive force to the tissue T captured within and/or positioned around the staples 22030, for example. In various circumstances, the expansion of the medicament can cause the cavities 22222 to burst. In certain embodiments, a first group of cavities 22222 can comprise a first medicament therein while a second group of cavities 22222 can comprise a second medicament therein, for example. In at least one such embodiment, the first medicament can be configured to expand a first amount and/or at a first rate while the second medicament can be configured to expand a second amount and/or at a second rate, for example, wherein the first amount can be different than the second amount and/or the first rate can be different than the second rate. Further to the above, in various embodiments, one or more cavities 22222 can include two or more medicaments stored in each cavity wherein the medicaments can comprise a first medicament and a second medicament, for example. In certain embodiments, a cavity 22222 can maintain the first medicament and the second medicament in a dry, or an at least substantially dry, state before being ruptured. After the cavity 22222 has been ruptured, as described above, blood, for example, can enter into the cavity 22222 and mix with the first and second medicaments wherein, in at least one embodiment, the first and second medicaments can form a gel which expands.

Figure 122:
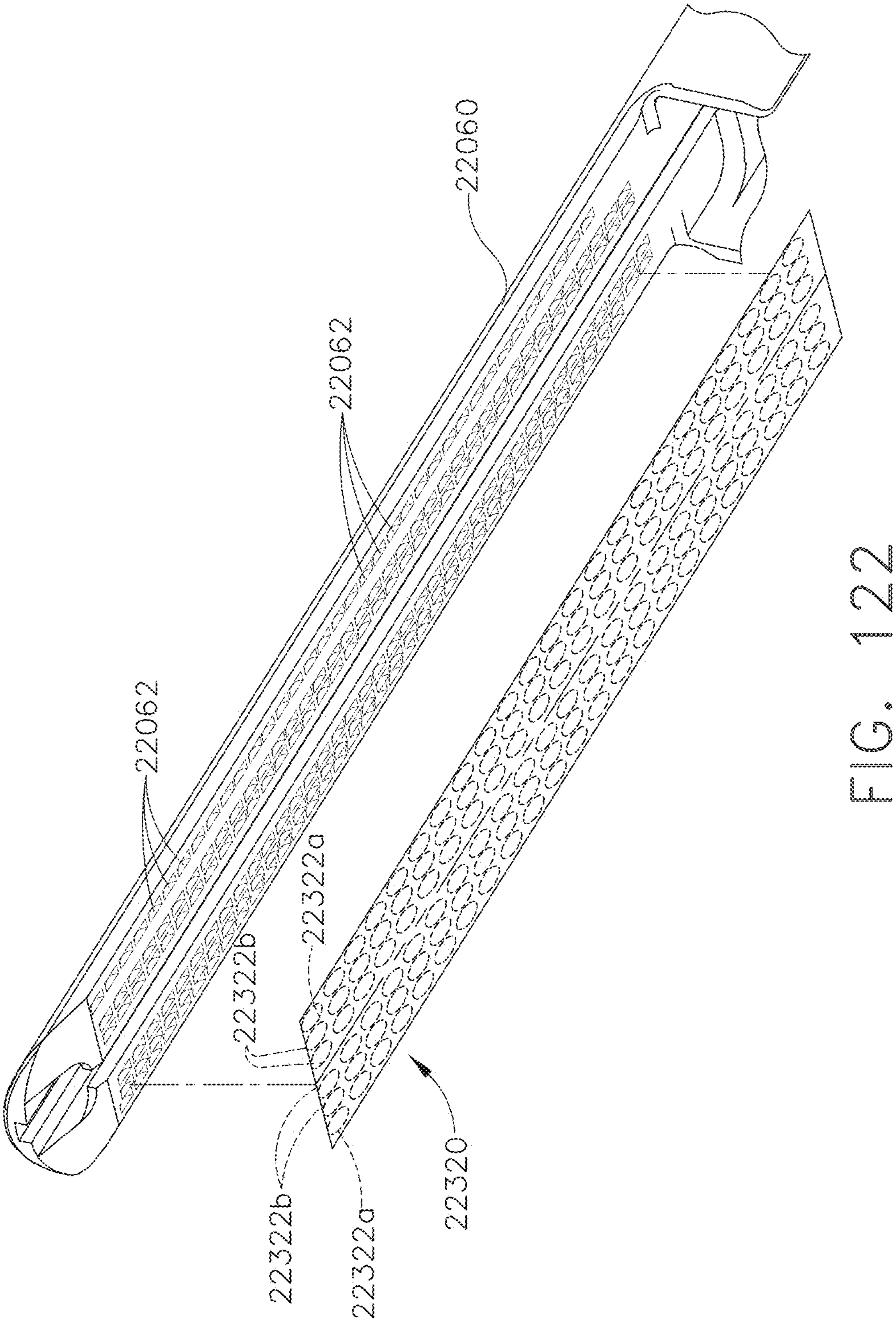

In various embodiments, referring now to FIGS. 122-124, a tissue thickness compensator, such as compensator 22320, for example, can comprise a plurality of first cavities 22322*a* and a plurality of second cavities 22322*b* which can be aligned with staple forming pockets 22062*a* and 22062*b*, respectively. In at least one embodiment, referring primarily to FIG. 123, the staple forming pockets 22062*a* and 22062*b* may be defined in separate stepped surfaces on the anvil 22060. More particularly, the forming pockets 22062*a* can be defined in first surfaces 22069*a* of anvil 22060 and the forming pockets 22062*b* can be defined in second surfaces 22069*b* wherein the first surfaces 22069*a* can be positioned offset, or higher, with respect to the second surfaces 22069*b*, for example. In various embodiments, the first cavities 22322*a* of the tissue thickness compensator 22320 can be larger than the second cavities 22322*b* wherein, in at least one such embodiment, the first cavities 22322*a* can extend higher than the second cavities 22322*b*. As a result of the above, the first cavities 22322*a* can extend upwardly into the first staple forming pockets 22062*a* while, concurrently, the second cavities 22322*b* can extend upwardly into the second staple forming pockets 22062*b*. In various embodiments, each of the first cavities 22322*a* can be configured to contain a larger quantity of a medicament than the second cavities 22322*b*, for example. In other embodiments, the first cavities 22322*a* and the second cavities 22322*b* can contain the same, or at least substantially the same, amount of medicament therein even though the cavities 22322*a* and 22322*b* may have different sizes.

In various embodiments, further to the above, the first cavities 22322*a* can be arranged in certain rows while the second cavities 22322*b* can be arranged in different rows. In certain embodiments, a tissue thickness compensator can comprise cavities aligned with each forming pocket while, in other embodiments, referring to FIG. 130, a tissue thickness compensator, such as compensator 22420, for example, may comprise cavities aligned with only some of the forming pockets. In various embodiments, referring again to FIG. 123, the compensator 22320 can be attached to the anvil 22060. In at least one embodiment, the cavities 22322*a* and/or the cavities 22322*b* can be configured such that fit snugly within staple forming pockets 22062*a* and/or 22062*b*, respectively. In certain embodiments, the compensator 22320 can be assembled to the anvil 22060 such that the second layer 22327 of the compensator 22320 is positioned against the second surfaces 22069*b* of the anvil 22060. In certain other embodiments, referring now to FIGS. 125 and 126, the compensator 22320 can be positioned adjacent to the anvil 22060 such that the compensator 22320 can abut the anvil 22060 when the anvil 22060 is displaced toward the staple cartridge 22000 to compress the tissue T therebetween. Once the staples 22030 have been fired from the staple cartridge 22000 and deformed by the anvil 22060, referring now to FIG. 127, the compensator 22320 can be trapped against the tissue T by the staples 22030 and the anvil 22060 can be moved away from the compensator 22320. In certain circumstances, referring now to FIG. 128, one or more of the staples 22030 may not be properly deformed by the anvil 22030. In such circumstances, referring now to FIG. 129, the cavities in the tissue thickness compensator which overlie the misfired or misformed staples may not be pierced when the staples are fired. In at least one such embodiment, the tissue thickness compensator may be comprised of a bioabsorbable material which can dissolve and subsequently release the medicament contained in the unpierced cavities.

In various embodiments, further to the above, the first cavities 22322*a* and/or the second cavities 22322*b* of the tissue thickness compensator 22320 can comprise a gas, such as air, carbon dioxide, and/or nitrogen, for example, sealed therein. In certain embodiments, the cavities 22322*a* and/or 22322*b* can comprise bubbles which can be popped when the staples 22030 are fired through the cavities 22322*a* and 22322*b* to release the gas contained therein. In at least one embodiment, such popping can provide an audio feedback to the surgeon that the cavities 22322*a* and 22322*b* are being ruptured. In some circumstances, however, some of the staples 22030 may be misfired, as described above, and the cavities 22322*a* and 22322*b* associated therewith may not be popped. In various circumstances, the surgeon can scan the stapled tissue for any unpopped bubbles, or cavities 22322*a* and 22322*b*, and determine whether any corrective action needs to be taken.

As discussed above, referring now to FIG. 131, a surgical stapling instrument can comprise a firing member, such as firing member 22080, for example, which can include a cutting member, or cutting edge, 22081 which can be advanced through the tissue T and one or more tissue thickness compensators as the firing member 22080 is advanced through the cartridge 22000 to deploy the staples 22030 therefrom. In various embodiments, referring primarily to FIG. 133, a compensator, such as compensator 22520, for example, can be attached to the anvil 22060 of the surgical stapling instrument wherein the anvil 22060 can include a knife slot 22061 sized and configured to receive at least a portion of the cutting member 22081. Similarly, the staple cartridge 22000 can comprise a knife slot 22011 which can also be sized and configured to receive at least a portion of the cutting member 22081. In various embodiments, referring again to FIG. 131, the compensator 22520 can comprise one or more cavities, such as cavities 22522, for example, positioned along a cutting line 22521 of the compensator 22520 wherein the cavities 22522 can be aligned with the knife slot 22061 defined in the anvil 22060. As the cutting member 22081 is progressed distally through the staple cartridge 22000 to deploy the staples 22030, the cutting member 22081 can incise the tissue T and the cavities 22522 of the compensator 22520. Similar to the above, referring primarily to FIG. 132, each cavity 22522 can define a sealed cavity 22524 which can contain one or more medicaments 22525 therein. In at least one embodiment, one or more of the cavities 22522 can be configured to contain a fluid which can be released when the cavities 22522 are at least partially incised by the cutting member 22081. In various circumstances, the cutting member 22081 can sequentially incise the cavities 22522 and, as a result, sequentially release the medicaments contained therein.

In various embodiments, referring primarily to FIG. 133, the compensator 22520 can comprise lateral projections, or wings, 22529 that extend along the sides thereof. In at least one embodiment, the projections 22529 can be secured to the anvil surfaces 22069*a* and/or anvil surfaces 22069*b* utilizing one or more adhesives, for example. In certain embodiments, the projections 22522 can be sized and configured to fit snugly within the knife slot 22061 of the anvil 22060 such that, in at least one such embodiment, the projections 22522 can retain the compensator 22520 to the anvil 22060. In various embodiments, the lateral projections 22529 can be sized and configured such that they extend over, or overlie, the staple forming pockets 22062*b* and/or the staple forming pockets 22062*a*. In certain other embodiments, referring now to FIGS. 134 and 135, a compensator 22620 can comprise lateral projections 22629 that do not extend over, or overlie, the staple forming pockets 22062*a* and 22062*b* of the anvil 22060 and/or any other staple forming pockets, for example. In at least one such embodiment, the compensator 22620 may not be captured within a staple 22030 ejected from the staple cartridge 22030. In any event, referring again to FIG. 131, the cutting member 22081 can transect the compensator 22520 as the compensator 22520 is being secured to the tissue T by the staples 22030. In such embodiments, the compensator 22520 can detach from the anvil 22060 and remain with the tissue T. Referring again to the compensator 22620 illustrated in FIGS. 134 and 135, the staples 22030 may not secure the compensator 22620 to the anvil 22060 and, in at least one embodiment, may remain attached to the anvil 22060 after the cutting member 22081 has transected the compensator 22620.

In various embodiment, referring now to FIGS. 136 and 137, an end effector of a surgical stapling instrument can comprise a tissue thickness compensator, such as compensator 22720, for example, which can be attached to, or can be configured to be attached to, an anvil, such as anvil 22760, among others. In at least one embodiment, similar to the above, the anvil 22760 can comprise a plurality of staple forming pockets 22762 and a longitudinal knife slot 22761 configured to receive a cutting member therein as the cutting member is advanced through the end effector. In certain embodiments, the compensator 22720 can comprise a first film layer 22726 and a second film layer 22727 which can be attached to one another to define a cavity 22724. In at least one such embodiment, the first film layer 22726 can be attached to the second film layer 22727 along a sealed outer perimeter 22728 wherein the sealed outer perimeter 22728 can contain at least one medicament 22725 in the cavity 22724, for example. As illustrated in FIG. 137, the cavity 22724 and the medicament 22725 can extend under all of the staple cavities 22762 and, in at least one embodiment, the sealed perimeter 22728 can be positioned laterally with respect to the outermost staple cavities 22762. In various embodiments, the compensator 22720 can further comprise a longitudinal rib 22721, for example, which can be configured to extend upwardly into the knife slot 22761. In at least one such embodiment, the rib 22721 can be sized and configured to fit snugly within the knife slot 22761 in order to secure the compensator 22720 to the anvil 22760. In certain embodiments, the rib 22721 can be configured to align or center the compensator 22720 with the anvil 22760. Similarly, referring to FIG. 138, a tissue thickness compensator 22820 can comprise a retention rib 22821 which can be positioned within the knife slot 22761, for example, in order to secure the compensator 22820 to the anvil 22760. Referring again to FIG. 137, as a cutting member is advanced through the knife slot 22761, in various circumstances, the cutting member can transect the rib 22721 and release the compensator 22720 from the anvil 22760. Such a cutting member is depicted in FIG. 138 as part of firing member 22080, for example.

In various embodiments, referring again to FIG. 138, the tissue thickness compensator 22820 can comprise a first layer 22826 and a second layer 22827 which can be configured and arranged to define a plurality of first packets 22824*a* and a plurality of second packets 22824*b*. In at least one embodiment, each of the first packets 22824*a* can be configured to contain a first medicament and each of the second packets 22824*b* can be configured to contain a second medicament, wherein the second medicament can be different than the first medicament. In various embodiments, the first packets 22824*a* and the second packets 22824*b* can be arranged in an alternating arrangement. In at least one such embodiment, the first packets 22824*a* and the second packets 22824*b* can extend laterally across the tissue thickness compensator 22820 such that a second packet 22824*b* is positioned intermediate two first packets 22824*a* and a first packet 22824*a* is positioned intermediate two second packets 22824*b*, for example. As the cutting member 22080 is progressed through the compensator 22820, as illustrated in FIG. 138, the cutting member 22080 can transect a first packet 22824*a*, followed by a second packet 22824*b*, followed by a first packet 22824*a*, followed by a second packet 22824*b*, and so forth. Correspondingly, in such embodiments, the cutting member 22080 can sequentially release the first medicament contained in a first packet 22824*a* and the second medicament contained in a second packet 22824*b* in an alternating arrangement, for example. In embodiments where the first packets 22824*a* and the second packets 22824*b* are positioned adjacent to one another, the first medicament can be configured to mix with the second medicament when they are released from their respective first packets 22824*a* and second packets 22824*b*. In at least one such embodiment, the advancement of the cutting member through the compensator 22820 can mix the first medicament with the second medicament.

In various embodiments, further to the above, the first medicament can comprise a first powder while the second medicament can comprise a second powder. In at least one embodiment, the first medicament and/or the second medicament can be comprised of a haemostatic material, oxidized regenerated cellulose, alginate, and/or calcium, for example. In certain embodiments, the first medicament and/or the second medicament can comprise a fluid. In at least one embodiment, one or more of the first packets 22824*a* and/or one or more of the second packets 22824*b* can comprise a lubricant which can reduce the force needed to advance the firing member 22080 through the compensator 22820 and/or the tissue T. In various embodiments, the first film layer 22826 and/or the second film layer 22827 can be comprised of a bioabsorbable material, such as PDS, for example. In certain embodiments, the first film layer 22826 and the second film layer 22827 can be attached to one another such that the first packets 22824*a* are sealed from the second packets 22824*b* prior to being incised by the firing member 22080. In certain embodiments, the first packets 22824*a* and/or the second packets 22825*b* can comprise a certain burst strength in order to withstand a certain burst pressure. More particularly, when an anvil, such as anvil 22760, for example, moves the compensator 22820 toward a staple cartridge positioned opposite the anvil 22760, the packets 22824*a*, 22824*b* can be positioned against the tissue positioned intermediate the packets 22824*a*, 22824*b* and the staple cartridge wherein the anvil 22760 can then be pushed, or clamped, downwardly toward the staple cartridge in order to compress the tissue positioned therebetween. In such circumstances, the packets 22824*a*, 22824*b* may be subjected to compressive pressures. In some circumstances, it may be desirable for the packets 22824*a* and/or packets 22824*b* to remain intact until they are incised by the cutting member 22080 and/or punctured by staples fired from the staple cartridge. In certain other circumstances, it may be desirable for the packets 22824*a* and/or the packets 22824*b* to burst from the compressive clamping load applied thereto.

As discussed above, the first packets 22824*a* and the second packets 22842*b* can extend laterally across the compensator 22820. In various embodiments, the first packets 22824*a* can extend along transverse axes 22823*a* while the second packets 22824*b* can extend along transverse axes 22823*b*, for example. In at least one embodiment, the first axes 22823*a* and/or the second axes 22823*b* can be perpendicular, or at least substantially perpendicular, to a longitudinal axis 22083 of the compensator 22820. In at least one such embodiment, the longitudinal axis 22083 can define the cutting path of the firing member 22080. In certain embodiments, the first axes 22823*a* and/or the second axes 22823*b* may not be perpendicular to the longitudinal axis 22083 and may be skew with respect to the longitudinal axis 22083. In various embodiments, as discussed above, the first packets 22824*a* and the second packets 22824*b* can be arranged in an alternating arrangement. In certain other embodiments, any other suitable arrangement of the first packets 22824*a* and the second packets 22824*b* may be utilized. For instance, a sequence of packets arranged in a tissue thickness compensator could include a first packet 22824*a*, a second packet 22824*b*, a second packet 22824*b*, and a first packet 22824*a*. In certain embodiments, a tissue thickness compensator can further comprise a plurality of third packets comprising a third medicament which is different than the first medicament and the second medicament. In at least one such embodiment, the first packets, the second packets, and the third packets can be arranged in an alternating arrangement. For instance, a sequence of packets arranged in a tissue thickness compensator could include a first packet, followed by a second packet, which is followed by a third packet, for example.

In various embodiments, referring again to FIG. 138, the first packets 22824*a* and/or the second packets 22824*b* of the tissue thickness compensator 22820 can define U-shaped, or at least substantially U-shaped, cross-sections, for example. In certain embodiments, referring now to FIG. 139, the packets 22924 of a tissue thickness compensator 22920 can define circular, or at least substantially circular, cross-sections, for example. In some embodiments, referring now to FIG. 140, the packets 23024 of a tissue thickness compensator 23020 can define oval and/or elliptical cross-sections, for example. In various embodiments, referring again to FIG. 138, the first cavities 22824*a* and the second cavities 22824*b* can comprise symmetrical, or at least nearly symmetrical, configurations which are defined in parallel, or at least substantially parallel, rows. In certain other embodiments, referring now to FIG. 141, a tissue thickness compensator, such as compensator 23120, for example, can comprise asymmetrical cavities 23122 defined therein which can have an irregular and/or non-repeating pattern, for example. In at least one such embodiment, each of the cavities 23122 can contain one or more different medicaments therein.

In various embodiments, referring now to FIG. 142, a tissue thickness compensator, such as tissue thickness compensator 23220, for example, can comprise a casing 23226 which defines a cavity 23224 therein and a material 23225 positioned within the cavity 23224. In certain embodiments, the casing 23226 can be comprised of a resorbable polymer, PDS, PGA, PLLA, Cap Gly, and/or PCL, for example, while the material 23225 could be comprised of a haemostatic agent, oxidized regenerated cellulose, Hercules, fibrin, and/or thrombin, for example, which can take any suitable form such as a powder, a fiber, and/or a gel, for example. In at least one embodiment, the casing 23226 can be manufactured utilizing an extrusion process. In such embodiments, the casing 23226 can comprise a constant, or an at least substantially constant, cross-section along the length thereof which can be created without having to weld a seam together. In at least one such embodiment, the cavity 23224 can be defined by a sidewall extending around the entire perimeter thereof without openings defined therein. In certain embodiments, the casing 23226 can be comprised of a mesh and/or a straw-like material having openings defined therein. In at least one embodiment, openings can be cut in the casing 23226 by a laser cutting process and/or a die cutting process, for example.

As part of manufacturing the material 23225, referring now to FIGS. 145-147, a yarn strand can be created utilizing fibers and/or a fibrous material, such as oxidized regenerated cellulose, for example. In certain embodiments, longer fibers 23325, depicted in FIG. 145, and shorter fibers 23425, depicted in FIG. 146, can be mixed together as illustrated in FIG. 147 to form the yarn strand of material 23225. In various embodiments, the yarn strand can be drawn and/or placed under tension in order to stretch the fibers contained therein in a longitudinal direction. In certain embodiments, referring now to FIG. 148, the yarn strand of material 23225 can be fluffed by graspers 23290 which can grasp and twist the material 23225 to increase the volume of the yarn strand. In at least one such embodiment, the graspers 23290 can fluff the material 23225 as the yarn strand is moving relative to the graspers 23290, for example. In some embodiments, referring again to FIG. 148, cutting members 23291 could be utilized to make small incisions and/or micro-cuts, for example, in the yarn strand of material 23225. Similar to the above, the cutting members 23291 can cut the material 23225 as the yarn strand is moving relative to the cutting members 23291. In certain embodiments, the yarn strand of material 23225 can be fluffed before the above-described incisions are made while, in other embodiments, the yarn strand of material 23225 could be incised before it is fluffed.

Once the yarn strand of material 23225 has been suitably prepared, the material 23225 can be positioned within the casing 23226. In at least one embodiment, referring now to FIG. 149, two or more casings 23226 could be formed together as part of an extrusion process, discussed above, wherein the casings 23226 can be connected together as part of a tube 23227. In various embodiments, the yarn strand of material 23225 can be positioned within, or drawn into, the cavity 23224 defined in the tube 23227. In at least one embodiment, the yarn strand of material 23225 can be positioned adjacent to and/or within a first open end 23221 of the cavity 23224 wherein a grasper 23292 can be inserted through a second open end 23222 of the cavity 23224. The grasper 23292 can then be pushed through the cavity 23224 until the jaws 23292*a* of the grasper 23292 pass through, and/or are positioned relative to, the first open end 23222 such that grasper jaws 23292*a* can be manipulated to grasp the yarn strand of material 23225. In certain embodiments, a grasper may comprise a hook member, for example, which can be configured to grasp the yarn strand of material 23225. In any event, once the grasper 23292 has sufficiently grasped the yarn strand of material 23225, the grasper 23292 can be drawn back into the cavity 23224 in order to pull the yarn strand of material 23225 into the cavity 23224. In various embodiments, the grasper 23292 can be configured to twist the yarn strand of material 23225 before, during, and/or after the yarn strand is pulled into the tube 23227.

Once the yarn strand of material 23225 has been suitably positioned within the tube 23227, the grasper 23292 can then be operated to release the yarn strand of material 23225. In various embodiments, the yarn strand can be released before the yarn strand has been pulled through the second open end 23222 of the tube 23227 while, in other embodiments, the yarn strand can be released after the yarn strand has been pulled through the second open end 23222, as illustrated in FIG. 150. In certain circumstances, the yarn strand can be pulled through the second open end 23222 such that, when the yarn strand is released, the yarn strand can shrink, or spring back, into the tube 23227 through the second open end 23222. In various circumstances, the yarn strand can be cut at a location adjacent to the first open end 23221 such that, similar to the above, the yarn strand can shrink, or spring back, into the tube 23227 through the first open end 23222. In various circumstances, further to the above, the grasper 23292 can apply a tension force to the yarn strand of material 23225 such that when the grasper 23292 releases the yarn strand and/or when the yarn strand is cut, the tension force within the yarn strand can be relieved thereby allowing the yarn strand to contract.

Once the yarn strand of material 23225 has been sufficiently positioned within the tube 23227, referring now to FIG. 151, the tube 23227 and the material 23225 can be cut into a plurality of segments, wherein each segment can be made into a tissue thickness compensator 23220, for example. In various embodiments, the cavity 23224 extending through the cover 23226 of each such segment can comprise an open end on opposite ends thereof. In at least one such embodiment, one or both of the open ends can be closed and/or sealed by a heat-staking, heat-welding, and/or laser welding process, for example. Referring to FIG. 152, a segment comprising a cover 23226 and a portion of the material 23225 therein can be positioned within a die configured to close and/or seal the open ends of the cover 23226. More particularly, in at least one embodiment, the die can comprise a base 23294 and a movable portion 23296, for example, wherein the segment can be positioned within a cavity 23295 defined in the base 23294. Once positioned, the movable portion 23296 can be moved downwardly to apply a force to the segment. In various embodiments, heat can be applied to the segment via the base 23294 and/or the movable portion 23296 wherein the heat and/or the force applied to the segment can distort the cover 23226. More specifically, in at least one embodiment, the movable portion 23296 can define a pocket 23297 which can be contoured to apply a clamping force to certain portions of the cover 23226, such as the open ends thereof, in order to close, flatten, and/or neck down such portions of the tissue thickness compensator 23220. For instance, the pocket 23297 can be configured to form the closed ends 23228 of the tissue thickness compensator 23220 and flatten the portion of the tissue thickness compensator 23220 positioned intermediate the closed ends 23228. After the tissue thickness compensator 23220 has been suitably formed, the movable portion 23296 can be moved to an open position and the tissue thickness compensator 23220 can be removed from the die. In various embodiments, the tissue thickness compensator 23220 can then be positioned in a cooling container wherein the compensator 23220 can be permitted to cool to room temperature and/or any other suitable temperature.

In certain alternative embodiments, further to the above, the tube 23227 can be positioned within a heat-forming die after the material 23225 has been positioned therein. After the tube 23227, and the material 23225 positioned therein, have been formed, the tube 23227 and the material 23225 can then be segmented into a plurality of tissue thickness compensators 23220, for example. In various embodiments, referring again to FIG. 142, the tissue thickness compensator 23220 can comprise lateral wings, or clips, 23229 which can be configured to be attached to the anvil 22060, for example. In at least one such embodiment, the lateral wings 23229 can be formed in the cover 23226 when the tissue thickness compensator 23220 is formed between the die portions 23294 and 23296, as described above. Referring now to FIG. 143, a tissue thickness compensator 23320 can comprise lateral wings 23329 extending from cover 23326. In certain embodiments, referring now to FIG. 144, a tissue thickness compensator 23420 can comprise a cover 23426 having one or more lateral flexible joints 23428, for example, which can permit the cover 23426 to flex and flatten when it is subjected to a compressive pressure in the heat-forming die described above. In various embodiments, as a result of the above, the tissue thickness compensator 23220 may not comprise lateral seams. In such embodiments, referring again to FIG. 142, the material 23225 may extend to the lateral edges of the anvil 22060, for example.

As described above, a yarn strand can be pulled through a tube and then cut to length to form one or more tissue thickness compensators. In various embodiments, further to the above, a yarn strand can be pulled or pushed through a tube utilizing a rigid strand of material. In at least one embodiment, a rigid strand of polymer material, such as PCL, for example, can be heated above its glass transition temperature and stretched into a deformed shape. In at least one such embodiment, the rigid strand can comprise an undeformed serpentine shape which, when stretched into its deformed shape, can comprise a straight, or at least substantially straight, shape, for example. Thereafter, the rigid strand can be cooled below the glass transition temperature of the material while the rigid strand is constrained so that the rigid strand can maintain its deformed shape. Once the rigid strand is in its deformed shape, in various embodiments, ORC fibers, for example, can be formed around the rigid strand. In certain embodiments, an ORC yarn strand, for example, can be wound around, flocked, and/or folded over the rigid strand. Alternatively, the rigid strand can be inserted into ORC fibers, for example. In certain embodiments, the rigid strand can comprise a sticky surface which can be rolled and/or dipped within the ORC fibers. In any event, the rigid strand and the ORC fibers can then be inserted into a tube, similar to the above, and reheated above the glass transition temperature of the rigid strand. In such circumstances, the rigid strand can be unconstrained, or at least substantially unconstrained, and can be permitted to return, or at least substantially return, to its original undeformed shape. In at least one such embodiment, the rigid strand can contract when returning to its original shape and retract the ORC fibers into the tube. In certain embodiments, the center of the tube can be clamped to hold the rigid strand and the ORC fibers in the center of the tube as the rigid tube contracts. Similar to the above, the ends of the tube can be sealed to enclose the rigid strand and the ORC fibers therein.

In various embodiments, referring now to FIG. 244, a tissue thickness compensator 33320 can comprise a shell 33326, a compressible core positioned within the shell 33326, and closed ends 33328 which can be configured to contain the compressible core within the shell 33326. In at least one embodiment, further to the above, the shell 33326 can be produced from a continuous extruding process and can comprise a continuous cross-sectional shape along the length thereof. In certain embodiments, referring now to FIGS. 245-247, a tissue thickness compensator 33420 can comprise a shell 33426, a cavity 33424 defined in the shell 33426, and a core 33425 positioned within the cavity 33424. In at least one such embodiment, the shell 33426 can comprise a film body formed from a continuous extruded shape and the core 33425 can comprise a fibrous medicament core, such as ORC, for example. In at least one embodiment, the shell 33426 can comprise one or more flexible legs 33423 which can be configured to extend into a knife slot 22063 defined in the anvil 22060 and releasably retain the tissue thickness compensator 33420 to the anvil 22060. In certain embodiments, referring now to FIGS. 248-250, a tissue thickness compensator 33520 can comprise a shell 33526, a cavity 33524 defined in the shell 33526, and a core 33425 positioned within the cavity 33524. In at least one such embodiment, the shell 33526 can comprise a film body formed from a continuous extruded shape and the core 33425 can comprise a fibrous medicament core, such as ORC, for example. In at least one embodiment, the shell 33526 can comprise one or more retention members 33528 which can be configured to extend around the outside surface of the anvil 22060 and releasably retain the tissue thickness compensator 33520 to the anvil 22060. In at least one such embodiment, referring primarily to FIG. 250, the shell 33526 can comprise movable portions 33527 and a gap 33523 defined between the movable portions 33527 wherein, after the tissue thickness compensator 33520 has detached from the anvil 22060, the movable portions 33527 can spring open to expose the core 33425 contained therein. In certain embodiments, referring now to FIGS. 251-252, a tissue thickness compensator 33620 can comprise a shell 33626, a cavity 33424 defined in the shell 33626, and a core 33425 positioned within the cavity 33424. In at least one such embodiment, the shell 33626 can comprise a film body formed from a continuous extruded shape and the core 33425 can comprise a fibrous medicament core, such as ORC, for example. In at least one embodiment, the shell 33626 can comprise a thin section 33623 which can be aligned with the knife slot 22063 defined in the anvil 22060 such that a cutting member passing through the tissue thickness compensator 33620 can pass through the thin section 33623 and reduce the force or energy needed to transect the tissue thickness compensator 33620. In certain embodiments, referring now to FIGS. 253-254, a tissue thickness compensator 33720 can comprise a shell 33726, a cavity 33424 defined in the shell 33726, and a core 33425 positioned within the cavity 33424. In at least one such embodiment, the shell 33726 can comprise a film body formed from a continuous extruded shape and the core 33425 can comprise a fibrous medicament core, such as ORC, for example. In at least one embodiment, the shell 33726 can comprise one or more retention members 33723 which can be configured to wrap around the outside surface of the anvil 22060 and releasably retain the tissue thickness compensator 33720 to the anvil 22060. In certain embodiments, referring now to FIGS. 255-256, a tissue thickness compensator 33820 can comprise a shell 33826, a cavity 33424 defined in the shell 33826, and a core 33425 positioned within the cavity 33424. In at least one such embodiment, the shell 33826 can comprise a film body formed from a continuous extruded shape and the core 33425 can comprise a fibrous medicament core, such as ORC, for example. In at least one embodiment, the shell 33826 can comprise a substantially rectangular cavity 33424 and a substantially flat tissue contacting surface 33829 as opposed to the arcuate cavity 33424 and tissue contacting surface depicted in FIG. 254, for example. In certain embodiments, referring now to FIGS. 257-258, a tissue thickness compensator 33920 can comprise a shell 33926, a plurality of cavities 33924 defined in the shell 33926, and a core 33925 positioned within each of the cavities 33924. In at least one such embodiment, the shell 33926 can comprise a film body formed from a continuous extruded shape and the cores 33925 can each comprise a fibrous medicament core, such as ORC, for example. In certain embodiments, the cores 33925 can be comprised of different materials. In at least one embodiment, the shell 33926 can comprise one or more retention members 33923 which can be configured to extend into the knife slot 22063 of the anvil 22060.

Referring now to FIG. 153, a tissue thickness compensator can be formed utilizing a folding process. In various embodiments, a material 23525, such as oxidized regenerated cellulose, for example, can be placed on a cover sheet 23526 which can be folded and then sealed in order to encapsulate the material 23525. In at least one such embodiment, the cover sheet 23526 can be comprised of cap gly, for example. In certain embodiments, a continuous process can be utilized in which the cover sheet 23526 can be passed under a hopper 23592 which is configured to dispense the material 23525 onto the cover sheet 23526. In at least one such embodiment, the cover sheet 23526 can be flattened between a roller 23591 and an anvil 23590 before the material 23525 is placed onto the cover sheet 23526. In certain embodiments, the material 23525 may be placed on one side, or half, of the cover sheet 23526 wherein the other side, or half, of the cover sheet 23526 can be folded, or flipped, over the material 23525. Before, during, and/or after the material 23525 has been placed on the cover sheet 23526, the cover sheet 23526 can be folded, or at least partially folded. In various embodiments, the anvil 23590, for example, can comprise a cam surface 23594 which can be configured to lift an edge or side of the longitudinally moving cover sheet 23526 and then fold the cover sheet 23526 in half, for example. In at least one embodiment, the cam surface 23594 can comprise a three-dimensional cam, or barrel cam, which progressively lifts and turns a portion of the cover sheet 23526 as the cover sheet 23526 passes by the cam surface 23594.

After the cover sheet 23526 has been folded over the material 23525, the folded cover sheet 23526 and the material 23525 positioned therein can pass through a die 23593 which can, in at least one embodiment, compress and/or compact the folded cover sheet 23526 and the material 23525 to form a tube 23527. In certain embodiments, the edges of the folded cover sheet 23526 can be sealed closed utilizing any suitable process such as thermal welding and/or laser welding, for example. In various embodiments, the tube 23527 can be further flattened by one or more rollers 23595, for example, before the sidewall of the tube 23527 has been sealed. In certain embodiments, the tube 23527 can be further flattened by one or more rollers after the sidewall of the tube 23527 has been sealed. In any event, the tube

23527 can be segmented into portions to create separate tissue thickness compensators. In various embodiments, the ends of the tissue thickness compensators can be sealed utilizing any suitable process such as thermal welding and/or laser welding, for example, while, in other embodiments, one or both of the ends of the tissue thickness compensator can remain in an open configuration, for example.

In various embodiments, referring now to FIG. 154, a compensator can be attached to an anvil, such as anvil 22060, for example, wherein the compensator can be configured to store at least one medicament therein. In at least one embodiment, a compensator 23620 can comprise a central body portion 23626 and lateral attachment portions 23628 which can be configured to be attached to the anvil 22060. In certain embodiments, the compensator 23620 can further comprise an array of capillary channels 23627 defined in a tissue contacting surface 23625 of the compensator 23620 wherein the capillary channels 23627 can be configured to store one or medicaments therein. In at least one such embodiment, the medicament can comprise a fluid which, owing to fluid tension forces, can be retained between the sidewalls of the capillary channels 23627. In various circumstances, the medicament can be applied to the compensator 23620 before the compensator 23620 is attached to the anvil 22060 while, in some circumstances, the medicament can be applied to the compensator 23620 after it has been attached to the anvil 22060, for example. In any event, the compensator 23620 can be configured to contact tissue positioned between the anvil 22060 and a staple cartridge positioned opposite the anvil 22060 wherein the medicament stored in the capillary channels 23627 can flow onto the tissue. In various circumstances, the medicament can flow within the capillary channels 23627.

In various embodiments, referring again to the compensator 23620 illustrated in FIG. 154, the array of capillary channels 23627 can be constructed and arranged in a cross-hatched pattern wherein a first quantity of channels 23627 can extend in a first direction and a second quantity of channels 23627 can extend in a second direction. In at least one embodiment, the first quantity of channels 23627 can intersect and can be in fluid communication with the second quantity of channels 23627. Referring now to FIG. 155, a compensator 23920 can comprise a body 23926 which includes an array of capillary channels 23927 defined in a tissue-contacting surface 23925. In various embodiments, the channels 23927 can be defined along linear paths while, in certain embodiments, the channels 23927 can be defined along non-linear paths. In at least one embodiment, a first quantity of channels 23927 can extend along axes 23923 while a second quantity of channels 23927 can extend along axes 23924, for example, wherein the axes 23923 can extend in different directions than the axes 23924. In various embodiments, the axes 23923 can be perpendicular, or at least substantially perpendicular, to the axes 23924 wherein, in at least one embodiment, the channels 23627 can define islands 23922 therebetween. In at least one such embodiment, the top surfaces of the islands 23922 can define the tissue contacting surface 23925 of the compensator 23920. In various embodiments, the compensator 23920 can comprise a longitudinal axis 23921 and the channels 23627 can extend in directions which are transverse or skew with respect to the longitudinal axis 23921. In certain embodiments, referring again to FIG. 154, a compensator 23720 can comprise a body 23726 and a plurality of capillary channels 23727 defined in the body 23726. In at least one embodiment, the compensator 23720 can further comprise a longitudinal channel 23721 which can be in fluid communication with the capillary channels 23727. In various embodiments, one or medicaments can be stored in the longitudinal channel 23721 wherein the medicaments can flow between the channel 23721 and the capillary channels 23727, for example. In at least one embodiment, the channel 23721 can define a longitudinal protrusion which can extend upwardly into a longitudinal knife slot 22061 defined in the anvil 22060.

As discussed above, referring again to FIG. 154, an array of capillary channels defined in a compensator can comprise a cross-hatched pattern. In various other embodiments, however, an array of capillary channels can comprise any suitable shape or configuration. For example, referring to compensator 23820 illustrated in FIG. 154, the channels 23827 defined in the body 23826 of the compensator 23820 can comprise parallel, diagonal channels which converge toward and/or diverge away from a central channel 23821, for example. Referring now to FIG. 158, an end effector of a surgical stapling instrument can include a staple cartridge 24000 including a tissue thickness compensator 24010 wherein, in at least one embodiment, the tissue thickness compensator 24010 can include at least one medicament, such as medicament 24001, for example, therein and/or thereon. Referring now to FIG. 159, a compensator 24020 attached to an anvil 24060, for example, can be moved into a closed position in order to place the compensator 24020 in contact with the tissue thickness compensator 24010. In such circumstances, the medicament 24001, for example, can be transferred from the tissue thickness compensator 24010 to the compensator 24020. In at least one embodiment, referring now to FIG. 160, the compensator 24020 can comprise a tissue contacting surface 24025 which can be brought into contact with the tissue thickness compensator 24010 wherein, in certain embodiments, the medicament 24001 can flow into capillary channels 24027 defined in the tissue contacting surface 24025. In certain embodiments, referring now to FIG. 157, the compensator 24020 can include at least one medicament, such as medicament 24002, for example, thereon and/or therein which can be transferred from the compensator 24020 to the tissue thickness compensator 24010.

In various embodiments, referring now to FIGS. 240 and 241, a tissue thickness compensator 33020 can comprise a plurality of channels and/or wells defined in the surface thereof. In at least one embodiment, the tissue thickness compensator 33020 can comprise a longitudinal channel 33026 that extends along a longitudinal axis defined through the tissue thickness compensator 33020. In at least one such embodiment, the end of the longitudinal channel 33026 can be in fluid communication with the perimeter of the tissue thickness compensator 33020. The tissue thickness compensator 33020 can further comprise a plurality of wells 33022 and, in addition, a plurality of diagonal channels 33024 which are in fluid communication with the wells 33022 and the longitudinal channel 33026. In certain embodiments, the tissue thickness compensator 33020 can further comprise a plurality of inlet-outlet channels 33027 which can be in fluid communication with the wells 33022 and the perimeter of the tissue thickness compensator 33020. In various embodiments, as a result of the above, fluids can flow into and/or out of the tissue thickness compensator 33020 before, during, and/or after it has been implanted against a patient's tissue. In certain embodiments, the pattern of channels 33024, 33026, and 33027 and the wells 33022 defined in the tissue-contacting surface 33025 of the tissue thickness compensator 33020 can define gripping edges which can be configured to contact the tissue and limit slipping between the tissue thickness compensator 33020 and the tissue. Referring now to the alternative embodiment illustrated in FIGS. 240A and 241A, a tissue thickness compensator 33120 can comprise a plurality of circular channels defined in the surface thereof. In various embodiments, the tissue thickness compensator 33120 can comprise concentric circular channels 33127 which comprise openings defined in the perimeter of the tissue thickness compensator 33120. Similar to the above, fluids can flow into and/or out of the tissue thickness compensator 33120 through the channels 33127. In at least one embodiment, the tissue thickness compensator 33120 can comprise concentric circular channels 33122 which may not include openings defined in the perimeter of the tissue thickness compensator 33120. Referring now to the alternative embodiment illustrated in FIGS. 242 and 243, a tissue thickness compensator 33220 can comprise a plurality of ridges 33227 extending therefrom which can be configured to grip tissue that is positioned against the tissue thickness compensator 33220. In at least one embodiment, the ridges 33227 can be straight while, in some embodiments, the ridges 33227 can comprise a curved contour, for example. Although the ridges and channels described above may be useful for tissue thickness compensators, in various embodiments, such ridges and channels could be utilized with any suitable bioabsorbable and/or biocompatible layer.

In various embodiments, a compensator can be comprised of a plurality of layers. In at least one embodiment, the compensator can comprise a first layer and a second layer attached to the first layer, for example. In certain embodiments, the first layer can comprise a tissue contacting surface and a plurality of capillary channels defined in the tissue contacting surface. In at least one embodiment, the first layer can also comprise capillary channels defined in a side which faces the second layer and faces opposite the tissue contacting surface. In certain embodiments, the second layer can comprise capillary channels defined therein. In at least one embodiment, wells can be defined between the first layer and the second layer of the compensator. In various embodiments, the capillary channels can be formed in the layers of the compensator utilizing any suitable process, such as during a molding process in which the layers are formed and/or during a heat-staking process, for example. In at least one embodiment, a heat-staking process can be utilized to attach the layers of the compensator to one another, for example. In at least one such embodiment, the layers can be comprised of a material which can become deformable when heat is applied thereto, such as CAP/GLY (36/64), for example. In any event, in various embodiments, the capillary channels defined in the tissue contacting surface of the compensator can define gripping surfaces therebetween which can improve the grip, or control, that can be applied to tissue positioned between the anvil and the staple cartridge of the surgical stapling instrument. Stated another way, the capillary channels defined in the tissue-contacting surface of a compensator can decrease the area in which the compensator can contact the tissue. In such circumstances, the smaller contact area can result in higher contact pressures between the compensator and the tissue for a given force. In various circumstances, the higher contact pressures can reduce slipping between the compensator and the tissue.

In various embodiments, one or medicaments can be positioned within the capillary channels and/or voids defined within and/or between the first layer and the second layer. In certain embodiments, the plurality of layers comprising a compensator can comprise a pack of therapeutic layers, or therapies. For instance, a first layer can be comprised of a first medicament and a second layer can be comprised of a second medicament, wherein the first medicament can be different than the second medicament. In at least one such embodiment, capillary channels defined in the first layer can store a third medicament and capillary channels defined in the second layer can store a fourth medicament, wherein the first, second, third, and/or fourth medicaments can be different, for example. In at least one embodiment, the first, second, third, and/or fourth medicaments can be different, for example. In various embodiments, referring now to FIG. 161, a compensator 24120 can comprise a plurality of layers, such as layers 24121-24125, for example. In at least one embodiment, the first layer 24121 and/or the fifth layer 24125 can comprise a flat sheet of material between which the second layer 24122, the third layer 24123, and/or the fourth layer 24124 can be sandwiched. In various embodiments, one or more of the layers 24121-24125 can comprise one or more channels 24127 defined therein. In at least one embodiment, the channels 24127 can extend from one end of the compensator 24120 to the other end and, in certain embodiments, the channels 24127 can extend between one side of the compensator 24120 to the other. In certain other embodiments, the channels 24127 can extend in any suitable direction between any suitable sides and/or ends of the compensator 24120. In various embodiments, referring now to FIGS. 164 and 165, a compensator 24820 can comprise two or more inner layers 24827 which can define lateral channels 24822, for example, which extend from one side of the compensator 24820 to the other. In certain embodiments, referring again to FIG. 161, the channels 24127 defined in one of the layers 24121-24125 can be aligned with the channels defined in a layer positioned adjacent thereto. In some embodiments, the channels 24127 defined in one of the layers 24121-24125 can face, or open toward, a flat surface on a layer positioned adjacent thereto. In various embodiments, referring again to FIG. 161, one or more of the layers 24121-24125 can comprise at least one well 24129 defined therein. In at least one embodiment, the wells 24129 can be in fluid communication with one or more of the channels 24127 defined in the layer. Similar to the above, the wells 24129 can comprise an opening which opens toward, or faces, an adjacent layer wherein the adjacent layer can cover the opening.

In various embodiments, further to the above, the channels 24127 and/or the wells 24129 can be configured to contain one or medicaments therein. In at least one embodiment, the channels 24127 can comprise one or more open ends which can permit a medicament to flow out of the channels 24127. Similarly, in at least one embodiment, the channels 24127 can include one or more openings which can be configured to permit a fluid, such as blood, for example, to flow into the channels 24127. In such embodiments, the fluid can flow into the compensator 24120, absorb at least a portion of a medicament and/or a layer 24121-24125, and then flow out of the compensator 24120. Referring again to FIGS. 164 and 165, the compensator 24820 can comprise apertures 24828 defined in outer layers 24826, for example. In various embodiments, referring again to FIG. 161, the layers 24121-24125 can be comprised of any suitable material, such as a bioabsorbable polymer, PLA, and/or PGA, for example. In certain embodiments, all of the layers 24121-24125 can be comprised of the same material. In certain other embodiments, one or more of the layers 24121-24125 could be comprised of different materials. In various embodiments, one or more of the layers 24121-24125 can include through holes 24128 extending therethrough which can be configured to permit fluids, such as blood, for example, to flow into the channels 24127, wells 24126, and/or between two or more of the layers 24121-21135, for example. In certain embodiments, one or more of the layers 24121-24125 can be connected to each other utilizing a heat-welding and/or laser-welding process, for example. In such embodiments, the fluid, or fluids, flowing into the compensator 24120 can dissolve the welded portions of the layers 24121-24125 and permit the layers 24121-24125 to separate and/or delaminate. In certain embodiments, one or more of the layers 24121-24125 can be comprised of a material which dissolves at a faster rate and/or a slower rate than the material, or materials, comprising the other layers 24121-24125. In at least one such embodiment, the inner layers 24122-24124 of the compensator 24120 can be comprised of a material which dissolves at a faster rate than the material, or materials, which comprise the outer layers 24121 and 24125, for example. In such embodiments, the compensator 24120 can maintain a consistent, or at least substantially consistent, general shape while the interior of the compensator 24120 is dissolved away. In certain other embodiments, the outermost layers of a compensator can be comprised of a material which dissolves at a faster rate than the material, or materials, which comprise the innermost layers of the compensator, for example. In various embodiments, the layers can comprise sheets of material having a thickness between approximately 1 mil and approximately 4 mils, for example.

In various embodiments, referring now to FIGS. 162 and 163, a compensator, such as compensator 24220, for example, can comprise a support layer 24226 which can be configured to be attached to an anvil, such as anvil 22060, for example, and/or a staple cartridge. In certain embodiments, the compensator 24220 can further comprise a scaffold 24222 attached to the support layer 24226 wherein the scaffold 24222 can comprise a plurality of scaffold layers 24227. In at least one embodiment, the scaffold can comprise a three-dimensional structural matrix, for example. In various embodiments, each of the scaffold layers 24227 can be comprised of a plurality of fibers. In at least one embodiment, referring now to FIG. 166, each scaffold layer 24227 can be comprised of a fiber weave including a first plurality of fibers 24228 extending in a first direction and a second plurality of fibers 24229 extending in a second, or different, direction. In certain embodiments, each fiber weave can comprise a plurality of pockets, or cavities, 24223 wherein the layers 24227, the fibers 24228, 24229, and the cavities 24223 can define a matrix favorable to tissue and cellular ingrowth. In various embodiments, the fibers 24228, 24229, and/or any other suitable fibers, can be comprised of a bioabsorbable material. In at least one embodiment, the fibers can be comprised of a haemostatic agent, bound active agents such as those that are biologically and/or pharmacologically active, and/or support members, for example, which can be interweaved with one another. In any event, the material of the fibers can be selected to induce a desirable biologic response such as cellular migration into the scaffold 24222, ECM secretion, and/or the proliferation of structural support cells, for example.

In various embodiments, further to the above, the support layer 24226 can be configured to structurally support the scaffold 24222. In at least one embodiment, the scaffold 24222 can be attached to the support layer 24226 utilizing one or more bioabsorbable adhesives, for example. Similarly, in certain embodiments, the support layer 24226 can be attached to an anvil or a staple cartridge utilizing one or more biocompatible adhesives, for example. In various embodiments, the layers 24227 of the scaffold 24222 can be arranged, or stacked, in any suitable manner. In certain embodiments, each layer 24227 can comprise a pattern of fibers wherein the layers 24227 can be arranged in the scaffold 24222 such that the patterns of the layers 24227 are aligned with each other. In at least one embodiment, referring to FIG. 167, the layers 24227 can be stacked on one another such that the fibers 24228 in a first layer 24227 are aligned with the fibers 24228 in a second layer 24227. Likewise, the layers 24227 can be stacked on one another such that the fibers 24229 in the first layer 24227 are aligned with the fibers 24229 in the second layer 24227. In certain embodiments, referring now to FIG. 168, a scaffold 24422 can comprise a plurality of scaffold layers 24427 wherein the fibers 24429 in each scaffold layer 24427 are oriented in the same direction, such as a longitudinal direction, for example. In certain embodiments, referring now to FIG. 170, each scaffold layer 24227 can comprise a pattern of fibers wherein the layers 24227 can be arranged in a scaffold 24322 such that the patterns of the layers 24227 are not aligned with each other. In at least one embodiment, the layers 24227 can be stacked on one another such that the fibers 24228 in a first layer 24227 extend in a direction which is transverse to or oblique with the fibers 24228 in a second layer 24227. Likewise, the layers 24227 can be stacked on one another such that the fibers 24229 in the first layer 24227 extend in a direction which is transverse to or oblique with the fibers 24229 in the second layer 24227. In certain embodiments, referring now to FIG. 171, a scaffold 24522 can comprise a plurality of scaffold layers 24427 which are oriented such that the fibers 24229 in each scaffold layer 24427 are oriented in different directions, for example.

In various embodiments, further to the above, a first scaffold layer 24227 of a scaffold 24222, for example, can be comprised of a first material while a second scaffold layer 24227 of the scaffold 24222 can be comprised of a second, or different, material. In at least one embodiment, the first material can comprise a first medicament while the second material can comprise a second, or different, medicament, for example. In various embodiments, further to the above, a first scaffold layer 24227 of a scaffold 24222, for example, can comprise a first medicament absorbed into the fibers thereof while a second scaffold layer 24227 of the scaffold 24222 can comprise a second, or different, medicament absorbed into the fibers thereof, for example. In at least one embodiment, the first material can comprise a first medicament while the second material can comprise a second, or different, medicament, for example. In certain embodiments, a scaffold can comprise any suitable number of layers having any suitable density of fibers which are comprised of any suitable number of materials.

Tissue thickness compensators may be installed in a surgical device, such as a surgical cutting and stapling device, for example, utilizing a retainer. The retainer can include a gripping surface and enable a surgeon, nurse, technician, or other person to align one or more of the tissue thickness compensators with features of the surgical instrument, such as an anvil and/or a staple cartridge, for example. In various embodiments, the retainer may include features that align the one or more tissue thickness compensators by engaging a staple cartridge of the surgical instrument. In certain embodiments, the retainer may include features that align one or more tissue thickness compensators by engaging an anvil of a surgical instrument. In certain embodiments, a staple cartridge for the surgical instrument may be included with the retainer and engaging the retainer with the surgical instrument can install the staple cartridge in the surgical instrument and align one or more of the tissue thickness compensators. After the tissue thickness compensators have been aligned with and attached to the surgical instrument, the retainer may be detached from the tissue thickness compensators and then removed from the surgical instrument.

FIGS. 61-67 illustrate an embodiment of a retainer 19000 that may be used to attach a first tissue thickness compensator 19002 to an anvil 19040 and a second tissue thickness compensator 19004 to a staple cartridge 19050 of a surgical stapler, for example. A retainer assembly 19060 can be provided which includes the retainer 19000, the first tissue thickness compensator 19002, and the second tissue thickness compensator 19004. In use, generally, the retainer assembly 19060 may be inserted between the anvil 19040 and a channel configured to support the staple cartridge 19050. Thereafter, the anvil 19040 can be closed. By closing the anvil 19040, the anvil 19040 can push downwardly onto the first tissue thickness compensator 19002 such that the first tissue thickness compensator 19002 may be attached to the anvil 19040. In at least one embodiment, closing the anvil 19040 pushes downwardly on the retainer 19000 and seats the staple cartridge 19050 into the channel of the surgical instrument. When the anvil 19040 is reopened, the first tissue thickness compensator 19002 can detach from the retainer 19000 and when the retainer 19000 is subsequently removed from the surgical device, the retainer 19000 can detach from the second tissue thickness compensator 19004. The surgical device is then ready for use with the first tissue thickness compensator 19002 attached to the anvil 19040 and the second tissue thickness compensator 19004 attached to the staple cartridge 19050.

Figure 61:
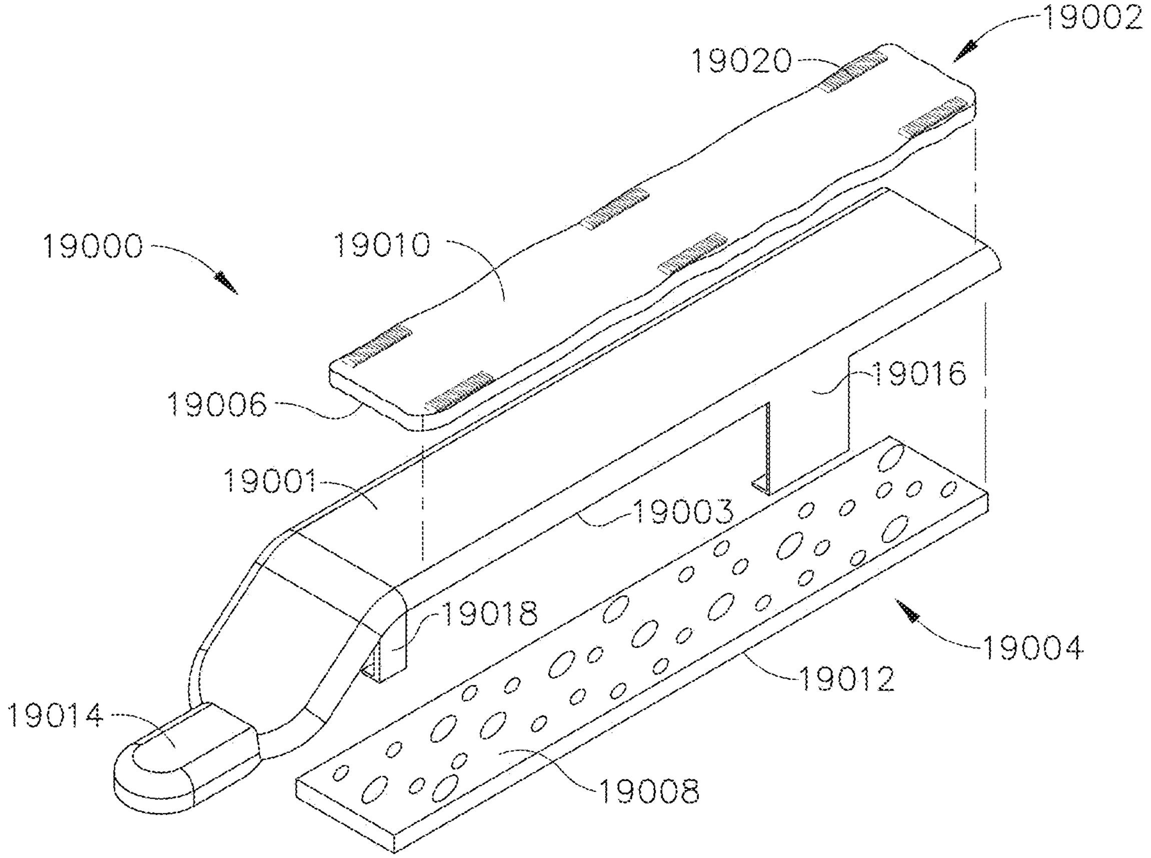
FIG. 61 is an exploded view of a retainer assembly including a retainer and two tissue thickness compensators in accordance with at least one embodiment.
Figure 62:
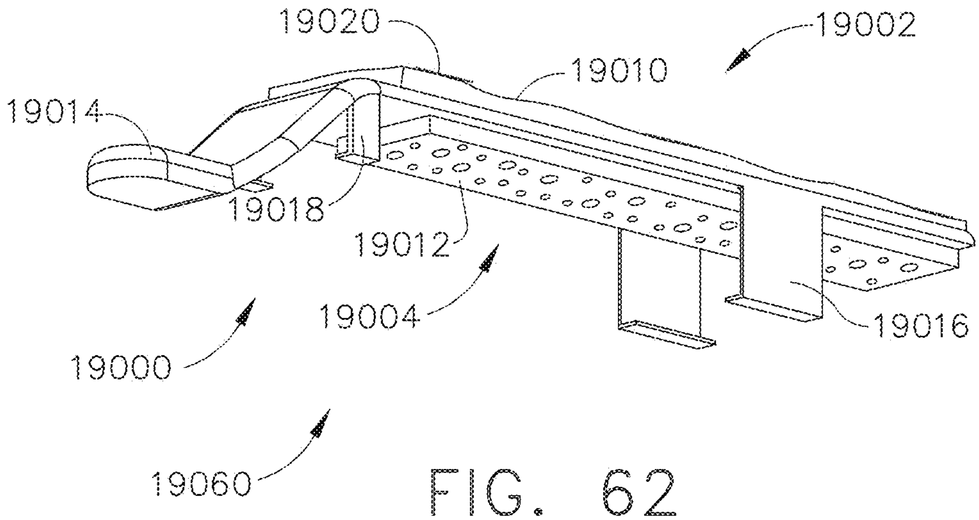
FIG. 62 is a perspective view of the retainer assembly shown in FIG. 61.
Figure 63:
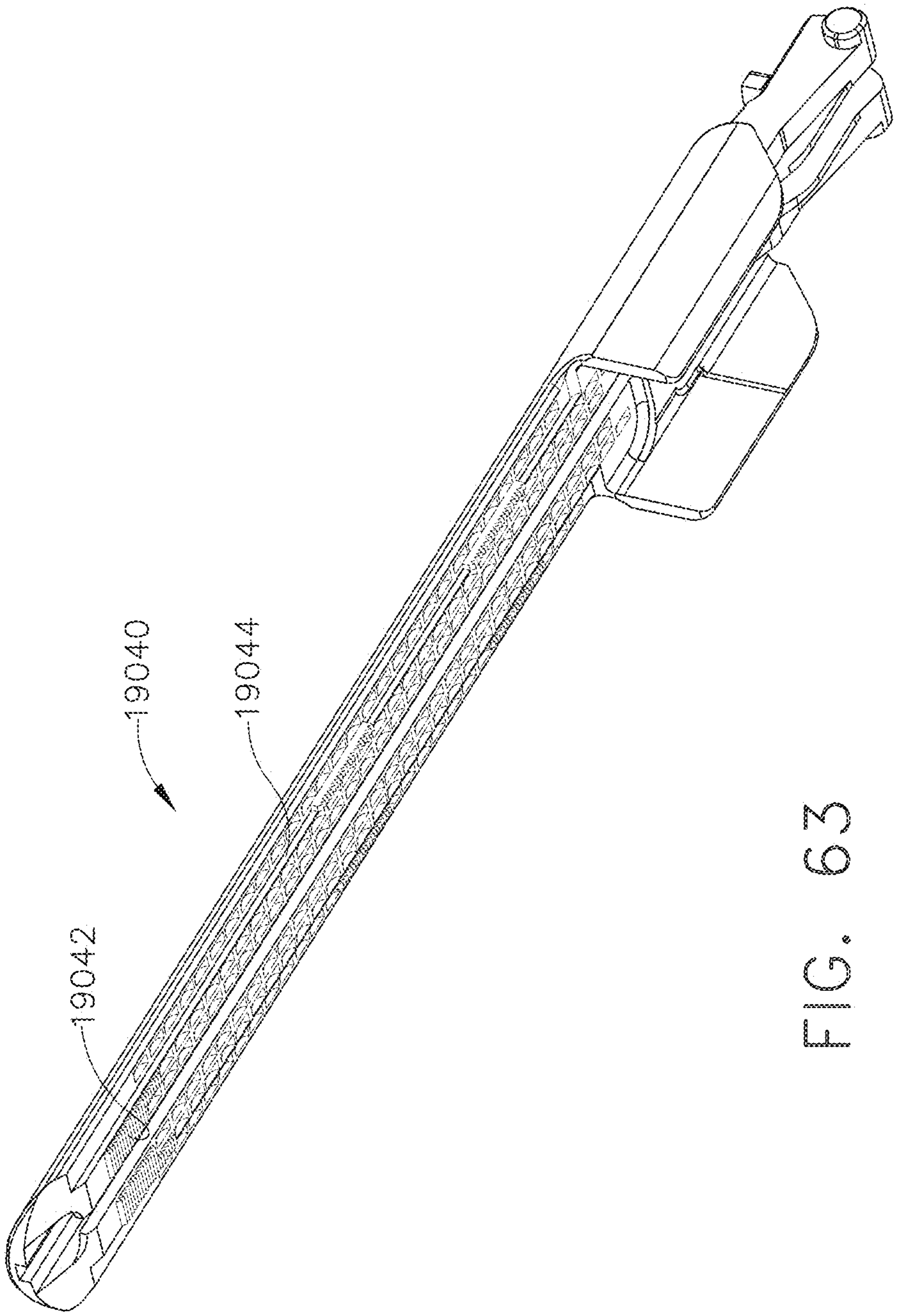
FIG. 63 is a perspective view of an anvil with which the retainer assembly of FIG. 61 may be used.

Referring to FIG. 61, the retainer 19000 may include a grip 19014 by which a person, such as a surgeon, nurse, or technician preparing surgical instruments may grasp the retainer 19000. The retainer 19000 may include a first surface 19001 on which a first tissue thickness compensator 19002 may be positioned and an opposing second surface 19003 on which a second tissue thickness compensator 19004 may be positioned. In various embodiments, one or more adhesives can be applied to the first surface 19001 and/or the second surface 19003 for attaching the first and second tissue thickness compensators 19002 and 19004 thereto. The retainer 19000 also may include clips that can engage a staple cartridge 19050 of the surgical device, for example. In at least one embodiment, referring to FIG. 64, the retainer 19000 may include distal clips 19108 configured to engage a recess 19056 at a distal end of the staple cartridge 19050 and/or proximal clips 19106 configured engage a ridge or edge 19054 on the staple cartridge 19050.

Referring to FIG. 61, in various embodiments, the first tissue thickness compensator 19002 may include a retainer-facing surface 19006 and an anvil-facing surface 19010. The retainer-facing surface 19006 can be attached to the first surface 19001 of the retainer 19000 by adhesives and/or engagement features, for example. The anvil-facing surface 19010 may include at least one adhesive thereon which can attach the first tissue thickness compensator 19002 to the anvil 19040 of the surgical device. For example, the adhesive can comprise an activatable adhesive that may adhere to a staple forming surface 19044 (FIG. 63) of the anvil 19040.

Referring to FIGS. 61 and 63-66, the anvil-facing surface 19010 of the first tissue thickness compensator may include engagement features 19020 that engage similar engagement features 19042 on the anvil 19040. Thus, in various embodiments, a first retention force can retain the first tissue thickness compensator 19002 to the retainer 19000 and a second retention force can retain the first tissue thickness compensator 19002 to the anvil 19040. In various embodiments, the second retention force can be greater than the first retention force such that the first tissue thickness compensator 19002 can remain attached to the anvil 19040 and separate from the retainer 19000 when the retainer 19000 is removed from the end effector.

Referring again to FIG. 61, the second tissue thickness compensator 19004 may include a retainer-facing surface 19008 and a staple-cartridge-facing surface 19012. The retainer-facing surface 19006 can be attached to the first surface 19001 of the retainer 19000 by one or more adhesives and/or engagement features. The staple-cartridge-facing surface 19012 may include an adhesive thereon which can attach the second tissue thickness compensator 19004 to the staple cartridge 19050 of the surgical device. For example, referring to FIG. 64, the adhesive may adhere the second tissue thickness compensator 19004 to a staple deck 19052 of the staple cartridge 19050. The staple-cartridge-facing surface 19012 also may include engagement features that engage co-operating engagement features on the staple cartridge 19050. Thus, in various embodiments, a first retention force can retain the second tissue thickness compensator 19004 to the retainer 19000 and a second retention force can retain the second tissue thickness compensator 19004 to the staple cartridge 19050. In various embodiments, the second retention force can be greater than the first retention force such that the second tissue thickness compensator 19004 can remain attached to the staple cartridge 19050 and separate from the retainer 19000 when the retainer 19000 is removed from the end effector.

Figure 64:
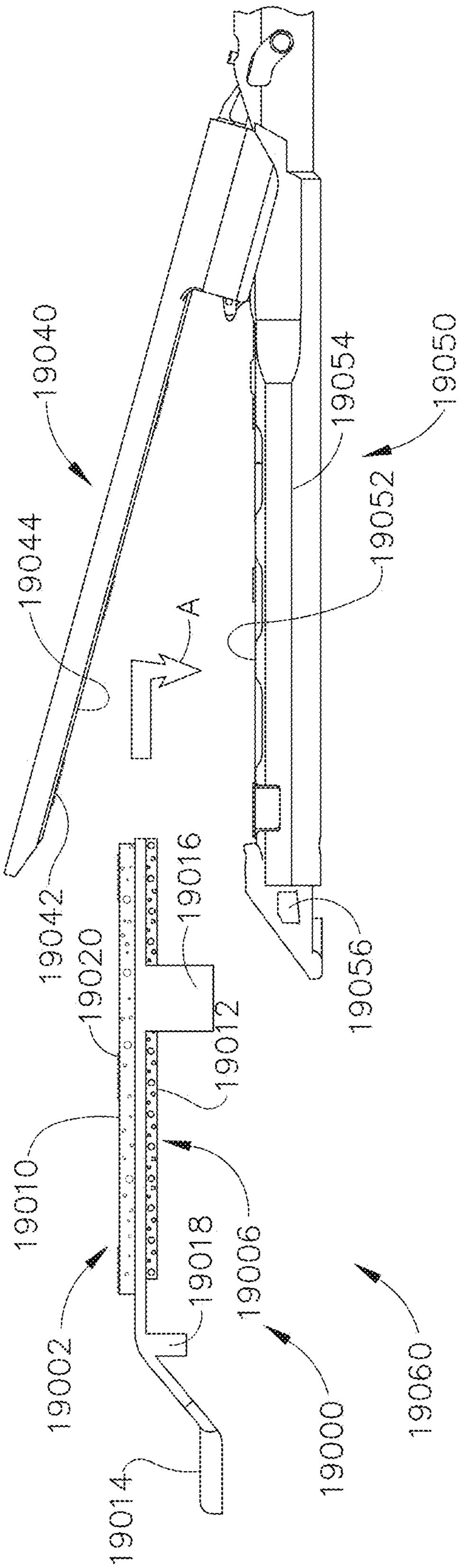
FIG. 64 is an illustration depicting the retainer assembly shown in FIG. 61 being inserted in an end effector of a surgical stapler which includes an anvil and a staple cartridge.
Figure 65:
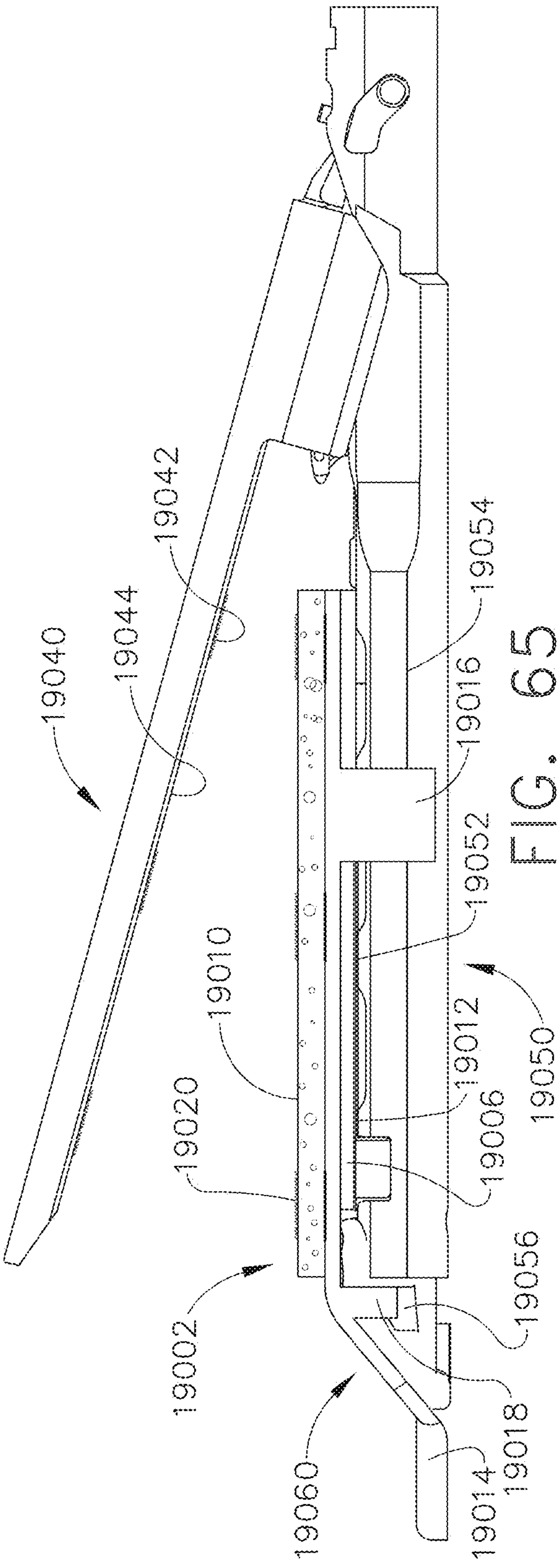
FIG. 65 is a side view of the retainer assembly shown in FIG. 61 engaged with the staple cartridge of FIG. 64.
Figure 66:
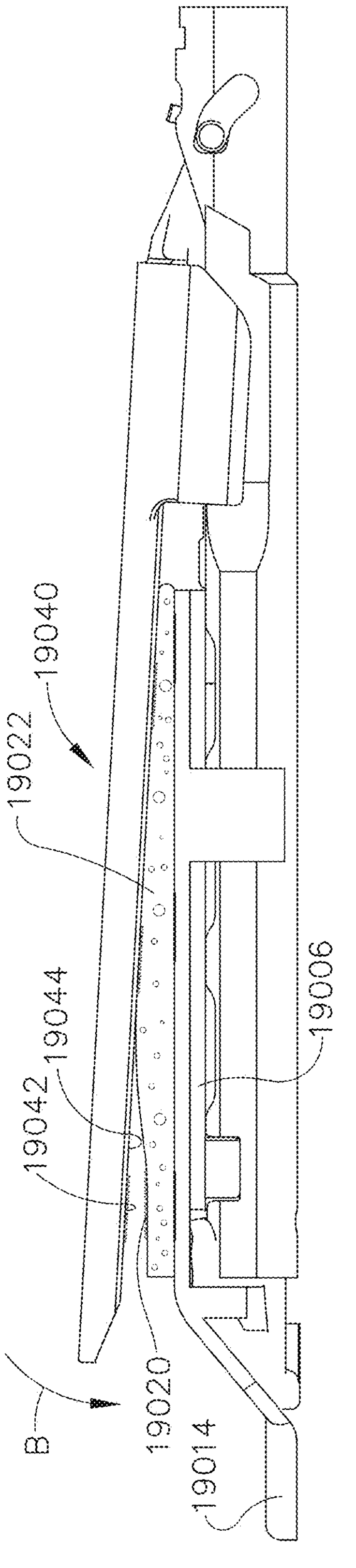
FIG. 66 is a side view of the retainer assembly shown in FIG. 61 engaged with the staple cartridge and the anvil of FIG. 64 illustrating the anvil in a closed position.

As shown in FIG. 64, the retainer assembly 19060 may be attached to a staple cartridge 19050 as indicated by arrow A. As described above, distal clips 19018 on the retainer 19000 may engage a recess 19056 in the staple cartridge and proximal clips 19016 on the retainer may engage the edge or ridge 19054 on the staple cartridge 19050. At such point, the retainer 19000 is attached to the staple cartridge 19050, as shown in FIG. 65, and the second tissue thickness compensator 19004 can be attached to the staple cartridge 19050. As shown in FIG. 66, closure of the anvil 19040 of the surgical device in the direction of arrow B may bring a surface 19044 of the anvil, such as a staple-forming surface and/or a tissue contacting surface, for example, into contact with the first tissue thickness compensator 19002. As described above, the anvil 19040 contacting the first tissue thickness compensator 19002 can cause the first tissue thickness compensator 19002 to become attached to the anvil 19040.

Figure 67:
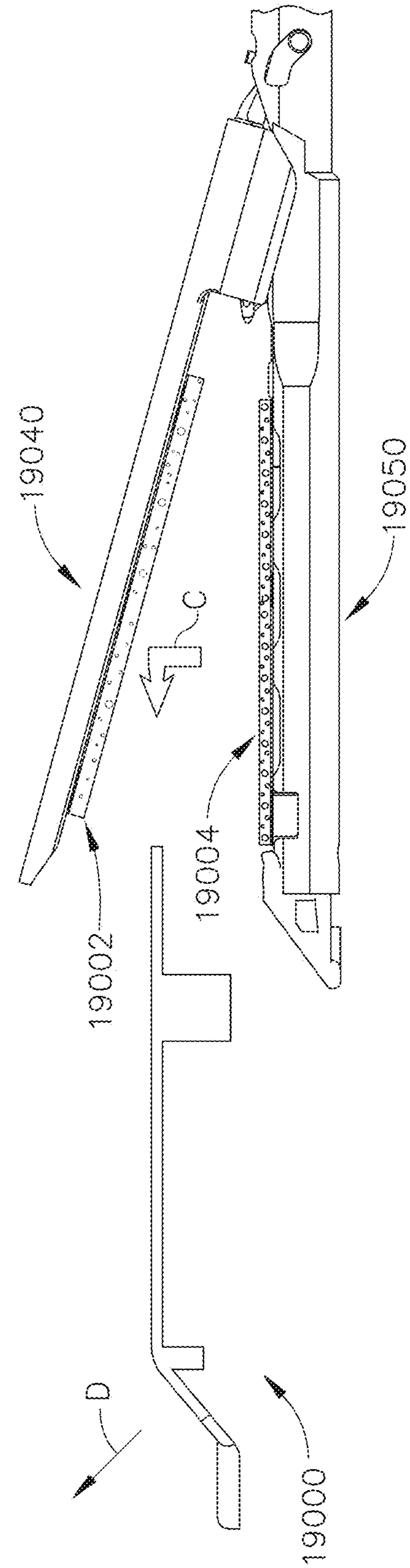
FIG. 67 is a side view of the retainer assembly of FIG. 61 being removed from the end effector of FIG. 64.

After the retainer assembly 19060 has been attached to the staple cartridge 19050 and the anvil 19040 has been closed, the first tissue thickness compensator 19002 can be attached to the anvil 19040 and the second tissue thickness compensator 19004 can be attached to the staple cartridge 19050. As described above, the retention force retaining the first tissue thickness compensator 19002 to the retainer 19000 can be less than the retention force holding the first tissue thickness compensator 19002 to the anvil 19040. Thus, when the anvil 19040 is reopened, the first tissue thickness compensator 19002 can detach from the retainer 19000 and remain with the anvil 19040, as shown in FIG. 67. As also described above, the retention force retaining the second tissue thickness compensator 19004 to the retainer 19000 can be less than the retention force holding the first tissue thickness compensator 19004 to the staple cartridge 19050. Thus, when the retainer 19000 is removed in the directions of arrows C and D in FIG. 67, the retainer 19000 can detach from the second tissue thickness compensator 19004. The surgical stapler shown in FIG. 67 includes the first tissue thickness compensator 19002 attached to the anvil 19040 and the second tissue thickness compensator 19004 attached to the staple cartridge 19050 and is ready for use.

FIGS. 390-396 show the retainer 19000 being used with a first tissue thickness compensator 19002 and a second tissue thickness compensator 19004. In various embodiments, the retainer 19000 may also be used with only one of the first tissue thickness compensator 19002 and the second tissue thickness compensator 19004. For example, the first tissue thickness compensator 19002 may be omitted.

Figure 68:
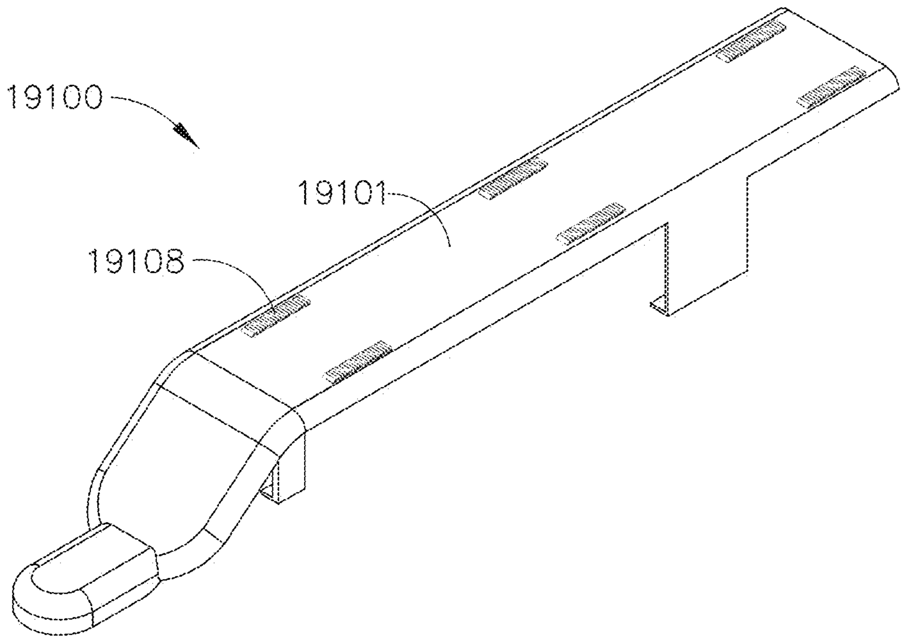
FIG. 68 is a perspective view of a retainer.
Figure 69:
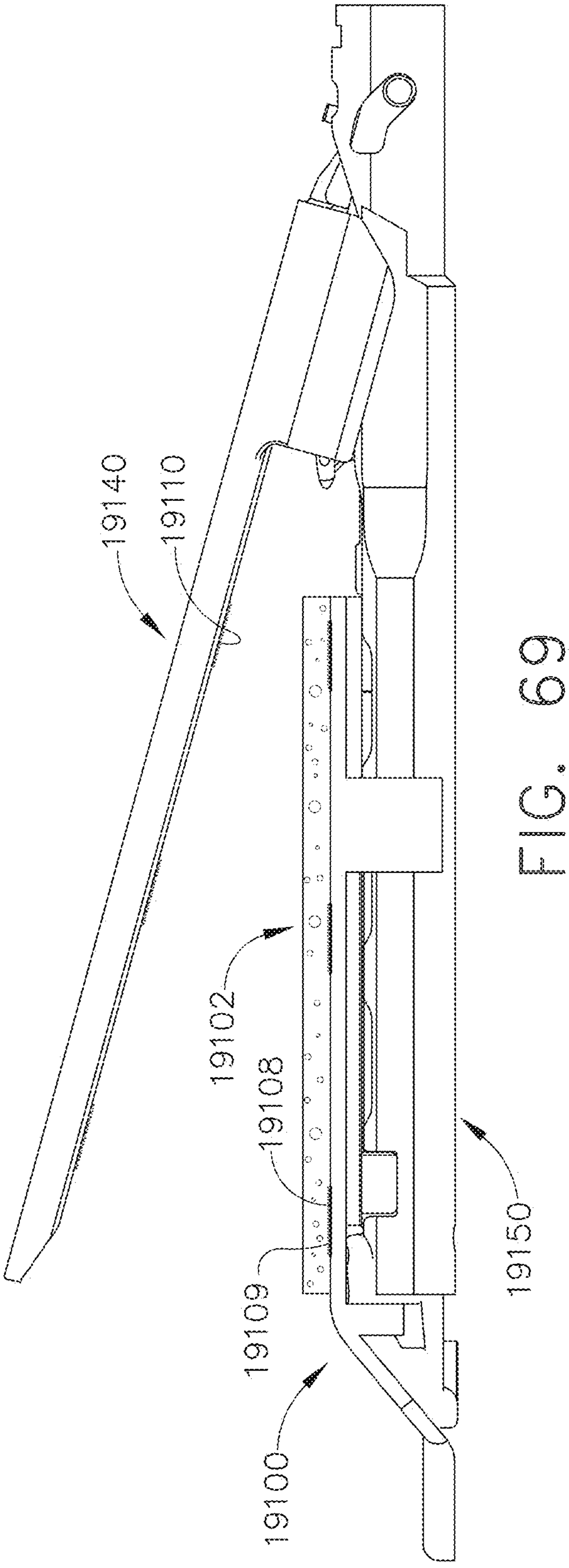
FIG. 69 is a side view of the retainer of FIG. 68 with tissue thickness compensators attached to bottom and top surfaces thereof illustrating one of the tissue thickness compensators engaged with a staple cartridge in a surgical stapler comprising an anvil.
Figure 70:
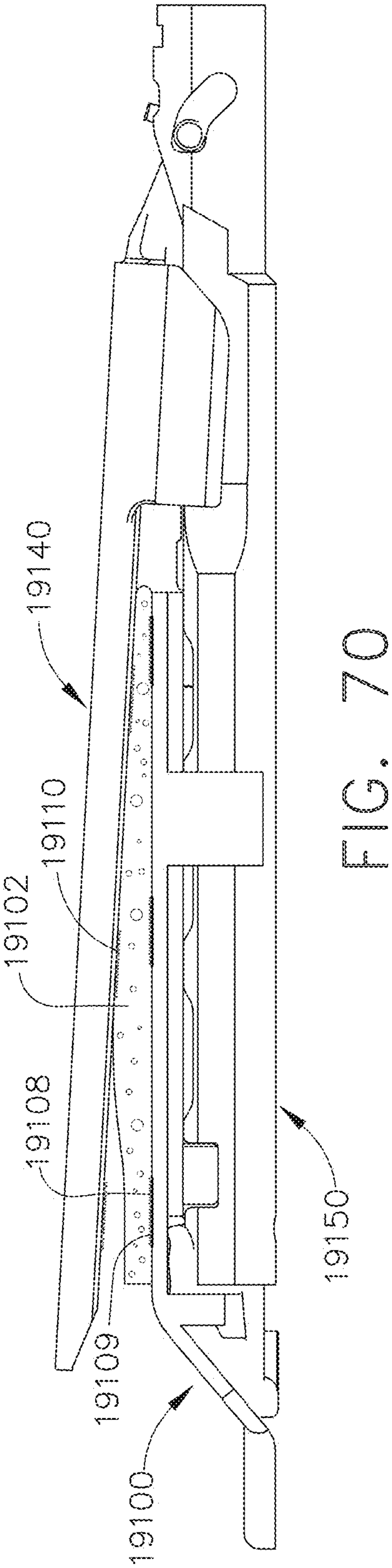
FIG. 70 is a side view illustrating the anvil of FIG. 69 in a closed position.

FIGS. 68-70 show an embodiment of a retainer 19100 that can include engagement features 19108 on a surface 19101. As shown in FIGS. 69 and 70, the engagement features 19108 on the retainer 19100 engage co-operating engagement features 19109 on a first tissue thickness compensator 19102.

Figure 71:
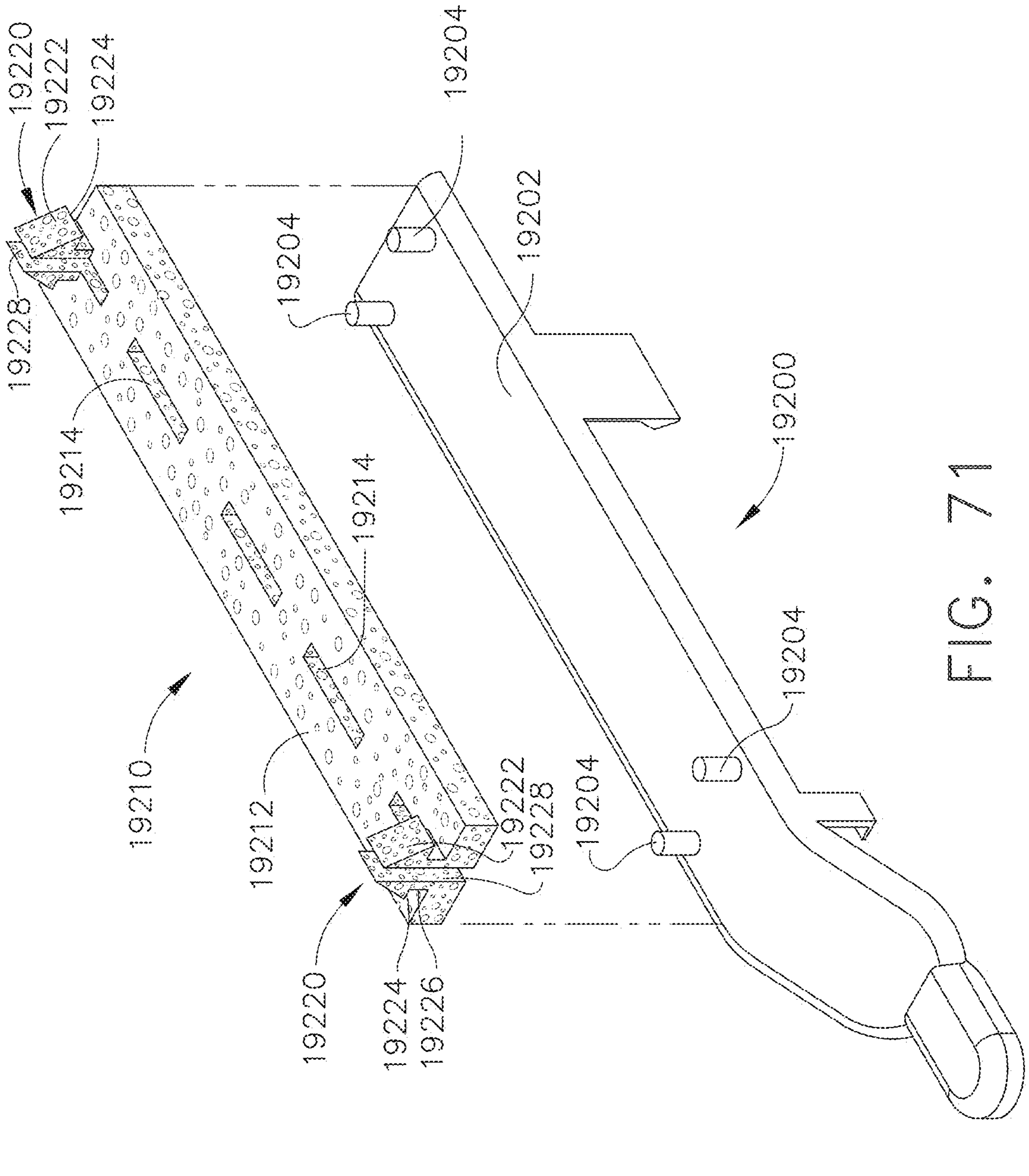
FIG. 71 is an exploded perspective view of a retainer and a tissue thickness compensator in accordance with at least one embodiment.
Figure 72:
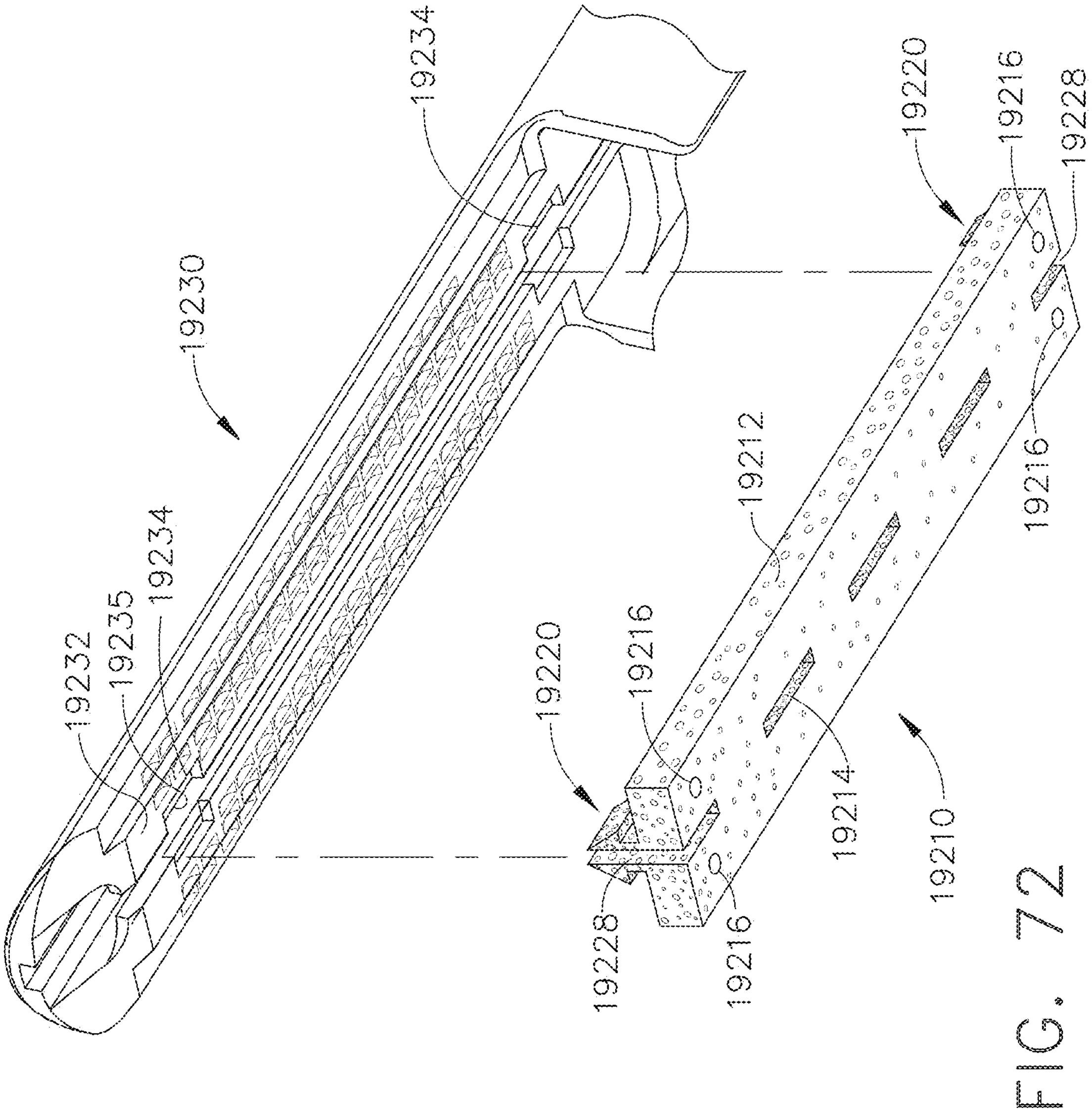
FIG. 72 is an exploded perspective view of the tissue thickness compensator of FIG. 71 and an anvil of a surgical stapler.
Figure 73:
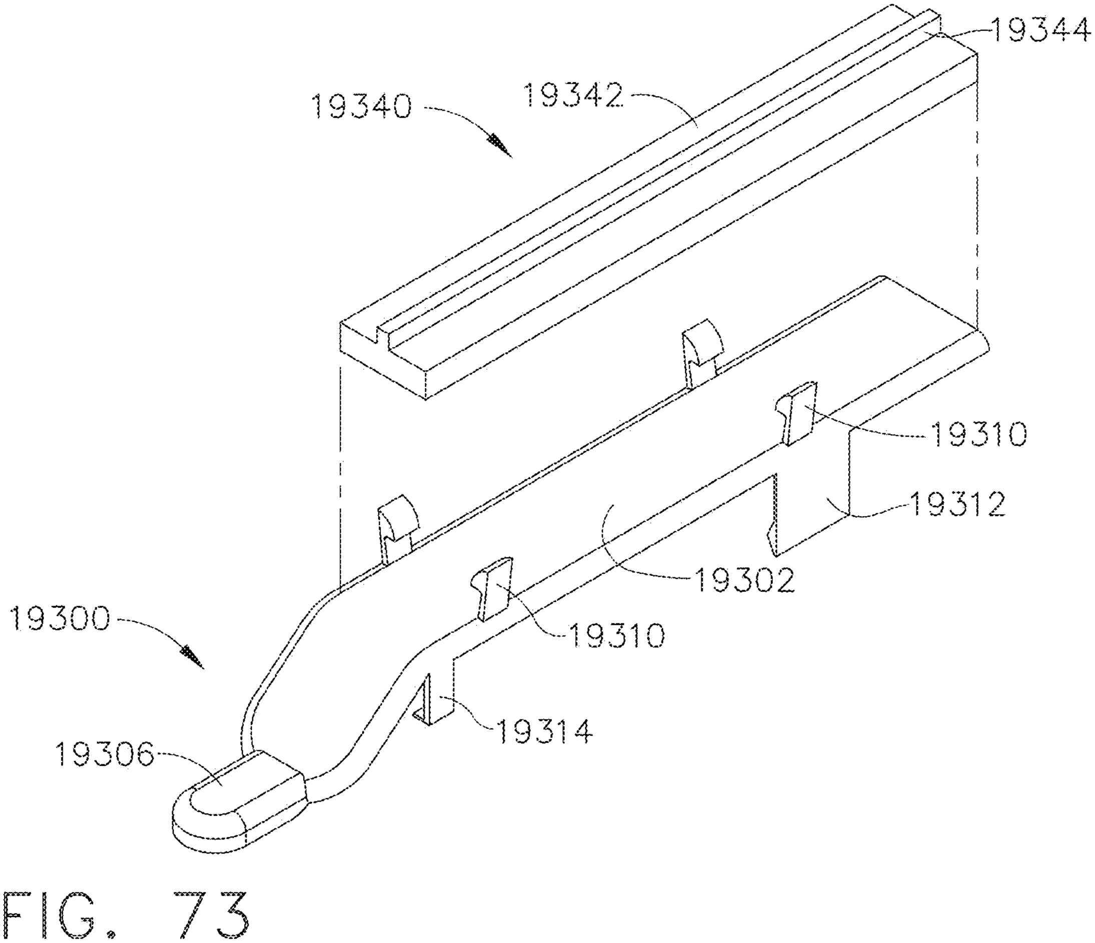
FIG. 73 is an exploded top perspective view of a retainer and a tissue thickness compensator in accordance with at least one embodiment.
Figure 74:
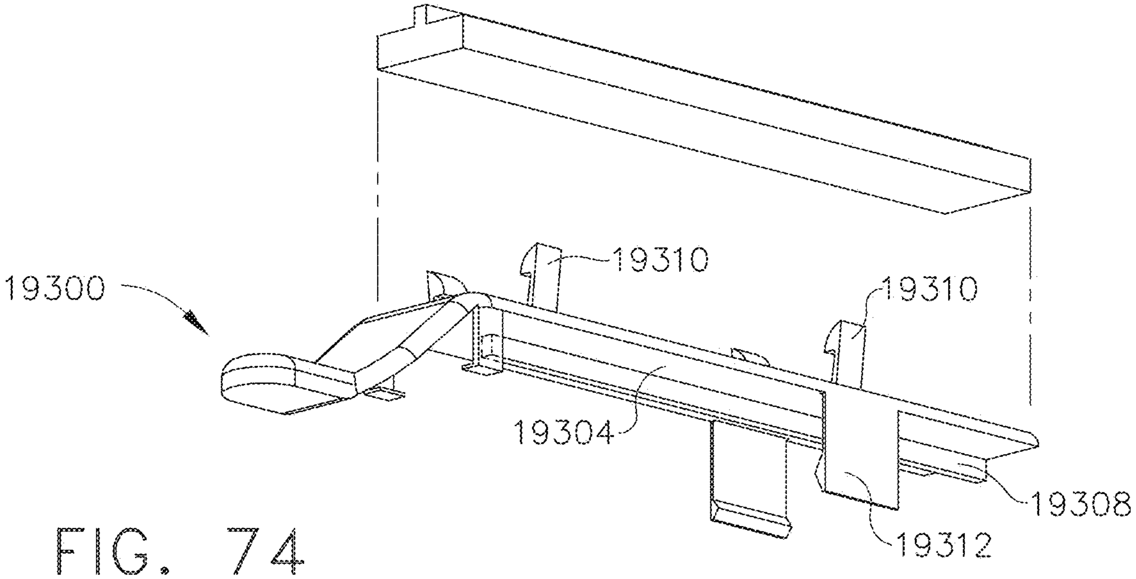
FIG. 74 is an exploded bottom perspective view of the retainer and tissue thickness compensator of FIG. 73.

FIGS. 71 and 72 show an embodiment of a retainer 19200 that may include a surface 19202 configured to align and attach a tissue thickness compensator 19210 to an anvil 19230. The retainer 19200 may include alignment pegs 19204 extending from the surface 19202. The retainer 19200 shown in FIGS. 71 and 72 includes four alignment pegs 19204, but more or fewer alignment pegs 19204 may be present. Referring to FIG. 72, the tissue thickness compensator 19210 can include a body 19212 that includes holes 19216 that can be located such that they that correspond to the locations of the alignment pegs 19204 extending from the retainer 19200. Each hole 19216 in the tissue thickness compensator 19210 fits over an alignment peg 19204, and owing to a close fit between the holes 19216 and the pegs 19204, the tissue thickness compensator 19210 can be aligned with the retainer 19200. In various embodiments, each hole 19216 may be slightly smaller than its corresponding peg 19204 such that each hole 19216 stretches when placed on its peg 19204. Such stretching can hold the holes 19216 on the pegs 19204. In certain embodiments, each hole 19216 may include an adhesive therein to create a releasable bond between the pegs 19204 and the tissue thickness compensator 19210.

The tissue thickness compensator 19220 may include tabs 19220 extending from a body 19212 of the tissue thickness compensator 19220 which can be configured to be received by slots 19234 in an anvil 19230. In various embodiments, the slots 19234 in the anvil 19230 may be located in a staple forming surface 19232, for example. After the retainer 19200 has been attached to a staple cartridge, similar to the embodiments described above, the anvil 19230 can be closed against the tissue thickness compensator 19210 on the retainer 19200. As the anvil 19230 is closed, referring to FIG. 72, the tabs 19220 on the tissue thickness compensator 19210 can engage the slots 19234, thereby attaching the tissue thickness compensator 19210 to the anvil 19230. Referring primarily to FIG. 71, each tab 19220 may include a tapered portion 19222 that guides the tab 19220 into the slots 19234 of the anvil 19230. The tapered portion 19222 can include sloped walls and may increase in cross-sectional area along the length thereof. A base portion 19226 of each tab 19220 may have a smaller cross-sectional area than the largest cross-sectional area of the tapered portion 19222. In various embodiments, the tapered portion 19222 may comprise a lock surface 19224 wherein, when a tab 19220 enters a slot 19234, the lock surface 19224 can catch on a lip 19235 in the slot 19234. As a result, the lock surface 19224 can hold the tab 19220 within the slot 19234 and thereby hold the tissue thickness compensator 19210 to the anvil 19230. Slots 19228 defined in the tissue thickness compensator 19210 and extending between the tabs 19220 can enable the tabs 19220 to flex inwardly and fit within the slots 19234. In various embodiments, the tabs 19220 being held with the slots 19234 can define a first retention force that retains the tissue thickness compensator 19210 to the anvil 19230 and the holes 19216 in the tissue thickness compensator 19210 being held on the pegs 19204 can define a second retention force. In various embodiments, the first retention force can be greater than the second retention force such that the tissue thickness compensator 19210 can remain attached to the anvil 19230 and separate from the retainer 19200 when the retainer 19200 is removed from the end effector.

The body 19212 of the tissue thickness compensator 19210 in FIGS. 71 and 72 also may define slots 19214 therewithin. The slots 19214 may be aligned along a longitudinal axis of the tissue thickness compensator 19210. For example, the slots 19214 may be arranged on a longitudinal axis such that the slots 19214 are aligned with a longitudinal path of a cutting blade of the surgical device when the tissue thickness compensator 19210 is attached to an anvil 19230. The slots 19214 may reduce the amount of energy required by the cutting blade to cut through the tissue thickness compensator 19210.

FIGS. 73-83 show an embodiment of a retainer 19300 that includes clips 19310 which are configured to retain a tissue thickness compensator 19340 on a first surface 19302 of the retainer 19300. When an anvil 19360 is closed on the retainer 19300, similar to the above, the anvil 19360 can push and displace the clips 19310 outwardly and, as a result, disengage the retainer 19300 from the tissue thickness compensator 19340. In various embodiments, the tissue thickness compensator 19340 can attach to the anvil 19360 when the anvil 19360 is pressed against the tissue thickness compensator 19340 and moved away from the retainer 19300 when the anvil 19360 is reopened.

The retainer 19300 may include staple cartridge mounting clips 19312 and 19314 which can be similar to those described above with respect to FIGS. 61-70. In addition to the first surface 19302 described above, the retainer 19300 also may include a second surface 19304 that may be configured to carry a second tissue thickness compensator. In various embodiments, the second surface 19304 may include an alignment feature, such as, for example, a raised ridge 19308. The raised ridge 19308 may engage a slot in a second tissue thickness compensator and/or a slot in a staple cartridge 19370, for example.

Figure 75:
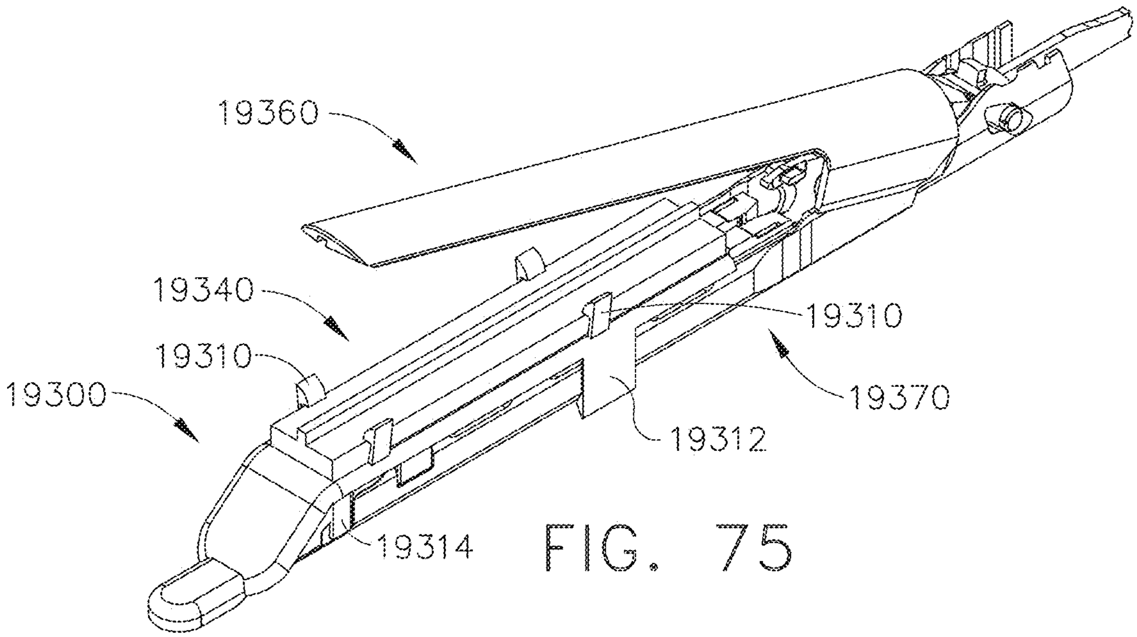
FIG. 75 is a top perspective view of the retainer and tissue thickness compensator of FIG. 73 engaged with a surgical stapler.
Figure 76:
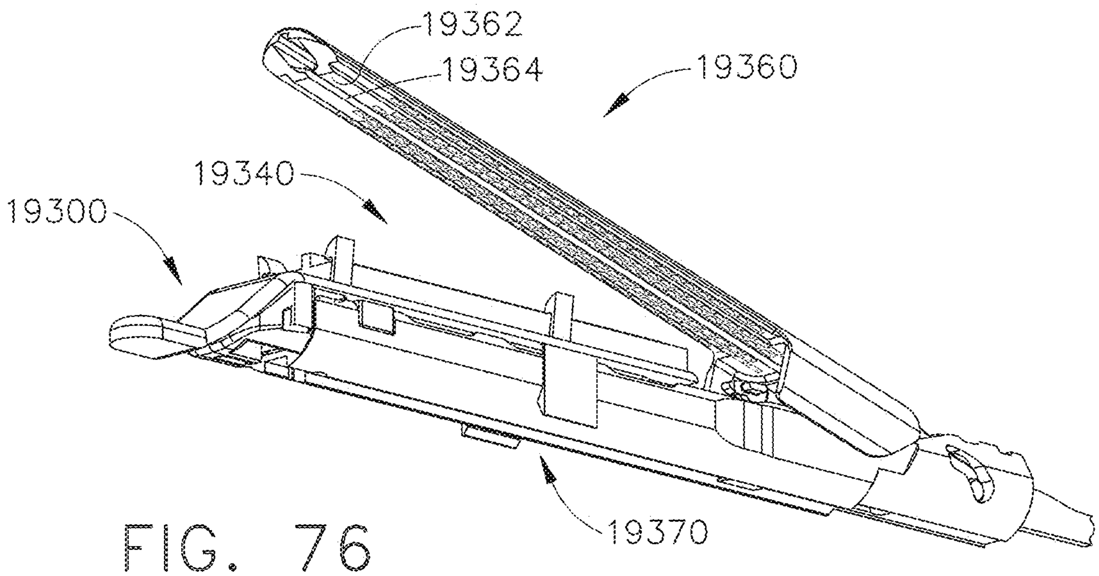
FIG. 76 is a bottom perspective view of the retainer and tissue thickness compensator of FIG. 73 engaged with the surgical stapler of FIG. 75.
Figure 77:
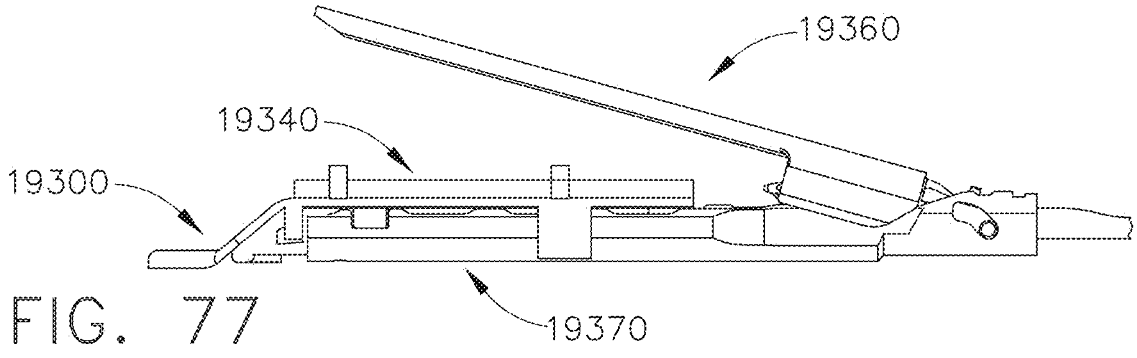
FIG. 77 is a side view of the retainer and tissue thickness compensator of FIG. 73 engaged with the surgical stapler of FIG. 75.
Figure 78:
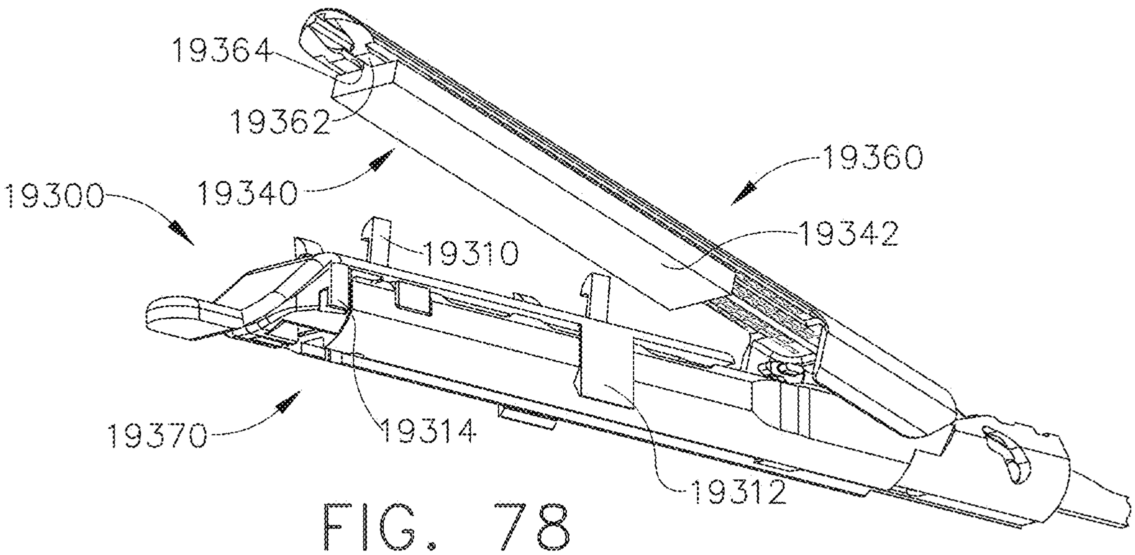
FIG. 78 is a bottom perspective view of the retainer and tissue thickness compensator of FIG. 73 illustrating the tissue thickness compensator attached to the anvil of the surgical stapler of FIG. 75.
Figure 79:
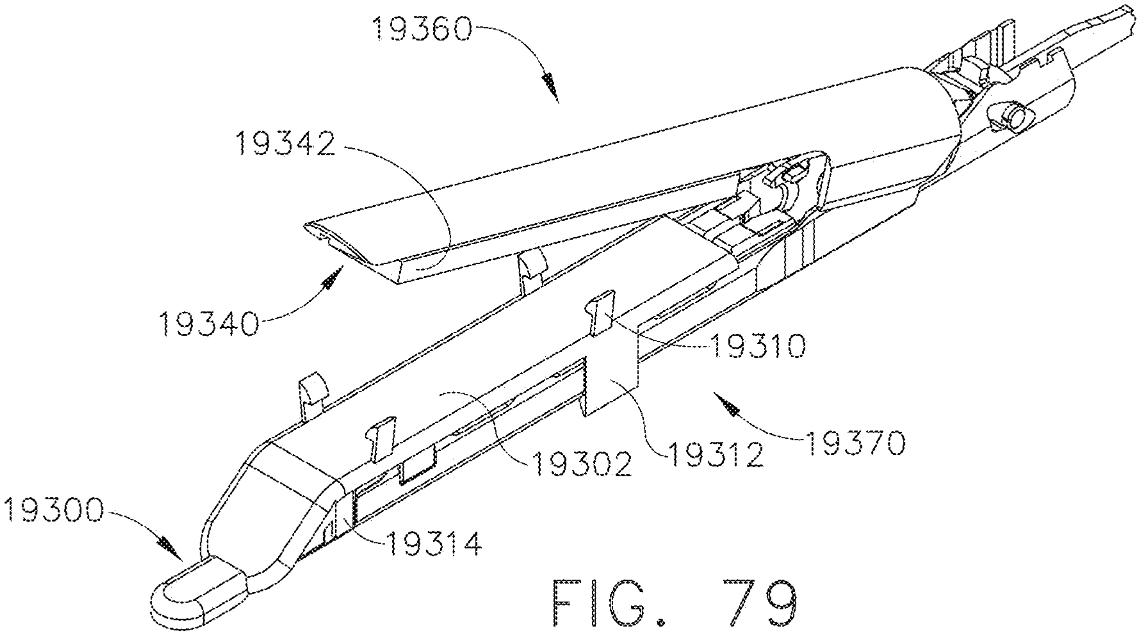
FIG. 79 is a top perspective view of the retainer and tissue thickness compensator of FIG. 73 illustrating the tissue thickness compensator attached to the anvil of FIG. 78.
Figure 80:
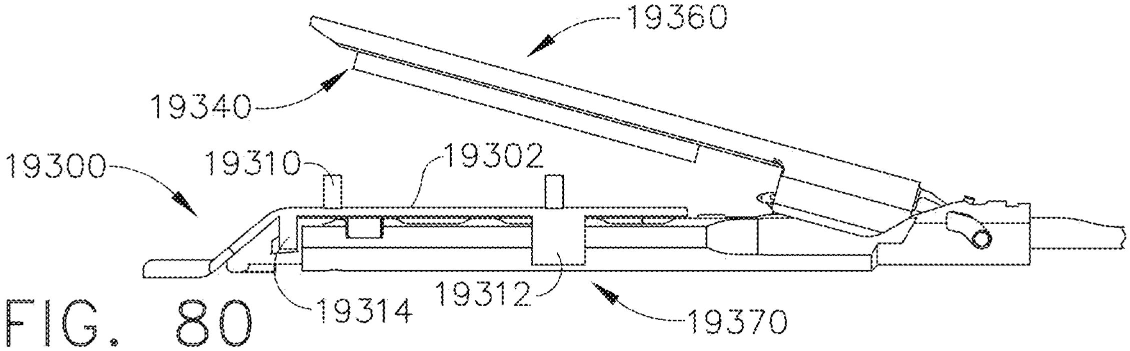
FIG. 80 is a side view of the tissue thickness compensator of FIG. 73 attached to the anvil of FIG. 78.
Figure 81:
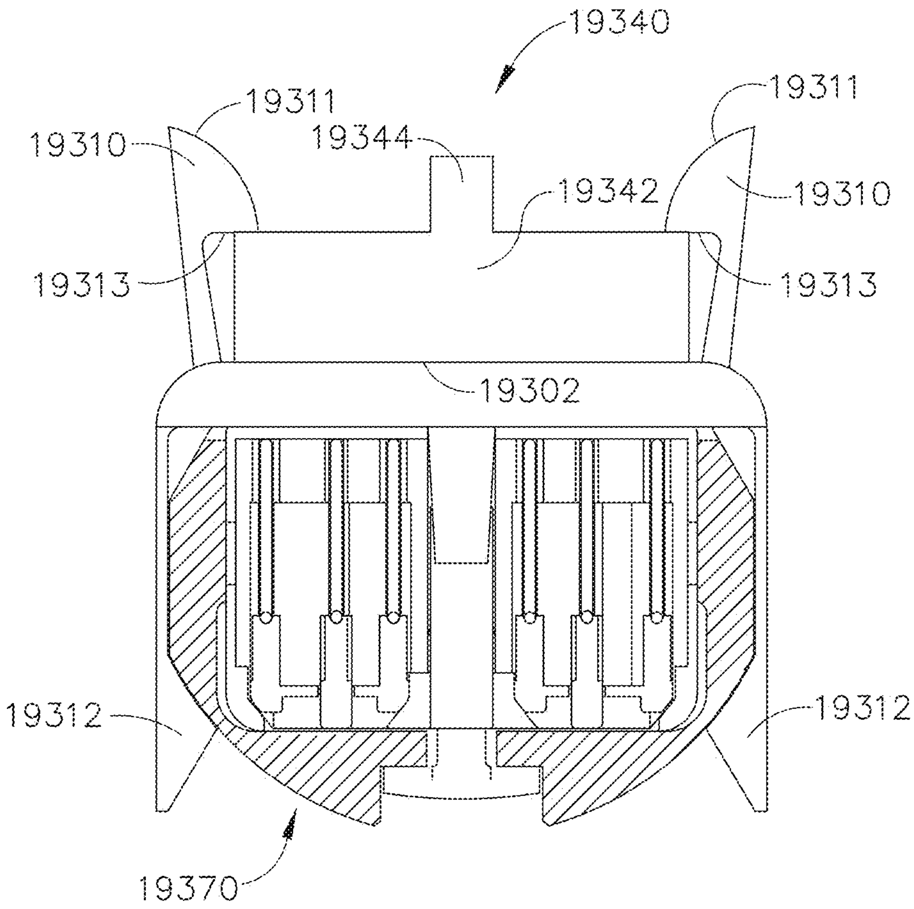
FIG. 81 is a cross-sectional view of the retainer and tissue thickness compensator of FIGS. 73 and 74 attached to a staple cartridge and channel of a surgical stapler.
Figure 82:
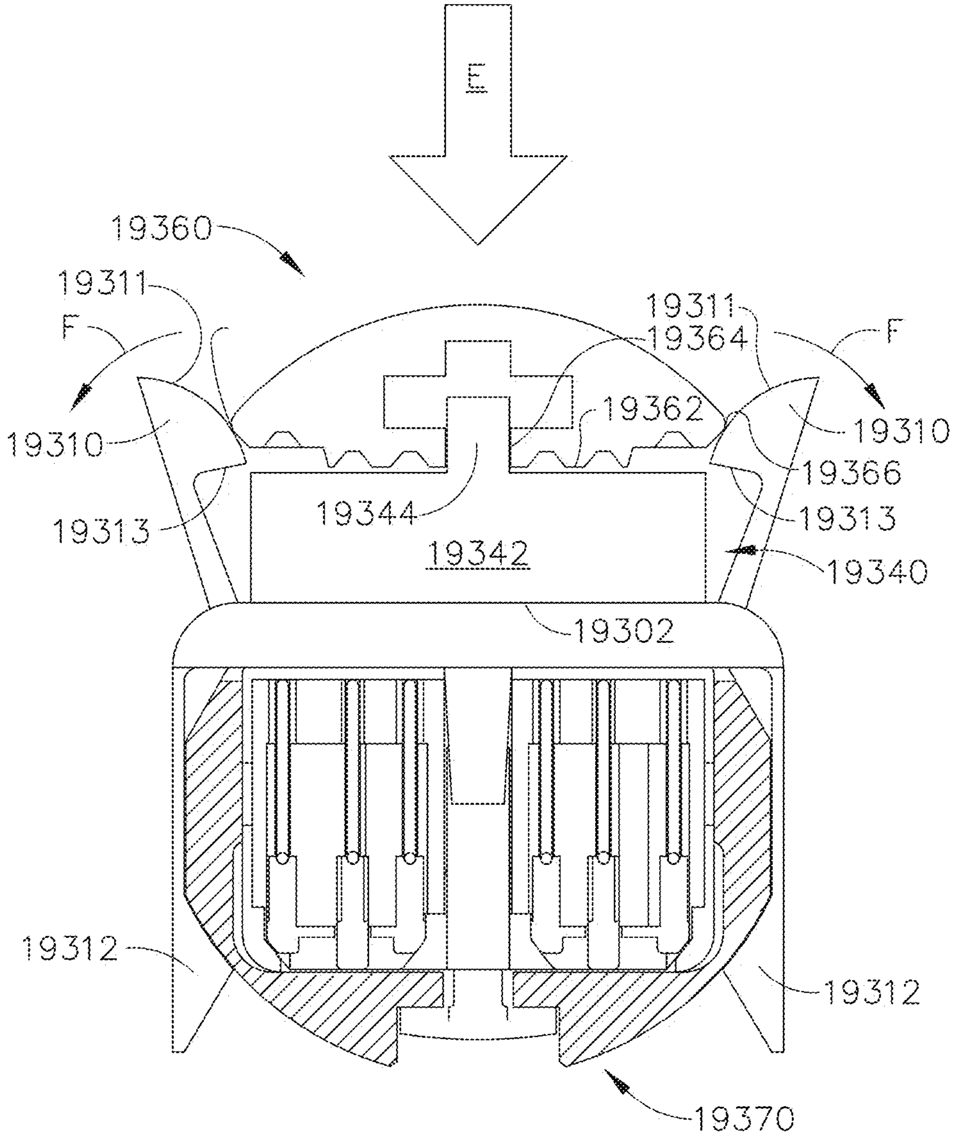
FIG. 82 is a cross-sectional view of the retainer and tissue thickness compensator of FIGS. 73 and 74 attached to the staple cartridge and channel of the surgical stapler of FIG. 81 illustrating an anvil of the surgical stapler engaged with the tissue thickness compensator.
Figure 83:
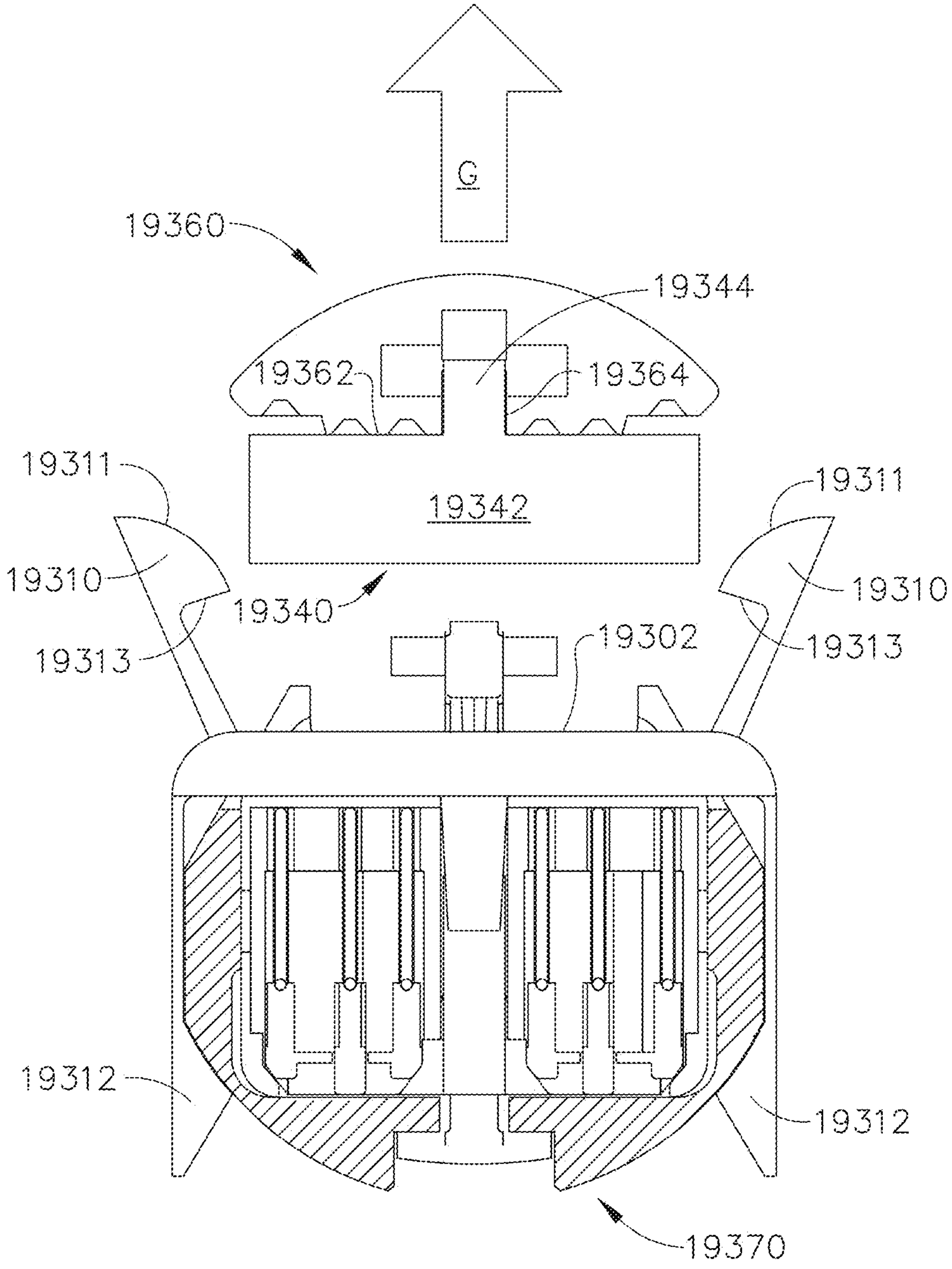
FIG. 83 is a cross-sectional view of the tissue thickness compensator of FIG. 73 attached to the anvil of the surgical stapler and being moved away from the retainer.

Referring to FIGS. 75-77, in use, the retainer 19300 may be attached to a staple cartridge 19370 by clips 19314 and 19312. The first tissue thickness compensator 19340 can be positioned on the first surface 19302 at the retainer 19300 and can be held in place by clips 19310. Referring primarily to FIGS. 81-83, each clip includes a flat 19313 that can clamp the first tissue thickness compensator 19340 against the first surface 19302 of the retainer 19300. Each clip 19310 can include an inward-facing tapered or curved surface 19311. As the anvil 19360 moves in the direction of arrow E, referring to FIG. 82, edges 19366 of the anvil 19360 can contact the inward-facing curved surfaces 19311 of the clips 19310. As the anvil 19360 continues to move in the direction of arrow E, interference between the edges 19366 of the anvil 19360 and the curved surfaces 19311 of the clips 19310 can push the clips 19310 outwardly in the direction of arrow F, as illustrated in FIG. 82. As the clips 19310 move in the direction of arrow F, the first tissue thickness compensator 19340 is freed from the flats 19313 of the clips 19310.

As the anvil 19360 continues to move in the direction of arrow E, it also contacts and attaches to the tissue thickness compensator 19340. For example, as the anvil 19360 moves in the direction of arrow E, an engagement feature, such as, for example, a raised ridge 19344, on the tissue thickness compensator 19340 engages a channel 19364 in the anvil 19360. The raised ridge 19344 may be configured to have an interference fit with the channel 19364 such that the tissue thickness compensator 19340 becomes attached to the anvil 19360. The tissue thickness compensator 19340 may include an adhesive that adheres to surfaces of the anvil 19360. In at least one embodiment, the raised ridge 19344 may include an adhesive that adheres to surfaces of the channel 19364. Likewise, surfaces of the body 19342 of the tissue thickness compensator 19340 may include an adhesive that adheres to a surface 19362 of the anvil 19360. After the tissue thickness compensator 19340 is attached to the anvil 19360, the tissue thickness compensator 19340 can lift from the retainer 19300 and remain with the anvil 19360 as the anvil 19360 returns to its open position by moving in the direction of arrow G, as illustrated in FIG. 83.

Figure 84:
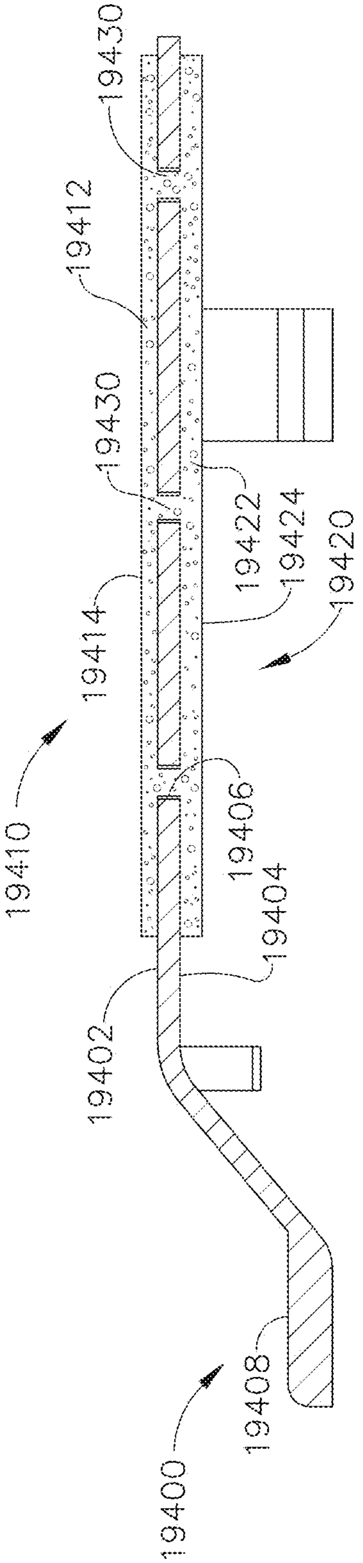
FIG. 84 is a side cross-sectional view of a retainer assembly comprising a retainer, tissue thickness compensators mounted on first and second surfaces of the retainer, and connectors passing through holes in the retainer in accordance with at least one embodiment.
Figure 85:
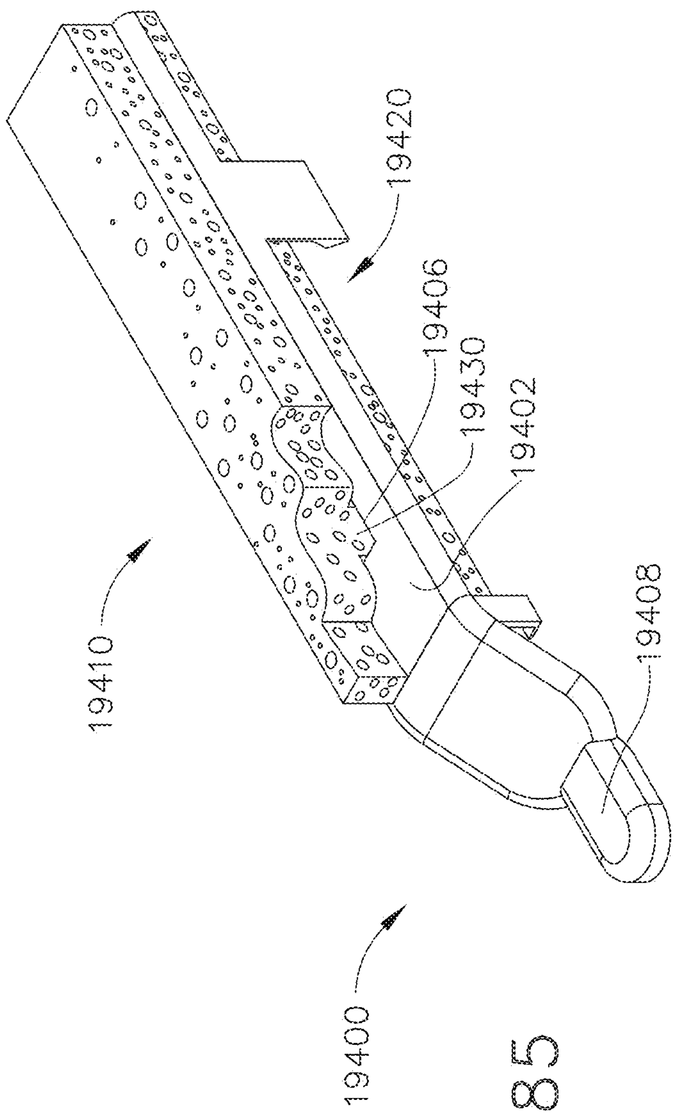
FIG. 85 is a perspective view of the retainer assembly of FIG. 84 illustrated with a portion of a tissue thickness compensator removed for the purposes of illustration.

FIG. 84 shows a cross-sectional side view of an embodiment of a retainer 19400. A first tissue thickness compensator 19410 is positioned on a first side 19402 of the retainer 19400 and a second tissue thickness compensator 19420 is positioned on an opposing second side 19404 of the retainer 19400. The retainer 19400 defines one or more holes 19406 extending therethrough. The first tissue thickness compensator 19410 and the second tissue thickness compensator 19420 are connected through the holes by connectors 19430 which extend through the holes 19406. In various embodiments, the first tissue thickness compensator 19410, the second tissue thickness compensator 19420, and the connectors 19430 all may be formed of a unitary material. For example, the first tissue thickness compensator 19410, the second tissue thickness compensator 19420, and the connectors 19430 may be overmolded onto the retainer 19400. In various other embodiments, the connectors 19430 may be formed as part of one of the tissue thickness compensators, such as, for example, the first tissue thickness compensator 19410. The connectors 19430 may be passed through the holes 19406 and then attached to the remaining tissue thickness compensator, such as, for example, the second tissue thickness compensator 19420. The connectors 19430 may be attached to the second tissue thickness compensator 19420, for example, by using an adhesive or by using an interference fit between an end of the connector and a receiving port (not shown) in the second tissue thickness compensator 19420. In various embodiments, the connectors 19430 may be separate components that are placed into the holes 19406 and to which the first tissue thickness compensator 19410 and the second tissue thickness compensator 19410 may be attached, for example, by using adhesives or interference fits between ends of the connectors 19430 and receiving ports in the first tissue thickness compensator 19410 and the second tissue thickness compensator 19420.

Figures 86, 87, 88:
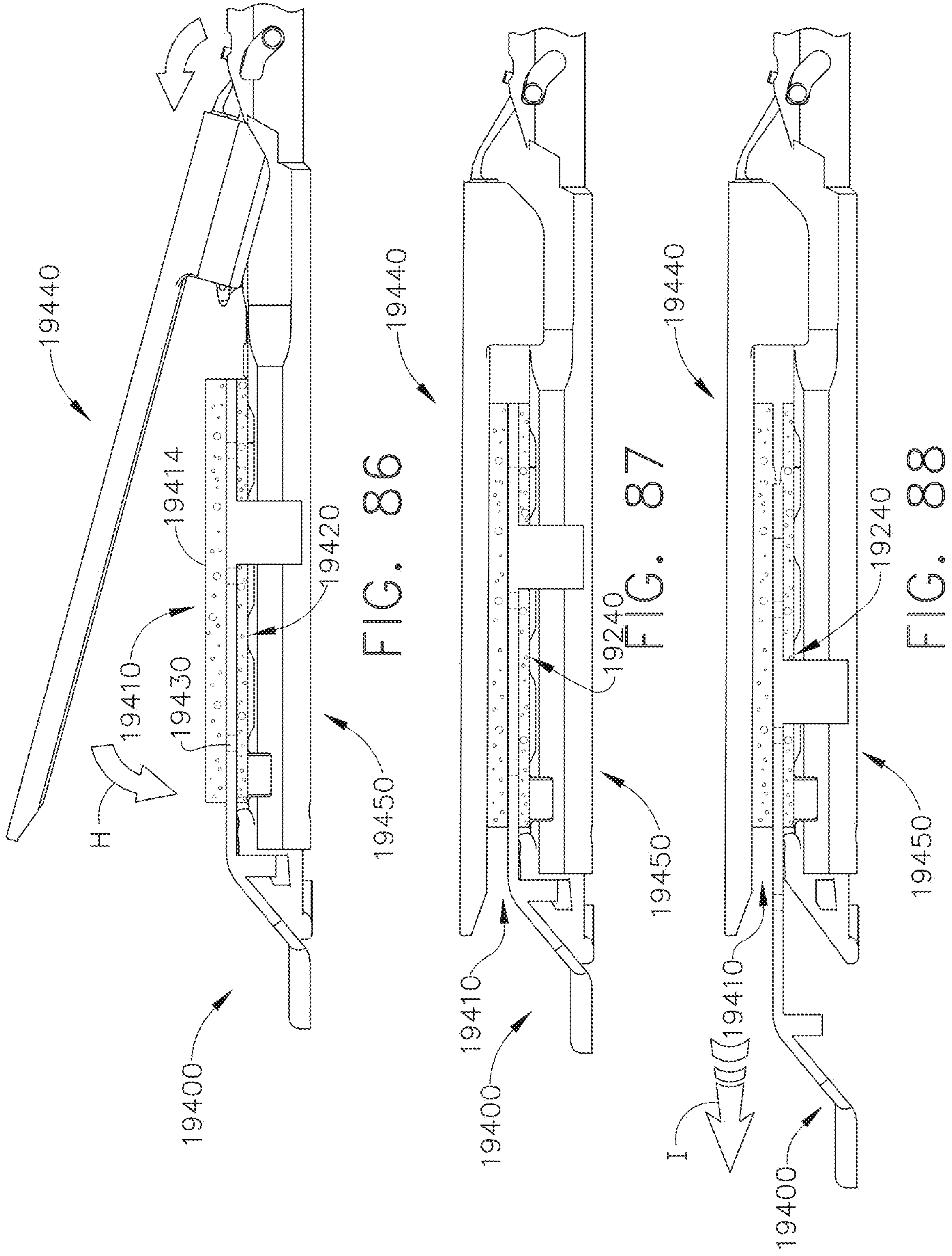
FIG. 86 is a side view of the retainer assembly of FIG. 84 engaged with a surgical stapler comprising an anvil illustrated in an open position.
FIG. 87 is a side view of the retainer assembly of FIG. 84 and the anvil of FIG. 86 illustrated in a closed position.
FIG. 88 is a side view of the retainer assembly of FIG. 84 illustrating the retainer being removed from between the tissue thickness compensators of the retainer assembly.
Figure 89:
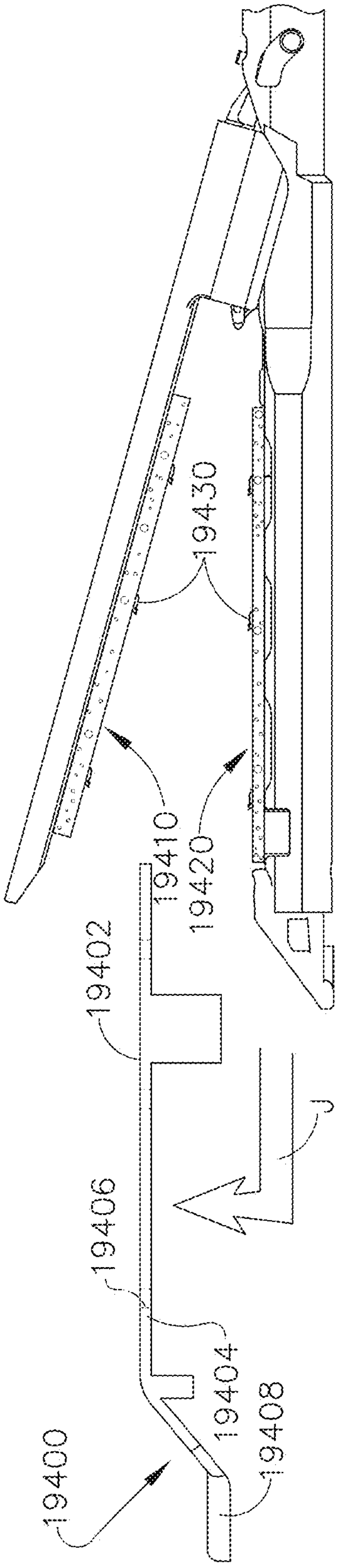
FIG. 89 is a side view of the retainer removed from the tissue thickness compensators of FIG. 84.
Figure 90:
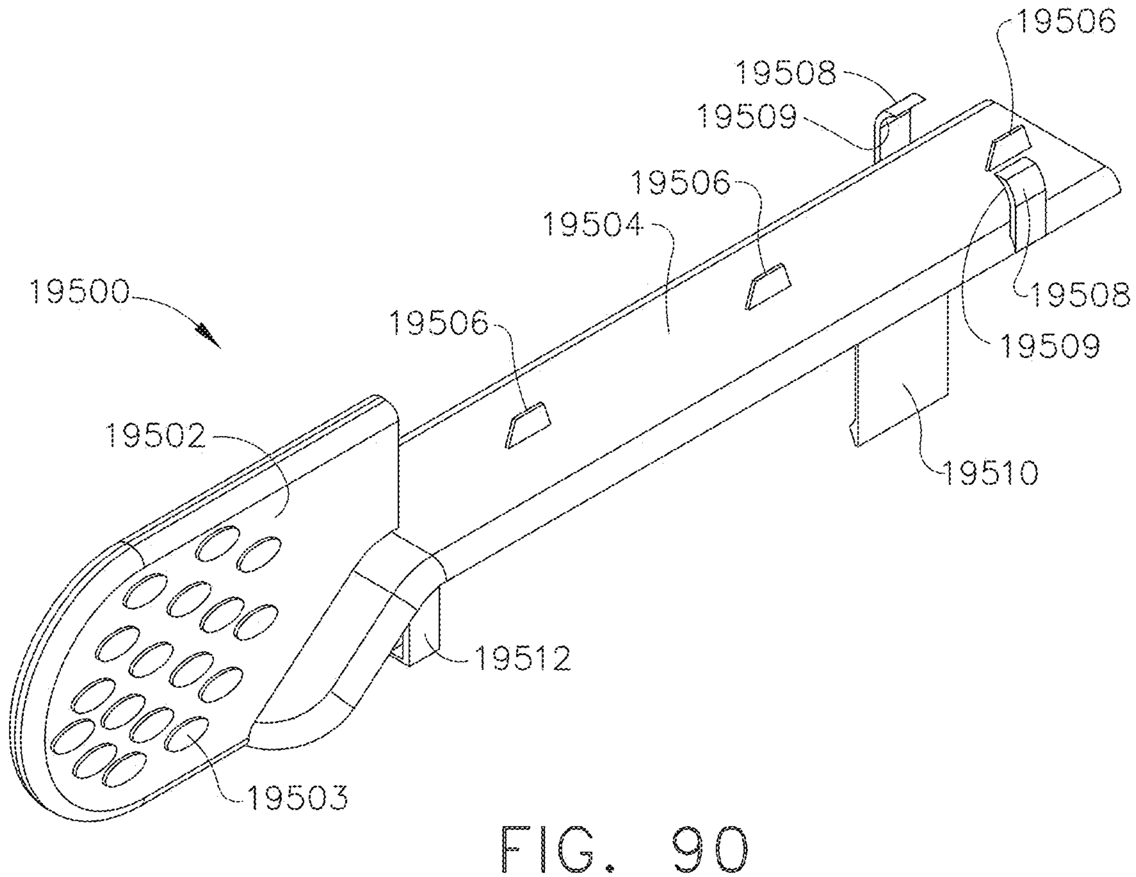
FIG. 90 is a perspective view of a retainer configured to engage an anvil of a surgical stapler in accordance with at least one embodiment.
Figure 91:
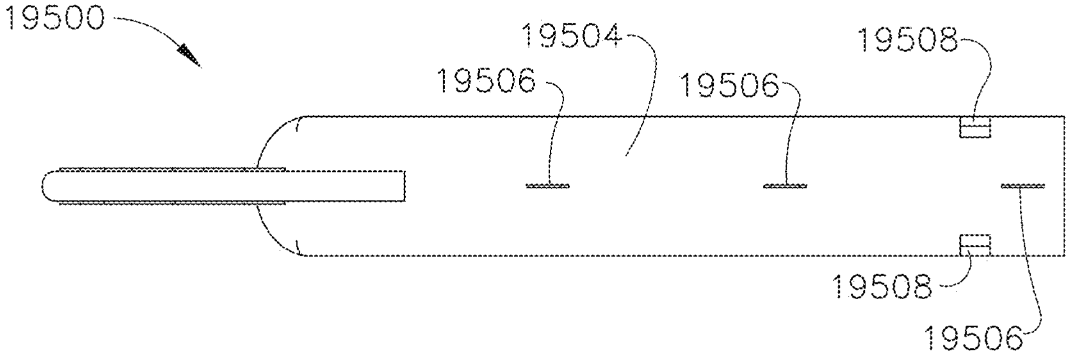
FIG. 91 is a top view of the retainer of FIG. 90.
Figure 92:
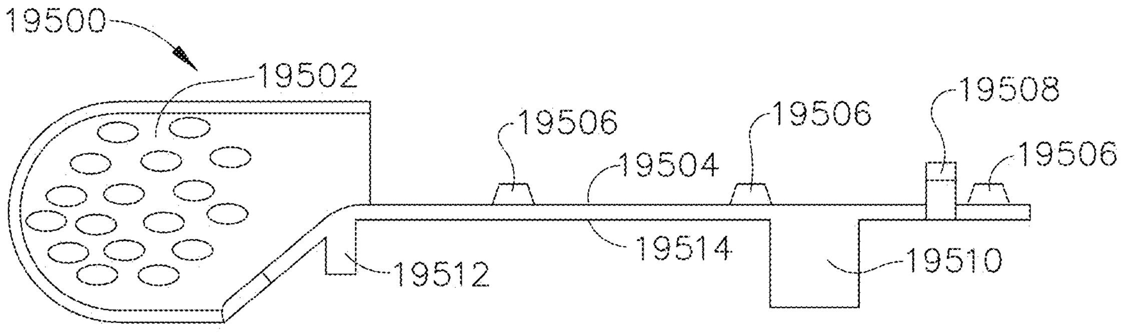
FIG. 92 is a side view of the retainer of FIG. 90.
Figure 93:
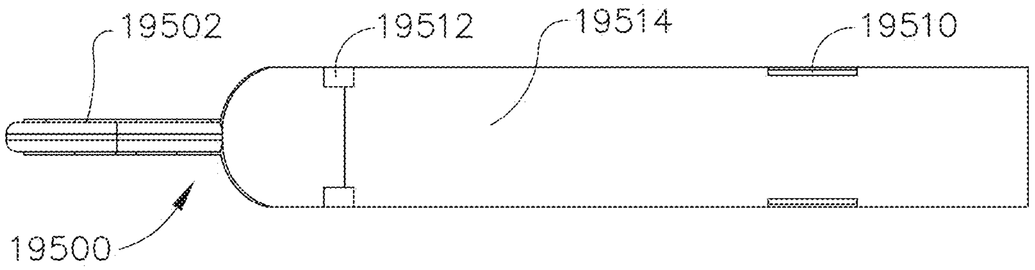
FIG. 93 is a bottom view of the retainer of FIG. 90.

After the retainer 19400 has been placed on a staple cartridge 19450, for example, an anvil 19440 of the surgical device can be moved in the direction of arrow H into a closed position. An adhesive and/or engagement features on a surface 19414 of the first tissue thickness compensator 19410 can attach the first tissue thickness compensator 19410 to the anvil 19440 when the anvil 19440 closes. Likewise, an adhesive and/or engagement features on a surface 19424 of the second tissue thickness compensator 19420 can attach the second tissue thickness compensator 19420 to the staple cartridge 19450. After the anvil 19440 is closed and the first and second tissue thickness compensators 19410 and 19420 are attached to the anvil 19440 and staple cartridge 19450, respectively, the retainer 19400 may be pulled in the direction of arrow I (FIG. 88) to remove the retainer 19400 from between the first tissue thickness compensator 19410 and the second tissue thickness compensator 19420 and to break the connectors 19430. As shown in FIG. 89, after the connectors 19430 are broken and the retainer 19400 has been removed, the anvil 19440 may be reopened, and the first tissue thickness compensator 19410 will be attached to the anvil 19440 and the second tissue thickness compensator 19420 will be attached to the staple cartridge 19450.

In various embodiments, a proximal portion 19407 of each hole 19406 in the retainer 19400 may include a cutting edge. When the retainer is pulled in the direction of arrow I (FIG. 88), a pulling force is transmitted through the proximal portion 19407 of the holes 19406 to break the connectors. A cutting edge at the proximal portion 19407 of each hole 19406 will concentrate the transmitted force on a relatively small area of each connector. As a result, the connectors will break more easily and a lower pulling force may be required to remove the retainer 19400 from between the first tissue thickness compensator 19410 and the second tissue thickness compensator 19420.

As described above, a retainer assembly can comprise a retainer positioned between a first tissue thickness compensator and a second tissue thickness compensator wherein, after the two tissue thickness compensators have been inserted into and attached to an end effector of a surgical instrument, the retainer can be pulled from between the tissue thickness compensators and removed from the end effector. In certain embodiments, the retainer can provide a barrier between the first and second tissue thickness compensators. Once the retainer is removed from between the first and second tissue thickness compensators, substances in and/or on the first tissue thickness compensator can react with substances in and/or on the second tissue thickness compensator, for example. In some embodiments, one or both of the tissue thickness compensators can include a film that can encase substances within the tissue thickness compensators. In certain embodiments, the films can be attached to the retainer wherein, when the retainer is pulled from between the tissue thickness compensators, as described above, the retainer can pull the films away from the tissue thickness compensators to expose the substances contained therein. At such point, the substances within each of the tissue thickness compensators can interact with each other.

FIGS. 90-100 illustrate an embodiment of a retainer that engages an anvil of a surgical device, such as, for example, a surgical stapler. The retainer may align a first tissue thickness compensator with the anvil and a second tissue thickness compensator with a staple cartridge. Closing the anvil causes the first tissue thickness compensator to attach to the anvil and the second tissue thickness compensator to attach to the staple cartridge. The retainer also may carry the staple cartridge with a tissue thickness compensator optionally disposed between the retainer and the staple cartridge. Closing the anvil causes the staple cartridge to attach to a channel of the surgical stapler and causes the first tissue thickness compensator to attach to the anvil.

FIGS. 90-93 show an embodiment of a retainer 19500. The retainer 19500 includes a grip 19502 by which a surgeon, nurse, technician, or other person may manipulate the retainer 19500. The grip 19502 may include a textured surface, such as raised portions 19503, for example, which may provide a better gripping surface. In various embodiments, the retainer 19500 can include a surface 19504 on which a tissue thickness compensator may be mounted. The surface 19504 may include one or more projections 19506 wherein the projections 19506 may engage recesses in the tissue thickness compensator and align the tissue thickness compensator relative to the surface 19504 of the retainer 19500. The recesses in the tissue thickness compensator may be slightly smaller than the projections 19506 such that, when engaged with the recesses, the projections 19506 can hold the tissue thickness compensator to the surface 19504. In various embodiments, the projections 19506 may pass through holes in the tissue thickness compensator and engage a slot, such as, for example, a cutting blade slot 19558 in anvil 19550 shown in FIG. 95, thereby aligning the tissue thickness compensator with the retainer 19500 and also providing additional alignment of the retainer 19500 with the anvil 19550. The tissue thickness compensator 19540 may include an adhesive and/or engagement features, described above, on a surface 19542 for attaching the tissue thickness compensator to an anvil 19550.

Figure 94:
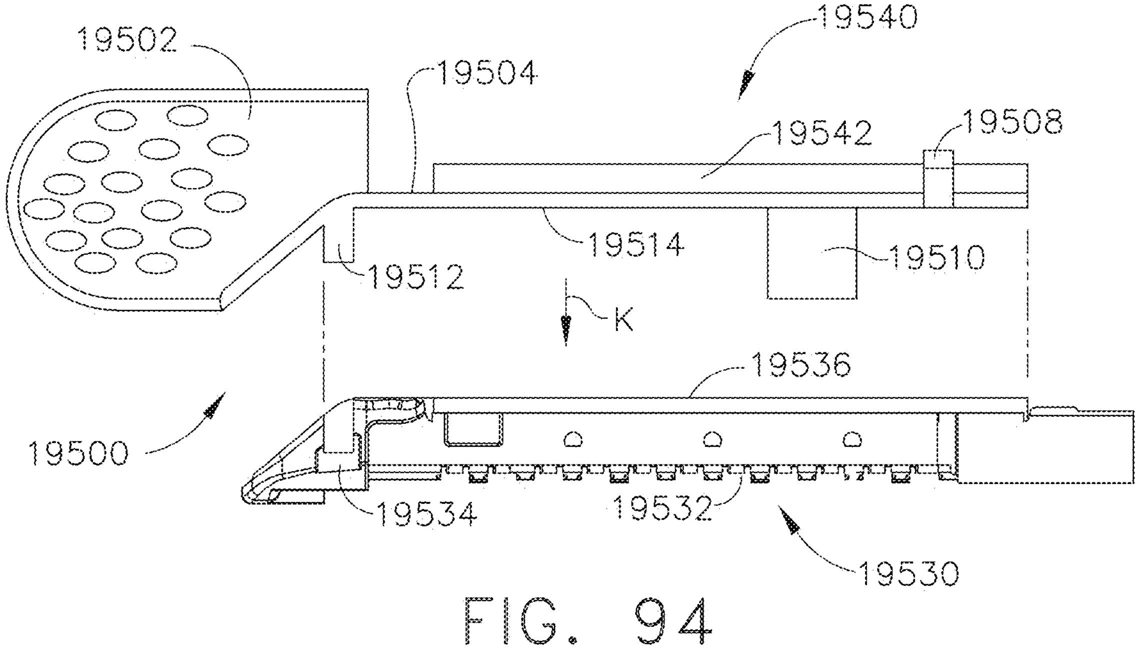
FIG. 94 illustrates a retainer assembly comprising the retainer of FIG. 90 and a tissue thickness compensator being attached to a staple cartridge for a surgical stapler.

As shown in FIG. 94, in various embodiments, a staple cartridge 19530 may be attached to the retainer 19500. The staple cartridge 19530 can be attached to the retainer 19500 by clips 19510 and 19512 extending from the retainer 19500. Clips 19512 on the retainer 19500 can engage a slot 19534 in the staple cartridge 19530. Clips 19510 of the retainer 19500 can surround the bottom 19532 of the staple cartridge 19532. In various embodiments, a second tissue thickness compensator may be attached to the staple cartridge 19530. In at least one embodiment, a second tissue thickness compensator may be attached to a staple deck 19536 of the staple cartridge 19530.

Figure 95:
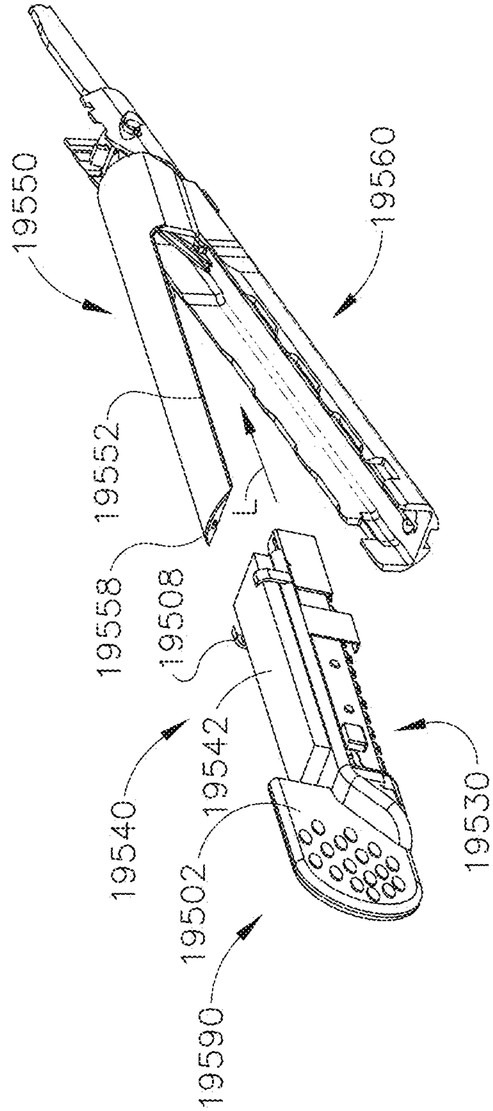
FIG. 95 illustrates the retainer assembly and staple cartridge of FIG. 94 engaging an anvil of an end effector of a surgical stapler.
Figure 96:
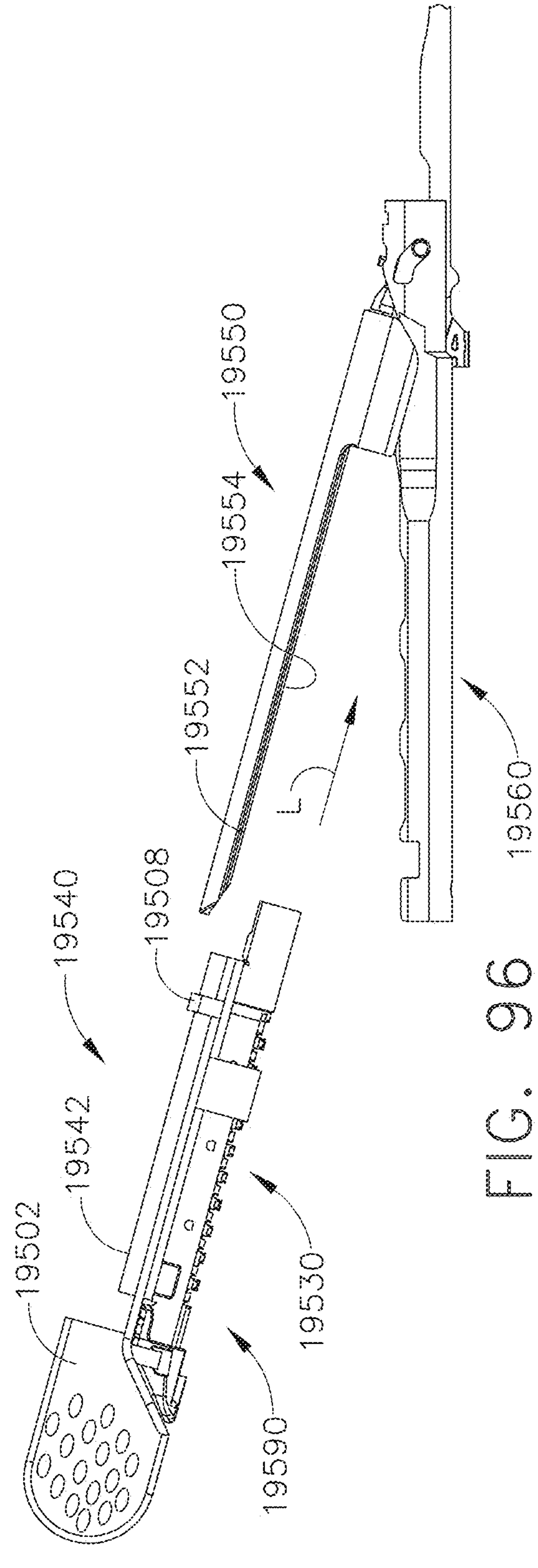
FIG. 96 illustrates the retainer assembly and staple cartridge of FIG. 94 engaging the anvil of the end effector of the surgical stapler of FIG. 95.
Figure 97:
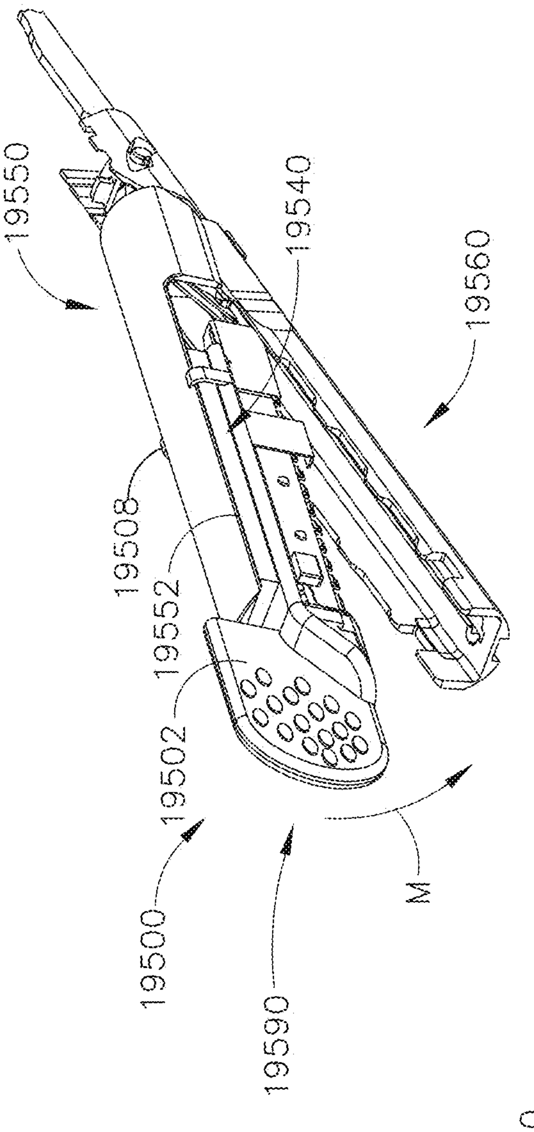
FIG. 97 illustrates the retainer assembly and staple cartridge of FIG. 94 engaged on the anvil of the surgical stapler of FIG. 95.
Figure 98:
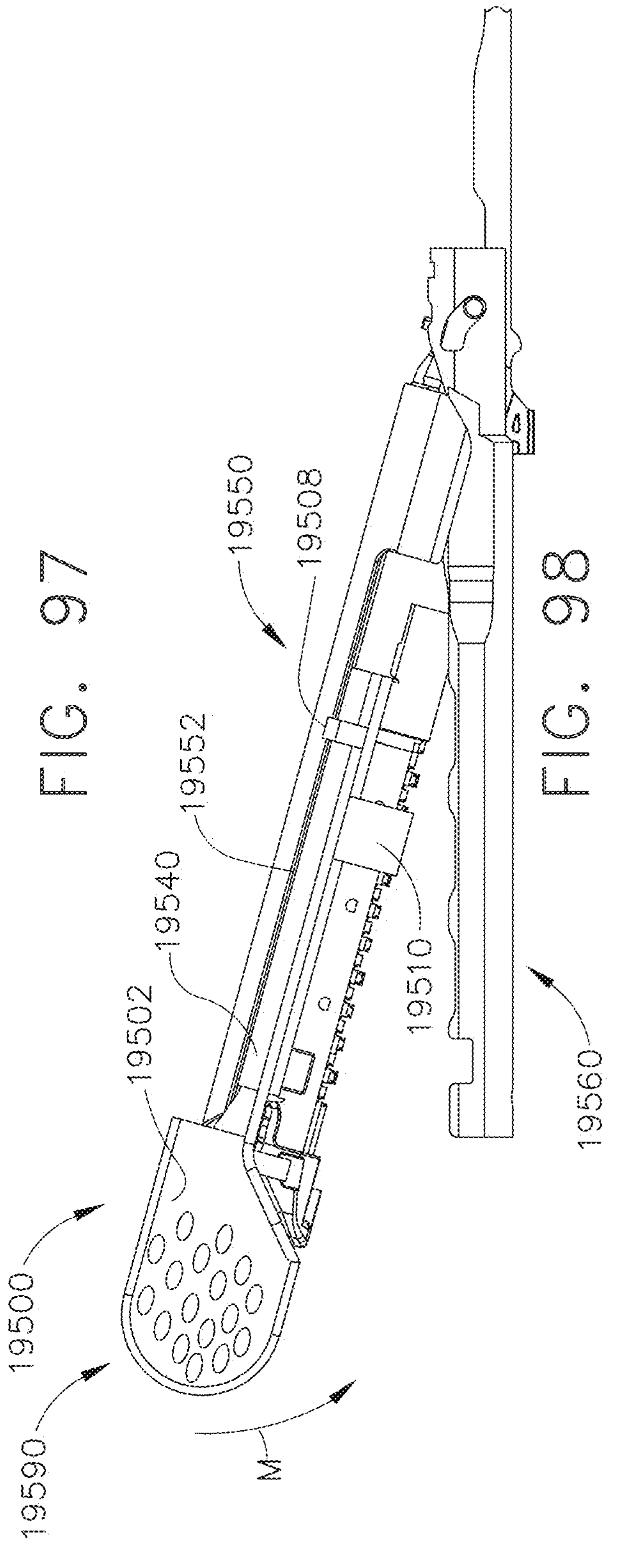
FIG. 98 illustrates the retainer assembly and staple cartridge of FIG. 94 engaged on the anvil of the surgical stapler of FIG. 95 and the anvil being moved into a closed position.
Figure 99:
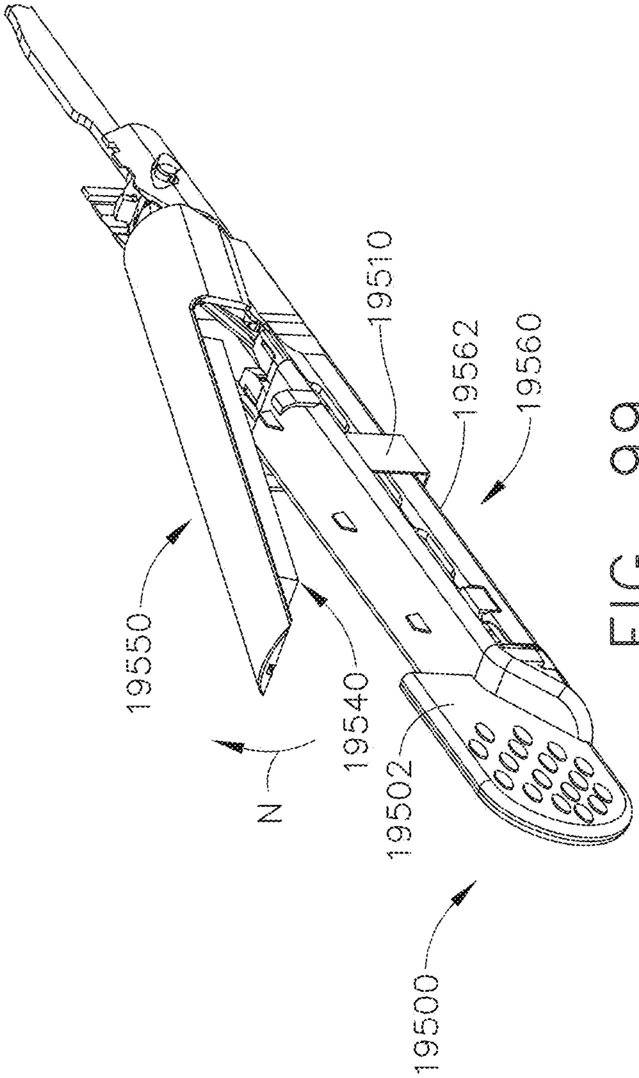
FIG. 99 illustrates the anvil of the surgical stapler of FIG. 95 in an open position with the tissue thickness compensator attached thereto and the retainer engaged with the staple cartridge channel of the surgical stapler.
Figure 100:
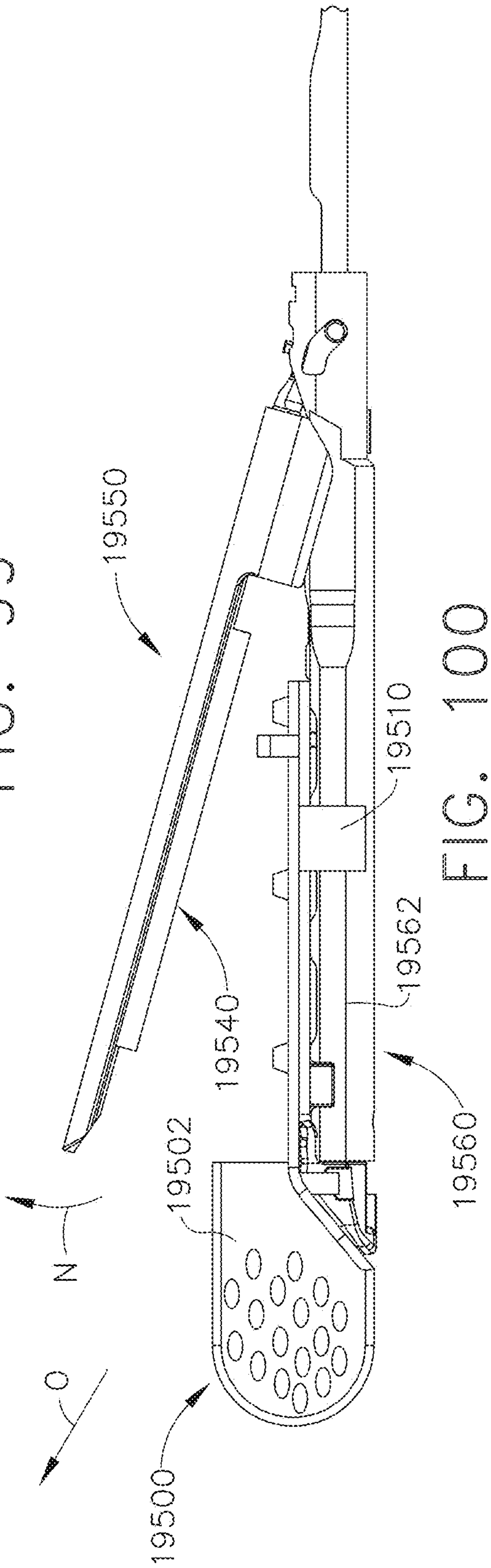
FIG. 100 illustrates the retainer of FIG. 94 engaged with the staple cartridge channel of the surgical stapler of FIG. 95 and the anvil in an open position.

As shown in FIGS. 95 and 96, a retainer assembly 19590 comprising the retainer 19500, a tissue thickness compensator 19540, and a staple cartridge 19530, can slide onto the anvil 19550 of a surgical device, such as a surgical stapler, in the direction of arrow L. The guide tabs 19508 on the retainer 19500 can surround edges 19552 of the anvil 19550 and position the retainer assembly 19590 relative to the anvil 19550. After the retainer assembly 19590 is engaged on the anvil 19550, as shown in FIGS. 97 and 98, the anvil can be closed in the direction of arrow M. Closure of the anvil 19550 can position the staple cartridge 19530 in a channel 19560 of the surgical device. In at least one embodiment, closure of the anvil 19550 can cause the clips 19510 extending from the retainer 19500 to engage a ridge 19562 of the channel 19560 in order to securely position the staple cartridge 19530 in the channel 19560. When the anvil 19550 is reopened in the direction of arrow N, referring now to FIGS. 99 and 100, the tissue thickness compensator 19540 can remain attached to the anvil 19550 and separates from the retainer 19500. The retainer 19500 then can be removed from the surgical instrument in the direction of arrow O (FIGS. 99 and 100) leaving the staple cartridge 19530 in the channel 19560 of the surgical device and a tissue thickness compensator 19540 attached to the anvil 19550.

Figure 101:
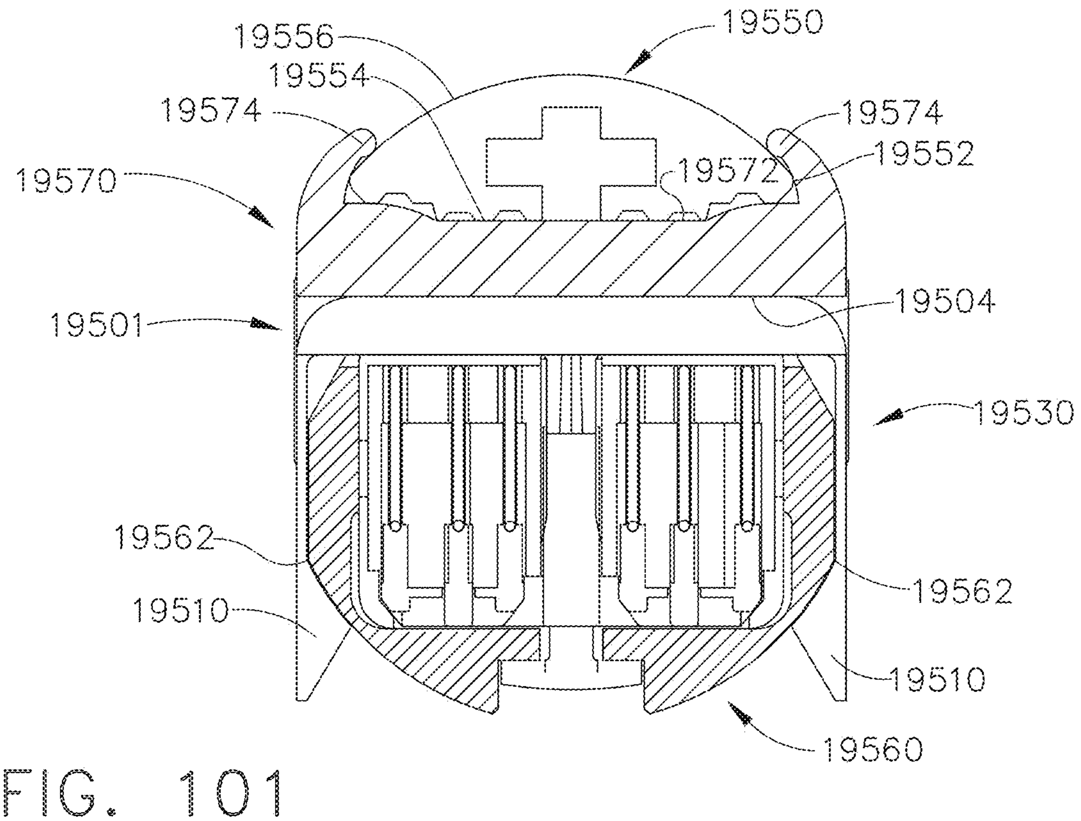
FIG. 101 is a cross-sectional view of a retainer including a tissue thickness compensator comprising protrusions or wings configured to engage an anvil of a surgical stapler.
Figure 102:
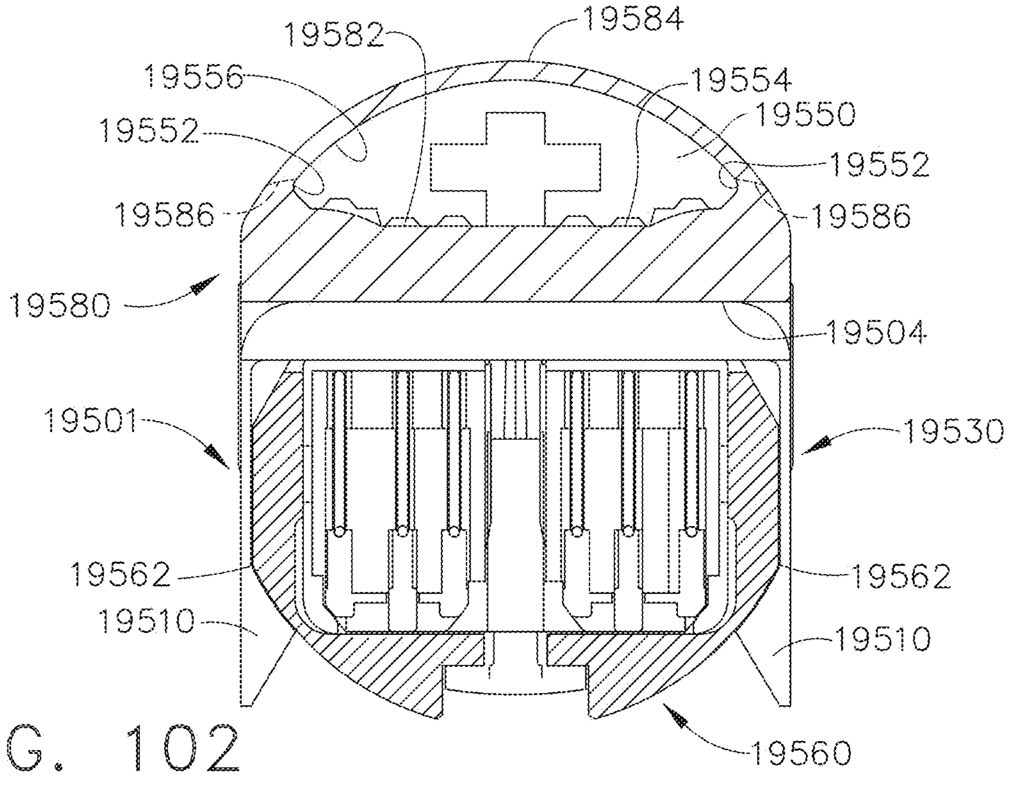
FIG. 102 is a cross-sectional view of a retainer including a tissue thickness compensator comprising a sock configured to engage an anvil of a surgical stapler.

FIGS. 101 and 102 show examples of two alternative embodiments of tissue thickness compensators 19570 and 19580, respectively. FIG. 101 is a cross-sectional view of a tissue thickness compensator 19570 attached to a retainer 19501 wherein the tissue thickness compensator 19570 can include protrusions 19574 which can contact edges 19552 of the anvil 19550 and partially surround an exterior surface 19556 of the anvil 19550. In various embodiments, the protrusions can grip the anvil 19550 and/or be attached to the anvil 19550 utilizing one or more adhesives. In order to release the tissue thickness compensator 19570 from the anvil 19550 after the compensator 19570 has been implanted against a patient's tissue, the protrusions 19574 can flex outwardly from the anvil 19550 thereby enabling the tissue thickness compensator 19570 to be pulled away from the anvil 19550. FIG. 102 is a cross-sectional view of a tissue thickness compensator 19580 attached to the retainer 19501 shown in FIG. 101. The tissue thickness compensator 19580 includes a sock 19584 that can surround the anvil 19550 to align the tissue thickness compensator 19580 with the anvil 19550 and/or to retain the tissue thickness compensator 19580 on the anvil 19550. In various embodiments, the sock 19584 can retain the tissue thickness compensator 19580 on the anvil 19550. In order to detach the sock 19584 from the anvil 19550, in various embodiments, the tissue thickness compensator 19580 can tear away from the sock 19584 at perforations 19586, for example. Thus, the sock 19584 can remain on the anvil 19550 while the remainder of the tissue thickness compensator 19580 can remain stapled to the patient tissue.

In certain embodiments, a tissue thickness compensator, such as tissue thickness compensator 19570, for example, can include an interior portion that comprises a biocompatible substance positioned therein. In various embodiments, the biocompatible substance can include an anti-inflammatory, a coagulant, and/or an antibiotic, for example. In various embodiments, a body, such as a wafer, for example can be inserted into the interior portion within the tissue thickness compensator. In at least one such embodiment, the wafer may be inserted through an open end of the tissue thickness compensator into a cavity defined therein. In certain embodiments, the wafer may be held within the cavity of the tissue thickness compensator by an interference fit. In certain embodiments, steps for assembling the wafer into the tissue thickness compensator can include a first step of heating the tissue thickness compensator such that the tissue thickness compensator expands. When the tissue thickness compensator expands, in various embodiments, the cavity defined therein can also expand. When the tissue thickness compensator is in an expanded state, according to a second step, the wafer may be inserted into the cavity. Then, as the tissue thickness compensator cools, according to a third step, the cavity can shrink onto the wafer and hold the wafer in place within the cavity.

Figure 103:
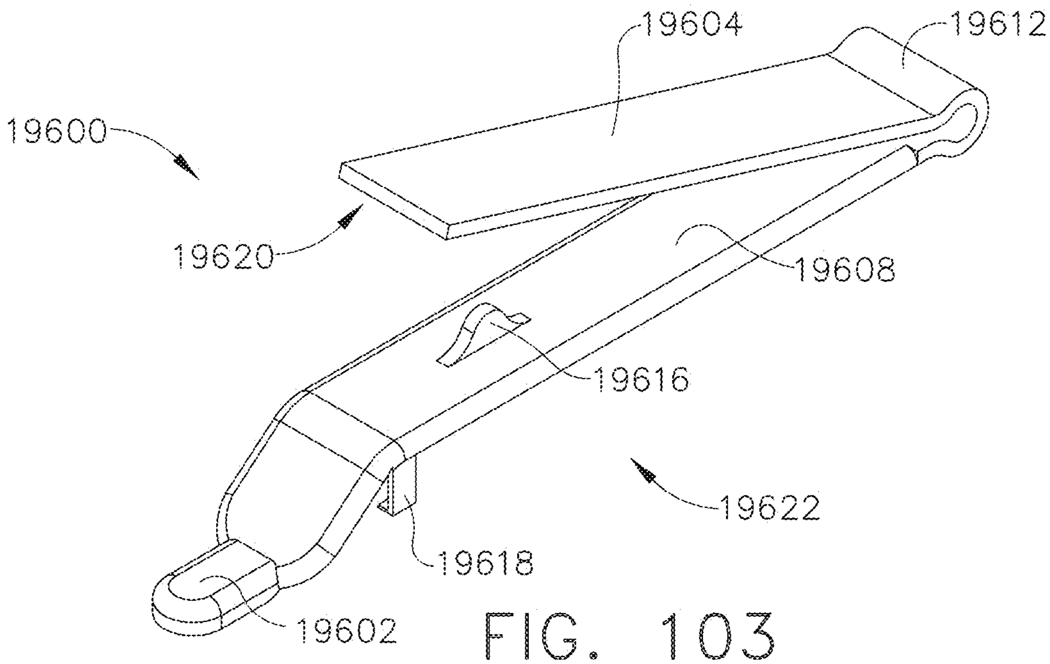
FIG. 103 is a perspective view of a retainer that includes two plates connected by a hinge according to at least one embodiment.
Figure 104:
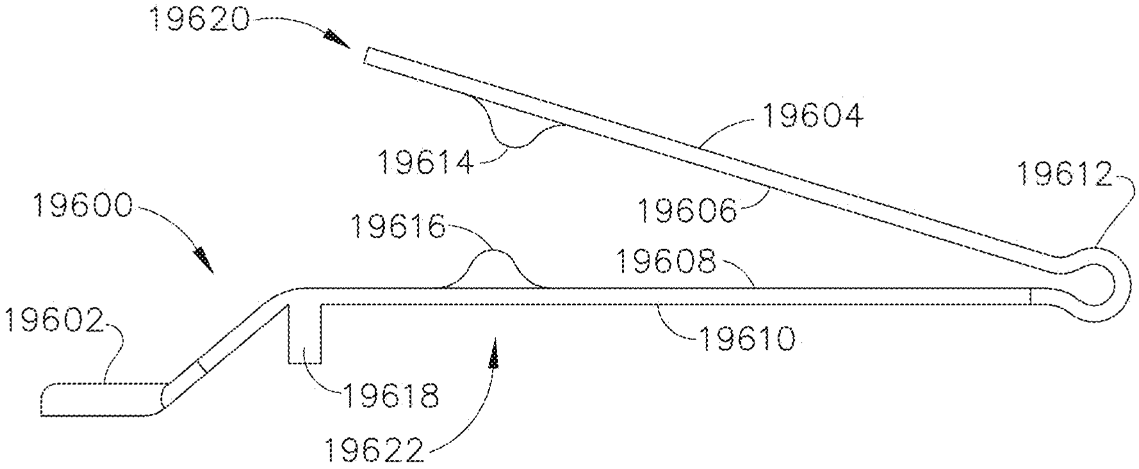
FIG. 104 is a side view of the retainer of FIG. 103.
Figure 106:
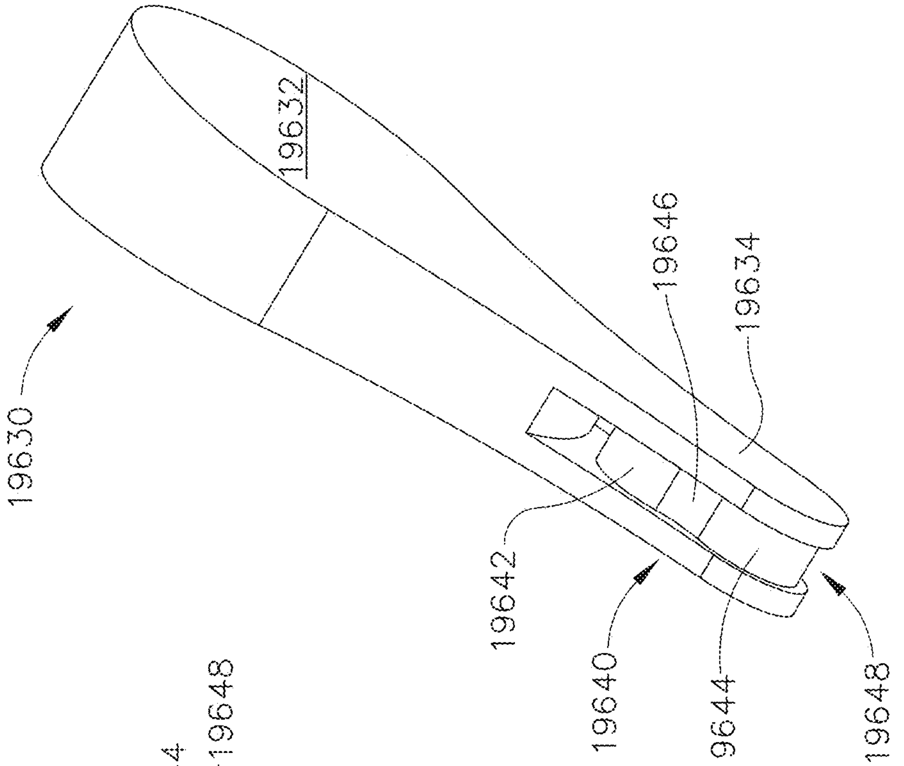
FIG. 106 is a top perspective view of the insertion tool of FIG. 105.
Figure 105:
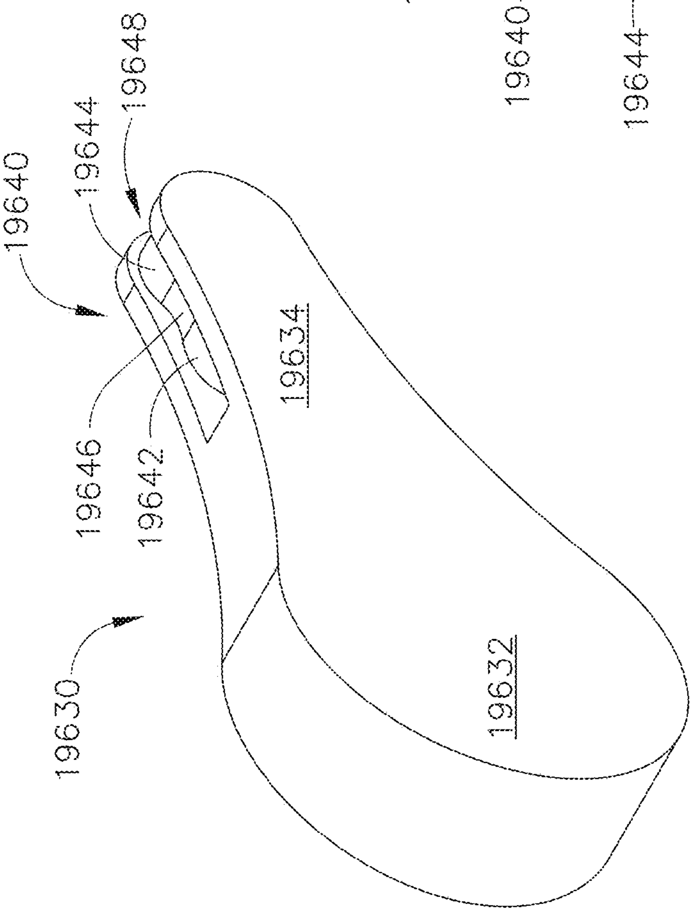
FIG. 105 is a rear perspective view of an embodiment of an insertion tool configured for use with the retainer of FIG. 103.
Figure 107:
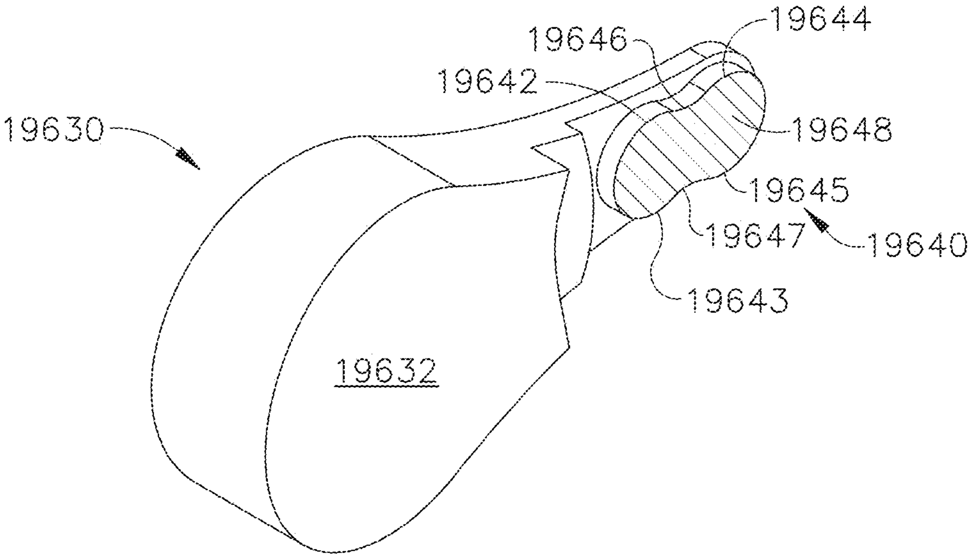
FIG. 107 is a rear perspective view of the insertion tool of FIG. 105 with a portion of the insertion tool removed for purposes of illustration.
Figure 108:
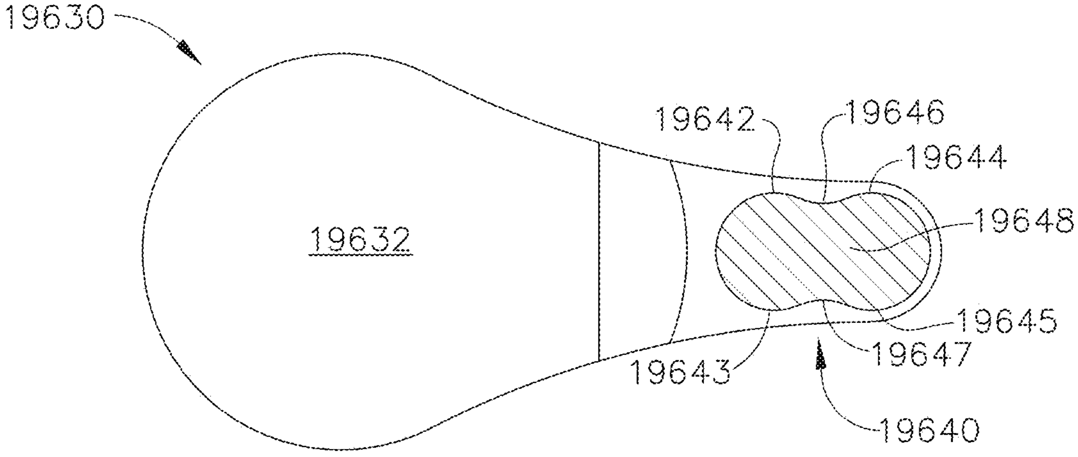
FIG. 108 is a side view of the insertion tool of FIG. 105 with a portion of the insertion tool removed for purposes of illustration.
Figure 109:
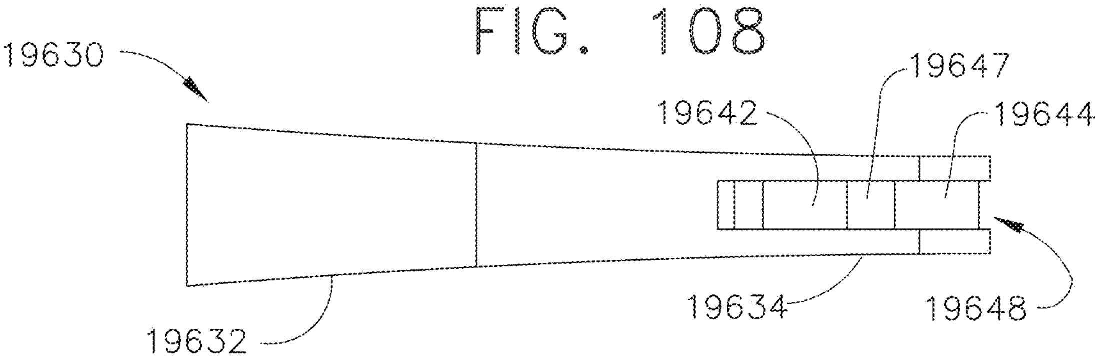
FIG. 109 is a top view of the insertion tool of FIG. 105.
Figure 110:
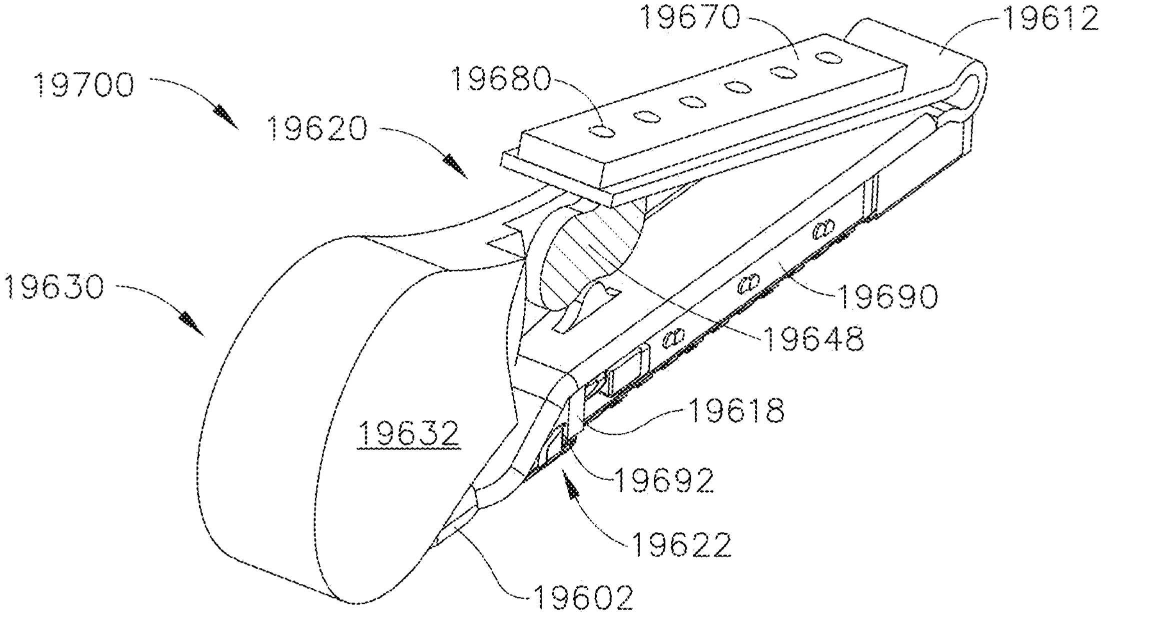
FIG. 110 is a perspective view of a retainer assembly comprising the retainer of FIG. 103, a tissue thickness compensator positioned on the retainer, a staple cartridge positioned on the retainer, and the insertion tool of FIG. 105 engaged with the retainer, wherein a portion of the insertion tool is removed for purposes of illustration.
Figure 111:
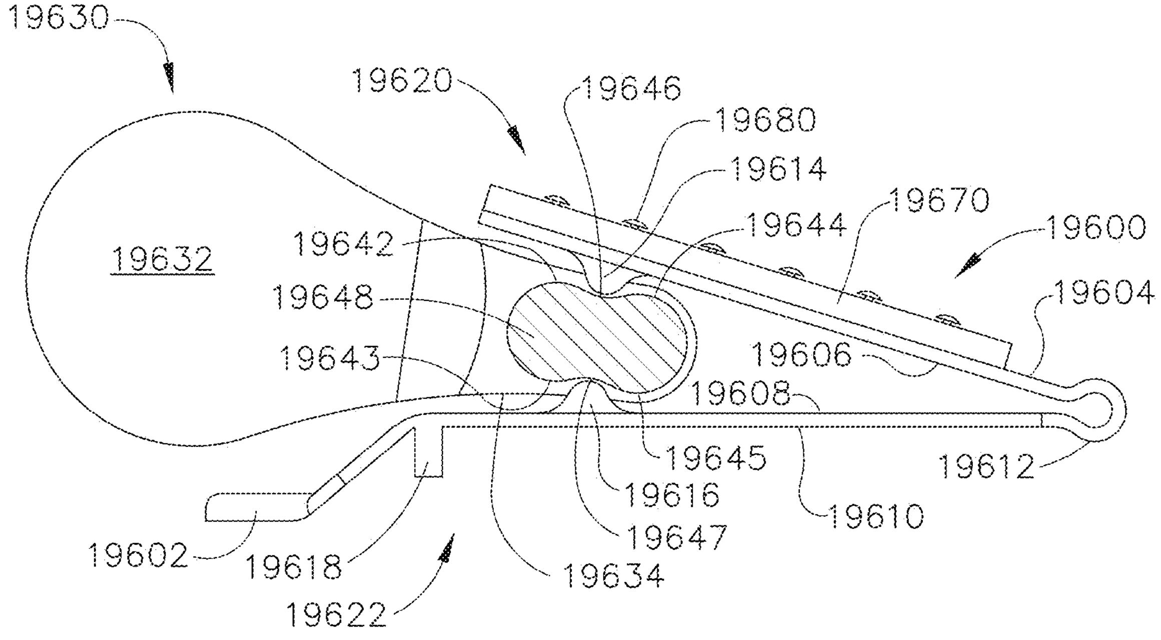
FIG. 111 is a side view of a retainer assembly comprising the retainer of FIG. 103, a tissue thickness compensator positioned on the retainer, and the insertion tool of FIG. 105 engaged with the retainer, wherein a portion of the insertion tool is removed for purposes of illustration.

FIGS. 103-115 illustrate an embodiment of a retainer comprising a separate insertion tool. The insertion tool can be used to insert an assembly into a surgical instrument, such as a surgical stapler, for example. The insertion tool can also press a staple cartridge and one or more tissue thickness compensators of the retainer assembly into position within the surgical instrument. Referring to FIGS. 103 and 104, a retainer 19600 may include a first plate 19620 and a second plate 19622. The first plate 19620 and the second plate 19622 may be connected by a hinge 19612. The hinge 19612 can position the first plate 19620 at an angle relative to the second plate 19622 and can also enable the first plate 19620 to rotate relative to the second plate 19622 about the hinge 19612.

In various embodiments, the first plate 19620 can include an outward-facing surface 19604 and an inward-facing surface 19606. Likewise, the second plate 19622 may include an outward-facing surface 19610 and an inward-facing surface 19608. In at least one embodiment, the inward-facing surface 19606 of the first plate 19620 may include a cam protrusion 19614. Similarly, the inward-facing surface 19608 of the second plate 19622 may include a cam protrusion 19616. Referring to FIGS. 110-115, outward-facing surface 19604 of the first plate may include a tissue thickness compensator positioned thereon. Outward-facing surface 19601 of the second plate 19622 may also include a tissue thickness compensator positioned thereon. The tissue thickness compensators may be attached to the outer surfaces 19604 and 19610 using adhesives, engagement features, and/or other suitable attachment means, for example. In various embodiments, the retainer 19600 can include clips 19618 extending from the second plate 19622 which can be configured to engage a staple cartridge 19690, as shown in FIGS. 110 and 112-115.

Referring now to FIGS. 105-109, an insertion tool 19630 can include a first end 19632 and a second end 19634. The first end 19632 can be large enough to be gripped by a surgeon, nurse, and/or technician, for example. In various embodiments, the second end 19634 defines a cavity 19640 wherein the cavity can include a cam 19648 positioned therein. A first side of the cam 19648 may include a first lobe 19642, a second lobe 19644, and a first anti-lobe 19646 positioned therebetween. A second side of the cam 19648 can include a third lobe 19643, a fourth lobe 19645, and a second anti-lobe 19647 positioned therebetween. In at least one such embodiment, the lobes and the anti-lobes can be arranged in a mirror-image manner. In other words, the first lobe 19642 may be arranged on the first side of the cam 19648 directly opposite the third lobe 19643 on the second side of the cam 19648. Likewise, the second lobe 19644 may be arranged on the first side of the cam 19648 directly opposite the fourth lobe 19645 on the second side of the cam 19648. Further, the first anti-lobe 19464 may be arranged on the first side of the cam 19648 directly opposite the second anti-lobe 19647 on the second side of the cam 19648.

Figure 112:
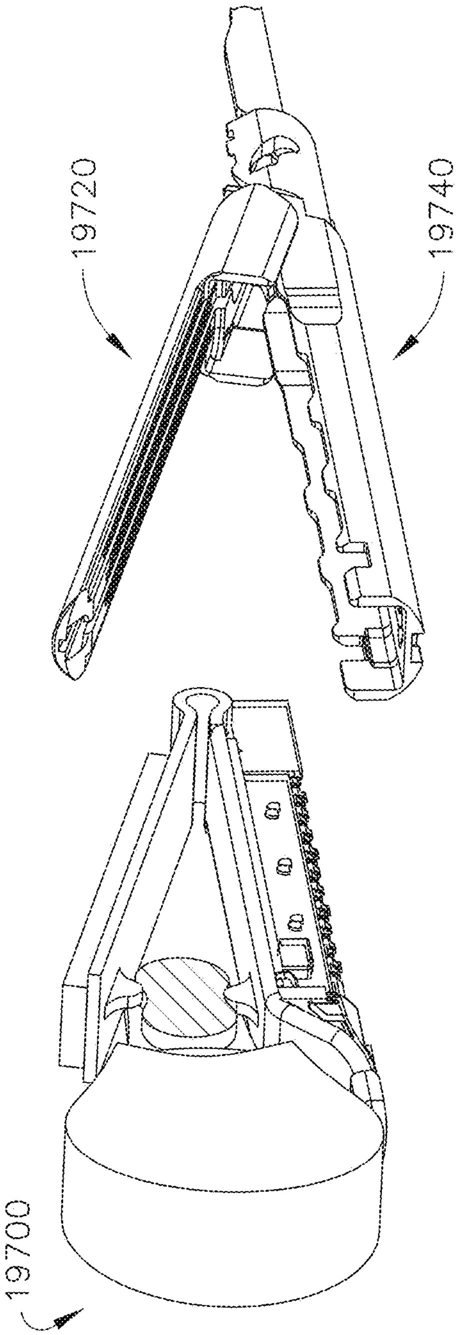
FIG. 112 illustrates the retainer assembly of FIG. 110 being inserted into a surgical instrument comprising an anvil and a staple cartridge channel, wherein a portion of the insertion tool is removed for the purposes of illustration.
Figure 113:
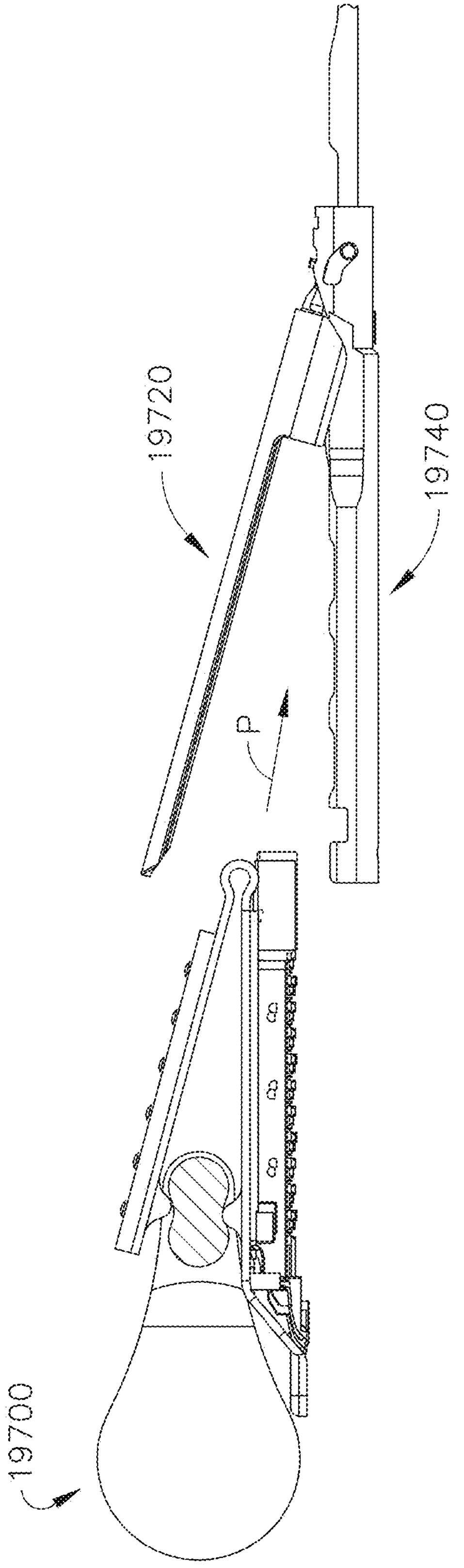

In use, the second end 19634 of the insertion tool 19630 is placed between the first plate 19620 and the second plate 19622 of the retainer 19600 such that the cam protrusion 19614 on the first plate 19620 is engaged with anti-lobe 19646 and cam protrusion 19616 on the second plate 19622 is engaged with anti-lobe 19647, for example. As shown in FIGS. 112 and 113, an insertion assembly 19700, which includes the retainer 19600, the insertion tool 19630, one or more tissue thickness compensators, and staple cartridge 19690 can be inserted into a surgical instrument. The surgical instrument, such as a surgical stapler, may include a channel 19740, which is configured to receive the staple cartridge 19690, and an anvil 19720. The insertion assembly 19700 can be inserted into the surgical instrument in the direction of arrow P (FIG. 113) to lock the staple cartridge 19690 into the channel 19740. In such a position, the cams 19614 and 19616 can be aligned with the anti-lobes 19646 and 19647, respectively.

Figure 114:
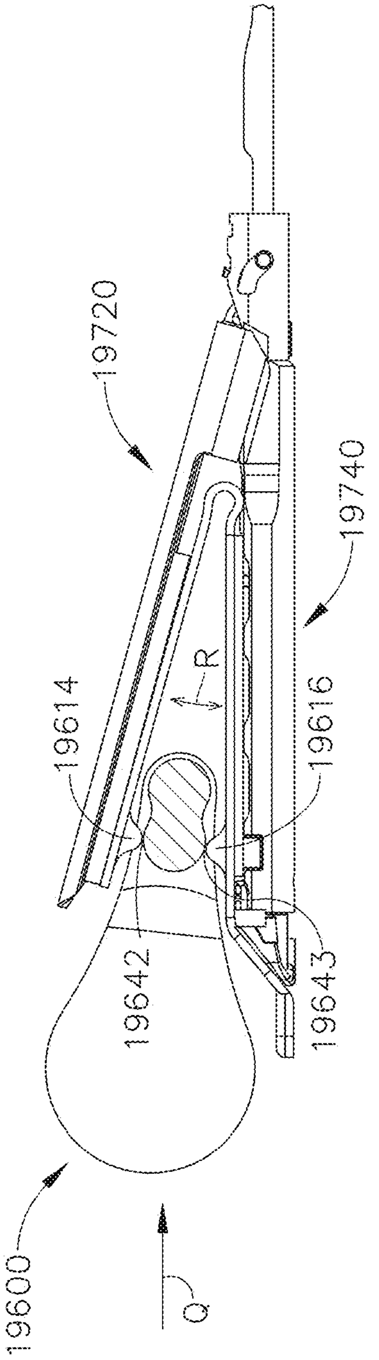
Figure 115:
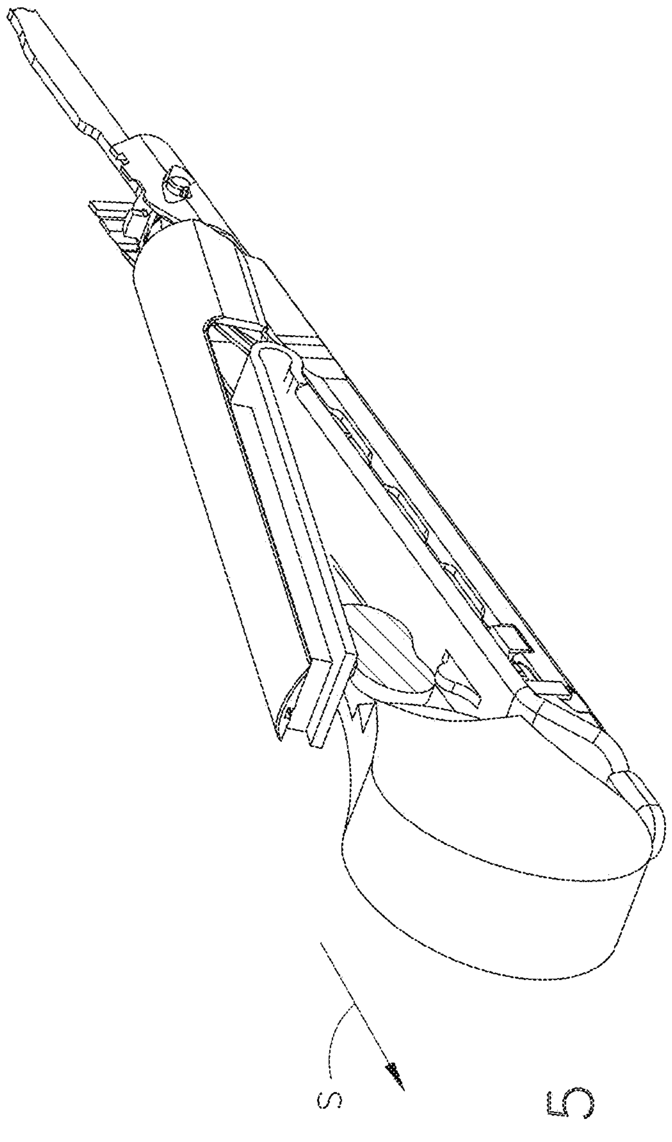

After the staple cartridge 19690 is locked into the channel 19740, as shown in FIG. 114, the insertion tool 19600 can continue to be moved in the direction of arrow Q relative to the surgical instrument. Further movement of the insertion tool 19600 in the direction of arrow Q can align the first lobe 19642 with the first cam protrusion 19614 and the third lobe 19634 with the second cam protrusion 19616. Such an alignment can cause the retainer plates 19620 and 19622 to rotate away from each other about the hinge 19612 in the direction of arrow R (FIG. 114). In such circumstances, the retainer plate 19620 and the tissue thickness compensator 19670 can move toward the anvil 19720 and the retainer plate 19622 can move toward and contact the anvil 19720. In various embodiments, as a result of the above, the tissue thickness compensator 19670 can be seated on the anvil 19720. After the tissue thickness compensator 19670 is attached to the anvil 19720, the insertion tool 19630 may be retracted or moved in the direction of arrow S (shown in FIG. 115). Movement of the insertion tool 19630 in the direction of arrow S can causes the cam protrusions 19614 an 19616 to disengage from the first lobe 19642 and the third lobe 19643, respectively, and become re-aligned with the first anti-lobe 19646 and the second anti-lobe 19647, respectively. In various embodiments, the second lobe 19642 and the fourth lobe 19645 can abut the cam protrusions 19614 and 19616, respectively, and, in at least one embodiment, can prevent the insertion tool 19630 from completely separating from the retainer 19600. With the cam protrusions 19614 and 19616 realigned with the anti-lobes 19646 and 19647, the first plate 19620 can at least partially rotate toward the second plate 19622 about the hinge 19612 and away from the anvil 19720. The retainer 19600 can also be detached from the channel 19740, in various embodiments, and then removed in the direction of arrow S leaving the tissue thickness compensator 19670 attached to the anvil 19720, for example.

In the embodiments described herein, a retainer assembly can be utilized to install one or more tissue thickness compensators into an end effector of a surgical stapling instrument. In certain embodiments, a retainer assembly can install layers besides tissue thickness compensators into a surgical instrument. In at least one embodiment, the layers may include an absorbable material and/or a biocompatible material, for example.

Referring to FIG. 172, an end effector 12 can be configured to receive an end effector insert 25002. In various embodiments, the end effector 12 can comprise a lower jaw 25070 and an anvil 25060 that is configured to pivot relative to the lower jaw 25070. In some embodiments, the end effector insert 25002 can comprise a staple cartridge 25000 that is pivotably connected to an anvil insert 25004. The end effector 12 can be configured to receive the end effector insert 25002 such that the staple cartridge 25000 fits within a staple cartridge channel 25072 of the lower jaw 25070, for example, and the anvil insert 25004 contacts the anvil 25060, for example. In various embodiments, the lower jaw 25070 can comprise a plurality of securing members 25074 configured to secure the staple cartridge 25000 to the staple cartridge channel 25072. In some embodiments, the anvil insert 25004 can comprise at least one retaining protrusion configured to engage at least one retaining groove in the anvil 25060. The anvil insert 25004 can be configured to correspondingly pivot towards the staple cartridge 25000 when the anvil 25060 pivots towards the lower jaw 25070, as described in greater detail herein.

Referring still to FIG. 172, the end effector insert 25002 can further comprise a retainer 25010. In various embodiments, the retainer 25010 can securely engage at least one of the staple cartridge 25000 and the anvil insert 25004. In at least one embodiment, the retainer 25010 can comprise at least one securing clip 25012 that can clip, engage, snap, clamp, and/or hook the staple cartridge 25000. As illustrated in FIG. 172, the retainer 25010 can comprise two securing clips 25012 on each longitudinal side thereof, for example. In at least one such embodiment, the securing clips 25012 can be configured to clip onto a portion of the staple cartridge 25000, for example. In various embodiments, a tissue thickness compensator can be held in position relative to the end effector insert 25002 by the retainer 25010. For example, a tissue thickness compensator can be positioned between the retainer 25010 and the staple cartridge 25000.

In various embodiments, when an operator is inserting the end effector insert 25002 into the end effector 12, the retainer 25010 can provide a solid or substantially solid element for the operator to grasp. Furthermore, the retainer 25010 can prevent premature deformation of a tissue thickness compensator that is confined by the retainer 25010, for example. In various embodiments, the retainer 25010 can be removed from the end effector 12 prior to utilizing the end effector 12 to cut and/or fasten tissue. In other embodiments, the retainer 25010 can remain positioned in the end effector 12. For example, the retainer 25010 can be transected by the cutting element 25052 (FIG. 207) as staples are fired from staples cavities 25002 (FIG. 207) in the staple cartridge 25000. In various embodiments, the retainer 25010 can comprise a polymeric composition, such as a bioabsorbable, biocompatible elastomeric polymer, for example. The retainer 25010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the retainer 25010 can comprise at least one therapeutic agent such as a pharmaceutically active agent or medicament.

Referring to FIG. 173, an end effector 26012 can comprise an anvil 26060 and a lower jaw 26070. In various embodiments, a tissue compensator 26020 can be releasably secured to the anvil 26060, the lower jaw 26070, and/or both the anvil 26060 and the lower jaw 26070. For example, a first tissue compensator 26020 can be releasably secured to a staple cartridge 26000 in the lower jaw 26070 and a second tissue compensator 26022 can be releasably secured to the anvil 26060. In various embodiments, the first and second tissue compensators 26020, 26022 can be deformable and/or resilient, similar to at least one tissue thickness compensator described herein. For example, the first and second tissue compensators 26020, 26022 can comprise a polymeric composition, such as a bioabsorbable, biocompatible elastomeric polymer, for example. The first and second tissue compensators 26020, 26022 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the first and second tissue compensators 26020, 26022 can comprise at least one therapeutic agent such as a pharmaceutically active agent or medicament.

In some embodiments, the tissue compensator 26020, 26022 can comprise a firm or substantially firm tip 26024, 26026. For example, a first tip 26024 can be positioned at the distal end of the first tissue compensator 26020 and a second tip 26026 can be positioned at the distal end of the second tissue compensator 26022. In various embodiments, the tips 26024, 26026 may prevent or limit premature deformation of the tissue compensators 26020, 26022. For example, the tips 26024, 26026 can protect the tissue compensators 26020, 26022 when the tissue compensators 26020, 26022 are moved through a trocar and/or maneuvered around a patient's tissue, for example. Similarly, referring to FIG. 174, the end effector 12 can comprise a first tissue compensator 25020 releasably secured to the staple cartridge 25000 in the lower jaw 25070 and a second tissue compensator 25022 releasably secured to the anvil 25060. In various embodiments, a tip 25026 can be positioned at the distal end of the second tissue compensator 25022. The tip 25026 can be positioned adjacent to a deformable and/or resilient portion of the tissue compensator 25022. In some embodiments, the tip 25026 can extend over and/or around a portion of the tissue compensator 25022, such that the tip 25026 protects the distal end and an intermediate portion of the tissue compensator 25022.

Referring to FIGS. 175-202, a sleeve 27010 can be configured to engage the anvil 25060 of the end effector 12 of a surgical instrument, for example. In various embodiments, the sleeve 27010 can comprise a pronged portion 27040 (FIGS. 176-179), a nose 27080 (FIGS. 186-189) and a compensator 27120 (FIGS. 180-182). In some embodiments, the sleeve 27010 can be configured to release a compensator 27020 when a translating firing bar 25052 (FIG. 196) approaches the distal end of the end effector 12. In various embodiments, the compensator 27020 can be deformable and/or resilient, similar to at least one tissue thickness compensator described herein. For example, the compensator 27020 can comprise a polymeric composition, such as a bioabsorbable, biocompatible elastomeric polymer, for example. The compensator 27020 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the compensator 27020 can comprise at least one therapeutic agent such as a pharmaceutically active agent or medicament. Referring primarily to FIG. 175, the pronged portion 27040 can be positioned on and/or around an outer surface 25061 of the anvil 25060. In various embodiments, the nose 27080 of the sleeve 27010 can be positioned at and/or around a distal portion of the anvil 25060. In some embodiments, the compensator 27020 can be positioned on and/or around an inner surface of the anvil 25060.

Referring still to FIG. 175, the pronged portion 27040 can comprise at least one prong 27042*a*. In various embodiments, as illustrated in FIGS. 505-508, the pronged portion 27040 can comprise a first prong 27042*a* and a second prong 27042*b*. The prongs 27042*a*, 27042*b* can be symmetrical or substantially symmetrical, for example. In some embodiments, the first prong 27042*a* can be asymmetrical relative to the second prong 27042*b*. In various embodiments, the first and/or second prongs 27042*a*, 27042*b* can narrow at the distal end thereof. For example, each prong 27042*a*, 27042*b* can comprise a narrowed end 27048. Referring primarily to FIG. 178, the pronged portion 27040 can be contoured, for example. In various embodiments, referring again to FIG. 175, the contour of the pronged portion 27040 can match or substantially match a contour of the outer surface 25061 of the anvil 25060, for example. Referring primarily to FIGS. 178 and 179, the pronged portion 27040 can also comprise at least one catch 27044*a* extending from the first prong 27042*a*. In some embodiments, a first catch 27044*a* can be positioned on a first side of the pronged portion 27040 and a second catch 27044*b* can be positioned on a second side of the pronged portion 27040. In various embodiments, the catches 27044*a*, 27044*b* can be positioned at or near the proximal end of the pronged portion 27040, for example. In some embodiments, the catches 27044*a*, 27044*b* can be positioned at or near the distal end of the pronged portion 27040, such as along the first and/or second prongs 27042*a*, 27042*b*, for example. In various embodiments, the catches 27044*a*, 27044*b* can extend along a substantial length of the pronged portion 27040 and/or along a shorter length of the pronged portion 27040. In some embodiments, a plurality of catches 27044*a*, 27044*b* can be positioned along each longitudinal side of the pronged portion, for example. Referring primarily to FIG. 179, the first catch 27044*a* can comprise a first catch extension 27046*a* and/or the second catch 27044*b* can comprise a second catch extension 27046*b*. In various embodiments, the first catch extension 27046*a* can protrude from at least a portion of the catch 27044*a* and the second catch extension 27046*b* can protrude from at least a portion of the catch 27044*b*, for example. Further, the first catch extension 27046*a* and the second catch extension

27046*b* can each be configured to engage a gap 27128 (FIG. 181) in the compensator 27020, as described in greater detail herein.

Referring now to FIG. 201, the compensator 27020 for the sleeve 27010 can comprise a longitudinal protrusion 27024 and an edge 27026 on each longitudinal side of the compensator 27020. In various embodiments, the compensator 27020 can be positioned adjacent to an inner surface 25063 of the anvil 25060. Further, when the sleeve 27010 is positioned on the anvil 25060, the longitudinal protrusion 27024 can be substantially aligned with and/or positioned within a longitudinal slot 25062 in the anvil 25060. The edges 27026 of the compensator 27020 can at least partially wrap around the anvil 25060 towards the outer surface 25061 thereof. Referring primarily to FIGS. 180-181, a compensator 27120 for a sleeve 27110 can comprise a body 27122 having a longitudinal protrusion 27124 that extends along at least a portion of the body 27122. The longitudinal protrusion 27124 can define a longitudinal path along the midline of the body 27122, for example. In various embodiments, the longitudinal protrusion 27124 can be received by the longitudinal slot 25062 (FIG. 201) in the anvil 25060 when the sleeve 27110 is positioned on the anvil 25060. Referring primarily to FIG. 182, the longitudinal protrusion 27124 can comprise a rounded projection. For example, the cross-section of the longitudinal protrusion 27124 can form an arc and/or partial ring. In other embodiments, the longitudinal protrusion 27124 can comprise an angular and/or stepped projection. The compensator 27120 can further comprise an edge 27126, which can be straight, bent, fluted, wavy, and/or zigzagged, for example. In various embodiments, the edge 27126 can comprise gaps 27128 that can be configured to receive the catch extensions 27046*a*, 27046*b* (FIG. 179) when the assembled sleeve 27110 is positioned on the anvil 25060. The catch extensions 27046*a*, 27046*b* can fit through the gap 27128 to engage the anvil 25060 such that the catch extensions 27046*a*, 27046*b* help to secure the sleeve 27110 to the anvil 25060, for example.

Referring primarily to FIGS. 183-185, a compensator 27220 for a sleeve 27210 can comprise a body 27222 comprising a longitudinal protrusion 27224 extending along at least a portion of the body 27222. In various embodiments, similar to the above, the longitudinal protrusion 27224 can be received by the longitudinal slot 25062 (FIG. 202) in the anvil 25060 when the sleeve 27210 is positioned on the anvil 25060. Referring primarily to FIG. 185, the longitudinal protrusion 27224 can comprise an angular projection such that the cross-section of the protrusion 70224 forms a substantially rectangular shape. The compensator 27220 can further comprise an edge 27226, which can be straight, bent, fluted, wavy, and/or zigzagged, for example. In various embodiments, the edge 27226 can comprise gaps 27228 that can be configured to receive the catch extensions 27046*a*, 27046*b* (FIG. 179) when the assembled sleeve 27210 is positioned on the anvil 25060. The catch extensions 27046*a*, 27046*b* can fit through the gaps 27228 and engage the anvil 25060 such that the catch extensions 27046*a*, 27046*b* help to secure the sleeve 27210 to the anvil 25060, for example. In various embodiments, the compensator 27220 can further comprise a plurality of ribs 27229 that laterally traverse the body 27222 of the compensator 27220. The ribs 27229 can support the body 27222 of the compensator 27220 when the sleeve 27210 is positioned on the anvil 25060 and/or when the compensator 27220 contacts tissue.

Referring to FIGS. 386-390, the nose 27080 of the sleeve 27010 can comprise an alignment ridge 27082 that can be substantially aligned with the longitudinal slot 25062 (FIG. 201) in the anvil 25060. When the alignment ridge 27082 is aligned with the longitudinal slot 25062 and when the sleeve 27010 is positioned on the anvil 25060, the nose 27082 can at least partially surround a distal portion of the pronged portion 27040 of the sleeve 27010. For example, the narrowed end 27048 of each prong 27042*a*, 27042*b* can be positioned within the nose 27080 when the sleeve 27010 is positioned on the anvil 25060. As described in greater detail herein, the nose 27080 can flex the prongs 27042*a*, 27042*b* closer together and/or downward when the pronged portion 27042 is engaged with the nose 27080. Furthermore, as illustrated in FIG. 190, when the narrowed ends 27048 of the pronged portion 27040 are positioned within the nose 27080, the catches 27044*a*, 27044*b* on the pronged portion 27040 can engage the edges 27026 of the compensator 27020, for example. As a result of such engagement, the compensator 27010 can be secured to the anvil 25060.

Referring to FIGS. 191-195, when the nose 27080 is engaged with the pronged portion 27040 of the sleeve 27010, the compensator 27020 can be secured to the anvil 25060. The nose 27080 can remain engaged with the pronged portion 27040 as the firing bar 25050 translates along a portion of the longitudinal slot 25062 in the anvil 25060. Referring now to FIGS. 195-200, when the cutting element 25052 on the firing bar 25050, and/or any other suitable portion of the firing bar 25050, such as retaining flange 25054, for example, approaches the distal end of the anvil 25060, the firing bar 25050 can disengage the nose 27080 from the pronged portion 27040. The firing bar 25050 can, for example, contact the nose 27080 and push the nose 27080 off of the anvil 25060 such that the nose 27080 becomes disconnected from the pronged portion 27040 of the sleeve 27010. Referring now to FIG. 202, when the nose 27080 is disengaged with the pronged portion 27040, the first and second prongs 27042*a*, 27042*b* can be configured to flex away from the anvil 25060. For example, when the pronged portion 27070 is engaged with the nose 27080, the prongs 27042*a*, 27042*b* can be flexed closer together and/or downwards towards the anvil 25060 and held in such a position by the nose 27080. In various embodiments, the prongs 27042*a*, 27042*b* can be held under a spring load by the nose 27080 such that the prongs 27042*a*, 27042*b* seek to rebound to a neutral configuration once the nose 27080 is disengaged from the prongs 27042*a*, 27042*b*. In other embodiments, the prongs 27042*a*, 27042*b* can be sufficiently deformable such that the prongs 27042*a*, 27042*b* can be deformed or splayed outwardly by the firing bar 25050 once the nose 27080 is disengaged therefrom. When the prongs 27042*a*, 27042*b* move away from the anvil 25060, the catches 27044*a*, 27044*b* along a longitudinal side of each prong 27042*a*, 27042*b* can disengage the compensator 27020, which can allow the compensator 27020 to be released from the anvil 25060.

Referring to FIGS. 203-209, the end effector 12 of a surgical instrument, for example, can be configured to receive an end effector insert 28010. In various embodiments, the end effector insert 28010 can comprise a compensator body 28012 and at least one clip 28014*a*, 28014*b*. In various embodiments, the end effector insert 28010 can comprise a proximal clip 28014*b* at the proximal end of the compensator body 28012 and a distal clip 28014*a* at the distal end of the compensator body 28012, for example. Referring primarily to FIG. 206, the distal clip 28014*a* can be secured to the anvil 25060 of the end effector 12 at or near the distal end of the anvil 25060. For example, the distal clip 28014*a* can be substantially aligned with and/or partially positioned within the longitudinal slot 25062 of the anvil 25060. Referring primarily to FIG. 207, the proximal clip 28014*b* can be secured to a staple cartridge 25000 in the lower jaw 25070 of the end effector 12 (FIG. 208). The proximal clip 28014*b* can be secured to the staple cartridge 25000 at or near the proximal end of the staple cartridge 25000. For example, the proximal clip 28014*b* can be substantially aligned with and/or positioned within a longitudinal slot 25004 in the staple cartridge 25000.

Referring now to FIGS. 208 and 209, the end effector insert 28010 can be inserted into the end effector 12 of a surgical instrument. In various embodiments, at least a portion of the end effector insert 28010, such as the compensator body 28012, distal clips 28014*a*, and/or proximal clip 28014*b*, can be deformable and/or resilient, for example. When the end effector insert 28010 is inserted into the end effector 12, the distal and/or the proximal clips 28014*a*, 28014*b* can bend or flex. When the clips 28014*a*, 28014*b* are flexed, for example, the clips 28014*a*, 28014*b* can seek to return to their initial, undeformed configuration and can generate a corresponding springback or restoring force, for example. In various embodiments, when the end effector insert 28010 is positioned within the end effector 12, the end effector insert 28010 can apply a spring load to the end effector 12. In some embodiments, the end effector insert 28010 can be solid or substantially solid such that an operator can grasp the insert 28010 when the operator is inserting the end effector insert 28010 and staple cartridge 25000 into the end effector 12.

In some embodiments, the end effector insert 28010 can be removed from the end effector 12 prior to cutting and/or fastening operations of the end effector 12. In other embodiments, the end effector insert 28010 can remain positioned in the end effector 12 during cutting and/or firing operations. For example, the end effector insert 28010 can be transected by the cutting element 25052 as staples are fired from their staples cavities 25002 (FIG. 207) in the staple cartridge 25000. In various embodiments, the end effector insert 28010 can comprise a tissue thickness compensation material, similar to at least one of the tissue thickness compensators described herein. For example, the end effector insert 28010 can comprise a polymeric composition, such as a bioabsorbable, biocompatible elastomeric polymer, for example. The end effector insert 28010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the end effector insert 28010 can comprise at least one therapeutic agent such as a pharmaceutically active agent or medicament.

Referring to FIGS. 210-215, a tissue thickness compensator 29020 can be positioned in the end effector 12 of a surgical instrument. The tissue thickness compensator 29020 can be substantially similar to at least one of the tissue thickness compensators described herein. For example, the tissue thickness compensator 29020 can be sufficiently deformable and resilient such that deformation of the tissue thickness compensator 29020 generates a springback or restoring force. In various embodiments, referring primarily to FIG. 211, a static charge can attract the tissue thickness compensator 29020 to the anvil 25060 of the end effector 12 such that the static charge secures the tissue thickness compensator 29020 to the anvil 25060. In various embodiments, the static charge can be neutralized such that the anvil 25060 releases the tissue thickness compensator 29020. Additionally or alternatively, referring now to FIG. 212, the tissue thickness compensator 29020 can be secured to the anvil 25060 by at least one suction element 29022. For example, a plurality of micro-suction elements 29022 on a surface of the tissue thickness compensator 29020 can releasably secure the tissue thickness compensator 29020 to the anvil 25060. Additionally or alternatively, referring to FIG. 213, hook and loop fasteners 29024 can secure the tissue thickness compensator 29020 to the anvil 25060. For example, a surface of the tissue thickness compensator 29020 can comprise a plurality of hook fasteners 29024*a* and a surface of the anvil 25060 can comprise a plurality of loop fasteners 29024*b*, for example. The hook fasteners 29024*a* can engage the loop fasteners 29024*b* such that the tissue thickness compensator 29020 is releasably secured to the anvil 25060.

Additionally or alternatively, referring now to FIG. 214, the tissue thickness compensator 29020 can be secured to the anvil 25060 by a band 29026. In some embodiments, the band 29026 can comprise an elastomeric polymer and/or can be tied or knotted around the anvil 25060. When the band 29026 is removed from the anvil 25060, the tissue thickness compensator 29020 can be released from the anvil 25060. To facilitate removal of the band 29026, it can be stretched and/or cut, for example. In various embodiments, a plurality of bands 29026 can secure the tissue thickness compensator 29020 to the anvil 25060. Alternatively or additionally, referring now to FIG. 215, the tissue thickness compensator 29020 can be secured to the anvil 25060 by a sock 29028 positioned at the distal end of the tissue thickness compensator 29020. The sock 29028 can be configured to receive the distal end of the anvil 25060 therein, for example. In some embodiments, an alignment ledge 29029 on the tissue thickness compensator 29020 can be aligned with and/or positioned within the longitudinal slot 25062 in the anvil 25060. For example, the alignment ledge 29029 can slide within the longitudinal slot 25062 as the tissue thickness compensator 29020 is positioned on and/or removed from the anvil 25060.

Referring to FIGS. 216-218, a tissue thickness compensator 30020 can be positioned on the anvil 25060 of the end effector 12 of the surgical instrument. In various embodiments, the tissue thickness compensator 30020 can comprise a body 30022 and a pocket 30024. In at least one embodiment, a compensator material 30026 can be retained between the body 30022 and the pocket 30024, for example. In some embodiments, the compensator material 30026 can comprise a bioabsorbable polymer, such as, for example, lyophilized polysaccharide, glycoprotein, elastin, proteoglycan, gelatin, collagen, and/or oxidized regenerated cellulose (ORC), for example. Additionally or alternatively, the compensator material 30026 can comprise at least one therapeutic agent such as a pharmaceutically active agent or medicament. In various embodiments, the tissue thickness compensator 30020 can be deformable and/or resilient, similar to at least one tissue thickness compensator described herein. For example, the tissue thickness compensator 30020 can comprise a polymeric composition, such as a bioabsorbable, biocompatible elastomeric polymer, for example. The tissue thickness compensator 30020 can further comprise a bioabsorbable polymer, such as, for example, lyophilized polysaccharide, glycoprotein, elastin, proteoglycan, gelatin, collagen, and/or oxidized regenerated cellulose (ORC), for example.

Referring primarily to FIG. 217, the body 30022 of the tissue thickness compensator 30020 can comprise an alignment element 30028 that can be received within the longitudinal slot 25062 of the anvil 25060 when the tissue thickness compensator 30020 is secured to the anvil 25060.

In some embodiments, the body 30022 can comprise a stepped thickness such that the geometry of the body 30022 substantially corresponds with the geometry of the anvil 25060. Further, in various embodiments, the body 30022 can comprise longitudinal flanges 30029. In at least one such embodiment, a longitudinal flange 30029 can extend along each longitudinal side of the body 30022 of the tissue thickness compensator 30020, for example. In various embodiments, the longitudinal flanges 30029 can at least partially wrap around the anvil 25060 to secure the tissue thickness compensator 30020 to the anvil 25060. Further, the longitudinal flanges 30029 can be sufficiently resilient such that the longitudinal flanges 30029 can flex to accommodate and/or engage the anvil 25060, for example. In various embodiments, the longitudinal flanges 30029 can exert a clamping force on the anvil 25060 when the flanges 30029 engage the anvil 25060. In some embodiments, the pocket 30024 can comprise an indentation 30025. When the tissue thickness compensator 30020 is secured to the anvil 25060, the indentation 30025 can be substantially aligned with the longitudinal slot 25062 in the anvil 25060, for example. In various embodiments, the tissue thickness compensator 30020 can be thinner at the indentation 30025 such that the translating cutting element 25052 (FIG. 207) severs the tissue thickness compensator 30020 where it is thinner.

Referring now to FIGS. 219 and 220, a tissue thickness compensator 30120 can comprise a body 30122 that is configured to retain compensation material 30026 therein. In various embodiments, the tissue thickness compensator 30120 can comprise an alignment element 30128, an indentation 30125, and/or longitudinal flanges 30129, similar to at least one of the embodiments described herein. In some embodiments, the tissue thickness compensator 30120 can also comprise a latch 30124 that can be moved between an open position and a closed position. When the latch 30124 is in the closed position, as illustrated in FIG. 219, the compensation material 30026 can be enclosed within the body 30122 of the tissue thickness compensator 30120 and, when the latch 30124 is in the open position, as illustrated in FIG. 220, the compensation material 30026 can escape from the body 30122. Similar to at least one of the tissue thickness compensators described herein, the tissue thickness compensator 30120 can be deformable and/or resilient. For example, the tissue thickness compensator 30120 can comprise a polymeric composition, such as a bioabsorbable, biocompatible elastomeric polymer, for example. The tissue thickness compensator 30120 can further comprise a bioabsorbable polymer, such as, for example, lyophilized polysaccharide, glycoprotein, elastin, proteoglycan, gelatin, collagen, and/or oxidized regenerated cellulose (ORC), for example. Owing to the resiliency of the tissue thickness compensator 30120, at least a portion of the body 30122 can be flexed to move the latch 30124 between the open position and the closed position. In at least one embodiment, the body 30122 of the tissue thickness compensator 30120 can remain attached to the anvil when the anvil is removed from the surgical site. In at least one such embodiment, the body 30122 can be configured to tear away from any staples that may have captured the body 30122 therein.

Referring to FIG. 221, a tissue thickness compensator 30220 can comprise a body 30222 and a pocket 30224. The compensator material 30026 can be retained between the body 30222 and the pocket 30224, for example. In various embodiments, the tissue thickness compensator 30220 can comprise an alignment element, an indentation, and/or longitudinal flanges 30229, similar to at least one of the embodiments described herein. Further, at least one longitudinal flange 30229 can comprise a groove, or slot, 30228, which can be configured to receive a tab 30225 extending from the pocket 30224 of the tissue thickness compensator 30220. In such an embodiment, engagement of the groove 30228 and the tab 30225 can connect the body 30222 and the pocket 30224. Further, in such an embodiment, the groove 30028 and tab 30025 connection can enclose and/or retain the compensation material 30026 within the tissue thickness compensator 30220. Referring now to FIG. 222, in various embodiments, a pocket 30324 of a tissue thickness compensator 30320 can comprise an anchor 30325 extending therefrom. Further, the tissue thickness compensator 30320 can comprise a body 30322 having an opening 30328. In various embodiments, the anchor 30325 can extend from the pocket 30324 to engage the opening 30328 in the body 30322. In such an arrangement, the pocket 30324 and the body 30222 can encase the compensation material 30026 therebetween. In at least one embodiment, the tissue thickness compensator 30320 can further comprise one or more flanges 30229 which can be mounted to the anvil in order to retain the body 30322 to the anvil.

Referring now to FIG. 223, a tissue thickness compensator 30420 can comprise a body 30422 and a pocket 30424. In various embodiments, the compensation material 30026 can be retained between the body 30422 and the pocket 30424 of the tissue thickness compensator 30420. In some embodiments, the body 30422 can comprise an orifice 30428 and the pocket 30424 can comprise an anchor 30425. The anchor 30425 can extend from the pocket 30424 and through the orifice 30428 of the body 30422, for example. In various embodiments, the anchor 30425 can engage the anvil 25060 when the tissue thickness compensator 30420 is secured to the anvil 25060, for example. The anchor 30525 can be sufficiently deformable and resilient such that the anchor 30425 flexes when it engages the anvil 25060. Further, in some embodiments, the flexed anchor 30425 can apply a clamping force to the anvil 25060 to secure or assist in securing the tissue thickness compensator 30420 to the anvil 25060. In other embodiments, an anchor may not extend completely through an orifice in the compensator body. Referring to FIG. 224, an anchor 30525 on a pocket 30524 of a tissue thickness compensator 30520 can engage an orifice 30528 in a body 30522 of the tissue thickness compensator 30520. In various embodiments, the anchor 30525 can engage the orifice 30528 to secure the pocket 30524 to the body 30522. For example, the orifice 30528 can comprise a necked portion that extends to a socket. The anchor 30525 can comprise securing edge, which can pass through the necked portion and engage the socket to secure the anchor 20525 within the orifice 30528. Similar to at least one of the embodiments described herein, the tissue thickness compensator 30520 can also comprise an alignment element, an indentation, and/or longitudinal flanges 30529, for example.

Referring to FIGS. 225-227, a tissue thickness compensator 31020 can be configured to engage an anvil 31060 of an end effector 31012 of a surgical instrument. In various embodiments, the tissue thickness compensator 31020 can comprise an outer film 31022, an inner film 31024 and a compensation material 31026 positioned therebetween. In various embodiments, the tissue thickness compensator 31020 can be deformable and/or resilient, similar to at least one of the tissue thickness compensators described herein. For example, the compensation material 31026 can comprise a polymeric composition, such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In some embodiments, the tissue thickness compensator 31020 can comprise at least one therapeutic agent such as a pharmaceutically active agent or medicament. In various embodiments, the compensation material 31206 of the tissue thickness compensator 31020 can comprise a therapeutic agent.

The inner film 31024 can be positioned adjacent to staple forming pockets 31066 in the anvil 31060, for example. Referring primarily to FIG. 225, the inner film 31024 can comprise a stepped geometry such that the geometry of the inner film 31024 substantially corresponds to the geometry of the anvil 31060. The inner film 31024 can further comprise an alignment ridge 31028, which can be substantially aligned with and/or parallel to a longitudinal slot 31062 in the anvil 31060, for example. As described in greater detail herein, the inner film 31024 can comprise an inner flange 31025 extending from each longitudinal side of the inner film 31024 and terminating in a catch 31027. The outer film 31022 can comprise a body 31021 and at least one outer flange 31023, for example. In various embodiments, an outer flange 31023 can extend from each longitudinal side of the body 31021, for example. In various embodiments, the outer flange 31023 can be secured to the inner flange 31025 such that the compensation material 31026 is retained between the outer film 31022 and the inner film 31024.

Referring primarily to FIG. 227, the anvil 31060 can comprise an outer surface 31061 and at least one groove 31064 along at least a portion of the outer surface 31061. In various embodiments, a catch 31027 on the inner flange 31025 of the inner film 31024 can be positioned within a groove 31064. Referring to FIG. 226, for example, the tissue thickness compensator 31020 can be slid around the anvil 31060. In various embodiments, the grooves 31064 on the anvil 31060 can extend to the distal end of the anvil 31060. In such embodiments, the catches 31027 of the tissue thickness compensator 31020 can slide into the grooves 31064 and along a length of the tissue thickness compensator 31020.

In various embodiments, referring now to FIGS. 228 and 229, a tissue thickness compensator 31120 can comprise a compensation material 31026 and at least one connector 31124. Each connector 31124 can extend around the compensation material 31026 and can terminate in a catch 31127 on opposite ends thereof. In various embodiments, the catches 31127 can be positioned within the grooves 31064 of the anvil 31060 to fasten the tissue thickness compensator 31120 to the anvil 31060. In various embodiments, the grooves 31164 on the anvil 31060 can extend to the distal end of the anvil 31060. In such embodiments, the catches 31127 of the connectors 31124 can slide into the grooves 31064. In other embodiments, the connectors 31224 can be resilient such that they can flex and snap around the anvil 31060. In use, the connectors 31224 can hold the compensation material 31026 in place until the compensation material 31026 detaches from the anvil 31060. In certain circumstances, the connectors 31224 can remain attached to the anvil 31060 and can be removed from the surgical site with the anvil. In certain other circumstances, the connectors 31224 can detach from the anvil 31060 and can be implanted with the compensation material 31026.

Referring to FIGS. 230-236, a tissue thickness compensator 32020 can comprise a body portion 32022, at least one longitudinal flange 32024, and at least one pocket 32026. In various embodiments, the tissue thickness compensator 31020 can be deformable and/or resilient, similar to at least one of the tissue thickness compensators described herein. For example, the compensation material 31026 can comprise a polymeric composition such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In various embodiments, the longitudinal flange 32024 can extend along each longitudinal side of the body portion 32022. Referring primarily to FIG. 233, the longitudinal flanges 32024 of the tissue thickness compensator 32020 can be configured to engage the anvil 25060. For example, the tissue thickness compensator 32020 can slide onto the anvil 25060 and the longitudinal flanges 32024 and can at least partially wrap around a portion of the anvil 25060. In such embodiments, the flanges 32024 can secure the tissue thickness compensator 32020 to the anvil 25060, for example. In various embodiments, when the tissue thickness compensator 32020 is secured to the anvil, the body portion 32022 of the tissue thickness compensator 32020 can overlap staple forming pockets 25066 on the inner surface of the anvil 25060.

Further to the above, in various embodiments, a plurality of pockets 32026 can laterally traverse the body portion 32022. Referring primarily to FIG. 234, the plurality of pockets 32026 can comprise at least one therapeutic agent such as a pharmaceutically active agent or medicament. In various embodiments, a plurality of first pockets *32026a* can comprise a first therapeutic agent or combination thereof and a plurality of second pockets *32026b* can comprise a second therapeutic agent or combination thereof. The first pockets *32026a* and the second pockets *32026b* can be alternatingly positioned along the body portion 32022, for example. Further, in various embodiments, when the first therapeutic agent is released from the first pocket *32026a* and the second therapeutic agent is released from the second pocket *32026b*, the first and second therapeutic agents can be configured to react with each other. Referring to FIG. 236, the pockets 32026 can release the therapeutic agent(s) retained therein when the cutting element 25052 on the firing bar 25050 translates along the longitudinal slot 25062 in the anvil 25060, for example.

In various embodiments, referring now to FIG. 237, an end effector of a surgical stapling instrument can comprise an anvil 32560 and a staple cartridge 32500 comprising a tissue thickness compensator 32520. Similar to the above, the staple cartridge 32500 can comprise a plurality of staples 32530 at least partially contained therein which can be ejected therefrom to capture the tissue thickness compensator 32520 therein. Also similar to the above, the staples 32530 can penetrate the tissue thickness compensator 32520 and contact staple forming pockets 32562 defined in the anvil 32560. In certain embodiments, referring now to FIG. 239, the anvil 32560 can further comprise a layer 32570 attached thereto which can be configured to retain a tissue thickness compensator 32580 to the anvil 32560. In at least one such embodiment, the layer 32570 can comprise a chargeable layer which can be configured to hold and/or generate an electrostatic charge and attract the tissue thickness compensator 32580 thereto. More specifically, in various embodiments, Van der Waals molecular forces, whether actively or passively actuated, for example, can hold the tissue thickness compensator 32580 to the layer 32570. In certain embodiments, the chargeable layer 32570 can be in electrical communication with a handle of the surgical stapling instrument which can comprise a control configured to selectively couple the chargeable layer 32570 with a power source and, as a result, allow an electrostatic charge to be selectively generated within the chargeable layer 32570. In at least one such embodiment, the chargeable layer 32570 can comprise conductive electrodes embedded within a polymer, for example. In any event, the statically-charged layer 32570 can attract oppositely-charged particles in the tissue thickness compensator 32580 and hold the tissue thickness compensator 32580 to the anvil. In certain embodiments, referring now to FIG. 238, the chargeable layer 32570 can comprise a grid, or lattice, of conductors 32571 which are in electrical communication with one another. In at least one such embodiment, the conductors can be positioned and arranged such that they surround the staple forming pockets 32562 defined in the anvil 32560. In such embodiments, staples 32530 can be ejected from the staple cartridge 32500 and then deformed by the anvil 32560 without capturing the conductors 32571 therein. In various circumstances, the chargeable layer 32570 can be uncoupled from the power source after the staples 32530 have been engaged with the tissue thickness compensator 32580 such that the electrostatic charge in the layer 32570 can dissipate. In certain other circumstances, the chargeable layer 32570 can be uncoupled from the power source prior to the staples 32530 being fired. In any event, as the electrostatic charge dissipates, the anvil 32560 can be re-opened and the layer 32570 can be moved away from the tissue thickness compensator 32580. In some embodiments, the electrostatic charge may need to dissipate completely before the layer 32570 can be detached from the tissue thickness compensator 32580 while, in other embodiments, the layer 32570 can be detached from the tissue thickness compensator 32580 before the electrostatic charge in the layer 32570 has completely dissipated. In certain embodiments, as a result of the above, the tissue thickness compensator 32580 can be attached to the anvil 32560 without the use of a chemical adhesive.

In various embodiments, further to the above, the layer 32570 can also provide feedback capability to the handle of the surgical stapling instrument. In at least one such embodiment, the layer 32570 can be pressure sensitive and can be configured to detect the clamping pressure being applied thereto by the anvil 32560, for example.

Referring to FIGS. 259 and 260, in various embodiments, a staple cartridge 70100 may comprise a tissue thickness compensator 70105 and a plurality of staples 70110 each comprising staple legs 70112. As shown in FIG. 259, tissue thickness compensator 70105 may have an initial thickness or compressed height that is less than the fired height of the staples 70110. The tissue thickness compensator 70100 may be configured to expand in situ and/or in vivo when contacted with a fluid 70102, such as bodily fluids, saline, and/or an activator for example, to push the tissue T against the legs 70112 of the staple 70110. As shown in FIG. 260, the tissue thickness compensator 70100 may expand and/or swell when contacted with a fluid 70102. The tissue thickness compensator 70105 can compensate for the thickness of the tissue T captured within each staple 70110. As shown in FIG. 260, tissue thickness compensator 70105 may have an expanded thickness or an uncompressed height that is less than the fired height of the staples 70110.

Referring to FIGS. 261 and 262, for example, a tissue thickness compensator 70000 may comprise at least one hydrogel precursor 70010 selected to form a hydrogel in situ and/or in vivo to expand the tissue thickness compensator 70000. FIG. 261 illustrates a tissue thickness compensator 70000 comprising an encapsulation comprising a first hydrogel precursor 70010A and a second hydrogel precursor 70010B prior to expansion. In certain embodiments, as shown in FIG. 261, the first hydrogel precursor 70010A and second hydrogel precursor 70010B may be physically separated from other in the same encapsulation. In certain embodiments, a first encapsulation may comprise the first hydrogel precursor 70010A and a second encapsulation may comprise the second hydrogel precursor 70010B. FIG. 262 illustrates the expansion of the thickness tissue compensator 70000 when the hydrogel is formed in situ and/or in vivo. As shown in FIG. 262, the encapsulation may be ruptured, and the first hydrogel precursor 70010A may contact the second hydrogel precursor 70010B to form the hydrogel 70020. In certain embodiments, the hydrogel may comprise an expandable material. In certain embodiments, the hydrogel may expand up to 72 hours, for example.

In various embodiments, the tissue thickness compensator may expand when contacted with an activator, such as a fluid, for example. Referring to FIG. 263, for example, a tissue thickness compensator 70050 may comprise a swellable material, such as a hydrogel, that expands when contacted with a fluid 70055, such as bodily fluids, saline, water and/or an activator, for example. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, bile, and/or gas (e.g., $CO_2$). In certain embodiments, the tissue thickness compensator 70050 may expand when the tissue thickness compensator 70050 absorbs the fluid. In another example, the tissue thickness compensator 70050 may comprise a non-crosslinked hydrogel that expands when contacted with an activator 70055 comprising a cross-linking agent to form a crosslinked hydrogel. In various embodiments, the tissue thickness compensator may expand when contacted with an activator. In various embodiments, the tissue thickness compensator may expand or swell from contact up to 72 hours, such as from 24-72 hours, up to 24 hours, up to 48 hours, and up to 72 hours, for example, to provide continuously increasing pressure and/or compression to the tissue. As shown in FIG. 263, the initial thickness of the tissue thickness compensator 70050 may be less than an expanded thickness after the fluid 70055 contacts the tissue thickness compensator 70050.

Referring to FIGS. 264-266, stapling apparatus 70118 may comprise an anvil 70120 and a staple cartridge 70122 comprising a firing member 70124, a plurality of staples 70128, a knife edge 70129, and a tissue thickness compensator 70130. The tissue thickness compensator 70130 may comprise at least one encapsulated component. The encapsulated component may be ruptured when the tissue thickness compensator is compressed, stapled, and/or cut. Referring to FIG. 265, for example, the staples 70128 can be deployed between an unfired position and a fired position such that the staple legs move through the tissue thickness compensator 70130, penetrate through a bottom surface and a top surface of the tissue thickness compensator 70130, penetrate the tissue T, and contact an anvil 70120 positioned opposite the staple cartridge 70118. The encapsulated components may react with each other, a hydrophilic powder embedded or dispersed in the tissue thickness compensator, and/or bodily fluids to expand or swell the tissue thickness compensator 70130. As the legs are deformed against the anvil, the legs of each staple can capture a portion of the tissue thickness compensator 70130 and a portion of the tissue T within each staple 70128 and apply a compressive force to the tissue T. As shown in FIGS. 265 and 266, the tissue thickness compensator 70130 can compensate for the thickness of the tissue T captured within each staple 70128.

In various embodiments, further to the above, a tissue thickness compensator can be comprised of a biocompatible material. The biocompatible material, such as, a foam, may comprise tackifiers, surfactants, fillers, cross-linkers, pigments, dyes, antioxidants and other stabilizers and/or combinations thereof to provide desired properties to the material. In certain embodiments, a biocompatible foam may comprise a surfactant. The surfactant may be applied to the surface of the material and/or dispersed within the material. Without wishing to be bound to any particular theory, the surfactant applied to the biocompatible material may reduce the surface tension of the fluids contacting the material. For example, the surfactant may reduce the surface tension of water contacting the material to accelerate the penetration of water into the material. In various embodiments, the water may act as a catalyst. The surfactant may increase the hydrophilicity of the material.

In various embodiments, the surfactant may comprise an anionic surfactant, a cationic surfactant, and/or a non-ionic surfactant. Examples surfactants include, but are not limited to polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers, and combinations thereof. In at least one embodiment, the surfactant may comprise a copolymer of polyethylene glycol and polypropylene glycol. In at least one embodiment, the surfactant may comprise a phospholipid surfactant. The phospholipid surfactant may provide antibacterial stabilizing properties and/or disperse other materials in the biocompatible material. In various embodiments, the tissue thickness compensator may comprise at least one medicament. The tissue thickness compensator may comprise one or more of the natural materials, non-synthetic materials, and/or synthetic materials described herein. In certain embodiments, the tissue thickness compensator may comprise a biocompatible foam comprising gelatin, collagen, hyaluronic acid, oxidized regenerated cellulose, polyglycolic acid, polycaprolactone, polylactic acid, polydioxanone, polyhydroxyalkanoate, poliglecaprone, and combinations thereof. In certain embodiments, the tissue thickness compensator may comprise a film comprising the at least one medicament. In certain embodiments, the tissue thickness compensator may comprise a biodegradable film comprising the at least one medicament. In certain embodiments, the medicament may comprise a liquid, gel, and/or powder. In various embodiments, the medicaments may comprise anticancer agents, such as, for example, cisplatin, mitomycin, and/or adriamycin.

In various embodiments, the tissue thickness compensator may comprise a biodegradable material to provide controlled elution or release of the at least one medicament as the biodegradable material degrades. In various embodiments, the biodegradable material may degrade may decompose, or loses structural integrity, when the biodegradable material contacts an activator, such as, for example an activator fluid. In various embodiments, the activator fluid may comprise saline or any other electrolyte solution, for example. The biodegradable material may contact the activator fluid by conventional techniques, including, but not limited to spraying, dipping, and/or brushing. In use, for example, a surgeon may dip an end effector and/or a staple cartridge comprising the tissue thickness compensator comprising the at least one medicament into an activator fluid comprising a salt solution, such as sodium chloride, calcium chloride, and/or potassium chloride. The tissue thickness compensator may release the medicament as the tissue thickness compensator degrades. In certain embodiments, the elution or release of the medicament from the tissue thickness compensator may be characterized by a rapid initial elution or release rate and a slower sustained elution or release rate.

In various embodiments, a tissue thickness compensator, for example, can be comprised of a biocompatible material which may comprise an oxidizing agent. In various embodiments, the oxidizing agent may be an organic peroxide and/or an inorganic peroxide. Examples of oxidizing agents may include, but are not limited to, hydrogen peroxide, urea peroxide, calcium peroxide, and magnesium peroxide, and sodium percarbonate. In various embodiments, the oxidizing agent may comprise peroxygen-based oxidizing agents and hypohalite-based oxidizing agents, such as, for example, hydrogen peroxide, hypochlorous acid, hypochlorites, hypocodites, and percarbonates. In various embodiments, the oxidizing agent may comprise alkali metal chlorites, hypochlorites and perborates, such as, for example, sodium chlorite, sodium hypochlorite and sodium perborate. In certain embodiments, the oxidizing agent may comprise vanadate. In certain embodiments, the oxidizing agent may comprise ascorbic acid. In certain embodiments, the oxidizing agent may comprise an active oxygen generator. In various embodiments, a tissue scaffold may comprise the biocompatible material comprising an oxidizing agent.

In various embodiments, the biocompatible material may comprise a liquid, gel, and/or powder. In certain embodiments, the oxidizing agent may comprise microparticles and/or nanoparticles, for example. For example, the oxidizing agent may be milled into microparticles and/or nanoparticles. In certain embodiments, the oxidizing agent may be incorporated into the biocompatible material by suspending the oxidizing agent in a polymer solution. In certain embodiments, the oxidizing agent may be incorporated into the biocompatible material during the lyophylization process. After lyophylization, the oxidizing agent may be attached to the cell walls of the biocompatible material to interact with the tissue upon contact. In various embodiments, the oxidizing agent may not be chemically bonded to the biocompatible material. In at least one embodiment, a percarbonate dry power may be embedded within a biocompatible foam to provide a prolonged biological effect by the slow release of oxygen. In at least one embodiment, a percarbonate dry power may be embedded within a polymeric fiber in a non-woven structure to provide a prolonged biological effect by the slow release of oxygen. In various embodiments, the biocompatible material may comprise an oxidizing agent and a medicament, such as, for example, doxycycline and ascorbic acid.

In various embodiments, the biocompatible material may comprise a rapid release oxidizing agent and/or a slower sustained release oxidizing agent. In certain embodiments, the elution or release of the oxidizing agent from the biocompatible material may be characterized by a rapid initial elution or release rate and a slower sustained elution or release rate. In various embodiments, the oxidizing agent may generate oxygen when the oxidizing agent contacts bodily fluid, such as, for example, water. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, and/or bile. Without wishing to be bound to any particular theory, the oxidizing agent may reduce cell death, enhance tissue viability and/or maintain the mechanical strength of the tissue to tissue that may be damaged during cutting and/or stapling.

In various embodiments, the biocompatible material may comprise at least one microparticle and/or nanoparticle. The biocompatible material may comprise one or more of the natural materials, non-synthetic materials, and synthetic materials described herein. In various embodiments, the biocompatible material may comprise particles having a mean diameter of about 10 nm to about 100 nm and/or about 10 μm to about 100 μm, such as, for example, 45-50 nm and/or 45-50 μm. In various embodiments, the biocompatible material may comprise biocompatible foam comprising at least one microparticle and/or nanoparticle embedded therein. The microparticle and/or nanoparticle may not be chemically bonded to the biocompatible material. The microparticle and/or nanoparticle may provide controlled release of the medicament. In certain embodiments, the microparticle and/or nanoparticle may comprise at least one medicament. In certain embodiments, the microparticle and/or nanoparticle may comprise a hemostatic agent, an anti-microbial agent, and/or an oxidizing agent, for example. In certain embodiments, the tissue thickness compensator may comprise a biocompatible foam comprising an hemostatic agent comprising oxidized regenerated cellulose, an anti-microbial agent comprising doxycline and/or Gentamicin, and/or an oxidizing agent comprising a percarbant. In various embodiments, the microparticle and/or nanoparticle may provide controlled release of the medicament up to three days, for example.

In various embodiments, the microparticle and/or nanoparticle may be embedded in the biocompatible material during a manufacturing process. For example, a biocompatible polymer, such as, for example, a PGA/PCL, may contact a solvent, such as, for example, dioxane to form a mixture. The biocompatible polymer may be ground to form particles. Dry particles, with or without ORC particles, may be contacted with the mixture to form a suspension. The suspension may be lyophilized to form a biocompatible foam comprising PGA/PCL having dry particles and/or ORC particles embedded therein.

In various embodiments, the tissue thickness compensators or layers disclosed herein can be comprised of an absorbable polymer, for example. In certain embodiments, a tissue thickness compensator can be comprised of foam, film, fibrous woven, fibrous non-woven PGA, PGA/PCL (Poly(glycolic acid-co-caprolactone)), PLA/PCL (Poly(lactic acid-co-polycaprolactone)), PLLA/PCL, PGA/TMC (Poly(glycolic acid-co-trimethylene carbonate)), PDS, PEPBO or other absorbable polyurethane, polyester, polycarbonate, Polyorthoesters, Polyanhydrides, Polyesteramides, and/or Polyoxaesters, for example. In various embodiments, a tissue thickness compensator can be comprised of PGA/PLA (Poly(glycolic acid-co-lactic acid)) and/or PDS/PLA (Poly(p-dioxanone-co-lactic acid)), for example. In various embodiments, a tissue thickness compensator can be comprised of an organic material, for example. In certain embodiments, a tissue thickness compensator can be comprised of Carboxymethyl Cellulose, Sodium Alginate, Cross-linked Hyaluronic Acid, and/or Oxidized regenerated cellulose, for example. In various embodiments, a tissue thickness compensator can comprise a durometer in the 3-7 Shore A (30-50 Shore OO) ranges with a maximum stiffness of 15 Shore A (65 Shore OO), for example. In certain embodiments, a tissue thickness compensator can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the tissue thickness compensator. In at least one embodiment, a tissue thickness compensator can comprise beads therein which comprise between approximately 50% and approximately 75% of the material stiffness comprising the tissue thickness compensator.

In various embodiments, a tissue thickness compensator can comprise hyaluronic acid, nutrients, fibrin, thrombin, platelet rich plasma, Sulfasalazine (Azulfidine®-5ASA+Sulfapyridine diazo bond))-prodrug-colonic bacterial (Azoreductase), Mesalamine (5ASA with different prodrug configurations for delayed release), Asacolo (5ASA+Eudragit-S coated—pH>7 (coating dissolution)), Pentasa® (5ASA+ethylcellulose coated-time/pH dependent slow release), Mesasal® (5ASA+Eudragit-L coated—pH>6), Olsalazine (5ASA+5ASA-colonic bacterial (Azoreductase)), Balsalazide (5ASA+4Aminobenzoyl-B-alanine)-colonic bacterial (Azoreductase)), Granulated mesalamine, Lialda (delay and SR formulation of mesalamine), HMPL-004 (herbal mixture that may inhibit TNF-alpha, interleukin-1 beta, and nuclear-kappa B activation), CCX282-B (oral chemokine receptor antagonist that interferes with trafficking of T lymphocytes into the intestinal mucosa), Rifaximin (nonabsorbable broad-spectrum antibiotic), Infliximab, murine chymieric (monoclonal antibody directed against TNF-alpha-approved for reducing signs/symptoms and maintaining clinical remission in adult/pediatric patients with moderate/severe luminal and fistulizing Crohn's disease who have had inadequate response to conventional therapy), Adalimumab, Total Human IgG1 (anti-TNF-alpha monoclonal antibody—approved for reducing signs/symptoms of Crohn's disease, and for the induction and maintenance of clinical remission in adult patients with moderate/severe active Crohn's disease with inadequate response to conventional therapies, or who become intolerant to Infliximab), Certolizumab pegoll, humanized anti-TNF FAB' (monoclonal antibody fragment linked to polyethylene glycol—approved for reducing signs/symptoms of Crohn's disease and for the induction and maintenance of response in adult patients w/moderate/severe disease with inadequate response to conventional therapies), Natalizumab, First non-TNF-alpha inhibitor (biologic compound approved for Crohn's disease), Humanized monoclonal IgG4 antibody (directed against alpha-4 integrin—FDA approved for inducing and maintaining clinical response and remission in patients with moderate/severe disease with evidence of inflammation and who have had inadequate response to or are unable to tolerate conventional Crohn's therapies and inhibitors of TNF-alpha), concomitant Immunomodulators potentially given with Infliximab, Azathioprine 6-Mercaptopurine (purine synthesis inhibitor—prodrug), Methotrexate (binds dihydrofolate reductase (DHFR) enzyme that participates in tetrahydrofolate synthesis, inhibits all purine synthesis), Allopurinol and Thioprine therapy, PPI, H2 for acid suppression to protect the healing line, C-Diff—Flagyl, Vancomycin (fecal translocation treatment; probiotics; repopulation of normal endoluminal flora), and/or Rifaximin (treatment of bacterial overgrowth (notably hepatic encephalopathy); not absorbed in GI tract with action on intraluminal bacteria), for example.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of creating a tissue thickness compensator, the method comprising:

dispensing oxidized regenerated cellulose onto a cover sheet;

folding the cover sheet to at least partially capture the oxidized regenerated cellulose therein; and creating the tissue thickness compensator by applying a seal to the folded cover sheet.

2. The method of claim 1, further comprising flattening the cover sheet with a roller prior to dispensing the oxidized regenerated cellulose onto the cover sheet.

3. The method of claim 1, further comprising flattening the cover sheet after applying the seal to the folded cover sheet.

4. The method of claim 1, further comprising flatting the cover sheet prior to applying the seal to the folded cover sheet.

5. The method of claim 1, further comprising:

compressing the folded cover sheet; and flattening the cover sheet after compressing the folded cover sheet.

6. The method of claim 1, wherein the cover sheet is comprised of Cap Gly.

7. The method of claim 1, wherein applying a seal to the folded cover sheet comprises welding at least one edge of the folded cover sheet.

8. A method of creating tissue thickness compensators, the method comprising:

dispensing oxidized regenerated cellulose onto a first portion of a cover sheet;

progressively folding a second portion of the cover sheet over the first portion of the cover sheet to at least partially capture the oxidized regenerated cellulose within the cover sheet;

applying a seal to the folded cover sheet; and segmenting the sealed cover sheet into a plurality of portions to create the tissue thickness compensators.

9. The method of claim 8, further comprising flattening the cover sheet with a roller prior to dispensing the oxidized regenerated cellulose onto the first portion of the cover sheet.

10. The method of claim 8, further comprising flattening the cover sheet after applying the seal to the folded cover sheet.

11. The method of claim 8, further comprising flatting the cover sheet prior to applying the seal to the folded cover sheet.

12. The method of claim 8, wherein the cover sheet is comprised of Cap Gly.

13. The method of claim 8, wherein applying a seal to the folded cover sheet comprises welding at least one edge of the folded cover sheet.

* * * * *